(12) United States Patent
Kumar et al.

(10) Patent No.: US 10,227,393 B2
(45) Date of Patent: Mar. 12, 2019

(54) TGF-BETA SUPERFAMILY TYPE I AND TYPE II RECEPTOR HETEROMULTIMERS AND USES THEREOF

(71) Applicant: Acceleron Pharma Inc., Cambridge, MA (US)

(72) Inventors: Ravindra Kumar, Acton, MA (US); Asya Grinberg, Lexington, MA (US); Dianne Sako, Medford, MA (US); Robert Scott Pearsall, North Reading, MA (US); Roselyne Castonguay, Watertown, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

(21) Appl. No.: 15/092,609

(22) Filed: Apr. 6, 2016

(65) Prior Publication Data

US 2016/0298093 A1    Oct. 13, 2016

Related U.S. Application Data

(60) Provisional application No. 62/143,579, filed on Apr. 6, 2015.

(51) Int. Cl.
| C07K 14/71 | (2006.01) |
| A61K 38/00 | (2006.01) |
| A61K 38/45 | (2006.01) |
| C12N 9/12  | (2006.01) |

(52) U.S. Cl.
CPC ............. *C07K 14/71* (2013.01); *A61K 38/45* (2013.01); *C12N 9/12* (2013.01); *C12Y 207/1103* (2013.01); *A61K 38/00* (2013.01); *C07K 2319/30* (2013.01)

(58) Field of Classification Search
CPC ..... C07K 14/71; C07K 2319/30; A61K 38/00
See application file for complete search history.

(56) References Cited

U.S. PATENT DOCUMENTS

| 7,612,041 B2 | 11/2009 | Knopf et al. |
| 7,709,605 B2 | 5/2010 | Knopf et al. |
| 7,820,620 B2 | 10/2010 | Vale et al. |
| 7,842,663 B2 | 11/2010 | Knopf et al. |
| 7,951,771 B2 | 5/2011 | Knopf et al. |
| 8,067,360 B2 | 11/2011 | Knopf et al. |
| 8,252,900 B2 | 8/2012 | Knopf et al. |
| 8,293,881 B2 | 10/2012 | Seehra et al. |
| 8,343,933 B2 | 1/2013 | Knopf et al. |
| 8,361,957 B2 | 1/2013 | Seehra et al. |
| 8,629,109 B2 | 1/2014 | Knopf et al. |
| 8,734,760 B2 | 5/2014 | O'Connor-McCourt et al. |
| 9,138,459 B2 | 9/2015 | Knopf et al. |
| 9,163,075 B2 | 10/2015 | Knopf et al. |
| 9,181,533 B2 | 11/2015 | Seehra et al. |
| 9,399,669 B2 | 7/2016 | Knopf et al. |
| 9,611,306 B2 | 4/2017 | Hinck et al. |
| 9,809,638 B2 | 11/2017 | Sun et al. |
| 2010/0266612 A1 | 10/2010 | Seehra |
| 2010/0330657 A1 | 12/2010 | Miyazono et al. |
| 2011/0236309 A1 | 9/2011 | O'Connor-Mccourt et al. |
| 2016/0289292 A1 | 10/2016 | Kumar et al. |
| 2016/0289298 A1 | 10/2016 | Kumar et al. |
| 2016/0297867 A1 | 10/2016 | Kumar et al. |
| 2017/0306027 A1 | 10/2017 | Knopf et al. |
| 2018/0008672 A1 | 1/2018 | Chalothorn et al. |
| 2018/0072791 A1 | 3/2018 | Sun et al. |
| 2018/0111991 A1 | 4/2018 | Miller et al. |

(Continued)

FOREIGN PATENT DOCUMENTS

| EP | 3 101 029 A1 | 12/2016 |
| WO | WO-93/11162 A1 | 6/1993 |
| WO | WO-94/11502 A2 | 5/1994 |

(Continued)

OTHER PUBLICATIONS

Pending U.S. Appl. No. 15/092,573.
Pending U.S. Appl. No. 15/092,577.
Pending U.S. Appl. No. 15/092,600.
Pending U.S. Appl. No. 15/726,255.
Pending U.S. Appl. No. 15/480,726.
Allendorph, et al., "Structure of the ternary signaling complex of a TGF-β superfamily member," Proceedings of the National Academy of Sciences, vol. 103(20): 7643-7648 (2006).

(Continued)

*Primary Examiner* — Ruixiang Li
(74) *Attorney, Agent, or Firm* — White & Case LLP

(57) ABSTRACT

In certain aspects, the disclosure provides soluble heteromeric polypeptide complexes comprising an extracellular domain of a type I serine/threonine kinase receptor of the TGF-beta family and an extracellular domain of a type II serine/threonine kinase receptor of the TGF-beta family. In some embodiments, the disclosure provides soluble polypeptide complexes comprising an extracellular domain of a type II receptor selected from: ActRIIA, ActRIIB, TGFBRII, BMPRII, and MISRII. In some embodiments, the disclosure provides soluble polypeptide complexes comprising an extracellular domain of a type I receptor selected from: ALK1, ALK2, ALK3, ALK4, ALK5, ALK6, and ALK7. Optionally the soluble complex is a heterodimer. In certain aspects, such soluble polypeptide complexes may be used to regulate (promote or inhibit) growth of tissues or cells including, for example, muscle, bone, cartilage, fat, neural tissue, tumors, cancerous cells, and/or cells of hematopoietic lineages, including red blood cells. In certain aspects, such soluble polypeptide complexes are can be used to improve muscle formation, bone formation, hematopoiesis, metabolic parameters, and disorders associated with these tissues, cellular networks, and endocrine systems.

27 Claims, 32 Drawing Sheets
(31 of 32 Drawing Sheet(s) Filed in Color)
Specification includes a Sequence Listing.

(56) References Cited

U.S. PATENT DOCUMENTS

2018/0148491 A1     5/2018   Han et al.

FOREIGN PATENT DOCUMENTS

| WO | WO-00/43781 A2 | 7/2000 |
|---|---|---|
| WO | WO-2004/039948 A2 | 5/2004 |
| WO | WO-2005/028433 A2 | 3/2005 |
| WO | WO-2005/084699 A1 | 9/2005 |
| WO | WO-2006/012627 A2 | 2/2006 |
| WO | WO-2007/147901 A1 | 12/2007 |
| WO | WO-2008/073351 A2 | 6/2008 |
| WO | WO-2008/076437 A2 | 6/2008 |
| WO | WO-2008/097541 A2 | 8/2008 |
| WO | WO-2009/089004 A1 | 7/2009 |
| WO | WO-2009/134428 A2 | 11/2009 |
| WO | WO-2010/019261 A1 | 2/2010 |
| WO | WO-2010/083034 A1 | 7/2010 |
| WO | WO-2010/114860 A1 | 10/2010 |
| WO | WO-2010/151426 A1 | 12/2010 |
| WO | WO-2011/034605 A2 | 3/2011 |
| WO | WO-2011/045497 A1 | 4/2011 |
| WO | WO-2012/027065 A2 | 3/2012 |
| WO | WO-2013/000234 A1 | 1/2013 |
| WO | WO-2013/063536 A1 | 5/2013 |
| WO | WO-2015/027082 A1 | 2/2015 |
| WO | WO-2016/164089 A2 | 10/2016 |
| WO | WO-2016/205370 A1 | 12/2016 |
| WO | WO-2017/037634 A1 | 3/2017 |
| WO | WO-2018/009624 A1 | 1/2018 |
| WO | WO-2018/075747 A1 | 4/2018 |

OTHER PUBLICATIONS

Andersson, et al., "Growth/differentiation factor 3 signals through ALK7 and regulates accumulation of adipose tissue and diet-induced obesity," Proceedings of the National Academy of Sciences, vol. 105(20): 7252-7256 (2008).

Ashmore, et al., "Comparative Aspects of Muscle Fiber Types in Fetuses of the Normal and "Double-Muscled" Cattle," Growth, vol. 38: 501-506 (1974).

Attie, et al., "A phase 1 study of ACE-536, a regulator of erythroid differentiation, in healthy volunteers," American Journal of Hematology, vol. 89(7): 766-770 (2014).

Attisano, et al., "Novel Activin Receptors: Distinct Genes and Alternative mRNA Splicing Generate a Repertoire of Serine/Threonine Kinase Receptors," Cell, vol. 68: 97-108 (1992).

Berasi, et al., "Divergent activities of osteogenic BMP2, and tenogenic BMP12 and BMP13 independent of receptor binding affinities," Growth Factors, vol. 29(4): 128-139 (2011).

Bogdanovich, et al., "Functional improvement of dystrophic muscle by myostatin blockade," Nature, vol. 420: 418-421 (2002).

Brown, et al., "Physicochemical Activation of Recombinant Latent Transforming Growth Factor-beta's 1, 2, and 3," Growth Factors, vol. 3: 35-43 (1990).

Castonguay, et al., "Soluble Endoglin Specifically Binds Bone Morphogenetic Proteins 9 and 10 via Its Orphan Domain, Inhibits Blood Vessel Formation, and Suppresses Tumor Growth," The Journal of Biological Chemistry, vol. 286(34): 30034-30046 (2011).

Clouthier, et al., "Hepatic Fibrosis, Glomerulosclerosis, and a Lipodystrophy-like Syndrome in PEPCK-TGF-β1 Transgenic Mice," Journal of Clinical Investigation, vol. 100(11): 2697-2713 (1997).

Cunha, et al., "ALK1 as an emerging target for antiangiogenic therapy of cancer," Blood, vol. 117(26): 6999-7006 (2011).

Demirhan, et al., "A homozygous BMPR1B mutation causes a new subtype of acromesomelic chondrodysplasia with genital anomalies," Journal of Medical Genetics, vol. 42: 314-317 (2005).

DePaolo, et al., "Follistatin and Activin: A Potential Intrinsic Regulatory System with Diverse Tissues," Proceedings of the Society for Experimental Biology and Medicine: 500-512 (1991).

di Clemente, et al., "Processing of Anti-Mullerian Hormone Regulates Receptor Activation by a Mechanism Distinct from TGF-β," Moleular Endocrinology, vol. 24(11): 2193-2206 (2010).

Dyson, et al., "Activin signalling has a necessary function in Xenopus early development," Current Biology, vol. 7(1): 81-84 (1997).

Fukuda, et al., "Constitutively Activated ALK2 and Increased SMAD1/5 Cooperatively Induce Bone Morphogenetic Protein Signaling in Fibrodysplasia Ossificans Progressiva," The Journal of Biological Chemistry, vol. 284(11): 7149-7156 (2009).

Gamer, et al., "A Novel BMP Expressed in Developing Mouse Limb, Spinal Cord, and Tail Bud Is a Potent Mesoderm Inducer in Xenopus Embryos," Developmental Biology, vol. 208: 222-232 (1999).

Gamer, et al., "Gdf11 Is a Negative Regulator of Chrondrogenesis and Myogenesis in the Developing Chick Limb," Developmental Biology, vol. 229: 407-420 (2001).

Gonzalez-Cadavid, et al., "Organization of the human myostatin gene and expression in healthy men and HIV-infected men with muscle wasting," Proceedings of the National Academy of Sciences, vol. 95: 14938-14943 (1998).

Goumans, et al., "Activin Receptor-like Kinase (ALK)1 Is an Antagonistic Mediator of Lateral TGFβ/ALK5 Signaling," Molecular Cell, vol. 12: 817-828 (2003).

Greenwald, et al., "Three-finger toxin fold for the extracellular ligand-binding domain of the type II activin receptor serine kinase," Nature Structural Biology, vol. 6(1): 18-22 (1999).

Grobet, et al., "A deletion in the bovine myostatin gene causes the double-muscled phenotype in cattle," Nature Genetics, vol. 17: 71-74 (1997).

Hildén, et al., "Expression of Type II Activin Receptor Genes During Differentiation of Human K562 Cells and cDNA Cloning of the Human Type IIB Activin Receptor," Blood, vol. 83(8): 2163-2170 (1994).

Hinck, "Structural studies of the TGF-βs and their receptors—insights into evolution of the TGF-β superfamily," Federation of European Biochemical Societies Letters, vol. 586: 1860-1870 (2012).

Kabat, et al., "Sequences of Proteins of Immunological Interest," Fifth Edition, Public Health Service National Institutes of Health, NIH Publication No. 91-3242: 688-696 (1991).

Kambadur, et al., "Mutations in myostatin (GDF8) in Double-Muscled Belgian Blue and Piedmontese Cattle," Genome Research, vol. 7: 910-915 (1997).

Kamiya, et al., "Disruption of Bmp Signaling in Osteoblasts Through Type IA Receptor (BMPRIA) Increases Bone Mass," Journal of Bone and Mineral Research, vol. 23(12): 2007-2017 (2008).

Kamiya, et al., "BMP signaling negatively regulates bone mass through sclerostin by inhibiting the canonical Wnt pathway," Development, vol. 135: 3801-3811 (2008).

Kaplan, et al., "Fibrodysplasia ossificans progressive: a blueprint for metamorphosis," Annals of the New York Academy of Sciences, vol. 1237: 5-10 (2011).

Klein, et al., "Progress in overcoming the chain association issue in bispecific heterodimeric IgG antibodies," mAbs, vol. 4(6): 653-663 (2012).

Konrad, et al., "Alternative splicing of TGF-betas and their high-affinity receptors TβRI, TβRII and TβRIII (betaglycan) reveal new variants in human prostatic cells," BMC Genomics, vol. 8(318): 13 pages (2007).

Kubiczkova, et al., "TGF-β—an excellent servant but a bad master," Journal of Translational Medicine, vol. 10(183): 24 pages (2012).

Larsson, et al., "Abnormal angiogenesis but intact hematopoietic potential in TGF-β type I receptor-deficient mice," The EMBO Journal, vol. 20(7): 1663-1673 (2001).

Lavery, et al., "BMP-2/4 and BMP-6/7 Differentially Utilize Cell Surface Receptors to Induce Osteoblastic Differentiation of Human Bone Marrow-derived Mesenchymal Stem Cells," The Journal of Biological Chemistry, vol. 283(30): 20948-20958 (2008).

Li, et al., "Transforming Growth Factor-β Controls Development, Homeostasis, and Tolerance of T Cells by Regulatory T Cell-Dependent and -Independent Mechanisms," Immunity, vol. 25: 455-471 (2006).

Macías-Silva, et al., "Specific Activation of Smad1 Signaling Pathways by the BMP7 Type I Receptor, ALK2," The Journal of Biological Chemistry, vol. 273(40): 25628-25636 (1998).

(56) References Cited

OTHER PUBLICATIONS

Massagué, "How Cells Read TGF-β Signals," Nature Reviews Molecular Cell Biology, vol. 1(3): 169-178 (2000).
McPherron, et al., "Double muscling in cattle due to mutations in the myostatin gene," Proceedings of the National Academy of Sciences, vol. 94: 12457-12461 (1997).
McPherron, et al., "Regulation of skeletal muscle mass in mice by a new TGF-β superfamily member," Nature, vol. 387: 83-90 (1997).
McPherron, et al., "Regulation of anterior/posterior patterning of the axial skeleton by growth/differentiation factor 11," Nature Genetics, vol. 22: 260-264 (1999).
Mishina, et al., "Multiple Roles for Activin-Like Kinase-2 Signaling during Mouse Embryogenesis," Developmental Biology, vol. 213: 314-326 (1999).
Mitchell, et al., "ALK1-Fc Inhibits Multiple Mediators of Angiogenesis and Suppresses Tumor Growth," Molecular Cancer Therapeutics, vol. 9(2): 379-380 (2010).
Miyazono, et al., "Latent High Molecular Weight Complex of Transforming Growth Factor β1," The Journal of Biological Chemistry, vol. 263(13): 6407-6415 (1998).
Nakashima, et al., "Expression of growth/differentiation factor 11, a new member of the BMP/TGFβ superfamily during mouse embryogenesis," Mechanisms of Development, vol. 80: 185-189 (1999).
Pack, et al., "Miniantibodies: Use of Amphipathic Helices to Produce Functional, Flexibly Linked Dimeric Fv Fragments with High Avidity in *Escherichia coli*," Biochemistry, vol. 31(6): 1579-1584 (1992).
Pack, et al., "Improved Bivalent Miniantibodies, with Identical Avidity as Whole Antibodies, Produced by High Cell Density Fermentation of *Escherichia coli*," Bio/Technology, vol. 11: 1271-1277 (1993).
Pistilli, et al., "Targeting the Activin Type IIB Receptor to Improve Muscle Mass and Function in the mdx Mouse Model of Duchenne Muscular Dystrophy," The American Journal of Pathology, vol. 178(3): 1287-1297 (2011).
Ridgway, et al., "'Knobs-into-holes' engineering of antibody CH3 domains for heavy chain heterodimerization," Protein Engineering, vol. 19(7): 617-621 (1996).
Rosenzweig, et al., "Cloning and characterization of a human type II receptor for bone morphogenetic proteins," Proceedings of the National Academy of Sciences, vol. 92: 7632-7636 (1995).
Sakuma, et al., "Inhibition of Nodal signalling by Lefty mediated through interaction with common receptors and efficient diffusion," Genes to Cells, vol. 7: 401-412 (2002).
Schaefer, et al., "Immunoglobulin domain crossover as a generic approach for the production of bispecific IgG antibodies," Proceedings of the National Academy of Sciences, vol. 108(27): 11187-11192 (2011).
Schuelke, et al., "Myostatin Mutation Associated with Gross Muscle Hypertrophy in a Child," The New England Journal of Medicine, vol. 350(26): 2682-2688 (2004).
Spiess, et al., "Alternative molecular formats and therapeutic applications for bispecific antibodies," Molecular Immunology, vol. 67: 95-106 (2015).
Swatland, et al., "Fetal Development of the Double Muscled Condition in Cattle," Journal of Animal Science, vol. 38(4): 752-757 (1974).
Ten Dijke, et al., "Activin receptor-like kinases: a novel subclass of cell-surface receptors with predicted serine/threonine kinase activity," Oncogene, vol. 8(10): 2879-2887 (1993).
Thompson, et al., "Structures of an ActRIIB: activin A complex reveal a novel binding mode for TGF-β ligand: receptor interactions," The EMBO Journal, vol. 22(7): 1555-1566 (2003).
Tsuchida, et al., "Signal Transduction Pathway through Activin Receptors as a Therapeutic Target of Musculoskeletal Diseases and Cancer," Endocrine Journal, vol. 55(1): 11-21 (2007).
Wakefield, et al., "Latent Transforming Growth Factor-β from Human Platelets," The Journal of Biological Chemistry, vol. 263(16): 7646-7654 (1988).
Weiss, et al., "The TGFbeta Superfamily Signaling Pathway," Developmental Biology, vol. 2: 47-63 (2013).
Woodruff, "Regulation of Cellular and System Function by Activin," Biochemical Pharmacology, vol. 55: 953-963 (1998).
Wranik, et al., "LUZ-Y, a Novel Platform for the Mammalian Cell Production of Full-length IgG-bispecific Antibodies," The Journal of Biological Chemistry, vol. 287(52): 43331-43339 (2012).
Wu, et al., "Autoregulation of Neurogenesis by GDF11," Neuron, vol. 37: 197-207 (2003).
Yi, et al., "The type I BMP receptor BMPRIB is required for chondrogenesis in the mouse limb," Development, vol. 127: 621-630 (2000).
Zec, et al., "Anti-Müllerian hormone: A unique biochemical marker of gonadal development and fertility in humans," Biochemia Medica, vol. 21(3): 219-230 (2011).
Zimmers, et al., "Induction of Cachexia in Mice by Systemically Administered Myostatin," Science, vol. 296: 1486-1488 (2002).
Cheng, et al., "Transforming Growth Factor-β1 (TGF-β1) Induces Mouse Precartilaginous Stem Cell Proliferation through TGF-β Recptor II (TGFRII)-Akt-β-Catenin Signaling," International Journal of Molecular Sciences, vol. 15: 12664-12676 (2014).
Das, et al., "Macromolecular Modeling with Rosetta," Annual Review of Biochemistry, vol. 77: 363-382 (2008).
Davis, et al., "SEEDbodies: fusion proteins based on strand-exchange engineered domain (SEED) CH3 heterodimers in an Fc analogue platform for asymmetric binders or immunofusions and bispecific antibodies," Protein Engineering, Design & Selection, vol. 23(4): 195-202 (2010).
De Silva, et al., "Nodal promotes glioblastoma cell growth," Frontiers in Endocrinology, vol. 3, Article 59: 1-6 (2012).
Fenn, et al., "Crystal Structure of an Anti-Ang2 CrossFab Demonstrates Complete Structural and Functional Integrity of the Variable Domain," PLoSONE, vol. 8(4): e61953 (2013).
Gunasekaran, et al., "Enhancing Antibody Fc Heterodimer Formation through Electrostatic Steering Effects," The Journal of Biological Chemistry, vol. 285(25): 19637-19646 (2010).
Kemaladewi, et al., "Targeting TGF-β Signaling by Antisense Oligonucleotide-mediated Knockdown of TGF-β Type I Receptor," Molecular Therapy—Nucleic Acids, vol. 3(e156): 1-8 (2014).
Lewis, et al., "Generation of bispecific IgG antibodies by structure-based design of an orthogonal Fab interface," Nature Biotechnology, vol. 32(2): 191-198 (2014).
Lin, et al., "The structural basis of TGF-β, bone morphogenetic protein, and activin ligand binding," Reproduction, vol. 132: 179-190 (2006).
Merchant, et al., "An efficient route to human bispecific IgG," Nature Biotechnology, vol. 16: 677-681 (1998).
Rider, et al., "Bone morphogenetic protein and growth differentiation factor cytokine families and their protein antagonists," Biochemical Journal, vol. 429: 1-12 (2010).
Qin et al., "A novel highly potent trivalent TGF-β receptor trap inhibits early-stage tumorigenesis and tumor cell invasion in murine Pten-deficient prostate glands," Oncotarget, Advance Publications: 1-16 (2016).
Zwaagstra et al., "Engineering and Therapeutic Application of Single-Chain Bivalent TGF-β Family Traps," Molecular Cancer Therapeutics; vol. 11(7): 1477-1487 (2012).
Pending U.S. Appl. No. 14/836,684, Knopf et al.
Pending U.S. Appl. No. 14/849,313, Knopf et al.
Pending U.S. Appl. No. 15/201,031, Knopf et al.
Pending U.S. Appl. No. 15/092,573, Kumar et al.
Pending U.S. Appl. No. 15/480,726, Knopf et al.
Pending U.S. Appl. No. 15/092,600, Kumar et al.
Pending U.S. Appl. No. 15/092,577, Kumar et al.
Pending U.S. Appl. No. 15/726,255, Kumar et al.

ActRIIa    ILGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

EVTQPTSNPV TPKPP
           GGPEVTYEPP PTAPT

FIG. 3

```
IgG1    --------THTCPPCPAPELLGGPSVFLFPPKPKDTLMISRTPEVTCVVVDVSHEDPEVKF  53
IgG4    ----ESKYGPPCPSCPAPEFLGGPSVFLFPPKPKDTLMISRTPEVTCVVVDVSQEDPEVQF  57
IgG2    ---------VECPPCPAPPVAG-PSVFLFPPKPKDTLMISRTPEVTCVVVDVSHEDPEVQF  51
IgG3    EPKSCDTPPPCPRCPAPELLGGPSVFLFPPKPKDTLMISRTPEVTCVVVDVSHEDPEVQF  60
                 **.****. .* ****************************.*****.*

IgG1    NWYVDGVEVHNAKTKPREEQYNSTYRVVSVLTVLHQDWLNGKEYKCKVSNKALPAPIEKT  113
IgG4    NWYVDGVEVHNAKTKPREEQFNSTYRVVSVLTVLHQDWLNGKEYKCKVSNKGLPSSIEKT  117
IgG2    NWYVDGVEVHNAKTKPREEQFNSTFRVVSVLTVVHQDWLNGKEYKCKVSNKGLPAPIEKT  111
IgG3    KWYVDGVEVHNAKTKPREEQYNSTFRVVSVLTVLHQDWLNGKEYKCKVSNKALPAPIEKT  120
        .****************** ***.********.****************.**..****

IgG1    ISKAKGQPREPQVYTLPPSREEMTKNQVSLTCLVKGFYPSDIAVEWESNGQPENNYKTTP  173
IgG4    ISKAKGQPREPQVYTLPPSQEEMTKNQVSLTCLVKGFYPSDIAVEWESNGQPENNYKTTP  177
IgG2    ISKTKGQPREPQVYTLPPSREEMTKNQVSLTCLVKGFYPSDIAVEWESNGQPENNYKTTP  171
IgG3    ISKTKGQPREPQVYTLPPSREEMTKNQVSLTCLVKGFYPSDIAVEWESSGQPENNYNTTP  180
        ***.*************** ***************************.*******.***

IgG1    PVLDSDGSFFLYSKLTVDKSRWQQGNVFSCSVMHEALHNHYTQKSLSLSPGK  225
IgG4    PVLDSDGSFFLYSRLTVDKSRWQEGNVFSCSVMHEALHNHYTQKSLSLSLGK  229
IgG2    PMLDSDGSFFLYSKLTVDKSRWQQGNVFSCSVMHEALHNHYTQKSLSLSPGK  223
IgG3    PMLDSDGSFFLYSKLTVDKSRWQQGNIFSCSVMHEALHNRFTQKSLSLSPGK  232
        *.***********.********* **.***********..********* **
```

FIG. 5

TGF-BETA SUPERFAMILY TYPE I AND TYPE II RECEPTOR HETEROMULTIMERS AND USES THEREOF

CROSS-REFERENCE TO RELATED APPLICATIONS

This application claims the benefit of priority to U.S. provisional application Ser. No. 62/143,579, filed Apr. 6, 2015. The disclosure of the foregoing applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 31, 2016, is named PHPH080101_SL.txt and is 605,625 bytes in size.

BACKGROUND OF THE INVENTION

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general phylogenetic clades: the more recently evolved members of the superfamily, which includes TGF-betas, Activins, and nodal and the Glade of more distantly related proteins of the superfamily, which includes a number of BMPs and GDFs. Hinck (2012) FEBS Letters 586:1860-1870. TGF-beta family members have diverse, often complementary biological effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al. (1997) Nat Genet., 17(1):71-4. Furthermore, in humans, inactive alleles of GDF8 are associated with increased muscle mass and, reportedly, exceptional strength. Schuelke et al. (2004) N Engl J Med, 350:2682-8.

Changes in muscle, bone, fat, red blood cells, and other tissues may be achieved by enhancing or inhibiting signaling (e.g., SMAD 1, 2, 3, 5, and/or 8) that is mediated by ligands of the TGF-beta family. Thus, there is a need for agents that regulate the activity of various ligands of the TGF-beta superfamily.

SUMMARY OF THE INVENTION

In part, the disclosure provides heteromultimeric complexes comprising at least one TGF-beta superfamily type I serine/threonine kinase receptor polypeptide (e.g., an ALK1, ALK2, ALK3, ALK4, ALK5, ALK6, and ALK7 polypeptide), including fragments and variants thereof, and at least one TGF-beta superfamily type II serine/threonine kinase receptor polypeptide (e.g., ActRIIA, ActRIIB, TGFBRII, BMPRII, and MISRII), including fragments and variants thereof. In other aspects, the disclosure provides heteromultimeric complexes comprising at least two different TGF-beta superfamily type I serine/threonine kinase receptor polypeptide (e.g., an ALK1, ALK2, ALK3, ALK4, ALK5, ALK6, and ALK7 polypeptide), including fragments and variants thereof. In still other aspects, the disclosure provides heteromultimeric complexes comprising at least two different TGF-beta superfamily type II serine/threonine kinase receptor polypeptide (e.g., ActRIIA, ActRIIB, TGF-BRII, BMPRII, and MISRII), including fragments and variants thereof. Optionally, heteromultimeric complexes disclosed herein (e.g., an ActRIIBALK4 heterodimer) have different ligand binding specificities/profiles compared to their corresponding homomultimer complexes (e.g., an ActRIIB homodimer and ALK4 homodimer). Novel properties, including novel ligand binding attributes, are exhibited by heteromultimeric polypeptide complexes comprising type I and type II receptor polypeptides of the TGF-beta superfamily, as shown by Examples herein.

Heteromultimeric structures include, for example, heterodimers, heterotrimers, and higher order complexes. See, e.g., FIGS. 1, 2, 15, 16, 17, 18, 19. In some embodiments heteromultimers of the disclosure are heterodimers. Preferably, TGF-beta superfamily type I and type II receptor polypeptides as described herein comprise a ligand-binding domain of the receptor, for example, an extracellular domain of a TGF-beta superfamily type I or type II receptor. Accordingly, in certain aspects, protein complexes described herein comprise an extracellular domain of a type II TGF-beta superfamily receptor selected from: ActRIIA, ActRIIB, TGFBRII, BMPRII, and MISRII, as well as truncations and variants thereof, and an extracellular domain of a type I TGF-beta superfamily receptor selected from: ALK1, ALK2, ALK3, ALK4, ALK5, ALK6, and ALK7, as well as truncations and variants thereof. Preferably, TGF-beta superfamily type I and type II polypeptides as described herein, as well as protein complexes comprising the same, are soluble. In certain aspects, heteromultimer complexes of the disclosure bind to one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, Müllerian-inhibiting substance (MIS), and Lefty). Optionally, protein complexes of the disclosure bind to one or more of these ligands with a $K_D$ of greater than or equal to $10^{-8}$, $10^{-9}$, $10^{-10}$, $10^{-11}$, or $10^{-12}$. In general, heteromultimers of the disclosure antagonize (inhibit) one or more activities of at least one TGF-beta superfamily ligand, and such alterations in activity may be measured using various assays known in the art, including, for example, a cell-based assay as described herein. Preferably heteromultimers of the disclosure exhibit a serum half-life of at least 4, 6, 12, 24, 36, 48, or 72 hours in a mammal (e.g., a mouse or a human). Optionally, heteromultimers of the disclosure may exhibit a serum half-life of at least 6, 8, 10, 12, 14, 20, 25, or 30 days in a mammal (e.g., a mouse or a human).

In certain aspects, heteromultimers described herein comprise a first polypeptide covalently or non-covalently associated with a second polypeptide wherein the first polypeptide comprises the amino acid sequence of a TGF-beta superfamily type I receptor polypeptide and the amino acid sequence of a first member of an interaction pair and the second polypeptide comprises the amino acid sequence of a TGF-beta superfamily type II receptor polypeptide and the amino acid sequence of a second member of the interaction pair. In other aspects, heteromultimers described herein comprise a first polypeptide covalently or non-covalently associated with a second polypeptide wherein the first polypeptide comprises the amino acid sequence of a TGF-beta superfamily type I receptor polypeptide and the amino acid sequence of a first member of an interaction pair and the second polypeptide comprises the amino acid sequence of a different TGF-beta superfamily type I receptor polypeptide and the amino acid sequence of a second member of the interaction pair. In still other aspects, heteromultimers described herein comprise a first polypeptide covalently or non-covalently associated with a second polypeptide wherein the first polypeptide comprises the amino acid sequence of a TGF-beta superfamily type II receptor polypeptide and the amino acid sequence of a first member of an interaction pair and the second polypeptide comprises the amino acid sequence of a different TGF-beta superfamily type II receptor polypeptide and the amino acid sequence of a second member of the interaction pair. Optionally, the TGF-beta superfamily type I receptor polypeptide is connected directly to the first member of the interaction pair, or an intervening sequence, such as a linker, may be positioned between the amino acid sequence of the TGF-beta superfamily type I receptor polypeptide and the amino acid sequence of the first member of the interaction pair. Similarly, the TGF-beta superfamily type II receptor polypeptide may be connected directly to the second member of the interaction pair, or an intervening sequence, such as a linker, may be positioned between the amino acid sequence of the TGF-beta superfamily type II receptor polypeptide and the amino acid sequence of the second member of the interaction pair. Examples of linkers include, but are not limited to, the sequences TGGG (SEQ ID NO: 62), TGGGG (SEQ ID NO: 60), SGGGG (SEQ ID NO: 61), GGGG (SEQ ID NO: 59), and GGG (SEQ ID NO: 58).

Interaction pairs described herein are designed to promote dimerization or form higher order multimers. In some embodiments, the interaction pair may be any two polypeptide sequences that interact to form a complex, particularly a heterodimeric complex although operative embodiments may also employ an interaction pair that forms a homodimeric sequence. The first and second members of the interaction pair may be an asymmetric pair, meaning that the members of the pair preferentially associate with each other rather than self-associate. Accordingly, first and second members of an asymmetric interaction pair may associate to form a heterodimeric complex. Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction action pair (e.g., an asymmetric pair or an unguided interaction pair) associates covalently with the second member of the interaction pair. Optionally, the first member of the interaction action pair (e.g., an asymmetric pair or an unguided interaction pair) associates non-covalently with the second member of the interaction pair. Optionally, the first member of the interaction pair (e.g., an asymmetrical or an unguided interaction pair) associates through both covalent and non-covalent mechanisms with the second member of the interaction pair.

In some embodiments, TGF-beta superfamily type I receptor polypeptides are fusion proteins that comprise an Fc domain of an immunoglobulin. Similarly, in some embodiments, TGF-beta superfamily type II receptor polypeptides are fusion proteins that comprise an Fc domain of an immunoglobulin. Traditional Fc fusion proteins and antibodies are examples of unguided interaction pairs, whereas a variety of engineered Fc domains have been designed as asymmetric interaction pairs [Spiess et al (2015) Molecular Immunology 67(2A): 95-106]. Therefore, a first member and/or a second member of an interaction pair described herein may comprise a constant domain of an immunoglobulin, including, for example, the Fc portion of an immunoglobulin. For example, a first member of an interaction pair may comprise an amino acid sequence that is derived from an Fc domain of an IgG (IgG1, IgG2, IgG3, or IgG4), IgA (IgA1 or IgA2), IgE, or IgM immunoglobulin. For example, the first member of an interaction pair may comprise, consist essentially of, or consist of an amino acid sequence that is at least 80%, 85%, 90%, 91%, 92%, 93%, 94%, 95%, 96%, 97%, 98%, 99% or 100% identical to any one of SEQ ID NOs: 200-214. Optionally, a second member of an interaction pair may comprise an amino acid sequence that is derived from an Fc domain of an IgG (IgG1, IgG2, IgG3, or IgG4), IgA (IgA1 or IgA2), IgE, or IgM. Such immunoglobulin domains may comprise one or more amino acid modifications (e.g., deletions, additions, and/or substitutions) that promote heterodimer formation. For example, the second member of an interaction pair may comprise, consist essentially of, or consist of an amino acid sequence that is at least 80%, 85%, 90%, 91%, 92%, 93%, 94%, 95%, 96%, 97%, 98%, 99% or 100% identical to any one of SEQ ID NOs: 200-214. In some embodiments, a first member and a second member of an interaction pair comprise Fc domains derived from the same immunoglobulin class and subtype. In other embodiments, a first member and a second member of an interaction pair comprise Fc domains derived from different immunoglobulin classes or subtypes. Similarly, a first member and/or a second member of an interaction pair (e.g., an asymmetric pair or an unguided interaction pair) comprise a modified constant domain of an immunoglobulin, including, for example, a modified Fc portion of an immunoglobulin. For example, protein complexes of the disclosure may comprise a first modified Fc portion of an immunoglobulin comprising an amino acid sequence that is at least 80%, 85%, 90%, 91%, 92%, 93%, 94%, 95%, 96%, 97%, 98%, or 99% identical to an amino acid sequence selected from the group: SEQ ID NOs: 200-214 and a second modified Fc portion of an immunoglobulin, which may be the same or different from the amino acid sequence of the first modified Fc portion of the immunoglobulin, comprising an amino acid sequence that is at least 80%, 85%, 90%, 91%, 92%, 93%, 94%, 95%, 96%, 97%, 98%, or 99% identical to an amino acid sequence selected from the group: SEQ ID NOs: 200-214. Such immunoglobulin domains may comprise one or more amino acid modifications (e.g., deletions, additions, and/or substitutions) that promote heterodimer formation.

In some embodiments, the disclosure provides heteromeric polypeptide complexes comprising a type I and type II TGF-beta superfamily receptor polypeptide, wherein the type II TGF-beta superfamily receptor polypeptide is derived from an ActRIIA receptor. In some embodiments, the disclosure provides heteromeric polypeptide complexes comprising at least two different type II TGF-beta superfamily receptor polypeptide, wherein at least one of the type II TGF-beta superfamily receptor polypeptide is derived from an ActRIIA receptor. For example, ActRIIA polypeptides may comprise, consist essentially of, or consist of an amino acid sequence that is at least 70%, 80%, 85%, 90%, 95%, 97%, 98%, 99% or 100% identical to an ActRIIA sequence disclosed herein (e.g., SEQ ID NOs: 9, 10, 11, 118, 120, 151, 152, 409, 410, 451, and 452). Optionally, ActRIIA polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 21-30 (e.g., amino acid residues 21, 22, 23, 24, 25, 26, 27, 28, 29, or 30) SEQ ID NO: 9, and b) ends at any one of amino acids 110-135 (e.g., 110, 111, 112, 113, 114, 115, 116, 117, 118, 119, 120, 121, 122, 123, 124, 125, 126, 127, 128, 129, 130, 131, 132, 133, 134 or 135) of SEQ ID NO: 9. Optionally, ActRIIA polypeptides of the disclosure may be fusion proteins that further comprise one or more portions (domains) that are heterologous to ActRIIA. For example, an ActRIIA polypeptide may be fused to a heterologous polypeptide that comprises a multimerization domain, optionally with a linker domain positioned between the ActRIIA polypeptide and the heterologous polypeptide. In some embodiments, multimerization domains described herein comprise one component of an interaction pair. In certain aspects, heteromeric complexes that comprise an ActRIIA polypeptide further comprise at least one type I TGF-beta superfamily receptor polypeptide. For example, an ActRIIA heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464. Optionally, ALK1 polypeptides in this and other embodiments may comprise, consist essentially of, or consist of an amino acid sequence that is at least 70%, 80%, 85%, 90%, 95%, 97%, 98%, 99% or 100% identical to a polypeptide that a) begins at any one of amino acids of 22-34 (e.g., amino acid residues 22, 23, 24, 25, 26, 27, 28, 29, 30, 31, 32, 33, and 34) SEQ ID NO: 14, and b) ends at any one of amino acids 95-118 (e.g., amino acid residues 95, 96, 97, 98, 99, 100, 101, 102, 103, 104, 105, 106, 107, 108, 109, 110, 111, 112, 113, 114, 115, 116, 117, and 118) of SEQ ID NO: 14. In some embodiments, an ActRIIA heteromeric complex may further comprise an ALK2 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. Optionally, ALK2 polypeptides in this and other embodiments may comprise, consist essentially of, or consist of an amino acid sequence that is at least 70%, 80%, 85%, 90%, 95%, 97%, 98%, 99% or 100% identical to a polypeptide that a) begins at any one of amino acids of 21-35 (e.g., amino acid residues 21, 22, 23, 24, 25, 26, 27, 28, 29, 30, 31, 32, 33, 34, and 35) SEQ ID NO: 18, and b) ends at any one of amino acids 99-123 (e.g., amino acid residues 99, 100, 101, 102, 103, 104, 105, 106, 107, 108, 109, 110, 111, 112, 113, 114, 115, 116, 117, 118, 119, 120, 121, 122, and 123) of SEQ ID NO: 18. In some embodiments, an ActRIIA heteromeric complex may further comprise an ALK3 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. Optionally, in this and other embodiments ALK3 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 24-61 (e.g., amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, and 61) SEQ ID NO: 22, and b) ends at any one of amino acids 130-152 (e.g., amino acid residues 130, 131, 132, 133, 134, 135, 136, 137, 138, 139, 140, 141, 142, 143, 144, 145, 146, 147, 148, 149, 150, 151, and 152) of SEQ ID NO: 22. In some embodiments, an ActRIIA heteromeric complex may further comprise an ALK4 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. Optionally, in this and other embodiments ALK4 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 23-34 (e.g., amino acid residues 23, 24, 25, 26, 27, 28, 29, 30, 31, 32, 33, 34) SEQ ID NO: 26 or 83, and b) ends at any one of amino acids 101-126 (e.g., amino acid residues 101, 102, 103, 104, 105, 106, 107, 108, 109, 110, 111, 112, 113, 114, 115, 116, 117, 118, 119, 120, 121, 122, 123, 124, 125, and 126) of SEQ ID NO: 26 or 83. In some embodiments, an ActRIIA heteromeric complex may further comprise an ALK5 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. Optionally, in this and other embodiments ALK5 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 25-36 (e.g., amino acid residues 25, 26, 27, 28, 29, 30, 31, 32, 33, 34, 35, and 36) SEQ ID NO: 30 or 87, and b) ends at any one of amino acids 106-126 (e.g., amino acid residues 106, 107, 108, 109, 110, 111, 112, 113, 114, 115, 116, 117, 118, 119, 120, 121, 122, 123, 124, 125, and 126) of SEQ ID NO: 30 or 87. In some embodiments, an ActRIIA heteromeric complex may further comprise an ALK6 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. Optionally, in this and other embodiments ALK6 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 14-32 (e.g., amino acid residues 14, 15, 16, 17, 18, 19, 20, 21, 22, 23, 24, 25, 26, 27, 28, 29, 30, 31, and 32) SEQ ID NO: 34, and b) ends at any one of amino acids 102-126 (e.g., amino acid residues 102, 103, 104, 105, 106, 107, 108, 109, 110, 111, 112, 113, 114, 115, 116, 117, 118, 119, 120, 121, 122, 123, 124, 125, and 126) of SEQ ID NO: 34. Optionally, in this and other embodiments ALK6 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 26-62 (e.g., amino acid residues 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, and 62) SEQ ID NO: 91, and b) ends at any one of amino acids 132-156 (e.g., amino acid residues 132, 133, 134, 135, 136, 137, 138, 139, 140, 141, 142, 143, 144, 145, 146, 147, 148, 149, 150, 151, 152, 153, 154, 155, and 156) of SEQ ID NO: 91. In some embodiments, an ActRIIA heteromeric complex may further comprise an ALK7 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476. Optionally, in this and other embodiments, ALK7 polypeptides may comprise, consist essentially of, or consist of an amino acid sequence that is at least 70%, 80%, 85%, 90%, 95%, 97%, 98%, 99% or 100% identical to a polypeptide that begins at any one of amino acids 21-28 of SEQ ID NO: 38 (e.g., amino acids 21, 22, 23, 24, 25, 26, 27, or 28) and ends at any one of amino acids 92-113 of SEQ ID NO: 38 (e.g., amino acids 92, 93, 94, 95, 96, 97, 98, 99, 100, 101, 102, 103, 104, 105, 106, 107, 108, 109, 110, 111, 112, or 113 of SEQ ID NO: 38). In certain aspects, heteromeric complexes that comprise an ActRIIA polypeptide further comprise at least one different type II TGF-beta superfamily receptor polypeptide. For example, an ActRIIA heteromeric complex may further comprise an ActRIIB polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 1, 2, 3, 4, 5, 6, 100, 102, 153, 154, 401, 402, 453, and 454. In some embodiments, an ActRIIA heteromeric complex may further comprise an BMPRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 46, 47, 71, 72, 121, 123, 155, 156, 411, 412, 455, and 456. In some embodiments, an ActRIIA heteromeric complex may further comprise an MISRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 50, 51, 75, 76, 79, 80, 133, 135, 161, 162, 419, 420, 457, and 458. In some embodiments, an ActRIIA heteromeric complex may further comprise an TGFBRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 42, 43, 67, 68, 127, 129, 130, 132, 157, 158, 159, 160, 415, 416, 417, 418, 459, 460, 461, and 462.

In some embodiments, the disclosure provides heteromeric polypeptide complexes comprising a type I and type II TGF-beta superfamily receptor polypeptide, wherein the type II TGF-beta superfamily receptor polypeptide is derived from an ActRIIB receptor. In some embodiments, the disclosure provides heteromeric polypeptide complexes comprising at least two different type II TGF-beta superfamily receptor polypeptide, wherein at least one of the type II TGF-beta superfamily receptor polypeptide is derived from an ActRIIB receptor. For example, ActRIIB polypeptides may comprise, consist essentially of, or consist of an amino acid sequence that is at least 70%, 80%, 85%, 90%, 95%, 97%, 98%, 99% or 100% identical to an ActRIIB sequence disclosed herein (e.g., SEQ ID NOs: 1, 2, 3, 4, 5, 6, 100, 102, 153, 154, 401, 402, 453, and 454). Optionally, ActRIIB polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 20-29 (e.g., amino acid residues 20, 21, 22, 23, 24, 25, 26, 27, 28, or 29) SEQ ID NO: 1, and b) ends at any one of amino acids 109-134 (e.g., amino acid residues 109, 110, 111, 112, 113, 114, 115, 116, 117, 118, 119, 120, 121, 122, 123, 124, 125, 126, 127, 128, 129, 130, 131, 132, 133, or 134 of SEQ ID NO: 1. Optionally, ActRIIB polypeptides of the disclosure may be fusion proteins that further comprise one or more portions (domains) that are heterologous to ActRIIB. For example, an ActRIIB polypeptide may be fused to a heterologous polypeptide that comprises a multimerization domain, optionally with a linker domain positioned between the ActRIIB polypeptide and the heterologous polypeptide. In some embodiments, multimerization domains described herein comprise one component of an interaction pair. Preferably, heteromeric complexes that comprise an ActRIIB polypeptide further comprise at least one type I TGF-beta superfamily receptor polypeptide. For example, an ActRIIB heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464. In some embodiments, an ActRIIB heteromeric complex may further comprise an ALK2 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. In some embodiments, an ActRIIB heteromeric complex may further comprise an ALK3 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. In some embodiments, an ActRIIB heteromeric complex may further comprise an ALK4 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. In some embodiments, an ActRIIB heteromeric complex may further comprise an ALK5 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. In some embodiments, an ActRIIB heteromeric complex may further comprise an ALK6 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. In some embodiments, an ActRIIB heteromeric complex may further comprise an ALK7 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476. In certain aspects, heteromeric complexes that comprise an ActRIIB polypeptide further comprise at least one different type II TGF-beta superfamily receptor polypeptide. For example, an ActRIIA heteromeric complex may further comprise an ActRIIB polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 1, 2, 3, 4, 5, 6, 100, 102, 153, 154, 401, 402, 453, and 454. For example, an ActRIIB heteromeric complex may further comprise an ActRIIA polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 9, 10, 11, 118, 120, 151, 152, 409, 410, 451, and 452. In some embodiments, an ActRIIB heteromeric complex may further comprise an BMPRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 46, 47, 71, 72, 121, 123, 155, 156, 411, 412, 455, and 456. In some embodiments, an ActRIIB heteromeric complex may further comprise an MISRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 50, 51, 75, 76, 79, 80, 133, 135, 161, 162, 419, 420, 457, and 458. In some embodiments, an ActRIIB heteromeric complex may further comprise an TGFBRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 42, 43, 67, 68, 127, 129, 130, 132, 157, 158, 159, 160, 415, 416, 417, 418, 459, 460, 461, and 462.

In some embodiments, the disclosure provides heteromeric polypeptide complexes comprising a type I and type II TGF-beta superfamily receptor polypeptide, wherein the type II TGF-beta superfamily receptor polypeptide is derived from a TGFBRII receptor. In some embodiments, the disclosure provides heteromeric polypeptide complexes comprising at least two different type II TGF-beta superfamily receptor polypeptide, wherein at least one of the type II TGF-beta superfamily receptor polypeptide is derived from an TGFBRII receptor. For example, TGFBRII polypeptides may comprise, consist essentially of, or consist of an amino acid sequence that is at least 70%, 80%, 85%, 90%, 95%, 97%, 98%, 99% or 100% identical to an TGFBRII sequence disclosed herein (e.g., SEQ ID NOs: 42, 43, 67, 68, 127, 129, 130, 132, 157, 158, 159, 160, 415, 416, 417, 418, 459, 460, 461, and 462). Optionally, TGFBRII polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 23, 24, 25, 26, 27, 28, 29, 30, 31, 32, 33, 34, 35, 36, 37, 38, 39, 40, 41, 42, 43, 44, 45, 46, 47, 48, 49, 50 or 51 of SEQ ID NO: 42, and b) ends at any one of amino acids 143, 144, 145, 146, 147, 148, 149, 150, 151, 152, 153, 154, 155, 156, 157, 158, 159, 160, 161, 162, 163, 164, 165 or 166 of SEQ ID NO: 42. Optionally, TGFBRII polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 23, 24, 25, 26, 27, 28, 29, 30, 31, 32, 33, 34, 35, 36, 37, 38, 39, 40, 41, 42, 43 or 44 of SEQ ID NO: 67, and b) ends at any one of amino acids 163, 164, 165, 166, 167, 168, 169, 170, 171, 172, 173, 174, 175, 176, 177, 178, 179, 180, 181, 182, 183, 184, 185, 186, 187, 188, 189, 190 or 191 of SEQ ID NO: 67. Optionally, TGFBRII polypeptides of the disclosure may be fusion proteins that further comprise one or more portions (domains) that are heterologous to TGFBRII. For example, a TGFBRII polypeptide may be fused to a heterologous polypeptide that comprises a multimerization domain, optionally with a linker domain positioned between the TGFBRII polypeptide and the heterologous polypeptide. In some embodiments, multimerization domains described herein comprise one component of an interaction pair. Preferably, heteromeric complexes that comprise a TGFBRII polypeptide further comprise at least one type I TGF-beta superfamily receptor polypeptide. For example, a TGFBRII heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464. In some embodiments, a TGFBRII heteromeric complex may further comprise an ALK2 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. In some embodiments, a TGFBRII heteromeric complex may further comprise an ALK3 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. In some embodiments, a TGFBRII heteromeric complex may further comprise an ALK4 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. In some embodiments, a TGFBRII heteromeric complex may further comprise an ALK5 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. In some embodiments, a TGFBRII heteromeric complex may further comprise an ALK6 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. In some embodiments, a TGFBRII heteromeric complex may further comprise an ALK7 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476. Optionally, heteromeric complexes comprising a TGFBRII polypeptide may further comprise one or more additional type II TGF-beta superfamily receptor polypeptides, including, for example ActRIIA, ActRIIB, BMPRII, and MISRII polypeptides described herein (e.g., a polypeptide comprising, consisting essentially of, or consisting of an amino acid sequence selected from SEQ ID NOs: 1, 2, 3, 4, 5, 6, 9, 10, 11 46, 47, 50, 51, 71, 72, 75, 76, 79, 80, 100, 102, 118, 120, 121, 123, 401, 402, 409, 410, 411, and 412). In certain aspects, heteromeric complexes that comprise a TGFBRII polypeptide further comprise at least one different type II TGF-beta superfamily receptor polypeptide. For example, an TGFBRII heteromeric complex may further comprise an ActRIIA polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 9, 10, 11, 118, 120, 151, 152, 409, 410, 451, and 452. In some embodiments, a TGFBRII heteromeric complex may further comprise an ActRIIB polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 1, 2, 3, 4, 5, 6, 100, 102, 153, 154, 401, 402, 453, and 454. In some embodiments, a TGFBRII heteromeric complex may further comprise an MISRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 50, 51, 75, 76, 79, 80, 133, 135, 161, 162, 419, 420, 457, and 458. In some embodiments, a TGFBRII heteromeric complex may further comprise an BMPRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 46, 47, 71, 72, 121, 123, 155, 156, 411, 412, 455, and 456.

In some embodiments, the disclosure provides heteromeric polypeptide complexes comprising a type I and type II TGF-beta superfamily receptor polypeptide, wherein the type II TGF-beta superfamily receptor polypeptide is derived from a BMPRII receptor. In some embodiments, the disclosure provides heteromeric polypeptide complexes comprising at least two different type II TGF-beta superfamily receptor polypeptide, wherein at least one of the type II TGF-beta superfamily receptor polypeptide is derived from an BMPRII receptor. For example, BMPRII polypeptides may comprise, consist essentially of, or consist of an amino acid sequence that is at least 70%, 80%, 85%, 90%, 95%, 97%, 98%, 99% or 100% identical to a BMPRII sequence disclosed herein (e.g., SEQ ID NOs: 46, 47, 71, 72, 121, 123, 155, 156, 411, 412, 455, and 456). Optionally, BMPRII polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 27-34 (e.g., amino acid residues 27, 28, 29, 30, 31, 32, 33, and 34) SEQ ID NO: 46 or 71, and b) ends at any one of amino acids 123-150 (e.g., amino acid residues 123, 124, 125, 126, 127, 128, 129, 130, 131, 132, 133, 134, 135, 136, 137, 138, 139, 140, 141, 142, 143, 144, 145, 146, 147, 148, 149, and 150) of SEQ ID NO: 46 or 71. Optionally, BMPRII polypeptides of the disclosure may be fusion proteins that further comprise one or more portions (domains) that are heterologous to BMPRII. For example, a BMPRII polypeptide may be fused to a heterologous polypeptide that comprises a multimerization domain, optionally with a linker domain positioned between the BMPRII polypeptide and the heterologous polypeptide. In some embodiments, multimerization domains described herein comprise one component of an interaction pair. Preferably, heteromeric complexes that comprise a BMPRII polypeptide further comprise at least one type I TGF-beta superfamily receptor polypeptide. For example, a BMPRII heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464. In some embodiments, a BMPRII heteromeric complex may further comprise an ALK2 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. In some embodiments, a BMPRII heteromeric complex may further comprise an ALK3 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. In some embodiments, a BMPRII heteromeric complex may further comprise an ALK4 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. In some embodiments, a BMPRII heteromeric complex may further comprise an ALK5 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. In some embodiments, a BMPRII heteromeric complex may further comprise an ALK6 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. In some embodiments, a BMPRII heteromeric complex may further comprise an ALK7 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476. In certain aspects, heteromeric complexes that comprise an BMPRII polypeptide further comprise at least one different type II TGF-beta superfamily receptor polypeptide. For example, an BMPRII heteromeric complex may further comprise an ActRIIA polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 9, 10, 11, 118, 120, 151, 152, 409, 410, 451, and 452. In some embodiments, a BMPRII heteromeric complex may further comprise an ActRIIB polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 1, 2, 3, 4, 5, 6, 100, 102, 153, 154, 401, 402, 453, and 454. In some embodiments, a BMPRII heteromeric complex may further comprise an MISRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 50, 51, 75, 76, 79, 80, 133, 135, 161, 162, 419, 420, 457, and 458. In some embodiments, a BMPRII heteromeric complex may further comprise an TGFBRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 42, 43, 67, 68, 127, 129, 130, 132, 157, 158, 159, 160, 415, 416, 417, 418, 459, 460, 461, and 462.

In some embodiments, the disclosure provides heteromeric polypeptide complexes comprising a type I and type II TGF-beta superfamily receptor polypeptide, wherein the type II TGF-beta superfamily receptor polypeptide is derived from an MISRII receptor. In some embodiments, the disclosure provides heteromeric polypeptide complexes comprising at least two different type II TGF-beta superfamily receptor polypeptide, wherein at least one of the type II TGF-beta superfamily receptor polypeptide is derived from an MISRII receptor. In some embodiments, the disclosure provides heteromeric polypeptide complexes comprising at least two different type II TGF-beta superfamily receptor polypeptide, wherein at least one of the type II TGF-beta superfamily receptor polypeptide is derived from an MISRII receptor. For example, MISRII polypeptides may comprise, consist essentially of, or consist of an amino acid sequence that is at least 70%, 80%, 85%, 90%, 95%, 97%, 98%, 99% or 100% identical to an MISRII sequence disclosed herein (e.g., SEQ ID NOs: 50, 51, 75, 76, 79, 80, 133, 135, 161, 162, 419, 420, 457, and 458). Optionally, MISRII polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 17-24 (e.g., amino acid residues 17, 18, 19, 20, 21, 22, 23, and 24) SEQ ID NO: 50, 75, or 79, and b) ends at any one of amino acids 116-149 (e.g., amino acid residues 116, 117, 118, 119, 120, 121, 122 123, 124, 125, 126, 127, 128, 129, 130, 131, 132, 133, 134, 135, 136, 137, 138, 139, 140, 141, 142, 143, 144, 145, 146, 147, 148, and 149) of SEQ ID NO: 50, 75, or 79. Optionally, MISRII polypeptides of the disclosure may be fusion proteins that further comprise one or more portions (domains) that are heterologous to MISRII. For example, an MISRII polypeptide may be fused to a heterologous polypeptide that comprises a multimerization domain, optionally with a linker domain positioned between the MISRII polypeptide and the heterologous polypeptide. In some embodiments, multimerization domains described herein comprise one component of an interaction pair. Preferably, heteromeric complexes that comprise an MISRII polypeptide further comprise at least one type I TGF-beta superfamily polypeptide. For example, an MISRII heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464. In some embodiments, an MISRII heteromeric complex may further comprise an ALK2 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. In some embodiments, an MISRII heteromeric complex may further comprise an ALK3 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. In some embodiments, an MISRII heteromeric complex may further comprise an ALK4 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. In some embodiments, an MISRII heteromeric complex may further comprise an ALK5 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. In some embodiments, an MISRII heteromeric complex may further comprise an ALK6 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. In some embodiments, an MISRII heteromeric complex may further comprise an ALK7 polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476. In certain aspects, heteromeric complexes that comprise an MISRII polypeptide further comprise at least one different type II TGF-beta superfamily receptor polypeptide. For example, an MISRII heteromeric complex may further comprise an ActRIIA polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 9, 10, 11, 118, 120, 151, 152, 409, 410, 451, and 452. In some embodiments, an MISRII heteromeric complex may further comprise an ActRIIB polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 1, 2, 3, 4, 5, 6, 100, 102, 153, 154, 401, 402, 453, and 454. In some embodiments, an MISRII heteromeric complex may further comprise an BMPRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 46, 47, 71, 72, 121, 123, 155, 156, 411, 412, 455, and 456. In some embodiments, an MISRII heteromeric complex may further comprise an TGFBRII polypeptide as described herein, including, for example, a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 42, 43, 67, 68, 127, 129, 130, 132, 157, 158, 159, 160, 415, 416, 417, 418, 459, 460, 461, and 462.

In some embodiments, the disclosure provides heteromeric polypeptide complexes comprising at least two different type I TGF-beta superfamily receptor polypeptide, wherein at least one of the type I TGF-beta superfamily receptor polypeptide is derived from an ALK1 receptor. For example, ALK1 polypeptides may comprise, consist essentially of, or consist of an amino acid sequence that is at least 70%, 80%, 85%, 90%, 95%, 97%, 98%, 99% or 100% identical to an ALK1 sequence disclosed herein (e.g., 14, 15, 124, 126, 171, 172, 413, 414, 463, and 464). Optionally, ALK1 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 22-34 (e.g., amino acid residues 22, 23, 24, 25, 26, 27, 28, 29, 30, 31, 32, 33, and 34) SEQ ID NO: 14, and b) ends at any one of amino acids 95-118 (e.g., amino acid residues 95, 96, 97, 98, 99, 100, 101, 102, 103, 104, 105, 106, 107, 108, 109, 110, 111, 112, 113, 114, 115, 116, 117, and 118) of SEQ ID NO: 14. Optionally, ALK1 polypeptides of the disclosure may be fusion proteins that further comprise one or more portions (domains) that are heterologous to ALK1. For example, an ALK1 polypeptide may be fused to a heterologous polypeptide that comprises a multimerization domain, optionally with a linker domain positioned between the ALK1 polypeptide and the heterologous polypeptide. In some embodiments, multimerization domains described herein comprise one component of an interaction pair. In some embodiments, heteromeric complexes that comprise an ALK1 polypeptide further comprise at least one different type I TGF-beta superfamily polypeptide. For example, an ALK1 heteromeric complex may further comprise an ALK2 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. In some embodiments, an ALK1 heteromeric complex may further comprise an ALK3 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. In some embodiments, an ALK1 heteromeric complex may further comprise an ALK4 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. In some embodiments, an ALK1 heteromeric complex may further comprise an ALK5 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. In some embodiments, an ALK1 heteromeric complex may further comprise an ALK6 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. In some embodiments, an ALK1 heteromeric complex may further comprise an ALK7 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476.

In some embodiments, the disclosure provides heteromeric polypeptide complexes comprising at least two different type I TGF-beta superfamily receptor polypeptide, wherein at least one of the type I TGF-beta superfamily receptor polypeptide is derived from an ALK2 receptor. For example, ALK2 polypeptides may comprise, consist essentially of, or consist of an amino acid sequence that is at least 70%, 80%, 85%, 90%, 95%, 97%, 98%, 99% or 100% identical to an ALK2 sequence disclosed herein (e.g., 18, 19, 136, 138, 173, 174, 421, 422, 465, and 466). Optionally, ALK2 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 21-35 (e.g., amino acid residues 21, 22, 23, 24, 25, 26, 27, 28, 29, 30, 31, 32, 33, 34, and 35) SEQ ID NO: 18, and b) ends at any one of amino acids 99-123 (e.g., amino acid residues 99, 100, 101, 102, 103, 104, 105, 106, 107, 108, 109, 110, 111, 112, 113, 114, 115, 116, 117, 118, 119, 120, 121, 122, and 123) of SEQ ID NO: 18. Optionally, ALK2 polypeptides of the disclosure may be fusion proteins that further comprise one or more portions (domains) that are heterologous to ALK2. For example, an ALK2 polypeptide may be fused to a heterologous polypeptide that comprises a multimerization domain, optionally with a linker domain positioned between the ALK2 polypeptide and the heterologous polypeptide. In some embodiments, multimerization domains described herein comprise one component of an interaction pair. In some embodiments, heteromeric complexes that comprise an ALK2 polypeptide further comprise at least one different type I TGF-beta superfamily polypeptide. For example, an ALK2 heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464. In some embodiments, an ALK2 heteromeric complex may further comprise an ALK3 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. In some embodiments, an ALK2 heteromeric complex may further comprise an ALK4 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. In some embodiments, an ALK2 heteromeric complex may further comprise an ALK5 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. In some embodiments, an ALK2 heteromeric complex may further comprise an ALK6 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. In some embodiments, an ALK2 heteromeric complex may further comprise an ALK7 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476.

In some embodiments, the disclosure provides heteromeric polypeptide complexes comprising at least two different type I TGF-beta superfamily receptor polypeptide, wherein at least one of the type I TGF-beta superfamily receptor polypeptide is derived from an ALK3 receptor. For example, ALK3 polypeptides may comprise, consist essentially of, or consist of an amino acid sequence that is at least 70%, 80%, 85%, 90%, 95%, 97%, 98%, 99% or 100% identical to an ALK3 sequence disclosed herein (e.g., 22, 23, 115, 117, 175, 176, 407, 408, 467, and 468). Optionally, ALK3 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 24-61 (e.g., amino acid residues 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, and 61) SEQ ID NO: 22, and b) ends at any one of amino acids 130-152 (e.g., amino acid residues 130, 131, 132, 133, 134, 135, 136, 137, 138, 139, 140, 141, 142, 143, 144, 145, 146, 147, 148, 149, 150, 151, and 152) of SEQ ID NO: 22. Optionally, ALK3 polypeptides of the disclosure may be fusion proteins that further comprise one or more portions (domains) that are heterologous to ALK3. For example, an ALK3 polypeptide may be fused to a heterologous polypeptide that comprises a multimerization domain, optionally with a linker domain positioned between the ALK3 polypeptide and the heterologous polypeptide. In some embodiments, multimerization domains described herein comprise one component of an interaction pair. In some embodiments, heteromeric complexes that comprise an ALK3 polypeptide further comprise at least one different type I TGF-beta superfamily polypeptide. For example, an ALK3 heteromeric complex may further comprise an ALK2 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. In some embodiments, an ALK3 heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464. In some embodiments, an ALK3 heteromeric complex may further comprise an ALK4 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. In some embodiments, an ALK3 heteromeric complex may further comprise an ALK5 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. In some embodiments, an ALK3 heteromeric complex may further comprise an ALK6 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. In some embodiments, an ALK3 heteromeric complex may further comprise an ALK7 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476.

In some embodiments, the disclosure provides heteromeric polypeptide complexes comprising at least two different type I TGF-beta superfamily receptor polypeptide, wherein at least one of the type I TGF-beta superfamily receptor polypeptide is derived from an ALK4 receptor. For example, ALK4 polypeptides may comprise, consist essentially of, or consist of an amino acid sequence that is at least 70%, 80%, 85%, 90%, 95%, 97%, 98%, 99% or 100% identical to an ALK4 sequence disclosed herein (e.g., 26, 27, 83, 84, 104, 106, 177, 178, 403, 404, 469, and 470).). Optionally, ALK4 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 23-34 (e.g., amino acid residues 23, 24, 25, 26, 27, 28, 29, 30, 31, 32, 33, 34) SEQ ID NO: 26 or 83, and b) ends at any one of amino acids 101-126 (e.g., amino acid residues 101, 102, 103, 104, 105, 106, 107, 108, 109, 110, 111, 112, 113, 114, 115, 116, 117, 118, 119, 120, 121, 122, 123, 124, 125, and 126) of SEQ ID NO: 26 or 83. Optionally, ALK4 polypeptides of the disclosure may be fusion proteins that further comprise one or more portions (domains) that are heterologous to ALK4. For example, an ALK4 polypeptide may be fused to a heterologous polypeptide that comprises a multimerization domain, optionally with a linker domain positioned between the ALK4 polypeptide and the heterologous polypeptide. In some embodiments, multimerization domains described herein comprise one component of an interaction pair. In some embodiments, heteromeric complexes that comprise an ALK4 polypeptide further comprise at least one different type I TGF-beta superfamily polypeptide. For example, an ALK4 heteromeric complex may further comprise an ALK2 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. In some embodiments, an ALK4 heteromeric complex may further comprise an ALK3 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. In some embodiments, an ALK4 heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464. In some embodiments, an ALK4 heteromeric complex may further comprise an ALK5 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. In some embodiments, an ALK4 heteromeric complex may further comprise an ALK6 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. In some embodiments, an ALK4 heteromeric complex may further comprise an ALK7 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476.

In some embodiments, the disclosure provides heteromeric polypeptide complexes comprising at least two different type I TGF-beta superfamily receptor polypeptide, wherein at least one of the type I TGF-beta superfamily receptor polypeptide is derived from an ALK5 receptor. For example, ALK5 polypeptides may comprise, consist essentially of, or consist of an amino acid sequence that is at least 70%, 80%, 85%, 90%, 95%, 97%, 98%, 99% or 100% identical to an ALK5 sequence disclosed herein (e.g., 30, 31, 87, 88, 139, 141, 179, 180, 423, 424, 471, and 472). Optionally, ALK5 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 25-36 (e.g., amino acid residues 25, 26, 27, 28, 29, 30, 31, 32, 33, 34, 35, and 36) SEQ ID NO: 30 or 87, and b) ends at any one of amino acids 106-126 (e.g., amino acid residues 106, 107, 108, 109, 110, 111, 112, 113, 114, 115, 116, 117, 118, 119, 120, 121, 122, 123, 124, 125, and 126) of SEQ ID NO: 30 or 87. Optionally, ALK5 polypeptides of the disclosure may be fusion proteins that further comprise one or more portions (domains) that are heterologous to ALK5. For example, an ALK5 polypeptide may be fused to a heterologous polypeptide that comprises a multimerization domain, optionally with a linker domain positioned between the ALK5 polypeptide and the heterologous polypeptide. In some embodiments, multimerization domains described herein comprise one component of an interaction pair. In some embodiments, heteromeric complexes that comprise an ALK5 polypeptide further comprise at least one different type I TGF-beta superfamily polypeptide. For example, an ALK5 heteromeric complex may further comprise an ALK2 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. In some embodiments, an ALK5 heteromeric complex may further comprise an ALK3 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. In some embodiments, an ALK5 heteromeric complex may further comprise an ALK4 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. In some embodiments, an ALK5 heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464. In some embodiments, an ALK5 heteromeric complex may further comprise an ALK6 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. In some embodiments, an ALK5 heteromeric complex may further comprise an ALK7 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476.

In some embodiments, the disclosure provides heteromeric polypeptide complexes comprising at least two different type I TGF-beta superfamily receptor polypeptide, wherein at least one of the type I TGF-beta superfamily receptor polypeptide is derived from an ALK6 receptor. For example, ALK6 polypeptides may comprise, consist essentially of, or consist of an amino acid sequence that is at least 70%, 80%, 85%, 90%, 95%, 97%, 98%, 99% or 100% identical to an ALK6 sequence disclosed herein (e.g., 34, 35, 91, 92, 142, 144, 181, 182, 425, 426, 473, and 474). Optionally, ALK6 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 14-32 (e.g., amino acid residues 14, 15, 16, 17, 18, 19, 20, 21, 22, 23, 24, 25, 26, 27, 28, 29, 30, 31, and 32) SEQ ID NO: 34, and b) ends at any one of amino acids 102-126 (e.g., amino acid residues 102, 103, 104, 105, 106, 107, 108, 109, 110, 111, 112, 113, 114, 115, 116, 117, 118, 119, 120, 121, 122, 123, 124, 125, and 126) of SEQ ID NO: 34. Optionally, ALK6 polypeptides may comprise, consist essentially of, or consist of an amino acid sequence that is at least 70%, 80%, 85%, 90%, 95%, 97%, 98%, 99% or 100% identical to a polypeptide that a) begins at any one of amino acids of 26-62 (e.g., amino acid residues 26, 27, 28, 29, 30, 31, 32, 33, 34, 35, 36, 37, 38, 39, 40, 41, 42, 43, 44, 45, 46, 47, 48, 49, 50, 52, 53, 54, 55, 56, 57, 58, 59, 60, 61, and 62) SEQ ID NO: 91, and b) ends at any one of amino acids 132-156 (e.g., amino acid residues 132, 133, 134, 135, 136, 137, 138, 139, 140, 141, 142, 143, 144, 145, 146, 147, 148, 149, 150, 151, 152, 153, 154, 155, and 156) of SEQ ID NO: 91. Optionally, ALK6 polypeptides of the disclosure may be fusion proteins that further comprise one or more portions (domains) that are heterologous to ALK6. For example, an ALK6 polypeptide may be fused to a heterologous polypeptide that comprises a multimerization domain, optionally with a linker domain positioned between the ALK6 polypeptide and the heterologous polypeptide. In some embodiments, multimerization domains described herein comprise one component of an interaction pair. In some embodiments, heteromeric complexes that comprise an ALK6 polypeptide further comprise at least one different type I TGF-beta superfamily polypeptide. For example, an ALK6 heteromeric complex may further comprise an ALK2 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. In some embodiments, an ALK6 heteromeric complex may further comprise an ALK3 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. In some embodiments, an ALK6 heteromeric complex may further comprise an ALK4 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. In some embodiments, an ALK6 heteromeric complex may further comprise an ALK5 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. In some embodiments, an ALK6 heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464. In some embodiments, an ALK6 heteromeric complex may further comprise an ALK7 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 38, 39, 301, 302, 305, 306, 309, 310, 313, 112, 114, 183, 184, 405, 406, 475, and 476.

In some embodiments, the disclosure provides heteromeric polypeptide complexes comprising at least two different type I TGF-beta superfamily receptor polypeptide, wherein at least one of the type I TGF-beta superfamily receptor polypeptide is derived from an ALK7 receptor. For example, ALK7 polypeptides may comprise, consist essentially of, or consist of an amino acid sequence that is at least 70%, 80%, 85%, 90%, 95%, 97%, 98%, 99% or 100% identical to an ALK7 sequence disclosed herein (e.g., 38, 39, 301, 302, 305, 306, 309, 310, 313, 112, 114, 183, 184, 405, 406, 475, and 476). Optionally, ALK7 polypeptides may comprise, consist essentially of, or consist of an amino acid sequence that is at least 70%, 80%, 85%, 90%, 95%, 97%, 98%, 99% or 100% identical to a polypeptide that begins at any one of amino acids 21-28 of SEQ ID NO: 38 (e.g., amino acids 21, 22, 23, 24, 25, 26, 27, or 28) and ends at any one of amino acids 92-113 of SEQ ID NO: 38 (e.g., amino acids 92, 93, 94, 95, 96, 97, 98, 99, 100, 101, 102, 103, 104, 105, 106, 107, 108, 109, 110, 111, 112, or 113 of SEQ ID NO: 38). Optionally, ALK7 polypeptides of the disclosure may be fusion proteins that further comprise one or more portions (domains) that are heterologous to ALK7. For example, an ALK7 polypeptide may be fused to a heterologous polypeptide that comprises a multimerization domain, optionally with a linker domain positioned between the ALK7 polypeptide and the heterologous polypeptide. In some embodiments, multimerization domains described herein comprise one component of an interaction pair. In some embodiments, heteromeric complexes that comprise an ALK7 polypeptide further comprise at least one different type I TGF-beta superfamily polypeptide. For example, an ALK7 heteromeric complex may further comprise an ALK2 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 18, 19, 136, 138, 173, 174, 421, 422, 465, and 466. In some embodiments, an ALK7 heteromeric complex may further comprise an ALK3 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 22, 23, 115, 117, 175, 176, 407, 408, 467, and 468. In some embodiments, an ALK7 heteromeric complex may further comprise an ALK4 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 26, 27, 83, 84, 104, 106, 177, 178, 403, 404, 469, and 470. In some embodiments, an ALK7 heteromeric complex may further comprise an ALK5 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 30, 31, 87, 88, 139, 141, 179, 180, 423, 424, 471, and 472. In some embodiments, an ALK7 heteromeric complex may further comprise an ALK6 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 34, 35, 91, 92, 142, 144, 181, 182, 425, 426, 473, and 474. In some embodiments, an ALK7 heteromeric complex may further comprise an ALK1 polypeptide as described herein, including, e.g., a polypeptide comprising, consisting essentially of, or consisting of an amino acid sequence that is at least 70%, 80%, 85%, 90%, 95%, 97%, 98%, 99% or 100% identical to a sequence selected from SEQ ID NOs: 14, 15, 124, 126, 171, 172, 413, 414, 463, and 464.

In some embodiments, the TGF-beta superfamily type I and/or type II receptor polypeptides disclosed herein comprise one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. In some embodiments, the TGF-beta superfamily type I and/or type II polypeptides described herein are glycosylated and have a glycosylation pattern obtainable from the expression of the polypeptides in a mammalian cell, including, for example, a CHO cell.

In certain aspects the disclosure provides nucleic acids encoding any of the TGF-beta superfamily type I and/or type II polypeptides described herein. Nucleic acids disclosed herein may be operably linked to a promoter for expression, and the disclosure further provides cells transformed with such recombinant polynucleotides. Preferably the cell is a mammalian cell such as a COS cell or a CHO cell.

In certain aspects, the disclosure provides methods for making any of the TGF-beta superfamily type I and/or type II polypeptides described herein as well as protein complexes comprising such polypeptides. Such a method may include expressing any of the nucleic acids disclosed herein in a suitable cell (e.g., CHO cell or a COS cell). Such a method may comprise: a) culturing a cell under conditions suitable for expression of the TGF-beta superfamily type I or type II polypeptides described herein, wherein said cell is transformed with a type I or type II polypeptide expression construct; and b) recovering the type I or type II polypeptides so expressed. TGF-beta superfamily type I and/or type II polypeptides described herein, as well as protein complexes of the same, may be recovered as crude, partially purified, or highly purified fractions using any of the well-known techniques for obtaining protein from cell cultures.

In certain aspects, the disclosure provides methods for making any of the heteromultimeric complexes disclosed herein. Such a method may include expressing any of the nucleic acids disclosed herein in a suitable cell (e.g., CHO cell or a COS cell). Such a method may comprise: a) obtaining a cell that comprises a nucleic acid comprising the coding sequence for a TGF-beta superfamily type I receptor polypeptide disclosed herein and a nucleic acid comprising the coding sequence for a TGF-beta superfamily type II receptor polypeptide disclosed herein; (b) culturing such cell under conditions suitable for expression of the TGF-beta superfamily type I and type II polypeptides described herein; and c) recovering the heteromeric complex comprising such type I and type II polypeptides so expressed. Heteromultimeric complexes disclosed herein as crude, partially purified, or highly purified fractions using any of the well-known techniques for obtaining protein from cell cultures.

Any of the protein complexes described herein may be incorporated into a pharmaceutical preparation. Optionally, such pharmaceutical preparations are at least 80%, 85%, 90%, 95%, 97%, 98% or 99% pure with respect to other polypeptide components. Optionally, pharmaceutical preparations disclosed herein may comprise one or more additional active agents. In some embodiments, heteromultimers of the disclosure comprise less than 10%, 9%, 8%, 7%, 5%, 4%, 3%, 2%, or less than 1% type I receptor polypeptide homomultimers. In some embodiments, heteromultimers of the disclosure comprise less than 10%, 9%, 8%, 7%, 5%, 4%, 3%, 2%, or less than 1% type II receptor polypeptide homomultimers. In some embodiments, heteromultimers of the disclosure comprise less than 10%, 9%, 8%, 7%, 5%, 4%, 3%, 2%, or less than 1% type I receptor polypeptide homomultimers and less than 10%, 9%, 8%, 7%, 5%, 4%, 3%, 2%, or less than 1% type II receptor polypeptide homomultimers.

The disclosure further provides methods and heteromultimeric complexes for use in the treatment or prevention of various disease and disorders associated with, for example, muscle, bone, fat, red blood cells, and other tissues that are affected by one or more ligands of the TGF-beta superfamily. Such disease and disorders include, but are not limited to, disorders associated with muscle loss or insufficient muscle growth (e.g., muscle atrophy; muscular dystrophy, including Duchenne muscular dystrophy, Becker muscular dystrophy, and facioscapulohumeral muscular dystrophy; amyotrophic lateral sclerosis; and cachexia) and disorders associated with undesirable weight gain (e.g., obesity, type 2 diabetes or non-insulin dependent diabetes mellitus (NIDDM), cardiovascular disease, hypertension, osteoarthritis, stroke, respiratory problems, and gall bladder disease). In some embodiments, heteromultimeric complexes disclosed herein may be used to decrease body fat content or reduce the rate of increase in body fat content in a subject in need thereof. In some embodiments, heteromultimeric complexes disclosed herein may be used to reduce cholesterol and/or triglyceride levels in a patient.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A depicts a heterodimeric protein complex comprising one type I receptor fusion polypeptide and one type II receptor fusion polypeptide, which can be assembled covalently or noncovalently via a multimerization domain contained within each polypeptide chain. Two assembled multimerization domains constitute an interaction pair, which can be either guided or unguided. FIG. 2A depicts a heterotetrameric protein complex comprising two heterodimeric complexes as in FIG. 1A. Complexes of higher order can be envisioned.

FIG. 3 shows an alignment of extracellular domains of human ActRIIA (SEQ ID NO: 500) and human ActRIIB (SEQ ID NO: 2) with the residues that are deduced herein, based on composite analysis of multiple ActRIIB and ActRIIA crystal structures, to directly contact ligand indicated with boxes.

FIG. 5 shows multiple sequence alignment of Fc domains from human IgG isotypes using Clustal 2.1 (SEQ ID NOS 208, 212, 210 and 209, respectively, in order of appearance). Hinge regions are indicated by dotted underline. Double underline indicates examples of positions engineered in IgG1 Fc to promote asymmetric chain pairing and the corresponding positions with respect to other isotypes IgG2, IgG3 and IgG4.

Figure 6:
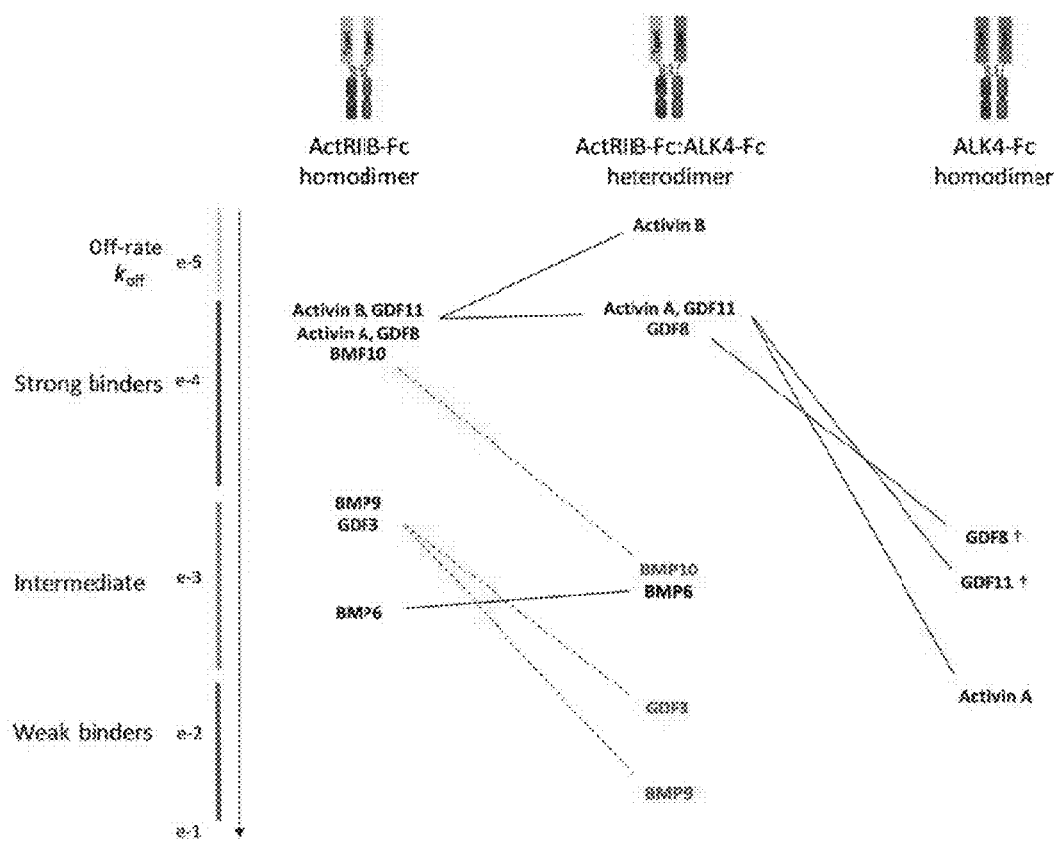
FIG. 6 shows ligand binding data for an ActRIIB-Fc:ALK4-Fc heterodimeric protein complex as compared to ActRIIB-Fc homodimer and ALK4-Fc homodimer. For each protein complex, ligands are ranked by $k_{off}$, a kinetic constant that correlates well with ligand signaling inhibition, and listed in descending order of binding affinity (ligands bound most tightly are listed at the top). At left, yellow, red, green, and blue lines indicate magnitude of the off-rate constant. Solid black lines indicate ligands whose binding to heterodimer is enhanced or unchanged compared with homodimer, whereas dashed red lines indicate substantially reduced binding compared with homodimer. As shown, the ActRIIB-Fc:ALK4-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. Like ActRIIB-Fc homodimer, the heterodimer retains intermediate-level binding to BMP6.
Figure 12:
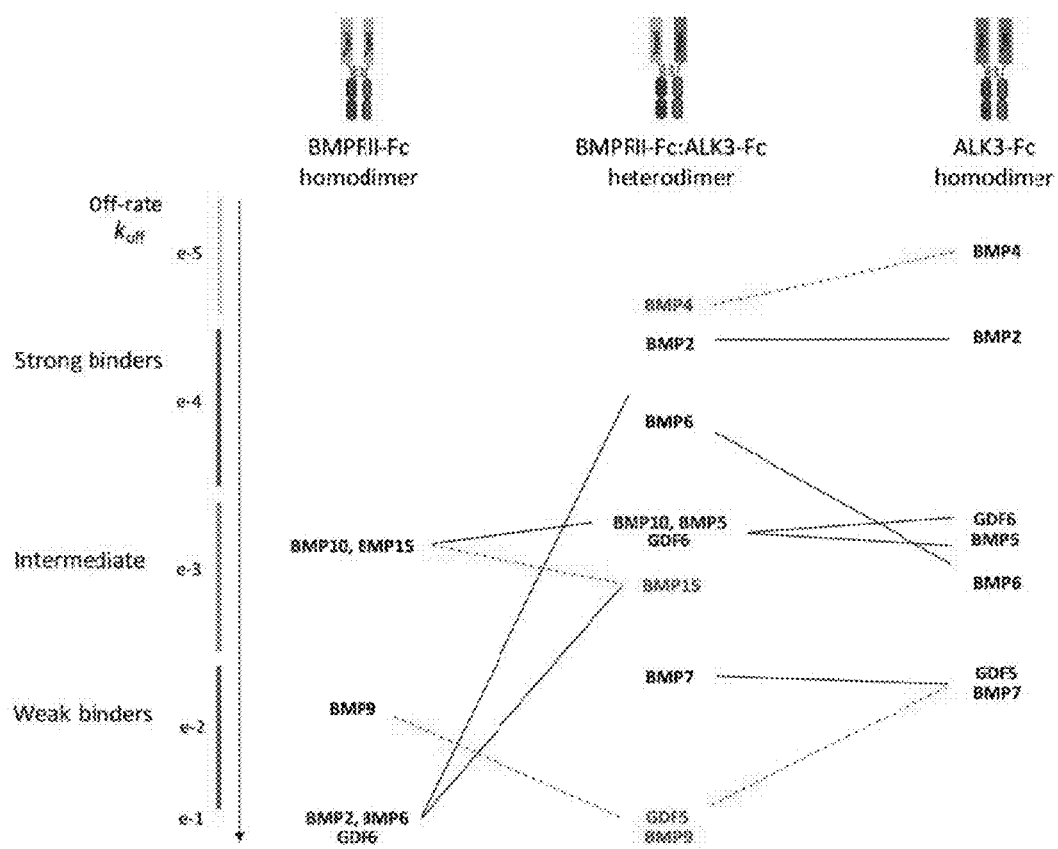

FIG. 12 shows ligand binding data for a BMPRII-Fc: ALK3-Fc heterodimeric protein complex as compared to BMPRII-Fc homodimer and ALK3-Fc homodimer. Format is the same as in FIG. 6. As shown, the BMPRII-Fc:ALK3-Fc heterodimer binds much more strongly to BMP6 than does ALK3-Fc homodimer, reflecting an off-rate nearly ten times slower. With its largely unchanged binding to BMP2 and BMP4, the BMPRII-Fc:ALK3 heterodimer can therefore be considered a joint inhibitor of BMP2, BMP4, and BMP6. This binding profile contrasts with that of ALK3-Fc homodimer, whose exceptionally strongly binding to BMP4 and BMP2 identifies it as highly selective for this ligand pair compared to four ligands with intermediate-level binding, including BMP6.

Figure 13:
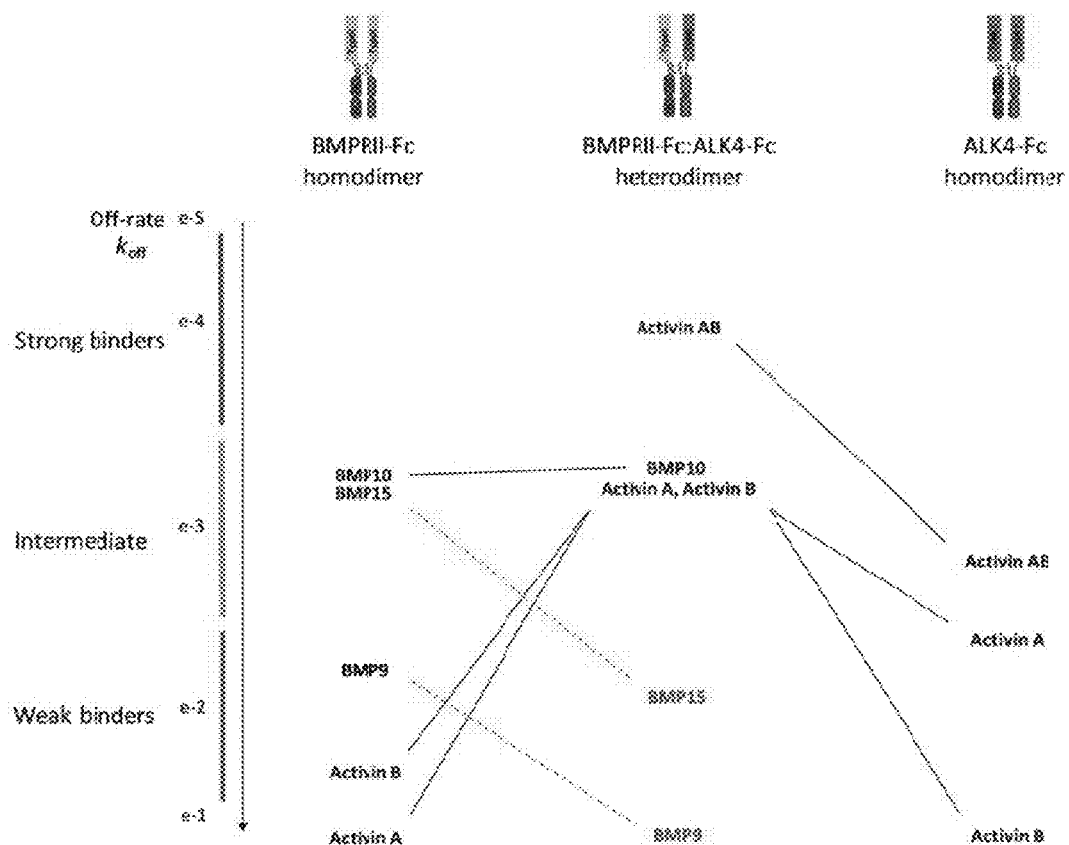

FIG. 13 shows ligand binding data for a BMPRII-Fc: ALK4-Fc heterodimeric protein complex as compared to BMPRII-Fc homodimer and ALK4-Fc homodimer. Format is the same as in FIG. 6. BMPRII-Fc:ALK4-Fc heterodimer differs from both homodimers by binding several activin ligands with high or intermediate strength and differs from BMPRII-Fc homodimer by binding BMP15 only weakly. Most notably, BMPRII-Fc:ALK4-Fc heterodimer binds strongly and with high selectivity to the heterodimeric ligand activin AB.

Figure 14:
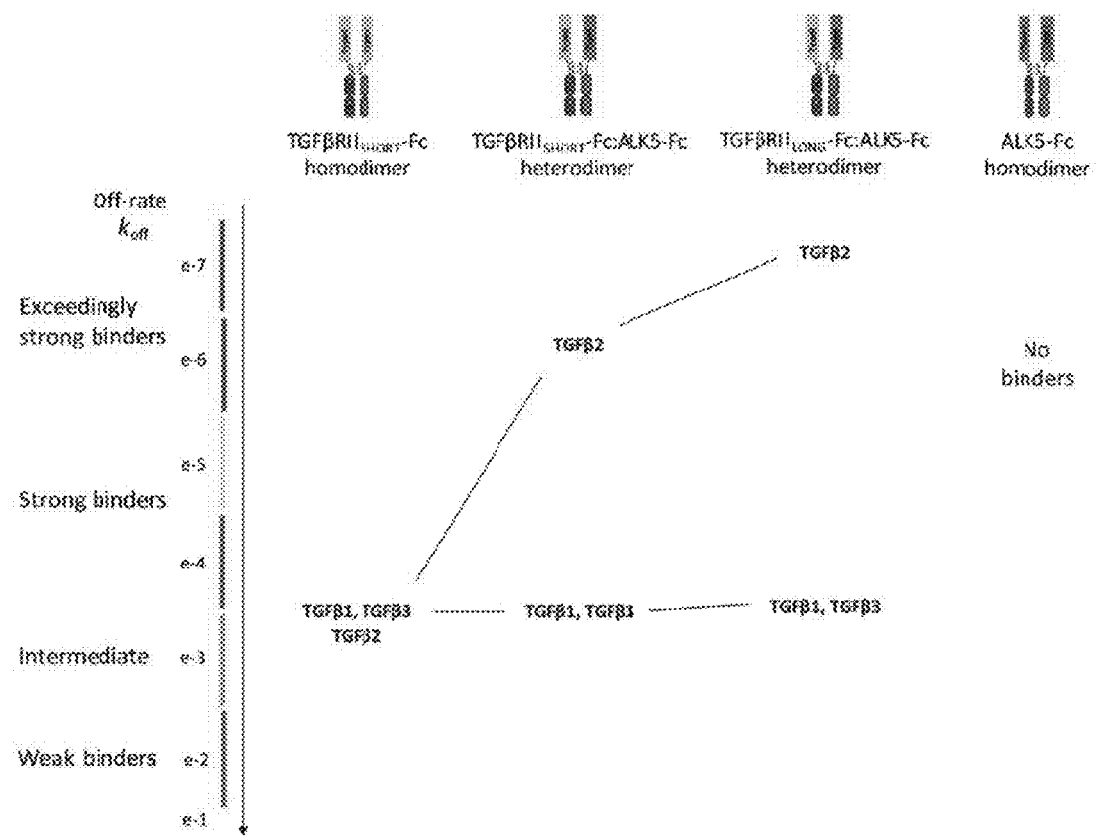
Figure 15A:
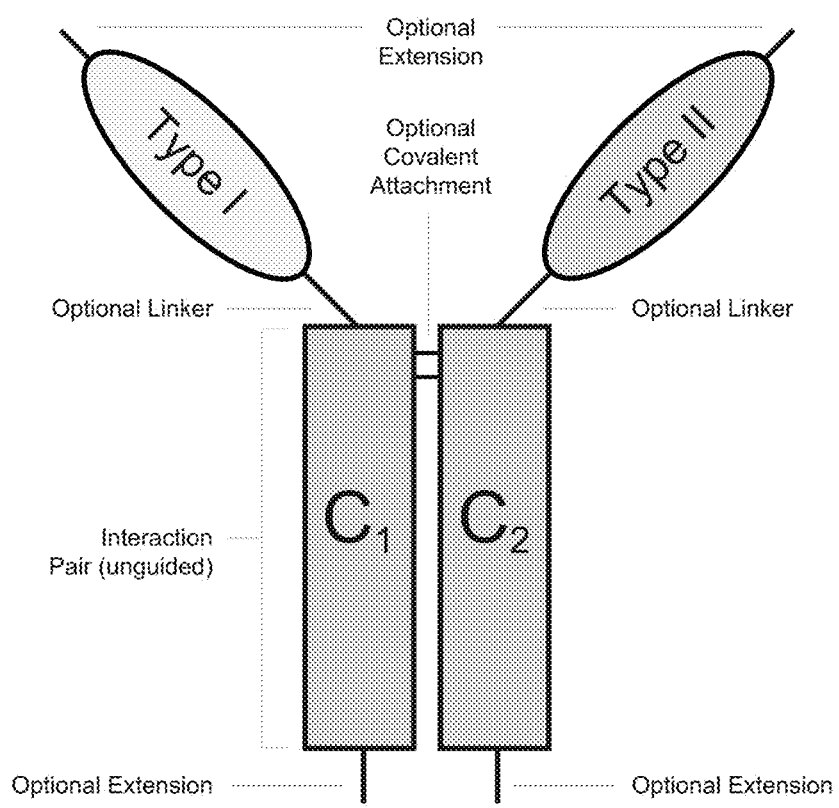
Figure 15B:
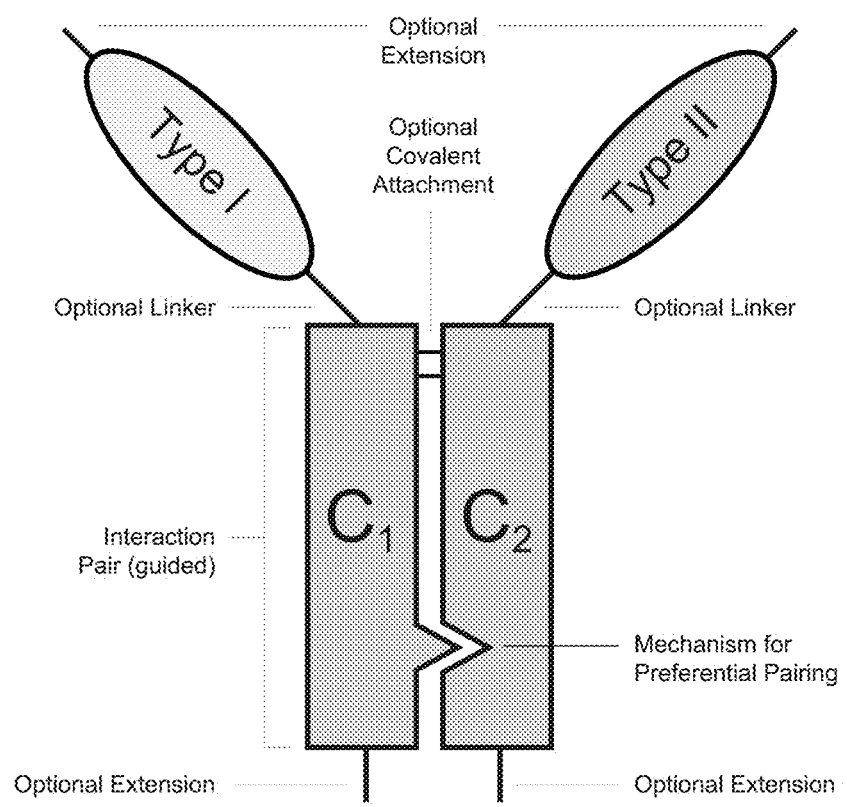
Figure 15C:
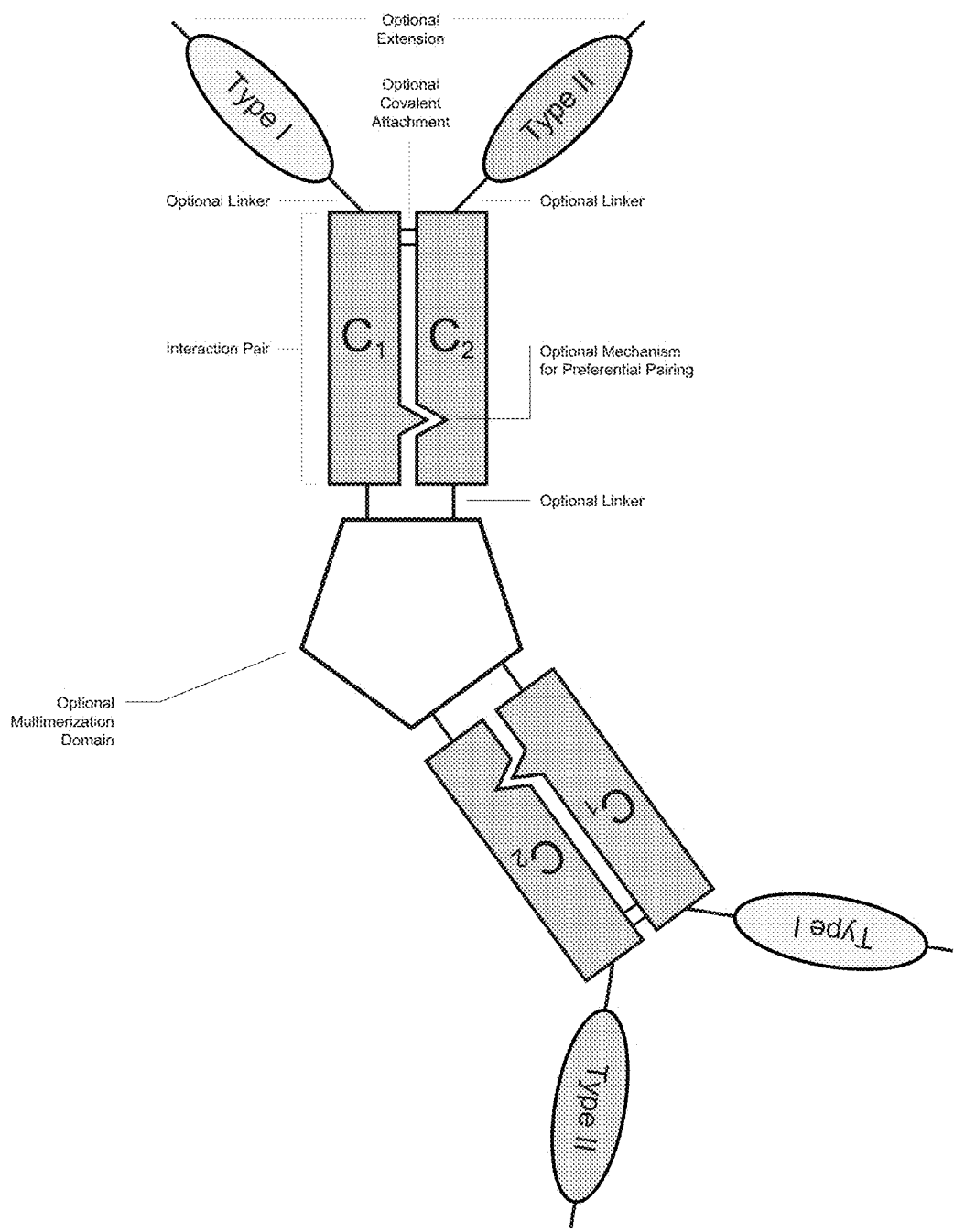
Figure 15D:
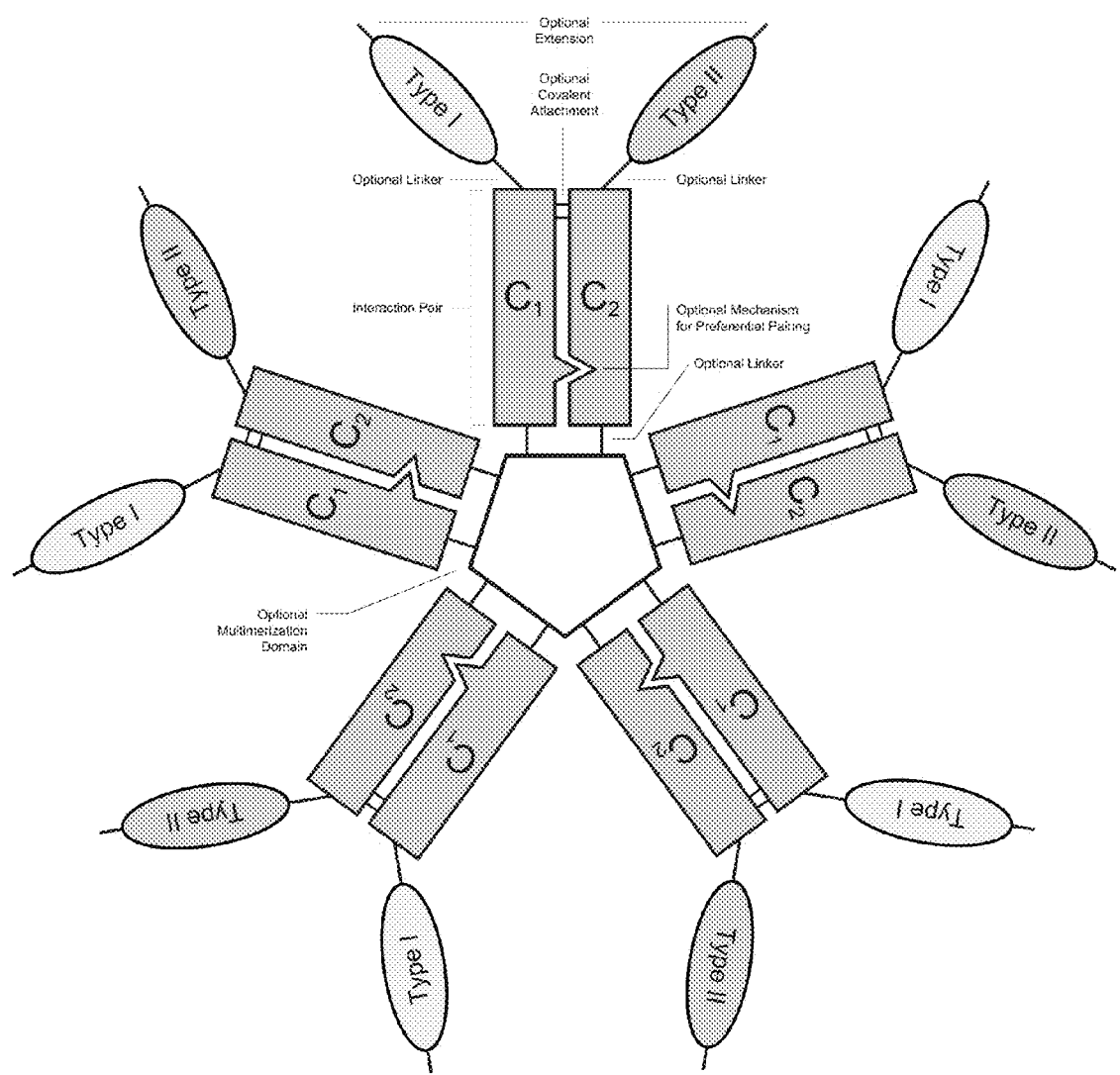

FIG. 14 shows ligand binding data for two different TGFβRII-Fc:ALK5-Fc heterodimeric protein complexes as compared to TGFβRII-Fc homodimer and ALK5-Fc homodimer. Format is the same as in FIG. 6. As shown, TGFβRII-Fc:ALK5-Fc heterodimers differ markedly from TGFβRII-Fc homodimer in their high selectivity for TGFβ2 while still retaining considerable affinity for TGFβ1 and TGFβ3. The heterodimer incorporating the long isoform of TGFβRII bound TGFβ2 more strongly and selectively than did its short-isoform counterpart. No ligands tested bind to ALK5-Fc homodimer.

FIGS. 15A-15D show schematic examples of heteromeric protein complexes comprising a type I receptor polypeptide (indicated as "I") (e.g. a polypeptide that is at least 80%, 85%, 90%, 95%, 97%, 98%, 99% or 100% identical to an extracellular domain of an ALK1, ALK2, ALK3, ALK4, ALK5, ALK6 or ALK7 protein from humans or other species such as those described herein, e.g., SEQ ID Nos: 14, 15, 124, 126, 171, 172, 413, 414, 463, 464, 18, 19, 136, 138, 173, 174, 421, 422, 465, 466, 22, 23, 115, 117, 175, 176, 407, 408, 467, 468, 26, 27, 83, 84, 104, 106, 177, 178, 403, 404, 469, 470, 30, 31, 87, 88, 139, 141, 179, 180, 423, 424, 471, 472, 34, 35, 91, 92, 142, 144, 181, 182, 425, 426, 473, 474, 38, 39, 301, 302, 305, 306, 309, 310, 313, 112, 114, 183, 184, 405, 406, 475, and 476) and a type II receptor polypeptide (indicated as "II") (e.g. a polypeptide that is at least 80%, 85%, 90%, 95%, 97%, 98%, 99% or 100% identical to an extracellular domain of an ActRIIA, ActRIIB, MISRII, BMPRII, or TGFBRII protein from humans or other species such as those described herein, e.g., 9, 10, 11, 118, 120, 151, 152, 409, 410, 451, 452, 1, 2, 3, 4, 5, 6, 100, 102, 153, 154, 401, 402, 453, 454, 46, 47, 71, 72, 121, 123, 155, 156, 411, 412, 455, 456, 50, 51, 75, 76, 79, 80, 133, 135, 161, 162, 419, 420, 457, 458, 42, 43, 67, 68, 127, 129, 130, 132, 157, 158, 159, 160, 415, 416, 417, 418, 459, 460, 461, and 462). In the illustrated embodiments, the a type I receptor polypeptide is part of a fusion polypeptide that comprises a first member of an interaction pair ("C₁"), and a type II receptor polypeptide is part of a fusion polypeptide that comprises a second member of an interaction pair ("C₂"). Suitable interaction pairs included, for example, heavy chain and/or light chain immunoglobulin interaction pairs, truncations, and variants thereof such as those described herein [e.g., Spiess et al (2015) Molecular Immunology 67(2A): 95-106]. In each fusion polypeptide, a linker may be positioned between the a type I receptor polypeptide or a type II receptor polypeptide and the corresponding member of the interaction pair. The first and second members of the interaction pair may be unguided, meaning that the members of the pair may associate with each other or self-associate without substantial preference, and they may have the same or different amino acid sequences. See FIG. 15A. Alternatively, the interaction pair may be a guided (asymmetric) pair, meaning that the members of the pair associate preferentially with each other rather than self-associate. See FIG. 15B. Complexes of higher order can be envisioned. See FIGS. 15C and 15D.

FIGS. 16A-16G show schematic examples of heteromeric protein complexes comprising two type I receptor polypeptide (indicated as "I") (e.g. a polypeptide that is at least 80%, 85%, 90%, 95%, 97%, 98%, 99% or 100% identical to an extracellular domain of an ALK1, ALK2, ALK3, ALK4, ALK5, ALK6 or ALK7 protein from humans or other species such as those described herein, e.g., SEQ ID Nos: 14, 15, 124, 126, 171, 172, 413, 414, 463, 464, 18, 19, 136, 138, 173, 174, 421, 422, 465, 466, 22, 23, 115, 117, 175, 176, 407, 408, 467, 468, 26, 27, 83, 84, 104, 106, 177, 178, 403, 404, 469, 470, 30, 31, 87, 88, 139, 141, 179, 180, 423, 424, 471, 472, 34, 35, 91, 92, 142, 144, 181, 182, 425, 426, 473, 474, 38, 39, 301, 302, 305, 306, 309, 310, 313, 112, 114, 183, 184, 405, 406, 475, and 476) and two type II receptor polypeptide (indicated as "II") (e.g. a polypeptide that is at least 80%, 85%, 90%, 95%, 97%, 98%, 99% or 100% identical to an extracellular domain of an ActRIIA, ActRIIB, MISRII, BMPRII, or TGFBRII protein from humans or other species such as those described herein, e.g., 9, 10, 11, 118, 120, 151, 152, 409, 410, 451, 452, 1, 2, 3, 4, 5, 6, 100, 102, 153, 154, 401, 402, 453, 454, 46, 47, 71, 72, 121, 123, 155, 156, 411, 412, 455, 456, 50, 51, 75, 76, 79, 80, 133, 135, 161, 162, 419, 420, 457, 458, 42, 43, 67, 68, 127, 129, 130, 132, 157, 158, 159, 160, 415, 416, 417, 418, 459, 460, 461, and 462).

Figure 16A:
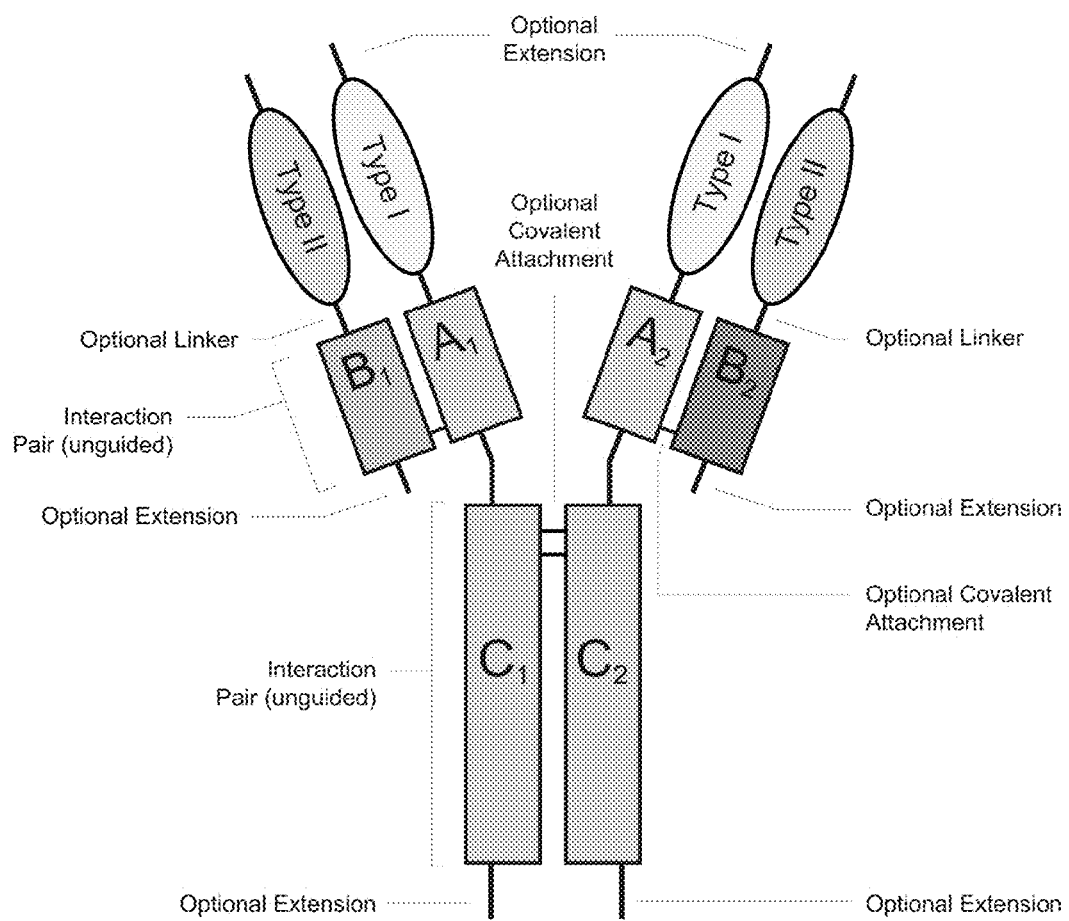

In the illustrated embodiment FIG. 16A, the first type I receptor polypeptide (from left to right) is part of a fusion polypeptide that comprises a first member of an interaction pair ("C₁") and further comprises an additional first member of an interaction pair ("A₁"); and the second type I receptor polypeptide is part of a fusion polypeptide that comprises a second member of an interaction pair ("C₂") and further comprises an first member of an interaction pair ("A₂"). The first type II receptor polypeptide (from left to right) is part of a fusion polypeptide that comprises a second member of an interaction pair ("B₁"); and the second type II receptor polypeptide is part of a fusion polypeptide that comprises a second member of an interaction pair ("B₂"). A₁ and A₂ may be the same or different; B₁ and B₂ may be the same or different, and C₁ and C₂ may be the same or different. In each fusion polypeptide, a linker may be positioned between the type I receptor polypeptide or type II receptor polypeptide and the corresponding member of the interaction pair as well as between interaction pairs. FIG. 16A is an example of an association of unguided interaction pairs, meaning that the members of the pair may associate with each other or self-associate without substantial preference and may have the same or different amino acid sequences.

Figure 16B:
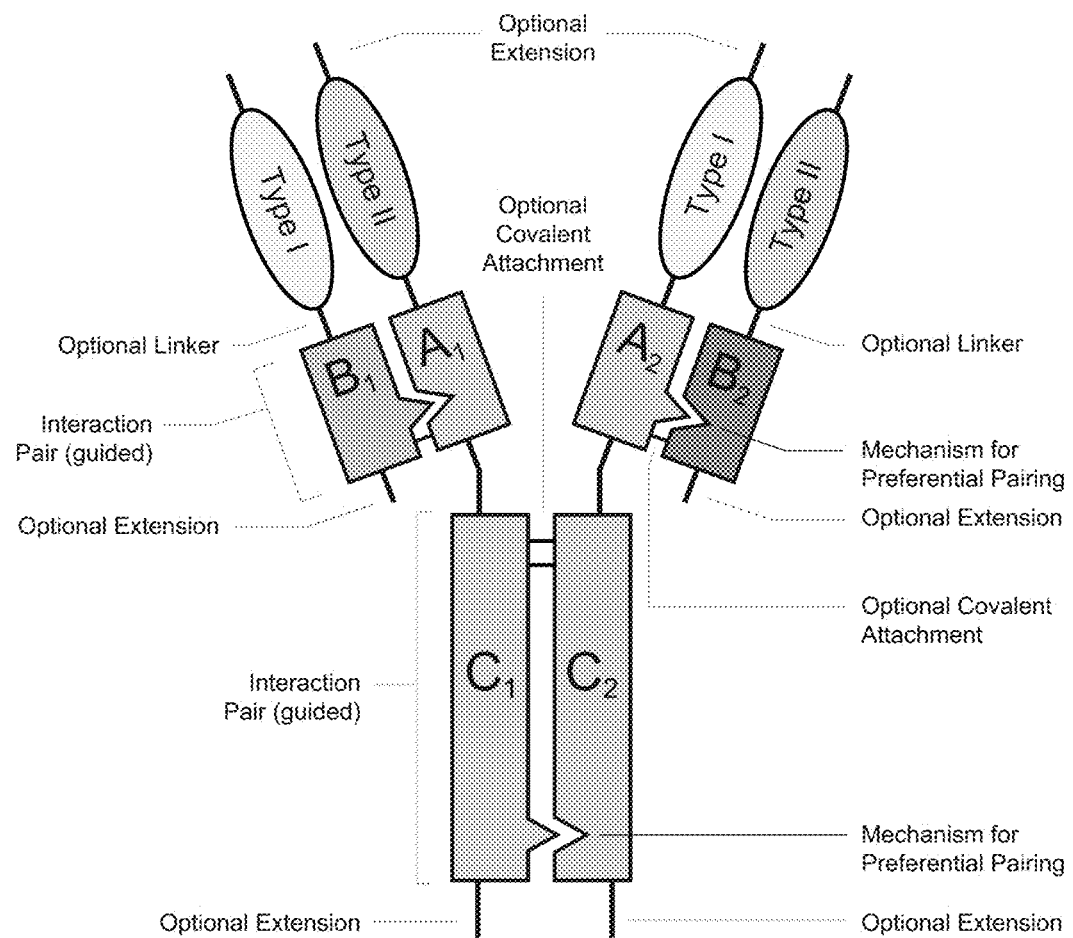
Figure 16C:
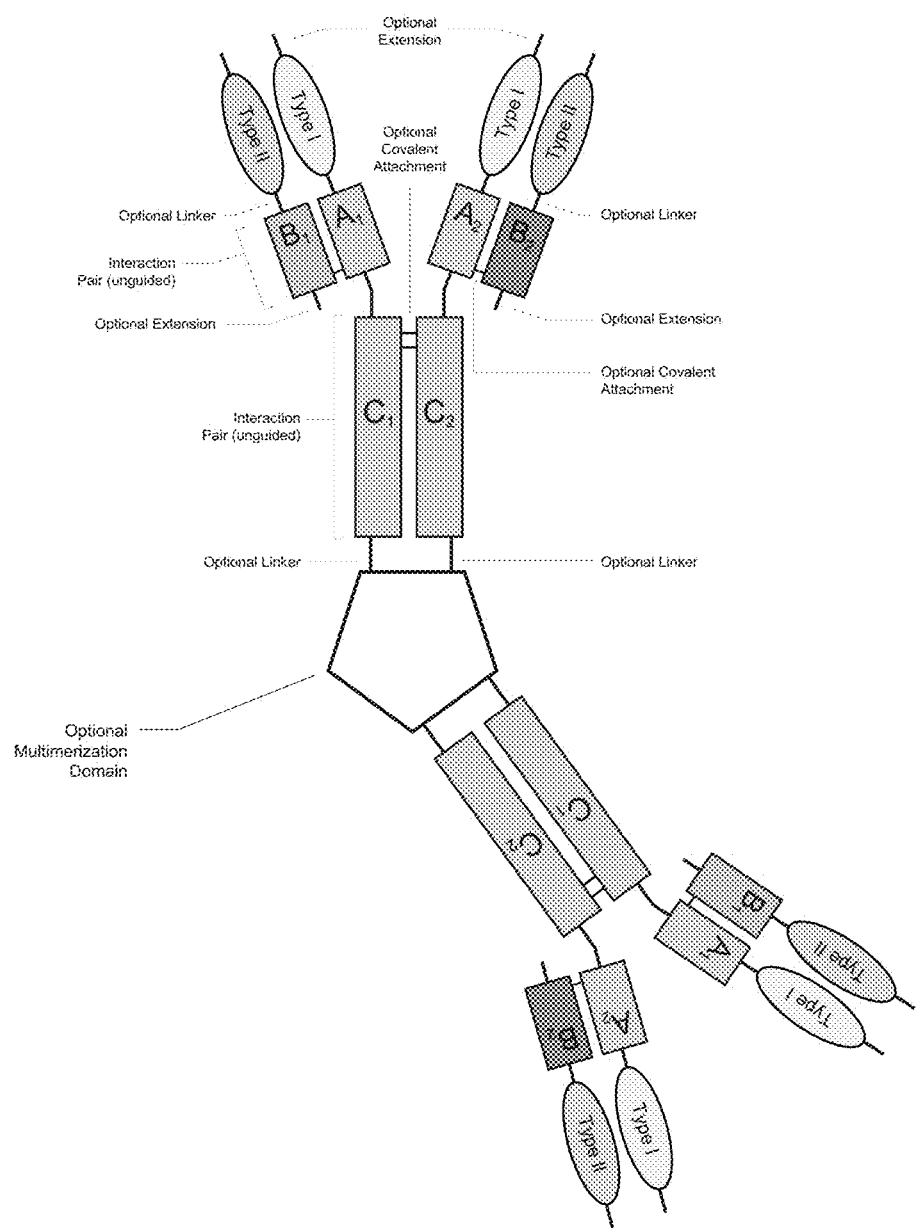
Figure 16D:
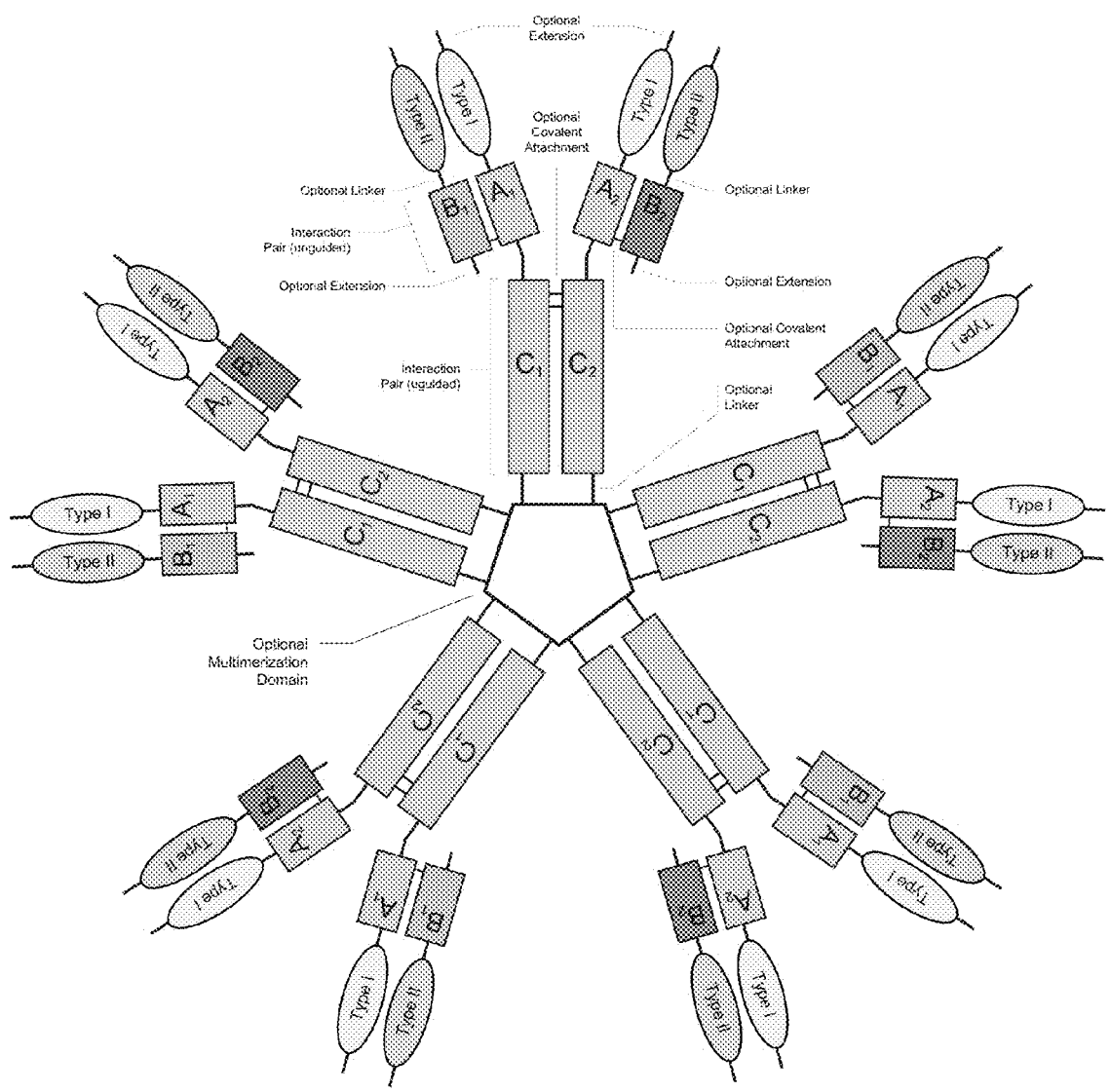
Figure 16E:
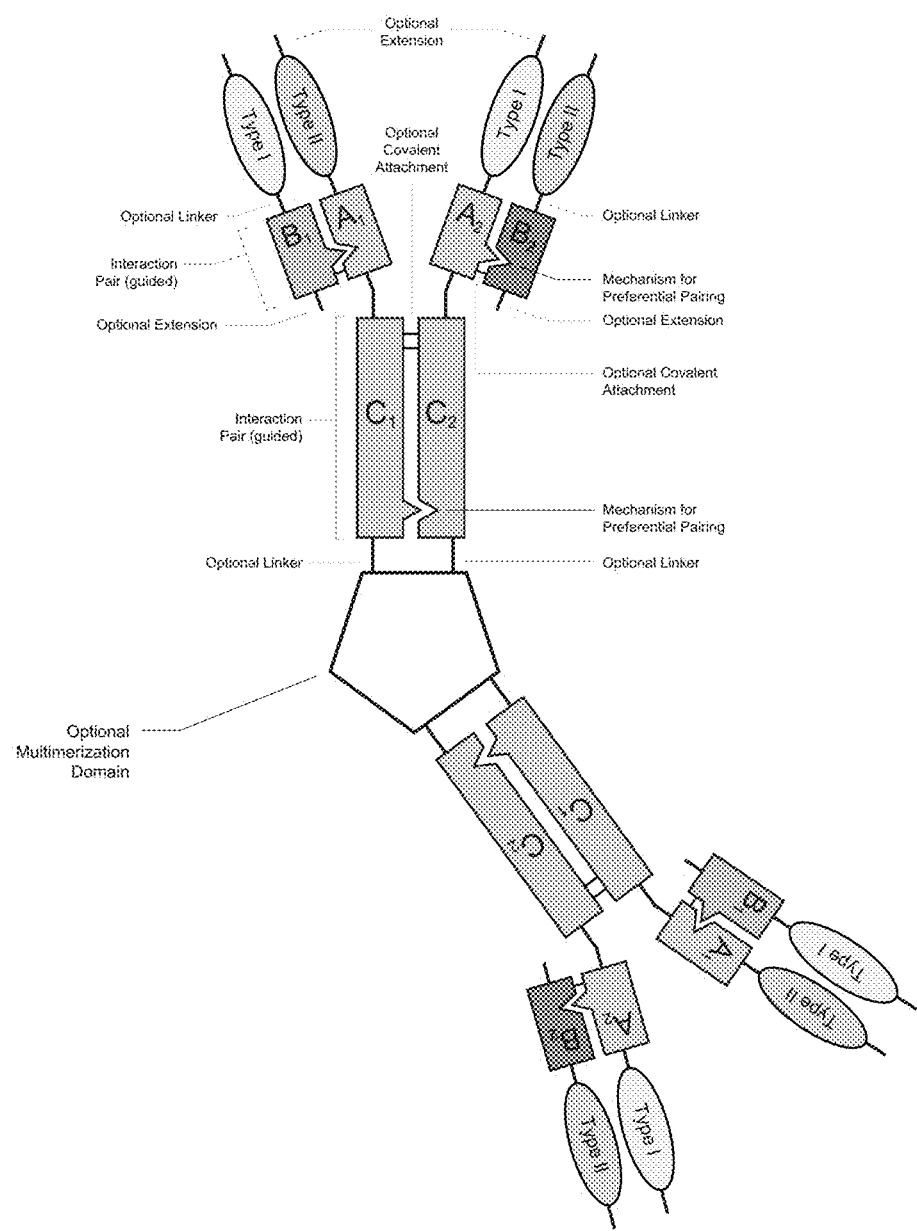
Figure 16F:
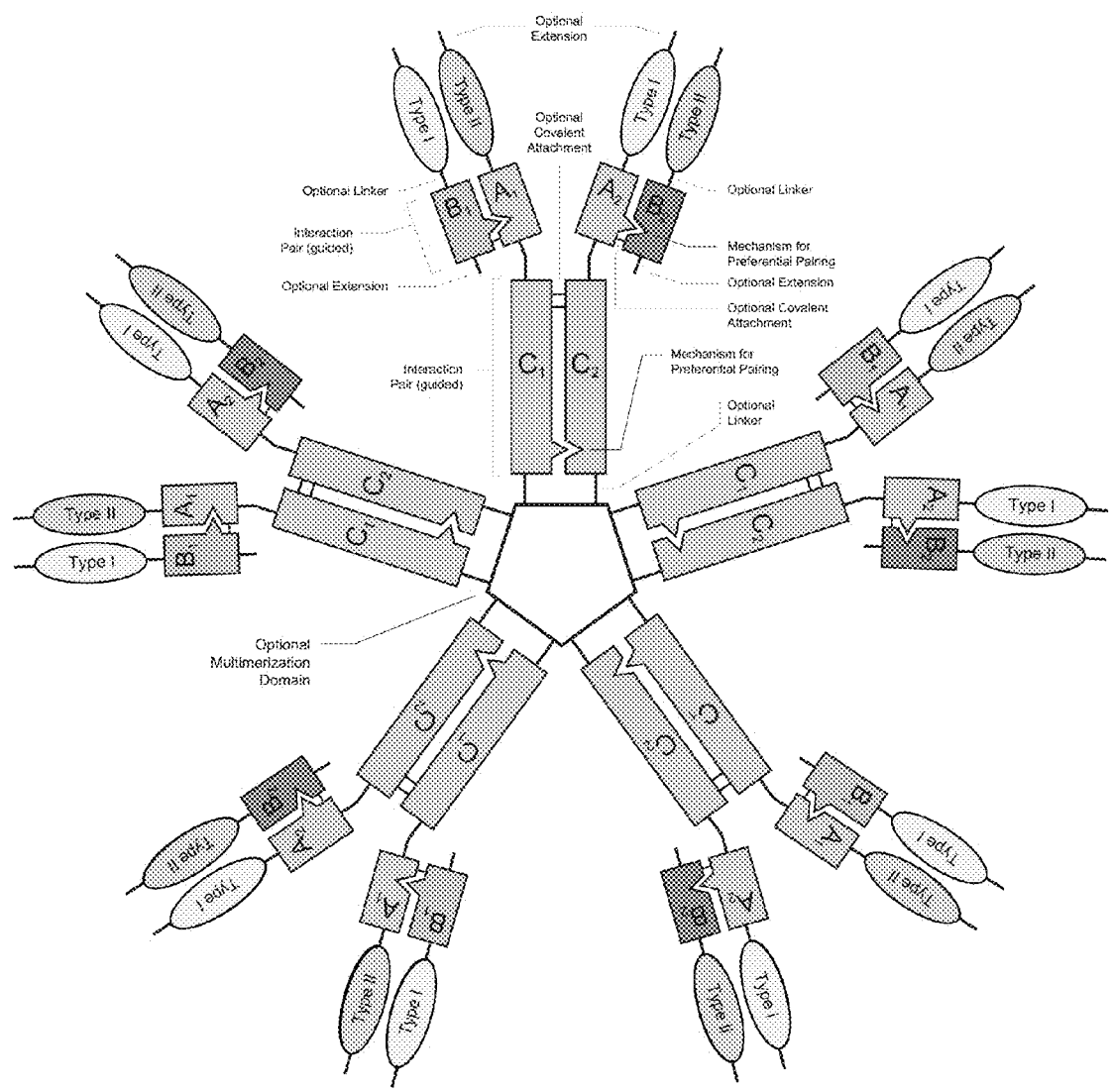
Figure 16G:
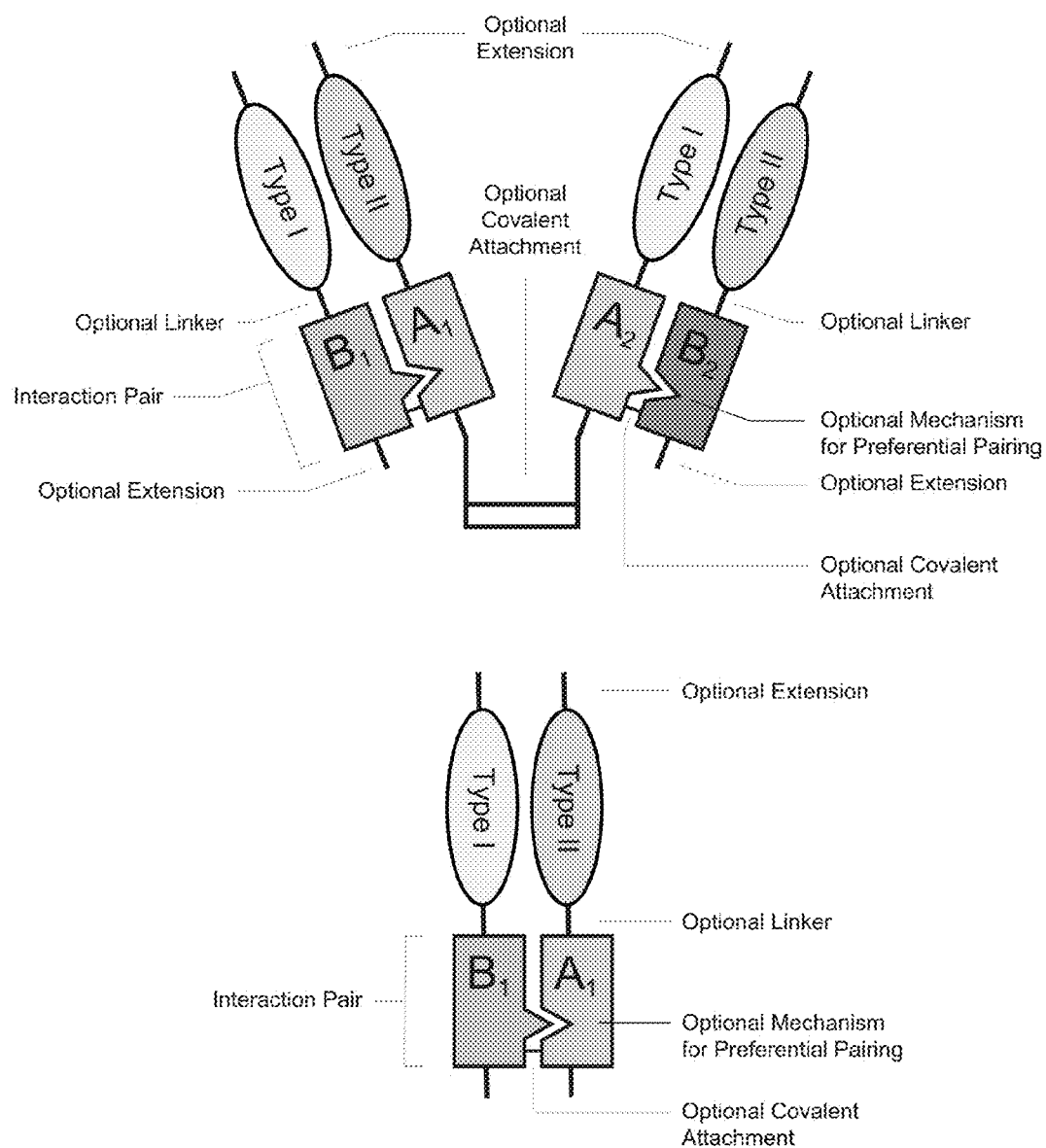

In the illustrated embodiment FIG. 16B, the first type II receptor polypeptide (from left to right) is part of a fusion polypeptide that comprises a first member of an interaction pair ("$C_1$") and further comprises an additional first member of an interaction pair ("$A_1$"); and the second type II receptor ActRIIB polypeptide is part of a fusion polypeptide that comprises a second member of an interaction pair ("$B_2$"). The first type I receptor polypeptide (from left to right) is part of a fusion polypeptide that comprises a second member of an interaction pair ("$B_1$"); and the second type I receptor polypeptide is part of a fusion polypeptide that comprises a second member of an interaction pair ("$C_2$") and further comprises a first member of an interaction pair ("$A_2$"). In each fusion polypeptide, a linker may be positioned between the type I receptor or type II receptor polypeptide and the corresponding member of the interaction pair as well as between interaction pairs. FIG. 16B is an example of an association of guided (asymmetric) interaction pairs, meaning that the members of the pair associate preferentially with each other rather than self-associate.

Suitable interaction pairs included, for example, heavy chain and/or light chain immunoglobulin interaction pairs, truncations, and variants thereof as described herein [e.g., Spiess et al (2015) Molecular Immunology 67(2A): 95-106]. Complexes of higher order can be envisioned. See FIGS. 16C-16F. Using similar methods, particularly those that employ light and/or heavy chain immunoglobulins, truncations, or variants thereof, interaction pairs may be used to produce heterodimers that resemble antibody Fab and F(ab')$_2$ complexes [e.g., Spiess et al (2015) Molecular Immunology 67(2A): 95-106]. See FIG. 16G.

Figure 17A:
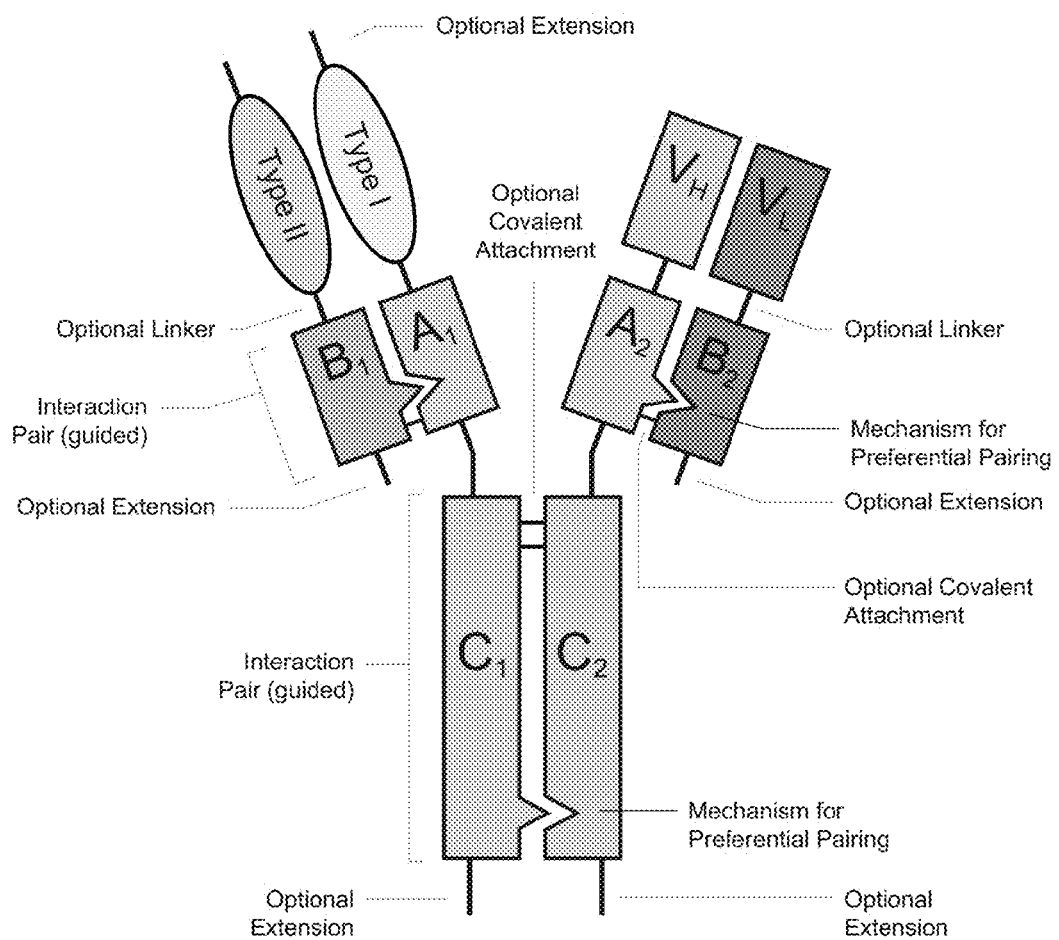
Figure 17B:
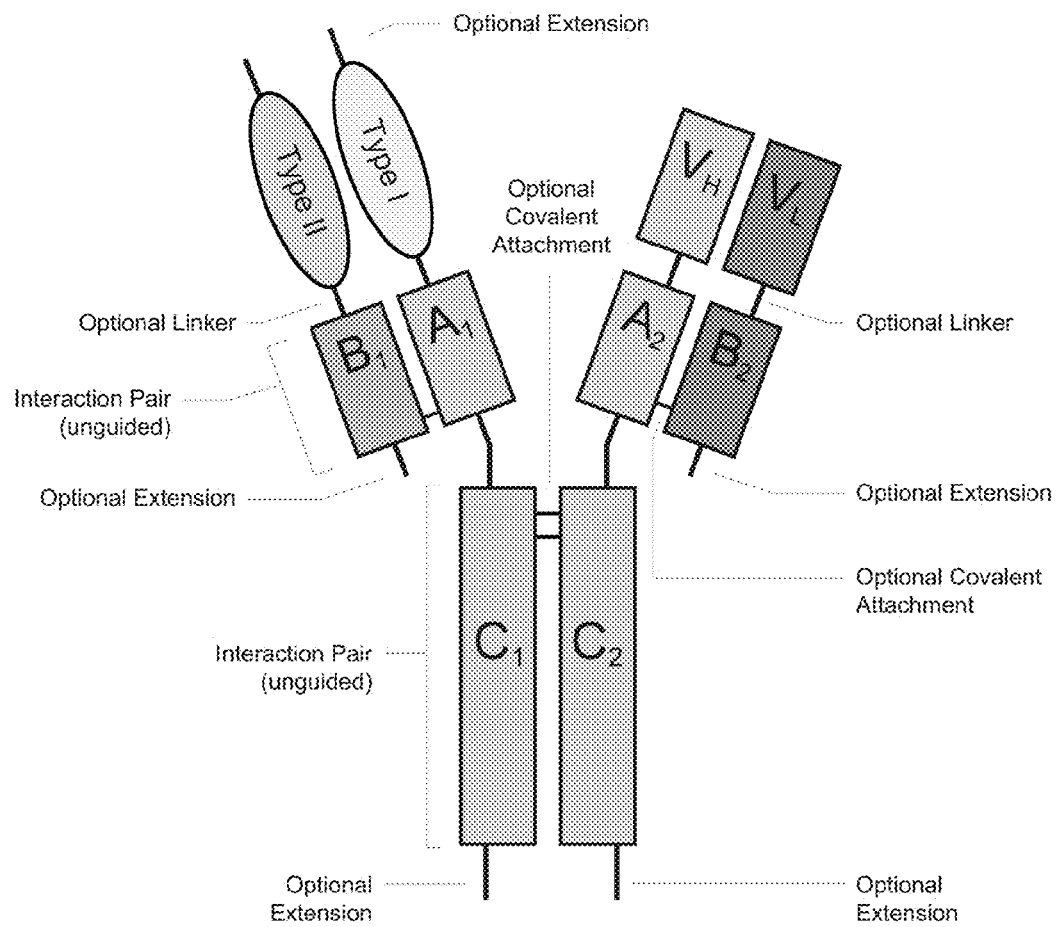

FIGS. 17A and 17B show schematic examples of a heteromeric protein complex comprising a type I receptor polypeptide (indicated as "I") (e.g. a polypeptide that is at least 80%, 85%, 90%, 95%, 97%, 98%, 99% or 100% identical to an extracellular domain of an ALK1, ALK2, ALK3, ALK4, ALK5, ALK6 or ALK7 protein from humans or other species such as those described herein, e.g., SEQ ID Nos: 14, 15, 124, 126, 171, 172, 413, 414, 463, 464, 18, 19, 136, 138, 173, 174, 421, 422, 465, 466, 22, 23, 115, 117, 175, 176, 407, 408, 467, 468, 26, 27, 83, 84, 104, 106, 177, 178, 403, 404, 469, 470, 30, 31, 87, 88, 139, 141, 179, 180, 423, 424, 471, 472, 34, 35, 91, 92, 142, 144, 181, 182, 425, 426, 473, 474, 38, 39, 301, 302, 305, 306, 309, 310, 313, 112, 114, 183, 184, 405, 406, 475, and 476) and a type II receptor polypeptide (indicated as "II") (e.g. a polypeptide that is at least 80%, 85%, 90%, 95%, 97%, 98%, 99% or 100% identical to an extracellular domain of an ActRIIA, ActRIIB, MISRII, BMPRII, or TGFBRII protein from humans or other species such as those described herein, e.g., 9, 10, 11, 118, 120, 151, 152, 409, 410, 451, 452, 1, 2, 3, 4, 5, 6, 100, 102, 153, 154, 401, 402, 453, 454, 46, 47, 71, 72, 121, 123, 155, 156, 411, 412, 455, 456, 50, 51, 75, 76, 79, 80, 133, 135, 161, 162, 419, 420, 457, 458, 42, 43, 67, 68, 127, 129, 130, 132, 157, 158, 159, 160, 415, 416, 417, 418, 459, 460, 461, and 462), and a ligand-binding domain of an antibody (e.g., a ligand binding domain derived form an antibody that binds to one or more TGF-beta superfamily ligands). In the illustrated embodiments, the type I receptor polypeptide is part of a fusion polypeptide that comprises a first member of an interaction pair ("$C_1$"), and further comprises an additional first member of an interaction pair ("$A_1$"). The type II receptor polypeptide is part of a fusion polypeptide that comprises a second member of an interaction pair ("$B_1$"). The variable heavy chain ($V_H$) polypeptide is part of a fusion polypeptide that comprises a second member of an interaction pair ("$C_2$"), and further comprises a first member of an interaction pair ("$A_2$"). The variable heavy chain ($V_L$) polypeptide is part of a fusion polypeptide that comprises a second member of an interaction pair ("$B_2$"). In each fusion polypeptide, a linker may be positioned between the type I receptor or type II receptor polypeptide and the corresponding member of the interaction pair, between interaction pairs, and between the $V_H$ and $V_L$ polypeptides and a member of the interaction pair. $A_1$ and $A_2$ may be the same or different; $B_1$ and $B_2$ may be the same or different, and $C_1$ and $C_2$ may be the same or different. Suitable interaction pairs included, for example, constant heavy chain and/or light chain immunoglobulin interaction pairs, truncations, and variants thereof as described herein [e.g., Spiess et al (2015) Molecular Immunology 67(2A): 95-106]. FIG. 17A is an example of an association of guided (asymmetric) interaction pairs, meaning that the members of the pair associate preferentially with each other rather than self-associate. FIG. 17B is an example of an association of unguided interaction pairs, meaning that the members of the pair may associate with each other or self-associate without substantial preference and may have the same or different amino acid sequences.

Figure 18:
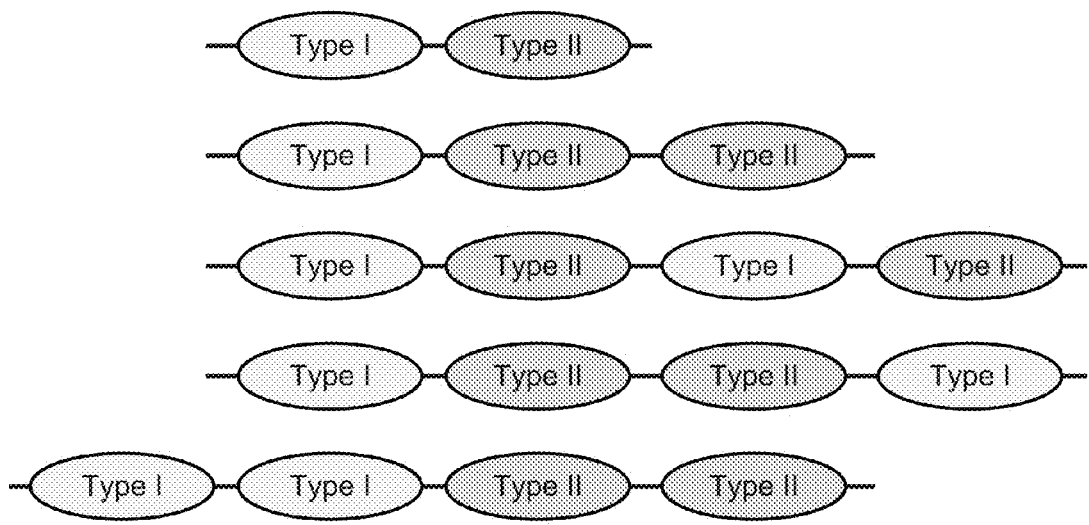

FIG. 18 shows schematic examples of type I receptor: type II receptor single-trap polypeptides. Type I receptor: type II receptor single-trap polypeptides may contain multiple type I receptor domains (e.g., 1, 2, 3, 4, 5, 6, 7, 9, 10 or more domains), having the same or different sequences, and multiple type II receptor domains (e.g., 1, 2, 3, 4, 5, 6, 7, 9, 10 or more domains), having the same or different sequences. These type I receptor and type II receptor domains may be arranged in any order and may comprise one or more linker domains positions between one or more of the type I1 receptor and type II receptor domains. Such ligand traps may be useful as therapeutic agents to treat or prevent diseases or disorders described herein.

Figure 19A:
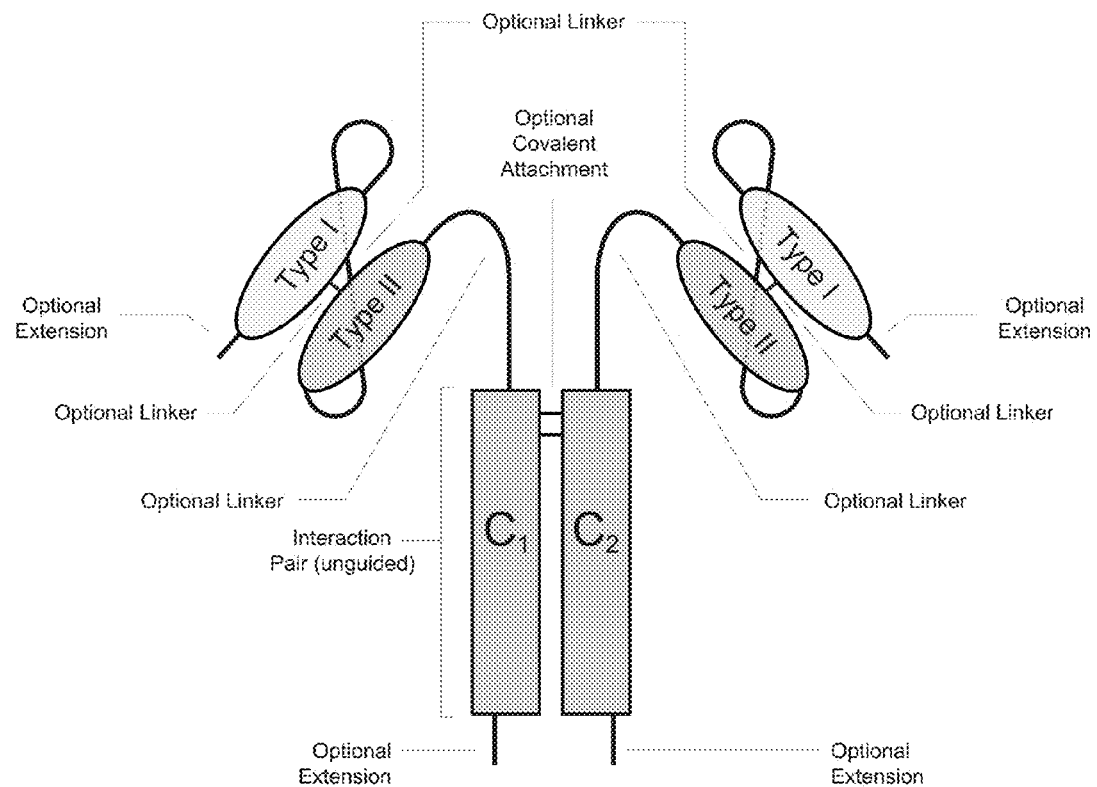
Figure 19B:
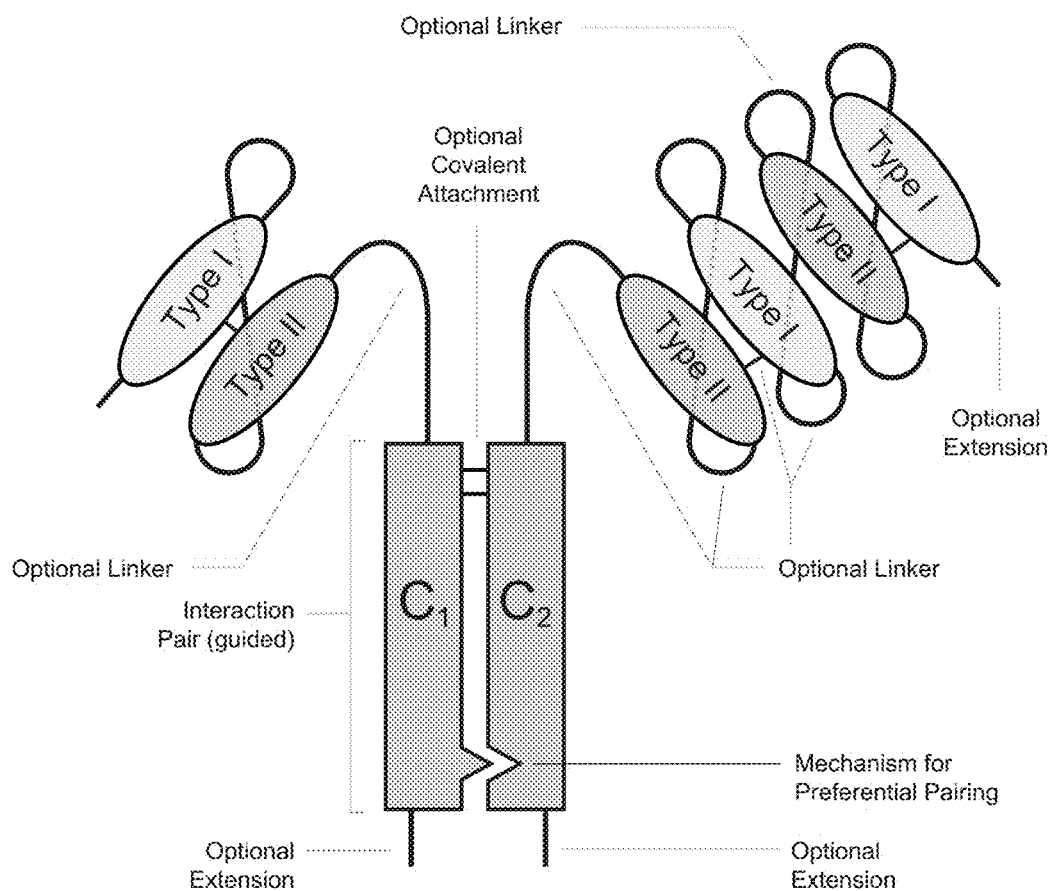
Figure 19C:
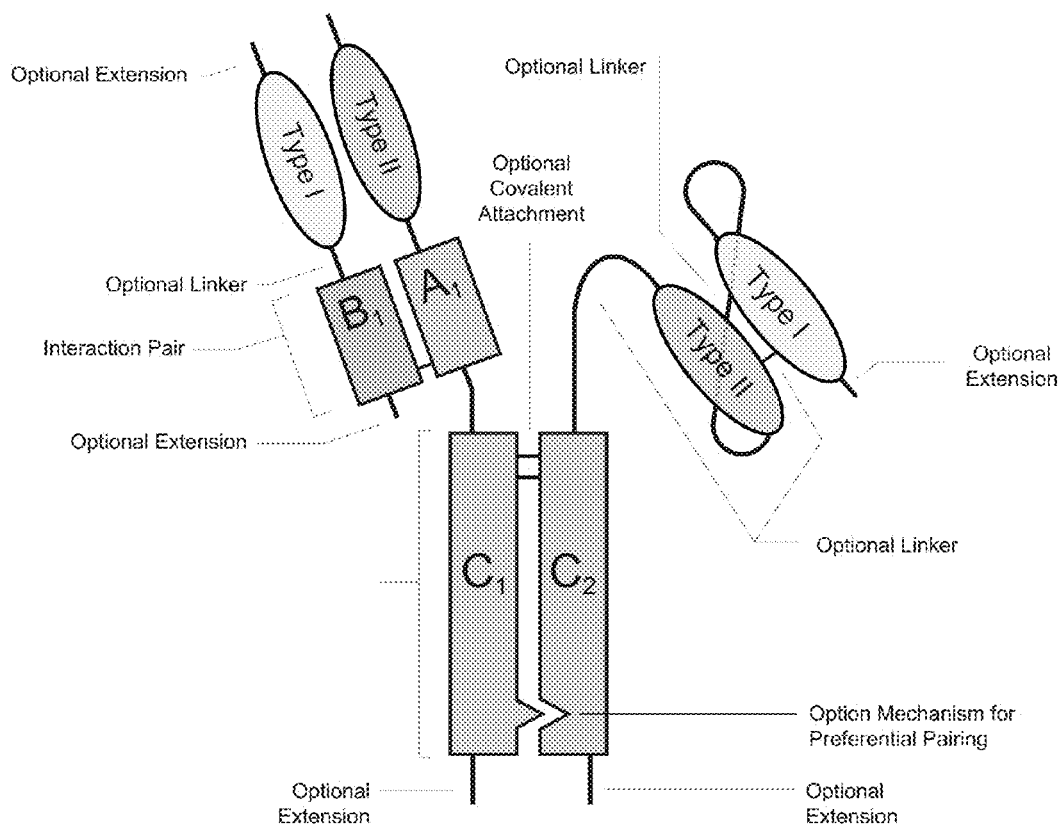
Figure 19D:
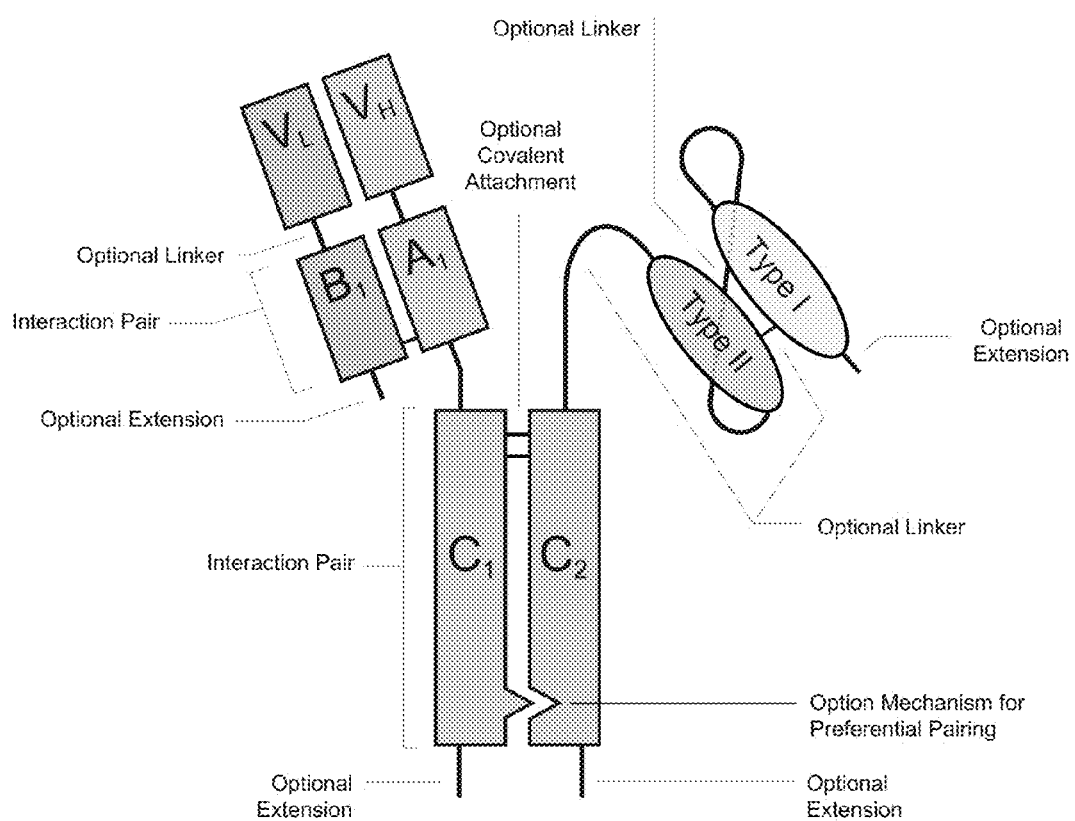

FIGS. 19A-19D show schematic examples of multimeric protein complexes comprising at least one type I receptor: type II receptor single-chain trap polypeptide. In the illustrated embodiments 19A and 19B, a first type I receptor: type II receptor single-chain trap polypeptide (from left to right) is part of a fusion polypeptide that comprises a first member of an interaction pair ("$C_1$"); and a second type I receptor: type II receptor single-chain trap polypeptide is part of a fusion polypeptide that comprises a second member of an interaction pair ("$C_2$"). $C_1$ and $C_2$ may be the same or different. The first and second type I receptor: type II receptor single-chain trap polypeptides may be the same or different. In each fusion polypeptide, a linker may be positioned between the type I receptor: type II receptor single-chain trap polypeptide and the corresponding member of the interaction pair. Suitable interaction pairs included, for example, heavy chain and/or light chain immunoglobulin interaction pairs, truncations, and variants thereof as described herein [e.g., Spiess et al (2015) Molecular Immunology 67(2A): 95-106]. FIG. 19A is an example of an association of unguided interaction pairs, meaning that the members of the pair may associate with each other or self-associate without substantial preference and may have the same or different amino acid sequences. FIG. 19B is an example of an association of guided (asymmetric) interaction pairs, meaning that the members of the pair associate preferentially with each other rather than self-associate. Complexes of higher order can be envisioned. In addition, such type I receptor: type II receptor single-chain trap polypeptides may be similarly be associated, covalently or non-covalently, with one or more type I receptor polypeptides and/or one or more type II receptor polypeptides. See FIG. 19C. Also, such type I receptor: type II receptor single-chain trap polypeptides may be similarly be associated, covalently or non-covalently, with one or more ligand-binding domain of an antibody (e.g., a ligand binding domain of an antibody that binds to one or more type I receptor: type II receptor heteromultimer binding-ligands). See FIG. 19D.

DETAILED DESCRIPTION OF THE INVENTION

1. Overview

In part, the present disclosure relates to heteromultimer complexes comprising an extracellular domain of a TGFβ superfamily type I receptor polypeptide and an extracellular domain of a TGFβ superfamily type II receptor polypeptide, heteromultimer complexes comprising an extracellular domain of at least two different TGFβ superfamily type I receptor polypeptides, heteromultimer complexes comprising an extracellular domain of at least two different TGFβ superfamily type II receptor polypeptides, methods of making such heteromultimer complexes, and uses thereof. As described herein, in some embodiments, heteromultimer complexes may comprise an extracellular domain of a TGFβ superfamily type I receptor polypeptide selected from: ALK1, ALK2, ALK3, ALK4, ALK5, ALK6, and ALK7. Similarly, in some embodiments, these heteromultimer complexes may comprise an extracellular domain of a TGFβ superfamily type II receptor polypeptide selected from: ActRIIA, ActRIIB, TGFBRII, BMPRII, and MISRII. In certain preferred embodiments, heteromultimer complexes of the disclosure have an altered TGFβ superfamily ligand binding specificity/profile relative to a corresponding sample of a homomultimer complex (e.g., an ActRIIB: ALK4 heterodimer compared to an ActRIIB:ActRIIB homodimer complex or an ALK4:ALK4 homodimer complex).

The TGF-β superfamily is comprised of over 30 secreted factors including TGF-betas, activins, nodals, bone morphogenetic proteins (BMPs), growth and differentiation factors (GDFs), and anti-Mullerian hormone (AMH). See, e.g., Weiss et al. (2013) Developmental Biology, 2(1): 47-63. Members of the superfamily, which are found in both vertebrates and invertebrates, are ubiquitously expressed in diverse tissues and function during the earliest stages of development throughout the lifetime of an animal. Indeed, TGF-β superfamily proteins are key mediators of stem cell self-renewal, gastrulation, differentiation, organ morphogenesis, and adult tissue homeostasis. Consistent with this ubiquitous activity, aberrant TGF-beta superfamily signaling is associated with a wide range of human pathologies including, for example, autoimmune disease, cardiovascular disease, fibrotic disease, and cancer.

Ligands of the TGF-beta superfamily share the same dimeric structure in which the central 3½ turn helix of one monomer packs against the concave surface formed by the beta-strands of the other monomer. The majority of TGF-beta family members are further stabilized by an intermolecular disulfide bonds. This disulfide bond traverses through a ring formed by two other disulfide bonds generating what has been termed a 'cysteine knot' motif. See, e.g., Lin et al., (2006) Reproduction 132: 179-190 and Hinck et al. (2012) FEBS Letters 586: 1860-1870.

TGF-beta superfamily signaling is mediated by heteromeric complexes of type I and type II serine/threonine kinase receptors, which phosphorylate and activate downstream SMAD proteins (e.g., SMAD proteins 1, 2, 3, 5, and 8) upon ligand stimulation. See, e.g., Massagué (2000) Nat. Rev. Mol. Cell Biol. 1:169-178. These type I and type II receptors are transmembrane proteins, composed of a ligand-binding extracellular domain with cysteine-rich region, a transmembrane domain, and a cytoplasmic domain with predicted serine/threonine kinase specificity. In general, type I receptors mediate intracellular signaling while the type II receptors are required for binding TGF-beta superfamily ligands. Type I and II receptors form a stable complex after ligand binding, resulting in phosphorylation of type I receptors by type II receptors.

The TGF-beta family can be divided into two phylogenetic branches based on the type I receptors they bind and the Smad proteins they activate. One is the more recently evolved branch, which includes, e.g., the TGF-betas, activins, GDF8, GDF9, GDF11, BMP3 and nodal, which signal through type I receptors that activate Smads 2 and 3 [Hinck (2012) FEBS Letters 586:1860-1870]. The other branch comprises the more distantly related proteins of the superfamily and includes, e.g., BMP2, BMP4, BMP5, BMP6, BMP7, BMP8a, BMP8b, BMP9, BMP10, GDF1, GDF5, GDF6, and GDF7, which signal through Smads 1, 5, and 8.

TGF-beta isoforms are the founding members of the TGF-beta superfamily, of which there are 3 known isoforms in mammals designated as TGF-beta1, TGF-beta2 and TGF-beta3. Mature bioactive TGF-beta ligands function as homodimers and predominantly signal through the type I receptor ALK5, but have also been found to additionally signal through ALK1 in endothelial cells. See, e.g., Goumans et al. (2003) Mol Cell 12(4): 817-828. TGF-beta1 is the most abundant and ubiquitously expressed isoform. TGF-beta1 is known to have an important role in wound healing, and mice expressing a constitutively active TGF-beta1 transgene develop fibrosis. See e.g., Clouthier et al., (1997) J Clin. Invest. 100(11): 2697-2713. TGF-beta1 is also involved in T cell activation and maintenance of T regulatory cells. See, e.g., Li et al., (2006) Immunity 25(3): 455-471. TGF-beta2 expression was first described in human glioblastoma cells, and is occurs in neurons and astroglial cells of the embryonic nervous system. TGF-beta2 is known to suppress interleukin-2-dependent growth of T lymphocytes. TGF-beta3 was initially isolated from a human rhabdomyosarcoma cell line and since has been found in lung adenocarcinoma and kidney carcinoma cell lines. TGF-beta3 is known to be important for palate and lung morphogenesis. See, e.g., Kubiczkova et al., (2012) Journal of Translational Medicine 10:183.

Activins are members of the TGF-beta superfamily and were initially discovered as regulators of secretion of follicle-stimulating hormone, but subsequently various reproductive and non-reproductive roles have been characterized. There are three principal activin forms (A, B, and AB) that are homo/heterodimers of two closely related β subunits ($β_Aβ_A$, $β_Bβ_B$, and $β_Aβ_B$, respectively). The human genome also encodes an activin C and an activin E, which are primarily expressed in the liver, and heterodimeric forms containing $β_C$ or $β_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos. See, e.g., DePaolo et al. (1991) Proc Soc Ep Biol Med. 198:500-512; Dyson et al. (1997) Curr Biol. 7:81-84; and Woodruff (1998) Biochem Pharmacol. 55:953-963. In several tissues, activin signaling is antagonized by its related heterodimer, inhibin. For example, in the regulation of follicle-stimulating hormone (FSH) secretion from the pituitary, activin promotes FSH synthesis and secretion, while inhibin reduces FSH synthesis and secretion. Other proteins that may regulate activin bioactivity and/or bind to activin include follistatin (FS), follistatin-related protein (FSRP, also known as FLRG or FSTL3), and $\alpha_2$-macroglobulin.

As described herein, agents that bind to "activin A" are agents that specifically bind to the $\beta_A$ subunit, whether in the context of an isolated PA subunit or as a dimeric complex (e.g., a $\beta_A\beta_A$ homodimer or a $\beta_A\beta_B$ heterodimer). In the case of a heterodimer complex (e.g., a $\beta_A\beta_B$ heterodimer), agents that bind to "activin A" are specific for epitopes present within the $\beta_A$ subunit, but do not bind to epitopes present within the non-$\beta_A$ subunit of the complex (e.g., the $\beta_B$ subunit of the complex). Similarly, agents disclosed herein that antagonize (inhibit) "activin A" are agents that inhibit one or more activities as mediated by a $\beta_A$ subunit, whether in the context of an isolated $\beta_A$ subunit or as a dimeric complex (e.g., a $\beta_A\beta_A$ homodimer or a $\beta_A\beta_B$ heterodimer). In the case of $\beta_A\beta_B$ heterodimers, agents that inhibit "activin A" are agents that specifically inhibit one or more activities of the $\beta_A$ subunit, but do not inhibit the activity of the non-$\beta_A$ subunit of the complex (e.g., the $\beta_B$ subunit of the complex). This principle applies also to agents that bind to and/or inhibit "activin B", "activin C", and "activin E". Agents disclosed herein that antagonize "activin AB", "activin AC", "activin AE", "activin BC", or "activin BE" are agents that inhibit one or more activities as mediated by the $\beta_A$ subunit and one or more activities as mediated by the $\beta_B$ subunit. The same principle applies to agents that bind to and/or inhibit "activin AC", "activin AE", "activin BC", or "activin BE".

Nodal proteins have functions in mesoderm and endoderm induction and formation, as well as subsequent organization of axial structures such as heart and stomach in early embryogenesis. It has been demonstrated that dorsal tissue in a developing vertebrate embryo contributes predominantly to the axial structures of the notochord and pre-chordal plate while it recruits surrounding cells to form non-axial embryonic structures. Nodal appears to signal through both type I and type II receptors and intracellular effectors known as SMAD proteins. Studies support the idea that ActRIIA and ActRIIB serve as type II receptors for nodal. See, e.g., Sakuma et al. (2002) Genes Cells. 2002, 7:401-12. It is suggested that Nodal ligands interact with their co-factors (e.g., Cripto or Cryptic) to activate activin type I and type II receptors, which phosphorylate SMAD2. Nodal proteins are implicated in many events critical to the early vertebrate embryo, including mesoderm formation, anterior patterning, and left-right axis specification. Experimental evidence has demonstrated that nodal signaling activates pAR3-Lux, a luciferase reporter previously shown to respond specifically to activin and TGF-beta. However, nodal is unable to induce pTlx2-Lux, a reporter specifically responsive to bone morphogenetic proteins. Recent results provide direct biochemical evidence that nodal signaling is mediated by SMAD2 and SMAD3, which also mediate signaling by TGF-betas and activins. Further evidence has shown that the extracellular protein Cripto or Cryptic is required for nodal signaling, making it distinct from activin or TGF-beta signaling.

The BMPs and GDFs together form a family of cysteine-knot cytokines sharing the characteristic fold of the TGF-beta superfamily. See, e.g., Rider et al. (2010) Biochem J., 429(1):1-12. This family includes, for example, BMP2, BMP4, BMP6, BMP7, BMP2a, BMP3, BMP3b (also known as GDF10), BMP4, BMP5, BMP6, BMP7, BMP8, BMP8a, BMP8b, BMP9 (also known as GDF2), BMP10, BMP11 (also known as GDF11), BMP12 (also known as GDF7), BMP13 (also known as GDF6), BMP14 (also known as GDF5), BMP15, GDF1, GDF3 (also known as VGR2), GDF8 (also known as myostatin), GDF9, GDF15, and decapentaplegic. Besides the ability to induce bone formation, which gave the BMPs their name, the BMP/GDFs display morphogenetic activities in the development of a wide range of tissues. BMP/GDF homo- and hetero-dimers interact with combinations of type I and type II receptor dimers to produce multiple possible signaling complexes, leading to the activation of one of two competing sets of SMAD transcription factors. BMP/GDFs have highly specific and localized functions. These are regulated in a number of ways, including the developmental restriction of BMP/GDF expression and through the secretion of several specific BMP antagonist proteins that bind with high affinity to the cytokines. Curiously, a number of these antagonists resemble TGF-beta superfamily ligands.

Growth and differentiation factor-8 (GDF8) is also known as myostatin. GDF8 is a negative regulator of skeletal muscle mass and is highly expressed in developing and adult skeletal muscle. The GDF8 null mutation in transgenic mice is characterized by a marked hypertrophy and hyperplasia of skeletal muscle. See, e.g., McPherron et al., Nature (1997) 387:83-90. Similar increases in skeletal muscle mass are evident in naturally occurring mutations of GDF8 in cattle and, strikingly, in humans. See, e.g., Ashmore et al. (1974) Growth, 38:501-507; Swatland and Kieffer, J. Anim. Sci. (1994) 38:752-757; McPherron and Lee, Proc. Natl. Acad. Sci. USA (1997) 94:12457-12461; Kambadur et al., Genome Res. (1997) 7:910-915; and Schuelke et al. (2004) N Engl J Med, 350:2682-8. Studies have also shown that muscle wasting associated with HIV-infection in humans is accompanied by increases in GDF8 protein expression. See, e.g., Gonzalez-Cadavid et al., PNAS (1998) 95:14938-43. In addition, GDF8 can modulate the production of muscle-specific enzymes (e.g., creatine kinase) and modulate myoblast cell proliferation. See, e.g., International Patent Application Publication No. WO 00/43781). The GDF8 propeptide can noncovalently bind to the mature GDF8 domain dimer, inactivating its biological activity. See, e.g., Miyazono et al. (1988) J. Biol. Chem., 263: 6407-6415; Wakefield et al. (1988) J. Biol. Chem., 263; 7646-7654; and Brown et al. (1990) Growth Factors, 3: 35-43. Other proteins which bind to GDF8 or structurally related proteins and inhibit their biological activity include follistatin, and potentially, follistatin-related proteins. See, e.g., Gamer et al. (1999) Dev. Biol., 208: 222-232.

GDF11, also known as BMP11, is a secreted protein that is expressed in the tail bud, limb bud, maxillary and mandibular arches, and dorsal root ganglia during mouse development. See, e.g., McPherron et al. (1999) Nat. Genet., 22: 260-264; and Nakashima et al. (1999) Mech. Dev., 80: 185-189. GDF11 plays a unique role in patterning both mesodermal and neural tissues. See, e.g., Gamer et al. (1999) Dev Biol., 208:222-32. GDF11 was shown to be a negative regulator of chondrogenesis and myogenesis in developing chick limb. See, e.g., Gamer et al. (2001) Dev Biol., 229:407-20. The expression of GDF11 in muscle also suggests its role in regulating muscle growth in a similar way to GDF8. In addition, the expression of GDF11 in brain suggests that GDF11 may also possess activities that relate to the function of the nervous system. Interestingly, GDF11 was found to inhibit neurogenesis in the olfactory epithelium. See, e.g., Wu et al. (2003) Neuron., 37:197-207. Hence, GDF11 may have in vitro and in vivo applications in the treatment of diseases such as muscle diseases and neurodegenerative diseases (e.g., amyotrophic lateral sclerosis).

BMP7, also called osteogenic protein-1 (OP-1), is well known to induce cartilage and bone formation. In addition, BMP7 regulates a wide array of physiological processes. For example, BMP7 may be the osteoinductive factor responsible for the phenomenon of epithelial osteogenesis. It is also found that BMP7 plays a role in calcium regulation and bone homeostasis. Like activin, BMP7 binds to type II receptors, ActRIIA and ActRIIB However, BMP7 and activin recruit distinct type I receptors into heteromeric receptor complexes. The major BMP7 type I receptor observed was ALK2, while activin bound exclusively to ALK4 (ActRIIB) BMP7 and activin elicited distinct biological responses and activated different SMAD pathways. See, e.g., Macias-Silva et al. (1998) J Biol Chem. 273:25628-36.

Anti-Mullerian hormone (AMH), also known as Mullerian-inhibiting substance (MIS), is a TGF-beta family glycoprotein. One AMH-associated type II receptor has been identified and is designated as AMHRII, or alternatively MISRII. AMH induces regression of the Mullerian ducts in the human male embryo. AMH is expressed in reproductive age women and does not fluctuate with cycle or pregnancy, but was found to gradual decrease as both oocyte quantity and quality decrease, suggesting AMH could serve as a biomarker for ovarian physiology. See e.g. Zec et al., (2011) Biochemia Medica 21(3): 219-30.

Activin receptor-like kinase-1 (ALK1), the product of the ACVRL1 gene known alternatively as ACVRLK1, is a type I receptor whose expression is predominantly restricted to endothelial cells. See, e.g., OMIM entry 601284. ALK1 is activated by the binding of TGF-beta family ligands such as BMP9 and BMP10, and ALK1 signaling is critical in the regulation of both developmental and pathological blood vessel formation. ALK1 expression overlaps with sites of vasculogenesis and angiogenesis in early mouse development, and ALK1 knockout mice die around embryonic day 11.5 because of severe vascular abnormalities (see e.g., Cunha and Pietras (2011) Blood 117(26):6999-7006.) ALK1 expression has also been described in other cell types such as hepatic stellate cells and chondrocytes. Additionally, ALK1 along with activin receptor-like kinase-2 (ALK2) have been found to be important for BMP9-induced osteogenic signaling in mesenchymal stem cells. See e.g., Cunha and Pietras (2011) Blood 117(26):6999-7006.

ALK2, the product of the ACVR1 gene known alternatively as ActRIA or ACVRLK2, is a type I receptor that has been shown to bind activins and BMPs. ALK2 is critical for embryogenesis as ALK2 knockout mice die soon after gastrulation. See, e.g., Mishina et al. (1999) Dev Biol. 213: 314-326 and OMIM entry 102576. Constitutively active mutations in ALK2 are associated with fibrodysplasia ossificans progressiva (FOP). FOP is rare genetic disorder that causes fibrous tissue, including muscle, tendon and ligament, to be ossified spontaneously or when damaged. An arginine to histidine mutation in codon 206 of ALK2 is naturally occurring mutation associated with FOP in humans. This mutation induces BMP-specific signaling via ALK2 without the binding of ligand. See, e.g., Fukuda et al., (2009) J Biol Chem. 284(11):7149-7156 and Kaplan et al., (2011) Ann N.Y. Acad Sci. 1237: 5-10.

Activin receptor-like kinase-3 (ALK3), the product of the BMPR1A gene known alternatively as ACVRLK3, is a type I receptor mediating effects of multiple ligands in the BMP family. Unlike several type I receptors with ubiquitous tissue expression, ALK3 displays a restricted pattern of expression consistent with more specialized functionality. See, e.g., ten Dijke (1993) Oncogene, 8: 2879-2887 and OMIM entry 601299. ALK3 is generally recognized as a high affinity receptor for BMP2, BMP4, BMP7 and other members of the BMP family. BMP2 and BMP7 are potent stimulators of osteoblastic differentiation, and are now used clinically to induce bone formation in spine fusions and certain non-union fractures. ALK3 is regarded as a key receptor in mediating BMP2 and BMP4 signaling in osteoblasts. See, e.g., Lavery et al. (2008) J. Biol. Chem. 283: 20948-20958. A homozygous ALK3 knockout mouse dies early in embryogenesis (~day 9.5), however, adult mice carrying a conditional disruption of ALK3 in osteoblasts have been recently reported to exhibit increased bone mass, although the newly formed bone showed evidence of disorganization. See, e.g., Kamiya (2008) J. Bone Miner. Res., 23:2007-2017; and Kamiya (2008) Development 135: 3801-3811. This finding is in startling contrast to the effectiveness of BMP2 and BMP7 (ligands for ALK3) as bone building agents in clinical use.

Activin receptor-like kinase-4 (ALK4), the product of the ACVR1B gene alternatively known as ACVRLK4, is a type I receptor that transduces signaling for a number of TGF-beta family ligands including activins, nodal and GDFs. ALK4 mutations are associated with pancreatic cancer and expression of dominant negative truncated ALK4 isoforms are highly expressed in human pituitary tumors. See, e.g., Tsuchida et al., (2008) Endocrine Journal 55(1):11-21 and OMIM entry 601300.

Activin receptor-like kinase-5 (ALK5), the product of the TGFBR1 gene, is widely expressed in most cell types. Several TGF-beta superfamily ligands, including TGF-betas, activin, and GDF-8, signal via ALK5 and activate downstream Smad 2 and Smad 3. Mice deficient in ALK5 exhibit severe defects in the vascular development of the yolk sac and placenta, lack circulating red blood cells, and die mid-gestation. It was found that these embryos had normal hematopoietic potential, but enhanced proliferation and improper migration of endothelial cells. Thus, ALK5-dependent signaling is important for angiogenesis, but not for the development of hematopoietic progenitor cells and functional hematopoiesis. See, e.g. Larsson et al., (2001) The EMBO Journal, 20(7): 1663-1673 and OMIM entry 190181. In endothelial cells, ALK5 acts cooperatively and opposite to ALK1 signaling. ALK5 inhibits cell migration and proliferation, notably the opposite effect of ALK1. See, e.g., Goumans et al. (2003) Mol Cell 12(4): 817-828. Additionally, ALK5 is believed to negatively regulate muscle growth. Knockdown of ALK5 in the muscle a mouse model of muscular dystrophy was found to decrease fibrosis and increase expression of genes associate with muscle growth. See, e.g. Kemaladewi et al., (2014) Mol Ther Nucleic Acids 3, e156.

Activin receptor-like kinase-6 (ALK6) is the product of the BMPR1B gene, whose deficiency is associated with chrondodysplasia and limb defects in both humans and mice. See, e.g., Demirhan et al., (2005) J Med Genet. 42:314-317. ALK6 is widely expressed throughout the developing skeleton, and is required for chondrogenesis in mice. See, e.g., Yi et al., (2000) Development 127:621-630 and OMIM entry 603248.

Activin receptor-like kinase-7 (ALK7) is the product of the ACVR1C gene. ALK7 null mice are viable, fertile, and display no skeletal or limb malformations. GDF3 signaling through ALK7 appears to play a role in insulin sensitivity and obesity. This is supported by results that Alk7 null mice show reduced fat accumulation and resistance to diet-induced obesity. See, e.g., Andersson et al., (2008) PNAS 105(20): 7252-7256. ALK7-mediated Nodal signaling has been implicated to have both tumor promoting and tumor suppressing effects in a variety of different cancer cell lines. See, e.g., De Silva et al., (2012) Frontiers in Endocrinology 3:59 and OMIM entry 608981.

As used herein the term "ActRII" refers to the family of type II activin receptors. This family includes both the activin receptor type IIA (ActRIIA), encoded by the ACVR2A gene, and the activin receptor type IIB (ActRIIB), encoded by the ACVR2B gene. ActRII receptors are TGF-beta superfamily type II receptors that bind a variety of TGF-beta superfamily ligands including activins, GDF8 (myostatin), GDF11, and a subset of BMPs, notably BMP6 and BMP7. ActRII receptors are implicated in a variety of biological disorders including muscle and neuromuscular disorders (e.g., muscular dystrophy, amyotrophic lateral sclerosis (ALS), and muscle atrophy), undesired bone/cartilage growth, adipose tissue disorders (e.g., obesity), metabolic disorders (e.g., type 2 diabetes), and neurodegenerative disorders. See, e.g., Tsuchida et al., (2008) Endocrine Journal 55(1):11-21, Knopf et al., U.S. Pat. No. 8,252,900, and OMIM entries 102581 and 602730.

Transforming growth factor beta receptor II (TGFBRII), encoded by the TGFBR2 gene, is a type II receptor that is known to bind TGF-beta ligands and activate downstream Smad 2 and Smad 3 effectors. See, e.g., Hinck (2012) FEBS Letters 586: 1860-1870 and OMIM entry 190182. TGF-beta signaling through TGFBRII is critical in T-cell proliferation, maintenance of T regulatory cells and proliferation of pre-cartilaginous stem cells. See, e.g., Li et al., (2006) Immunity 25(3): 455-471 and Cheng et al., Int. J. Mol. Sci. 2014, 15, 12665-12676.

Bone morphogenetic protein receptor II (BMPRII), encoded by the BMPR2 gene, is a type II receptor that is thought to bind certain BMP ligands. In some instances, efficient ligand binding to BMPRII is dependent on the presence of the appropriate TGFBR type I receptors. See, e.g., Rosenzweig et al., (1995) PNAS 92:7632-7636. Mutations in BMPRII are associated pulmonary hypertension in humans. See OMIM entry 600799.

Müllerian-inhibiting substance receptor II (MISRII), the product of the AMHR2 gene known alternatively as anti-Müllerian hormone type II receptor, is a type II TGF-beta receptor. MISRII binds the MIS ligand, but requires the presence of an appropriate type I receptor, such as ALK3 or ALK6, for signal transduction. See, e.g., Hinck (2012) FEBS Letters 586:1860-1870 and OMIM entry 600956. MISRII is involved in sex differentiation in humans and is required for Müllerian regression in the human male. AMH is expressed in reproductive age women and does not fluctuate with cycle or pregnancy, but was found to gradual decrease as both oocyte quantity and quality decrease, suggesting AMH could serve as a biomarker of ovarian physiology. See, e.g., Zec et al., (2011) Biochemia Medica 21(3): 219-30 and OMIM entry 600956.

In certain aspects, the present disclosure relates to the use of a) heteromultimer complexes comprising an extracellular domain of a TGFβ superfamily type I receptor polypeptide (e.g., ALK1, ALK2, ALK3, ALK4, ALK5, ALK6, and ALK7) and an extracellular domain of a TGFβ superfamily type II receptor polypeptide (e.g., ActRIIA, ActRIIB, TGF-BRII, BMPRII, and MISRII) b) heteromultimer complexes comprising an extracellular domain of at least two TGFβ superfamily type I receptor polypeptide (e.g., ALK1, ALK2, ALK3, ALK4, ALK5, ALK6, and ALK7), and heteromultimer complexes comprising an extracellular domain of at least two TGFβ superfamily type II receptor polypeptide (e.g., ActRIIA, ActRIIB, TGFBRII, BMPRII, and MISRII), preferably soluble heteromultimer complexes, to antagonize intracellular signaling transduction (e.g., Smad 2/3 and/or Smad 1/5/8 signaling) initiated by one or more TGFβ superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, Müllerian-inhibiting substance (MIS), and Lefty). As described herein, such antagonist heteromultimer complexes may be useful in the treatment or prevention of various disorders/conditions associated with, e.g., muscle loss, insufficient muscle growth, neurodegeneration, bone loss, reduced bone density and/or mineralization, insufficient bone growth, metabolic disorders such as obesity and red blood cell disorders such as anemia.

In particular, the data of the present disclosure demonstrates that heteromultimer complexes comprising an extracellular domain of a TGFβ superfamily type I receptor polypeptide and an extracellular domain of a TGFβ superfamily type II receptor polypeptide have different ligand binding specificities/profiles in comparison to their corresponding homomultimer complexes.

The terms used in this specification generally have their ordinary meanings in the art, within the context of this disclosure and in the specific context where each term is used. Certain terms are discussed below or elsewhere in the specification to provide additional guidance to the practitioner in describing the compositions and methods of the disclosure and how to make and use them. The scope or meaning of any use of a term will be apparent from the specific context in which it is used.

The terms "heteromer" or "heteromultimer" is a complex comprising at least a first polypeptide and a second polypeptide, wherein the second polypeptide differs in amino acid sequence from the first polypeptide by at least one amino acid residue. The heteromer can comprise a "heterodimer" formed by the first and second polypeptide or can form higher order structures where polypeptides in addition to the first and second polypeptide are present. Exemplary structures for the heteromultimer include heterodimers, heterotrimers, heterotetramers and further oligomeric structures. Heterodimers are designated herein as X:Y or equivalently as X-Y, where X represents a first polypeptide and Y represents a second polypeptide. Higher-order heteromers and oligomeric structures are designated herein in a corresponding manner. In certain embodiments a heteromultimer is recombinant (e.g., one or more polypeptide components may be a recombinant protein), isolated and/or purified.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. However, in common usage and in the instant application, the term "homologous," when modified with an adverb such as "highly," may refer to sequence similarity and may or may not relate to a common evolutionary origin.

The term "sequence similarity," in all its grammatical forms, refers to the degree of identity or correspondence between nucleic acid or amino acid sequences that may or may not share a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

As used herein, unless otherwise stated, "does not substantially bind to X" is intended to mean that an agent has a $K_D$ that is greater than about $10^{-7}$, $10^{-6}$, $10^{-5}$, $10^{-4}$, or greater (e.g., no detectable binding by the assay used to determine the $K_D$) for "X", wherein "X" is a specified agent such as protein or nucleic acid.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers.

2. TGF-Beta Superfamily Type I Receptor and Type II Receptor Complexes

In certain aspects, the present disclosure relates to heteromultimer complexes comprising one or more TGF-beta superfamily type I receptor polypeptides (e.g., ALK1, ALK2, ALK3, ALK4, ALK5, ALK6, and ALK7 proteins from humans or other species such as those described herein, e.g., SEQ ID NOs: 14, 15, 124, 126, 171, 172, 413, 414, 463, 464, 18, 19, 136, 138, 173, 174, 421, 422, 465, 466, 22, 23, 115, 117, 175, 176, 407, 408, 467, 468, 26, 27, 83, 84, 104, 106, 177, 178, 403, 404, 469, 470, 30, 31, 87, 88, 139, 141, 179, 180, 423, 424, 471, 472, 34, 35, 91, 92, 142, 144, 181, 182, 425, 426, 473, 474, 38, 39, 301, 302, 305, 306, 309, 310, 313, 112, 114, 183, 184, 405, 406, 475, and 476) and one or more TGF-beta superfamily type II receptor polypeptides (e.g., ActRIIA, ActRIIB, TGFBRII, BMPRII, and MISRII proteins from humans or other species such as those described herein, e.g., SEQ ID NOs: 9, 10, 11, 118, 120, 151, 152, 409, 410, 451, 452, 1, 2, 3, 4, 5, 6, 100, 102, 153, 154, 401, 402, 453, 454, 46, 47, 71, 72, 121, 123, 155, 156, 411, 412, 455, 456, 50, 51, 75, 76, 79, 80, 133, 135, 161, 162, 419, 420, 457, 458, 42, 43, 67, 68, 127, 129, 130, 132, 157, 158, 159, 160, 415, 416, 417, 418, 459, 460, 461, and 462); heteromultimer complexes comprising at least two different TGF-beta superfamily type I receptor polypeptides (e.g., ALK1, ALK2, ALK3, ALK4, ALK5, ALK6, and ALK7 proteins from humans or other species such as those described herein, e.g., SEQ ID NOs: 14, 15, 124, 126, 171, 172, 413, 414, 463, 464, 18, 19, 136, 138, 173, 174, 421, 422, 465, 466, 22, 23, 115, 117, 175, 176, 407, 408, 467, 468, 26, 27, 83, 84, 104, 106, 177, 178, 403, 404, 469, 470, 30, 31, 87, 88, 139, 141, 179, 180, 423, 424, 471, 472, 34, 35, 91, 92, 142, 144, 181, 182, 425, 426, 473, 474, 38, 39, 301, 302, 305, 306, 309, 310, 313, 112, 114, 183, 184, 405, 406, 475, and 476); and heteromultimer complexes comprising at least two different TGF-beta superfamily type II receptor polypeptides (e.g., ActRIIA, ActRIIB, TGFBRII, BMPRII, and MISRII proteins from humans or other species such as those described herein, e.g., SEQ ID NOs: 9, 10, 11, 118, 120, 151, 152, 409, 410, 451, 452, 1, 2, 3, 4, 5, 6, 100, 102, 153, 154, 401, 402, 453, 454, 46, 47, 71, 72, 121, 123, 155, 156, 411, 412, 455, 456, 50, 51, 75, 76, 79, 80, 133, 135, 161, 162, 419, 420, 457, 458, 42, 43, 67, 68, 127, 129, 130, 132, 157, 158, 159, 160, 415, 416, 417, 418, 459, 460, 461, and 462), which are generally referred to herein as "heteromultimer complexes" or "heteromultimers". Preferably, heteromultimers are soluble, e.g., a heteromultimer comprises a soluble portion of at least one TGFβ superfamily type I receptor polypeptide and a soluble portion (domain) of at least one TGFβ superfamily type II receptor polypeptide. In general, the extracellular domains of TGFβ superfamily type I and type II receptors correspond to a soluble portion of the type I and type II receptor. Therefore, in some embodiments, heteromultimers of the disclosure comprise an extracellular domain of a TGFβ superfamily type I receptor polypeptide (e.g., one or more ALK1, ALK2, ALK3, ALK4, ALK5, ALK6, and/or ALK7 receptor extracellular domains) and/or an extracellular domain of a TGFβ superfamily type II receptor polypeptide (e.g., one or more ActRIIA, ActRIIB, TGFBRII, BMPRII, and/or MISRII receptor extracellular domains). Exemplary extracellular domains of ALK1, ALK2, ALK3, ALK4, ALK5, ALK6, ALK7, ActRIIA, ActRIIB, TGFBRII, BMPRII, and MISRII are disclosed herein and such sequences, as well as fragments, functional variants, and modified forms thereof, may be used in accordance with the inventions of the present disclosure (e.g., heteromultimers compositions and uses thereof). Heteromultimers of the disclosure include, e.g., heterodimers, heterotrimers, heterotetramers, and higher order oligomeric structures. See, e.g., FIGS. 1, 2, and 15-17. In certain preferred embodiments, heteromultimers of the disclosure are heterodimers.

A defining structural motif known as a three-finger toxin fold is important for ligand binding by type I and type II receptors and is formed by 10, 12, or 14 conserved cysteine residues located at varying positions within the extracellular domain of each monomeric receptor. See, e.g., Greenwald et al. (1999) Nat Struct Biol 6:18-22; Hinck (2012) FEBS Lett 586:1860-1870. The core ligand-binding domains of TGFβ superfamily receptors, as demarcated by the outermost of these conserved cysteines, corresponds to positions 29-109 of SEQ ID NO: 1 (ActRIIB precursor); positions 30-110 of SEQ ID NO: 9 (ActRIIA precursor); positions 34-95 of SEQ ID NO: 14 (ALK1 precursor); positions 35-99 of SEQ ID NO: 18 (ALK2 precursor); positions 61-130 of SEQ ID NO: 22 (ALK3 precursor); positions 34-101 of SEQ ID NOs: 26 and 83 (ALK4 precursors); positions 36-106 of SEQ ID NOs: 30 and 87 (ALK5 precursors); positions 32-102 of SEQ ID NO: 34 (ALK6 isoform B precursor); positions 28-92 of SEQ ID NOs: 38, 305, and 309 (ALK7 precursors); positions 51-143 of SEQ ID NO: 42 (TGFBRII isoform B precursor); positions 34-123 of SEQ ID NO: 46 and 71 (BMPRII precursors); positions 24-116 of SEQ ID NO: 50, 75, and 79 (MISRII precursors); positions 44-168 of SEQ ID NO: 67 (TGFBRII isoform A precursor); and positions 62-132 of SEQ ID NO: 91 (ALK6 isoform A precursor). The structurally less-ordered amino acids flanking these cysteine-demarcated core sequences can be truncated by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 residues on either terminus without necessarily altering ligand binding. Exemplary extracellular domains for N-terminal and/or C-terminal truncation include SEQ ID NOs: 2, 3, 5, 6, 10, 11, 15, 19, 23, 27, 31, 35, 39, 43, 47, 51, 68, 72, 76, 80, 84, 88, 92, 302, 306, 310, and 313.

In preferred embodiments, heteromultimers of the disclosure bind to and/or inhibit (antagonize) activity of one or more TGF-beta superfamily ligands including, but not limited to, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty. In particular, heteromultimer complexes of the disclosure may be used to antagonize signaling transduction (e.g., Smad 2/3 and/or Smad 1/5/8 signaling) initiated by one or more TGFβ superfamily ligands, which may be determined, for example, using a cell-based assay such as those described herein. As described herein, such antagonist heteromultimer complexes may be useful in the treatment or prevention of various disorders/conditions associated with, e.g., muscle loss, insufficient muscle growth, neurodegeneration, bone loss, reduced bone density and/or mineralization, insufficient bone growth, and/or obesity. In some embodiments, heteromultimer complexes of the disclosure have different ligand binding specificities/profiles in comparison to their corresponding homomultimer complex (e.g., an ALK4:ActRIIB heterodimer vs. a corresponding ActRIIB or ALK4 homodimer).

As used herein, the term "ActRIIB" refers to a family of activin receptor type IIB (ActRIIB) proteins from any species and variants derived from such ActRIIB proteins by mutagenesis or other modification. Reference to ActRIIB herein is understood to be a reference to any one of the currently identified forms. Members of the ActRIIB family are generally transmembrane proteins, composed of a ligand-binding extracellular domain comprising a cysteine-rich region, a transmembrane domain, and a cytoplasmic domain with predicted serine/threonine kinase activity.

The term "ActRIIB polypeptide" includes polypeptides comprising any naturally occurring polypeptide of an ActRIIB family member as well as any variants thereof (including mutants, fragments, fusions, and peptidomimetic forms) that retain a useful activity. Examples of such variant ActRIIB polypeptides are provided throughout the present disclosure as well as in International Patent Application Publication Nos. WO 2006/012627, WO 2008/097541, and Wo 2010/151426, which are incorporated herein by reference in their entirety. Numbering of amino acids for all ActRIIB-related polypeptides described herein is based on the numbering of the human ActRIIB precursor protein sequence provided below (SEQ ID NO: 1), unless specifically designated otherwise.

The human ActRIIB precursor protein sequence is as follows:

(SEQ ID NO: 1)

```
  1 MTAPWVALAL LWGSLCAGSG RGEAETRECI YYNANWELER TNQSGLERCE

51 GEQDKRLHCY ASWRNSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA
```

```
251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI
```

The signal peptide is indicated with a single underline; the extracellular domain is indicated in bold font; and the potential, endogenous N-linked glycosylation sites are indicated with a double underline.

The processed (mature) extracellular ActRIIB polypeptide sequence is as follows:

(SEQ ID NO: 2)
GRGEAETRECIYYNANWELERTNQSGLERCEGEQDKRLHCYASWRNSSGT
IELVKKGCWLDDFNCYDRQECVATEENPQVYFCCCEGNFCNERFTHLPEA
GGPEVTYEPPPTAPT.

In some embodiments, the protein may be produced with an "SGR . . . " sequence at the N-terminus. The C-terminal "tail" of the extracellular domain is indicated by a single underline. The sequence with the "tail" deleted (a Δ15 sequence) is as follows:

(SEQ ID NO: 3)
BGRGEAETRECIYYNANWELERTNQSGLERCEGEQDKRLHCYASWRNSSG
TIELVKKGCWLDDFNCYDRQECVATEENPQVYFCCCEGNFCNERFTHLP
EA.

A form of ActRIIB with an alanine at position 64 of SEQ ID NO: 1 (A64) is also reported in the literature. See, e.g., Hilden et al. (1994) Blood, 83(8): 2163-2170. Applicants have ascertained that an ActRIIB-Fc fusion protein comprising an extracellular domain of ActRIIB with the A64 substitution has a relatively low affinity for activin and GDF11. By contrast, the same ActRIIB-Fc fusion protein with an arginine at position 64 (R64) has an affinity for activin and GDF11 in the low nanomolar to high picomolar range. Therefore, sequences with an R64 are used as the "wild-type" reference sequence for human ActRIIB in this disclosure.

The form of ActRIIB with an alanine at position 64 is as follows:

(SEQ ID NO: 4)
```
  1 MTAPWVALAL LWGSLCAGSG RGEAETRECI YYNANWELER TNQSGLERCE

51 GEQDKRLHCY ASWANSSGTI ELVKKGCWLD DFNCYDRQEC VATEENPQVY

101 FCCCEGNFCN ERFTHLPEAG GPEVTYEPPP TAPTLLTVLA YSLLPIGGLS

151 LIVLLAFWMY RHRKPPYGHV DIHEDPGPPP PSPLVGLKPL QLLEIKARGR

201 FGCVWKAQLM NDFVAVKIFP LQDKQSWQSE REIFSTPGMK HENLLQFIAA

251 EKRGSNLEVE LWLITAFHDK GSLTDYLKGN IITWNELCHV AETMSRGLSY

301 LHEDVPWCRG EGHKPSIAHR DFKSKNVLLK SDLTAVLADF GLAVRFEPGK

351 PPGDTHGQVG TRRYMAPEVL EGAINFQRDA FLRIDMYAMG LVLWELVSRC

401 KAADGPVDEY MLPFEEEIGQ HPSLEELQEV VVHKKMRPTI KDHWLKHPGL

451 AQLCVTIEEC WDHDAEARLS AGCVEERVSL IRRSVNGTTS DCLVSLVTSV

501 TNVDLPPKES SI
```

The signal peptide is indicated by single underline and the extracellular domain is indicated by bold font.

The processed (mature) extracellular ActRIIB polypeptide sequence of the alternative A64 form is as follows:

(SEQ ID NO: 5)
GRGEAETRECIYYNANWELERTNQSGLERCEGEQDKRLHCYASWANSSGT
IELVKKGCWLDDFNCYDRQECVATEENPQVYFCCCEGNFCNERFTHLPEA
GGPEVTYEPPPTAPT

In some embodiments, the protein may be produced with an "SGR . . . " sequence at the N-terminus. The C-terminal "tail" of the extracellular domain is indicated by single underline. The sequence with the "tail" deleted (a Δ15 sequence) is as follows:

(SEQ ID NO: 6)
GRGEAETRECIYYNANWELERTNQSGLERCEGEQDKRLHCYASWANSSGT
IELVKKGCWLDDFNCYDRQECVATEENPQVYFCCCEGNFCNERFTHLPEA

A nucleic acid sequence encoding the human ActRIIB precursor protein is shown below (SEQ ID NO: 7), representing nucleotides 25-1560 of Genbank Reference Sequence NM_001106.3, which encode amino acids 1-513 of the ActRIIB precursor. The sequence as shown provides an arginine at position 64 and may be modified to provide an alanine instead. The signal sequence is underlined.

(SEQ ID NO: 7)
```
   1 ATGACGGCGC CCTGGGTGGC CCTCGCCCTC CTCTGGGGAT CGCTGTGCGC

51 CGGCTCTGGG CGTGGGGAGG CTGAGACACG GGAGTGCATC TACTACAACG

101 CCAACTGGGA GCTGGAGCGC ACCAACCAGA GCGGCCTGGA GCGCTGCGAA

151 GGCGAGCAGG ACAAGCGGCT GCACTGCTAC GCCTCCTGGC GCAACAGCTC

201 TGGCACCATC GAGCTCGTGA AGAAGGGCTG CTGGCTAGAT GACTTCAACT

251 GCTACGATAG GCAGGAGTGT GTGGCCACTG AGGAGAACCC CCAGGTGTAC

301 TTCTGCTGCT GTGAAGGCAA CTTCTGCAAC GAACGCTTCA CTCATTTGCC

351 AGAGGCTGGG GGCCCGGAAG TCACGTACGA GCCACCCCCG ACAGCCCCCA

401 CCCTGCTCAC GGTGCTGGCC TACTCACTGC TGCCCATCGG GGGCCTTTCC

451 CTCATCGTCC TGCTGGCCTT TTGGATGTAC CGGCATCGCA AGCCCCCCTA

501 CGGTCATGTG GACATCCATG AGGACCCTGG GCCTCCACCA CCATCCCCTC

551 TGGTGGGCCT GAAGCCACTG CAGCTGCTGG AGATCAAGGC TCGGGGGCGC

601 TTTGGCTGTG TCTGGAAGGC CCAGCTCATG AATGACTTTG TAGCTGTCAA

651 GATCTTCCCA CTCCAGGACA AGCAGTCGTG GCAGAGTGAA CGGGAGATCT

701 TCAGCACACC TGGCATGAAG CACGAGAACC TGCTACAGTT CATTGCTGCC

751 GAGAAGCGAG GCTCCAACCT CGAAGTAGAG CTGTGGCTCA TCACGGCCTT

801 CCATGACAAG GGCTCCCTCA CGGATTACCT CAAGGGGAAC ATCATCACAT

851 GGAACGAACT GTGTCATGTA GCAGAGACGA TGTCACGAGG CCTCTCATAC

901 CTGCATGAGG ATGTGCCCTG GTGCCGTGGC GAGGGCCACA AGCCGTCTAT

951 TGCCCACAGG GACTTTAAAA GTAAGAATGT ATTGCTGAAG AGCGACCTCA

1001 CAGCCGTGCT GGCTGACTTT GGCTTGGCTG TTCGATTTGA GCCAGGGAAA

1051 CCTCCAGGGG ACACCCACGG ACAGGTAGGC ACGAGACGGT ACATGGCTCC

1101 TGAGGTGCTC GAGGGAGCCA TCAACTTCCA GAGAGATGCC TTCCTGCGCA

1151 TTGACATGTA TGCCATGGGG TTGGTGCTGT GGGAGCTTGT GTCTCGCTGC

1201 AAGGCTGCAG ACGGACCCGT GGATGAGTAC ATGCTGCCCT TTGAGGAAGA

1251 GATTGGCCAG CACCCTTCGT TGGAGGAGCT GCAGGAGGTG GTGGTGCACA

1301 AGAAGATGAG GCCCACCATT AAAGATCACT GGTTGAAACA CCCGGGCCTG

1351 GCCCAGCTTT GTGTGACCAT CGAGGAGTGC TGGGACCATG ATGCAGAGGC

1401 TCGCTTGTCC GCGGGCTGTG TGGAGGAGCG GGTGTCCCTG ATTCGGAGGT

1451 CGGTCAACGG CACTACCTCG GACTGTCTCG TTTCCCTGGT GACCTCTGTC

1501 ACCAATGTGG ACCTGCCCCC TAAAGAGTCA AGCATC
```

A nucleic acid sequence encoding processed extracellular human ActRIIB polypeptide is as follows (SEQ ID NO: 8). The sequence as shown provides an arginine at position 64, and may be modified to provide an alanine instead.

(SEQ ID NO: 8)
```
  1 GGGCGTGGGG AGGCTGAGAC ACGGGAGTGC ATCTACTACA ACGCCAACTG

51 GGAGCTGGAG CGCACCAACC AGAGCGGCCT GGAGCGCTGC GAAGGCGAGC

101 AGGACAAGCG GCTGCACTGC TACGCCTCCT GGCGCAACAG CTCTGGCACC

151 ATCGAGCTCG TGAAGAAGGG CTGCTGGCTA GATGACTTCA ACTGCTACGA

201 TAGGCAGGAG TGTGTGGCCA CTGAGGAGAA CCCCCAGGTG TACTTCTGCT
```

```
251 GCTGTGAAGG CAACTTCTGC AACGAACGCT TCACTCATTT GCCAGAGGCT

301 GGGGGCCCGG AAGTCACGTA CGAGCCACCC CCGACAGCCC CCACC
```

An alignment of the amino acid sequences of human ActRIIB extracellular domain and human ActRIIA extracellular domain are illustrated in FIG. 3. This alignment indicates amino acid residues within both receptors that are believed to directly contact ActRII ligands. For example, the composite ActRII structures indicated that the ActRIIB-ligand binding pocket is defined, in part, by residues Y31, N33, N35, L38 through T41, E47, E50, Q53 through K55, L57, H58, Y60, S62, K74, W78 through N83, Y85, R87, A92, and E94 through F101. At these positions, it is expected that conservative mutations will be tolerated.

Figure 1A:
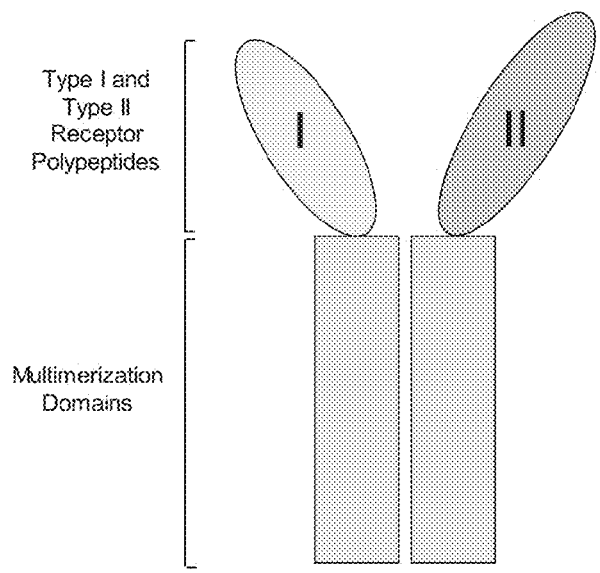
FIGS. 1A and 1B show two schematic examples of heteromeric protein complexes comprising type I receptor and type II receptor polypeptides.
Figure 1B:
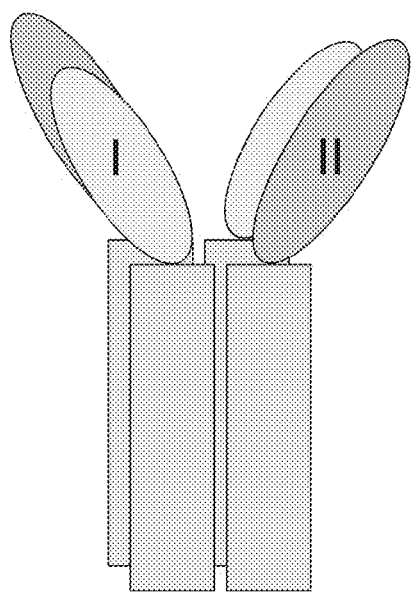
Figure 2:
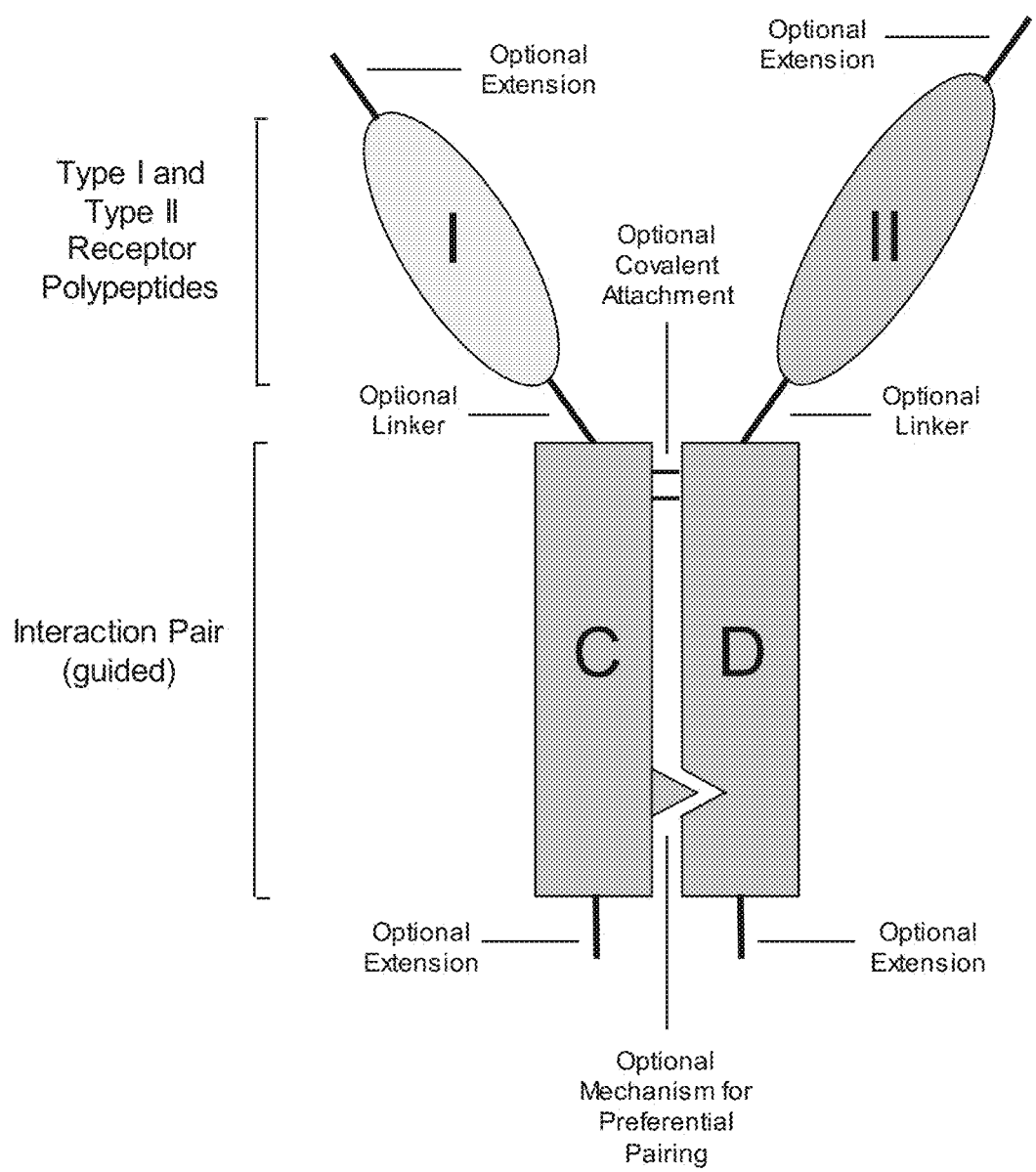
FIG. 2 shows a schematic example of a heteromeric protein complex comprising a type I receptor polypeptide (indicated as "I") (e.g. a polypeptide that is at least 80%, 85%, 90%, 95%, 97%, 98%, 99% or 100% identical to an extracellular domain of an ALK1, ALK2, ALK3, ALK4, ALK5, ALK6 or ALK7 protein from humans or other species such as those described herein, e.g., SEQ ID Nos: 14, 15, 124, 126, 171, 172, 413, 414, 463, 464, 18, 19, 136, 138, 173, 174, 421, 422, 465, 466, 22, 23, 115, 117, 175, 176, 407, 408, 467, 468, 26, 27, 83, 84, 104, 106, 177, 178, 403, 404, 469, 470, 30, 31, 87, 88, 139, 141, 179, 180, 423, 424, 471, 472, 34, 35, 91, 92, 142, 144, 181, 182, 425, 426, 473, 474, 38, 39, 301, 302, 305, 306, 309, 310, 313, 112, 114, 183, 184, 405, 406, 475, and 476) and a type II receptor polypeptide (indicated as "II") (e.g. a polypeptide that is at least 80%, 85%, 90%, 95%, 97%, 98%, 99% or 100% identical to an extracellular domain of an ActRIIA, ActRIIB, MISRII, BMPRII, or TGFBRII protein from humans or other species such as those described herein, e.g., 9, 10, 11, 118, 120, 151, 152, 409, 410, 451, 452, 1, 2, 3, 4, 5, 6, 100, 102, 153, 154, 401, 402, 453, 454, 46, 47, 71, 72, 121, 123, 155, 156, 411, 412, 455, 456, 50, 51, 75, 76, 79, 80, 133, 135, 161, 162, 419, 420, 457, 458, 42, 43, 67, 68, 127, 129, 130, 132, 157, 158, 159, 160, 415, 416, 417, 418, 459, 460, 461, and 462). In the illustrated embodiment, the type I receptor polypeptide is part of a fusion polypeptide that comprises a first member of an interaction pair ("C"), and the type II receptor polypeptide is part of a fusion polypeptide that comprises a second member of an interaction pair ("D"). In each fusion polypeptide, a linker may be positioned between the type I or type II receptor polypeptide and the corresponding member of the interaction pair. The first and second members of the interaction pair (C, D) may be a guided (asymmetric) pair, meaning that the members of the pair associate preferentially with each other rather than self-associate, or the interaction pair may be unguided, meaning that the members of the pair may associate with each other or self-associate without substantial preference and may have the same or different amino acid sequences. Traditional Fc fusion proteins and antibodies are examples of unguided interaction pairs, whereas a variety of engineered Fc domains have been designed as guided (asymmetric) interaction pairs [e.g., Spiess et al (2015) Molecular Immunology 67(2A): 95-106].
Figure 4:
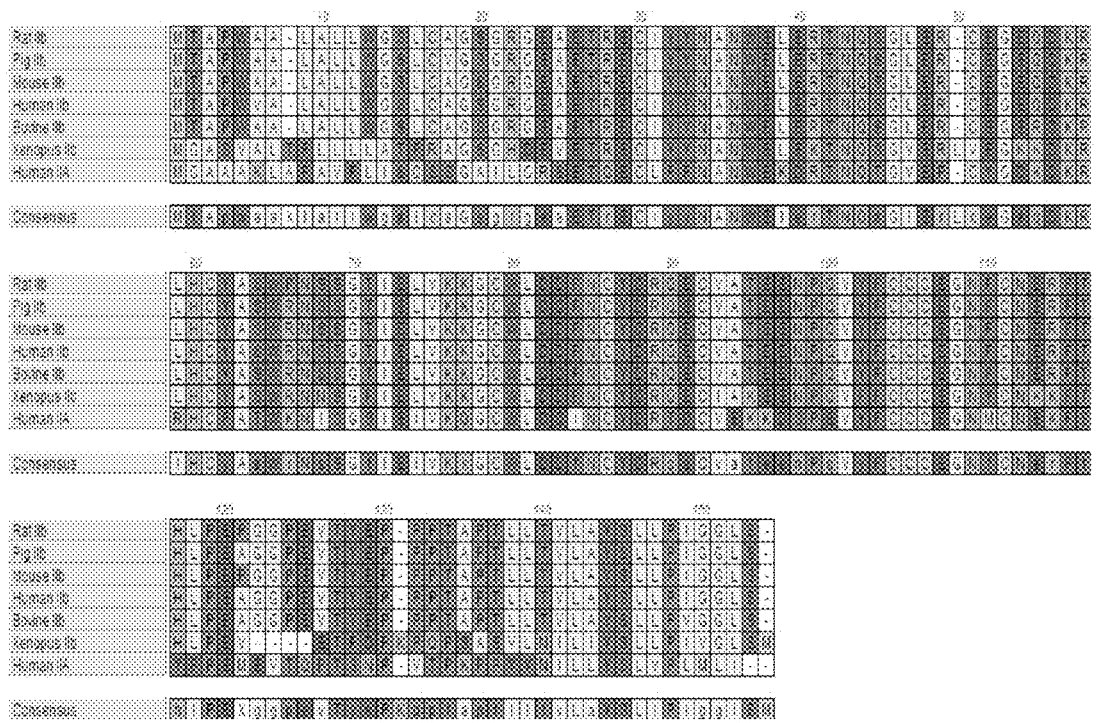
FIG. 4 shows a multiple sequence alignment of various vertebrate ActRIIB precursor proteins without their intracellular domains (SEQ ID NOs: 501, 502, 503, 504, 505, and 506, respectively), human ActRIIA precursor protein without its intracellular domain (SEQ ID NO: 507), and a consensus ActRII precursor protein (SEQ ID NO: 508).

In addition, ActRIIB is well-conserved among vertebrates, with large stretches of the extracellular domain completely conserved. For example, FIG. 4 depicts a multi-sequence alignment of a human ActRIIB extracellular domain compared to various ActRIIB orthologs. Many of the ligands that bind to ActRIIB are also highly conserved. Accordingly, from these alignments, it is possible to predict key amino acid positions within the ligand-binding domain that are important for normal ActRIIB-ligand binding activities as well as to predict amino acid positions that are likely to be tolerant of substitution without significantly altering normal ActRIIB-ligand binding activities. Therefore, an active, human ActRIIB variant polypeptide useful in accordance with the presently disclosed methods may include one or more amino acids at corresponding positions from the sequence of another vertebrate ActRIIB, or may include a residue that is similar to that in the human or other vertebrate sequences. Without meaning to be limiting, the following examples illustrate this approach to defining an active ActRIIB variant. L46 in the human extracellular domain (SEQ ID NO: 2) is a valine in Xenopus ActRIIB (SEQ ID NO: 506), and so this position may be altered, and optionally may be altered to another hydrophobic residue, such as V, I or F, or a non-polar residue such as A. E52 in the human extracellular domain is a K in Xenopus, indicating that this site may be tolerant of a wide variety of changes, including polar residues, such as E, D, K, R, H, S, T, P, G, Y and probably A. T93 in the human extracellular domain is a K in Xenopus, indicating that a wide structural variation is tolerated at this position, with polar residues favored, such as S, K, R, E, D, H, G, P, G and Y. F108 in the human extracellular domain is a Y in Xenopus, and therefore Y or other hydrophobic group, such as I, V or L should be tolerated. E111 in the human extracellular domain is K in Xenopus, indicating that charged residues will be tolerated at this position, including D, R, K and H, as well as Q and N. R112 in the human extracellular domain is K in Xenopus, indicating that basic residues are tolerated at this position, including R and H. A at position 119 in the human extracellular domain is relatively poorly conserved, and appears as P in rodents and V in Xenopus, thus essentially any amino acid should be tolerated at this position.

Moreover, ActRII proteins have been characterized in the art in terms of structural and functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663]. In addition to the teachings herein, these references provide amply guidance for how to generate ActRIIB variants that retain one or more normal activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRIIB, as demarcated by the outermost of these conserved cysteines, corresponds to positions 29-109 of SEQ ID NO: 1 (ActRIIB precursor). Thus, the structurally less-ordered amino acids flanking these cysteine-demarcated core sequences can be truncated by about 1, 2, 3, 4, 5, 6, 7, 8, 9, 10, 11, 12, 13, 14, 15, 16, 17, 18, 19, 20, 21, 22, 23, 24, 25, 26, 27, or 28 residues at the N-terminus and/or by about 1, 2, 3, 4, 5, 6, 7, 8, 9, 10, 11, 12, 13, 14, 15, 16, 17, 18, 19, 20, 21, 22, 23, 24, or 25 residues a the C-terminus without necessarily altering ligand binding. Exemplary ActRIIB extracellular domains for N-terminal and/or C-terminal truncation include SEQ ID NOs: 2, 3, 5, and 6.

Attisano et al. showed that a deletion of the proline knot at the C-terminus of the extracellular domain of ActRIIB reduced the affinity of the receptor for activin. An ActRIIB-Fc fusion protein containing amino acids 20-119 of present SEQ ID NO: 1, "ActRIIB(20-119)-Fc", has reduced binding to GDF11 and activin relative to an ActRIIB(20-134)-Fc, which includes the proline knot region and the complete juxtamembrane domain (see, e.g., U.S. Pat. No. 7,842,663). However, an ActRIIB(20-129)-Fc protein retains similar, but somewhat reduced activity, relative to the wild-type, even though the proline knot region is disrupted.

Thus, ActRIIB extracellular domains that stop at amino acid 134, 133, 132, 131, 130 and 129 (with respect to SEQ ID NO: 1) are all expected to be active, but constructs stopping at 134 or 133 may be most active. Similarly, mutations at any of residues 129-134 (with respect to SEQ ID NO: 1) are not expected to alter ligand-binding affinity by large margins. In support of this, it is known in the art that mutations of P129 and P130 (with respect to SEQ ID NO: 1) do not substantially decrease ligand binding. Therefore, an ActRIIB polypeptide of the present disclosure may end as early as amino acid 109 (the final cysteine), however, forms ending at or between 109 and 119 (e.g., 109, 110, 111, 112, 113, 114, 115, 116, 117, 118, or 119) are expected to have reduced ligand binding. Amino acid 119 (with respect to present SEQ ID NO: 1) is poorly conserved and so is readily altered or truncated. ActRIIB polypeptides ending at 128 (with respect to SEQ ID NO: 1) or later should retain ligand-binding activity. ActRIIB polypeptides ending at or between 119 and 127 (e.g., 119, 120, 121, 122, 123, 124, 125, 126, or 127), with respect to SEQ ID NO: 1, will have an intermediate binding ability. Any of these forms may be desirable to use, depending on the clinical or experimental setting.

At the N-terminus of ActRIIB, it is expected that a protein beginning at amino acid 29 or before (with respect to SEQ ID NO: 1) will retain ligand-binding activity. Amino acid 29 represents the initial cysteine. An alanine-to-asparagine mutation at position 24 (with respect to SEQ ID NO: 1) introduces an N-linked glycosylation sequence without substantially affecting ligand binding [U.S. Pat. No. 7,842,663]. This confirms that mutations in the region between the signal cleavage peptide and the cysteine cross-linked region, corresponding to amino acids 20-29, are well tolerated. In particular, ActRIIB polypeptides beginning at position 20, 21, 22, 23, and 24 (with respect to SEQ ID NO: 1) should retain general ligand-biding activity, and ActRIIB polypeptides beginning at positions 25, 26, 27, 28, and 29 (with respect to SEQ ID NO: 1) are also expected to retain ligand-biding activity. It has been demonstrated, e.g., U.S. Pat. No. 7,842,663, that, surprisingly, an ActRIIB construct beginning at 22, 23, 24, or 25 will have the most activity.

Taken together, a general formula for an active portion (e.g., ligand-binding portion) of ActRIIB comprises amino acids 29-109 of SEQ ID NO: 1. Therefore ActRIIB polypeptides may, for example, comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to any one of amino acids 20-29 (e.g., beginning at any one of amino acids 20, 21, 22, 23, 24, 25, 26, 27, 28, or 29) of SEQ ID NO: 1 and ending at a position corresponding to any one amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. Other examples include polypeptides that begin at a position from 20-29 (e.g., any one of positions 20, 21, 22, 23, 24, 25, 26, 27, 28, or 29) or 21-29 (e.g., any one of positions 21, 22, 23, 24, 25, 26, 27, 28, or 29) of SEQ ID NO: 1 and end at a position from 119-134 (e.g., any one of positions 119, 120, 121, 122, 123, 124, 125, 126, 127, 128, 129, 130, 131, 132, 133, or 134), 119-133 (e.g., any one of positions 119, 120, 121, 122, 123, 124, 125, 126, 127, 128, 129, 130, 131, 132, or 133), 129-134 (e.g., any one of positions 129, 130, 131, 132, 133, or 134), or 129-133 (e.g., any one of positions 129, 130, 131, 132, or 133) of SEQ ID NO: 1. Other examples include constructs that begin at a position from 20-24 (e.g., any one of positions 20, 21, 22, 23, or 24), 21-24 (e.g., any one of positions 21, 22, 23, or 24), or 22-25 (e.g., any one of positions 22, 22, 23, or 25) of SEQ ID NO: 1 and end at a position from 109-134 (e.g., any one of positions 109, 110, 111, 112, 113, 114, 115, 116, 117, 118, 119, 120, 121, 122, 123, 124, 125, 126, 127, 128, 129, 130, 131, 132, 133, or 134), 119-134 (e.g., any one of positions 119, 120, 121, 122, 123, 124, 125, 126, 127, 128, 129, 130, 131, 132, or 134) or 129-134 (e.g., any one of positions 129, 130, 131, 132, 133, or 134) of SEQ ID NO: 1. Variants within these ranges are also contemplated, particularly those having at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 1.

The variations described herein may be combined in various ways. In some embodiments, ActRIIB variants comprise no more than 1, 2, 5, 6, 7, 8, 9, 10 or 15 conservative amino acid changes in the ligand-binding pocket, and zero, one, or more non-conservative alterations at positions 40, 53, 55, 74, 79 and/or 82 in the ligand-binding pocket. Sites outside the binding pocket, at which variability may be particularly well tolerated, include the amino and carboxy termini of the extracellular domain (as noted above), and positions 42-46 and 65-73 (with respect to SEQ ID NO: 1). An asparagine-to-alanine alteration at position 65 (N65A) actually improves ligand binding in the A64 background, and is thus expected to have no detrimental effect on ligand binding in the R64 background [U.S. Pat. No. 7,842,663]. This change probably eliminates glycosylation at N65 in the A64 background, thus demonstrating that a significant change in this region is likely to be tolerated. While an R64A change is poorly tolerated, R64K is well-tolerated, and thus another basic residue, such as H may be tolerated at position 64 [U.S. Pat. No. 7,842,663]. Additionally, the results of the mutagenesis program described in the art indicate that there are amino acid positions in ActRIIB that are often beneficial to conserve. With respect to SEQ ID NO: 1, these include position 80 (acidic or hydrophobic amino acid), position 78 (hydrophobic, and particularly tryptophan), position 37 (acidic, and particularly aspartic or glutamic acid), position 56 (basic amino acid), position 60 (hydrophobic amino acid, particularly phenylalanine or tyrosine). Thus, the disclosure provides a framework of amino acids that may be conserved in ActRIIB polypeptides. Other positions that may be desirable to conserve are as follows: position 52 (acidic amino acid), position 55 (basic amino acid), position 81 (acidic), 98 (polar or charged, particularly E, D, R or K), all with respect to SEQ ID NO: 1.

In certain embodiments, the disclosure relates to heteromultimers that comprise at least one ActRIIB polypeptide, which includes fragments, functional variants, and modified forms thereof. Preferably, ActRIIB polypeptides for use in accordance with the disclosure are soluble (e.g., an extracellular domain of ActRIIB) In other preferred embodiments, ActRIIB polypeptides for use in accordance with the disclosure bind to one or more TGF-beta superfamily ligands. Therefore, in some embodiments, ActRIIB polypeptides for use in accordance with the disclosure inhibit (antagonize) activity (e.g., inhibition of Smad signaling) of one or more TGF-beta superfamily ligands. In some embodiments, heteromultimers of the disclosure comprise at least one ActRIIB polypeptide that comprises, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRIIB beginning at a residue corresponding to amino acids 20-29 (e.g., beginning at any one of amino acids 20, 21, 22, 23, 24, 25, 26, 27, 28, or 29) of SEQ ID NO: 1 and ending at a position corresponding to amino acids 109-134 (e.g., ending at any one of amino acids 109, 110, 111, 112, 113, 114, 115, 116, 117, 118, 119, 120, 121, 122, 123, 124, 125, 126, 127, 128, 129, 130, 131, 132, 133, or 134) of SEQ ID NO: 1. In certain preferred embodiments, heteromultimers of the disclosure comprise at least one ActRIIB polypeptide that comprises, consists, or consists essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 29-109 of SEQ ID NO: 1 In other preferred embodiments, heteromultimers of the disclosure comprise at least one ActRIIB polypeptide that comprises, consists, or consists essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 25-131 of SEQ ID NO: 1 In some embodiments, heteromultimers of the disclosure comprise at least one ActRIIB polypeptide that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 4, 5, 6, 100, 102, 153, 154, 401, 402, 453, and 454. In certain embodiments, heteromultimers of the disclosure comprise at least one ActRIIB polypeptide wherein the amino acid position corresponding to L79 of SEQ ID NO: 1 is not an acidic amino acid (i.e., is not a naturally occurring D or E amino acid residue or artificial acidic amino acid).

In certain embodiments, the present disclosure relates to a protein complex comprising an ActRIIA polypeptide. As used herein, the term "ActRIIA" refers to a family of activin receptor type IIA (ActRIIA) proteins from any species and variants derived from such ActRIIA proteins by mutagenesis or other modification. Reference to ActRIIA herein is understood to be a reference to any one of the currently identified forms. Members of the ActRIIA family are generally transmembrane proteins, composed of a ligand-binding extracellular domain comprising a cysteine-rich region, a transmembrane domain, and a cytoplasmic domain with predicted serine/threonine kinase activity.

The term "ActRIIA polypeptide" includes polypeptides comprising any naturally occurring polypeptide of an ActRIIA family member as well as any variants thereof (including mutants, fragments, fusions, and peptidomimetic forms) that retain a useful activity. Examples of such variant ActRIIA polypeptides are provided throughout the present disclosure as well as in International Patent Application Publication No. WO 2006/012627, which is incorporated herein by reference in its entirety. Numbering of amino acids for all ActRIIA-related polypeptides described herein is based on the numbering of the human ActRIIA precursor protein sequence provided below (SEQ ID NO: 9), unless specifically designated otherwise.

The human ActRIIA precursor protein sequence is as follows:

```
                                                              (SEQ ID NO: 9)
  1 MGAAAKLAFA VFLISCSSGA ILGRSETQEC LFFNANWEKD RTNQTGVEPC

51 YGDKDKRRHC FATWKNISGS IEIVKQGCWL DDINCYDRTD CVEKKDSPEV

101 YFCCCEGNMC NEKFSYFPEM EVTQPTSNPV TPKPPYYNIL LYSLVPLMLI

151 AGIVICAFWV YRHHKMAYPP VLVPTQDPGP PPPSPLLGLK PLQLLEVKAR

201 GRFGCVWKAQ LLNEYVAVKI FPIQDKQSWQ NEYEVYSLPG MKHENILQFI

251 GAEKRGTSVD VDLWLITAFH EKGSLSDFLK ANVVSWNELC HIAETMARGL

301 AYLHEDIPGL KDGHKPAISH RDIKSKNVLL KNNLTACIAD FGLALKFEAG

351 KSAGDTHGQV GTRRYMAPEV LEGAINFQRD AFLRIDMYAM GLVLWELASR

401 CTAADGPVDE YMLPFEEEIG QHPSLEDMQE VVVHKKKRPV LRDYWQKHAG

451 MAMLCETIEE CWDHDAEARL SAGCVGERIT QMQRLTNIIT TEDIVTVVTM

501 VTNVDFPPKE SSL
```

The signal peptide is indicated by a single underline; the extracellular domain is indicated in bold font; and the potential, endogenous N-linked glycosylation sites are indicated by a double underline.

The processed extracellular human ActRIIA polypeptide sequence is as follows:

```
                                                              (SEQ ID NO: 10)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP
```

The C-terminal "tail" of the extracellular domain is indicated by a single underline. The sequence with the "tail" deleted (a Δ15 sequence) is as follows:

```
                                                              (SEQ ID NO: 11)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM
```

A nucleic acid sequence encoding the human ActRIIA precursor protein is shown below (SEQ ID NO: 12), corresponding to nucleotides 159-1700 of Genbank Reference Sequence NM_001616.4. The signal sequence is underlined.

```
                                                              (SEQ ID NO: 12)
  1 ATGGGAGCTG CTGCAAAGTT GGCGTTTGCC GTCTTTCTTA TCTCCTGTTC

51 TTCAGGTGCT ATACTTGGTA GATCAGAAAC TCAGGAGTGT CTTTTCTTTA
```

-continued

```
 101 ATGCTAATTG GGAAAAAGAC AGAACCAATC AAACTGGTGT TGAACCGTGT

151 TATGGTGACA AAGATAAACG GCGGCATTGT TTTGCTACCT GGAAGAATAT

201 TTCTGGTTCC ATTGAAATAG TGAAACAAGG TTGTTGGCTG GATGATATCA

251 ACTGCTATGA CAGGACTGAT TGTGTAGAAA AAAAAGACAG CCCTGAAGTA

301 TATTTTTGTT GCTGTGAGGG CAATATGTGT AATGAAAAGT TTTCTTATTT

351 TCCGGAGATG GAAGTCACAC AGCCCACTTC AAATCCAGTT ACACCTAAGC

401 CACCCTATTA CAACATCCTG CTCTATTCCT TGGTGCCACT TATGTTAATT

451 GCGGGGATTG TCATTTGTGC ATTTTGGGTG TACAGGCATC ACAAGATGGC

501 CTACCCTCCT GTACTTGTTC CAACTCAAGA CCCAGGACCA CCCCCACCTT

551 CTCCATTACT AGGTTTGAAA CCACTGCAGT TATTAGAAGT GAAAGCAAGG

601 GGAAGATTTG GTTGTGTCTG GAAAGCCCAG TTGCTTAACG AATATGTGGC

651 TGTCAAAATA TTTCCAATAC AGGACAAACA GTCATGGCAA AATGAATACG

701 AAGTCTACAG TTTGCCTGGA ATGAAGCATG AGAACATATT ACAGTTCATT

751 GGTGCAGAAA AACGAGGCAC CAGTGTTGAT GTGGATCTTT GGCTGATCAC

801 AGCATTTCAT GAAAAGGGTT CACTATCAGA CTTTCTTAAG GCTAATGTGG

851 TCTCTTGGAA TGAACTGTGT CATATTGCAG AAACCATGGC TAGAGGATTG

901 GCATATTTAC ATGAGGATAT ACCTGGCCTA AAAGATGGCC ACAAACCTGC

951 CATATCTCAC AGGGACATCA AAAGTAAAAA TGTGCTGTTG AAAAACAACC

1001 TGACAGCTTG CATTGCTGAC TTTGGGTTGG CCTTAAAATT TGAGGCTGGC

1051 AAGTCTGCAG GCGATACCCA TGGACAGGTT GGTACCCGGA GGTACATGGC

1101 TCCAGAGGTA TTAGAGGGTG CTATAAACTT CCAAAGGGAT GCATTTTTGA

1151 GGATAGATAT GTATGCCATG GGATTAGTCC TATGGGAACT GGCTTCTCGC

1201 TGTACTGCTG CAGATGGACC TGTAGATGAA TACATGTTGC CATTTGAGGA

1251 GGAAATTGGC CAGCATCCAT CTCTTGAAGA CATGCAGGAA GTTGTTGTGC

1301 ATAAAAAAAA GAGGCCTGTT TTAAGAGATT ATTGGCAGAA ACATGCTGGA

1351 ATGGCAATGC TCTGTGAAAC CATTGAAGAA TGTTGGGATC ACGACGCAGA

1401 AGCCAGGTTA TCAGCTGGAT GTGTAGGTGA AGAATTACC CAGATGCAGA

1451 GACTAACAAA TATTATTACC ACAGAGGACA TTGTAACAGT GGTCACAATG

1501 GTGACAAATG TTGACTTTCC TCCCAAAGAA TCTAGTCTA
```

The nucleic acid sequence encoding processed extracellular ActRIIA polypeptide is as follows:

```
                                                 (SEQ ID NO: 13)
  1 ATACTTGGTA GATCAGAAAC TCAGGAGTGT CTTTTCTTTA ATGCTAATTG

51 GGAAAAAGAC AGAACCAATC AAACTGGTGT TGAACCGTGT TATGGTGACA

101 AAGATAAACG GCGGCATTGT TTTGCTACCT GGAAGAATAT TTCTGGTTCC

151 ATTGAAATAG TGAAACAAGG TTGTTGGCTG GATGATATCA ACTGCTATGA

201 CAGGACTGAT TGTGTAGAAA AAAAAGACAG CCCTGAAGTA TATTTTTGTT

251 GCTGTGAGGG CAATATGTGT AATGAAAAGT TTTCTTATTT TCCGGAGATG

301 GAAGTCACAC AGCCCACTTC AAATCCAGTT ACACCTAAGC CACCC
```

A general formula for an active (e.g., ligand binding) ActRIIA polypeptide is one that comprises a polypeptide that starts at amino acid 30 and ends at amino acid 110 of SEQ ID NO: 9. Accordingly, ActRIIA polypeptides of the present disclosure may comprise a polypeptide that is at least 80%, 85%, 90%, 95%, 96%, 97%, 98%, 99%, or 100% identical to amino acids 30-110 of SEQ ID NO: 9. Optionally, ActRIIA polypeptides of the present disclosure comprise a polypeptide that is at least 80%, 85%, 90%, 95%, 96%, 97%, 98%, 99%, or 100% identical to amino acids amino acids 12-82 of SEQ ID NO: 9 optionally beginning at a position ranging from 1-5 (e.g., 1, 2, 3, 4, or 5) or 3-5 (e.g., 3, 4, or 5) and ending at a position ranging from 110-116 (e.g., 110, 111, 112, 113, 114, 115, or 116) or 110-115 (e.g., 110, 111, 112, 113, 114, or 115), respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand-binding pocket with respect to SEQ ID NO: 9.

In certain embodiments, the disclosure relates to heteromultimer complexes that comprise at least one ActRIIA polypeptide, which includes fragments, functional variants, and modified forms thereof. Preferably, ActRIIA polypeptides for use in accordance with inventions of the disclosure (e.g., heteromultimer complexes comprising an ActRIIA polypeptide and uses thereof) are soluble (e.g., an extracellular domain of ActRIIA). In other preferred embodiments, ActRIIA polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one ActRIIA polypeptide that is at least 70%, 75%, 80%, 85%, 90%, 95%, 97%, 98%, or 99% identical to the amino acid sequence of any one of SEQ ID NOs: 9, 10, 11, 118, 120, 409, or 410. In some embodiments, heteromultimer complexes of the disclosure comprise, consist, or consist essentially of at least one ActRIIA polypeptide that is at least 70%, 75%, 80%, 85%, 90%, 95%, 97%, 98%, or 99% identical to the amino acid sequence of any one of SEQ ID NOs: 9, 10, 11, 118, 120, 409, or 410.

In certain aspects, the present disclosure relates to protein complexes that comprise a TGFBRII polypeptide. As used herein, the term "TGFBRII" refers to a family of transforming growth factor-beta receptor II (TGFBRII) proteins from any species and variants derived from such proteins by mutagenesis or other modification. Reference to TGFBRII herein is understood to be a reference to any one of the currently identified forms. Members of the TGFBRII family are generally transmembrane proteins, composed of a ligand-binding extracellular domain with a cysteine-rich region, a transmembrane domain, and a cytoplasmic domain with predicted serine/threonine kinase activity.

The term "TGFBRII polypeptide" includes polypeptides comprising any naturally occurring polypeptide of a TGFBRII family member as well as any variants thereof (including mutants, fragments, fusions, and peptidomimetic forms) that retain a useful activity. Numbering of amino acids for all TGFBRII-related polypeptides described herein is based on the numbering of the human TGFBRII precursor protein sequence below (SEQ ID NO: 42), unless specifically designated otherwise.

The canonical human TGFBRII precursor protein sequence (NCBI Ref Seq NP_003233.4) is as follows:

```
                                                        (SEQ ID NO: 42)
  1 MGRGLLRGLW PLHIVLWTRI ASTIPPHVQK SVNNDMIVTD NNGAVKFPQL

51 CKFCDVRFST CDNQKSCMSN CSITSICEKP QEVCVAVWRK NDENITLETV

101 CHDPKLPYHD FILEDAASPK CIMKEKKKPG ETFFMCSCSS DECNDNIIFS

151 EEYNTSNPDL LLVIFQVTGI SLLPPLGVAI SVIIIFYCYR VNRQQKLSST

201 WETGKTRKLM EFSEHCAIIL EDDRSDISST CANNINHNTE LLPIELDTLV

251 GKGRFAEVYK AKLKQNTSEQ FETVAVKIFP YEEYASWKTE KDIFSDINLK

301 HENILQFLTA EERKTELGKQ YWLITAFHAK GNLQEYLTRH VISWEDLRKL

351 GSSLARGIAH LHSDHTPCGR PKMPIVHRDL KSSNILVKND LTCCLCDFGL

401 SLRLDPTLSV DDLANSGQVG TARYMAPEVL ESRMNLENVE SFKQTDVYSM

451 ALVLWEMTSR CNAVGEVKDY EPPFGSKVRE HPCVESMKDN VLRDRGRPEI

501 PSFWLNHQGI QMVCETLTEC WDHDPEARLT AQCVAERFSE LEHLDRLSGR

551 SCSEEKIPED GSLNTTK
```

The signal peptide is indicated by a single underline and the extracellular domain is indicated in bold font.

The processed extracellular TGFBRII polypeptide sequence is as follows:

```
                                                        (SEQ ID NO: 43)
TIPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKCI

MKEKKKPGETFFMCSCSSDECNDNIIFSEEYNTSNPDLLLVIFQ
```

The nucleic acid sequence encoding TGFBRII precursor protein is shown below (SEQ ID NO:44), corresponding to nucleotides 383-2083 of Genbank Reference Sequence NM_003242.5. The signal sequence is underlined.

```
                                                        (SEQ ID NO: 44)
ATGGGTCGGGGGCTGCTCAGGGGCCTGTGGCCGCTGCACATCGTCCTGTG

GACGCGTATCGCCAGCACGATCCCACCGCACGTTCAGAAGTCGGTTAATA
```

```
ACGACATGATAGTCACTGACAACAACGGTGCAGTCAAGTTTCCACAACTG
TGTAAATTTTGTGATGTGAGATTTTCCACCTGTGACAACCAGAAATCCTG
CATGAGCAACTGCAGCATCACCTCCATCTGTGAGAAGCCACAGGAAGTCT
GTGTGGCTGTATGGAGAAAGAATGACGAGAACATAACACTAGAGACAGTT
TGCCATGACCCCAAGCTCCCCTACCATGACTTTATTCTGGAAGATGCTGC
TTCTCCAAAGTGCATTATGAAGGAAAAAAAAAAGCCTGGTGAGACTTTCT
TCATGTGTTCCTGTAGCTCTGATGAGTGCAATGACAACATCATCTTCTCA
GAAGAATATAACACCAGCAATCCTGACTTGTTGCTAGTCATATTTCAAGT
GACAGGCATCAGCCTCCTGCCACCACTGGGAGTTGCCATATCTGTCATCA
TCATCTTCTACTGCTACCGCGTTAACCGGCAGCAGAAGCTGAGTTCAACC
TGGGAAACCGGCAAGACGCGGAAGCTCATGGAGTTCAGCGAGCACTGTGC
CATCATCCTGGAAGATGACCGCTCTGACATCAGCTCCACGTGTGCCAACA
ACATCAACCACAACACAGAGCTGCTGCCCATTGAGCTGGACACCCTGGTG
GGGAAAGGTCGCTTTGCTGAGGTCTATAAGGCCAAGCTGAAGCAGAACAC
TTCAGAGCAGTTTGAGACAGTGGCAGTCAAGATCTTTCCCTATGAGGAGT
ATGCCTCTTGGAAGACAGAGAAGGACATCTTCTCAGACATCAATCTGAAG
CATGAGAACATACTCCAGTTCCTGACGGCTGAGGAGCGGAAGACGGAGTT
GGGGAAACAATACTGGCTGATCACCGCCTTCCACGCCAAGGGCAACCTAC
AGGAGTACCTGACGCGGCATGTCATCAGCTGGGAGGACCTGCGCAAGCTG
GGCAGCTCCCTCGCCCGGGGGATTGCTCACCTCCACAGTGATCACACTCC
ATGTGGGAGGCCCAAGATGCCCATCGTGCACAGGGACCTCAAGAGCTCCA
ATATCCTCGTGAAGAACGACCTAACCTGCTGCCTGTGTGACTTTGGGCTT
TCCCTGCGTCTGGACCCTACTCTGTCTGTGGATGACCTGGCTAACAGTGG
```

```
GCAGGTGGGAACTGCAAGATACATGGCTCCAGAAGTCCTAGAATCCAGGA
TGAATTTGGAGAATGTTGAGTCCTTCAAGCAGACCGATGTCTACTCCATG
GCTCTGGTGCTCTGGGAAATGACATCTCGCTGTAATGCAGTGGGAGAAGT
AAAAGATTATGAGCCTCCATTTGGTTCCAAGGTGCGGGAGCACCCCTGTG
TCGAAAGCATGAAGGACAACGTGTTGAGAGATCGAGGGCGACCAGAAATT
CCCAGCTTCTGGCTCAACCACCAGGGCATCCAGATGGTGTGTGAGACGTT
GACTGAGTGCTGGGACCACGACCCAGAGGCCCGTCTCACAGCCCAGTGTG
TGGCAGAACGCTTCAGTGAGCTGGAGCATCTGGACAGGCTCTCGGGGAGG
AGCTGCTCGGAGGAGAAGATTCCTGAAGACGGCTCCCTAAACACTACCAA
A
```

The nucleic acid sequence encoding processed extracellular TGFBRII polypeptide is as follows:

(SEQ ID NO: 45)
```
ACGATCCCACCGCACGTTCAGAAGTCGGTTAATAACGACATGATAGTCAC
TGACAACAACGGTGCAGTCAAGTTTCCACAACTGTGTAAATTTTGTGATG
TGAGATTTTCCACCTGTGACAACCAGAAATCCTGCATGAGCAACTGCAGC
ATCACCTCCATCTGTGAGAAGCCACAGGAAGTCTGTGTGGCTGTATGGAG
AAAGAATGACGAGAACATAACACTAGAGACAGTTTGCCATGACCCCAAGC
TCCCCTACCATGACTTTATTCTGGAAGATGCTGCTTCTCCAAAGTGCATT
ATGAAGGAAAAAAAAAAGCCTGGTGAGACTTTCTTCATGTGTTCCTGTAG
CTCTGATGAGTGCAATGACAACATCATCTTCTCAGAAGAATATAACACCA
GCAATCCTGACTTGTTGCTAGTCATATTTCAA
```

An alternative isoform of TGFBRII, isoform A (NP_001020018.1), is as follows:

(SEQ ID NO: 67)
```
  1 MGRGLLRGLW PLHIVLWTRI ASTIPPHVQK SDVEMEAQKD EIICPSCNRT
 51 AHPLRHINND MIVTDNNGAV KFPQLCKFCD VRFSTCDNQK SCMSNCSITS
101 ICEKPQEVCV AVWRKNDENI TLETVCHDPK LPYHDFILED AASPKCIMKE
151 KKKPGETFFM CSCSSDECND NIIFSEEYNT SNPDLLLVIF QVTGISLLPP
201 LGVAISVIII FYCYRVNRQQ KLSSTWETGK TRKLMEFSEH CAIILEDDRS
251 DISSTCANNI NHNTELLPIE LDTLVGKGRF AEVYKAKLKQ NTSEQFETVA
301 VKIFPYEEYA SWKTEKDIFS DINLKHENIL QFLTAEERKT ELGKQYWLIT
351 AFHAKGNLQE YLTRHVISWE DLRKLGSSLA RGIAHLHSDH TPCGRPKMPI
401 VHRDLKSSNI LVKNDLTCCL CDFGLSLRLD PTLSVDDLAN SGQVGTARYM
451 APEVLESRMN LENVESFKQT DVYSMALVLW EMTSRCNAVG EVKDYEPPFG
501 SKVREHPCVE SMKDNVLRDR GRPEIPSFWL NHQGIQMVCE TLTECWDHDP
551 EARLTAQCVA ERFSELEHLD RLSGRSCSEE KIPEDGSLNT TK
```

The signal peptide is indicated by a single underline and the extracellular domain is indicated in bold font.

The processed extracellular TGFBRII polypeptide sequence (isoform A) is as follows:

(SEQ ID NO: 68)
TIPPHVQKSDVEMEAQKDEIICPSCNRTAHPLRHINNDMIVTDNNGAVKF

PQLCKFCDVRFSTCDNQKSCMSNCSITSICEKPQEVCVAVWRKNDENITL

ETVCHDPKLPYHDFILEDAASPKCIMKEKKKPGETFFMCSCSSDECNDNI

IFSEEYNTSNPDLLLVIFQ

A nucleic acid sequence encoding the TGFBRII precursor protein (isoform A) is shown below (SEQ ID NO: 69), corresponding to nucleotides 383-2158 of Genbank Reference Sequence NM_001024847.2. The signal sequence is underlined.

(SEQ ID NO: 69)
ATGGGTCGGGGCTGCTCAGGGGCCTGTGGCCGCTGCACATCGTCCTGTG

GACGCGTATCGCCAGCACGATCCCACCGCACGTTCAGAAGTCGGATGTGG

AAATGGAGGCCCAGAAAGATGAAATCATCTGCCCCAGCTGTAATAGGACT

GCCCATCCACTGAGACATATTAATAACGACATGATAGTCACTGACAACAA

CGGTGCAGTCAAGTTTCCACAACTGTGTAAATTTTGTGATGTGAGATTTT

CCACCTGTGACAACCAGAAATCCTGCATGAGCAACTGCAGCATCACCTCC

ATCTGTGAGAAGCCACAGGAAGTCTGTGTGGCTGTATGGAGAAAGAATGA

CGAGAACATAACACTAGAGACAGTTTGCCATGACCCCAAGCTCCCCTACC

ATGACTTTATTCTGGAAGATGCTGCTTCTCCAAAGTGCATTATGAAGGAA

AAAAAAAAGCCTGGTGAGACTTTCTTCATGTGTTCCTGTAGCTCTGATGA

GTGCAATGACAACATCATCTTCTCAGAAGAATATAACACCAGCAATCCTG

ACTTGTTGCTAGTCATATTTCAAGTGACAGGCATCAGCCTCCTGCCACCA

CTGGGAGTTGCCATATCTGTCATCATCATCTTCTACTGCTACCGCGTTAA

CCGGCAGCAGAAGCTGAGTTCAACCTGGGAAACCGGCAAGACGCGGAAGC

TCATGGAGTTCAGCGAGCACTGTGCCATCATCCTGGAAGATGACCGCTCT

GACATCAGCTCCACGTGTGCCAACAACATCAACCACAACACAGAGCTGCT

GCCCATTGAGCTGGACACCCTGGTGGGGAAAGGTCGCTTTGCTGAGGTCT

ATAAGGCCAAGCTGAAGCAGAACACTTCAGAGCAGTTTGAGACAGTGGCA

GTCAAGATCTTTCCCTATGAGGAGTATGCCTCTTGGAAGACAGAGAAGGA

CATCTTCTCAGACATCAATCTGAAGCATGAGAACATACTCCAGTTCCTGA

CGGCTGAGGAGCGGAAGACGGAGTTGGGGAAACAATACTGGCTGATCACC

GCCTTCCACGCCAAGGGCAACCTACAGGAGTACCTGACGCGGCATGTCAT

CAGCTGGGAGGACCTGCGCAAGCTGGGCAGCTCCCTCGCCCGGGGGATTG

CTCACCTCCACAGTGATCACACTCCATGTGGGAGGCCCAAGATGCCCATC

GTGCACAGGGACCTCAAGAGCTCCAATATCCTCGTGAAGAACGACCTAAC

CTGCTGCCTGTGTGACTTTGGGCTTTCCCTGCGTCTGGACCCTACTCTGT

CTGTGGATGACCTGGCTAACAGTGGGCAGGTGGGAACTGCAAGATACATG

GCTCCAGAAGTCCTAGAATCCAGGATGAATTTGGAGAATGTTGAGTCCTT

CAAGCAGACCGATGTCTACTCCATGGCTCTGGTGCTCTGGGAAATGACAT

CTCGCTGTAATGCAGTGGGAGAAGTAAAAGATTATGAGCCTCCATTTGGT

TCCAAGGTGCGGGAGCACCCCTGTGTCGAAAGCATGAAGGACAACGTGTT

GAGAGATCGAGGGCGACCAGAAATTCCCAGCTTCTGGCTCAACCACCAGG

GCATCCAGATGGTGTGTGAGACGTTGACTGAGTGCTGGGACCACGACCCA

GAGGCCCGTCTCACAGCCCAGTGTGTGGCAGAACGCTTCAGTGAGCTGGA

GCATCTGGACAGGCTCTCGGGGAGGAGCTGCTCGGAGGAGAAGATTCCTG

AAGACGGCTCCCTAAACACTACCAAA

A nucleic acid sequence encoding the processed extracellular TGFBRII polypeptide (isoform A) is as follows:

(SEQ ID NO: 70)
ACGATCCCACCGCACGTTCAGAAGTCGGATGTGGAAATGGAGGCCCAGAA

AGATGAAATCATCTGCCCCAGCTGTAATAGGACTGCCCATCCACTGAGAC

ATATTAATAACGACATGATAGTCACTGACAACAACGGTGCAGTCAAGTTT

CCACAACTGTGTAAATTTTGTGATGTGAGATTTTCCACCTGTGACAACCA

GAAATCCTGCATGAGCAACTGCAGCATCACCTCCATCTGTGAGAAGCCAC

AGGAAGTCTGTGTGGCTGTATGGAGAAAGAATGACGAGAACATAACACTA

GAGACAGTTTGCCATGACCCCAAGCTCCCCTACCATGACTTTATTCTGGA

AGATGCTGCTTCTCCAAAGTGCATTATGAAGGAAAAAAAAAAGCCTGGTG

AGACTTTCTTCATGTGTTCCTGTAGCTCTGATGAGTGCAATGACAACATC

ATCTTCTCAGAAGAATATAACACCAGCAATCCTGACTTGTTGCTAGTCAT

ATTTCAA.

Either of the foregoing TGFβRII isoforms (SEQ ID NOs: 42, 43, 67, and 68) could incorporate an insertion of 36 amino acids (SEQ ID NO: 95) between the pair of glutamate residues (positions 151 and 152 of SEQ ID NO: 42; positions 129 and 130 of SEQ ID NO: 43; positions 176 and 177 of SEQ ID NO: 67; or positions 154 and 155 of SEQ ID NO: 68) located near the C-terminus of the TGFβRII ECD, as occurs naturally in the TGFβRII isoform C (Konrad et al., BMC Genomics 8:318, 2007).

(SEQ ID NO: 95)
GRCKIRHIGS NNRLQRSTCQ NTGWESAHVM KTPGFR

In certain embodiments, the disclosure relates to heteromultimer complexes that comprise at least one TGFBRII polypeptide, which includes fragments, functional variants, and modified forms thereof. Preferably, TGFBRII polypeptides for use in accordance with inventions of the disclosure (e.g., heteromultimer complexes comprising a TGFBRII polypeptide and uses thereof) are soluble (e.g., an extracellular domain of TGFBRII). In other preferred embodiments, TGFBRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one TGFBRII polypeptide that is at least 70%, 75%, 80%, 85%, 90%, 95%, 97%, 98%, or 99% identical to the amino acid sequence of SEQ ID NOs: 42, 43, 67, or 68, with or without insertion of SEQ ID NO: 95 as described above. In some embodiments, heteromultimer complexes of the disclosure consist or consist essentially of at least one TGFBRII polypeptide that is at least 70%, 75%, 80%, 85%, 90%, 95%, 97%, 98%, or 99% identical to the amino acid sequence of SEQ ID NOs: 42, 43, 67, or 68, with or without insertion of SEQ ID NO: 95.

In certain aspects, the present disclosure relates to protein complexes that comprise a BMPRII polypeptide. As used herein, the term "BMPRII" refers to a family of bone morphogenetic protein receptor type II (BMPRII) proteins from any species and variants derived from such BMPRII proteins by mutagenesis or other modification. Reference to BMPRII herein is understood to be a reference to any one of the currently identified forms. Members of the BMPRII family are generally transmembrane proteins, composed of a ligand-binding extracellular domain with a cysteine-rich region, a transmembrane domain, and a cytoplasmic domain with predicted serine/threonine kinase activity.

The term "BMPRII polypeptide" includes polypeptides comprising any naturally occurring polypeptide of a BMPRII family member as well as any variants thereof (including mutants, fragments, fusions, and peptidomimetic forms) that retain a useful activity. Numbering of amino acids for all BMPRII-related polypeptides described herein is based on the numbering of the human BMPRII precursor protein sequence below (SEQ ID NO: 46), unless specifically designated otherwise.

The canonical human BMPRII precursor protein sequence (NCBI Ref Seq NP_001195.2) is as follows:

The signal peptide is indicated by a single underline and the extracellular domain is indicated in bold font.

The processed extracellular BMPRII polypeptide sequence is as follows:

```
                                         (SEQ ID NO: 47)
SQNQERLCAFKDPYQQDLGIGESRISHENGTILCSKGSTCYGLWEKSKGD

INLVKQGCWSHIGDPQECHYEECVVTTTPPSIQNGTYRFCCCSTDLCNVN

FTENFPPPDTTPLSPPHSFNRDET
```

A nucleic acid sequence encoding BMPRII precursor protein is shown below (SEQ ID NO: 48), as follows nucleotides 1149-4262 of Genbank Reference Sequence NM_001204.6. The signal sequence is underlined.

```
                                         (SEQ ID NO: 48)
ATGACTTCCTCGCTGCAGCGGCCCTGGCGGGTGCCCTGGCTACCATGGAC

CATCCTGCTGGTCAGCACTGCGGCTGCTTCGCAGAATCAAGAACGGCTAT

GTGCGTTTAAAGATCCGTATCAGCAAGACCTTGGGATAGGTGAGAGTAGA

ATCTCTCATGAAAATGGGACAATATTATGCTCGAAAGGTAGCACCTGCTA

TGGCCTTTGGGAGAAATCAAAAGGGGACATAAATCTTGTAAAACAAGGAT

GTTGGTCTCACATTGGAGATCCCCAAGAGTGTCACTATGAAGAATGTGTA
```

```
                                         (SEQ ID NO: 46)
   1 MTSSLQRPWR VPWLPWTILL VSTAAASQNQ ERLCAFKDPY QQDLGIGESR

51 ISHENGTILC SKGSTCYGLW EKSKGDINLV KQGCWSHIGD PQECHYEECV

101 VTTTPPSIQN GTYRFCCCST DLCNVNFTEN FPPPDTTPLS PPHSFNRDET

151 IIIALASVSV LAVLIVALCF GYRMLTGDRK QGLHSMNMME AAASEPSLDL

201 DNLKLLELIG RGRYGAVYKG SLDERPVAVK VFSFANRQNF INEKNIYRVP

251 LMEHDNIARF IVGDERVTAD GRMEYLLVME YYPNGSLCKY LSLHTSDWVS

301 SCRLAHSVTR GLAYLHTELP RGDHYKPAIS HRDLNSRNVL VKNDGTCVIS

351 DFGLSMRLTG NRLVRPGEED NAAISEVGTI RYMAPEVLEG AVNLRDCESA

401 LKQVDMYALG LIYWEIFMRC TDLFPGESVP EYQMAFQTEV GNHPTFEDMQ

451 VLVSREKQRP KFPEAWKENS LAVRSLKETI EDCWDQDAEA RLTAQCAEER

501 MAELMMIWER NKSVSPTVNP MSTAMQNERN LSHNRRVPKI GPYPDYSSSS

551 YIEDSIHHTD SIVKNISSEH SMSSTPLTIG EKNRNSINYE RQQAQARIPS

601 PETSVTSLST NTTTTNTTGL TPSTGMTTIS EMPYPDETNL HTTNVAQSIG

651 PTPVCLQLTE EDLETNKLDP KEVDKNLKES SDENLMEHSL KQFSGPDPLS

701 STSSSLLYPL IKLAVEATGQ QDFTQTANGQ ACLIPDVLPT QIYPLPKQQN

751 LPKRPTSLPL NTKNSTKEPR LKFGSKHKSN LKQVETGVAK MNTINAAEPH

801 VVTVTMNGVA GRNHSVNSHA ATTQYANGTV LSGQTTNIVT HRAQEMLQNQ

851 FIGEDTRLNI NSSPDEHEPL LRREQQAGHD EGVLDRLVDR RERPLEGGRT

901 NSNNNNSNPC SEQDVLAQGV PSTAADPGPS KPRRAQRPNS LDLSATNVLD

951 GSSIQIGEST QDGKSGSGEK IKKRVKTPYS LKRWRPSTWV ISTESLDCEV

1001 NNNGSNRAVH SKSSTAVYLA EGGTATTMVS KDIGMNCL
```

-continued
```
GTAACTACCACTCCTCCCTCAATTCAGAATGGAACATACCGTTTCTGCTG
TTGTAGCACAGATTTATGTAATGTCAACTTTACTGAGAATTTTCCACCTC
CTGACACAACACCACTCAGTCCACCTCATTCATTTAACCGAGATGAGACA
ATAATCATTGCTTTGGCATCAGTCTCTGTATTAGCTGTTTTGATAGTTGC
CTTATGCTTTGGATACAGAATGTTGACAGGAGACCGTAAACAAGGTCTTC
ACAGTATGAACATGATGGAGGCAGCAGCATCCGAACCCTCTCTTGATCTA
GATAATCTGAAACTGTTGGAGCTGATTGGCCGAGGTCGATATGGAGCAGT
ATATAAAGGCTCCTTGGATGAGCGTCCAGTTGCTGTAAAAGTGTTTTCCT
TTGCAAACCGTCAGAATTTTATCAACGAAAAGAACATTTACAGAGTGCCT
TTGATGGAACATGACAACATTGCCCGCTTTATAGTTGGAGATGAGAGAGT
CACTGCAGATGGACGCATGGAATATTTGCTTGTGATGGAGTACTATCCCA
ATGGATCTTTATGCAAGTATTTAAGTCTCCACACAAGTGACTGGGTAAGC
TCTTGCCGTCTTGCTCATTCTGTTACTAGAGGACTGGCTTATCTTCACAC
AGAATTACCACGAGGAGATCATTATAAACCTGCAATTTCCCATCGAGATT
TAAACAGCAGAAATGTCCTAGTGAAAAATGATGGAACCTGTGTTATTAGT
GACTTTGGACTGTCCATGAGGCTGACTGGAAATAGACTGGTGCGCCCAGG
GGAGGAAGATAATGCAGCCATAAGCGAGGTTGGCACTATCAGATATATGG
CACCAGAAGTGCTAGAAGGAGCTGTGAACTTGAGGGACTGTGAATCAGCT
TTGAAACAAGTAGACATGTATGCTCTTGGACTAATCTATTGGGAGATATT
TATGAGATGTACAGACCTCTTCCCAGGGGAATCCGTACCAGAGTACCAGA
TGGCTTTTCAGACAGAGGTTGGAAACCATCCCACTTTTGAGGATATGCAG
GTTCTCGTGTCTAGGGAAAAACAGAGACCCAAGTTCCCAGAAGCCTGGAA
AGAAAATAGCCTGGCAGTGAGGTCACTCAAGGAGACAATCGAAGACTGTT
GGGACCAGGATGCAGAGGCTCGGCTTACTGCACAGTGTGCTGAGGAAAGG
ATGGCTGAACTTATGATGATTTGGGAAAGAAACAAATCTGTGAGCCCAAC
AGTCAATCCAATGTCTACTGCTATGCAGAATGAACGCAACCTGTCACATA
ATAGGCGTGTGCCAAAAATTGGTCCTTATCCAGATTATTCTTCCTCCTCA
TACATTGAAGACTCTATCCATCATACTGACAGCATCGTGAAGAATATTTC
CTCTGAGCATTCTATGTCCAGCACACCTTTGACTATAGGGGAAAAAAACC
GAAATTCAATTAACTATGAACGACAGCAAGCACAAGCTCGAATCCCCAGC
CCTGAAACAAGTGTCACCAGCCTCTCCACCAACACAACAACCACAAACAC
CACAGGACTCACGCCAAGTACTGGCATGACTACTATATCTGAGATGCCAT
ACCCAGATGAAACAAATCTGCATACCACAAATGTTGCACAGTCAATTGGG
CCAACCCCTGTCTGCTTACAGCTGACAGAAGAAGACTTGGAAACCAACAA
GCTAGACCCAAAAGAAGTTGATAAGAACCTCAAGGAAAGCTCTGATGAGA
ATCTCATGGAGCACTCTCTTAAACAGTTCAGTGGCCCAGACCCACTGAGC
AGTACTAGTTCTAGCTTGCTTTACCCACTCATAAAACTTGCAGTAGAAGC
AACTGGACAGCAGGACTTCACACAGACTGCAAATGGCCAAGCATGTTTGA
TTCCTGATGTTCTGCCTACTCAGATCTATCCTCTCCCCAAGCAGCAGAAC
CTTCCCAAGAGACCTACTAGTTTGCCTTTGAACACCAAAAATTCAACAAA
AGAGCCCCGGCTAAAATTTGGCAGCAAGCACAAATCAAACTTGAAACAAG
```
-continued
```
TCGAAACTGGAGTTGCCAAGATGAATACAATCAATGCAGCAGAACCTCAT
GTGGTGACAGTCACCATGAATGGTGTGGCAGGTAGAAACCACAGTGTTAA
CTCCCATGCTGCCACAACCCAATATGCCAATGGGACAGTACTATCTGGCC
AAACAACCAACATAGTGACACATAGGGCCCAAGAAATGTTGCAGAATCAG
TTTATTGGTGAGGACACCCGGCTGAATATTAATTCCAGTCCTGATGAGCA
TGAGCCTTTACTGAGACGAGAGCAACAAGCTGGCCATGATGAAGGTGTTC
TGGATCGTCTTGTGGACAGGAGGGAACGGCCACTAGAAGGTGGCCGAACT
AATTCCAATAACAACAGCAATCCATGTTCAGAACAAGATGTTCTTGC
ACAGGGTGTTCCAAGCACAGCAGCAGATCCTGGGCCATCAAAGCCCAGAA
GAGCACAGAGGCCTAATTCTCTGGATCTTTCAGCCACAAATGTCCTGGAT
GGCAGCAGTATACAGATAGGTGAGTCAACACAAGATGGCAAATCAGGATC
AGGTGAAAAGATCAAGAAACGTGTGAAAACTCCCTATTCTCTTAAGCGGT
GGCGCCCCTCCACCTGGGTCATCTCCACTGAATCGCTGGACTGTGAAGTC
AACAATAATGGCAGTAACAGGGCAGTTCATTCCAAATCCAGCACTGCTGT
TTACCTTGCAGAAGGAGGCACTGCTACAACCATGGTGTCTAAAGATATAG
GAATGAACTGTCTG
```

The nucleic acid sequence encoding the extracellular BMPRII polypeptide is as follows:

(SEQ ID NO: 49)
```
TCGCAGAATCAAGAACGGCTATGTGCGTTTAAAGATCCGTATCAGCAAGA
CCTTGGGATAGGTGAGAGTAGAATCTCTCATGAAAATGGGACAATATTAT
GCTCGAAAGGTAGCACCTGCTATGGCCTTTGGGAGAAATCAAAAGGGGAC
ATAAATCTTGTAAAACAAGGATGTTGGTCTCACATTGGAGATCCCCAAGA
GTGTCACTATGAAGAATGTGTAGTAACTACCACTCCTCCCTCAATTCAGA
ATGGAACATACCGTTTCTGCTGTTGTAGCACAGATTTATGTAATGTCAAC
TTTACTGAGAATTTTCCACCTCCTGACACAACACCACTCAGTCCACCTCA
TTCATTTAACCGAGATGAGACA
```

An alternative isoform of BMPRII, isoform 2 (GenBank: AAA86519.1) is as follows:

(SEQ ID NO: 71)
```
  1 MTSSLQRPWR VPWLPWTILL VSTAAASQNQ ERLCAFKDPY QQDLGIGESR

51 ISHENGTILC SKGSTCYGLW EKSKGDINLV KQGCWSHIGD PQECHYEECV

101 VTTTPPSIQN GTYRFCCCST DLCNVNFTEN FPPPDTTPLS PPHSFNRDET

151 IIIALASVSV LAVLIVALCF GYRMLTGDRK QGLHSMNMME AAASEPSLDL

201 DNLKLLELIG RGRYGAVYKG SLDERPVAVK VFSFANRQNF INEKNIYRVP

251 LMEHDNIARF IVGDERVTAD GRMEYLLVME YYPNGSLCKY LSLHTSDWVS

301 SCRLAHSVTR GLAYLHTELP RGDHYKPAIS HRDLNSRNVL VKNDGTCVIS

351 DFGLSMRLTG NRLVRPGEED NAAISEVGTI RYMAPEVLEG AVNLRDCESA

401 LKQVDMYALG LIYWEIFMRC TDLFPGESVP EYQMAFQTEV GNHPTFEDMQ

451 VLVSREKQRP KFPEAWKENS LAVRSLKETI EDCWDQDAEA RLTAQCAEER

501 MAELMMIWER NKSVSPTVNP MSTAMQNERR
```

The signal peptide is indicated by a single underline and the extracellular domain is indicated in bold font.

The processed extracellular BMPRII polypeptide sequence (isoform 2) is as follows:

(SEQ ID NO: 72)
```
SQNQERLCAFKDPYQQDLGIGESRISHENGTILCSKGSTCYGLWEKSKGD

INLVKQGCWSHIGDPQECHYEECVVTTTPPSIQNGTYRFCCCSTDLCNVN

FTENFPPPDTTPLSPPHSFNRDET
```

A nucleic acid sequence encoding human BMPRII precursor protein (isoform 2) is shown below (SEQ ID NO:73), corresponding to nucleotides 163-1752 of Genbank Reference Sequence U25110.1. The signal sequence is underlined.

(SEQ ID NO: 73)
```
ATGACTTCCTCGCTGCAGCGGCCCTGGCGGGTGCCCTGGCTACCATGGAC

CATCCTGCTGGTCAGCACTGCGGCTGCTTCGCAGAATCAAGAACGGCTAT

GTGCGTTTAAAGATCCGTATCAGCAAGACCTTGGGATAGGTGAGAGTAGA

ATCTCTCATGAAAATGGGACAATATTATGCTCGAAAGGTAGCACCTGCTA

TGGCCTTTGGGAGAAATCAAAAGGGGACATAAATCTTGTAAAACAAGGAT

GTTGGTCTCACATTGGAGATCCCCAAGAGTGTCACTATGAAGAATGTGTA

GTAACTACCACTCCTCCCTCAATTCAGAATGGAACATACCGTTTCTGCTG

TTGTAGCACAGATTTATGTAATGTCAACTTTACTGAGAATTTTCCACCTC

CTGACACAACACCACTCAGTCCACCTCATTCATTTAACCGAGATGAGACA

ATAATCATTGCTTTGGCATCAGTCTCTGTATTAGCTGTTTTGATAGTTGC

CTTATGCTTTGGATACAGAATGTTGACAGGAGACCGTAAACAAGGTCTTC

ACAGTATGAACATGATGGAGGCAGCAGCATCCGAACCCTCTCTTGATCTA

GATAATCTGAAACTGTTGGAGCTGATTGGCCGAGGTCGATATGGAGCAGT

ATATAAAGGCTCCTTGGATGAGCGTCCAGTTGCTGTAAAAGTGTTTTCCT

TTGCAAACCGTCAGAATTTTATCAACGAAAAGAACATTTACAGAGTGCCT
```

-continued
```
TTGATGGAACATGACAACATTGCCCGCTTTATAGTTGGAGATGAGAGAGT

CACTGCAGATGGACGCATGGAATATTTGCTTGTGATGGAGTACTATCCCA

ATGGATCTTTATGCAAGTATTTAAGTCTCCACACAAGTGACTGGGTAAGC

TCTTGCCGTCTTGCTCATTCTGTTACTAGAGGACTGGCTTATCTTCACAC

AGAATTACCACGAGGAGATCATTATAAACCTGCAATTTCCCATCGAGATT

TAAACAGCAGAAATGTCCTAGTGAAAAATGATGGAACCTGTGTTATTAGT

GACTTTGGACTGTCCATGAGGCTGACTGGAAATAGACTGGTGCGCCCAGG

GGAGGAAGATAATGCAGCCATAAGCGAGGTTGGCACTATCAGATATATGG

CACCAGAAGTGCTAGAAGGAGCTGTGAACTTGAGGGACTGTGAATCAGCT

TTGAAACAAGTAGACATGTATGCTCTTGGACTAATCTATTGGGAGATATT

TATGAGATGTACAGACCTCTTCCCAGGGGAATCCGTACCAGAGTACCAGA

TGGCTTTTCAGACAGAGGTTGGAAACCATCCCACTTTTGAGGATATGCAG

GTTCTCGTGTCTAGGGAAAAACAGAGACCCAAGTTCCCAGAAGCCTGGAA

AGAAAATAGCCTGGCAGTGAGGTCACTCAAGGAGACAATCGAAGACTGTT

GGGACCAGGATGCAGAGGCTCGGCTTACTGCACAGTGTGCTGAGGAAAGG

ATGGCTGAACTTATGATGATTTGGGAAAGAAACAAATCTGTGAGCCCAAC

AGTCAATCCAATGTCTACTGCTATGCAGAATGAACGTAGG
```

A nucleic acid sequence encoding an extracellular BMPRII polypeptide (isoform 2) is as follows:

(SEQ ID NO: 74)
```
TCGCAGAATCAAGAACGGCTATGTGCGTTTAAAGATCCGTATCAGCAAGA

CCTTGGGATAGGTGAGAGTAGAATCTCTCATGAAAATGGGACAATATTAT

GCTCGAAAGGTAGCACCTGCTATGGCCTTTGGGAGAAATCAAAAGGGGAC

ATAAATCTTGTAAAACAAGGATGTTGGTCTCACATTGGAGATCCCCAAGA

GTGTCACTATGAAGAATGTGTAGTAACTACCACTCCTCCCTCAATTCAGA

ATGGAACATACCGTTTCTGCTGTTGTAGCACAGATTTATGTAATGTCAAC
```

-continued

```
TTTACTGAGAATTTTCCACCTCCTGACACAACACCACTCAGTCCACCTCA

TTCATTTAACCGAGATGAGACA
```

In certain embodiments, the disclosure relates to heteromultimer complexes that comprise at least one BMPRII polypeptide, which includes fragments, functional variants, and modified forms thereof. Preferably, BMPRII polypeptides for use in accordance with inventions of the disclosure (e.g., heteromultimer complexes comprising a BMPRII polypeptide and uses thereof) are soluble (e.g., an extracellular domain of BMPRII). In other preferred embodiments, BMPRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one BMPRII polypeptide that is at least 70%, 75%, 80%, 85%, 90%, 95%, 97%, 98%, or 99% identical to the amino acid sequence of SEQ ID NO: 46, 47, 71, 72, 121, 123, 411, or 412. In some embodiments, heteromultimer complexes of the disclosure consist or consist essentially of at least one BMPRII polypeptide that is at least 70%, 75%, 80%, 85%, 90%, 95%, 97%, 98%, or 99% identical to the amino acid sequence of SEQ ID NO: 46, 47, 71, 72, 121, 123, 411, or 412.

In certain aspects, the present disclosure relates to protein complexes that comprise an MISRII polypeptide. As used herein, the term "MISRII" refers to a family of Müllerian inhibiting substance receptor type II (MISRII) proteins from any species and variants derived from such MISRII proteins by mutagenesis or other modification. Reference to MISRII herein is understood to be a reference to any one of the currently identified forms. Members of the MISRII family are generally transmembrane proteins, composed of a ligand-binding extracellular domain with a cysteine-rich region, a transmembrane domain, and a cytoplasmic domain with predicted serine/threonine kinase activity.

The term "MISRII polypeptide" includes polypeptides comprising any naturally occurring polypeptide of an MISRII family member as well as any variants thereof (including mutants, fragments, fusions, and peptidomimetic forms) that retain a useful activity. Numbering of amino acids for all MISRII-related polypeptides described herein is based on the numbering of the human MISRII precursor protein sequence below (SEQ ID NO: 50), unless specifically designated otherwise.

The canonical human MISRII precursor protein sequence (NCBI Ref Seq NP_065434.1) is as follows:

```
                                                   (SEQ ID NO: 50)
  1 MLGSLGLWAL LPTAVEAPPN RRTCVFFEAP GVRGSTKTLG ELLDTGTELP

51 RAIRCLYSRC CFGIWNLTQD RAQVEMQGCR DSDEPGCESL HCDPSPRAHP

101 SPGSTLFTCS CGTDFCNANY SHLPPPGSPG TPGSQGPQAA PGESIWMALV

151 LLGLFLLLLL LLGSIILALL QRKNYRVRGE PVPEPRPDSG RDWSVELQEL

201 PELCFSQVIR EGGHAVVWAG QLQGKLVAIK AFPPRSVAQF QAERALYELP

251 GLQHDHIVRF ITASRGGPGR LLSGPLLVLE LHPKGSLCHY LTQYTSDWGS

301 SLRMALSLAQ GLAFLHEERW QNGQYKPGIA HRDLSSQNVL IREDGSCAIG

351 DLGLALVLPG LTQPPAWTPT QPQGPAAIME AGTQRYMAPE LLDKTLDLQD

401 WGMALRRADI YSLALLLWEI LSRCPDLRPD SSPPPFQLAY EAELGNTPTS

451 DELWALAVQE RRRPYIPSTW RCFATDPDGL RELLEDCWDA DPEARLTAEC

501 VQQRLAALAH PQESHPFPES CPRGCPPLCP EDCTSIPAPT ILPCRPQRSA

551 CHFSVQQGPC SRNPQPACTL SPV
```

The signal peptide is indicated by a single underline and the extracellular domain is indicated in bold font.

The processed extracellular MISRII polypeptide sequence is as follows:

```
                                                   (SEQ ID NO: 51)
PPNRRTCVFFEAPGVRGSTKTLGELLDTGTELPRAIRCLYSRCCFGIWNL

TQDRAQVEMQGCRDSDEPGCESLHCDPSPRAHPSPGSTLFTCSCGTDFCN

ANYSHLPPPGSPGTPGSQGPQAAPGESIWMAL
```

A nucleic acid sequence encoding the MISRII precursor protein is shown below (SEQ ID NO: 52), corresponding to nucleotides 81-1799 of Genbank Reference Sequence NM_020547.2. The signal sequence is underlined.

```
                                                   (SEQ ID NO: 52)
ATGCTAGGGTCTTTGGGGCTTTGGGCATTACTTCCCACAGCTGTGGAAGC

ACCCCCAAACAGGCGAACCTGTGTGTTCTTTGAGGCCCCTGGAGTGCGGG

GAAGCACAAAGACACTGGGAGAGCTGCTAGATACAGGCACAGAGCTCCCC

AGAGCTATCCGCTGCCTCTACAGCCGCTGCTGCTTTGGGATCTGGAACCT

GACCCAAGACCGGGCACAGGTGGAAATGCAAGGATGCCGAGACAGTGATG

AGCCAGGCTGTGAGTCCCTCCACTGTGACCCAAGTCCCCGAGCCCACCCC

AGCCCTGGCTCCACTCTCTTCACCTGCTCCTGTGGCACTGACTTCTGCAA

TGCCAATTACAGCCATCTGCCTCCTCCAGGGAGCCCTGGGACTCCTGGCT

CCCAGGGTCCCCAGGCTGCCCCAGGTGAGTCCATCTGGATGGCACTGGTG

CTGCTGGGGCTGTTCCTCCTCCTCCTGCTGCTGCTGGGCAGCATCATCTT
```

```
GGCCCTGCTACAGCGAAAGAACTACAGAGTGCGAGGTGAGCCAGTGCCAG

AGCCAAGGCCAGACTCAGGCAGGGACTGGAGTGTGGAGCTGCAGGAGCTG

CCTGAGCTGTGTTTCTCCCAGGTAATCCGGGAAGGAGGTCATGCAGTGGT

TTGGGCCGGGCAGCTGCAAGGAAAACTGGTTGCCATCAAGGCCTTCCCAC

CGAGGTCTGTGGCTCAGTTCCAAGCTGAGAGAGCATTGTACGAACTTCCA

GGCCTACAGCACGACCACATTGTCCGATTTATCACTGCCAGCCGGGGGGG

TCCTGGCCGCCTGCTCTCTGGGCCCCTGCTGGTACTGGAACTGCATCCCA

AGGGCTCCCTGTGCCACTACTTGACCCAGTACACCAGTGACTGGGGAAGT

TCCCTGCGGATGGCACTGTCCCTGGCCCAGGGCCTGGCATTTCTCCATGA

GGAGCGCTGGCAGAATGGCCAATATAAACCAGGTATTGCCCACCGAGATC
```

```
                                              (SEQ ID NO: 53)
CCCCCAAACAGGCGAACCTGTGTGTTCTTTGAGGCCCCTGGAGTGCGGGG

AAGCACAAAGACACTGGGAGAGCTGCTAGATACAGGCACAGAGCTCCCCA

GAGCTATCCGCTGCCTCTACAGCCGCTGCTGCTTTGGGATCTGGAACCTG

ACCCAAGACCGGGCACAGGTGGAAATGCAAGGATGCCGAGACAGTGATGA

GCCAGGCTGTGAGTCCCTCCACTGTGACCCAAGTCCCCGAGCCCACCCCA

GCCCTGGCTCCACTCTCTTCACCTGCTCCTGTGGCACTGACTTCTGCAAT

GCCAATTACAGCCATCTGCCTCCTCCAGGGAGCCCTGGGACTCCTGGCTC

CCAGGGTCCCCAGGCTGCCCCAGGTGAGTCCATCTGGATGGCACTG
```

An alternative isoform of the human MISRII precursor protein sequence, isoform 2 (NCBI Ref Seq NP_001158162.1), is as follows:

```
                                              (SEQ ID NO: 75)
  1 MLGSLGLWAL LPTAVEAPPN RRTCVFFEAP GVRGSTKTLG ELLDTGTELP

51 RAIRCLYSRC CFGIWNLTQD RAQVEMQGCR DSDEPGCESL HCDPSPRAHP

101 SPGSTLFTCS CGTDFCNANY SHLPPPGSPG TPGSQGPQAA PGESIWMALV

151 LLGLFLLLLL LLGSIILALL QRKNYRVRGE PVPEPRPDSG RDWSVELQEL

201 PELCFSQVIR EGGHAVVWAG QLQGKLVAIK AFPPRSVAQF QAEPALYELP

251 GLQHDHIVRF ITASRGGPGR LLSGPLLVLE LHPKGSLCHY LTQYTSDWGS

301 SLRMALSLAQ GLAFLHEERW QNGQYKPGIA HRDLSSQNVL IREDGSCAIG

351 DLGLALVLPG LTQPPAWTPT QPQGPAAIME AGTQRYMAPE LLDKTLDLQD

401 WGMALRRADI YSLALLLWEI LSRCPDLRPA VHHPSNWPMR QNWAIPLPLM

451 SYGPWQCRRG GVPTSHPPGA ALPQTLMG
```

The signal peptide is indicated by a single underline and the extracellular domain is indicated in bold font.

The processed extracellular MISRII polypeptide sequence (isoform 2) is as follows:

```
                                              (SEQ ID NO: 76)
PPNRRTCVFFEAPGVRGSTKTLGELLDTGTELPRAIRCLYSRCCFGIWNL

TQDRAQVEMQGCRDSDEPGCESLHCDPSPRAHPSPGSTLFTCSCGTDFCN

ANYSHLPPPGSPGTPGSQGPQAAPGESIWMAL
```

A nucleic acid sequence encoding the MISRII precursor protein (isoform 2) is shown below (SEQ ID NO: 77), corresponding to nucleotides 81-1514 of Genbank Reference Sequence NM_001164690.1. The signal sequence is underlined.

```
                                              (SEQ ID NO: 77)
ATGCTAGGGTCTTTGGGGCTTTGGGCATTACTTCCCACAGCTGTGGAAGC

ACCCCCAAACAGGCGAACCTGTGTGTTCTTTGAGGCCCCTGGAGTGCGGG

GAAGCACAAAGACACTGGGAGAGCTGCTAGATACAGGCACAGAGCTCCCC

AGAGCTATCCGCTGCCTCTACAGCCGCTGCTGCTTTGGGATCTGGAACCT

GACCCAAGACCGGGCACAGGTGGAAATGCAAGGATGCCGAGACAGTGATG

AGCCAGGCTGTGAGTCCCTCCACTGTGACCCAAGTCCCCGAGCCCACCCC
```

A nucleic acid sequence encoding the extracellular human MISRII polypeptide is as follows:

```
TGAGCAGCCAGAATGTGCTCATTCGGGAAGATGGATCGTGTGCCATTGGA

GACCTGGGCCTTGCCTTGGTGCTCCCTGGCCTCACTCAGCCCCCTGCCTG

GACCCCTACTCAACCACAAGGCCCAGCTGCCATCATGGAAGCTGGCACCC

AGAGGTACATGGCACCAGAGCTCTTGGACAAGACTCTGGACCTACAGGAT

TGGGGCATGGCCCTCCGACGAGCTGATATTTACTCTTTGGCTCTGCTCCT

GTGGGAGATACTGAGCCGCTGCCCAGATTTGAGGCCTGACAGCAGTCCAC

CACCCTTCCAACTGGCCTATGAGGCAGAACTGGGCAATACCCCTACCTCT

GATGAGCTATGGGCCTTGGCAGTGCAGGAGAGGAGGCGTCCCTACATCCC

ATCCACCTGGCGCTGCTTTGCCACAGACCCTGATGGGCTGAGGGAGCTCC

TAGAAGACTGTTGGGATGCAGACCCAGAAGCACGGCTGACAGCTGAGTGT

GTACAGCAGCGCCTGGCTGCCTTGGCCCATCCTCAAGAGAGCCACCCCTT

TCCAGAGAGCTGTCCACGTGGCTGCCCACCTCTCTGCCCAGAAGACTGTA

CTTCAATTCCTGCCCCTACCATCCTCCCCTGTAGGCCTCAGCGGAGTGCC

TGCCACTTCAGCGTTCAGCAAGGCCCTTGTTCCAGGAATCCTCAGCCTGC

CTGTACCCTTTCTCCTGTG
```

-continued
```
AGCCCTGGCTCCACTCTCTTCACCTGCTCCTGTGGCACTGACTTCTGCAA

TGCCAATTACAGCCATCTGCCTCCTCCAGGGAGCCCTGGGACTCCTGGCT

CCCAGGGTCCCCAGGCTGCCCCAGGTGAGTCCATCTGGATGGCACTGGTG

CTGCTGGGGCTGTTCCTCCTCCTCCTGCTGCTGCTGGGCAGCATCATCTT

GGCCCTGCTACAGCGAAAGAACTACAGAGTGCGAGGTGAGCCAGTGCCAG

AGCCAAGGCCAGACTCAGGCAGGGACTGGAGTGTGGAGCTGCAGGAGCTG

CCTGAGCTGTGTTTCTCCCAGGTAATCCGGGAAGGAGGTCATGCAGTGGT

TTGGGCCGGGCAGCTGCAAGGAAAACTGGTTGCCATCAAGGCCTTCCCAC
```

-continued
```
CGAGGTCTGTGGCTCAGTTCCAAGCTGAGAGAGCATTGTACGAACTTCCA

GGCCTACAGCACGACCACATTGTCCGATTTATCACTGCCAGCCGGGGGG

TCCTGGCCGCCTGCTCTCTGGGCCCCTGCTGGTACTGGAACTGCATCCCA

AGGGCTCCCTGTGCCACTACTTGACCCAGTACACCAGTGACTGGGGAAGT

TCCCTGCGGATGGCACTGTCCCTGGCCCAGGGCCTGGCATTTCTCCATGA

GGAGCGCTGGCAGAATGGCCAATATAAACCAGGTATTGCCCACCGAGATC

TGAGCAGCCAGAATGTGCTCATTCGGGAAGATGGATCGTGTGCCATTGGA

GACCTGGGCCTTGCCTTGGTGCTCCCTGGCCTCACTCAGCCCCCTGCCTG

GACCCCTACTCAACCACAAGGCCCAGCTGCCATCATGGAAGCTGGCACCC

AGAGGTACATGGCACCAGAGCTCTTGGACAAGACTCTGGACCTACAGGAT

TGGGGCATGGCCCTCCGACGAGCTGATATTTACTCTTTGGCTCTGCTCCT

GTGGGAGATACTGAGCCGCTGCCCAGATTTGAGGCCTGCAGTCCACCACC

CTTCCAACTGGCCTATGAGGCAGAACTGGGCAATACCCCTACCTCTGATG

AGCTATGGGCCTTGGCAGTGCAGGAGAGGAGGCGTCCCTACATCCCATCC

ACCTGGCGCTGCTTTGCCACAGACCCTGATGGGC
```

The nucleic acid sequence encoding processed soluble (extracellular) human MISRII polypeptide (isoform 2) is as follows:

(SEQ ID NO: 78)
```
CCCCCAAACAGGCGAACCTGTGTGTTCTTTGAGGCCCCTGGAGTGCGGG

AAGCACAAAGACACTGGGAGAGCTGCTAGATACAGGCACAGAGCTCCCCA
```

-continued
```
GAGCTATCCGCTGCCTCTACAGCCGCTGCTGCTTTGGGATCTGGAACCTG

ACCCAAGACCGGGCACAGGTGGAAATGCAAGGATGCCGAGACAGTGATGA

GCCAGGCTGTGAGTCCCTCCACTGTGACCCAAGTCCCCGAGCCCACCCCA

GCCCTGGCTCCACTCTCTTCACCTGCTCCTGTGGCACTGACTTCTGCAAT

GCCAATTACAGCCATCTGCCTCCTCCAGGGAGCCCTGGGACTCCTGGCTC

CCAGGGTCCCCAGGCTGCCCCAGGTGAGTCCATCTGGATGGCACTG
```

An alternative isoform of the human MISRII precursor protein sequence, isoform 3 (NCBI Ref Seq NP_001158163.1), is as follows:

(SEQ ID NO: 79)
```
  1 MLGSLGLWAL LPTAVEAPPN RRTCVFFEAP GVRGSTKTLG ELLDTGTELP

51 RAIRCLYSRC CFGIWNLTQD RAQVEMQGCR DSDEPGCESL HCDPSPRAHP

101 SPGSTLFTCS CGTDFCNANY SHLPPPGSPG TPGSQGPQAA PGESIWMALV

151 LLGLFLLLLL LLGSIILALL QRKNYRVRGE PVPEPRPDSG RDWSVELQEL

201 PELCFSQVIR EGGHAVVWAG QLQGKLVAIK AFPPRSVAQF QAERALYELP

251 GLQHDHIVRF ITASRGGPGR LLSGPLLVLE LHPKGSLCHY LTQYTSDWGS

301 SLRMALSLAQ GLAFLHEERW QNGQYKPGIA HRDLSSQNVL IREDGSCAIG

351 DLGLALVLPG LTQPPAWTPT QPQGPAAIME DPDGLRELLE DCWDADPEAR

401 LTAECVQQRL AALAHPQESH PFPESCPRGC PPLCPEDCTS IPAPTILPCR

451 PQRSACHFSV QQGPCSRNPQ PACTLSPV
```

The signal peptide is indicated by a single underline and the extracellular domain is indicated in bold font.

The processed extracellular MISRII polypeptide sequence (isoform 3) is as follows:

(SEQ ID NO: 80)
```
PPNRRTCVFFEAPGVRGSTKTLGELLDTGTELPRAIRCLYSRCCFGIWNL

TQDRAQVEMQGCRDSDEPGCESLHCDPSPRAHPSPGSTLFTCSCGTDFCN

ANYSHLPPPGSPGTPGSQGPQAAPGESIWMAL
```

A nucleic acid sequence encoding human MISRII precursor protein (isoform 3) is shown below (SEQ ID NO: 81), corresponding to nucleotides 81-1514 of Genbank Reference Sequence NM_001164691.1. The signal sequence is underlined.

(SEQ ID NO: 81)
```
ATGCTAGGGTCTTTGGGGCTTTGGGCATTACTTCCCACAGCTGTGGAAGC

ACCCCCAAACAGGCGAACCTGTGTGTTCTTTGAGGCCCCTGGAGTGCGGG

GAAGCACAAAGACACTGGGAGAGCTGCTAGATACAGGCACAGAGCTCCCC

AGAGCTATCCGCTGCCTCTACAGCCGCTGCTGCTTTGGGATCTGGAACCT

GACCCAAGACCGGGCACAGGTGGAAATGCAAGGATGCCGAGACAGTGATG

AGCCAGGCTGTGAGTCCCTCCACTGTGACCCAAGTCCCCGAGCCCACCCC

AGCCCTGGCTCCACTCTCTTCACCTGCTCCTGTGGCACTGACTTCTGCAA

TGCCAATTACAGCCATCTGCCTCCTCCAGGGAGCCCTGGGACTCCTGGCT
```

```
CCCAGGGTCCCCAGGCTGCCCCAGGTGAGTCCATCTGGATGGCACTGGTG

CTGCTGGGGCTGTTCCTCCTCCTCCTGCTGCTGCTGGGCAGCATCATCTT

GGCCCTGCTACAGCGAAAGAACTACAGAGTGCGAGGTGAGCCAGTGCCAG

AGCCAAGGCCAGACTCAGGCAGGGACTGGAGTGTGGAGCTGCAGGAGCTG

CCTGAGCTGTGTTTCTCCCAGGTAATCCGGGAAGGAGGTCATGCAGTGGT

TTGGGCCGGGCAGCTGCAAGGAAAACTGGTTGCCATCAAGGCCTTCCCAC

CGAGGTCTGTGGCTCAGTTCCAAGCTGAGAGAGCATTGTACGAACTTCCA

GGCCTACAGCACGACCACATTGTCCGATTTATCACTGCCAGCCGGGGGG

TCCTGGCCGCCTGCTCTCTGGGCCCCTGCTGGTACTGGAACTGCATCCCA

AGGGCTCCCTGTGCCACTACTTGACCCAGTACACCAGTGACTGGGGAAGT

TCCCTGCGGATGGCACTGTCCCTGGCCCAGGGCCTGGCATTTCTCCATGA

GGAGCGCTGGCAGAATGGCCAATATAAACCAGGTATTGCCCACCGAGATC

TGAGCAGCCAGAATGTGCTCATTCGGGAAGATGGATCGTGTGCCATTGGA

GACCTGGGCCTTGCCTTGGTGCTCCCTGGCCTCACTCAGCCCCCTGCCTG

GACCCCTACTCAACCACAAGGCCCAGCTGCCATCATGGAAGACCCTGATG

GGCTGAGGGAGCTCCTAGAAGACTGTTGGGATGCAGACCCAGAAGCACGG

CTGACAGCTGAGTGTGTACAGCAGCGCCTGGCTGCCTTGGCCCATCCTCA

AGAGAGCCACCCCTTTCCAGAGAGCTGTCCACGTGGCTGCCCACCTCTCT

GCCCAGAAGACTGTACTTCAATTCCTGCCCCTACCATCCTCCCCTGTAGG

CCTCAGCGGAGTGCCTGCCACTTCAGCGTTCAGCAAGGCCCTTGTTCCAG

GAATCCTCAGCCTGCCTGTACCCTTTCTCCTGTG
```

A nucleic acid sequence encoding processed soluble (extracellular) human MISRII polypeptide (isoform 3) is as follows:

```
                                        (SEQ ID NO: 82)
CCCCCAAACAGGCGAACCTGTGTGTTCTTTGAGGCCCCTGGAGTGCGGGG

AAGCACAAAGACACTGGGAGAGCTGCTAGATACAGGCACAGAGCTCCCCA

GAGCTATCCGCTGCCTCTACAGCCGCTGCTGCTTTGGGATCTGGAACCTG

ACCCAAGACCGGGCACAGGTGGAAATGCAAGGATGCCGAGACAGTGATGA

GCCAGGCTGTGAGTCCCTCCACTGTGACCCAAGTCCCCGAGCCCACCCCA

GCCCTGGCTCCACTCTCTTCACCTGCTCCTGTGGCACTGACTTCTGCAAT

GCCAATTACAGCCATCTGCCTCCTCCAGGGAGCCCTGGGACTCCTGGCTC

CCAGGGTCCCCAGGCTGCCCCAGGTGAGTCCATCTGGATGGCACTG
```

In certain embodiments, the disclosure relates to heteromultimer complexes that comprise at least one MISRII polypeptide, which includes fragments, functional variants, and modified forms thereof. Preferably, MISRII polypeptides for use in accordance with inventions of the disclosure (e.g., heteromultimer complexes comprising a MISRII polypeptide and uses thereof) are soluble (e.g., an extracellular domain of MISRII). In other preferred embodiments, MISRII polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one MISRII polypeptide that is at least 70%, 75%, 80%, 85%, 90%, 95%, 97%, 98%, or 99% identical to the amino acid sequence of SEQ ID NOs: 50, 51, 75, 76, 79, or 80. In some embodiments, heteromultimer complexes of the disclosure consist or consist essentially of at least one MISRII polypeptide that is at least 70%, 75%, 80%, 85%, 90%, 95%, 97%, 98%, or 99% identical to the amino acid sequence of SEQ ID NOs: 50, 51, 75, 76, 79, or 80.

In certain aspects, the present disclosure relates to protein complexes that comprise an ALK1 polypeptide. As used herein, the term "ALK1" refers to a family of activin receptor-like kinase-1 proteins from any species and variants derived from such ALK1 proteins by mutagenesis or other modification. Reference to ALK1 herein is understood to be a reference to any one of the currently identified forms. Members of the ALK1 family are generally transmembrane proteins, composed of a ligand-binding extracellular domain with a cysteine-rich region, a transmembrane domain, and a cytoplasmic domain with predicted serine/threonine kinase activity.

The term "ALK1 polypeptide" includes polypeptides comprising any naturally occurring polypeptide of an ALK1 family member as well as any variants thereof (including mutants, fragments, fusions, and peptidomimetic forms) that retain a useful activity. Numbering of amino acids for all ALK1-related polypeptides described herein is based on the numbering of the human ALK1 precursor protein sequence below (SEQ ID NO: 14), unless specifically designated otherwise.

The human ALK1 precursor protein sequence (NCBI Ref Seq NP_000011.2) is as follows:

```
                                                    (SEQ ID NO: 14)
  1 MTLGSPRKGL LMLLMALVTQ GDPVKPSRGP LVTCTCESPH CKGPTCRGAW

51 CTVVLVREEG RHPQEHRGCG NLHRELCRGR PTEFVNHYCC DSHLCNHNVS

101 LVLEATQPPS EQPGTDGQLA LILGPVLALL ALVALGVLGL WHVRRRQEKQ

151 RGLHSELGES SLILKASEQG DSMLGDLLDS DCTTGSGSGL PFLVQRTVAR

201 QVALVECVGK GRYGEVWRGL WHGESVAVKI FSSRDEQSWF RETEIYNTVL

251 LRHDNILGFI ASDMTSRNSS TQLWLITHYH EHGSLYDFLQ RQTLEPHLAL

301 RLAVSAACGL AHLHVEIFGT QGKPAIAHRD FKSRNVLVKS NLQCCIADLG

351 LAVMHSQGSD YLDIGNNPRV GTKRYMAPEV LDEQIRTDCF ESYKWTDIWA

401 FGLVLWEIAR RTIVNGIVED YRPPFYDVVP NDPSFEDMKK VVCVDQQTPT
```

```
451 IPNRLAADPV LSGLAQMMRE CWYPNPSARL TALRIKKTLQ KISNSPEKPK

501 VIQ
```

The signal peptide is indicated by a single underline and the extracellular domain is indicated in bold font.

The processed extracelluar ALK1 polypeptide sequence is as follows:

(SEQ ID NO: 15)
DPVKPSRGPLVTCTCESPHCKGPTCRGAWCTVVLVREEGRHPQEHRGCGN
LHRELCRGRPTEFVNHYCCDSHLCNHNVSLVLEATQPPSEQPGTDGQ

A nucleic acid sequence encoding human ALK1 precursor protein is shown below (SEQ ID NO: 16), corresponding to nucleotides 284-1792 of Genbank Reference Sequence NM_000020.2. The signal sequence is underlined.

(SEQ ID NO: 16)
ATGACCTTGGGCTCCCCCAGGAAAGGCCTTCTGATGCTGCTGATGGCCTTT
GGTGACCCAGGGAGACCCTGTGAAGCCGTCTCGGGGCCCGCTGGTGACCT
GCACGTGTGAGAGCCCACATTGCAAGGGGCCTACCTGCCGGGGGCCTGG
TGCACAGTAGTGCTGGTGCGGGAGGAGGGGAGGCACCCCAGGAACATCG
GGGCTGCGGGAACTTGCACAGGGAGCTCTGCAGGGGGCGCCCCACCGAGT
TCGTCAACCACTACTGCTGCGACAGCCACCTCTGCAACCACAACGTGTCC
CTGGTGCTGGAGGCCACCCAACCTCCTTCGGAGCAGCCGGGAACAGATGG
CCAGCTGGCCCTGATCCTGGGCCCCGTGCTGGCCTTGCTGGCCCTGGTGG
CCCTGGGTGTCCTGGGCCTGTGGCATGTCCGACGGAGGCAGGAGAAGCAG
CGTGGCCTGCACAGCGAGCTGGGAGAGTCCAGTCTCATCCTGAAAGCATC
TGAGCAGGGCGACAGCATGTTGGGGGACCTCCTGGACAGTGACTGCACCA
CAGGGAGTGGCTCAGGGCTCCCCTTCCTGGTGCAGAGGACAGTGGCACGG
CAGGTTGCCTTGGTGGAGTGTGTGGGAAAAGGCCGCTATGGCGAAGTGTG
GCGGGGCTTGTGGCACGGTGAGAGTGTGGCCGTCAAGATCTTCTCCTCGA
GGGATGAACAGTCCTGGTTCCGGGAGACTGAGATCTATAACACAGTGTTG
CTCAGACACGACAACATCCTAGGCTTCATCGCCTCAGACATGACCTCCCG
CAACTCGAGCACGCAGCTGTGGCTCATCACGCACTACCACGAGCACGGCT
CCCTCTACGACTTTCTGCAGAGACAGACGCTGGAGCCCCATCTGGCTCTG
AGGCTAGCTGTGTCCGCGGCATGCGGCCTGGCGCACCTGCACGTGGAGAT
CTTCGGTACACAGGGCAAACCAGCCATTGCCCACCGCGACTTCAAGAGCC
GCAATGTGCTGGTCAAGAGCAACCTGCAGTGTTGCATCGCCGACCTGGGC
CTGGCTGTGATGCACTCACAGGGCAGCGATTACCTGGACATCGGCAACAA
CCCGAGAGTGGGCACCAAGCGGTACATGGCACCCGAGGTGCTGGACGAGC
AGATCCGCACGGACTGCTTTGAGTCCTACAAGTGGACTGACATCTGGGCC
TTTGGCCTGGTGCTGTGGGAGATTGCCCGCCGGACCATCGTGAATGGCAT
CGTGGAGGACTATAGACCACCCTTCTATGATGTGGTGCCCAATGACCCCA
GCTTTGAGGACATGAAGAAGGTGGTGTGTGTGGATCAGCAGACCCCCACC

ATCCCTAACCGGCTGGCTGCAGACCCGGTCCTCTCAGGCCTAGCTCAGAT
GATGCGGGAGTGCTGGTACCCAAACCCCTCTGCCCGACTCACCGCGCTGC
GGATCAAGAAGACACTACAAAAAATTAGCAACAGTCCAGAGAAGCCTAAA
GTGATTCAA
```

A nucleic acid sequence encoding processed extracelluar ALK1 polypeptide is as follows:

(SEQ ID NO: 17)
GACCCTGTGAAGCCGTCTCGGGGCCCGCTGGTGACCTGCACGTGTGAGAG
CCCACATTGCAAGGGGCCTACCTGCCGGGGGCCTGGTGCACAGTAGTGC
TGGTGCGGGAGGAGGGGAGGCACCCCCAGGAACATCGGGGCTGCGGGAAC
TTGCACAGGGAGCTCTGCAGGGGGCGCCCCACCGAGTTCGTCAACCACTA
CTGCTGCGACAGCCACCTCTGCAACCACAACGTGTCCCTGGTGCTGGAGG
CCACCCAACCTCCTTCGGAGCAGCCGGGAACAGATGGCCAG
```

In certain embodiments, the disclosure relates to heteromultimer complexes that comprise at least one ALK1 polypeptide, which includes fragments, functional variants, and modified forms thereof. Preferably, ALK1 polypeptides for use in accordance with inventions of the disclosure (e.g., heteromultimer complexes comprising an ALK1 polypeptide and uses thereof) are soluble (e.g., an extracellular domain of ALK1). In other preferred embodiments, ALK1 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one ALK1 polypeptide that is at least 70%, 75%, 80%, 85%, 90%, 95%, 97%, 98%, or 99% identical to the amino acid sequence of SEQ ID NO: 14, 15, 124, 126, 413, or 414. In some embodiments, heteromultimer complexes of the disclosure consist or consist essentially of at least one ALK1 polypeptide that is at least 70%, 75%, 80%, 85%, 90%, 95%, 97%, 98%, or 99% identical to the amino acid sequence of SEQ ID NO: 14, 15, 124, 126, 413, or 414.

In certain aspects, the present disclosure relates to protein complexes that comprise an ALK2 polypeptide. As used herein, the term "ALK2" refers to a family of activin receptor-like kinase-2 proteins from any species and variants derived from such ALK2 proteins by mutagenesis or other modification. Reference to ALK2 herein is understood to be a reference to any one of the currently identified forms. Members of the ALK2 family are generally transmembrane proteins, composed of a ligand-binding extracellular domain with a cysteine-rich region, a transmembrane domain, and a cytoplasmic domain with predicted serine/threonine kinase activity.

The term "ALK2 polypeptide" includes polypeptides comprising any naturally occurring polypeptide of an ALK2 family member as well as any variants thereof (including mutants, fragments, fusions, and peptidomimetic forms) that retain a useful activity. Numbering of amino acids for all ALK2-related polypeptides described herein is based on the numbering of the human ALK2 precursor protein sequence below (SEQ ID NO: 18), unless specifically designated otherwise.

The human ALK2 precursor protein sequence (NCBI Ref Seq NP_001096.1) is as follows:

(SEQ ID NO: 18)
```
  1 MVDGVMILPV LIMIALPSPS MEDEKPKVNP KLYMCVCEGL SCGNEDHCEG

51 QQCFSSLSIN DGFHVYQKGC FQVYEQGKMT CKTPPSPGQA VECCQGDWCN

101 RNITAQLPTK GKSFPGTQNF HLEVGLIILS VVFAVCLLAC LLGVALRKFK

151 RRNQERLNPR DVEYGTIEGL ITTNVGDSTL ADLLDHSCTS GSGSGLPFLV

201 QRTVARQITL LECVGKGRYG EVWRGSWQGE NVAVKIFSSR DEKSWFRETE

251 LYNTVMLRHE NILGFIASDM TSRHSSTQLW LITHYHEMGS LYDYLQLTTL

301 DTVSCLRIVL SIASGLAHLH IEIFGTQGKP AIAHRDLKSK NILVKKNGQC

351 CIADLGLAVM HSQSTNQLDV GNNPRVGTKR YMAPEVLDET IQVDCFDSYK

401 RVDIWAFGLV LWEVARRMVS NGIVEDYKPP FYDVVPNDPS FEDMRKVVCV

451 DQQRPNIPNR WFSDPTLTSL AKLMKECWYQ NPSARLTALR IKKTLTKIDN

501 SLDKLKTDC
```

The signal peptide is indicated by a single underline and the extracellular domain is indicated in bold font.

The processed extracellular ALK2 polypeptide sequence is as follows:

(SEQ ID NO: 19)
MEDEKPKVNPKLYMCVCEGLSCGNEDHCEGQQCFSSLSINDGFHVYQKGC
FQVYEQGKMTCKTPPSPGQAVECCQGDWCNRNITAQLPTKGKSFPGTQNF
HLE

A nucleic acid sequence encoding human ALK2 precursor protein is shown below (SEQ ID NO: 20), corresponding to nucleotides 431-1957 of Genbank Reference Sequence NM_001105.4. The signal sequence is underlined.

(SEQ ID NO: 20)
ATGGTAGATGGAGTGATGATTCTTCCTGTGCTTATCATGATTGCTCTCCC
CTCCCCTAGTATGGAAGATGAGAAGCCCAAGGTCAACCCCAAACTCTACA
TGTGTGTGTGTGAAGGTCTCTCCTGCGGTAATGAGGACCACTGTGAAGGC
CAGCAGTGCTTTTCCTCACTGAGCATCAACGATGGCTTCCACGTCTACCA
GAAAGGCTGCTTCCAGGTTTATGAGCAGGGAAAGATGACCTGTAAGACCC
CGCCGTCCCCTGGCCAAGCCGTGGAGTGCTGCCAAGGGGACTGGTGTAAC
AGGAACATCACGGCCCAGCTGCCCACTAAAGGAAAATCCTTCCCTGGAAC
ACAGAATTTCCACTTGGAGGTTGGCCTCATTATTCTCTCTGTAGTGTTCG
CAGTATGTCTTTTAGCCTGCCTGCTGGGAGTTGCTCTCCGAAAATTTAAA
AGGCGCAACCAAGAACGCCTCAATCCCCGAGACGTGGAGTATGGCACTAT
CGAAGGGCTCATCACCACCAATGTTGGAGACAGCACTTTAGCAGATTTAT
TGGATCATTCGTGTACATCAGGAAGTGGCTCTGGTCTTCCTTTTCTGGTA
CAAAGAACAGTGGCTCGCCAGATTACACTGTTGGAGTGTGTCGGGAAAGG
CAGGTATGGTGAGGTGTGGAGGGGCAGCTGGCAAGGGGAGAATGTTGCCG
TGAAGATCTTCTCCTCCCGTGATGAGAAGTCATGGTTCAGGGAAACGGAA
TTGTACAACACTGTGATGCTGAGGCATGAAAATATCTTAGGTTTCATTGC
TTCAGACATGACATCAAGACACTCCAGTACCCAGCTGTGGTTAATTACAC
ATTATCATGAAATGGGATCGTTGTACGACTATCTTCAGCTTACTACTCTG
GATACAGTTAGCTGCCTTCGAATAGTGCTGTCCATAGCTAGTGGTCTTGC
ACATTTGCACATAGAGATATTTGGGACCCAAGGGAAACCAGCCATTGCCC
ATCGAGATTTAAAGAGCAAAAATATTCTGGTTAAGAAGAATGGACAGTGT
TGCATAGCAGATTTGGGCCTGGCAGTCATGCATTCCCAGAGCACCAATCA
GCTTGATGTGGGGAACAATCCCCGTGTGGGCACCAAGCGCTACATGGCCC
CCGAAGTTCTAGATGAAACCATCCAGGTGGATTGTTTCGATTCTTATAAA
AGGGTCGATATTTGGGCCTTTGGACTTGTTTTGTGGGAAGTGGCCAGGCG
GATGGTGAGCAATGGTATAGTGGAGGATTACAAGCCACCGTTCTACGATG
TGGTTCCCAATGACCCAAGTTTTGAAGATATGAGGAAGGTAGTCTGTGTG
GATCAACAAAGGCCAAACATACCCAACAGATGGTTCTCAGACCCGACATT
AACCTCTCTGGCCAAGCTAATGAAAGAATGCTGGTATCAAAATCCATCCG
CAAGACTCACAGCACTGCGTATCAAAAAGACTTTGACCAAAATTGATAAT
TCCCTCGACAAATTGAAAACTGACTGT
```

A nucleic acid sequence encoding the extracellular ALK2 polypeptide is as follows (SEQ ID NO: 21)
ATGGAAGATGAGAAGCCCAAGGTCAACCCCAAACTCTACATGTGTGTGTG
TGAAGGTCTCTCCTGCGGTAATGAGGACCACTGTGAAGGCCAGCAGTGCT
TTTCCTCACTGAGCATCAACGATGGCTTCCACGTCTACCAGAAAGGCTGC
TTCCAGGTTTATGAGCAGGGAAAGATGACCTGTAAGACCCCGCCGTCCCC
TGGCCAAGCCGTGGAGTGCTGCCAAGGGGACTGGTGTAACAGGAACATCA
CGGCCCAGCTGCCCACTAAAGGAAAATCCTTCCCTGGAACACAGAATTTC
CACTTGGAG In certain embodiments, the disclosure relates to heteromultimer complexes that comprise at least one ALK2 polypeptide, which includes fragments, functional variants, and modified forms thereof. Preferably, ALK2 polypeptides for use in accordance with inventions of the disclosure (e.g., heteromultimer complexes comprising an ALK2 polypeptide and uses thereof) are soluble (e.g., an extracellular domain of ALK2). In other preferred embodiments, ALK2 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one ALK2 polypeptide that is at least 70%, 75%, 80%, 85%, 90%, 95%, 97%, 98%, or 99% identical to the amino acid sequence of SEQ ID NO: 18 or 19. In some embodiments, heteromultimer complexes of the disclosure consist or consist essentially of at least one ALK2 polypeptide that is at least 70%, 75%, 80%, 85%, 90%, 95%, 97%, 98%, or 99% identical to the amino acid sequence of SEQ ID NO: 18 or 19.

In certain aspects, the present disclosure relates to protein complexes that comprise an ALK3 polypeptide. As used herein, the term "ALK3" refers to a family of activin receptor-like kinase-3 proteins from any species and variants derived from such ALK3 proteins by mutagenesis or other modification. Reference to ALK3 herein is understood to be a reference to any one of the currently identified forms. Members of the ALK3 family are generally transmembrane proteins, composed of a ligand-binding extracellular domain with a cysteine-rich region, a transmembrane domain, and a cytoplasmic domain with predicted serine/threonine kinase activity.

The term "ALK3 polypeptide" includes polypeptides comprising any naturally occurring polypeptide of an ALK3 family member as well as any variants thereof (including mutants, fragments, fusions, and peptidomimetic forms) that retain a useful activity. Numbering of amino acids for all ALK3-related polypeptides described herein is based on the numbering of the human ALK3 precursor protein sequence below (SEQ ID NO: 22), unless specifically designated otherwise.

The human ALK3 precursor protein sequence (NCBI Ref Seq NP_004320.2) is as follows:

```
                                                           (SEQ ID NO: 22)
  1 MPQLYIYIRL LGAYLFIISR VQGQNLDSML HGTGMKSDSD QKKSENGVTL APEDTLPFLK

61 CYCSGHCPDD AINNTCITNG HCFAIIEEDD QGETTLASGC MKYEGSDFQC KDSPKAQLRR

121 TIECCRTNLC NQYLQPTLPP VVIGPFFDGS IRWLVLLISM AVCIIAMIIF SSCFCYKHYC

181 KSISSRRRYN RDLEQDEAFI PVGESLKDLI DQSQSSGSGS GLPLLVQRTI AKQIQMVRQV

241 GKGRYGEVWM GKWRGEKVAV KVFFTTEEAS WFRETEIYQT VLMRHENILG FIAADIKGTG

301 SWTQLYLITD YHENGSLYDF LKCATLDTRA LLKLAYSAAC GLCHLHTEIY GTQGKPAIAH

361 RDLKSKNILI KKNGSCCIAD LGLAVKFNSD TNEVDVPLNT RVGTKRYMAP EVLDESLNKN

421 HFQPYIMADI YSFGLIIWEM ARRCITGGIV EEYQLPYYNM VPSDPSYEDM REVVCVKRLR

481 PIVSNRWNSD ECLRAVLKLM SECWAHNPAS RLTALRIKKT LAKMVESQDV KI
```

The signal peptide is indicated by a single underline and the extracellular domain is indicated in bold font.

The processed extracellular ALK3 polypeptide sequence is as follows:

```
                                                           (SEQ ID NO: 23)
  1 QNLDSMLHGT GMKSDSDQKK SENGVTLAPE DTLPFLKCYC SGHCPDDAIN NTCITNGHCF

61 AIIEEDDQGE TTLASGCMKY EGSDFQCKDS PKAQLRRTIE CCRTNLCNQY LQPTLPPVVI

121 GPFFDGSIR
```

A nucleic acid sequence encoding human ALK3 precursor protein is shown below (SEQ ID NO: 24), corresponding to nucleotides 549-2144 of Genbank Reference Sequence NM_004329.2. The signal sequence is underlined and the extracellular domain is indicated in bold font.

```
                                                           (SEQ ID NO: 24)
  1 ATGCCTCAGC TATACATTTA CATCAGATTA TTGGGAGCCT ATTTGTTCAT CATTTCTCGT

61 GTTCAAGGAC AGAATCTGGA TAGTATGCTT CATGGCACTG GGATGAAATC AGACTCCGAC

121 CAGAAAAAGT CAGAAAATGG AGTAACCTTA GCACCAGAGG ATACCTTGCC TTTTTTAAAG

181 TGCTATTGCT CAGGGCACTG TCCAGATGAT GCTATTAATA ACACATGCAT AACTAATGGA

241 CATTGCTTTG CCATCATAGA AGAAGATGAC CAGGGAGAAA CCACATTAGC TTCAGGGTGT
```

-continued

```
 301 ATGAAATATG AAGGATCTGA TTTTCAGTGC AAAGATTCTC CAAAAGCCCA GCTACGCCGG
 361 ACAATAGAAT GTTGTCGGAC CAATTTATGT AACCAGTATT TGCAACCCAC ACTGCCCCCT
 421 GTTGTCATAG GTCCGTTTTT TGATGGCAGC ATTCGATGGC TGGTTTTGCT CATTTCTATG
 481 GCTGTCTGCA TAATTGCTAT GATCATCTTC TCCAGCTGCT TTTGTTACAA ACATTATTGC
 541 AAGAGCATCT CAAGCAGACG TCGTTACAAT CGTGATTTGG AACAGGATGA AGCATTTATT
 601 CCAGTTGGAG AATCACTAAA AGACCTTATT GACCAGTCAC AAAGTTCTGG TAGTGGGTCT
 661 GGACTACCTT TATTGGTTCA GCGAACTATT GCCAAACAGA TTCAGATGGT CCGGCAAGTT
 721 GGTAAAGGCC GATATGGAGA AGTATGGATG GGCAAATGGC GTGGCGAAAA AGTGGCGGTG
 781 AAAGTATTCT TTACCACTGA AGAAGCCAGC TGGTTTCGAG AAACAGAAAT CTACCAAACT
 841 GTGCTAATGC GCCATGAAAA CATACTTGGT TTCATAGCGG CAGACATTAA AGGTACAGGT
 901 TCCTGGACTC AGCTCTATTT GATTACTGAT TACCATGAAA ATGGATCTCT CTATGACTTC
 961 CTGAAATGTG CTACACTGGA CACCAGAGCC CTGCTTAAAT TGGCTTATTC AGCTGCCTGT
1021 GGTCTGTGCC ACCTGCACAC AGAAATTTAT GGCACCCAAG GAAAGCCCGC AATTGCTCAT
1081 CGAGACCTAA AGAGCAAAAA CATCCTCATC AAGAAAAATG GGAGTTGCTG CATTGCTGAC
1141 CTGGGCCTTG CTGTTAAATT CAACAGTGAC ACAAATGAAG TTGATGTGCC CTTGAATACC
1201 AGGGTGGGCA CCAAACGCTA CATGGCTCCC GAAGTGCTGG ACGAAAGCCT GAACAAAAAC
1261 CACTTCCAGC CCTACATCAT GGCTGACATC TACAGCTTCG GCCTAATCAT TTGGGAGATG
1321 GCTCGTCGTT GTATCACAGG AGGGATCGTG GAAGAATACC AATTGCCATA TTACAACATG
1381 GTACCGAGTG ATCCGTCATA CGAAGATATG CGTGAGGTTG TGTGTGTCAA ACGTTTGCGG
1441 CCAATTGTGT CTAATCGGTG GAACAGTGAT GAATGTCTAC GAGCAGTTTT GAAGCTAATG
1501 TCAGAATGCT GGGCCCACAA TCCAGCCTCC AGACTCACAG CATTGAGAAT TAAGAAGACG
1561 CTTGCCAAGA TGGTTGAATC CCAAGATGTA AAAATC
```

A nucleic acid sequence encoding the extracelluar human ALK3 polypeptide is as follows:

(SEQ ID NO: 25)
```
  1 CAGAATCTGG ATAGTATGCT TCATGGCACT GGGATGAAAT CAGACTCCGA CCAGAAAAAG
 61 TCAGAAAATG GAGTAACCTT AGCACCAGAG GATACCTTGC CTTTTTTAAA GTGCTATTGC
121 TCAGGGCACT GTCCAGATGA TGCTATTAAT AACACATGCA TAACTAATGG ACATTGCTTT
181 GCCATCATAG AAGAAGATGA CCAGGGAGAA ACCACATTAG CTTCAGGGTG TATGAAATAT
241 GAAGGATCTG ATTTTCAGTG CAAAGATTCT CCAAAAGCCC AGCTACGCCG GACAATAGAA
301 TGTTGTCGGA CCAATTTATG TAACCAGTAT TTGCAACCCA CACTGCCCCC TGTTGTCATA
361 GGTCCGTTTT TTGATGGCAG CATTCGA
```

A general formula for an active (e.g., ligand binding) ALK3 polypeptide is one that comprises a polypeptide that begins at any amino acid position 25-31 (i.e., position 25, 26, 27, 28, 29, 30, or 31) of SEQ ID NO: 22 and ends at any amino acid position 140-152 of SEQ ID NO: 22 (i.e., 140, 141, 142, 143, 144, 145, 146, 147, 148, 149, 150, 151, or 152). See U.S. Pat. No. 8,338,377, the teachings of which are incorporated herein by reference in their entirety.

In certain embodiments, the disclosure relates to heteromultimer complexes that comprise at least one ALK3 polypeptide, which includes fragments, functional variants, and modified forms thereof. Preferably, ALK3 polypeptides for use in accordance with inventions of the disclosure (e.g., heteromultimer complexes comprising an ALK3 polypeptide and uses thereof) are soluble (e.g., an extracellular domain of ALK3). In other preferred embodiments, ALK3 polypeptides for use in accordance with the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one ALK3 polypeptide that comprises, consists, or consists essentially of an amino acid beginning at any amino acid position 25-31 (i.e., position 25, 26, 27, 28, 29, 30, or 31) of SEQ ID NO: 22 and ending at any amino acid position 140-153 of SEQ ID NO: 22 (i.e., 140, 141, 142, 143, 144, 145, 146, 147, 148, 149, 150, 151, or 152) of SEQ ID NO: 22. In some embodiments, heteromultimer complexes of the disclosure comprise at least one ALK3 polypeptide that is at least 70%, 75%, 80%, 85%, 90%, 95%, 97%, 98%, or 99% identical to the amino acid sequence of SEQ ID NO: 22, 23, 115, 117, 407, or 408. In some embodiments, heteromultimer complexes of the disclosure consist or consist essentially of at least one ALK3 polypeptide that is at least 70%, 75%, 80%, 85%, 90%, 95%, 97%, 98%, or 99% identical to the amino acid sequence of SEQ ID NO: 22, 23, 115, 117, 407, or 408.

In certain aspects, the present disclosure relates to protein complexes that comprise an ALK4 polypeptide. As used herein, the term "ALK4" refers to a family of activin receptor-like kinase-4 proteins from any species and variants derived from such ALK4 proteins by mutagenesis or other modification. Reference to ALK4 herein is understood to be a reference to any one of the currently identified forms. Members of the ALK4 family are generally transmembrane proteins, composed of a ligand-binding extracellular domain with a cysteine-rich region, a transmembrane domain, and a cytoplasmic domain with predicted serine/threonine kinase activity.

The term "ALK4 polypeptide" includes polypeptides comprising any naturally occurring polypeptide of an ALK4 family member as well as any variants thereof (including mutants, fragments, fusions, and peptidomimetic forms) that retain a useful activity. Numbering of amino acids for all ALK4-related polypeptides described herein is based on the numbering of the human ALK4 precursor protein sequence below (SEQ ID NO: 26), unless specifically designated otherwise.

The canonical human ALK4 precursor protein sequence (NCBI Ref Seq NP_004293) is as follows:

```
                                                    (SEQ ID NO: 26)
  1 MAESAGASSFFPLVVLLLAGSGGSGPRGVQ ALLCACTSCL QANYTCETDG ACMVSIFNLD

61 GMEHHVRTCI PKVELVPAGK PFYCLSSEDL RNTHCCYTDY CNRIDLRVPS GHLKEPEHPS

121 MWGPVELVGI IAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK DNGTWTQLWL VSDYHEHGSL FDYLNRYTVT

301 IEGMIKLALS AASGLAHLHM EIVGTQGKPG IAHRDLKSKN ILVKKNGMCA IADLGLAVRH

361 DAVTDTIDIA PNQRVGTKRY MAPEVLDETI NMKHFDSFKC ADIYALGLVY WEIARRCNSG

421 GVHEEYQLPY YDLVPSDPSI EEMRKVVCDQ KLRPNIPNWW QSYEALRVMG KMMRECWYAN

481 GAARLTALRI KKTLSQLSVQ EDVKI
```

The signal peptide is indicated by a single underline and the extracellular domain is indicated in bold font.

The processed extracellular human ALK4 polypeptide sequence is as follows:

```
                                                    (SEQ ID NO: 27)
SGPRGVQALLCACTSCLQANYTCETDGACMVSIFNLDGMEHHVRTCIPKV

ELVPAGKPFYCLSSEDLRNTHCCYTDYCNRIDLRVPSGHLKEPEHPSMWG

PVE
```

A nucleic acid sequence encoding the ALK4 precursor protein is shown below (SEQ ID NO: 28), corresponding to nucleotides 78-1592 of Genbank Reference Sequence NM_004302.4. The signal sequence is underlined and the extracellular domain is indicated in bold font.

```
                                                    (SEQ ID NO: 28)
ATGGCGGAGTCGGCCGGAGCCTCCTCCTTCTTCCCCCTTGTTGTCCTCCT

GCTCGCCGGCAGCGGCGGGTCCGGGCCCCGGGGGGTCCAGGCTCTGCTGT

GTGCGTGCACCAGCTGCCTCCAGGCCAACTACACGTGTGAGACAGATGGG

GCCTGCATGGTTTCCATTTTCAATCTGGATGGGATGGAGCACCATGTGCG

CACCTGCATCCCCAAAGTGGAGCTGGTCCCTGCCGGGAAGCCCTTCTACT

GCCTGAGCTCGGAGGACCTGCGCAACACCCACTGCTGCTACACTGACTAC

TGCAACAGGATCGACTTGAGGGTGCCCAGTGGTCACCTCAAGGAGCCTGA

GCACCCGTCCATGTGGGGCCCGGTGGAGCTGGTAGGCATCATCGCCGGCC

CGGTGTTCCTCCTGTTCCTCATCATCATCATTGTTTTCCTTGTCATTAAC

TATCATCAGCGTGTCTATCACAACCGCCAGAGACTGGACATGGAAGATCC

CTCATGTGAGATGTGTCTCTCCAAAGACAAGACGCTCCAGGATCTTGTCT

ACGATCTCTCCACCTCAGGGTCTGGCTCAGGGTTACCCCTCTTTGTCCAG

CGCACAGTGGCCCGAACCATCGTTTTACAAGAGATTATTGGCAAGGGTCG

GTTTGGGGAAGTATGGCGGGGCCGCTGGAGGGGTGGTGATGTGGCTGTGA

AAATATTCTCTTCTCGTGAAGAACGGTCTTGGTTCAGGGAAGCAGAGATA

TACCAGACGGTCATGCTGCGCCATGAAAACATCCTTGGATTTATTGCTGC

TGACAATAAAGATAATGGCACCTGGACACAGCTGTGGCTTGTTTCTGACT

ATCATGAGCACGGGTCCCTGTTTGATTATCTGAACCGGTACACAGTGACA
```

-continued
```
ATTGAGGGGATGATTAAGCTGGCCTTGTCTGCTGCTAGTGGGCTGGCACA

CCTGCACATGGAGATCGTGGGCACCCAAGGGAAGCCTGGAATTGCTCATC

GAGACTTAAAGTCAAAGAACATTCTGGTGAAGAAAAATGGCATGTGTGCC

ATAGCAGACCTGGGCCTGGCTGTCCGTCATGATGCAGTCACTGACACCAT

TGACATTGCCCCGAATCAGAGGGTGGGGACCAAACGATACATGGCCCCTG

AAGTACTTGATGAAACCATTAATATGAAACACTTTGACTCCTTTAAATGT

GCTGATATTTATGCCCTCGGGCTTGTATATTGGGAGATTGCTCGAAGATG

CAATTCTGGAGGAGTCCATGAAGAATATCAGCTGCCATATTACGACTTAG

TGCCCTCTGACCCTTCCATTGAGGAAATGCGAAAGGTTGTATGTGATCAG

AAGCTGCGTCCCAACATCCCCAACTGGTGGCAGAGTTATGAGGCACTGCG
```

GGTGATGGGGAAGATGATGCGAGAGTGTTGGTATGCCAACGGCGCAGCCC

GCCTGACGGCCCTGCGCATCAAGAAGACCCTCTCCCAGCTCAGCGTGCAG

GAAGACGTGAAGATC

A nucleic acid sequence encoding the extracellular ALK4 polypeptide is as follows:

(SEQ ID NO: 29)
TCCGGGCCCCGGGGGGTCCAGGCTCTGCTGTGTGCGTGCACCAGCTGCCT

CCAGGCCAACTACACGTGTGAGACAGATGGGGCCTGCATGGTTTCCATTT

TCAATCTGGATGGGATGGAGCACCATGTGCGCACCTGCATCCCCAAAGTG

GAGCTGGTCCCTGCCGGGAAGCCCTTCTACTGCCTGAGCTCGGAGGACCT

GCGCAACACCCACTGCTGCTACACTGACTACTGCAACAGGATCGACTTGA

GGGTGCCCAGTGGTCACCTCAAGGAGCCTGAGCACCCGTCCATGTGGGGC

CCGGTGGAG

An alternative isoform of human ALK4 precursor protein sequence, isoform C (NCBI Ref Seq NP_064733.3), is as follows:

(SEQ ID NO: 83)
1 MAESAGASSF FPLVVLLLAG SGGSGPRGVQ ALLCACTSCL QANYTCETDG ACMVSIFNLD

61 GMEHHVRTCI PKVELVPAGK PFYCLSSEDL RNTHCCYTDY CNRIDLRVPS GHLKEPEHPS

121 MWGPVELVGI IAGPVFLLFL IIIIVFLVIN YHQRVYHNRQ RLDMEDPSCE MCLSKDKTLQ

181 DLVYDLSTSG SGSGLPLFVQ RTVARTIVLQ EIIGKGRFGE VWRGRWRGGD VAVKIFSSRE

241 ERSWFREAEI YQTVMLRHEN ILGFIAADNK ADCSFLTLPW EVVMVSAAPK LRSLRLQYKG

301 GRGRARFLFP LNNGTWTQLW LVSDYHEHGS LFDYLNRYTV TIEGMIKLAL SAASGLAHLH

361 MEIVGTQGKP GIAHRDLKSK NILVKKNGMC AIADLGLAVR HDAVTDTIDI APNQRVGTKR

421 YMAPEVLDET INMKHFDSFK CADIYALGLV YWEIARRCNS GGVHEEYQLP YYDLVPSDPS

481 IEEMRKVVCD QKLRPNIPNW WQSYEALRVM GKMMRECWYA NGAARLTALR IKKTLSQLSV

541 QEDVKI

The signal peptide is indicated by a single underline and the extracellular domain is indicated in bold font.

The processed extracellular ALK4 polypeptide sequence (isoform C) is as follows:

(SEQ ID NO: 84)
SGPRGVQALLCACTSCLQANYTCETDGACMVSIFNLDGMEHHVRTCIPKV

ELVPAGKPFYCLSSEDLRNTHCCYTDYCNRIDLRVPSGHLKEPEHPSMWG

PVE

A nucleic acid sequence encoding the ALK4 precursor protein (isoform C) is shown below (SEQ ID NO: 85), corresponding to nucleotides 78-1715 of Genbank Reference Sequence NM_020328.3. The signal sequence is underlined and the extracellular domain is indicated in bold font.

(SEQ ID NO: 85)
<u>ATGGCGGAGTCGGCCGGAGCCTCCTCCTTCTTCCCCCTTGTTGTCCTCCT</u>

<u>GCTCGCCGGCAGCGGCGGG</u>TCCGGGCCCCGGGGGGTCCAGGCTCTGCTGT

GTGCGTGCACCAGCTGCCTCCAGGCCAACTACACGTGTGAGACAGATGGG

GCCTGCATGGTTTCCATTTTCAATCTGGATGGGATGGAGCACCATGTGCG

CACCTGCATCCCCAAAGTGGAGCTGGTCCCTGCCGGGAAGCCCTTCTACT

GCCTGAGCTCGGAGGACCTGCGCAACACCCACTGCTGCTACACTGACTAC

TGCAACAGGATCGACTTGAGGGTGCCCAGTGGTCACCTCAAGGAGCCTGA

GCACCCGTCCATGTGGGGCCCGGTGGAGCTGGTAGGCATCATCGCCGGCC

CGGTGTTCCTCCTGTTCCTCATCATCATCATTGTTTTCCTTGTCATTAAC

TATCATCAGCGTGTCTATCACAACCGCCAGAGACTGGACATGGAAGATCC

CTCATGTGAGATGTGTCTCTCCAAAGACAAGACGCTCCAGGATCTTGTCT

ACGATCTCTCCACCTCAGGGTCTGGCTCAGGGTTACCCCTCTTTGTCCAG

CGCACAGTGGCCCGAACCATCGTTTTACAAGAGATTATTGGCAAGGGTCG

GTTTGGGGAAGTATGGCGGGGCCGCTGGAGGGGTGGTGATGTGGCTGTGA

AAATATTCTCTTCTCGTGAAGAACGGTCTTGGTTCAGGGAAGCAGAGATA

TACCAGACGGTCATGCTGCGCCATGAAAACATCCTTGGATTTATTGCTGC

TGACAATAAAGCAGACTGCTCATTCCTCACATTGCCATGGGAAGTTGTAA

TGGTCTCTGCTGCCCCAAGCTGAGGAGCCTTAGACTCCAATACAAGGGA

GGAAGGGGAAGAGCAAGATTTTTATTCCCACTGAATAATGGCACCTGGAC

ACAGCTGTGGCTTGTTTCTGACTATCATGAGCACGGGTCCCTGTTTGATT

ATCTGAACCGGTACACAGTGACAATTGAGGGGATGATTAAGCTGGCCTTG

TCTGCTGCTAGTGGGCTGGCACACCTGCACATGGAGATCGTGGGCACCCA

AGGGAAGCCTGGAATTGCTCATCGAGACTTAAAGTCAAAGAACATTCTGG

TGAAGAAAAATGGCATGTGTGCCATAGCAGACCTGGGCCTGGCTGTCCGT

CATGATGCAGTCACTGACACCATTGACATTGCCCCGAATCAGAGGGTGGG

GACCAAACGATACATGGCCCCTGAAGTACTTGATGAAACCATTAATATGA

AACACTTTGACTCCTTTAAATGTGCTGATATTTATGCCCTCGGGCTTGTA

TATTGGGAGATTGCTCGAAGATGCAATTCTGGAGGAGTCCATGAAGAATA

-continued
TCAGCTGCCATATTACGACTTAGTGCCCTCTGACCCTTCCATTGAGGAAA

TGCGAAAGGTTGTATGTGATCAGAAGCTGCGTCCCAACATCCCCAACTGG

TGGCAGAGTTATGAGGCACTGCGGGTGATGGGGAAGATGATGCGAGAGTG

TTGGTATGCCAACGGCGCAGCCCGCCTGACGGCCCTGCGCATCAAGAAGA

CCCTCTCCCAGCTCAGCGTGCAGGAAGACGTGAAGATC

A nucleic acid sequence encoding the extracelluar ALK4 polypeptide (isoform C) is as follows:

(SEQ ID NO: 86)
TCCGGGCCCCGGGGGGTCCAGGCTCTGCTGTGTGCGTGCACCAGCTGCCT

CCAGGCCAACTACACGTGTGAGACAGATGGGGCCTGCATGGTTTCCATTT

TCAATCTGGATGGGATGGAGCACCATGTGCGCACCTGCATCCCCAAAGTG

GAGCTGGTCCCTGCCGGGAAGCCCTTCTACTGCCTGAGCTCGGAGGACCT

GCGCAACACCCACTGCTGCTACACTGACTACTGCAACAGGATCGACTTGA

GGGTGCCCAGTGGTCACCTCAAGGAGCCTGAGCACCCGTCCATGTGGGGC

CCGGTGGAG

In certain embodiments, the disclosure relates to heteromultimer complexes that comprise at least one ALK4 polypeptide, which includes fragments, functional variants, and modified forms thereof. Preferably, ALK4 polypeptides for use in accordance with inventions of the disclosure (e.g., heteromultimer complexes comprising an ALK4 polypeptide and uses thereof) are soluble (e.g., an extracellular domain of ALK4). In other preferred embodiments, ALK4 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one ALK4 polypeptide that is at least 70%, 75%, 80%, 85%, 90%, 95%, 97%, 98%, or 99% identical to the amino acid sequence of SEQ ID NO: 26, 27, 83, 84, 104, 106, 403, or 404. In some embodiments, heteromultimer complexes of the disclosure consist or consist essentially of at least one ALK4 polypeptide that is at least 70%, 75%, 80%, 85%, 90%, 95%, 97%, 98%, or 99% identical to the amino acid sequence of SEQ ID NO: 26, 27, 83, 84, 104, 106, 403, or 404.

In certain aspects, the present disclosure relates to protein complexes that comprise an ALK5 polypeptide. As used herein, the term "ALK5" refers to a family of activin receptor-like kinase-5 proteins from any species and variants derived from such ALK4 proteins by mutagenesis or other modification. Reference to ALK5 herein is understood to be a reference to any one of the currently identified forms. Members of the ALK5 family are generally transmembrane proteins, composed of a ligand-binding extracellular domain with a cysteine-rich region, a transmembrane domain, and a cytoplasmic domain with predicted serine/threonine kinase activity.

The term "ALK5 polypeptide" includes polypeptides comprising any naturally occurring polypeptide of an ALK5 family member as well as any variants thereof (including mutants, fragments, fusions, and peptidomimetic forms) that retain a useful activity. Numbering of amino acids for all ALK5-related polypeptides described herein is based on the numbering of the human ALK5 precursor protein sequence below (SEQ ID NO: 30), unless specifically designated otherwise.

The canonical human ALK5 precursor protein sequence (NCBI Ref Seq NP_004603.1) is as follows:

(SEQ ID NO: 30)
```
  1 MEAAVAAPRP RLLLLVLAAA AAAAAALLPG ATALQCFCHL CTKDNFTCVT DGLCFVSVTE
 61 TTDKVIHNSM CIAEIDLIPR DRPFVCAPSS KTGSVTTTYC CNQDHCNKIE LPTTVKSSPG
121 LGPVELAAVI AGPVCFVCIS LMLMVYICHN RTVIHHRVPN EEDPSLDRPF ISEGTTLKDL
181 IYDMTTSGSG SGLPLLVQRT IARTIVLQES IGKGRFGEVW RGKWRGEEVA VKIFSSREER
241 SWFREAEIYQ TVMLRHENIL GFIAADNKDN GTWTQLWLVS DYHEHGSLFD YLNRYTVTVE
301 GMIKLALSTA SGLAHLHMEI VGTQGKPAIA HRDLKSKNIL VKKNGTCCIA DLGLAVRHDS
361 ATDTIDIAPN HRVGTKRYMA PEVLDDSINM KHFESFKRAD IYAMGLVFWE IARRCSIGGI
421 HEDYQLPYYD LVPSDPSVEE MRKVVCEQKL RPNIPNRWQS CEALRVMAKI MRECWYANGA
481 ARLTALRIKK TLSQLSQQEG IKM
```

The signal peptide is indicated by a single underline and the extracellular domain is indicated in bold font.

The processed extracellular ALK5 polypeptide sequence is as follows:

(SEQ ID NO: 31)
AALLPGATALQCFCHLCTKDNFTCVTDGLCFVSVTETTDKVIHNSMCIAE

IDLIPRDRPFVCAPSSKTGSVTTTYCCNQDHCNKIELPTTVKSSPGLGP

VEL

A nucleic acid sequence encoding the ALK5 precursor protein is shown below (SEQ ID NO: 32), corresponding to nucleotides 77-1585 of Genbank Reference Sequence NM_004612.2. The signal sequence is underlined and the extracellular domain is indicated in bold font.

(SEQ ID NO: 32)
ATGGAGGCGGCGGTCGCTGCTCCGCGTCCCCGGCTGCTCCTCCTCGTGCT

GGCGGCGGCGGCGGCGGCGGCGGCGGCGCTGCTCCCGGGGGCGACGGCGT

TACAGTGTTTCTGCCACCTCTGTACAAAAGACAATTTTACTTGTGTGACA

GATGGGCTCTGCTTTGTCTCTGTCACAGAGACCACAGACAAAGTTATACA

```
CAACAGCATGTGTATAGCTGAAATTGACTTAATTCCTCGAGATAGGCCGT

TTGTATGTGCACCCTCTTCAAAAACTGGGTCTGTGACTACAACATATTGC

TGCAATCAGGACCATTGCAATAAAATAGAACTTCCAACTACTGTAAAGTC

ATCACCTGGCCTTGGTCCTGTGGAACTGGCAGCTGTCATTGCTGGACCAG

TGTGCTTCGTCTGCATCTCACTCATGTTGATGGTCTATATCTGCCACAAC

CGCACTGTCATTCACCATCGAGTGCCAAATGAAGAGGACCCTTCATTAGA

TCGCCCTTTTATTTCAGAGGGTACTACGTTGAAAGACTTAATTTATGATA

TGACAACGTCAGGTTCTGGCTCAGGTTTACCATTGCTTGTTCAGAGAACA

ATTGCGAGAACTATTGTGTTACAAGAAAGCATTGGCAAAGGTCGATTTGG

AGAAGTTTGGAGAGGAAAGTGGCGGGGAGAAGAAGTTGCTGTTAAGATAT
```

```
                                          -continued
TCTCCTCTAGAGAAGAACGTTCGTGGTTCCGTGAGGCAGAGATTTATCAA

ACTGTAATGTTACGTCATGAAAACATCCTGGGATTTATAGCAGCAGACAA

TAAAGACAATGGTACTTGGACTCAGCTCTGGTTGGTGTCAGATTATCATG

AGCATGGATCCCTTTTTGATTACTTAAACAGATACACAGTTACTGTGGAA

GGAATGATAAAACTTGCTCTGTCCACGGCGAGCGGTCTTGCCCATCTTCA

CATGGAGATTGTTGGTACCCAAGGAAAGCCAGCCATTGCTCATAGAGATT

TGAAATCAAAGAATATCTTGGTAAAGAAGAATGGAACTTGCTGTATTGCA

GACTTAGGACTGGCAGTAAGACATGATTCAGCCACAGATACCATTGATAT

TGCTCCAAACCACAGAGTGGGAACAAAAAGGTACATGGCCCCTGAAGTTC

TCGATGATTCCATAAATATGAAACATTTTGAATCCTTCAAACGTGCTGAC

ATCTATGCAATGGGCTTAGTATTCTGGGAAATTGCTCGACGATGTTCCAT

TGGTGGAATTCATGAAGATTACCAACTGCCTTATTATGATCTTGTACCTT

CTGACCCATCAGTTGAAGAAATGAGAAAAGTTGTTTGTGAACAGAAGTTA

AGGCCAAATATCCCAAACAGATGGCAGAGCTGTGAAGCCTTGAGAGTAAT

GGCTAAAATTATGAGAGAATGTTGGTATGCCAATGGAGCAGCTAGGCTTA

CAGCATTGCGGATTAAGAAAACATTATCGCAACTCAGTCAACAGGAAGGC

ATCAAAATG
```

A nucleic acid sequence encoding the extracellular human ALK5 polypeptide is as follows:

```
                                          (SEQ ID NO: 33)
GCGGCGCTGCTCCCGGGGGCGACGGCGTTACAGTGTTTCTGCCACCTCTG

TACAAAAGACAATTTTACTTGTGTGACAGATGGGCTCTGCTTTGTCTCTG

TCACAGAGACCACAGACAAAGTTATACACAACAGCATGTGTATAGCTGAA

ATTGACTTAATTCCTCGAGATAGGCCGTTTGTATGTGCACCCTCTTCAAA

AACTGGGTCTGTGACTACAACATATTGCTGCAATCAGGACCATTGCAATA

AAATAGAACTTCCAACTACTGTAAAGTCATCACCTGGCCTTGGTCCTGTG

GAACTG
```

An alternative isoform of the human ALK5 precursor protein sequence, isoform 2 (NCBI Ref Seq XP_005252207.1), is as follows:

```
                                          (SEQ ID NO: 87)
  1 MEAVAAPRP RLLLLVLAAA AAAAAALLPG ATALQCFCHL CTKDNFTCVT DGLCFVSVTE

61 TTDKVIHNSM CIAEIDLIPR DRPFVCAPSS KTGSVTTTYC CNQDHCNKIE LPTTGPFSVK

121 SSPGLGPVEL AAVIAGPVCF VCISLMLMVY ICHNRTVIHH RVPNEEDPSL DRPFISEGTT

181 LKDLIYDMTT SGSGSGLPLL VQRTIARTIV LQESIGKGRF GEVWRGKWRG EEVAVKIFSS

241 REERSWFREA EIYQTVMLRH ENILGFIAAD NKDNGTWTQL WLVSDYHEHG SLFDYLNRYT

301 VTVEGMIKLA LSTASGLAHL HMEIVGTQGK PAIAHRDLKS KNILVKKNGT CCIADLGLAV

361 RHDSATDTID IAPNHRVGTK RYMAPEVLDD SINMKHFESF KRADIYAMGL VFWEIARRCS

421 IGGIHEDYQL PYYDLVPSDP SVEEMRKVVC EQKLRPNIPN RWQSCEALRV MAKIMRECWY

481 ANGAARLTAL RIKKTLSQLS QQEGIKM
```

The signal peptide is indicated by a single underline and the extracellular domain is indicated in bold font.

The processed extracellular ALK5 polypeptide sequence (isoform 2) is as follows:

```
                                          (SEQ ID NO: 88)
AALLPGATALQCFCHLCTKDNFTCVTDGLCFVSVTETTDKVIHNSMCIAE

IDLIPRDRPFVCAPSSKTGSVTTTYCCNQDHCNKIELPTTGPFSVKSSPG

LGPVEL
```

A nucleic acid sequence encoding human ALK5 precursor protein (isoform 2) is shown below (SEQ ID NO: 89), corresponding to nucleotides 77-1597 of Genbank Reference Sequence XM_0052521501 The signal sequence is underlined and the extracellular domain is indicated in bold font.

```
                                          (SEQ ID NO: 89)
ATGGAGGCGGCGGTCGCTGCTCCGCGTCCCCGGCTGCTCCTCCTCGTGCT

GGCGGCGGCGGCGGCGGCGGCGGCGGCGCTGCTCCCGGGGGCGACGGCGT

TACAGTGTTTCTGCCACCTCTGTACAAAAGACAATTTTACTTGTGTGACA

GATGGGCTCTGCTTTGTCTCTGTCACAGAGACCACAGACAAAGTTATACA

CAACAGCATGTGTATAGCTGAAATTGACTTAATTCCTCGAGATAGGCCGT

TTGTATGTGCACCCTCTTCAAAAACTGGGTCTGTGACTACAACATATTGC
```

```
TGCAATCAGGACCATTGCAATAAAATAGAACTTCCAACTACTGGCCCTTT

TTCAGTAAAGTCATCACCTGGCCTTGGTCCTGTGGAACTGGCAGCTGTCA

TTGCTGGACCAGTGTGCTTCGTCTGCATCTCACTCATGTTGATGGTCTAT

ATCTGCCACAACCGCACTGTCATTCACCATCGAGTGCCAAATGAAGAGGA

CCCTTCATTAGATCGCCCTTTTATTTCAGAGGGTACTACGTTGAAAGACT

TAATTTATGATATGACAACGTCAGGTTCTGGCTCAGGTTTACCATTGCTT

GTTCAGAGAACAATTGCGAGAACTATTGTGTTACAAGAAAGCATTGGCAA

AGGTCGATTTGGAGAAGTTTGGAGAGGAAAGTGGCGGGGAGAAGAAGTTG

CTGTTAAGATATTCTCCTCTAGAGAAGAACGTTCGTGGTTCCGTGAGGCA

GAGATTTATCAAACTGTAATGTTACGTCATGAAAACATCCTGGGATTTAT

AGCAGCAGACAATAAAGACAATGGTACTTGGACTCAGCTCTGGTTGGTGT

CAGATTATCATGAGCATGGATCCCTTTTTGATTACTTAAACAGATACACA

GTTACTGTGGAAGGAATGATAAAACTTGCTCTGTCCACGGCGAGCGGTCT

TGCCCATCTTCACATGGAGATTGTTGGTACCCAAGGAAAGCCAGCCATTG

CTCATAGAGATTTGAAATCAAAGAATATCTTGGTAAAGAAGAATGGAACT

TGCTGTATTGCAGACTTAGGACTGGCAGTAAGACATGATTCAGCCACAGA

TACCATTGATATTGCTCCAAACCACAGAGTGGGAACAAAAAGGTACATGG

CCCCTGAAGTTCTCGATGATTCCATAAATATGAAACATTTTGAATCCTTC

AAACGTGCTGACATCTATGCAATGGGCTTAGTATTCTGGGAAATTGCTCG

ACGATGTTCCATTGGTGGAATTCATGAAGATTACCAACTGCCTTATTATG

ATCTTGTACCTTCTGACCCATCAGTTGAAGAAATGAGAAAAGTTGTTTGT

GAACAGAAGTTAAGGCCAAATATCCCAAACAGATGGCAGAGCTGTGAAGC

CTTGAGAGTAATGGCTAAAATTATGAGAGAATGTTGGTATGCCAATGGAG

CAGCTAGGCTTACAGCATTGCGGATTAAGAAAACATTATCGCAACTCAGT

CAACAGGAAGGCATCAAAATG
```

A nucleic acid sequence encoding the processed extracellular ALK5 polypeptide is as follows:

```
                                          (SEQ ID NO: 90)
GCGGCGCTGCTCCCGGGGGCGACGGCGTTACAGTGTTTCTGCCACCTCTG

TACAAAAGACAATTTTACTTGTGTGACAGATGGGCTCTGCTTTGTCTCTG
```

```
TCACAGAGACCACAGACAAAGTTATACACAACAGCATGTGTATAGCTGAA

ATTGACTTAATTCCTCGAGATAGGCCGTTTGTATGTGCACCCTCTTCAAA

AACTGGGTCTGTGACTACAACATATTGCTGCAATCAGGACCATTGCAATA

AAATAGAACTTCCAACTACTGGCCCTTTTTCAGTAAAGTCATCACCTGGC

CTTGGTCCTGTGGAACTG
```

In certain embodiments, the disclosure relates to heteromultimer complexes that comprise at least one ALK5 polypeptide, which includes fragments, functional variants, and modified forms thereof. Preferably, ALK5 polypeptides for use in accordance with inventions of the disclosure (e.g., heteromultimer complexes comprising an ALK5 polypeptide and uses thereof) are soluble (e.g., an extracellular domain of ALK5). In other preferred embodiments, ALK5 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one ALK5 polypeptide that is at least 70%, 75%, 80%, 85%, 90%, 95%, 97%, 98%, or 99% identical to the amino acid sequence of SEQ ID NO: 30, 31, 87, or 88. In some embodiments, heteromultimer complexes of the disclosure consist or consist essentially of at least one ALK5 polypeptide that is at least 70%, 75%, 80%, 85%, 90%, 95%, 97%, 98%, or 99% identical to the amino acid sequence of SEQ ID NO: 30, 31, 87, or 88.

In certain aspects, the present disclosure relates to protein complexes that comprise an ALK6 polypeptide. As used herein, the term "ALK6" refers to a family of activin receptor-like kinase-6 proteins from any species and variants derived from such ALK6 proteins by mutagenesis or other modification. Reference to ALK6 herein is understood to be a reference to any one of the currently identified forms. Members of the ALK6 family are generally transmembrane proteins, composed of a ligand-binding extracellular domain with a cysteine-rich region, a transmembrane domain, and a cytoplasmic domain with predicted serine/threonine kinase activity.

The term "ALK6 polypeptide" includes polypeptides comprising any naturally occurring polypeptide of an ALK6 family member as well as any variants thereof (including mutants, fragments, fusions, and peptidomimetic forms) that retain a useful activity. Numbering of amino acids for all ALK6-related polypeptides described herein is based on the numbering of the human ALK6 precursor protein sequence below (SEQ ID NO: 34), unless specifically designated otherwise.

The canonical human ALK6 precursor protein sequence (NCBI Ref Seq NP_001194.1) is as follows:

```
                                                              (SEQ ID NO: 34)
  1 MLLRSAGKLN VGTKKEDGES TAPTPRPKVL RCKCHHHCPE DSVNNICSTD GYCFTMIEED

61 DSGLPVVTSG CLGLEGSDFQ CRDTPIPHQR RSIECCTERN ECNKDLHPTL PPLKNRDFVD

121 GPIHHRALLI SVTVCSLLLV LIILFCYFRY KRQETRPRYS IGLEQDETYI PPGESLRDLI

181 EQSQSSGSGS GLPLLVQRTI AKQIQMVKQI GKGRYGEVWM GKWRGEKVAV KVFFTTEEAS

241 WFRETEIYQT VLMRHENILG FIAADIKGTG SWTQLYLITD YHENGSLYDY LKSTTLDAKS

301 MLKLAYSSVS GLCHLHTEIF STQGKPAIAH RDLKSKNILV KKNGTCCIAD LGLAVKFISD

361 TNEVDIPPNT RVGTKRYMPP EVLDESLNRN HFQSYIMADM YSFGLILWEV ARRCVSGGIV
```

```
421 EEYQLPYHDL VPSDPSYEDM REIVCIKKLR PSFPNRWSSD ECLRQMGKLM TECWAHNPAS

481 RLTALRVKKT LAKMSESQDI KL
```

The signal peptide is indicated by a single underline and the extracellular domain is indicated in bold font.

The processed extracellular ALK6 polypeptide sequence is as follows:

```
                                            (SEQ ID NO: 35)
KKEDGESTAPTPRPKVLRCKCHHHCPEDSVNNICSTDGYCFTMIEEDDSG

LPVVTSGCLGLEGSDFQCRDTPIPHQRRSIECCTERNECNKDLHPTLPPL

KNRDFVDGPIHHR
```

A nucleic acid sequence encoding the ALK6 precursor protein is shown below (SEQ ID NO: 36), corresponding to nucleotides 275-1780 of Genbank Reference Sequence NM_001203.2. The signal sequence is underlined and the extracellular domain is indicated in bold font.

```
                                            (SEQ ID NO: 36)
ATGCTTTTGCGAAGTGCAGGAAAATTAAATGTGGGCACCAAGAAAGAGGA

TGGTGAGAGTACAGCCCCCACCCCCCGTCCAAAGGTCTTGCGTTGTAAAT

GCCACCACCATTGTCCAGAAGACTCAGTCAACAATATTTGCAGCACAGAC

GGATATTGTTTCACGATGATAGAAGAGGATGACTCTGGGTTGCCTGTGGT

CACTTCTGGTTGCCTAGGACTAGAAGGCTCAGATTTTCAGTGTCGGACA

CTCCCATTCCTCATCAAAGAAGATCAATTGAATGCTGCACAGAAAGGAAC

GAATGTAATAAAGACCTACACCCTACACTGCCTCCATTGAAAAACAGAGA

TTTTGTTGATGGACCTATACACCACAGGGCTTTACTTATATCTGTGACTG

TCTGTAGTTTGCTCTTGGTCCTTATCATATTATTTTGTTACTTCCGGTAT

AAAAGACAAGAAACCAGACCTCGATACAGCATTGGGTTAGAACAGGATGA

AACTTACATTCCTCCTGGAGAATCCCTGAGAGACTTAATTGAGCAGTCTC

AGAGCTCAGGAAGTGGATCAGGCCTCCCTCTGCTGGTCCAAAGGACTATA

GCTAAGCAGATTCAGATGGTGAAACAGATTGGAAAAGGTCGCTATGGGGA

AGTTTGGATGGGAAAGTGGCGTGGCGAAAAGGTAGCTGTGAAAGTGTTCT

TCACCACAGAGGAAGCCAGCTGGTTCAGAGAGACAGAAATATATCAGACA

GTGTTGATGAGGCATGAAAACATTTTGGGTTTCATTGCTGCAGATATCAA

AGGGACAGGGTCCTGGACCCAGTTGTACCTAATCACAGACTATCATGAAA

ATGGTTCCCTTTATGATTATCTGAAGTCCACCACCCTAGACGCTAAATCA

ATGCTGAAGTTAGCCTACTCTTCTGTCAGTGGCTTATGTCATTTACACAC

AGAAATCTTTAGTACTCAAGGCAAACCAGCAATTGCCCATCGAGATCTGA

AAAGTAAAAACATTCTGGTGAAGAAAAATGGAACTTGCTGTATTGCTGAC

CTGGGCCTGGCTGTTAAATTTATTAGTGATACAAATGAAGTTGACATACC

ACCTAACACTCGAGTTGGCACCAAACGCTATATGCCTCCAGAAGTGTTGG

ACGAGAGCTTGAACAGAAATCACTTCCAGTCTTACATCATGGCTGACATG

TATAGTTTTGGCCTCATCCTTTGGGAGGTTGCTAGGAGATGTGTATCAGG

AGGTATAGTGGAAGAATACCAGCTTCCTTATCATGACCTAGTGCCCAGTG

ACCCCTCTTATGAGGACATGAGGGAGATTGTGTGCATCAAGAAGTTACGC

CCCTCATTCCCAAACCGGTGGAGCAGTGATGAGTGTCTAAGGCAGATGGG

AAAACTCATGACAGAATGCTGGGCTCACAATCCTGCATCAAGGCTGACAG

CCCTGCGGGTTAAGAAAACACTTGCCAAAATGTCAGAGTCCCAGGACATT

AAACTC
```

A nucleic acid sequence encoding processed extracellular ALK6 polypeptide is as follows:

```
                                            (SEQ ID NO: 37)
AAGAAAGAGGATGGTGAGAGTACAGCCCCCACCCCCCGTCCAAAGGTCTT

GCGTTGTAAATGCCACCACCATTGTCCAGAAGACTCAGTCAACAATATTT

GCAGCACAGACGGATATTGTTTCACGATGATAGAAGAGGATGACTCTGGG

TTGCCTGTGGTCACTTCTGGTTGCCTAGGACTAGAAGGCTCAGATTTTCA

GTGTCGGGACACTCCCATTCCTCATCAAAGAAGATCAATTGAATGCTGCA

CAGAAAGGAACGAATGTAATAAAGACCTACACCCTACACTGCCTCCATTG

AAAAACAGAGATTTTGTTGATGGACCTATACACCACAGG
```

An alternative isoform of human ALK6 precursor protein sequence, isoform 2 (NCBI Ref Seq NP_001243722.1) is as follows:

```
                                            (SEQ ID NO: 91)
  1 MGWLEELNWQ LHIFLLILLS MHTRANFLDN MLLRSAGKLN VGTKKEDGES TAPTPRPKVL

61 RCKCHHHCPE DSVNNICSTD GYCFTMIEED DSGLPVVTSG CLGLEGSDFQ CRDTPIPHQR

121 RSIECCTERN ECNKDLHPTL PPLKNRDFVD GPIHHRALLI SVTVCSLLLV LIILFCYFRY

181 KRQETRPRYS IGLEQDETYI PPGESLRDLI EQSQSSGSGS GLPLLVQRTI AKQIQMVKQI
```

-continued

241 GKGRYGEVWM GKWRGEKVAV KVFFTTEEAS WFRETEIYQT VLMRHENILG FIAADIKGTG

301 SWTQLYLITD YHENGSLYDY LKSTTLDAKS MLKLAYSSVS GLCHLHTEIF STQGKPAIAH

361 RDLKSKNILV KKNGTCCIAD LGLAVKFISD TNEVDIPPNT RVGTKRYMPP EVLDESLNRN

421 HFQSYIMADM YSFGLILWEV ARRCVSGGIV EEYQLPYHDL VPSDPSYEDM REIVCIKKLR

481 PSFPNRWSSD ECLRQMGKLM TECWAHNPAS RLTALRVKKT LAKMSESQDI KL

The signal peptide is indicated by a single underline and the extracellular domain is indicated in bold font.

The processed extracellular ALK6 polypeptide sequence (isoform 2) is as follows:

(SEQ ID NO: 92)
NFLDNMLLRSAGKLNVGTKKEDGESTAPTPRPKVLRCKCHHHCPEDS
VNNICSTDGYCFTMIEEDDSGLPVVTSGCLGLEGSDFQCRDTPIPHQRR
SIECCTERNECNKDLHPTLPPLKNRDFVDGPIHHR

A nucleic acid sequence encoding human ALK6 precursor protein (isoform 2) is shown below, corresponding to nucleotides 22-1617 of Genbank Reference Sequence NM_001256793.1. The signal sequence is underlined and the extracellular domain is indicated in bold font.

(SEQ ID NO: 93)
ATGGGTTGGCTGGAAGAACTAAACTGGCAGCTTCACATTTTCTTGCTCAT
TCTTCTCTCTATGCACACAAGGGCA**AACTTCCTTGATAACATGCTTTTGC
GAAGTGCAGGAAAATTAAATGTGGGCACCAAGAAAGAGGATGGTGAGAGT
ACAGCCCCCACCCCCCGTCCAAAGGTCTTGCGTTGTAAATGCCACCACCA
TTGTCCAGAAGACTCAGTCAACAATATTTGCAGCACAGACGGATATTGTT
TCACGATGATAGAAGAGGATGACTCTGGGTTGCCTGTGGTCACTTCTGGT
TGCCTAGGACTAGAAGGCTCAGATTTTCAGTGTCGGGACACTCCCATTCC
TCATCAAAGAAGATCAATTGAATGCTGCACAGAAAGGAACGAATGTAATA
AAGACCTACACCCTACACTGCCTCCATTGAAAAACAGAGATTTTGTTGAT
GGACCTATACACCACAGG**GCTTTACTTATATCTGTGACTGTCTGTAGTTT
GCTCTTGGTCCTTATCATATTATTTTGTTACTTCCGGTATAAAAGACAAG
AAACCAGACCTCGATACAGCATTGGGTTAGAACAGGATGAAACTTACATT
CCTCCTGGAGAATCCCTGAGAGACTTAATTGAGCAGTCTCAGAGCTCAGG
AAGTGGATCAGGCCTCCCTCTGCTGGTCCAAAGGACTATAGCTAAGCAGA
TTCAGATGGTGAAACAGATTGGAAAAGGTCGCTATGGGGAAGTTTGGATG
GGAAAGTGGCGTGGCGAAAAGGTAGCTGTGAAAGTGTTCTTCACCACAGA
GGAAGCCAGCTGGTTCAGAGAGACAGAAATATATCAGACAGTGTTGATGA
GGCATGAAAACATTTTGGGTTTCATTGCTGCAGATATCAAAGGGACAGGG
TCCTGGACCCAGTTGTACCTAATCACAGACTATCATGAAAATGGTTCCCT
TTATGATTATCTGAAGTCCACCACCCTAGACGCTAAATCAATGCTGAAGT
TAGCCTACTCTTCTGTCAGTGGCTTATGTCATTTACACACAGAAATCTTT
AGTACTCAAGGCAAACCAGCAATTGCCCATCGAGATCTGAAAAGTAAAAA
CATTCTGGTGAAGAAAAATGGAACTTGCTGTATTGCTGACCTGGGCCTGG

-continued
CTGTTAAATTTATTAGTGATACAAATGAAGTTGACATACCACCTAACACT
CGAGTTGGCACCAAACGCTATATGCCTCCAGAAGTGTTGGACGAGAGCTT
GAACAGAAATCACTTCCAGTCTTACATCATGGCTGACATGTATAGTTTTG
GCCTCATCCTTTGGGAGGTTGCTAGGAGATGTGTATCAGGAGGTATAGTG
GAAGAATACCAGCTTCCTTATCATGACCTAGTGCCCAGTGACCCCTCTTA
TGAGGACATGAGGGAGATTGTGTGCATCAAGAAGTTACGCCCCTCATTCC
CAAACCGGTGGAGCAGTGATGAGTGTCTAAGGCAGATGGGAAAACTCATG
ACAGAATGCTGGGCTCACAATCCTGCATCAAGGCTGACAGCCCTGCGGGT
TAAGAAAACACTTGCCAAAATGTCAGAGTCCCAGGACATTAAACTC A nucleic acid sequence encoding the processed extracellular ALK6 polypeptide is as follows:

(SEQ ID NO: 94)
AACTTCCTTGATAACATGCTTTTGCGAAGTGCAGGAAAATTAAATGTGGG
CACCAAGAAAGAGGATGGTGAGAGTACAGCCCCCACCCCCCGTCCAAAGG
TCTTGCGTTGTAAATGCCACCACCATTGTCCAGAAGACTCAGTCAACAAT
ATTTGCAGCACAGACGGATATTGTTTCACGATGATAGAAGAGGATGACTC
TGGGTTGCCTGTGGTCACTTCTGGTTGCCTAGGACTAGAAGGCTCAGATT
TTCAGTGTCGGGACACTCCCATTCCTCATCAAAGAAGATCAATTGAATGC
TGCACAGAAAGGAACGAATGTAATAAAGACCTACACCCTACACTGCCTCC
ATTGAAAAACAGAGATTTTGTTGATGGACCTATACACCACAGG

In certain embodiments, the disclosure relates to heteromultimer complexes that comprise at least one ALK6 polypeptide, which includes fragments, functional variants, and modified forms thereof. Preferably, ALK6 polypeptides for use in accordance with inventions of the disclosure (e.g., heteromultimer complexes comprising an ALK6 polypeptide and uses thereof) are soluble (e.g., an extracellular domain of ALK6). In other preferred embodiments, ALK6 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one ALK6 polypeptide that is at least 70%, 75%, 80%, 85%, 90%, 95%, 97%, 98%, or 99% identical to the amino acid sequence of SEQ ID NO: 34, 35, 91, or 92. In some embodiments, heteromultimer complexes of the disclosure consist or consist essentially of at least one ALK6 polypeptide that is at least 70%, 75%, 80%, 85%, 90%, 95%, 97%, 98%, or 99% identical to the amino acid sequence of SEQ ID NO: 34, 35, 91, or 92.

In certain aspects, the present disclosure relates to protein complexes that comprise an ALK7 polypeptide. As used herein, the term "ALK7" refers to a family of activin receptor-like kinase-7 proteins from any species and variants derived from such ALK7 proteins by mutagenesis or other modification. Reference to ALK7 herein is understood to be a reference to any one of the currently identified forms. Members of the ALK7 family are generally transmembrane proteins, composed of a ligand-binding extracellular domain with a cysteine-rich region, a transmembrane domain, and a cytoplasmic domain with predicted serine/threonine kinase activity.

The term "ALK7 polypeptide" includes polypeptides comprising any naturally occurring polypeptide of an ALK7 family member as well as any variants thereof (including mutants, fragments, fusions, and peptidomimetic forms) that retain a useful activity. Numbering of amino acids for all ALK7-related polypeptides described herein is based on the numbering of the human ALK7 precursor protein sequence below (SEQ ID NO: 38), unless specifically designated otherwise.

Four naturally occurring isoforms of human ALK7 have been described. The sequence of canonical human ALK7 isoform 1 precursor protein (NCBI Ref Seq NP_660302.2) is as follows:

(SEQ ID NO: 38)
```
  1 MTRALCSALR QALLLLAAAAELSPGLKCVC LLCDSSNFTC QTEGACWASV MLTNGKEQVI

61 KSCVSLPELN AQVFCHSSNN VTKTECCFTD FCNNITLHLP TASPNAPKLG PMELAIIITV

121 PVCLLSIAAM LTVWACQGRQ CSYRKKKRPN VEEPLSECNL VNAGKTLKDL IYDVTASGSG

181 SGLPLLVQRT IARTIVLQEI VGKGRFGEVW HGRWCGEDVA VKIFSSRDER SWFREAEIYQ

241 TVMLRHENIL GFIAADNKDN GTWTQLWLVS EYHEQGSLYD YLNRNIVTVA GMIKLALSIA

301 SGLAHLHMEI VGTQGKPAIA HRDIKSKNIL VKKCETCAIA DLGLAVKHDS ILNTIDIPQN

361 PKVGTKRYMA PEMLDDTMNV NIFESFKRAD IYSVGLVYWE IARRCSVGGI VEEYQLPYYD

421 MVPSDPSIEE MRKVVCDQKF RPSIPNQWQS CEALRVMGRI MRECWYANGA ARLTALRIKK

481 TISQLCVKED CKA
```

The signal peptide is indicated by a single underline and the extracellular domain is indicated in bold font.

The processed extracellular ALK7 isoform 1 polypeptide sequence is as follows:

(SEQ ID NO: 39)
ELSPGLKCVCLLCDSSNFTCQTEGACWASVMLTNGKEQVIKSCVSL
PELNAQVFCHSSNNVTKTECCFTDFCNNITLHLPTASPNAPKLGPME

A nucleic acid sequence encoding human ALK7 isoform 1 precursor protein is shown below (SEQ ID NO: 40), corresponding to nucleotides 244-1722 of Genbank Reference Sequence NM_145259.2. The signal sequence is underlined and the extracellular domain is indicated in bold font.

(SEQ ID NO: 40)
ATGACCCGGGCGCTCTGCTCAGCGCTCCGCCAGGCTCTCCTGCTGCTCGC

AGCGGCCGCCGAGCTCTCGCCAGGACTGAAGTGTGTATGTCTTTTGTGTG

ATTCTTCAAACTTTACCTGCCAAACAGAAGGAGCATGTTGGGCATCAGTC

ATGCTAACCAATGGAAAAGAGCAGGTGATCAAATCCTGTGTCTCCCTTCC

AGAACTGAATGCTCAAGTCTTCTGTCATAGTTCCAACAATGTTACCAAAA

CCGAATGCTGCTTCACAGATTTTTGCAACAACATAACACTGCACCTTCCA

ACAGCATCACCAAATGCCCCAAAACTTGGACCCATGGAGCTGGCCATCAT

TATTACTGTGCCTGTTTGCCTCCTGTCCATAGCTGCGATGCTGACAGTAT

GGGCATGCCAGGGTCGACAGTGCTCCTACAGGAAGAAAAAGAGACCAAAT

GTGGAGGAACCACTCTCTGAGTGCAATCTGGTAAATGCTGGAAAAACTCT

GAAAGATCTGATTTATGATGTGACCGCCTCTGGATCTGGCTCTGGTCTAC

CTCTGTTGGTTCAAAGGACAATTGCAAGGACGATTGTGCTTCAGGAAATA

GTAGGAAAAGGTAGATTTGGTGAGGTGTGGCATGGAAGATGGTGTGGGGA

AGATGTGGCTGTGAAAATATTCTCCTCCAGAGATGAAAGATCTTGGTTTC

GTGAGGCAGAAATTTACCAGACGGTCATGCTGCGACATGAAAACATCCTT

GGTTTCATTGCTGCTGACAACAAAGATAATGGAACTTGGACTCAACTTTG

GCTGGTATCTGAATATCATGAACAGGGCTCCTTATATGACTATTTGAATA

GAAATATAGTGACCGTGGCTGGAATGATCAAGCTGGCGCTCTCAATTGCT

AGTGGTCTGGCACACCTTCATATGGAGATTGTTGGTACACAAGGTAAACC

TGCTATTGCTCATCGAGACATAAAATCAAAGAATATCTTAGTGAAAAAGT

GTGAAACTTGTGCCATAGCGGACTTAGGGTTGGCTGTGAAGCATGATTCA

ATACTGAACACTATCGACATACCTCAGAATCCTAAAGTGGGAACCAAGAG

GTATATGGCTCCTGAAATGCTTGATGATACAATGAATGTGAATATCTTTG

AGTCCTTCAAACGAGCTGACATCTATTCTGTTGGTCTGGTTTACTGGGAA

ATAGCCCGGAGGTGTTCAGTCGGAGGAATTGTTGAGGAGTACCAATTGCC

TTATTATGACATGGTGCCTTCAGATCCCTCGATAGAGGAAATGAGAAAGG

TTGTTTGTGACCAGAAGTTTCGACCAAGTATCCCAAACCAGTGGCAAAGT

TGTGAAGCACTCCGAGTCATGGGGAGAATAATGCGTGAGTGTTGGTATGC

CAACGGAGCGGCCCGCCTAACTGCTCTTCGTATTAAGAAGACTATATCTC

AACTTTGTGTCAAAGAAGACTGCAAAGCC

A nucleic acid sequence encoding the processed extracellular ALK7 polypeptide (isoform 1) is as follows:

(SEQ ID NO: 41)
GAGCTCTCGCCAGGACTGAAGTGTGTATGTCTTTTGTGTGATTCTTCAAA

CTTTACCTGCCAAACAGAAGGAGCATGTTGGGCATCAGTCATGCTAACCA

ATGGAAAAGAGCAGGTGATCAAATCCTGTGTCTCCCTTCCAGAACTGAAT

GCTCAAGTCTTCTGTCATAGTTCCAACAATGTTACCAAAACCGAATGCTG

CTTCACAGATTTTTGCAACAACATAACACTGCACCTTCCAACAGCATCAC

CAAATGCCCCAAAACTTGGACCCATGGAG

The amino acid sequence of an alternative isoform of human ALK7, isoform 2 (NCBI Ref Seq NP_001104501.1), is shown in its processed form as follows (SEQ ID NO: 301), where the extracellular domain is indicated in bold font.

```
                                        (SEQ ID NO: 301)
  1 MLTNGKEQVI KSCVSLPELN AQVFCHSSNN VTKTECCFTD FCNNITLHLP TASPNAPKLG

61 PMELAIIITV PVCLLSIAAM LTVWACQGRQ CSYRKKKRPN VEEPLSECNL VNAGKTLKDL

121 IYDVTASGSG SGLPLLVQRT IARTIVLQEI VGKGRFGEVW HGRWCGEDVA VKIFSSRDER

181 SWFREAEIYQ TVMLRHENIL GFIAADNKDN GTWTQLWLVS EYHEQGSLYD YLNRNIVTVA

241 GMIKLALSIA SGLAHLHMEI VGTQGKPAIA HRDIKSKNIL VKKCETCAIA DLGLAVKHDS

301 ILNTIDIPQN PKVGTKRYMA PEMLDDTMNV NIFESFKRAD IYSVGLVYWE IARRCSVGGI

361 VEEYQLPYYD MVPSDPSIEE MRKVVCDQKF RPSIPNQWQS CEALRVMGRI MRECWYANGA

421 ARLTALRIKK TISQLCVKED CKA
```

The amino acid sequence of the extracellular ALK7 polypeptide (isoform 2) is as follows:

(SEQ ID NO: 302)
MLTNGKEQVIKSCVSLPELNAQVFCHSSNNVTKTECCFTDFCNNITL

HLPTASPNAPKLGPME.

A nucleic acid sequence encoding the processed ALK7 polypeptide (isoform 2) is shown below (SEQ ID NO: 303), corresponding to nucleotides 279-1607 of NCBI Reference Sequence NM_001111031.1. The extracellular domain is indicated in bold font.

(SEQ ID NO: 303)
ATGCTAACCAATGGAAAAGAGCAGGTGATCAAATCCTGTGTCTCCCTTCC

AGAACTGAATGCTCAAGTCTTCTGTCATAGTTCCAACAATGTTACCAAAA

CCGAATGCTGCTTCACAGATTTTTGCAACAACATAACACTGCACCTTCCA

ACAGCATCACCAAATGCCCCAAAACTTGGACCCATGGAGCTGGCCATCAT

TATTACTGTGCCTGTTTGCCTCCTGTCCATAGCTGCGATGCTGACAGTAT

GGGCATGCCAGGGTCGACAGTGCTCCTACAGGAAGAAAAAGAGACCAAAT

GTGGAGGAACCACTCTCTGAGTGCAATCTGGTAAATGCTGGAAAAACTCT

GAAAGATCTGATTTATGATGTGACCGCCTCTGGATCTGGCTCTGGTCTAC

CTCTGTTGGTTCAAAGGACAATTGCAAGGACGATTGTGCTTCAGGAAATA

GTAGGAAAAGGTAGATTTGGTGAGGTGTGGCATGGAAGATGGTGTGGGGA

AGATGTGGCTGTGAAATATTCTCCTCCAGAGATGAAAGATCTTGGTTTC

GTGAGGCAGAAATTTACCAGACGGTCATGCTGCGACATGAAAACATCCTT

AGTCCTTCAAACGAGCTGACATCTATTCTGTTGGTCTGGTTTACTGGGAA

ATAGCCCGGAGGTGTTCAGTCGGAGGAATTGTTGAGGAGTACCAATTGCC

TTATTATGACATGGTGCCTTCAGATCCCTCGATAGAGGAAATGAGAAAGG

TTGTTTGTGACCAGAAGTTTCGACCAAGTATCCCAAACCAGTGGCAAAGT

TGTGAAGCACTCCGAGTCATGGGGAGAATAATGCGTGAGTGTTGGTATGC

CAACGGAGCGGCCCGCCTAACTGCTCTTCGTATTAAGAAGACTATATCTC

AACTTTGTGTCAAAGAAGACTGCAAAGCC

A nucleic acid sequence encoding the extracellular ALK7 polypeptide (isoform 2) is as follows (SEQ ID NO: 304):

(SEQ ID NO: 304)
ATGCTAACCAATGGAAAAGAGCAGGTGATCAAATCCTGTGTCTCCCTTCC

AGAACTGAATGCTCAAGTCTTCTGTCATAGTTCCAACAATGTTACCAAAA

CCGAATGCTGCTTCACAGATTTTTGCAACAACATAACACTGCACCTTCCA

ACAGCATCACCAAATGCCCCAAAACTTGGACCCATGGAG

The amino acid sequence of an alternative human ALK7 precursor protein, isoform 3 (NCBI Ref Seq NP_001104502.1), is shown as follows (SEQ ID NO: 305), where the signal peptide is indicated by a single underline.

(SEQ ID NO: 305)
```
  1 MTRALCSALR QALLLLAAAA ELSPGLKCVC LLCDSSNFTC QTEGACWASV MLTNGKEQVI

61 KSCVSLPELN AQVFCHSSNN VTKTECCFTD FCNNITLHLP TGLPLLVQRT IARTIVLQEI

121 VGKGRFGEVW HGRWCGEDVA VKIFSSRDER SWFREAEIYQ TVMLRHENIL GFIAADNKDN

181 GTWTQLWLVS EYHEQGSLYD YLNRNIVTVA GMIKLALSIA SGLAHLHMEI VGTQGKPAIA

241 HRDIKSKNIL VKKCETCAIA DLGLAVKHDS ILNTIDIPQN PKVGTKRYMA PEMLDDTMNV

301 NIFESFKRAD IYSVGLVYWE IARRCSVGGI VEEYQLPYYD MVPSDPSIEE MRKVVCDQKF

361 RPSIPNQWQS CEALRVMGRI MRECWYANGA ARLTALRIKK TISQLCVKED CKA
```

The amino acid sequence of the processed ALK7 polypeptide (isoform 3) is as follows (SEQ ID NO: 306). This isoform lacks a transmembrane domain and is therefore proposed to be soluble in its entirety (Roberts et al., 2003, Biol Reprod 68:1719-1726). N-terminal variants of SEQ ID NO: 306 are predicted as described below.

(SEQ ID NO: 306)
```
  1 ELSPGLKCVC LLCDSSNFTC QTEGACWASV MLTNGKEQVI KSCVSLPELN AQVFCHSSNN

61 VTKTECCFTD FCNNITLHLP TGLPLLVQRT IARTIVLQEI VGKGRFGEVW HGRWCGEDVA

121 VKIFSSRDER SWFREAEIYQ TVMLRHENIL GFIAADNKDN GTWTQLWLVS EYHEQGSLYD

181 YLNRNIVTVA GMIKLALSIA SGLAHLHMEI VGTQGKPAIA HRDIKSKNIL VKKCETCAIA

241 DLGLAVKHDS ILNTIDIPQN PKVGTKRYMA PEMLDDTMNV NIFESFKRAD IYSVGLVYWE

301 IARRCSVGGI VEEYQLPYYD MVPSDPSIEE MRKVVCDQKF RPSIPNQWQS CEALRVMGRI

361 MRECWYANGA ARLTALRIKK TISQLCVKED CKA
```

A nucleic acid sequence encoding the unprocessed ALK7 polypeptide precursor protein (isoform 3) is shown below (SEQ ID NO: 307), corresponding to nucleotides 244-1482 of NCBI Reference Sequence NM_001111032.1. The signal sequence is indicated by solid underline.

(SEQ ID NO: 307)
```
ATGACCCGGGCGCTCTGCTCAGCGCTCCGCCAGGCTCTCCTGCTGCTCGC
AGCGGCCGCCGAGCTCTCGCCAGGACTGAAGTGTGTATGTCTTTTGTGTG
ATTCTTCAAACTTTACCTGCCAAACAGAAGGAGCATGTTGGGCATCAGTC
ATGCTAACCAATGGAAAAGAGCAGGTGATCAAATCCTGTGTCTCCCTTCC
AGAACTGAATGCTCAAGTCTTCTGTCATAGTTCCAACAATGTTACCAAAA
CCGAATGCTGCTTCACAGATTTTTGCAACAACATAACACTGCACCTTCCA
ACAGGTCTACCTCTGTTGGTTCAAAGGACAATTGCAAGGACGATTGTGCT
TCAGGAAATAGTAGGAAAAGGTAGATTTGGTGAGGTGTGGCATGGAAGAT
GGTGTGGGGAAGATGTGGCTGTGAAAATATTCTCCTCCAGAGATGAAAGA
TCTTGGTTTCGTGAGGCAGAAATTTACCAGACGGTCATGCTGCGACATGA
AAACATCCTTGGTTTCATTGCTGCTGACAACAAAGATAATGGAACTTGGA
CTCAACTTTGGCTGGTATCTGAATATCATGAACAGGGCTCCTTATATGAC
TATTTGAATAGAAATATAGTGACCGTGGCTGGAATGATCAAGCTGGCGCT
CTCAATTGCTAGTGGTCTGGCACACCTTCATATGGAGATTGTTGGTACAC
AAGGTAAACCTGCTATTGCTCATCGAGACATAAAATCAAAGAATATCTTA
GTGAAAAAGTGTGAAACTTGTGCCATAGCGGACTTAGGGTTGGCTGTGAA
GCATGATTCAATACTGAACACTATCGACATACCTCAGAATCCTAAAGTGG
GAACCAAGAGGTATATGGCTCCTGAAATGCTTGATGATACAATGAATGTG
AATATCTTTGAGTCCTTCAAACGAGCTGACATCTATTCTGTTGGTCTGGT
TTACTGGGAAATAGCCCGGAGGTGTTCAGTCGGAGGAATTGTTGAGGAGT
ACCAATTGCCTTATTATGACATGGTGCCTTCAGATCCCTCGATAGAGGAA
ATGAGAAAGGTTGTTTGTGACCAGAAGTTTCGACCAAGTATCCCAAACCA
GTGGCAAAGTTGTGAAGCACTCCGAGTCATGGGGAGAATAATGCGTGAGT
GTTGGTATGCCAACGGAGCGGCCCGCCTAACTGCTCTTCGTATTAAGAAG
ACTATATCTCAACTTTGTGTCAAAGAAGACTGCAAAGCC
```

A nucleic acid sequence encoding the processed ALK7 polypeptide (isoform 3) is as follows (SEQ ID NO: 308):

(SEQ ID NO: 308)
```
GAGCTCTCGCCAGGACTGAAGTGTGTATGTCTTTTGTGTGATTCTTCAAA
CTTTACCTGCCAAACAGAAGGAGCATGTTGGGCATCAGTCATGCTAACCA
ATGGAAAAGAGCAGGTGATCAAATCCTGTGTCTCCCTTCCAGAACTGAAT
GCTCAAGTCTTCTGTCATAGTTCCAACAATGTTACCAAAACCGAATGCTG
CTTCACAGATTTTTGCAACAACATAACACTGCACCTTCCAACAGGTCTAC
CTCTGTTGGTTCAAAGGACAATTGCAAGGACGATTGTGCTTCAGGAAATA
GTAGGAAAAGGTAGATTTGGTGAGGTGTGGCATGGAAGATGGTGTGGGGA
AGATGTGGCTGTGAAAATATTCTCCTCCAGAGATGAAAGATCTTGGTTTC
```

```
GTGAGGCAGAAATTTACCAGACGGTCATGCTGCGACATGAAAACATCCTT

GGTTTCATTGCTGCTGACAACAAAGATAATGGAACTTGGACTCAACTTTG

GCTGGTATCTGAATATCATGAACAGGGCTCCTTATATGACTATTTGAATA

GAAATATAGTGACCGTGGCTGGAATGATCAAGCTGGCGCTCTCAATTGCT

AGTGGTCTGGCACACCTTCATATGGAGATTGTTGGTACACAAGGTAAACC

TGCTATTGCTCATCGAGACATAAAATCAAAGAATATCTTAGTGAAAAAGT

GTGAAACTTGTGCCATAGCGGACTTAGGGTTGGCTGTGAAGCATGATTCA

ATACTGAACACTATCGACATACCTCAGAATCCTAAAGTGGGAACCAAGAG

GTATATGGCTCCTGAAATGCTTGATGATACAATGAATGTGAATATCTTTG

AGTCCTTCAAACGAGCTGACATCTATTCTGTTGGTCTGGTTTACTGGGAA

ATAGCCCGGAGGTGTTCAGTCGGAGGAATTGTTGAGGAGTACCAATTGCC

TTATTATGACATGGTGCCTTCAGATCCCTCGATAGAGGAAATGAGAAAGG

TTGTTTGTGACCAGAAGTTTCGACCAAGTATCCCAAACCAGTGGCAAAGT

TGTGAAGCACTCCGAGTCATGGGGAGAATAATGCGTGAGTGTTGGTATGC

CAACGGAGCGGCCCGCCTAACTGCTCTTCGTATTAAGAAGACTATATCTC

AACTTTGTGTCAAAGAAGACTGCAAAGCC
```

The amino acid sequence of an alternative human ALK7 precursor protein, isoform 4 (NCBI Ref Seq NP_001104503.1), is shown as follows (SEQ ID NO: 309), where the signal peptide is indicated by a single underline.

A nucleic acid sequence encoding the unprocessed ALK7 polypeptide precursor protein (isoform 4) is shown below (SEQ ID NO: 311), corresponding to nucleotides 244-1244 of NCBI Reference Sequence NM_001111033.1. The signal sequence is indicated by solid underline.

```
                                                 (SEQ ID NO: 311)
ATGACCCGGGCGCTCTGCTCAGCGCTCCGCCAGGCTCTCCTGCTGCTCGC

AGCGGCCGCCGAGCTCTCGCCAGGACTGAAGTGTGTATGTCTTTTGTGTG

ATTCTTCAAACTTTACCTGCCAAACAGAAGGAGCATGTTGGGCATCAGTC

ATGCTAACCAATGGAAAAGAGCAGGTGATCAAATCCTGTGTCTCCCTTCC

AGAACTGAATGCTCAAGTCTTCTGTCATAGTTCCAACAATGTTACCAAAA

CCGAATGCTGCTTCACAGATTTTTGCAACAACATAACACTGCACCTTCCA

ACAGATAATGGAACTTGGACTCAACTTTGGCTGGTATCTGAATATCATGA

ACAGGGCTCCTTATATGACTATTTGAATAGAAATATAGTGACCGTGGCTG

GAATGATCAAGCTGGCGCTCTCAATTGCTAGTGGTCTGGCACACCTTCAT

ATGGAGATTGTTGGTACACAAGGTAAACCTGCTATTGCTCATCGAGACAT

AAAATCAAAGAATATCTTAGTGAAAAAGTGTGAAACTTGTGCCATAGCGG

ACTTAGGGTTGGCTGTGAAGCATGATTCAATACTGAACACTATCGACATA

CCTCAGAATCCTAAAGTGGGAACCAAGAGGTATATGGCTCCTGAAATGCT

TGATGATACAATGAATGTGAATATCTTTGAGTCCTTCAAACGAGCTGACA
```

```
                                                 (SEQ ID NO: 309)
  1 MTRALCSALR QALLLLAAAA ELSPGLKCVC LLCDSSNFTC QTEGACWASV MLTNGKEQVI

61 KSCVSLPELN AQVFCHSSNN VTKTECCFTD FCNNITLHLP TDNGTWTQLW LVSEYHEQGS

121 LYDYLNRNIV TVAGMIKLAL SIASGLAHLH MEIVGTQGKP AIAHRDIKSK NILVKKCETC

181 AIADLGLAVK HDSILNTIDI PQNPKVGTKR YMAPEMLDDT MNVNIFESFK RADIYSVGLV

241 YWEIARRCSV GGIVEEYQLP YYDMVPSDPS IEEMRKVVCD QKFRPSIPNQ WQSCEALRVM

301 GRIMRECWYA NGAARLTALR IKKTISQLCV KEDCKA
```

The amino acid sequence of the processed ALK7 polypeptide (isoform 4) is as follows (SEQ ID NO: 310). Like ALK7 isoform 3, isoform 4 lacks a transmembrane domain and is therefore proposed to be soluble in its entirety (Roberts et al., 2003, Biol Reprod 68:1719-1726). N-terminal variants of SEQ ID NO: 310 are predicted as described below.

```
-continued
TCTATTCTGTTGGTCTGGTTTACTGGGAAATAGCCCGGAGGTGTTCAGTC

GGAGGAATTGTTGAGGAGTACCAATTGCCTTATTATGACATGGTGCCTTC

AGATCCCTCGATAGAGGAAATGAGAAAGGTTGTTTGTGACCAGAAGTTTC
```

```
                                                 (SEQ ID NO: 310)
  1 ELSPGLKCVC LLCDSSNFTC QTEGACWASV MLTNGKEQVI KSCVSLPELN AQVFCHSSNN

61 VTKTECCFTD FCNNITLHLP TDNGTWTQLW LVSEYHEQGS LYDYLNRNIV TVAGMIKLAL

121 SIASGLAHLH MEIVGTQGKP AIAHRDIKSK NILVKKCETC AIADLGLAVK HDSILNTIDI

181 PQNPKVGTKR YMAPEMLDDT MNVNIFESFK RADIYSVGLV YWEIARRCSV GGIVEEYQLP

240 YYDMVPSDPS IEEMRKVVCD QKFRPSIPNQ WQSCEALRVM GRIMRECWYA NGAARLTALR

301 IKKTISQLCV KEDCKA
```

-continued

```
GACCAAGTATCCCAAACCAGTGGCAAAGTTGTGAAGCACTCCGAGTCATG

GGGAGAATAATGCGTGAGTGTTGGTATGCCAACGGAGCGGCCCGCCTAAC

TGCTCTTCGTATTAAGAAGACTATATCTCAACTTTGTGTCAAAGAAGACT

GCAAAGCCTAA
```

A nucleic acid sequence encoding the processed ALK7 polypeptide (isoform 4) is as follows (SEQ ID NO: 312):

```
                                         (SEQ ID NO: 312)
GAGCTCTCGCCAGGACTGAAGTGTGTATGTCTTTTGTGTGATTCTTCAAA

CTTTACCTGCCAAACAGAAGGAGCATGTTGGGCATCAGTCATGCTAACCA

ATGGAAAAGAGCAGGTGATCAAATCCTGTGTCTCCCTTCCAGAACTGAAT

GCTCAAGTCTTCTGTCATAGTTCCAACAATGTTACCAAAACCGAATGCTG

CTTCACAGATTTTTGCAACAACATAACACTGCACCTTCCAACAGATAATG

GAACTTGGACTCAACTTTGGCTGGTATCTGAATATCATGAACAGGGCTCC

TTATATGACTATTTGAATAGAAATATAGTGACCGTGGCTGGAATGATCAA

GCTGGCGCTCTCAATTGCTAGTGGTCTGGCACACCTTCATATGGAGATTG

TTGGTACACAAGGTAAACCTGCTATTGCTCATCGAGACATAAAATCAAAG

AATATCTTAGTGAAAAAGTGTGAAACTTGTGCCATAGCGGACTTAGGGTT

GGCTGTGAAGCATGATTCAATACTGAACACTATCGACATACCTCAGAATC

CTAAAGTGGGAACCAAGAGGTATATGGCTCCTGAAATGCTTGATGATACA

ATGAATGTGAATATCTTTGAGTCCTTCAAACGAGCTGACATCTATTCTGT

TGGTCTGGTTTACTGGGAAATAGCCCGGAGGTGTTCAGTCGGAGGAATTG

TTGAGGAGTACCAATTGCCTTATTATGACATGGTGCCTTCAGATCCCTCG

ATAGAGGAAATGAGAAAGGTTGTTTGTGACCAGAAGTTTCGACCAAGTAT

CCCAAACCAGTGGCAAAGTTGTGAAGCACTCCGAGTCATGGGGAGAATAA

TGCGTGAGTGTTGGTATGCCAACGGAGCGGCCCGCCTAACTGCTCTTCGT

ATTAAGAAGACTATATCTCAACTTTGTGTCAAAGAAGACTGCAAAGCCTA

A
```

Based on the signal sequence of full-length ALK7 (isoform 1) in the rat (see NCBI Reference Sequence NP_620790.1) and on the high degree of sequence identity between human and rat ALK7, it is predicted that a processed form of human ALK7 isoform 1 is as follows (SEQ ID NO: 313).

peptide, which includes fragments, functional variants, and modified forms thereof. Preferably, ALK7 polypeptides for use in accordance with inventions of the disclosure (e.g., heteromultimer complexes comprising an ALK7 polypeptide and uses thereof) are soluble (e.g., an extracellular domain of ALK7). In other preferred embodiments, ALK7 polypeptides for use in accordance with the inventions of the disclosure bind to and/or inhibit (antagonize) activity (e.g., induction of Smad 2/3 and/or Smad 1/5/8 signaling) of one or more TGF-beta superfamily ligands. In some embodiments, heteromultimer complexes of the disclosure comprise at least one ALK7 polypeptide that is at least 70%, 75%, 80%, 85%, 90%, 95%, 97%, 98%, or 99% identical to the amino acid sequence of SEQ ID NO: 38, 39, 112, 114, 301, 302, 305, 306, 309, 310, 313, 405, or 406. In some embodiments, heteromultimer complexes of the disclosure consist or consist essentially of at least one ALK7 polypeptide that is at least 70%, 75%, 80%, 85%, 90%, 95%, 97%, 98%, or 99% identical to the amino acid sequence of SEQ ID NO: 38, 39, 112, 114, 301, 302, 305, 306, 309, 310, 313, 405, or 406.

In certain aspects, the disclosure relates to heteromultimers that comprise at least one ALK1 polypeptide, which includes fragments, functional variants, and modified forms thereof, and at least one ActRIIB polypeptide, which includes fragments, functional variants, and modified forms thereof. In some embodiments, ALK1:ActRIIB heteromultimer complexes of the disclosure comprise at least one ALK1 polypeptide that comprises, consists of, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:ActRIIB heteromultimers of the disclosure comprises at least one ActRIIB polypeptide that comprises, consists, or consists essentially a sequence that is at least 70%, 75%, 80%, 85%, 90%, 91%, 92%, 93%, 94%, 95%, 96% 97%, 98%, 99%, or 100% identical to amino acids 29-109 of SEQ ID NO: 1. In some embodiments, ALK1:ActRIIB heteromultimer complexes of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 1, 2, 3, 4, 5, 6, 100, 102, 153, 154, 401, 402, 453, and 454. In certain preferred embodiments, ActRIIB polypeptides of the disclosure do not comprise an acidic amino acid (e.g., a naturally occurring D or E amino acid or artificially acidic amino acid). Preferably,

```
                                          (SEQ ID NO: 313)
  1 LKCVCLLCDS SNFTCQTEGA CWASVMLTNG KEQVIKSCVS LPELNAQVFC HSSNNVTKTE

61 CCFTDFCNNI TLHLPTASPN APKLGPME
```

Active variants of processed ALK7 isoform 1 are predicted in which SEQ ID NO: 39 is truncated by 1, 2, 3, 4, 5, 6, or 7 amino acids at the N-terminus and SEQ ID NO: 313 is truncated by 1 or 2 amino acids at the N-terminus. Consistent with SEQ ID NO: 313, it is further expected that leucine is the N-terminal amino acid in the processed forms of human ALK7 isoform 3 (SEQ ID NO: 306) and human ALK7 isoform 4 (SEQ ID NO: 310).

In certain embodiments, the disclosure relates to heteromultimer complexes that comprise at least one ALK7 poly- ALK1:ActRIIB heteromultimer complexes of the present disclosure are soluble (e.g., comprise an extracellular domain of ALK1 and/or ActRIIB) In other embodiments, ALK1:ActRIIB heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:ActRIIB heteromultimer complexes of the disclosure have different ligand binding specificities/profiles compared to their corresponding homomultimer complexes (i.e., ALK1 and ActRIIB homomultimers). ALK1:ActRIIB heteromultimer complexes of the disclosure include, e.g., heterodimers, heterotrimers, heterotetramers and further oligomeric structures. In certain preferred embodiments, ALK1:ActRIIB heteromultimer complexes of the disclosure are heterodimers.

In certain aspects, the disclosure relates to heteromultimers that comprise at least one ALK2 polypeptide, which includes fragments, functional variants, and modified forms thereof, and at least one ActRIIB polypeptide, which includes fragments, functional variants, and modified forms thereof. In some embodiments, ALK2:ActRIIB heteromultimer complexes of the disclosure comprise at least one ALK2 polypeptide that comprises, consists of, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 18, 19, 136, 138, 173, 174, 421, 422, 465, and 466 or amino acids 35-99 of SEQ ID NO: 18. In some embodiments, ALK2:ActRIIB heteromultimers of the disclosure comprises at least one ActRIIB polypeptide that comprises, consists, or consists essentially a sequence that is at least 70%, 75%, 80%, 85%, 90%, 91%, 92%, 93%, 94%, 95%, 96% 97%, 98%, 99%, or 100% identical to amino acids 29-109 of SEQ ID NO: 1. In some embodiments, ALK2:ActRIIB heteromultimer complexes of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 1, 2, 3, 4, 5, 6, 100, 102, 153, 154, 401, 402, 453, and 454. In certain preferred embodiments, ActRIIB polypeptides of the disclosure do not comprise an acidic amino acid (e.g., a naturally occurring D or E amino acid or artificially acidic amino acid). Preferably, ALK2:ActRIIB heteromultimer complexes of the present disclosure are soluble (e.g., comprise an extracellular domain of ALK2 and/or ActRIIB) In other embodiments, ALK2:ActRIIB heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK2:ActRIIB heteromultimer complexes of the disclosure have different ligand binding specificities/profiles compared to their corresponding homomultimer complexes (i.e., ALK2 and ActRIIB homomultimers). ALK2:ActRIIB heteromultimer complexes of the disclosure include, e.g., heterodimers, heterotrimers, heterotetramers and further oligomeric structures. In certain preferred embodiments, ALK2:ActRIIB heteromultimer complexes of the disclosure are heterodimers.

In certain aspects, the disclosure relates to heteromultimers that comprise at least one ALK3 polypeptide, which includes fragments, functional variants, and modified forms thereof, and at least one ActRIIB polypeptide, which includes fragments, functional variants, and modified forms thereof. In some embodiments, ALK3:ActRIIB heteromultimer complexes of the disclosure comprise at least one ALK3 polypeptide that comprises, consists of, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 22, 23, 115, 117, 175, 176, 407, 408, 467, and 468 or amino acids 61-130 of SEQ ID NO: 22. In some embodiments, ALK3:ActRIIB heteromultimers of the disclosure comprises at least one ActRIIB polypeptide that comprises, consists, or consists essentially a sequence that is at least 70%, 75%, 80%, 85%, 90%, 91%, 92%, 93%, 94%, 95%, 96% 97%, 98%, 99%, or 100% identical to amino acids 29-109 of SEQ ID NO: 1. In some embodiments, ALK3:ActRIIB heteromultimer complexes of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 1, 2, 3, 4, 5, 6, 100, 102, 153, 154, 401, 402, 453, and 454. In certain preferred embodiments, ActRIIB polypeptides of the disclosure do not comprise an acidic amino acid (e.g., a naturally occurring D or E amino acid or artificially acidic amino acid). Preferably, ALK3:ActRIIB heteromultimer complexes of the present disclosure are soluble (e.g., comprise an extracellular domain of ALK3 and/or ActRIIB) In other embodiments, ALK3:ActRIIB heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK3:ActRIIB heteromultimer complexes of the disclosure have different ligand binding specificities/profiles compared to their corresponding homomultimer complexes (i.e., ALK3 and ActRIIB homomultimers). ALK3:ActRIIB heteromultimer complexes of the disclosure include, e.g., heterodimers, heterotrimers, heterotetramers and further oligomeric structures. In certain preferred embodiments, ALK3:ActRIIB heteromultimer complexes of the disclosure are heterodimers.

In certain aspects, the disclosure relates to heteromultimers that comprise at least one ALK4 polypeptide, which includes fragments, functional variants, and modified forms thereof, and at least one ActRIIB polypeptide, which includes fragments, functional variants, and modified forms thereof. In some embodiments, ALK4:ActRIIB heteromultimer complexes of the disclosure comprise at least one ALK4 polypeptide that comprises, consists of, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 26, 27, 83, 84, 104, 106, 177, 178, 403, 404, 469, and 470 or amino acids 34-101 of SEQ ID NO: 26 or 83. In some embodiments, ALK4:ActRIIB heteromultimers of the disclosure comprises at least one ActRIIB polypeptide that comprises, consists, or consists essentially a sequence that is at least 70%, 75%, 80%, 85%, 90%, 91%, 92%, 93%, 94%, 95%, 96% 97%, 98%, 99%, or 100% identical to amino acids 29-109 of SEQ ID NO: 1. In some embodiments, ALK4:ActRIIB heteromultimer complexes of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 1, 2, 3, 4, 5, 6, 100, 102, 153, 154, 401, 402, 453, and 454. In certain preferred embodiments, ActRIIB polypeptides of the disclosure do not comprise an acidic amino acid (e.g., a naturally occurring D or E amino acid or artificially acidic amino acid). Preferably, ALK4:ActRIIB heteromultimer complexes of the present disclosure are soluble (e.g., comprise an extracellular domain of ALK4 and/or ActRIIB) In other embodiments, ALK4:ActRIIB heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK4:ActRIIB heteromultimer complexes of the disclosure have different ligand binding specificities/profiles compared to their corresponding homomultimer complexes (i.e., ALK4 and ActRIIB homomultimers). ALK4:ActRIIB heteromultimer complexes of the disclosure include, e.g., heterodimers, heterotrimers, heterotetramers and further oligomeric structures. In certain preferred embodiments, ALK4:ActRIIB heteromultimer complexes of the disclosure are heterodimers.

In certain aspects, the disclosure relates to heteromultimers that comprise at least one ALK5 polypeptide, which includes fragments, functional variants, and modified forms thereof, and at least one ActRIIB polypeptide, which includes fragments, functional variants, and modified forms thereof. In some embodiments, ALK5:ActRIIB heteromultimer complexes of the disclosure comprise at least one ALK5 polypeptide that comprises, consists of, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 30, 31, 87, 88, 139, 141, 179, 180, 423, 424, 471, and 472 or amino acids 36-106 of SEQ ID NO: 30 or 87. In some embodiments, ALK5:ActRIIB heteromultimers of the disclosure comprises at least one ActRIIB polypeptide that comprises, consists, or consists essentially a sequence that is at least 70%, 75%, 80%, 85%, 90%, 91%, 92%, 93%, 94%, 95%, 96% 97%, 98%, 99%, or 100% identical to amino acids 29-109 of SEQ ID NO: 1. In some embodiments, ALK5:ActRIIB heteromultimer complexes of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 1, 2, 3, 4, 5, 6, 100, 102, 153, 154, 401, 402, 453, and 454. In certain preferred embodiments, ActRIIB polypeptides of the disclosure do not comprise an acidic amino acid (e.g., a naturally occurring D or E amino acid or artificially acidic amino acid). Preferably, ALK5:ActRIIB heteromultimer complexes of the present disclosure are soluble (e.g., comprise an extracellular domain of ALK5 and/or ActRIIB) In other embodiments, ALK5:ActRIIB heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK5:ActRIIB heteromultimer complexes of the disclosure have different ligand binding specificities/profiles compared to their corresponding homomultimer complexes (i.e., ALK5 and ActRIIB homomultimers). ALK5:ActRIIB heteromultimer complexes of the disclosure include, e.g., heterodimers, heterotrimers, heterotetramers and further oligomeric structures. In certain preferred embodiments, ALK5:ActRIIB heteromultimer complexes of the disclosure are heterodimers.

In certain aspects, the disclosure relates to heteromultimers that comprise at least one ALK6 polypeptide, which includes fragments, functional variants, and modified forms thereof, and at least one ActRIIB polypeptide, which includes fragments, functional variants, and modified forms thereof. In some embodiments, ALK6:ActRIIB heteromultimer complexes of the disclosure comprise at least one ALK6 polypeptide that comprises, consists of, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 34, 35, 91, 92, 142, 144, 181, 182, 425, 426, 473, and 474 or amino acids 32-102 of SEQ ID NO: 34 or amino acids 62-132 of SEQ ID NO: 91. In some embodiments, ALK6:ActRIIB heteromultimers of the disclosure comprises at least one ActRIIB polypeptide that comprises, consists, or consists essentially a sequence that is at least 70%, 75%, 80%, 85%, 90%, 91%, 92%, 93%, 94%, 95%, 96% 97%, 98%, 99%, or 100% identical to amino acids 29-109 of SEQ ID NO: 1. In some embodiments, ALK6:ActRIIB heteromultimer complexes of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 1, 2, 3, 4, 5, 6, 100, 102, 153, 154, 401, 402, 453, and 454. In certain preferred embodiments, ActRIIB polypeptides of the disclosure do not comprise an acidic amino acid (e.g., a naturally occurring D or E amino acid or artificially acidic amino acid). Preferably, ALK6:ActRIIB heteromultimer complexes of the present disclosure are soluble (e.g., comprise an extracellular domain of ALK6 and/or ActRIIB) In other embodiments, ALK6:ActRIIB heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK6:ActRIIB heteromultimer complexes of the disclosure have different ligand binding specificities/profiles compared to their corresponding homomultimer complexes (i.e., ALK6 and ActRIIB homomultimers). ALK6:ActRIIB heteromultimer complexes of the disclosure include, e.g., heterodimers, heterotrimers, heterotetramers and further oligomeric structures. In certain preferred embodiments, ALK6:ActRIIB heteromultimer complexes of the disclosure are heterodimers.

In certain aspects, the disclosure relates to heteromultimers that comprise at least one ALK7 polypeptide, which includes fragments, functional variants, and modified forms thereof, and at least one ActRIIB polypeptide, which includes fragments, functional variants, and modified forms thereof. In some embodiments, ALK7:ActRIIB heteromultimer complexes of the disclosure comprise at least one ALK7 polypeptide that comprises, consists of, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 38, 39, 301, 302, 305, 306, 309, 310, 313, 112, 114, 183, 184, 405, 406, 475, and 476 or amino acids 28-92 of SEQ ID Nos: 38, 305, and 309. In some embodiments, ALK7:ActRIIB heteromultimers of the disclosure comprises at least one ActRIIB polypeptide that comprises, consists, or consists essentially a sequence that is at least 70%, 75%, 80%, 85%, 90%, 91%, 92%, 93%, 94%, 95%, 96% 97%, 98%, 99%, or 100% identical to amino acids 29-109 of SEQ ID NO: 1. In some embodiments, ALK7:ActRIIB heteromultimer complexes of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 1, 2, 3, 4, 5, 6, 100, 102, 153, 154, 401, 402, 453, and 454. In certain preferred embodiments, ActRIIB polypeptides of the disclosure do not comprise an acidic amino acid (e.g., a naturally occurring D or E amino acid or artificially acidic amino acid). Preferably, ALK7:ActRIIB heteromultimer complexes of the present disclosure are soluble (e.g., comprise an extracellular domain of ALK7 and/or ActRIIB) In other embodiments, ALK7:ActRIIB heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK7:ActRIIB heteromultimer complexes of the disclosure have different ligand binding specificities/profiles compared to their corresponding homomultimer complexes (i.e., ALK7 and ActRIIB homomultimers). ALK7:ActRIIB heteromultimer complexes of the disclosure include, e.g., heterodimers, heterotrimers, heterotetramers and further oligomeric structures. In certain preferred embodiments, ALK7:ActRIIB heteromultimer complexes of the disclosure are heterodimers.

In certain aspects, the disclosure relates to heteromultimers that comprise at least one ALK1 polypeptide, which includes fragments, functional variants, and modified forms thereof, and at least one ActRIIA polypeptide, which includes fragments, functional variants, and modified forms thereof. In some embodiments, ALK1:ActRIIA heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:ActRIIA heteromultimers of the disclosure comprises at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 9, 10, 11, 118, 120, 151, 152, 409, 410, 451, and 452 or amino acids 30-110 of SEQ ID NO: 9. Preferably, ALK1:ActRIIA heteromultimers of the present disclosure are soluble (e.g., comprise an extracellular domain of ALK1 and/or ActRIIA). In other preferred embodiments, ALK1:ActRIIA heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:ActRIIA heteromultimers of the disclosure have different ligand binding specificities/profiles compared to their corresponding homomultimer complexes (i.e., ALK1 and ActRIIA homomultimers). ALK1:ActRIIA heteromultimer complexes of the disclosure include, e.g., heterodimers, heterotrimers, heterotetramers and further oligomeric structures. In certain preferred embodiments, ALK1:ActRIIA heteromultimer complexes of the disclosure are heterodimers.

In certain aspects, the disclosure relates to heteromultimers that comprise at least one ALK2 polypeptide, which includes fragments, functional variants, and modified forms thereof, and at least one ActRIIA polypeptide, which includes fragments, functional variants, and modified forms thereof. In some embodiments, ALK2:ActRIIA heteromultimers of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 18, 19, 136, 138, 173, 174, 421, 422, 465, and 466 or amino acids 35-99 of SEQ ID NO: 18. In some embodiments, ALK2:ActRIIA heteromultimers of the disclosure comprises at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 9, 10, 11, 118, 120, 151, 152, 409, 410, 451, and 452 or amino acids 30-110 of SEQ ID NO: 9. Preferably, ALK2:ActRIIA heteromultimers of the present disclosure are soluble (e.g., comprise an extracellular domain of ALK2 and/or ActRIIA). In other preferred embodiments, ALK2:ActRIIA heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK2:ActRIIA heteromultimers of the disclosure have different ligand binding specificities/profiles compared to their corresponding homomultimer complexes (i.e., ALK2 and ActRIIA homomultimers). ALK2:ActRIIA heteromultimer complexes of the disclosure include, e.g., heterodimers, heterotrimers, heterotetramers and further oligomeric structures. In certain preferred embodiments, ALK2:ActRIIA heteromultimer complexes of the disclosure are heterodimers.

In certain aspects, the disclosure relates to heteromultimers that comprise at least one ALK3 polypeptide, which includes fragments, functional variants, and modified forms thereof, and at least one ActRIIA polypeptide, which includes fragments, functional variants, and modified forms thereof. In some embodiments, ALK3:ActRIIA heteromultimers of the disclosure comprise at least one ALK3 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 22, 23, 115, 117, 175, 176, 407, 408, 467, and 468 or amino acids 61-130 of SEQ ID NO: 22. In some embodiments, ALK3:ActRIIA heteromultimers of the disclosure comprises at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 9, 10, 11, 118, 120, 151, 152, 409, 410, 451, and 452 or amino acids 30-110 of SEQ ID NO: 9. Preferably, ALK3:ActRIIA heteromultimers of the present disclosure are soluble (e.g., comprise an extracellular domain of ALK3 and/or ActRIIA). In other preferred embodiments, ALK3:ActRIIA heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK3:ActRIIA heteromultimers of the disclosure have different ligand binding specificities/profiles compared to their corresponding homomultimer complexes (i.e., ALK3 and ActRIIA homomultimers). ALK3:ActRIIA heteromultimer complexes of the disclosure include, e.g., heterodimers, heterotrimers, heterotetramers and further oligomeric structures. In certain preferred embodiments, ALK3:ActRIIA heteromultimer complexes of the disclosure are heterodimers.

In certain aspects, the disclosure relates to heteromultimers that comprise at least one ALK4 polypeptide, which includes fragments, functional variants, and modified forms thereof, and at least one ActRIIA polypeptide, which includes fragments, functional variants, and modified forms thereof. In some embodiments, ALK4:ActRIIA heteromultimers of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 26, 27, 83, 84, 104, 106, 177, 178, 403, 404, 469, and 470 or amino acids 34-101 of SEQ ID NO: 26 or 83. In some embodiments, ALK4:ActRIIA heteromultimers of the disclosure comprises at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 9, 10, 11, 118, 120, 151, 152, 409, 410, 451, and 452 or amino acids 30-110 of SEQ ID NO: 9. Preferably, ALK4:ActRIIA heteromultimers of the present disclosure are soluble (e.g., comprise an extracellular domain of ALK4 and/or ActRIIA). In other preferred embodiments, ALK4:ActRIIA heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK4:ActRIIA heteromultimers of the disclosure have different ligand binding specificities/profiles compared to their corresponding homomultimer complexes (i.e., ALK4 and ActRIIA homomultimers). ALK4:ActRIIA heteromultimer complexes of the disclosure include, e.g., heterodimers, heterotrimers, heterotetramers and further oligomeric structures. In certain preferred embodiments, ALK4:ActRIIA heteromultimer complexes of the disclosure are heterodimers.

In certain aspects, the disclosure relates to heteromultimers that comprise at least one ALK5 polypeptide, which includes fragments, functional variants, and modified forms thereof, and at least one ActRIIA polypeptide, which includes fragments, functional variants, and modified forms thereof. In some embodiments, ALK5:ActRIIA heteromultimers of the disclosure comprise at least one ALK5 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 30, 31, 87, 88, 139, 141, 179, 180, 423, 424, 471, and 472 or amino acids 36-106 of SEQ ID NO: 30 or 87. In some embodiments, ALK5:ActRIIA heteromultimers of the disclosure comprises at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 9, 10, 11, 118, 120, 151, 152, 409, 410, 451, and 452 or amino acids 30-110 of SEQ ID NO: 9. Preferably, ALK5:ActRIIA heteromultimers of the present disclosure are soluble (e.g., comprise an extracellular domain of ALK5 and/or ActRIIA). In other preferred embodiments, ALK5:ActRIIA heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK5:ActRIIA heteromultimers of the disclosure have different ligand binding specificities/profiles compared to their corresponding homomultimer complexes (i.e., ALK5 and ActRIIA homomultimers). ALK5:ActRIIA heteromultimer complexes of the disclosure include, e.g., heterodimers, heterotrimers, heterotetramers and further oligomeric structures. In certain preferred embodiments, ALK5:ActRIIA heteromultimer complexes of the disclosure are heterodimers.

In certain aspects, the disclosure relates to heteromultimers that comprise at least one ALK6 polypeptide, which includes fragments, functional variants, and modified forms thereof, and at least one ActRIIA polypeptide, which includes fragments, functional variants, and modified forms thereof. In some embodiments, ALK6:ActRIIA heteromultimers of the disclosure comprise at least one ALK6 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 34, 35, 91, 92, 142, 144, 181, 182, 425, 426, 473, and 474 or amino acids 32-102 of SEQ ID NO: 34 or amino acids 62-132 of SEQ ID NO: 91. In some embodiments, ALK6:ActRIIA heteromultimers of the disclosure comprises at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 9, 10, 11, 118, 120, 151, 152, 409, 410, 451, and 452 or amino acids 30-110 of SEQ ID NO: 9. Preferably, ALK6:ActRIIA heteromultimers of the present disclosure are soluble (e.g., comprise an extracellular domain of ALK6 and/or ActRIIA). In other preferred embodiments, ALK6:ActRIIA heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK6:ActRIIA heteromultimers of the disclosure have different ligand binding specificities/profiles compared to their corresponding homomultimer complexes (i.e., ALK6 and ActRIIA homomultimers). ALK6:ActRIIA heteromultimer complexes of the disclosure include, e.g., heterodimers, heterotrimers, heterotetramers and further oligomeric structures. In certain preferred embodiments, ALK6:ActRIIA heteromultimer complexes of the disclosure are heterodimers.

In certain aspects, the disclosure relates to heteromultimers that comprise at least one ALK7 polypeptide, which includes fragments, functional variants, and modified forms thereof, and at least one ActRIIA polypeptide, which includes fragments, functional variants, and modified forms thereof. In some embodiments, ALK7:ActRIIA heteromultimers of the disclosure comprise at least one ALK7 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 38, 39, 301, 302, 305, 306, 309, 310, 313, 112, 114, 183, 184, 405, 406, 475, and 476 or amino acids 28-93 of SEQ ID Nos: 38, 305, or 309. In some embodiments, ALK7:ActRIIA heteromultimers of the disclosure comprises at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NOs: 9, 10, 11, 118, 120, 151, 152, 409, 410, 451, and 452 or amino acids 30-110 of SEQ ID NO: 9. Preferably, ALK7:ActRIIA heteromultimers of the present disclosure are soluble (e.g., comprise an extracellular domain of ALK7 and/or ActRIIA). In other preferred embodiments, ALK7:ActRIIA heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK7:ActRIIA heteromultimers of the disclosure have different ligand binding specificities/profiles compared to their corresponding homomultimer complexes (i.e., ALK7 and ActRIIA homomultimers). ALK7:ActRIIA heteromultimer complexes of the disclosure include, e.g., heterodimers, heterotrimers, heterotetramers and further oligomeric structures. In certain preferred embodiments, ALK7:ActRIIA heteromultimer complexes of the disclosure are heterodimers.

In certain aspects, the disclosure relates to heteromultimers that comprise at least one ALK1 polypeptide, which includes fragments, functional variants, and modified forms thereof, and at least one TGFBRII polypeptide, which includes fragments, functional variants, and modified forms thereof. In some embodiments, ALK1:TGFBRII heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:TGFBRII heteromultimer complexes of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. Preferably, ALK1:TGFBRII heteromultimer complexes of the present disclosure are soluble (e.g., comprise an extracellular domain of ALK1 and/or TGFBRII). In other preferred embodiments, ALK1:TGFBRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:TGFBRII heteromultimer complexes of the disclosure have different ligand binding specificities/profiles compared to their corresponding homomultimer complexes (i.e., ALK1 and TGFBRII homomultimers). ALK1:TGFBRII heteromultimer complexes of the disclosure include, e.g., heterodimers, heterotrimers, heterotetramers and further oligomeric structures. In certain preferred embodiments, ALK1:TGFBRII heteromultimer complexes of the disclosure are heterodimers.

In certain aspects, the disclosure relates to heteromultimers that comprise at least one ALK2 polypeptide, which includes fragments, functional variants, and modified forms thereof, and at least one TGFBRII polypeptide, which includes fragments, functional variants, and modified forms thereof. In some embodiments, ALK2:TGFBRII heteromultimers of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 18, 19, 136, 138, 173, 174, 421, 422, 465, and 466 or amino acids 35-99 of SEQ ID NO: 18. In some embodiments, ALK2:TGFBRII heteromultimer complexes of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. Preferably, ALK2:TGFBRII heteromultimer complexes of the present disclosure are soluble (e.g., comprise an extracellular domain of ALK2 and/or TGFBRII). In other preferred embodiments, ALK2:TGFBRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK2:TGFBRII heteromultimer complexes of the disclosure have different ligand binding specificities/profiles compared to their corresponding homomultimer complexes (i.e., ALK2 and TGFBRII homomultimers). ALK2:TGFBRII heteromultimer complexes of the disclosure include, e.g., heterodimers, heterotrimers, heterotetramers and further oligomeric structures. In certain preferred embodiments, ALK2:TGFBRII heteromultimer complexes of the disclosure are heterodimers.

In certain aspects, the disclosure relates to heteromultimers that comprise at least one ALK3 polypeptide, which includes fragments, functional variants, and modified forms thereof, and at least one TGFBRII polypeptide, which includes fragments, functional variants, and modified forms thereof. In some embodiments, ALK3:TGFBRII heteromultimers of the disclosure comprise at least one ALK3 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 22, 23, 115, 117, 175, 176, 407, 408, 467, and 468 or amino acids 61-130 of SEQ ID NO: 22. In some embodiments, ALK3:TGFBRII heteromultimer complexes of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. Preferably, ALK3:TGFBRII heteromultimer complexes of the present disclosure are soluble (e.g., comprise an extracellular domain of ALK3 and/or TGFBRII). In other preferred embodiments, ALK3:TGFBRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK3:TGFBRII heteromultimer complexes of the disclosure have different ligand binding specificities/profiles compared to their corresponding homomultimer complexes (i.e., ALK3 and TGFBRII homomultimers). ALK3:TGFBRII heteromultimer complexes of the disclosure include, e.g., heterodimers, heterotrimers, heterotetramers and further oligomeric structures. In certain preferred embodiments, ALK3:TGFBRII heteromultimer complexes of the disclosure are heterodimers.

In certain aspects, the disclosure relates to heteromultimers that comprise at least one ALK4 polypeptide, which includes fragments, functional variants, and modified forms thereof, and at least one TGFBRII polypeptide, which includes fragments, functional variants, and modified forms thereof. In some embodiments, ALK4:TGFBRII heteromultimers of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 26, 27, 83, 84, 104, 106, 177, 178, 403, 404, 469, and 470 or amino acids 34-101 of SEQ ID NO: 26 or 83. In some embodiments, ALK4:TGFBRII heteromultimer complexes of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. Preferably, ALK4:TGFBRII heteromultimer complexes of the present disclosure are soluble (e.g., comprise an extracellular domain of ALK4 and/or TGFBRII). In other preferred embodiments, ALK4:TGFBRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK4:TGFBRII heteromultimer complexes of the disclosure have different ligand binding specificities/profiles compared to their corresponding homomultimer complexes (i.e., ALK4 and TGFBRII homomultimers). ALK4:TGFBRII heteromultimer complexes of the disclosure include, e.g., heterodimers, heterotrimers, heterotetramers and further oligomeric structures. In certain preferred embodiments, ALK4:TGFBRII heteromultimer complexes of the disclosure are heterodimers.

In certain aspects, the disclosure relates to heteromultimers that comprise at least one ALK5 polypeptide, which includes fragments, functional variants, and modified forms thereof, and at least one TGFBRII polypeptide, which includes fragments, functional variants, and modified forms thereof. In some embodiments, ALK5:TGFBRII heteromultimers of the disclosure comprise at least one ALK5 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 30, 31, 87, 88, 139, 141, 179, 180, 423, 424, 471, and 472 or amino acids 36-106 of SEQ ID NO: 30 or 87. In some embodiments, ALK5:TGFBRII heteromultimer complexes of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. Preferably, ALK5:TGFBRII heteromultimer complexes of the present disclosure are soluble (e.g., comprise an extracellular domain of ALK5 and/or TGFBRII). In other preferred embodiments, ALK5:TGFBRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK5:TGFBRII heteromultimer complexes of the disclosure have different ligand binding specificities/profiles compared to their corresponding homomultimer complexes (i.e., ALK5 and TGFBRII homomultimers). ALK5:TGFBRII heteromultimer complexes of the disclosure include, e.g., heterodimers, heterotrimers, heterotetramers and further oligomeric structures. In certain preferred embodiments, ALK5:TGFBRII heteromultimer complexes of the disclosure are heterodimers.

In certain aspects, the disclosure relates to heteromultimers that comprise at least one ALK6 polypeptide, which includes fragments, functional variants, and modified forms thereof, and at least one TGFBRII polypeptide, which includes fragments, functional variants, and modified forms thereof. In some embodiments, ALK6:TGFBRII heteromultimers of the disclosure comprise at least one ALK6 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 34, 35, 91, 92, 142, 144, 181, 182, 425, 426, 473, and 474 or amino acids 32-102 of SEQ ID NO: 34 or amino acids 62-132 of SEQ ID NO: 91. In some embodiments, ALK6:TGFBRII heteromultimer complexes of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. Preferably, ALK6:TGFBRII heteromultimer complexes of the present disclosure are soluble (e.g., comprise an extracellular domain of ALK6 and/or TGFBRII). In other preferred embodiments, ALK6:TGFBRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK6:TGFBRII heteromultimer complexes of the disclosure have different ligand binding specificities/profiles compared to their corresponding homomultimer complexes (i.e., ALK6 and TGFBRII homomultimers). ALK6:TGFBRII heteromultimer complexes of the disclosure include, e.g., heterodimers, heterotrimers, heterotetramers and further oligomeric structures. In certain preferred embodiments, ALK6:TGFBRII heteromultimer complexes of the disclosure are heterodimers.

In certain aspects, the disclosure relates to heteromultimers that comprise at least one ALK7 polypeptide, which includes fragments, functional variants, and modified forms thereof, and at least one TGFBRII polypeptide, which includes fragments, functional variants, and modified forms thereof. In some embodiments, ALK7:TGFBRII heteromultimers of the disclosure comprise at least one ALK7 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 38, 39, 301, 302, 305, 306, 309, 310, 313, 112, 114, 183, 184, 405, 406, 475, and 476 or amino acids 28-93 of SEQ ID Nos: 38, 305, or 309. In some embodiments, ALK7:TGFBRII heteromultimer complexes of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. Preferably, ALK7:TGFBRII heteromultimer complexes of the present disclosure are soluble (e.g., comprise an extracellular domain of ALK7 and/or TGFBRII). In other preferred embodiments, ALK7:TGFBRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK7:TGFBRII heteromultimer complexes of the disclosure have different ligand binding specificities/profiles compared to their corresponding homomultimer complexes (i.e., ALK7 and TGFBRII homomultimers). ALK7:TGFBRII heteromultimer complexes of the disclosure include, e.g., heterodimers, heterotrimers, heterotetramers and further oligomeric structures. In certain preferred embodiments, ALK7:TGFBRII heteromultimer complexes of the disclosure are heterodimers.

In certain aspects, the disclosure relates to heteromultimers that comprise at least one ALK1 polypeptide, which includes fragments, functional variants, and modified forms thereof, and at least one MISRII polypeptide, which includes fragments, functional variants, and modified forms thereof. In some embodiments, ALK1:MISRII heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:MISRII heteromultimer complexes of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 50, 51, 75, 76, 79, 80, 133, 135, 161, 162, 419, 420, 457, and 458 or amino acids 24-116 of SEQ ID Nos: 50, 75, or 79. Preferably, ALK1:MISRII heteromultimer complexes of the present disclosure are soluble (e.g., comprise an extracellular domain of ALK1 and/or MISRII). In other preferred embodiments, ALK1:MISRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:MISRII heteromultimer complexes of the disclosure have different ligand binding specificities/profiles compared to their corresponding homomultimer complexes (i.e., ALK1 and MISRII homomultimers). ALK1:MISRII heteromultimers of the disclosure include, e.g., heterodimers, heterotrimers, heterotetramers and further oligomeric structures. In certain preferred embodiments, ALK1:MISRII heteromultimers of the disclosure are heterodimers.

In certain aspects, the disclosure relates to heteromultimers that comprise at least one ALK2 polypeptide, which includes fragments, functional variants, and modified forms thereof, and at least one MISRII polypeptide, which includes fragments, functional variants, and modified forms thereof. In some embodiments, ALK2:MISRII heteromultimers of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 18, 19, 136, 138, 173, 174, 421, 422, 465, and 466 or amino acids 35-99 of SEQ ID NO: 18. In some embodiments, ALK2:MISRII heteromultimer complexes of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 50, 51, 75, 76, 79, 80, 133, 135, 161, 162, 419, 420, 457, and 458 or amino acids 24-116 of SEQ ID Nos: 50, 75, or 79. Preferably, ALK2:MISRII heteromultimer complexes of the present disclosure are soluble (e.g., comprise an extracellular domain of ALK2 and/or MISRII). In other preferred embodiments, ALK2:MISRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK2:MISRII heteromultimer complexes of the disclosure have different ligand binding specificities/profiles compared to their corresponding homomultimer complexes (i.e., ALK2 and MISRII homomultimers). ALK2:MISRII heteromultimers of the disclosure include, e.g., heterodimers, heterotrimers, heterotetramers and further oligomeric structures. In certain preferred embodiments, ALK2:MISRII heteromultimers of the disclosure are heterodimers.

In certain aspects, the disclosure relates to heteromultimers that comprise at least one ALK3 polypeptide, which includes fragments, functional variants, and modified forms thereof, and at least one MISRII polypeptide, which includes fragments, functional variants, and modified forms thereof. In some embodiments, ALK3:MISRII heteromultimers of the disclosure comprise at least one ALK3 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 22, 23, 115, 117, 175, 176, 407, 408, 467, and 468 or amino acids 61-130 of SEQ ID NO: 22. In some embodiments, ALK3:MISRII heteromultimer complexes of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 50, 51, 75, 76, 79, 80, 133, 135, 161, 162, 419, 420, 457, and 458 or amino acids 24-116 of SEQ ID Nos: 50, 75, or 79. Preferably, ALK3:MISRII heteromultimer complexes of the present disclosure are soluble (e.g., comprise an extracellular domain of ALK3 and/or MISRII). In other preferred embodiments, ALK3:MISRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK3:MISRII heteromultimer complexes of the disclosure have different ligand binding specificities/profiles compared to their corresponding homomultimer complexes (i.e., ALK3 and MISRII homomultimers). ALK3:MISRII heteromultimers of the disclosure include, e.g., heterodimers, heterotrimers, heterotetramers and further oligomeric structures. In certain preferred embodiments, ALK3:MISRII heteromultimers of the disclosure are heterodimers.

In certain aspects, the disclosure relates to heteromultimers that comprise at least one ALK4 polypeptide, which includes fragments, functional variants, and modified forms thereof, and at least one MISRII polypeptide, which includes fragments, functional variants, and modified forms thereof. In some embodiments, ALK4:MISRII heteromultimers of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 26, 27, 83, 84, 104, 106, 177, 178, 403, 404, 469, and 470 or amino acids 34-101 of SEQ ID NO: 26 or 83. In some embodiments, ALK4:MISRII heteromultimer complexes of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 50, 51, 75, 76, 79, 80, 133, 135, 161, 162, 419, 420, 457, and 458 or amino acids 24-116 of SEQ ID Nos: 50, 75, or 79. Preferably, ALK4:MISRII heteromultimer complexes of the present disclosure are soluble (e.g., comprise an extracellular domain of ALK4 and/or MISRII). In other preferred embodiments, ALK4:MISRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK4:MISRII heteromultimer complexes of the disclosure have different ligand binding specificities/profiles compared to their corresponding homomultimer complexes (i.e., ALK4 and MISRII homomultimers). ALK4:MISRII heteromultimers of the disclosure include, e.g., heterodimers, heterotrimers, heterotetramers and further oligomeric structures. In certain preferred embodiments, ALK4:MISRII heteromultimers of the disclosure are heterodimers.

In certain aspects, the disclosure relates to heteromultimers that comprise at least one ALK5 polypeptide, which includes fragments, functional variants, and modified forms thereof, and at least one MISRII polypeptide, which includes fragments, functional variants, and modified forms thereof. In some embodiments, ALK5:MISRII heteromultimers of the disclosure comprise at least one ALK5 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 30, 31, 87, 88, 139, 141, 179, 180, 423, 424, 471, and 472 or amino acids 36-106 of SEQ ID NOs: 30 or 87. In some embodiments, ALK5:MISRII heteromultimer complexes of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 50, 51, 75, 76, 79, 80, 133, 135, 161, 162, 419, 420, 457, and 458 or amino acids 24-116 of SEQ ID Nos: 50, 75, or 79. Preferably, ALK5:MISRII heteromultimer complexes of the present disclosure are soluble (e.g., comprise an extracellular domain of ALK5 and/or MISRII). In other preferred embodiments, ALK5:MISRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK5:MISRII heteromultimer complexes of the disclosure have different ligand binding specificities/profiles compared to their corresponding homomultimer complexes (i.e., ALK5 and MISRII homomultimers). ALK5:MISRII heteromultimers of the disclosure include, e.g., heterodimers, heterotrimers, heterotetramers and further oligomeric structures. In certain preferred embodiments, ALK5:MISRII heteromultimers of the disclosure are heterodimers.

In certain aspects, the disclosure relates to heteromultimers that comprise at least one ALK6 polypeptide, which includes fragments, functional variants, and modified forms thereof, and at least one MISRII polypeptide, which includes fragments, functional variants, and modified forms thereof. In some embodiments, ALK6:MISRII heteromultimers of the disclosure comprise at least one ALK6 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 34, 35, 91, 92, 142, 144, 181, 182, 425, 426, 473, and 474 or amino acids 32-102 of SEQ ID NO: 34 or amino acids 62-132 SEQ ID NO: 91. In some embodiments, ALK6:MISRII heteromultimer complexes of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 50, 51, 75, 76, 79, 80, 133, 135, 161, 162, 419, 420, 457, and 458 or amino acids 24-116 of SEQ ID Nos: 50, 75, or 79. Preferably, ALK6:MISRII heteromultimer complexes of the present disclosure are soluble (e.g., comprise an extracellular domain of ALK6 and/or MISRII). In other preferred embodiments, ALK6:MISRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK6:MISRII heteromultimer complexes of the disclosure have different ligand binding specificities/profiles compared to their corresponding homomultimer complexes (i.e., ALK6 and MISRII homomultimers). ALK6:MISRII heteromultimers of the disclosure include, e.g., heterodimers, heterotrimers, heterotetramers and further oligomeric structures. In certain preferred embodiments, ALK6:MISRII heteromultimers of the disclosure are heterodimers.

In certain aspects, the disclosure relates to heteromultimers that comprise at least one ALK7 polypeptide, which includes fragments, functional variants, and modified forms thereof, and at least one MISRII polypeptide, which includes fragments, functional variants, and modified forms thereof. In some embodiments, ALK7:MISRII heteromultimers of the disclosure comprise at least one ALK7 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 38, 39, 301, 302, 305, 306, 309, 310, 313, 112, 114, 183, 184, 405, 406, 475, and 476 or amino acids 28-93 of SEQ ID NOs: 38, 305, or 309. In some embodiments, ALK7:MISRII heteromultimer complexes of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 50, 51, 75, 76, 79, 80, 133, 135, 161, 162, 419, 420, 457, and 458 or amino acids 24-116 of SEQ ID Nos: 50, 75, or 79. Preferably, ALK7:MISRII heteromultimer complexes of the present disclosure are soluble (e.g., comprise an extracellular domain of ALK7 and/or MISRII). In other preferred embodiments, ALK7:MISRII heteromultimer complexes of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK7:MISRII heteromultimer complexes of the disclosure have different ligand binding specificities/profiles compared to their corresponding homomultimer complexes (i.e., ALK7 and MISRII homomultimers). ALK7:MISRII heteromultimers of the disclosure include, e.g., heterodimers, heterotrimers, heterotetramers and further oligomeric structures. In certain preferred embodiments, ALK7:MISRII heteromultimers of the disclosure are heterodimers.

In certain aspects, the disclosure relates to heteromultimers that comprise at least one ALK1 polypeptide, which includes fragments, functional variants, and modified forms thereof, and at least one BMPRII polypeptide, which includes fragments, functional variants, and modified forms thereof. In some embodiments, ALK1:BMPRII heteromultimer complexes of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:BMPRII heteromultimer complexes of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 46, 47, 71, 72, 121, 123, 155, 156, 411, 412, 455, and 456 or amino acids 34-123 of SEQ ID NO: 46 or 71. Preferably, ALK1:BMPRII heteromultimers of the present disclosure are soluble (e.g., comprise an extracellular domain of ALK1 and/or BMPRII). In other preferred embodiments, ALK1:BMPRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:BMPRII heteromultimers of the disclosure have different ligand binding specificities/profiles compared to their corresponding homomultimer complexes (i.e., ALK1 and BMPRII homomultimers). ALK1:BMPRII heteromultimer complexes of the disclosure include, e.g., heterodimers, heterotrimers, heterotetramers and further oligomeric structures. In certain preferred embodiments, ALK1:BMPRII heteromultimer complexes of the disclosure are heterodimers.

In certain aspects, the disclosure relates to heteromultimers that comprise at least one ALK2 polypeptide, which includes fragments, functional variants, and modified forms thereof, and at least one BMPRII polypeptide, which includes fragments, functional variants, and modified forms thereof. In some embodiments, ALK2:BMPRII heteromultimer complexes of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 18, 19, 136, 138, 173, 174, 421, 422, 465, and 466 or amino acids 35-99 of SEQ ID NO: 18. In some embodiments, ALK2:BMPRII heteromultimer complexes of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 46, 47, 71, 72, 121, 123, 155, 156, 411, 412, 455, and 456 or amino acids 34-123 of SEQ ID NO: 46 or 71. Preferably, ALK2:BMPRII heteromultimers of the present disclosure are soluble (e.g., comprise an extracellular domain of ALK2 and/or BMPRII). In other preferred embodiments, ALK2:BMPRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin AB, activin AC, activin AE, activin BC, activin BE, nodal, glial cell-derived neurotrophic factor (GDNF), neurturin, artemin, persephin, MIS, and Lefty). In some embodiments, ALK2:BMPRII heteromultimers of the disclosure have different ligand binding specificities/profiles compared to their corresponding homomultimer complexes (i.e., ALK2 and BMPRII homomultimers). ALK2:BMPRII heteromultimer complexes of the disclosure include, e.g., heterodimers, heterotrimers, heterotetramers and further oligomeric structures. In certain preferred embodiments, ALK2:BMPRII heteromultimer complexes of the disclosure are heterodimers.

In certain aspects, the disclosure relates to heteromultimers that comprise at least one ALK3 polypeptide, which includes fragments, functional variants, and modified forms thereof, and at least one BMPRII polypeptide, which includes fragments, functional variants, and modified forms thereof. In some embodiments, ALK3:BMPRII heteromultimer complexes of the disclosure comprise at least one ALK3 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 22, 23, 115, 117, 175, 176, 407, 408, 467, and 468 or amino acids 61-130 of SEQ ID NO: 22. In some embodiments, ALK3:BMPRII heteromultimer complexes of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 46, 47, 71, 72, 121, 123, 155, 156, 411, 412, 455, and 456 or amino acids 34-123 of SEQ ID NO: 46 or 71. Preferably, ALK3:BMPRII heteromultimers of the present disclosure are soluble (e.g., comprise an extracellular domain of ALK3 and/or BMPRII). In other preferred embodiments, ALK3:BMPRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK3:BMPRII heteromultimers of the disclosure have different ligand binding specificities/profiles compared to their corresponding homomultimer complexes (i.e., ALK3 and BMPRII homomultimers). ALK3:BMPRII heteromultimer complexes of the disclosure include, e.g., heterodimers, heterotrimers, heterotetramers and further oligomeric structures. In certain preferred embodiments, ALK3:BMPRII heteromultimer complexes of the disclosure are heterodimers.

In certain aspects, the disclosure relates to heteromultimers that comprise at least one ALK4 polypeptide, which includes fragments, functional variants, and modified forms thereof, and at least one BMPRII polypeptide, which includes fragments, functional variants, and modified forms thereof. In some embodiments, ALK4:BMPRII heteromultimer complexes of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 26, 27, 83, 84, 104, 106, 177, 178, 403, 404, 469, and 470 or amino acids 34-101 of SEQ ID NOs: 26 or 83. In some embodiments, ALK4:BMPRII heteromultimer complexes of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 46, 47, 71, 72, 121, 123, 155, 156, 411, 412, 455, and 456 or amino acids 34-123 of SEQ ID NO: 46 or 71. Preferably, ALK4:BMPRII heteromultimers of the present disclosure are soluble (e.g., comprise an extracellular domain of ALK4 and/or BMPRII). In other preferred embodiments, ALK4:BMPRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK4:BMPRII heteromultimers of the disclosure have different ligand binding specificities/profiles compared to their corresponding homomultimer complexes (i.e., ALK4 and BMPRII homomultimers). ALK4:BMPRII heteromultimer complexes of the disclosure include, e.g., heterodimers, heterotrimers, heterotetramers and further oligomeric structures. In certain preferred embodiments, ALK4:BMPRII heteromultimer complexes of the disclosure are heterodimers.

In certain aspects, the disclosure relates to heteromultimers that comprise at least one ALK5 polypeptide, which includes fragments, functional variants, and modified forms thereof, and at least one BMPRII polypeptide, which includes fragments, functional variants, and modified forms thereof. In some embodiments, ALK5:BMPRII heteromultimer complexes of the disclosure comprise at least one ALK5 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: SEQ ID Nos: 30, 31, 87, 88, 139, 141, 179, 180, 423, 424, 471, and 472 or amino acids 36-106 of SEQ ID NOs: 30 or 87. In some embodiments, ALK5:BMPRII heteromultimer complexes of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 46, 47, 71, 72, 121, 123, 155, 156, 411, 412, 455, and 456 or amino acids 34-123 of SEQ ID NO: 46 or 71. Preferably, ALK5:BMPRII heteromultimers of the present disclosure are soluble (e.g., comprise an extracellular domain of ALK5 and/or BMPRII). In other preferred embodiments, ALK5:BMPRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK5:BMPRII heteromultimers of the disclosure have different ligand binding specificities/profiles compared to their corresponding homomultimer complexes (i.e., ALK5 and BMPRII homomultimers). ALK5:BMPRII heteromultimer complexes of the disclosure include, e.g., heterodimers, heterotrimers, heterotetramers and further oligomeric structures. In certain preferred embodiments, ALK5:BMPRII heteromultimer complexes of the disclosure are heterodimers.

In certain aspects, the disclosure relates to heteromultimers that comprise at least one ALK6 polypeptide, which includes fragments, functional variants, and modified forms thereof, and at least one BMPRII polypeptide, which includes fragments, functional variants, and modified forms thereof. In some embodiments, ALK6:BMPRII heteromultimer complexes of the disclosure comprise at least one ALK6 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 34, 35, 91, 92, 142, 144, 181, 182, 425, 426, 473, and 474 or amino acids 32-102 of SEQ ID NO: 34 or amino acids 62-132 of SEQ ID NO: 91. In some embodiments, ALK6:BMPRII heteromultimer complexes of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 46, 47, 71, 72, 121, 123, 155, 156, 411, 412, 455, and 456 or amino acids 34-123 of SEQ ID NO: 46 or 71. Preferably, ALK6:BMPRII heteromultimers of the present disclosure are soluble (e.g., comprise an extracellular domain of ALK6 and/or BMPRII). In other preferred embodiments, ALK6:BMPRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK6:BMPRII heteromultimers of the disclosure have different ligand binding specificities/profiles compared to their corresponding homomultimer complexes (i.e., ALK6 and BMPRII homomultimers). ALK6:BMPRII heteromultimer complexes of the disclosure include, e.g., heterodimers, heterotrimers, heterotetramers and further oligomeric structures. In certain preferred embodiments, ALK6:BMPRII heteromultimer complexes of the disclosure are heterodimers.

In certain aspects, the disclosure relates to heteromultimers that comprise at least one ALK7 polypeptide, which includes fragments, functional variants, and modified forms thereof, and at least one BMPRII polypeptide, which includes fragments, functional variants, and modified forms thereof. In some embodiments, ALK7:BMPRII heteromultimer complexes of the disclosure comprise at least one ALK7 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 38, 39, 301, 302, 305, 306, 309, 310, 313, 112, 114, 183, 184, 405, 406, 475, and 476 or amino acids 28-92 of SEQ ID NOs: 38, 305, or 309. In some embodiments, ALK7:BMPRII heteromultimer complexes of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 46, 47, 71, 72, 121, 123, 155, 156, 411, 412, 455, and 456 or amino acids 34-123 of SEQ ID NO: 46 or 71. Preferably, ALK7:BMPRII heteromultimers of the present disclosure are soluble (e.g., comprise an extracellular domain of ALK7 and/or BMPRII). In other preferred embodiments, ALK6:BMPRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK7:BMPRII heteromultimers of the disclosure have different ligand binding specificities/profiles compared to their corresponding homomultimer complexes (i.e., ALK7 and BMPRII homomultimers). ALK7:BMPRII heteromultimer complexes of the disclosure include, e.g., heterodimers, heterotrimers, heterotetramers and further oligomeric structures. In certain preferred embodiments, ALK7:BMPRII heteromultimer complexes of the disclosure are heterodimers.

In certain aspects, the disclosure relates to heteromultimers that comprise at least one ALK1 polypeptide, which includes fragments, functional variants, and modified forms thereof, and at least one ALK2 polypeptide, which includes fragments, functional variants, and modified forms thereof. In some embodiments, ALK1:ALK2 heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:ALK2 heteromultimers of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 18, 19, 136, 138, 173, 174, 421, 422, 465, and 466 or amino acids 35-99 of SEQ ID NO: 18. Preferably, ALK1:ALK2 heteromultimers of the present disclosure are soluble (e.g., comprise an extracellular domain of ALK1 and/or ALK2). In other preferred embodiments, ALK1:ALK2 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/

MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:ALK2 heteromultimers of the disclosure have different ligand binding specificities/profiles compared to their corresponding homomultimer complexes (i.e., ALK1 and ALK2 homomultimers). ALK1:ALK2 heteromultimers of the disclosure include, e.g., heterodimers, heterotrimers, heterotetramers and further oligomeric structures. In certain preferred embodiments, ALK1:ALK2 heteromultimers of the disclosure are heterodimers.

In certain aspects, the disclosure relates to heteromultimers that comprise at least one ALK1 polypeptide, which includes fragments, functional variants, and modified forms thereof, and at least one ALK2 polypeptide, which includes fragments, functional variants, and modified forms thereof. In some embodiments, ALK1:ALK2 heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:ALK2 heteromultimers of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 18, 19, 136, 138, 173, 174, 421, 422, 465, and 466 or amino acids 35-99 of SEQ ID NO: 18. Preferably, ALK1:ALK2 heteromultimers of the present disclosure are soluble (e.g., comprise an extracellular domain of ALK1 and/or ALK2). In other preferred embodiments, ALK1:ALK2 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/ MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:ALK2 heteromultimers of the disclosure have different ligand binding specificities/profiles compared to their corresponding homomultimer complexes (i.e., ALK1 and ALK2 homomultimers). ALK1:ALK2 heteromultimers of the disclosure include, e.g., heterodimers, heterotrimers, heterotetramers and further oligomeric structures. In certain preferred embodiments, ALK1:ALK2 heteromultimers of the disclosure are heterodimers.

In certain aspects, the disclosure relates to heteromultimers that comprise at least one ALK1 polypeptide, which includes fragments, functional variants, and modified forms thereof, and at least one ALK3 polypeptide, which includes fragments, functional variants, and modified forms thereof. In some embodiments, ALK1:ALK3 heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:ALK3 heteromultimers of the disclosure comprise at least one ALK3 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 22, 23, 115, 117, 175, 176, 407, 408, 467, and 468 or amino acids 61-130 of SEQ ID NO: 22. Preferably, ALK1:ALK3 heteromultimers of the present disclosure are soluble (e.g., comprise an extracellular domain of ALK1 and/or ALK3). In other preferred embodiments, ALK1:ALK3 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/ MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:ALK3 heteromultimers of the disclosure have different ligand binding specificities/profiles compared to their corresponding homomultimer complexes (i.e., ALK1 and ALK3 homomultimers). ALK1:ALK3 heteromultimers of the disclosure include, e.g., heterodimers, heterotrimers, heterotetramers and further oligomeric structures. In certain preferred embodiments, ALK1:ALK3 heteromultimers of the disclosure are heterodimers.

In certain aspects, the disclosure relates to heteromultimers that comprise at least one ALK1 polypeptide, which includes fragments, functional variants, and modified forms thereof, and at least one ALK4 polypeptide, which includes fragments, functional variants, and modified forms thereof. In some embodiments, ALK1:ALK4 heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:ALK4 heteromultimers of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 26, 27, 83, 84, 104, 106, 177, 178, 403, 404, 469, and 470 or amino acids 34-101 of SEQ ID NOs: 26 or 83. Preferably, ALK1:ALK4 heteromultimers of the present disclosure are soluble (e.g., comprise an extracellular domain of ALK1 and/or ALK4). In other preferred embodiments, ALK1:ALK4 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/ MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:ALK4 heteromultimers of the disclosure have different ligand binding specificities/profiles compared to their corresponding homomultimer complexes (i.e., ALK1 and ALK4 homomultimers). ALK1:ALK4 heteromultimers of the disclosure include, e.g., heterodimers, heterotrimers, heterotetramers and further oligomeric structures. In certain preferred embodiments, ALK1:ALK4 heteromultimers of the disclosure are heterodimers.

In certain aspects, the disclosure relates to heteromultimers that comprise at least one ALK1 polypeptide, which includes fragments, functional variants, and modified forms thereof, and at least one ALK4 polypeptide, which includes fragments, functional variants, and modified forms thereof. In some embodiments, ALK1:ALK4 heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:ALK4 heteromultimers of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 26, 27, 83, 84, 104, 106, 177, 178, 403, 404, 469, and 470 or amino acids 34-101 of SEQ ID NOs: 26 or 83. Preferably, ALK1:ALK4 heteromultimers of the present disclosure are soluble (e.g., comprise an extracellular domain of ALK1 and/or ALK4). In other preferred embodiments, ALK1:ALK4 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:ALK4 heteromultimers of the disclosure have different ligand binding specificities/profiles compared to their corresponding homomultimer complexes (i.e., ALK1 and ALK4 homomultimers). ALK1:ALK4 heteromultimers of the disclosure include, e.g., heterodimers, heterotrimers, heterotetramers and further oligomeric structures. In certain preferred embodiments, ALK1:ALK4 heteromultimers of the disclosure are heterodimers.

In certain aspects, the disclosure relates to heteromultimers that comprise at least one ALK1 polypeptide, which includes fragments, functional variants, and modified forms thereof, and at least one ALK5 polypeptide, which includes fragments, functional variants, and modified forms thereof. In some embodiments, ALK1:ALK5 heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:ALK5 heteromultimers of the disclosure comprise at least one ALK5 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 30, 31, 87, 88, 139, 141, 179, 180, 423, 424, 471, and 472 or amino acids 36-106 of SEQ ID NOs: 30 or 87. Preferably, ALK1:ALK5 heteromultimers of the present disclosure are soluble (e.g., comprise an extracellular domain of ALK1 and/or ALK5). In other preferred embodiments, ALK1:ALK5 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:ALK5 heteromultimers of the disclosure have different ligand binding specificities/profiles compared to their corresponding homomultimer complexes (i.e., ALK1 and ALK5 homomultimers). ALK1:ALK5 heteromultimers of the disclosure include, e.g., heterodimers, heterotrimers, heterotetramers and further oligomeric structures. In certain preferred embodiments, ALK1:ALK5 heteromultimers of the disclosure are heterodimers.

In certain aspects, the disclosure relates to heteromultimers that comprise at least one ALK1 polypeptide, which includes fragments, functional variants, and modified forms thereof, and at least one ALK6 polypeptide, which includes fragments, functional variants, and modified forms thereof. In some embodiments, ALK1:ALK6 heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:ALK6 heteromultimers of the disclosure comprise at least one ALK6 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 34, 35, 91, 92, 142, 144, 181, 182, 425, 426, 473, and 474 or amino acids 32-102 of SEQ ID NO: 34 or amino acids 62-132 of SEQ ID NO: 91. Preferably, ALK1:ALK6 heteromultimers of the present disclosure are soluble (e.g., comprise an extracellular domain of ALK1 and/or ALK6). In other preferred embodiments, ALK1:ALK6 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:ALK6 heteromultimers of the disclosure have different ligand binding specificities/profiles compared to their corresponding homomultimer complexes (i.e., ALK1 and ALK6 homomultimers). ALK1:ALK6 heteromultimers of the disclosure include, e.g., heterodimers, heterotrimers, heterotetramers and further oligomeric structures. In certain preferred embodiments, ALK1:ALK6 heteromultimers of the disclosure are heterodimers.

In certain aspects, the disclosure relates to heteromultimers that comprise at least one ALK1 polypeptide, which includes fragments, functional variants, and modified forms thereof, and at least one ALK7 polypeptide, which includes fragments, functional variants, and modified forms thereof. In some embodiments, ALK1:ALK7 heteromultimers of the disclosure comprise at least one ALK1 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID NO: 14, 15, 124, 126, 171, 172, 413, 414, 463, and 464 or amino acids 34-95 of SEQ ID NO: 14. In some embodiments, ALK1:ALK7 heteromultimers of the disclosure comprise at least one ALK7 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 38, 39, 301, 302, 305, 306, 309, 310, 313, 112, 114, 183, 184, 405, 406, 475, and 476 or amino acids 28-92 of SEQ ID NOs: 38, 305, or 309. Preferably, ALK1:ALK7 heteromultimers of the present disclosure are soluble (e.g., comprise an extracellular domain of ALK1 and/or ALK7). In other preferred embodiments, ALK1:ALK7 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK1:ALK7 heteromultimers of the disclosure have different ligand binding specificities/profiles compared to their corresponding homomultimer complexes (i.e., ALK1 and ALK7 homomultimers). ALK1:ALK7 heteromultimers of the disclosure include, e.g., heterodimers, heterotrimers, heterotetramers and further oligomeric structures. In certain preferred embodiments, ALK1:ALK7 heteromultimers of the disclosure are heterodimers.

In certain aspects, the disclosure relates to heteromultimers that comprise at least one ALK2 polypeptide, which includes fragments, functional variants, and modified forms thereof, and at least one ALK3 polypeptide, which includes fragments, functional variants, and modified forms thereof. In some embodiments, ALK2:ALK3 heteromultimers of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 18, 19, 136, 138, 173, 174, 421, 422, 465, and 466 or amino acids 35-99 of SEQ ID NO: 18. In some embodiments, ALK2:ALK3 heteromultimers of the disclosure comprise at least one ALK3 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 22, 23, 115, 117, 175, 176, 407, 408, 467, and 468 or amino acids 61-130 of SEQ ID NO: 22. Preferably, ALK2:ALK3 heteromultimers of the present disclosure are soluble (e.g., comprise an extracellular domain of ALK2 and/or ALK3). In other preferred embodiments, ALK2:ALK3 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK2:ALK3 heteromultimers of the disclosure have different ligand binding specificities/profiles compared to their corresponding homomultimer complexes (i.e., ALK2 and ALK3 homomultimers). ALK2:ALK3 heteromultimers of the disclosure include, e.g., heterodimers, heterotrimers, heterotetramers and further oligomeric structures. In certain preferred embodiments, ALK2:ALK3 heteromultimers of the disclosure are heterodimers.

In certain aspects, the disclosure relates to heteromultimers that comprise at least one ALK2 polypeptide, which includes fragments, functional variants, and modified forms thereof, and at least one ALK4 polypeptide, which includes fragments, functional variants, and modified forms thereof. In some embodiments, ALK2:ALK4 heteromultimers of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 18, 19, 136, 138, 173, 174, 421, 422, 465, and 466 or amino acids 35-99 of SEQ ID NO: 18. In some embodiments, ALK2:ALK4 heteromultimers of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 26, 27, 83, 84, 104, 106, 177, 178, 403, 404, 469, and 470 or amino acids 34-101 of SEQ ID NOs: 26 or 83. Preferably, ALK2:ALK4 heteromultimers of the present disclosure are soluble (e.g., comprise an extracellular domain of ALK2 and/or ALK4). In other preferred embodiments, ALK2:ALK4 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK2:ALK4 heteromultimers of the disclosure have different ligand binding specificities/profiles compared to their corresponding homomultimer complexes (i.e., ALK2 and ALK4 homomultimers). ALK2:ALK4 heteromultimers of the disclosure include, e.g., heterodimers, heterotrimers, heterotetramers and further oligomeric structures. In certain preferred embodiments, ALK2:ALK4 heteromultimers of the disclosure are heterodimers.

In certain aspects, the disclosure relates to heteromultimers that comprise at least one ALK2 polypeptide, which includes fragments, functional variants, and modified forms thereof, and at least one ALK5 polypeptide, which includes fragments, functional variants, and modified forms thereof. In some embodiments, ALK2:ALK5 heteromultimers of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 18, 19, 136, 138, 173, 174, 421, 422, 465, and 466 or amino acids 35-99 of SEQ ID NO: 18. In some embodiments, ALK2:ALK5 heteromultimers of the disclosure comprise at least one ALK5 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 30, 31, 87, 88, 139, 141, 179, 180, 423, 424, 471, and 472 or amino acids 36-106 of SEQ ID NOs: 30 or 87. Preferably, ALK2:ALK5 heteromultimers of the present disclosure are soluble (e.g., comprise an extracellular domain of ALK2 and/or ALK5). In other preferred embodiments, ALK2:ALK5 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK2:ALK5 heteromultimers of the disclosure have different ligand binding specificities/profiles compared to their corresponding homomultimer complexes (i.e., ALK2 and ALK5 homomultimers). ALK2:ALK5 heteromultimers of the disclosure include, e.g., heterodimers, heterotrimers, heterotetramers and further oligomeric structures. In certain preferred embodiments, ALK2:ALK5 heteromultimers of the disclosure are heterodimers.

In certain aspects, the disclosure relates to heteromultimers that comprise at least one ALK2 polypeptide, which includes fragments, functional variants, and modified forms thereof, and at least one ALK6 polypeptide, which includes fragments, functional variants, and modified forms thereof. In some embodiments, ALK2:ALK6 heteromultimers of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 18, 19, 136, 138, 173, 174, 421, 422, 465, and 466 or amino acids 35-99 of SEQ ID NO: 18. In some embodiments, ALK2:ALK6 heteromultimers of the disclosure comprise at least one ALK6 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 34, 35, 91, 92, 142, 144, 181, 182, 425, 426, 473, and 474 or amino acids 32-102 of SEQ ID NO: 34 or amino acids 62-132 of SEQ ID NO: 91. Preferably, ALK2:ALK6 heteromultimers of the present disclosure are soluble (e.g., comprise an extracellular domain of ALK2 and/or ALK6). In other preferred embodiments, ALK2: ALK6 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK2:ALK6 heteromultimers of the disclosure have different ligand binding specificities/profiles compared to their corresponding homomultimer complexes (i.e., ALK2 and ALK6 homomultimers). ALK2:ALK6 heteromultimers of the disclosure include, e.g., heterodimers, heterotrimers, heterotetramers and further oligomeric structures. In certain preferred embodiments, ALK2:ALK6 heteromultimers of the disclosure are heterodimers.

In certain aspects, the disclosure relates to heteromultimers that comprise at least one ALK2 polypeptide, which includes fragments, functional variants, and modified forms thereof, and at least one ALK7 polypeptide, which includes fragments, functional variants, and modified forms thereof. In some embodiments, ALK2:ALK7 heteromultimers of the disclosure comprise at least one ALK2 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 18, 19, 136, 138, 173, 174, 421, 422, 465, and 466 or amino acids 35-99 of SEQ ID NO: 18. In some embodiments, ALK2:ALK7 heteromultimers of the disclosure comprise at least one ALK7 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 38, 39, 301, 302, 305, 306, 309, 310, 313, 112, 114, 183, 184, 405, 406, 475, and 476 or amino acids 28-92 of SEQ ID NOs: 38, 305, or 309. Preferably, ALK2:ALK7 heteromultimers of the present disclosure are soluble (e.g., comprise an extracellular domain of ALK2 and/or ALK7). In other preferred embodiments, ALK2: ALK7 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK2:ALK7 heteromultimers of the disclosure have different ligand binding specificities/profiles compared to their corresponding homomultimer complexes (i.e., ALK2 and ALK7 homomultimers). ALK2:ALK7 heteromultimers of the disclosure include, e.g., heterodimers, heterotrimers, heterotetramers and further oligomeric structures. In certain preferred embodiments, ALK2:ALK7 heteromultimers of the disclosure are heterodimers.

In certain aspects, the disclosure relates to heteromultimers that comprise at least one ALK3 polypeptide, which includes fragments, functional variants, and modified forms thereof, and at least one ALK4 polypeptide, which includes fragments, functional variants, and modified forms thereof. In some embodiments, ALK3:ALK4 heteromultimers of the disclosure comprise at least one ALK3 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 22, 23, 115, 117, 175, 176, 407, 408, 467, and 468 or amino acids 61-130 of SEQ ID NO: 22. In some embodiments, ALK3:ALK4 heteromultimers of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 26, 27, 83, 84, 104, 106, 177, 178, 403, 404, 469, and 470 or amino acids 34-101 of SEQ ID NOs: 26 or 83. Preferably, ALK3:ALK4 heteromultimers of the present disclosure are soluble (e.g., comprise an extracellular domain of ALK3 and/or ALK4). In other preferred embodiments, ALK3:ALK4 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK3:ALK4 heteromultimers of the disclosure have different ligand binding specificities/profiles compared to their corresponding homomultimer complexes (i.e., ALK3 and ALK4 homomultimers). ALK3:ALK4 heteromultimers of the disclosure include, e.g., heterodimers, heterotrimers, heterotetramers and further oligomeric structures. In certain preferred embodiments, ALK3:ALK4 heteromultimers of the disclosure are heterodimers.

In certain aspects, the disclosure relates to heteromultimers that comprise at least one ALK3 polypeptide, which includes fragments, functional variants, and modified forms thereof, and at least one ALK5 polypeptide, which includes fragments, functional variants, and modified forms thereof. In some embodiments, ALK3:ALK5 heteromultimers of the disclosure comprise at least one ALK3 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 22, 23, 115, 117, 175, 176, 407, 408, 467, and 468 or amino acids 61-130 of SEQ ID NO: 22. In some embodiments, ALK3:ALK5 heteromultimers of the disclosure comprise at least one ALK5 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 30, 31, 87, 88, 139, 141, 179, 180, 423, 424, 471, and 472 or amino acids 36-106 of SEQ ID NOs: 30 or 87. Preferably, ALK3:ALK5 heteromultimers of the present disclosure are soluble (e.g., comprise an extracellular domain of ALK3 and/or ALK5). In other preferred embodiments, ALK3:ALK5 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK3:ALK5 heteromultimers of the disclosure have different ligand binding specificities/profiles compared to their corresponding homomultimer complexes (i.e., ALK3 and ALK5 homomultimers). ALK3:ALK5 heteromultimers of the disclosure include, e.g., heterodimers, heterotrimers, heterotetramers and further oligomeric structures. In certain preferred embodiments, ALK3:ALK5 heteromultimers of the disclosure are heterodimers.

In certain aspects, the disclosure relates to heteromultimers that comprise at least one ALK3 polypeptide, which includes fragments, functional variants, and modified forms thereof, and at least one ALK6 polypeptide, which includes fragments, functional variants, and modified forms thereof. In some embodiments, ALK3:ALK6 heteromultimers of the disclosure comprise at least one ALK3 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 22, 23, 115, 117, 175, 176, 407, 408, 467, and 468 or amino acids 61-130 of SEQ ID NO: 22. In some embodiments, ALK3:ALK6 heteromultimers of the disclosure comprise at least one ALK6 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 34, 35, 91, 92, 142, 144, 181, 182, 425, 426, 473, and 474 or amino acids 32-102 of SEQ ID NO: 34 or amino acids 62-132 of SEQ ID NO: 91. Preferably, ALK3:ALK6 heteromultimers of the present disclosure are soluble (e.g., comprise an extracellular domain of ALK3 and/or ALK6). In other preferred embodiments, ALK3:ALK6 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK3:ALK6 heteromultimers of the disclosure have different ligand binding specificities/profiles compared to their corresponding homomultimer complexes (i.e., ALK3 and ALK6 homomultimers). ALK3:ALK6 heteromultimers of the disclosure include, e.g., heterodimers, heterotrimers, heterotetramers and further oligomeric structures. In certain preferred embodiments, ALK3:ALK6 heteromultimers of the disclosure are heterodimers.

In certain aspects, the disclosure relates to heteromultimers that comprise at least one ALK3 polypeptide, which includes fragments, functional variants, and modified forms thereof, and at least one ALK7 polypeptide, which includes fragments, functional variants, and modified forms thereof. In some embodiments, ALK3:ALK7 heteromultimers of the disclosure comprise at least one ALK3 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 22, 23, 115, 117, 175, 176, 407, 408, 467, and 468 or amino acids 61-130 of SEQ ID NO: 22. In some embodiments, ALK3:ALK7 heteromultimers of the disclosure comprise at least one ALK7 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 38, 39, 301, 302, 305, 306, 309, 310, 313, 112, 114, 183, 184, 405, 406, 475, and 476 or amino acids 28-92 of SEQ ID NOs: 38, 305, or 309. Preferably, ALK3:ALK7 heteromultimers of the present disclosure are soluble (e.g., comprise an extracellular domain of ALK3 and/or ALK7). In other preferred embodiments, ALK3:ALK7 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK3:ALK7 heteromultimers of the disclosure have different ligand binding specificities/profiles compared to their corresponding homomultimer complexes (i.e., ALK3 and ALK7 homomultimers).

ALK3:ALK7 heteromultimers of the disclosure include, e.g., heterodimers, heterotrimers, heterotetramers and further oligomeric structures. In certain preferred embodiments, ALK3:ALK7 heteromultimers of the disclosure are heterodimers.

In certain aspects, the disclosure relates to heteromultimers that comprise at least one ALK4 polypeptide, which includes fragments, functional variants, and modified forms thereof, and at least one ALK5 polypeptide, which includes fragments, functional variants, and modified forms thereof. In some embodiments, ALK4:ALK5 heteromultimers of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 26, 27, 83, 84, 104, 106, 177, 178, 403, 404, 469, and 470 or amino acids 34-101 of SEQ ID NOs: 26 or 83. In some embodiments, ALK4:ALK5 heteromultimers of the disclosure comprise at least one ALK5 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 30, 31, 87, 88, 139, 141, 179, 180, 423, 424, 471, and 472 or amino acids 36-106 of SEQ ID NOs: 30 or 87. Preferably, ALK4:ALK5 heteromultimers of the present disclosure are soluble (e.g., comprise an extracellular domain of ALK4 and/or ALK5). In other preferred embodiments, ALK4:ALK5 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK4:ALK5 heteromultimers of the disclosure have different ligand binding specificities/profiles compared to their corresponding homomultimer complexes (i.e., ALK4 and ALK5 homomultimers). ALK4:ALK5 heteromultimers of the disclosure include, e.g., heterodimers, heterotrimers, heterotetramers and further oligomeric structures. In certain preferred embodiments, ALK4:ALK5 heteromultimers of the disclosure are heterodimers.

In certain aspects, the disclosure relates to heteromultimers that comprise at least one ALK4 polypeptide, which includes fragments, functional variants, and modified forms thereof, and at least one ALK6 polypeptide, which includes fragments, functional variants, and modified forms thereof. In some embodiments, ALK4:ALK6 heteromultimers of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 26, 27, 83, 84, 104, 106, 177, 178, 403, 404, 469, and 470 or amino acids 34-101 of SEQ ID NOs: 26 or 83. In some embodiments, ALK4:ALK6 heteromultimers of the disclosure comprise at least one ALK6 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 34, 35, 91, 92, 142, 144, 181, 182, 425, 426, 473, and 474 or amino acids 32-102 of SEQ ID NO: 34 or amino acids 62-132 of SEQ ID NO: 91. Preferably, ALK4:ALK6 heteromultimers of the present disclosure are soluble (e.g., comprise an extracellular domain of ALK4 and/or ALK6). In other preferred embodiments, ALK4:ALK6 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK4:ALK6 heteromultimers of the disclosure have different ligand binding specificities/profiles compared to their corresponding homomultimer complexes (i.e., ALK4 and ALK6 homomultimers). ALK4:ALK6 heteromultimers of the disclosure include, e.g., heterodimers, heterotrimers, heterotetramers and further oligomeric structures. In certain preferred embodiments, ALK4:ALK6 heteromultimers of the disclosure are heterodimers.

In certain aspects, the disclosure relates to heteromultimers that comprise at least one ALK4 polypeptide, which includes fragments, functional variants, and modified forms thereof, and at least one ALK7 polypeptide, which includes fragments, functional variants, and modified forms thereof. In some embodiments, ALK4:ALK7 heteromultimers of the disclosure comprise at least one ALK4 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 26, 27, 83, 84, 104, 106, 177, 178, 403, 404, 469, and 470 or amino acids 34-101 of SEQ ID NOs: 26 or 83. In some embodiments, ALK4:ALK7 heteromultimers of the disclosure comprise at least one ALK7 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 38, 39, 301, 302, 305, 306, 309, 310, 313, 112, 114, 183, 184, 405, 406, 475, and 476 or amino acids 28-92 of SEQ ID NOs: 38, 305, or 309. Preferably, ALK4:ALK7 heteromultimers of the present disclosure are soluble (e.g., comprise an extracellular domain of ALK4 and/or ALK7). In other preferred embodiments, ALK4:ALK7 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK4:ALK7 heteromultimers of the disclosure have different ligand binding specificities/profiles compared to their corresponding homomultimer complexes (i.e., ALK4 and ALK7 homomultimers). ALK4:ALK7 heteromultimers of the disclosure include, e.g., heterodimers, heterotrimers, heterotetramers and further oligomeric structures. In certain preferred embodiments, ALK4:ALK7 heteromultimers of the disclosure are heterodimers.

In certain aspects, the disclosure relates to heteromultimers that comprise at least one ALK5 polypeptide, which includes fragments, functional variants, and modified forms thereof, and at least one ALK6 polypeptide, which includes fragments, functional variants, and modified forms thereof. In some embodiments, ALK5:ALK6 heteromultimers of the disclosure comprise at least one ALK5 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 30, 31, 87, 88, 139, 141, 179, 180, 423, 424, 471, and 472 or amino acids 36-106 of SEQ ID NOs: 30 or 87. In some embodiments, ALK5:ALK6 heteromultimers of the disclosure comprise at least one ALK6 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 34, 35, 91, 92, 142, 144, 181, 182, 425, 426, 473, and 474 or amino acids 32-102 of SEQ ID NO: 34 or amino acids 62-132 of SEQ ID NO: 91. Preferably, ALK5:ALK6 heteromultimers of the present disclosure are soluble (e.g., comprise an extracellular domain of ALK5 and/or ALK6). In other preferred embodiments, ALK5:ALK6 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK5:ALK6 heteromultimers of the disclosure have different ligand binding specificities/profiles compared to their corresponding homomultimer complexes (i.e., ALK5 and ALK6 homomultimers). ALK5:ALK6 heteromultimers of the disclosure include, e.g., heterodimers, heterotrimers, heterotetramers and further oligomeric structures. In certain preferred embodiments, ALK5:ALK6 heteromultimers of the disclosure are heterodimers.

In certain aspects, the disclosure relates to heteromultimers that comprise at least one ALK5 polypeptide, which includes fragments, functional variants, and modified forms thereof, and at least one ALK7 polypeptide, which includes fragments, functional variants, and modified forms thereof. In some embodiments, ALK5:ALK7 heteromultimers of the disclosure comprise at least one ALK5 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 30, 31, 87, 88, 139, 141, 179, 180, 423, 424, 471, and 472 or amino acids 36-106 of SEQ ID NOs: 30 or 87. In some embodiments, ALK5:ALK7 heteromultimers of the disclosure comprise at least one ALK7 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 38, 39, 301, 302, 305, 306, 309, 310, 313, 112, 114, 183, 184, 405, 406, 475, and 476 or amino acids 28-92 of SEQ ID NOs: 38, 305, or 309. Preferably, ALK5:ALK7 heteromultimers of the present disclosure are soluble (e.g., comprise an extracellular domain of ALK5 and/or ALK7). In other preferred embodiments, ALK5:ALK7 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK5:ALK7 heteromultimers of the disclosure have different ligand binding specificities/profiles compared to their corresponding homomultimer complexes (i.e., ALK5 and ALK7 homomultimers). ALK5:ALK7 heteromultimers of the disclosure include, e.g., heterodimers, heterotrimers, heterotetramers and further oligomeric structures. In certain preferred embodiments, ALK5:ALK7 heteromultimers of the disclosure are heterodimers.

In certain aspects, the disclosure relates to heteromultimers that comprise at least one ALK6 polypeptide, which includes fragments, functional variants, and modified forms thereof, and at least one ALK7 polypeptide, which includes fragments, functional variants, and modified forms thereof. In some embodiments, ALK6:ALK7 heteromultimers of the disclosure comprise at least one ALK6 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 34, 35, 91, 92, 142, 144, 181, 182, 425, 426, 473, and 474 or amino acids 32-102 of SEQ ID NO: 34 or amino acids 62-132 of SEQ ID NO: 91. In some embodiments, ALK6:ALK7 heteromultimers of the disclosure comprise at least one ALK7 polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 38, 39, 301, 302, 305, 306, 309, 310, 313, 112, 114, 183, 184, 405, 406, 475, and 476 or amino acids 28-92 of SEQ ID NOs: 38, 305, or 309. Preferably, ALK5:ALK7 heteromultimers of the present disclosure are soluble (e.g., comprise an extracellular domain of ALK6 and/or ALK7). In other preferred embodiments, ALK6:ALK7 heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ALK6:ALK7 heteromultimers of the disclosure have different ligand binding specificities/profiles compared to their corresponding homomultimer complexes (i.e., ALK6 and ALK7 homomultimers). ALK6:ALK7 heteromultimers of the disclosure include, e.g., heterodimers, heterotrimers, heterotetramers and further oligomeric structures. In certain preferred embodiments, ALK6:ALK7 heteromultimers of the disclosure are heterodimers.

In certain aspects, the disclosure relates to heteromultimers that comprise at least one ActRIIA polypeptide, which includes fragments, functional variants, and modified forms thereof, and at least one ActRIIB polypeptide, which includes fragments, functional variants, and modified forms thereof. In some embodiments, ActRIIA:ActRIIB heteromultimers of the disclosure comprise at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 9, 10, 11, 118, 120, 151, 152, 409, 410, 451, and 452 or amino acids 30-110 of SEQ ID NO: 9. In some embodiments, ActRIIA:ActRIIB heteromultimers of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 1, 2, 3, 4, 5, 6, 100, 102, 153, 154, 401, 402, 453, and 454 or amino acids 29-109 of SEQ ID NO: 1 or 25-131 of SEQ ID NO: 1. Preferably, ActRIIA:ActRIIB heteromultimers of the present disclosure are soluble (e.g., comprise an extracellular domain of ActRIIA and/or ActRIIB) In other preferred embodiments, ActRIIA:ActRIIB heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ActRIIA:ActRIIB heteromultimers of the disclosure have different ligand binding specificities/profiles compared to their corresponding homomultimer complexes (i.e., ActRIIA and ActRIIB homomultimers). ActRIIA:ActRIIB heteromultimers of the disclosure include, e.g., heterodimers, heterotrimers, heterotetramers and further oligomeric structures. In certain preferred embodiments, ActRIIA:ActRIIB heteromultimers of the disclosure are heterodimers.

In certain aspects, the disclosure relates to heteromultimers that comprise at least one ActRIIA polypeptide, which includes fragments, functional variants, and modified forms thereof, and at least one BMPRII polypeptide, which includes fragments, functional variants, and modified forms thereof. In some embodiments, ActRIIA:BMPRII heteromultimers of the disclosure comprise at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 9, 10, 11, 118, 120, 151, 152, 409, 410, 451, and 452 or amino acids 30-110 of SEQ ID NO: 9. In some embodiments, ActRIIA:BMPRII heteromultimers of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 46, 47, 71, 72, 121, 123, 155, 156, 411, 412, 455, and 456 or amino acids 34-123 of SEQ ID NO: 46 and 71. Preferably, ActRIIA:BMPRII heteromultimers of the present disclosure are soluble (e.g., comprise an extracellular domain of ActRIIA and/or BMPRII). In other preferred embodiments, ActRIIA:BMPRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ActRIIA:BMPRII heteromultimers of the disclosure have different ligand binding specificities/profiles compared to their corresponding homomultimer complexes (i.e., ActRIIA and BMPRII homomultimers). ActRIIA:BMPRII heteromultimers of the disclosure include, e.g., heterodimers, heterotrimers, heterotetramers and further oligomeric structures. In certain preferred embodiments, ActRIIA:BMPRII heteromultimers of the disclosure are heterodimers.

In certain aspects, the disclosure relates to heteromultimers that comprise at least one ActRIIA polypeptide, which includes fragments, functional variants, and modified forms thereof, and at least one TGFBRII polypeptide, which includes fragments, functional variants, and modified forms thereof. In some embodiments, ActRIIA:TGFBRII heteromultimers of the disclosure comprise at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 9, 10, 11, 118, 120, 151, 152, 409, 410, 451, and 452 or amino acids 30-110 of SEQ ID NO: 9. In some embodiments, ActRIIA:TGFBRII heteromultimers of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. Preferably, ActRIIA:TGFBRII heteromultimers of the present disclosure are soluble (e.g., comprise an extracellular domain of ActRIIA and/or BMPRII). In other preferred embodiments, ActRIIA:TGFBRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ActRIIA:TGFBRII heteromultimers of the disclosure have different ligand binding specificities/profiles compared to their corresponding homomultimer complexes (i.e., ActRIIA and TGFBRII homomultimers). ActRIIA:TGFBRII heteromultimers of the disclosure include, e.g., heterodimers, heterotrimers, heterotetramers and further oligomeric structures. In certain preferred embodiments, ActRIIA:TGFBRII heteromultimers of the disclosure are heterodimers.

In certain aspects, the disclosure relates to heteromultimers that comprise at least one ActRIIA polypeptide, which includes fragments, functional variants, and modified forms thereof, and at least one MISRII polypeptide, which includes fragments, functional variants, and modified forms thereof. In some embodiments, ActRIIA:MISRII heteromultimers of the disclosure comprise at least one ActRIIA polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 9, 10, 11, 118, 120, 151, 152, 409, 410, 451, and 452 or amino acids 30-110 of SEQ ID NO: 9. In some embodiments, ActRIIA:MISRII heteromultimers of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 50, 51, 75, 76, 79, 80, 133, 135, 161, 162, 419, 420, 457, and 458 or amino acids 24-116 of SEQ ID NO: 50, 75, and 79. Preferably, ActRIIA:MISRII heteromultimers of the present disclosure are soluble (e.g., comprise an extracellular domain of ActRIIA and/or MISRII). In other preferred embodiments, ActRIIA:MISRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ActRIIA:MISRII heteromultimers of the disclosure have different ligand binding specificities/profiles compared to their corresponding homomultimer complexes (i.e., ActRIIA and MISRII homomultimers). ActRIIA:MISRII heteromultimers of the disclosure include, e.g., heterodimers, heterotrimers, heterotetramers and further oligomeric structures. In certain preferred embodiments, ActRIIA:MISRII heteromultimers of the disclosure are heterodimers.

In certain aspects, the disclosure relates to heteromultimers that comprise at least one ActRIIB polypeptide, which includes fragments, functional variants, and modified forms thereof, and at least one BMPRII polypeptide, which includes fragments, functional variants, and modified forms thereof. In some embodiments, ActRIIB. BMPRII heteromultimers of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 1, 2, 3, 4, 5, 6, 100, 102, 153, 154, 401, 402, 453, and 454 or amino acids 29-109 of SEQ ID NO: 1 or 25-131 of SEQ ID NO: 1. In some embodiments, ActRIIB:BMPRII heteromultimers of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 46, 47, 71, 72, 121, 123, 155, 156, 411, 412, 455, and 456 or amino acids 34-123 of SEQ ID NO: 46 and 71. Preferably, ActRIIB:BMPRII heteromultimers of the present disclosure are soluble (e.g., comprise an extracellular domain of ActRIIB and/or BMPRII). In other preferred embodiments, ActRIIB:BMPRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ActRIIB:BMPRII heteromultimers of the disclosure have different ligand binding specificities/profiles compared to their corresponding homomultimer complexes (i.e., ActRIIB and BMPRII homomultimers). ActRIIB:BMPRII heteromultimers of the disclosure include, e.g., heterodimers, heterotrimers, heterotetramers and further oligomeric structures. In certain preferred embodiments, ActRIIB:BMPRII heteromultimers of the disclosure are heterodimers.

In certain aspects, the disclosure relates to heteromultimers that comprise at least one ActRIIB polypeptide, which includes fragments, functional variants, and modified forms thereof, and at least one TGFBRII polypeptide, which includes fragments, functional variants, and modified forms thereof. In some embodiments, ActRIIB:TGFBRII heteromultimers of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 1, 2, 3, 4, 5, 6, 100, 102, 153, 154, 401, 402, 453, and 454 or amino acids 29-109 of SEQ ID NO: 1 or 25-131 of SEQ ID NO: 1. In some embodiments, ActRIIB:TGFBRII heteromultimers of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. Preferably, ActRIIB:TGFBRII heteromultimers of the present disclosure are soluble (e.g., comprise an extracellular domain of ActRIIB and/or TGF-BRII). In other preferred embodiments, ActRIIB:TGFBRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ActRIIB:TGFBRII heteromultimers of the disclosure have different ligand binding specificities/profiles compared to their corresponding homomultimer complexes (i.e., ActRIIB and TGFBRII homomultimers). ActRIIB:TGFBRII heteromultimers of the disclosure include, e.g., heterodimers, heterotrimers, heterotetramers and further oligomeric structures. In certain preferred embodiments, ActRIIB:TGFBRII heteromultimers of the disclosure are heterodimers.

In certain aspects, the disclosure relates to heteromultimers that comprise at least one ActRIIB polypeptide, which includes fragments, functional variants, and modified forms thereof, and at least one MISRII polypeptide, which includes fragments, functional variants, and modified forms thereof. In some embodiments, ActRIIB:MISRII heteromultimers of the disclosure comprise at least one ActRIIB polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 1, 2, 3, 4, 5, 6, 100, 102, 153, 154, 401, 402, 453, and 454 or amino acids 29-109 of SEQ ID NO: 1 or 25-131 of SEQ ID NO: 1. In some embodiments, ActRIIB:MISRII heteromultimers of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 50, 51, 75, 76, 79, 80, 133, 135, 161, 162, 419, 420, 457, and 458 or amino acids 24-116 of SEQ ID NO: 50, 75, and 79. Preferably, ActRIIB:MISRII heteromultimers of the present disclosure are soluble (e.g., comprise an extracellular domain of ActRIIB and/or MISRII). In other preferred embodiments, ActRIIB:MISRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, ActRIIB:MISRII heteromultimers of the disclosure have different ligand binding specificities/profiles compared to their corresponding homomultimer complexes (i.e., ActRIIB and MISRII homomultimers). ActRIIB:MISRII heteromultimers of the disclosure include, e.g., heterodimers, heterotrimers, heterotetramers and further oligomeric structures. In certain preferred embodiments, ActRIIB:MISRII heteromultimers of the disclosure are heterodimers.

In certain aspects, the disclosure relates to heteromultimers that comprise at least one BMPRII polypeptide, which includes fragments, functional variants, and modified forms thereof, and at least one TGFBRII polypeptide, which includes fragments, functional variants, and modified forms thereof. In some embodiments, BMPRII:TGFBRII heteromultimers of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 46, 47, 71, 72, 121, 123, 155, 156, 411, 412, 455, and 456 or amino acids 34-123 of SEQ ID NO: 46 or 71. In some embodiments, BMPRII:TGFBRII heteromultimers of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. Preferably, BMPRII:TGFBRII heteromultimers of the present disclosure are soluble (e.g., comprise an extracellular domain of BMPRII and/or TGFBRII). In other preferred embodiments, BMPRII:TGFBRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, BMPRII:TGFBRII heteromultimers of the disclosure have different ligand binding specificities/profiles compared to their corresponding homomultimer complexes (i.e., BMPRII and TGFBRII homomultimers). BMPRII:TGFBRII heteromultimers of the disclosure include, e.g., heterodimers, heterotrimers, heterotetramers and further oligomeric structures. In certain preferred embodiments, BMPRII:TGFBRII heteromultimers of the disclosure are heterodimers.

In certain aspects, the disclosure relates to heteromultimers that comprise at least one BMPRII polypeptide, which includes fragments, functional variants, and modified forms thereof, and at least one MISRII polypeptide, which includes fragments, functional variants, and modified forms thereof. In some embodiments, BMPRII:MISRII heteromultimers of the disclosure comprise at least one BMPRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 46, 47, 71, 72, 121, 123, 155, 156, 411, 412, 455, and 456 or amino acids 34-123 of SEQ ID NO: 46 or 71. In some embodiments, BMPRII:MISRII heteromultimers of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 50, 51, 75, 76, 79, 80, 133, 135, 161, 162, 419, 420, 457, and 458 or amino acids 24-116 of SEQ ID NO: 50, 75, or 79. Preferably, BMPRII:MISRII heteromultimers of the present disclosure are soluble (e.g., comprise an extracellular domain of BMPRII and/or MISRII). In other preferred embodiments, BMPRII:MISRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, BMPRII:MISRII heteromultimers of the disclosure have different ligand binding specificities/profiles compared to their corresponding homomultimer complexes (i.e., BMPRII and MISRII homomultimers). BMPRII:MISRII heteromultimers of the disclosure include, e.g., heterodimers, heterotrimers, heterotetramers and further oligomeric structures. In certain preferred embodiments, BMPRII:MISRII heteromultimers of the disclosure are heterodimers.

In certain aspects, the disclosure relates to heteromultimers that comprise at least one TGFBRII polypeptide, which includes fragments, functional variants, and modified forms thereof, and at least one MISRII polypeptide, which includes fragments, functional variants, and modified forms thereof. In some embodiments, TGFBRII:MISRII heteromultimers of the disclosure comprise at least one TGFBRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 42, 43, 67, 68, 127, 129, 130, 132, 157, 158, 159, 160, 415, 416, 417, 418, 459, 460, 461, and 462 or amino acids 44-168 of SEQ ID NO: 67 or amino acids 51-143 of SEQ ID NO: 42. In some embodiments, TGFBRII:MISRII heteromultimers of the disclosure comprise at least one MISRII polypeptide that comprises, consists, or consists essentially of a sequence that is at least 70%, 75%, 80%, 85%, 90%, 91%, 92%, 93%, 94%, 95%, 96% 97%, 98%, 99%, or 100% identical to the amino acid sequence of any one of SEQ ID Nos: 50, 51, 75, 76, 79, 80, 133, 135, 161, 162, 419, 420, 457, and 458 or amino acids 24-116 of SEQ ID NO: 50, 75, or 79. Preferably, TGFBRII:MISRII heteromultimers of the present disclosure are soluble (e.g., comprise an extracellular domain of TGFBII and/or MISRII). In other preferred embodiments, TGFBRII:MISRII heteromultimers of the disclosure bind to and/or inhibit (antagonize) activity (e.g., induction of Smad 2/3 and/or Smad 1/5/8 signaling) of one or more TGF-beta superfamily ligands (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). In some embodiments, TGFBRII:MISRII heteromultimers of the disclosure have different ligand binding specificities/profiles compared to their corresponding homomultimer complexes (i.e., TGFBRII and MISRII homomultimers). TGFBRII:MISRII heteromultimers of the disclosure include, e.g., heterodimers, heterotrimers, heterotetramers and further oligomeric structures. In certain preferred embodiments, TGFBRII:MISRII heteromultimers of the disclosure are heterodimers.

In some embodiments, the present disclosure contemplates making functional variants by modifying the structure of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) for such purposes as enhancing therapeutic efficacy or stability (e.g., shelf-life and resistance to proteolytic degradation in vivo). Variants can be produced by amino acid substitution, deletion, addition, or combinations thereof. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a polypeptide of the disclosure results in a functional homolog can be readily determined by assessing the ability of the variant polypeptide to produce a response in cells in a fashion similar to the wild-type polypeptide, or to bind to one or more TGF-beta superfamily ligands including, for example, BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty.

In some embodiments, the present disclosure contemplates making functional variants by modifying the structure of the TGF-beta superfamily type I receptor polypeptide and/or TGF-beta superfamily type II receptor polypeptide for such purposes as enhancing therapeutic efficacy or stability (e.g., increased shelf-life and/or increased resistance to proteolytic degradation).

In certain embodiments, the present disclosure contemplates specific mutations of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) receptor of the disclosure so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, TGF-beta superfamily type I and II receptor complexes of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of a TGF-beta superfamily type I receptor polypeptide (e.g., ALK1, ALK2, ALK3, ALK4, ALK5, ALK6, and ALK7) and/or a TGF-beta superfamily type II receptor polypeptide (e.g., ActRIIA, ActRIIB, TGFBRII, BMPRII, and MISRII) of the present disclosure, as well as truncation mutants. Pools of combinatorial mutants are especially useful for identifying functionally active (e.g., ligand binding) TGF-beta superfamily type I and/or TGF-beta superfamily type II receptor sequences. The purpose of screening such combinatorial libraries may be to generate, for example, polypeptides variants which have altered properties, such as altered pharmacokinetic or altered ligand binding. A variety of screening assays are provided below, and such assays may be used to evaluate variants. For example, TGF-beta superfamily type I and II receptor complex variants may be screened for ability to bind to a TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty), to prevent binding of a TGF-beta superfamily ligand to a TGF-beta superfamily receptor, and/or to interfere with signaling caused by an TGF-beta superfamily ligand.

The activity of a TGF-beta superfamily heteromultimer complex of the disclosure also may be tested, for example in a cell-based or in vivo assay. For example, the effect of a heteromultimer complex on the expression of genes or the activity of proteins involved in muscle production in a muscle cell may be assessed. This may, as needed, be performed in the presence of one or more recombinant TGF-beta superfamily ligand proteins (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty), and cells may be transfected so as to produce a TGF-beta superfamily type I and II receptor complex, and optionally, a TGF-beta superfamily ligand. Likewise, a heteromultimer complex of the disclosure may be administered to a mouse or other animal, and one or more measurements, such as muscle formation and strength may be assessed using art-recognized methods. Similarly, the activity of a heteromultimer, or variants thereof, may be tested in osteoblasts, adipocytes, and/or neuronal cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference TGF-beta superfamily heteromultimer complex. Such variants, when expressed from recombinant DNA constructs, can be used in gene therapy protocols. Likewise, mutagenesis can give rise to variants which have intracellular half-lives dramatically different than the corresponding unmodified TGF-beta superfamily heteromultimer complex. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter one or more activities of the TGF-beta superfamily heteromultimer complex including, for example, immunogenicity, half-life, and solubility.

A combinatorial library may be produced by way of a degenerate library of genes encoding a library of polypeptides which each include at least a portion of potential TGF-beta superfamily type I and/or II receptor sequences. For instance, a mixture of synthetic oligonucleotides can be enzymatically ligated into gene sequences such that the degenerate set of potential TGF-beta superfamily type I and/or II receptor encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art. See, e.g., Narang, S A (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; Ike et al. (1983) Nucleic Acid Res. 11:477. Such techniques have been employed in the directed evolution of other proteins. See, e.g., Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815.

Alternatively, other forms of mutagenesis can be utilized to generate a combinatorial library. For example, TGF-beta superfamily heteromultimer complexes of the disclosure can be generated and isolated from a library by screening using, for example, alanine scanning mutagenesis [see, e.g., Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218: 597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [see, e.g., Gustin et al. (1993) Virology 193:653-660; and Brown et al. (1992) Mol. Cell Biol. 12:2644-2652; McKnight et al. (1982) Science 232:316], by saturation mutagenesis [see, e.g., Meyers et al., (1986) Science 232:613]; by PCR mutagenesis [see, e.g., Leung et al. (1989) Method Cell Mol Biol 1:11-19]; or by random mutagenesis, including chemical mutagenesis [see, e.g., Miller et al. (1992) A Short Course in Bacterial Genetics, CSHL Press, Cold Spring Harbor, N.Y.; and Greener et al. (1994) Strategies in Mol Biol 7:32-34]. Linker scanning mutagenesis, particularly in a combinatorial setting, is an attractive method for identifying truncated (bioactive) forms of TGF-beta superfamily type I and/or II receptor polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of TGF-beta superfamily heteromultimer complexes of the disclosure. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty) binding assays and/or TGF-beta superfamily ligand-mediated cell signaling assays.

In certain embodiments, TGF-beta superfamily type I and II heteromultimer complexes of the disclosure may further comprise post-translational modifications in addition to any that are naturally present in the TGF-beta superfamily type I and/or II receptor polypeptide. Such modifications include, but are not limited to, acetylation, carboxylation, glycosylation, phosphorylation, lipidation, and acylation. As a result, the TGF-beta superfamily type I and II heteromultimer complex may comprise non-amino acid elements, such as polyethylene glycols, lipids, polysaccharide or monosaccharide, and phosphates. Effects of such non-amino acid elements on the functionality of a heteromultimer complex may be tested as described herein for other heteromultimer complex variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, WI38, NIH-3T3 or HEK293) have specific cellular machinery and characteristic mechanisms for such post-translational activities and may be chosen to ensure the correct modification and processing of the TGF-beta superfamily type I and/or type II receptor polypeptides as well as heteromultimers comprising the same.

In certain aspects, the polypeptides disclosed herein may form protein complexes comprising at least one TGF-beta superfamily type I polypeptide associated, covalently or non-covalently, with at least one type II receptor polypeptide. Preferably, polypeptides disclosed herein form heterodimeric complexes, although higher order heteromultimeric complexes (heteromultimers) are also included such as, but not limited to, heterotrimers, heterotetramers, and further oligomeric structures (see, e.g., FIGS. 1, 2, and 15-17). In some embodiments, TGF-beta superfamily type I and/or type II receptor polypeptides of the present disclosure comprise at least one multimerization domain. As disclosed herein, the term "multimerization domain" refers to an amino acid or sequence of amino acids that promote covalent or non-covalent interaction between at least a first polypeptide and at least a second polypeptide. Polypeptides disclosed herein may be joined covalently or non-covalently to a multimerization domain. Preferably, a multimerization domain promotes interaction between a first polypeptide (e.g., TGF-beta superfamily type I polypeptide) and a second polypeptide (e.g., TGF-beta superfamily type II polypeptide) to promote heteromultimer formation (e.g., heterodimer formation), and optionally hinders or otherwise disfavors homomultimer formation (e.g., homodimer formation), thereby increasing the yield of desired heteromultimer (see, e.g., FIG. 2).

Many methods known in the art can be used to generate TGF-beta superfamily complexes of the disclosure. For example, non-naturally occurring disulfide bonds may be constructed by replacing on a first polypeptide (e.g., TGF-beta superfamily type I polypeptide) a naturally occurring amino acid with a free thiol-containing residue, such as cysteine, such that the free thiol interacts with another free thiol-containing residue on a second polypeptide (e.g., TGF-beta superfamily type II polypeptide) such that a disulfide bond is formed between the first and second polypeptides. Additional examples of interactions to promote heteromultimer formation include, but are not limited to, ionic interactions such as described in Kjaergaard et al., WO2007147901; electrostatic steering effects such as described in Kannan et al., U.S. Pat. No. 8,592,562; coiled-coil interactions such as described in Christensen et al., U.S.20120302737; leucine zippers such as described in Pack & Plueckthun, (1992) Biochemistry 31: 1579-1584; and helix-turn-helix motifs such as described in Pack et al., (1993) Bio/Technology 11: 1271-1277. Linkage of the various segments may be obtained via, e.g., covalent binding such as by chemical cross-linking, peptide linkers, disulfide bridges, etc., or affinity interactions such as by avidin-biotin or leucine zipper technology.

In certain aspects, a multimerization domain may comprise one component of an interaction pair. In some embodiments, the polypeptides disclosed herein may form protein complexes comprising a first polypeptide covalently or non-covalently associated with a second polypeptide, wherein the first polypeptide comprises the amino acid sequence of a TGF-beta superfamily type I polypeptide and the amino acid sequence of a first member of an interaction pair; and the second polypeptide comprises the amino acid sequence of a TGF-beta superfamily type II polypeptide and the amino acid sequence of a second member of an interaction pair. The interaction pair may be any two polypeptide sequences that interact to form a complex, particularly a heterodimeric complex although operative embodiments may also employ an interaction pair that can form a homodimeric complex. One member of the interaction pair may be fused to a TGF-beta superfamily type I or type II polypeptide as described herein, including for example, a polypeptide sequence comprising, consisting essentially of, or consisting of an amino acid sequence that is at least 80%, 85%, 90%, 95%, 96%, 97%, 98%, 99%, or 100% identical to the sequence of any one of SEQ ID NOs: 14, 15, 124, 126, 171, 172, 413, 414, 463, 464, 18, 19, 136, 138, 173, 174, 421, 422, 465, 466, 22, 23, 115, 117, 175, 176, 407, 408, 467, 468, 26, 27, 83, 84, 104, 106, 177, 178, 403, 404, 469, 470, 30, 31, 87, 88, 139, 141, 179, 180, 423, 424, 471, 472, 34, 35, 91, 92, 142, 144, 181, 182, 425, 426, 473, 474, 38, 39, 301, 302, 305, 306, 309, 310, 313, 112, 114, 183, 184, 405, 406, 475, 476, 9, 10, 11, 118, 120, 151, 152, 409, 410, 451, 452, 1, 2, 3, 4, 5, 6, 100, 102, 153, 154, 401, 402, 453, 454, 46, 47, 71, 72, 121, 123, 155, 156, 411, 412, 455, 456, 50, 51, 75, 76, 79, 80, 133, 135, 161, 162, 419, 420, 457, 458, 42, 43, 67, 68, 127, 129, 130, 132, 157, 158, 159, 160, 415, 416, 417, 418, 459, 460, 461, and 462. An interaction pair may be selected to confer an improved property/activity such as increased serum half-life, or to act as an adaptor on to which another moiety is attached to provide an improved property/activity. For example, a polyethylene glycol moiety may be attached to one or both components of an interaction pair to provide an improved property/activity such as improved serum half-life.

The first and second members of the interaction pair may be an asymmetric pair, meaning that the members of the pair preferentially associate with each other rather than self-associate. Accordingly, first and second members of an asymmetric interaction pair may associate to form a heterodimeric complex (see, e.g., FIG. 2). Alternatively, the interaction pair may be unguided, meaning that the members of the pair may associate with each other or self-associate without substantial preference and thus may have the same or different amino acid sequences. Accordingly, first and second members of an unguided interaction pair may associate to form a homodimer complex or a heterodimeric complex. Optionally, the first member of the interaction pair (e.g., an asymmetric pair or an unguided interaction pair) associates covalently with the second member of the interaction pair. Optionally, the first member of the interaction pair (e.g., an asymmetric pair or an unguided interaction pair) associates non-covalently with the second member of the interaction pair.

As specific examples, the present disclosure provides fusion proteins comprising TGF-beta superfamily type I or type II polypeptides fused to a polypeptide comprising a constant domain of an immunoglobulin, such as a CH1, CH2, or CH3 domain of an immunoglobulin or an Fc domain. Fc domains derived from human IgG1, IgG2, IgG3, and IgG4 are provided herein. Other mutations are known that decrease either CDC or ADCC activity, and collectively, any of these variants are included in the disclosure and may be used as advantageous components of a heteromultimeric complex of the disclosure. Optionally, the IgG1 Fc domain of SEQ ID NO: 208 has one or more mutations at residues such as Asp-265, Lys-322, and Asn-434 (numbered in accordance with the corresponding full-length IgG1). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MEW class I-related Fc-receptor (FcRN) relative to a wildtype Fc domain.

An example of a native amino acid sequence that may be used for the Fc portion of human IgG1 (G1Fc) is shown below (SEQ ID NO: 208). Dotted underline indicates the hinge region, and solid underline indicates positions with naturally occurring variants. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 208. Naturally occurring variants in G1Fc would include E134D and M136L according to the numbering system used in SEQ ID NO: 208 (see Uniprot P01857).

```
                                                           (SEQ ID NO: 208)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
```

An example of a native amino acid sequence that may be used for the Fc portion of human IgG2 (G2Fc) is shown below (SEQ ID NO: 209). Dotted underline indicates the hinge region and double underline indicates positions where there are data base conflicts in the sequence (according to UniProt P01859). In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NO: 209.

```
                                                           (SEQ ID NO: 209)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP
```

```
151 SDIAVEWESN GQPENNYKTT PPMLDSDGSF FLYSKLTVDK SRWQQGNVFS

201 CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 210) contains a short hinge region consisting of a single 15-residue segment, whereas the second G3Fc sequence (SEQ ID NO: 211) contains a full-length hinge region. In each case, dotted underline indicates the hinge region, and solid underline indicates positions with naturally occurring variants according to UniProt P01859. In part, the disclosure provides polypeptides comprising, consisting of, or consisting essentially of an amino acid sequence with 70%, 80%, 85%, 86%, 87%, 88%, 89%, 90%, 91%, 92%, 93%, 94%, 95%, 96%, 97%, 98%, 99%, or 100% identity to SEQ ID NOs: 210 and 211.

7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 212). Dotted underline indicates the

```
                                                       (SEQ ID NO: 210)
  1 EPKSCDTPPP CPRCPAPELL GGPSVFLFPP KPKDTLMISR TPEVTCVVVD

51 VSHEDPEVQF KWYVDGVEVH NAKTKPREEQ YNSTFRVVSV LTVLHQDWLN

101 GKEYKCKVSN KALPAPIEKT ISKTKGQPRE PQVYTLPPSR EEMTKNQVSL

151 TCLVKGFYPS DIAVEWESSG QPENNYNTTP PMLDSDGSFF LYSKLTVDKS

201 RWQQGNIFSC SVMHEALHNR FTQKSLSLSP GK (SEQ ID NO: 211)
  1 ELKTPLGDTT HTCPRCPEPK SCDTPPPCPR CPEPKSCDTP PPCPRCPEPK

51 SCDTPPPCPR CPAPELLGGP SVFLFPPKPK DTLMISRTPE VTCVVVDVSH

101 EDPEVQFKWY VDGVEVHNAK TKPREEQYNS TFRVVSVLTV LHQDWLNGKE

151 YKCKVSNKAL PAPIEKTISK TKGQPREPQV YTLPPSREEM TKNQVSLTCL

201 VKGFYPSDIA VEWESSGQPE NNYNTTPPML DSDGSFFLYS KLTVDKSRWQ

251 QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 210, and the present disclosure provides fusion proteins comprising hinge region. In part, the disclosure provides polypeptides comprising, consisting of, or consisting essentially of an amino acid sequence with 70%, 80%, 85%, 86%, 8'7%, 88%, 89%, 90%, 91%, 92%, 93%, 94%, 95%, 96%, 97%, 98%, 99%, or 100% identity to SEQ ID NO: 212.

```
                                                       (SEQ ID NO: 212)
  1 ESKYGPPCPS CPAPEFLGGP SVFLFPPKPK DTLMISRTPE VTCVVVDVSQ

51 EDPEVQFNWY VDGVEVHNAK TKPREEQFNS TYRVVSVLTV LHQDWLNGKE

101 YKCKVSNKGL PSSIEKTISK AKGQPREPQV YTLPPSQEEM TKNQVSLTCL

151 VKGFYPSDIA VEWESNGQPE NNYKTTPPVL DSDGSFFLYS RLTVDKSRWQ

201 EGNVFSCSVM HEALHNHYTQ KSLSLSLGK
```

G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position A variety of engineered mutations in the Fc domain are presented herein with respect to the G1Fc sequence (SEQ ID NO: 208), and analogous mutations in G2Fc, G3Fc, and G4Fc can be derived from their alignment with G1Fc in FIG. 5. Due to unequal hinge lengths, analogous Fc positions based on isotype alignment (FIG. 5) possess different amino acid numbers in SEQ ID NOs: 208, 209, 210, and 212. It can also be appreciated that a given amino acid position in an immunoglobulin sequence consisting of hinge, $C_H2$, and $C_H3$ regions (e.g., SEQ ID NOs: 208, 209, 210, 211, or 212) will be identified by a different number than the same position when numbering encompasses the entire IgG1 heavy-chain constant domain (consisting of the $C_H1$, hinge, $C_H2$, and $C_H3$ regions) as in the Uniprot database. For example, correspondence between selected $C_H3$ positions in a human G1Fc sequence (SEQ ID NO: 208), the human IgG1 heavy chain constant domain (Uniprot P01857), and the human IgG1 heavy chain is as follows.

Correspondence of $C_H3$ Positions in Different Numbering Systems

| G1Fc (Numbering begins at first threonine in hinge region) | IgG1 heavy chain constant domain (Numbering begins at $C_H1$) | IgG1 heavy chain (EU numbering scheme of Kabat et al., 1991*) |
|---|---|---|
| Y127 | Y232 | Y349 |
| S132 | S237 | S354 |
| E134 | E239 | E356 |
| T144 | T249 | T366 |
| L146 | L251 | L368 |
| K170 | K275 | K392 |
| D177 | D282 | D399 |
| Y185 | Y290 | Y407 |
| K187 | K292 | K409 |

*Kabat et al. (eds) 1991; pp. 688-696 in *Sequences of Proteins of Immunological Interest*, 5th ed., Vol. 1, NIH, Bethesda, MD.

A problem that arises in large-scale production of asymmetric immunoglobulin-based proteins from a single cell line is known as the "chain association issue". As confronted prominently in the production of bispecific antibodies, the chain association issue concerns the challenge of efficiently producing a desired multichain protein from among the multiple combinations that inherently result when different heavy chains and/or light chains are produced in a single cell line [see, for example, Klein et al (2012) mAbs 4:653-663]. This problem is most acute when two different heavy chains and two different light chains are produced in the same cell, in which case there are a total of 16 possible chain combinations (although some of these are identical) when only one is typically desired. Nevertheless, the same principle accounts for diminished yield of a desired multichain fusion protein that incorporates only two different (asymmetric) heavy chains.

Various methods are known in the art that increase desired pairing of Fc-containing fusion polypeptide chains in a single cell line to produce a preferred asymmetric fusion protein at acceptable yields [see, for example, Klein et al (2012) mAbs 4:653-663; and Spiess et al (2015) Molecular Immunology 67(2A): 95-106]. Methods to obtain desired pairing of Fc-containing chains include, but are not limited to, charge-based pairing (electrostatic steering), "knobs-into-holes" steric pairing, SEEDbody pairing, and leucine zipper-based pairing. See, for example, Ridgway et al (1996) Protein Eng 9:617-621; Merchant et al (1998) Nat Biotech 16:677-681; Davis et al (2010) Protein Eng Des Sel 23:195-202; Gunasekaran et al (2010); 285:19637-19646; Wranik et al (2012) J Biol Chem 287:43331-43339; U.S. Pat. No. 5,932,448; WO 1993/011162; WO 2009/089004, and WO 2011/034605. As described herein, these methods may be used to generate heterodimers comprising TGF-beta superfamily type I and type II receptor polypeptides, at least two different TGF-beta superfamily type I receptor polypeptides, and at least two different TGF-beta superfamily type II receptor polypeptides. See FIGS. 15-17.

For example, one means by which interaction between specific polypeptides may be promoted is by engineering protuberance-into-cavity (knob-into-holes) complementary regions such as described in Arathoon et al., U.S. Pat. No. 7,183,076 and Carter et al., U.S. Pat. No. 5,731,168. "Protuberances" are constructed by replacing small amino acid side chains from the interface of the first polypeptide (e.g., a first interaction pair) with larger side chains (e.g., tyrosine or tryptophan). Complementary "cavities" of identical or similar size to the protuberances are optionally created on the interface of the second polypeptide (e.g., a second interaction pair) by replacing large amino acid side chains with smaller ones (e.g., alanine or threonine). Where a suitably positioned and dimensioned protuberance or cavity exists at the interface of either the first or second polypeptide, it is only necessary to engineer a corresponding cavity or protuberance, respectively, at the adjacent interface.

At neutral pH (7.0), aspartic acid and glutamic acid are negatively charged and lysine, arginine, and histidine are positively charged. These charged residues can be used to promote heterodimer formation and at the same time hinder homodimer formation. Attractive interactions take place between opposite charges and repulsive interactions occur between like charges. In part, protein complexes disclosed herein make use of the attractive interactions for promoting heteromultimer formation (e.g., heterodimer formation), and optionally repulsive interactions for hindering homodimer formation (e.g., homodimer formation) by carrying out site directed mutagenesis of charged interface residues.

For example, the IgG1 CH3 domain interface comprises four unique charge residue pairs involved in domain-domain interactions: Asp356-Lys439', Glu357-Lys370', Lys392-Asp399', and Asp399-Lys409' [residue numbering in the second chain is indicated by (')]. It should be noted that the numbering scheme used here to designate residues in the IgG1 CH3 domain conforms to the EU numbering scheme of Kabat. Due to the 2-fold symmetry present in the CH3-CH3 domain interactions, each unique interaction will represented twice in the structure (e.g., Asp-399-Lys409' and Lys409-Asp399'). In the wild-type sequence, K409-D399' favors both heterodimer and homodimer formation. A single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation.

The electrostatic steering effect on heterodimer formation and homodimer discouragement can be further enhanced by mutation of additional charge residues which may or may not be paired with an oppositely charged residue in the second chain including, for example, Arg355 and Lys360. The table below lists possible charge change mutations that can be used, alone or in combination, to enhance heteromultimer formation of the polypeptide complexes disclosed herein.

Examples of Pair-Wise Charged Residue Mutations
to Enhance Heterodimer Formation

| Position in first chain | Mutation in first chain | Interacting position in second chain | Corresponding mutation in second chain |
|---|---|---|---|
| Lys409 | Asp or Glu | Asp399' | Lys, Arg, or His |
| Lys392 | Asp or Glu | Asp399' | Lys, Arg, or His |
| Lys439 | Asp or Glu | Asp356' | Lys, Arg, or His |
| Lys370 | Asp or Glu | Glu357' | Lys, Arg, or His |
| Asp399 | Lys, Arg, or His | Lys409' | Asp or Glu |
| Asp399 | Lys, Arg, or His | Lys392' | Asp or Glu |
| Asp356 | Lys, Arg, or His | Lys439' | Asp or Glu |
| Glu357 | Lys, Arg, or His | Lys370' | Asp or Glu |

In some embodiments, one or more residues that make up the CH3-CH3 interface in a fusion protein of the instant application are replaced with a charged amino acid such that the interaction becomes electrostatically unfavorable. For example, a positive-charged amino acid in the interface (e.g., a lysine, arginine, or histidine) is replaced with a negatively charged amino acid (e.g., aspartic acid or glutamic acid). Alternatively, or in combination with the forgoing substitution, a negative-charged amino acid in the interface is replaced with a positive-charged amino acid. In certain embodiments, the amino acid is replaced with a non-naturally occurring amino acid having the desired charge characteristic. It should be noted that mutating negatively charged residues (Asp or Glu) to His will lead to increase in side chain volume, which may cause steric issues. Furthermore, His proton donor- and acceptor-form depends on the localized environment. These issues should be taken into consideration with the design strategy. Because the interface residues are highly conserved in human and mouse IgG subclasses, electrostatic steering effects disclosed herein can be applied to human and mouse IgG1, IgG2, IgG3, and IgG4. This strategy can also be extended to modifying uncharged residues to charged residues at the CH3 domain interface.

In part, the disclosure provides desired pairing of asymmetric Fc-containing polypeptide chains using Fc sequences engineered to be complementary on the basis of charge pairing (electrostatic steering). One of a pair of Fc sequences with electrostatic complementarity can be arbitrarily fused to the TGF-beta superfamily type I or type II receptor polypeptide of the construct, with or without an optional linker, to generate a TGF-beta superfamily type I or type II receptor fusion polypeptide This single chain can be coexpressed in a cell of choice along with the Fc sequence complementary to the first Fc to favor generation of the desired multichain construct (e.g., a TGF-beta superfamily heteromeric complex). In this example based on electrostatic steering, SEQ ID NO: 200 [human G1Fc(E134K/D177K)] and SEQ ID NO: 201 [human G1Fc(K170D/K187D)] are examples of complementary Fc sequences in which the engineered amino acid substitutions are double underlined, and the TGF-beta superfamily type I or type II receptor polypeptide of the construct can be fused to either SEQ ID NO: 200 or SEQ ID NO: 201, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 200 and 201).

```
                                             (SEQ ID NO: 200)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSRKEMTKNQ VSLTCLVKGF

151 YPSDIAVEWE SNGQPENNYK TTPPVLKSDG SFFLYSKLTV DKSRWQQGNV

201 FSCSVMHEAL HNHYTQKSLS LSPGK
                                             (SEQ ID NO: 201)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYD TTPPVLDSDG SFFLYSDLTV DKSRWQQGNV

201 FSCSVMHEAL HNHYTQKSLS LSPGK
```

In part, the disclosure provides desired pairing of asymmetric Fc-containing polypeptide chains using Fc sequences engineered for steric complementarity. In part, the disclosure provides knobs-into-holes pairing as an example of steric complementarity. One of a pair of Fc sequences with steric complementarity can be arbitrarily fused to the TGF-beta superfamily type I or type II polypeptide of the construct, with or without an optional linker, to generate a TGF-beta superfamily type I or type II fusion polypeptide. This single chain can be coexpressed in a cell of choice along with the Fc sequence complementary to the first Fc to favor generation of the desired multichain construct. In this example based on knobs-into-holes pairing, SEQ ID NO: 202 [human G1Fc(T144Y)] and SEQ ID NO: 203 [human G1Fc (Y185T)] are examples of complementary Fc sequences in which the engineered amino acid substitutions are double underlined, and the TGF-beta superfamily type I or type II polypeptide of the construct can be fused to either SEQ ID NO: 202 or SEQ ID NO: 203, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 202 and 203).

```
                                                    (SEQ ID NO: 202)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLYCLVKGF

151 YPSDIAVEWE SNGQPENNYK TTPPVLDSDG SFFLYSKLTV DKSRWQQGNV

201 FSCSVMHEAL HNHYTQKSLS LSPGK
                                                    (SEQ ID NO: 203)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLTSKLTV DKSRWQQGNV

201 FSCSVMHEAL HNHYTQKSLS LSPGK
```

An example of Fc complementarity based on knobs-into-holes pairing combined with an engineered disulfide bond is disclosed in SEQ ID NO: 204 [hG1Fc(S132C/T144W)] and SEQ ID NO: 205 [hG1Fc(Y127C/T144S/L146A/Y185V)]. The engineered amino acid substitutions in these sequences are double underlined, and the TGF-beta superfamily type I or type II polypeptide of the construct can be fused to either SEQ ID NO: 204 or SEQ ID NO: 205, but not both. Given the high degree of amino acid sequence identity between native hG1Fc, native hG2Fc, native hG3Fc, and native hG4Fc, it can be appreciated that amino acid substitutions at corresponding positions in hG2Fc, hG3Fc, or hG4Fc (see FIG. 5) will generate complementary Fc pairs which may be used instead of the complementary hG1Fc pair below (SEQ ID NOs: 204 and 205).

SEEDbody complementarity can be arbitrarily fused to the TGF-beta superfamily type I or type II polypeptide of the construct, with or without an optional linker, to generate a TGF-beta superfamily type I or type II fusion polypeptide. This single chain can be coexpressed in a cell of choice along with the Fc sequence complementary to the first Fc to favor generation of the desired multichain construct. In this example based on SEEDbody (Sb) pairing, SEQ ID NO: 206 [hG1Fc(Sb$_{AG}$)] and SEQ ID NO: 207 [hG1Fc(Sb$_{GA}$)] are examples of complementary IgG Fc sequences in which the engineered amino acid substitutions from IgA Fc are double underlined, and the TGF-beta superfamily type I or type II polypeptide of the construct can be fused to either SEQ ID

```
                                                    (SEQ ID NO: 204)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PCREEMTKNQ VSLWCLVKGF

151 YPSDIAVEWE SNGQPENNYK TTPPVLDSDG SFFLYSKLTV DKSRWQQGNV

201 FSCSVMHEAL HNHYTQKSLS LSPGK (SEQ ID NO: 205)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVCTLP PSREEMTKNQ VSLSCAVKGF

151 YPSDIAVEWE SNGQPENNYK TTPPVLDSDG SFFLVSKLTV DKSRWQQGNV

201 FSCSVMHEAL HNHYTQKSLS LSPGK
```

In part, the disclosure provides desired pairing of asymmetric Fc-containing polypeptide chains using Fc sequences engineered to generate interdigitating β-strand segments of human IgG and IgA $C_H3$ domains. Such methods include the use of strand-exchange engineered domain (SEED) $C_H3$ heterodimers allowing the formation of SEEDbody fusion proteins [see, for example, Davis et al (2010) Protein Eng Design Sel 23:195-202]. One of a pair of Fc sequences with NO: 206 or SEQ ID NO: 207, but not both. Given the high degree of amino acid sequence identity between native hG1Fc, native hG2Fc, native hG3Fc, and native hG4Fc, it can be appreciated that amino acid substitutions at corresponding positions in hG1Fc, hG2Fc, hG3Fc, or hG4Fc (see FIG. 5) will generate an Fc monomer which may be used in the complementary IgG-IgA pair below (SEQ ID NOs: 206 and 207).

```
                                                          (SEQ ID NO: 206)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PFRPEVHLLP PSREEMTKNQ VSLTCLARGF

151 YPKDIAVEWE SNGQPENNYK TIPSRQEPSQ GTTTFAVTSK LTVDKSRWQQ

201 GNVFSCSVMH EALHNHYTQK TISLSPGK (SEQ ID NO: 207)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PPSEELALNE LVTLTCLVKG

151 FYPSDIAVEW ESNGQELPRE KYLTWAPVLD SDGSFFLYSI LRVAAEDWKK

201 GDTFSCSVMH EALHNHYTQK SLDRSPGK
```

In part, the disclosure provides desired pairing of asymmetric Fc-containing polypeptide chains with a cleavable leucine zipper domain attached at the C-terminus of the Fc $C_H3$ domains. Attachment of a leucine zipper is sufficient to cause preferential assembly of heterodimeric antibody heavy chains. See, e.g., Wranik et al (2012) J Biol Chem 287:43331-43339. As disclosed herein, one of a pair of Fc sequences attached to a leucine zipper-forming strand can be arbitrarily fused to the TGF-beta superfamily type I or type II polypeptide of the construct, with or without an optional linker, to generate a TGF-beta superfamily type I or type II fusion polypeptide. This single chain can be coexpressed in a cell of choice along with the Fc sequence attached to a complementary leucine zipper-forming strand to favor generation of the desired multichain construct. Proteolytic digestion of the construct with the bacterial endoproteinase Lys-C post purification can release the leucine zipper domain, resulting in an Fc construct whose structure is identical to that of native Fc. In this example based on leucine zipper pairing, SEQ ID NO: 213 [hG1Fc-Ap1 (acidic)] and SEQ ID NO: 214 [hG1Fc-Bp1 (basic)] are examples of complementary IgG Fc sequences in which the engineered complementary leucine zipper sequences are underlined, and the TGF-beta superfamily type I or type II polypeptide of the construct can be fused to either SEQ ID NO: 213 or SEQ ID NO: 214, but not both. Given the high degree of amino acid sequence identity between native hG1Fc, native hG2Fc, native hG3Fc, and native hG4Fc, it can be appreciated that leucine zipper-forming sequences attached, with or without an optional linker, to hG1Fc, hG2Fc, hG3Fc, or hG4Fc (see FIG. 5) will generate an Fc monomer which may be used in the complementary leucine zipper-forming pair below (SEQ ID NOs: 213 and 214).

```
                                                          (SEQ ID NO: 213)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGKGGSAQ LEKELQALEK ENAQLEWELQ

251 ALEKELAQGA T (SEQ ID NO: 214)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGKGGSAQ LKKKLQALKK KNAQLKWKLQ

251 ALKKKLAQGA T
```

As described above, various methods are known in the art that increase desired pairing of Fc-containing fusion polypeptide chains in a single cell line to produce a preferred asymmetric fusion protein at acceptable yields [Klein et al (2012) mAbs 4:653-663; and Spiess et al (2015) Molecular Immunology 67(2A): 95-106]. In addition, heteromultimers as described herein may be generated using a combination of heavy and light chain fusion proteins comprising either an TGF-beta superfamily type I or TGF-beta superfamily type II polypeptide. For example, in some embodiments, a TGF-beta superfamily type I receptor polypeptide polypeptide may be fused, with or without a linker domain, to an immunoglobulin heavy chain (IgG1, IgG2, IgG3, IgG4, IgM, IgA1, or IgA2) that comprises at least a portion of the $C_H1$ domain. Similarly, a TGF-beta superfamily type II receptor polypeptide may be fused, with or without a linker domain, to an immunoglobulin light chain (kappa or lambda) that comprises at least a portion of the light chain constant domain ($C_L$). In alternative embodiments, a TGF-beta superfamily type I receptor polypeptide may be fused, with or without a linker domain, to an immunoglobulin heavy chain (IgG1, IgG2, IgG3, IgG4, IgM, IgA1, or IgA2) that comprises at least a portion of the $C_H1$ domain, and a TGF-beta superfamily type II receptor polypeptide may be fused, with or without a linker domain, to an immunoglobulin light chain (kappa or lambda) that comprises at least a portion of the light chain constant domain ($C_L$). This design takes advantage of the natural ability of the heavy chains to heterodimerize with light chains. In particular, heterodimerization of a heavy and light chain occurs between the $C_H1$ with the $C_L$, which is generally stabilized by covalent linking of the two domains via a disulfide bridge. Constructs employing the full-length heavy chain, or at least a portion of the heavy chain comprising the hinge region, could give rise to antibody-like molecules comprising two "light chains" and two "heavy chains". See FIG. 16. A potential advantage of this design is that it may more closely mimic the naturally occurring TGF-beta superfamily type I receptor polypeptide-ligand-TGF-beta superfamily type II receptor polypeptide complex and may display higher affinity for the ligand than comparable single heterodimers. In some embodiments, this design may be modified by incorporating various heavy chain truncations including, for example, truncations that comprise the $C_H1$ domain and some or all of the hinge domain (giving rise to F(ab')$_2$-like molecules) as well as truncations that only comprise the $C_H1$ domain or a fragment thereof (giving rise to Fab-like molecules). See FIG. 16G. Various methods for designing such heteromultimer constructs are described in US 2009/0010879, Klein et al [(2012) mAbs 4:653-663], and Spiess et al [(2015) Molecular Immunology 67(2A): 95-106] the contents of which are incorporated in their entirety herein.

In some embodiments, it is desirable to generate antibody-like heterodimers comprising at least one branch of the complex comprising an TGF-beta superfamily type I receptor polypeptide-$C_L$:TGF-beta superfamily type II receptor polypeptide-$C_H1$ heterodimer pair and at least a second branch comprising an TGF-beta superfamily type II receptor polypeptide-$C_L$:TGF-beta superfamily type I receptor polypeptide r-$C_H1$ heterodimer pair. See, e.g., FIG. 16B. Such heterodimer complexes can be generated, for example, using combinations of heavy chain and light chain asymmetrical pairing technologies [Spiess et al (2015) Molecular Immunology 67(2A): 95-106]. For example, in CrossMab technology, [Schaefer et al (2011). Proc. Natl. Acad. Sci. U.S.A. 108: 11187-11192] light chain mispairing is overcome using domain crossovers and heavy chains heterodimerized using knobs-into-holes [Merchant et al (1998) Nat. Biotechnol. 16: 677-681]. For the domain crossovers either the variable domains or the constant domains are swapped between light and heavy chains to create two asymmetric Fab arms that drive cognate light chain pairing while preserving the structural and functional integrity of the variable domain [Fenn et al (2013) PLoS ONE 8: e61953]. An alternative approach for overcoming light chain mispairing is designing heavy and light chains with orthogonal Fab interfaces [Lewis (2014) Nat. Biotechnol. 32: 191-198]. This has been accomplished by computational modeling [Das et al (2008) Annu. Rev. Biochem. 77: 363-382] in combination with X-ray crystallography to identify mutations at the $V_H/V_L$ and $C_H1/C_L$ interfaces. For the heterodimers generated using this methodology, it may be necessary to engineer mutations into both $V_H/V_L$ and $C_H1/C_L$ interfaces to minimize heavy/light chain mispairing. The designed orthogonal Fab interface may be used in conjunction with a heavy chain heterodimerization strategy to facilitate efficient IgG production in a single host cell. Electrostatic steering may also be used to generate orthogonal Fab interfaces to facilitate the construction of such heterodimers. Peptide linkers may be used to ensure cognate pairing of light and heavy chains in a format known as "LUZ-Y" [Wranik et al (2012) J. Biol. Chem. 287: 43331-43339], wherein heavy chain heterodimerization is accomplished using leucine zippers which may be subsequently removed by proteolysis in vitro.

Alternatively, heteromultimers may comprise one or more single-chain ligand traps as described herein, optionally which may be covalently or non-covalently associated with one or more TGF-beta superfamily type I receptor polypeptides or TGF-beta superfamily type I receptor polypeptides as well as additional TGF-beta superfamily type I receptor polypeptide:TGF-beta superfamily type II receptor polypeptide single chain ligand traps [US 2011/0236309 and US2009/0010879]. See FIG. 12. As described herein, single-chain ligand traps do not require fusion to any multimerization domain such as coiled-coil Fc domains to be multivalent. In general, single-chain ligand traps of the present disclosure comprise at least one TGF-beta superfamily type I receptor polypeptide domain and one TGF-beta superfamily type I receptor polypeptide domain. The TGF-beta superfamily type I receptor polypeptide and TGF-beta superfamily type I receptor polypeptide domains, generally referred to herein as binding domains (BD), optionally may be joined by a linker region.

For example, in one aspect, the present disclosure provides heteromultimers comprising a polypeptide having the following structure:

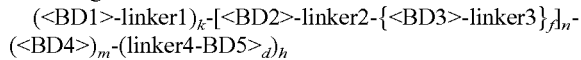

where: n and h are independently greater than or equal to one; d, f, m, and k are independently equal to or greater than zero; BD1, BD2, BD3, BD4, and BD5 are independently TGF-beta superfamily type I receptor polypeptide or TGF-beta superfamily type II receptor polypeptide domains, wherein at least one of BD1, BD2, BD3, and BD4 is an TGF-beta superfamily type I receptor polypeptide domain, and wherein at least one of BD1, BD2, BD3, and BD4 is an TGF-beta superfamily type II receptor polypeptide domain, and linker1, linker2, linker3, and linker 4 are independently greater than or equal to zero. In some embodiment, TGF-beta superfamily type I receptor polypeptide:TGF-beta superfamily type II receptor polypeptide single-chain traps comprise at least two different TGF-beta superfamily type I receptor polypeptide. In some embodiments, TGF-beta superfamily type I receptor polypeptide:TGF-beta superfamily type II receptor polypeptide single-chain traps comprise at least two different TGF-beta superfamily type II receptor polypeptide polypeptides. In some embodiment, TGF-beta superfamily type I receptor polypeptide:TGF-beta superfamily type I receptor polypeptide single-chain traps comprise at least two different linkers. Depending on the values of selected for d, f, h, k, m, and n, the heteromultimer structure may comprise a large number of repeating units in various combinations or may be a relatively simple structure.

In another aspect, the present disclosure provides heteromultimers comprising a polypeptide having the following structure:

<BD1>-linker1-<BD2>

In yet another aspect, the present disclosure provides heteromultimers comprising a polypeptide having the following structure:

<BD1>-(linker2-<BD2>)$_n$ where n is greater than or equal one.

Another aspect of the invention provides heteromultimers comprising a polypeptide having the following structure:

(<BD1>-linker1-<BD1>)$_f$-linker2-(<BD2>-linker3-<BD3>)$_g$ wherein f and g are greater than or equal to one.
In an embodiment where BD2 and BD3 are the same, and f and g are the same number, this can result in a substantially mirror symmetric structure around linker 2, subject to differences in the linkers. In instances where BD2 is different from BD3 and/or where f and g are different numbers, different structures will be produced. It is within the capacity of one of ordinary skill in the art to select suitable binding domains, linkers, and repeat frequencies in light of the disclosure herein and knowledge in the art. Specific, non-limiting examples of such single-chain ligand traps in accordance with the present disclosure are represented schematically in FIG. 18.

The linkers (1, 2, 3, and 4) may be the same or different. The linker region provides a segment that is distinct from the structured ligand-binding domains of TGF-beta superfamily type I receptor polypeptide and TGF-beta superfamily type II receptor polypeptide and thus can be used for conjugation to accessory molecules (e.g., molecules useful in increasing stability such as PEGylation moieties) without having to chemically modify the binding domains. The linker may include an unstructured amino acid sequence that may be either the same as or derived from conservative modifications to the sequence of a natural unstructured region in the extracellular portion of the receptor for the ligand of interest or another receptor in the TGF-β superfamily. In other instances, such linkers may be entirely artificial in composition and origin but will contain amino acids selected to provide an unstructured flexible linker with a low likelihood of encountering electrostatic or steric hindrance complications when brought into close proximity to the ligand of interest. Linker length will be considered acceptable when it permits binding domains located on each of the N- and C-termini of the linker to bind their natural binding sites on their natural ligand such that, with both binding domains so bound, the ligand is bound with a higher affinity than it would be bound by binding of only one of the binding domains. In some instances, the number of amino acid residues in the linker of either natural or artificial origin is selected to be equal to or greater than the minimum required distance for simultaneous (bridged) binding to two binding sites on the TGF-beta superfamily type I receptor polypeptide and/or TGF-beta superfamily type II receptor polypeptide ligand. For example, and without wishing to be limiting in any manner, the linker length may be between about 1-10 amino acids, 10-20 amino acids, 18-80 amino acids, 25-60 amino acids, 35-45 amino acids, or any other suitable length.

Linkers may be designed to facilitate purification of the polypeptide. The exact purification scheme chosen will determine what modifications are needed, for example and without wishing to be limiting, additions of purification "tags" such as His tags is contemplated; in other examples, the linker may include regions to facilitate the addition of cargo or accessory molecules. When such additions affect the unstructured nature of the linker or introduce potential electrostatic or steric concerns, appropriate increases to the linker length will be made to ensure that the two binding domains are able to bind their respective sites on the ligand. In light of the methods and teachings herein, such determinations could be made routinely by one skilled in the art.

In addition, the present design permits linkage of other cargo molecules (for example imaging agents like fluorescent molecules), toxins, etc. For example, and without wishing to be limiting in any manner, single-chain polypeptides can be modified to add one or more cargo and/or accessory molecules (referred to collectively herein by R1, R2, R3, R4, etc.):

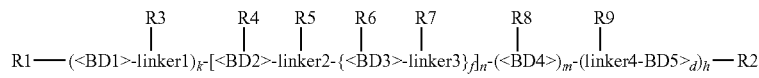

Without limiting the generality of R substituents available, R1, R2, R3, R4, R5, R6, R7, R8, R9, may or may not be present; when present, they may be the same or different, and may independently be one or more of: a fusion protein for targeting, for example, but not limited to such as an antibody fragment (e.g. single chain Fv) and/or a single domain antibody (sdAb); a radiotherapy and/or imaging agent, for example, but not limited to a radionuceotide (e.g. $^{123}$I $^{111}$In, $^{18}$F, $^{64}$C, $^{68}$Y, $^{124}$I, $^{131}$I, $^{90}$Y, $^{177}$Lu, $^{57}$Cu, $^{213}$Bi, $^{211}$At), a fluorescent dye (e.g. Alexa Fluor, Cy dye) and/or a fluorescent protein tag (e.g. GFP, DsRed); a cytotoxic agent for chemotherapy, for example, but not limited to doxorubicin, calicheamicin, a maytansinoid derivatives (e.g. DM1, DM4), a toxin (eg. truncated *Pseudomonas* endotoxin A, diphteria toxin); a nanoparticle-based carrier, for example, but not limited to polyethylene glycol (PEG), a polymer-conjugated to drug, nanocarrier or imaging agent (e.g. of a polymer N-(2-hydorxylpropyl) methacrylamide (HPMA), glutamic acid, PEG, dextran); a drug (for example, but not limited to doxorubicin, camptothecin, paclitaxel, palatinate); a nanocarrier, for example, but not limited to a nanoshell or liposome; an imaging agent, for example, but not limited to Supermagnetic Iron Oxide (SPIO); a dendrimer; and/or a solid support for use in ligand purification, concentration or sequestration (e.g. nanoparticles, inert resins, suitable silica supports).

In general, it will not be preferable to have cargo or accessory molecules in all possible positions, as this may cause steric or electrostatic complications. However, the effects of adding a cargo or accessory molecule to any given position or positions on the structure can be determined routinely in light of the disclosure herein by modeling the linker between the binding domains and carrying out molecular dynamics simulations to substantially minimize molecular mechanics energy and reduce steric and electrostatic incompatibility between the linker and the TGF-beta superfamily type I receptor polypeptide and TGF-beta superfamily type II receptor polypeptideas taught herein.

It may be preferable to add the cargo or accessory molecule to the linker portion of the agent, rather to the binding domain, to reduce the likelihood of interference in binding function. However, addition to the binding domain is possible and could be desirable in some instances and the effect of such an addition can be determined routinely in advance by modeling the binding agent and the linker with the proposed addition as described herein.

Conjugation methodologies may be performed using commercial kits that enable conjugation via common reactive groups such as primary amines, succinimidyl (NHS) esters and sulfhydral-reactive groups. Some non-limiting examples are: Alexa Fluor 488 protein labeling kit (Molecular Probes, Invitrogen detection technologies) and PEGylation kits (Pierce Biotechnology Inc.).

In certain aspects, TGF-beta superfamily type I receptor polypeptide:TGF-beta superfamily type II receptor polypeptide single-chain traps may be covalently or non-covalently associated with one or more TGF-beta superfamily type I receptor polypeptides or TGF-beta superfamily type II receptor polypeptide as well as additional TGF-beta superfamily type I receptor polypeptide:TGF-beta superfamily type II receptor polypeptide single chain ligand traps to form higher order heteromultimers, which may be used in accordance with the methods described herein. See, e.g., FIG. 19. For example, an TGF-beta superfamily type I receptor polypeptide: TGF-beta superfamily type II receptor polypeptide single chain ligand trap may further comprise a multimerization domain as described herein. In some embodiments, TGF-beta superfamily type I receptor polypeptide:TGF-beta superfamily type II receptor polypeptide single chain ligand traps comprise a constant domain of an Ig immunoglobulin. Such immunoglobulins constant domains may be selected to promote symmetrical or asymmetrical complexes comprising at least one single-chain TGF-beta superfamily type I receptor polypeptide:TGF-beta superfamily type II receptor polypeptide trap.

In certain aspects, an TGF-beta superfamily type I receptor polypeptide: TGF-beta superfamily type II receptor polypeptide single-chain trap, or combinations of such traps, may be used as TGF-beta superfamily antagonists to treat or prevent an TGF-beta superfamily disorder or disease as described herein (e.g., kidney disease and/or a metabolic disorder or condition).

It is understood that different elements of the fusion proteins (e.g., immunoglobulin Fc fusion proteins) may be arranged in any manner that is consistent with desired functionality. For example, a TGF-beta superfamily type I and/or type II receptor polypeptide domain may be placed C-terminal to a heterologous domain, or alternatively, a heterologous domain may be placed C-terminal to a TGF-beta superfamily type I and/or type II receptor polypeptide domain. The TGF-beta superfamily type I and/or type II receptor polypeptide domain and the heterologous domain need not be adjacent in a fusion protein, and additional domains or amino acid sequences may be included C- or N-terminal to either domain or between the domains.

For example, a TGF-beta superfamily type I and/or type II receptor fusion protein may comprise an amino acid sequence as set forth in the formula A-B-C. The B portion corresponds to a TGF-beta superfamily type I and/or type II receptor polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines, e.g., GGG (SEQ ID NO: 58), GGGG (SEQ ID NO: 59), TGGGG (SEQ ID NO: 60), SGGGG (SEQ ID NO: 61), TGGG (SEQ ID NO: 62), or SGGG (SEQ ID NO: 63) singlets, or repeats. In certain embodiments, a TGF-beta superfamily type I and/or type II receptor fusion protein comprises an amino acid sequence as set forth in the formula A-B-C, wherein A is a leader (signal) sequence, B consists of a TGF-beta superfamily type I and/or type II receptor polypeptide domain, and C is a polypeptide portion that enhances one or more of in vivo stability, in vivo half-life, uptake/administration, tissue localization or distribution, formation of protein complexes, and/or purification. In certain embodiments, a TGF-beta superfamily type I and/or type II receptor fusion protein comprises an amino acid sequence as set forth in the formula A-B-C, wherein A is a TPA leader sequence, B consists of a TGF-beta superfamily type I and/or type II receptor polypeptide domain, and C is an immunoglobulin Fc domain. Preferred fusion proteins comprise the amino acid sequence set forth in any one of SEQ ID NOs: 100, 102, 104, 106, 112, 114, 115, 117, 118, 120, 121, 123, 124, 126, 127, 129, 401, 402, 403, 404, 405, 406, 407, 408, 409, 410, 411, 412, 413, 414, 415, and 416.

In some embodiments, TGF-beta superfamily receptor heteromultimer complexes of the present disclosure further comprise one or more heterologous portions (domains) so as to confer a desired property. For example, some fusion domains are particularly useful for isolation of the fusion proteins by affinity chromatography. Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$ (SEQ ID NO: 509)) fusion partners. As another example, a fusion domain may be selected so as to facilitate detection of the ligand trap polypeptides. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for factor Xa or thrombin, which allows the relevant protease to partially digest the fusion proteins and thereby liberate the recombinant proteins therefrom. The liberated proteins can then be isolated from the fusion domain by subsequent chromatographic separation.

In certain embodiments, TGF-beta superfamily type I and/or type II receptor polypeptides of the present disclosure contain one or more modifications that are capable of stabilizing the polypeptides. For example, such modifications enhance the in vitro half-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising a TGF-beta superfamily type I and/or type II receptor polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol.

In preferred embodiments, TGF-beta superfamily heteromultimer complexes to be used in accordance with the methods described herein are isolated polypeptide complexes. As used herein, an isolated protein (or protein complex) or polypeptide (or polypeptide complex) is one which has been separated from a component of its natural environment. In some embodiments, a heteromultimer complex of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of antibody purity are well known in the art [See, e.g., Flatman et al., (2007) J. Chromatogr. B 848:79-87]. In some embodiments, heteromultimer preparations of the disclosure are substantially free of TGF-beta superfamily type I receptor polypeptide homomultimers and/or TGF-beta superfamily type II receptor polypeptide homomultimers. For example, in some embodiments, heteromultimer preparations comprise less than about 10%, 9%, 8%, 7%, 5%, 4%, 3%, 2%, or less than 1% of TGF-beta superfamily type I receptor polypeptide homomultimers. In some embodiments, heteromultimer preparations comprise less than about 10%, 9%, 8%, 7%, 5%, 4%, 3%, 2%, or less than 1% of TGF-beta superfamily type II receptor polypeptide homomultimers. In some embodiments, heteromultimer preparations comprise less than about 10%, 9%, 8%, 7%, 5%, 4%, 3%, 2%, or less than 1% of TGF-beta superfamily type I receptor polypeptide homomultimers and less than about 10%, 9%, 8%, 7%, 5%, 4%, 3%, 2%, or less than 1% of TGF-beta superfamily type II receptor polypeptide homomultimers.

In certain embodiments, TGFβ superfamily type I and/or type II receptor polypeptides, as well as heteromultimer complexes thereof, of the disclosure can be produced by a variety of art-known techniques. For example, polypeptides of the disclosure can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (see, e.g., Advanced ChemTech Model 396; Milligen/Biosearch 9600). Alternatively, the polypeptides and complexes of the disclosure, including fragments or variants thereof, may be recombinantly produced using various expression systems [e.g., E. coli, Chinese Hamster Ovary (CHO) cells, COS cells, baculovirus] as is well known in the art. In a further embodiment, the modified or unmodified polypeptides of the disclosure may be produced by digestion of recombinantly produced full-length TGFβ superfamily type I and/or type II receptor polypeptides by using, for example, a protease, e.g., trypsin, thermolysin, chymotrypsin, pepsin, or paired basic amino acid converting enzyme (PACE). Computer analysis (using a commercially available software, e.g., MacVector, Omega, PCGene, Molecular Simulation, Inc.) can be used to identify proteolytic cleavage sites.

With respect to antibodies that bind to and antagonize ligands that bind to TGF-beta type I receptor polypeptide: TGF-beta type II receptor polypeptide heteromultimers of the disclosure (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty) it is contemplated that an antibody may be designed as a bispecific antibody comprising a first portion that binds to an epitope of such ligand, such that the first portion of the antibody competes for binding with a type I receptor and comprising a second portion that binds to an epitope of such ligand, such that the second portion of the antibody competes for binding with a type II receptor. In this manner, a bispecific antibody targeting a single ligand can be designed to mimic the dual type I-type II receptor binding blockade that may be conferred by an ALK7:ActRIIB heteromultimer. Similarly it is contemplated that the same effect could be achieved using a combination of two or more antibodies wherein at least a first antibody binds to an epitope of such ligand, such that the first antibody competes for binding with a type I receptor and at least a second antibody binds to an epitope of such ligand, such that the second antibody competes for binding with a type II receptor.

B. Nucleic Acids Encoding TGFβ Superfamily Type I and/or Type II Receptor Polypeptides In certain embodiments, the present disclosure provides isolated and/or recombinant nucleic acids encoding TGFβ superfamily type I and/or type II receptors (including fragments, functional variants, and fusion proteins thereof) disclosed herein. For example, SEQ ID NO: 12 encodes the naturally occurring human ActRIIA precursor polypeptide, while SEQ ID NO: 13 encodes the mature, extracellular domain of ActRIIA. The subject nucleic acids may be single-stranded or double stranded. Such nucleic acids may be DNA or RNA molecules. These nucleic acids may be used, for example, in methods for making TGF-beta superfamily heteromultimer complexes of the present disclosure.

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding TGFβ superfamily type I and/or type II receptor polypeptides of the present disclosure are understood to include nucleic acids that are variants of any one of SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143. Variant nucleotide sequences include sequences that differ by one or more nucleotide substitutions, additions, or deletions including allelic variants, and therefore, will include coding sequences that differ from the nucleotide sequence designated in any one of SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143.

In certain embodiments, TGFβ superfamily type I and/or type II receptor polypeptides of the present disclosure are encoded by isolated or recombinant nucleic acid sequences that are at least 80%, 85%, 90%, 95%, 96%, 97%, 98%, 99%, or 100% identical to SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143. One of ordinary skill in the art will appreciate that nucleic acid sequences that are at least 80%, 85%, 90%, 95%, 96%, 97%, 98%, or 99% identical to the sequences complementary to SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143 are also within the scope of the present disclosure. In further embodiments, the nucleic acid sequences of the disclosure can be isolated, recombinant, and/or fused with a heterologous nucleotide sequence or in a DNA library.

In other embodiments, nucleic acids of the present disclosure also include nucleotide sequences that hybridize under highly stringent conditions to the nucleotide sequence designated in SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143, the complement sequence of SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143, or fragments thereof. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 7, 8, 12, 13, 16, 17, 20, 21, 24, 25, 28, 29, 32, 33, 36, 37, 40, 41, 44, 45, 48, 49, 52, 53, 69, 70, 73, 74, 77, 78, 81, 82, 85, 86, 89, 90, 93, 94, 303, 304, 307, 308, 311, 312, 101, 105, 113, 116, 119, 122, 125, 128, 131, 134, 137, 140, and 143 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and will vary with the host cell used.

In certain aspects of the present disclosure, the subject nucleic acid is provided in an expression vector comprising a nucleotide sequence encoding a TGFβ superfamily type I and/or type II receptor polypeptide and operably linked to at least one regulatory sequence. Regulatory sequences are art-recognized and are selected to direct expression of the TGFβ superfamily type I and/or type II receptor polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a TGFβ superfamily type I and/or type II receptor polypeptides. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant TGFβ superfamily type I and/or type II receptor polypeptide include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject TGFβ superfamily type I and/or type II receptor polypeptides in CHO cells, such as a Pcmv-Script vector (Stratagene, La Jolla, Calif), pcDNA4 vectors (Invitrogen, Carlsbad, Calif.) and pCI-neo vectors (Promega, Madison, Wis.). As will be apparent, the subject gene constructs can be used to cause expression of the subject TGFβ superfamily type I and/or type II receptor polypeptide in cells propagated in culture, e.g., to produce proteins, including fusion proteins or variant proteins, for purification.

This disclosure also pertains to a host cell transfected with a recombinant gene including a coding sequence for one or more of the subject TGFβ superfamily type I and/or type II receptor polypeptides. The host cell may be any prokaryotic or eukaryotic cell. For example, a TGFβ superfamily type I and/or type II receptor polypeptide of the disclosure may be expressed in bacterial cells such as *E. coli*, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject TGFβ superfamily type I and/or type II receptor polypeptides. For example, a host cell transfected with an expression vector encoding a TGFβ superfamily type I and/or type II receptor polypeptide can be cultured under appropriate conditions to allow expression of the TGFβ superfamily type I and/or type II receptor polypeptide to occur. The polypeptide may be secreted and isolated from a mixture of cells and medium containing the polypeptide. Alternatively, the TGFβ superfamily type I and/or type II receptor polypeptide may be isolated from a cytoplasmic or membrane fraction obtained from harvested and lysed cells. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the TGFβ superfamily type I and/or type II receptor polypeptides and affinity purification with an agent that binds to a domain fused to TGFβ superfamily type I and/or type II receptor polypeptide (e.g., a protein A column may be used to purify a TGFβ superfamily type I receptor-Fc and/or type II receptor-Fc fusion protein). In some embodiments, the TGFβ superfamily type I and/or type II receptor polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. A TGFβ superfamily type I receptor-Fc and/or type II receptor-Fc fusion protein may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant TGFβ superfamily type I and/or type II receptor polypeptide, can allow purification of the expressed fusion protein by affinity chromatography using a $Ni^{2+}$ metal resin. The purification leader sequence can then be subsequently removed by treatment with enterokinase to provide the purified TGFβ superfamily type I and/or type II receptor polypeptide. See, e.g., Hochuli et al. (1987) *J. Chromatography* 411:177; and Janknecht et al. (1991) *PNAS USA* 88:8972.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

4. Screening Assays

In certain aspects, the present disclosure relates to the use of TGFβ superfamily type I and type II receptor heteromultimer complexes to identify compounds (agents) which are agonists or antagonists of TGFβ superfamily receptors. Compounds identified through this screening can be tested to assess their ability to modulate tissues such as bone, cartilage, muscle, fat, and/or neurons, to assess their ability to modulate tissue growth in vivo or in vitro. These compounds can be tested, for example, in animal models.

There are numerous approaches to screening for therapeutic agents for modulating tissue growth by targeting TGFβ superfamily ligand signaling (e.g., SMAD 2/3 and/or SMAD 1/5/8 signaling). In certain embodiments, high-throughput screening of compounds can be carried out to identify agents that perturb TGFβ superfamily receptor-mediated effects on a selected cell line. In certain embodiments, the assay is carried out to screen and identify compounds that specifically inhibit or reduce binding of a TGF-beta superfamily heteromultimer complex to its binding partner, such as a TGFβ superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). Alternatively, the assay can be used to identify compounds that enhance binding of a TGF-beta superfamily heteromultimer complex to its binding partner such as a TGFβ superfamily ligand. In a further embodiment, the compounds can be identified by their ability to interact with a TGF-beta superfamily heteromultimer complex of the disclosure.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In certain embodiments, the test agent is a small organic molecule having a molecular weight of less than about 2,000 Daltons.

The test compounds of the disclosure can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S-transferase (GST), photoactivatible crosslinkers or any combinations thereof.

In many drug-screening programs which test libraries of compounds and natural extracts, high-throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a TGF-beta superfamily heteromultimer complex and its binding partner (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty).

Merely to illustrate, in an exemplary screening assay of the present disclosure, the compound of interest is contacted with an isolated and purified TGF-beta superfamily heteromultimer complex which is ordinarily capable of binding to a TGF-beta superfamily ligand, as appropriate for the intention of the assay. To the mixture of the compound and TGF-beta superfamily heteromultimer complex is then added to a composition containing the appropriate TGF-beta superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). Detection and quantification of heteromultimer-superfamily ligand complexes provides a means for determining the compound's efficacy at inhibiting (or potentiating) complex formation between the TGF-beta superfamily heteromultimer complex and its binding protein. The efficacy of the compound can be assessed by generating dose-response curves from data obtained using various concentrations of the test compound. Moreover, a control assay can also be performed to provide a baseline for comparison. For example, in a control assay, isolated and purified TGF-beta superfamily ligand is added to a composition containing the TGF-beta superfamily heteromultimer complex, and the formation of heteromultimer-ligand complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Binding of a TGF-beta superfamily heteromultimer complex to another protein may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled TGF-beta superfamily heteromultimer complex and/or its binding protein, by immunoassay, or by chromatographic detection.

In certain embodiments, the present disclosure contemplates the use of fluorescence polarization assays and fluorescence resonance energy transfer (FRET) assays in measuring, either directly or indirectly, the degree of interaction between a TGF-beta superfamily heteromultimer complex and its binding protein. Further, other modes of detection, such as those based on optical waveguides (see, e.g., PCT Publication WO 96/26432 and U.S. Pat. No. 5,677,196), surface plasmon resonance (SPR), surface charge sensors, and surface force sensors, are compatible with many embodiments of the disclosure.

Moreover, the present disclosure contemplates the use of an interaction trap assay, also known as the "two-hybrid assay," for identifying agents that disrupt or potentiate interaction between a TGF-beta superfamily heteromultimer complex and its binding partner. See, e.g., U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present disclosure contemplates the use of reverse two-hybrid systems to identify compounds (e.g., small molecules or peptides) that dissociate interactions between a TGF-beta superfamily heteromultimer complex and its binding protein [see, e.g., Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368].

In certain embodiments, the subject compounds are identified by their ability to interact with a TGF-beta superfamily heteromultimer complex of the disclosure. The interaction between the compound and the TGF-beta superfamily heteromultimer complex may be covalent or non-covalent. For example, such interaction can be identified at the protein level using in vitro biochemical methods, including photo-crosslinking, radiolabeled ligand binding, and affinity chromatography. See, e.g., Jakoby W B et al. (1974) Methods in Enzymology 46:1. In certain cases, the compounds may be screened in a mechanism-based assay, such as an assay to detect compounds which bind to a TGF-beta superfamily heteromultimer complex. This may include a solid-phase or fluid-phase binding event. Alternatively, the gene encoding a TGF-beta superfamily heteromultimer complex can be transfected with a reporter system (e.g., β-galactosidase, luciferase, or green fluorescent protein) into a cell and screened against the library preferably by high-throughput screening or with individual members of the library. Other mechanism-based binding assays may be used; for example, binding assays which detect changes in free energy. Binding assays can be performed with the target fixed to a well, bead or chip or captured by an immobilized antibody or resolved by capillary electrophoresis. The bound compounds may be detected usually using colorimetric endpoints or fluorescence or surface plasmon resonance.

5. Exemplary Therapeutic Uses

In certain embodiments, a TGF-beta superfamily heteromultimer complex, or combinations of TGF-beta superfamily heteromultimer complexes, of the present disclosure can be used to treat or prevent a disease or condition that is associated with abnormal activity of a TGFβ superfamily receptor (e.g., ALK1, ALK2, ALK3, ALK4, ALK5, ALK6, ALK7, ActRIIA, ActRIIB, BMPRII, TGFBRII, and MIS-RII) and/or a TGFβ superfamily ligand (e.g., BMP2, BMP2/7, BMP3, BMP4, BMP4/7, BMP5, BMP6, BMP7, BMP8a, BMP8b, BMP9, BMP10, GDF3, GDF5, GDF6/BMP13, GDF7, GDF8, GDF9b/BMP15, GDF11/BMP11, GDF15/MIC1, TGF-β1, TGF-β2, TGF-β3, activin A, activin B, activin C, activin E, activin AB, activin AC, activin AE, activin BC, activin BE, nodal, glial cell-derived neurotrophic factor (GDNF), neurturin, artemin, persephin, MIS, and Lefty). These diseases, disorders or conditions are generally referred to herein as "TGFβ superfamily-associated conditions" or "TGFβ superfamily-associated disorders." In certain embodiments, the present invention provides methods of treating or preventing an individual in need thereof through administering to the individual a therapeutically effective amount of a TGF-beta superfamily heteromultimer complex, or combinations of TGF-beta superfamily heteromultimer complexes, as described herein. Any of the TGF-beta superfamily heteromultimer complexes of the present disclosure can potentially be employed individually or in combination for therapeutic uses disclosed herein. These methods are particularly aimed at therapeutic and prophylactic treatments of mammals including, for example, rodents, primates, and humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes amelioration or elimination of the condition once it has been established. In either case, prevention or treatment may be discerned in the diagnosis provided by a physician or other health care provider and the intended result of administration of the therapeutic agent.

TGFβ superfamily receptor-ligand complexes play essential roles in tissue growth as well as early developmental processes such as the correct formation of various structures or in one or more post-developmental capacities including sexual development, pituitary hormone production, and creation of bone and cartilage. Thus, TGFβ superfamily-associated conditions/disorders include abnormal tissue growth and developmental defects. In addition, TGFβ superfamily-associated conditions include, but are not limited to, disorders of cell growth and differentiation such as inflammation, allergy, autoimmune diseases, infectious diseases, and tumors.

Exemplary TGFβ superfamily-associated conditions include neuromuscular disorders (e.g., muscular dystrophy and muscle atrophy), congestive obstructive pulmonary disease (and muscle wasting associated with COPD), muscle wasting syndrome, sarcopenia, cachexia, adipose tissue disorders (e.g., obesity), type 2 diabetes (NIDDM, adult-onset diabetes), and bone degenerative disease (e.g., osteoporosis). Other exemplary TGFβ superfamily-associated conditions include musculodegenerative and neuromuscular disorders, tissue repair (e.g., wound healing), neurodegenerative diseases (e.g., amyotrophic lateral sclerosis), and immunologic disorders (e.g., disorders related to abnormal proliferation or function of lymphocytes).

In certain embodiments, a TGF-beta superfamily heteromultimer complex, or combinations of TGF-beta superfamily heteromultimer complexes, of the disclosure are used as part of a treatment for a muscular dystrophy. The term "muscular dystrophy" refers to a group of degenerative muscle diseases characterized by gradual weakening and deterioration of skeletal muscles and sometimes the heart and respiratory muscles. Muscular dystrophies are genetic disorders characterized by progressive muscle wasting and weakness that begin with microscopic changes in the muscle. As muscles degenerate over time, the person's muscle strength declines. Exemplary muscular dystrophies that can be treated with a regimen including the subject TGF-beta superfamily heteromultimer complexes include: Duchenne muscular dystrophy (DMD), Becker muscular dystrophy (BMD), Emery-Dreifuss muscular dystrophy (EDMD), limb-girdle muscular dystrophy (LGMD), facioscapulohumeral muscular dystrophy (FSH or FSHD) (also known as Landouzy-Dejerine), myotonic dystrophy (MMD; also known as Steinert's Disease), oculopharyngeal muscular dystrophy (OPMD), distal muscular dystrophy (DD), congenital muscular dystrophy (CMD).

Duchenne muscular dystrophy (DMD) was first described by the French neurologist Guillaume Benjamin Amand Duchenne in the 1860s. Becker muscular dystrophy (BMD) is named after the German doctor Peter Emil Becker, who first described this variant of DMD in the 1950s. DMD is one of the most frequent inherited diseases in males, affecting one in 3,500 boys. DMD occurs when the dystrophin gene, located on the short arm of the X chromosome, is defective. Since males only carry one copy of the X chromosome, they only have one copy of the dystrophin gene. Without the dystrophin protein, muscle is easily damaged during cycles of contraction and relaxation. While early in the disease muscle compensates by regeneration, later on muscle progenitor cells cannot keep up with the ongoing damage and healthy muscle is replaced by non-functional fibro-fatty tissue.

BMD results from different mutations in the dystrophin gene. BMD patients have some dystrophin, but it is either of insufficient quantity or poor quality. The presence of some dystrophin protects the muscles of patients with BMD from degenerating as severely or as quickly as those of patients with DMD.

Studies in animals indicate that inhibition of the GDF8 signaling pathway may effectively treat various aspects of disease in DMD and BMD patients (Bogdanovich et al., 2002, Nature 420:418-421; Pistilli et al., 2011, Am J Pathol 178:1287-1297). Thus, TGF-beta superfamily heteromultimer complexes of the disclosure may act as GDF8 inhibitors (antagonists), and constitute an alternative means of blocking signaling by GDF8 and/or related TGFβ superfamily ligands in vivo in DMD and BMD patients.

Similarly, TGF-beta superfamily heteromultimer complexes of the disclosure may provide an effective means to increase muscle mass in other disease conditions that are in need of muscle growth. For example, amyotrophic lateral sclerosis (ALS), also called Lou Gehrig's disease or motor neuron disease, is a chronic, progressive, and incurable CNS disorder that attacks motor neurons, which are components of the central nervous system required for initiation of skeletal muscle contraction. In ALS, motor neurons deteriorate and eventually die, and though a person's brain normally remains fully functioning and alert, initiation of muscle contraction is blocked at the spinal level. Individuals who develop ALS are typically between 40 and 70 years old, and the first motor neurons to degenerate are those innervating the arms or legs. Patients with ALS may have trouble walking, may drop things, fall, slur their speech, and laugh or cry uncontrollably. As the disease progresses, muscles in the limbs begin to atrophy from disuse. Muscle weakness becomes debilitating, and patients eventually require a wheel chair or become confined to bed. Most ALS patients die from respiratory failure or from complications of ventilator assistance like pneumonia 3-5 years from disease onset.

Promotion of increased muscle mass by TGF-beta superfamily heteromultimer complexes might also benefit those suffering from muscle wasting diseases. Gonzalez-Cadavid et al. (supra) reported that GDF8 expression correlates inversely with fat-free mass in humans and that increased expression of the GDF8 gene is associated with weight loss in men with AIDS wasting syndrome. By inhibiting the function of GDF8 in AIDS patients, at least certain symptoms of AIDS may be alleviated, if not completely eliminated, thus significantly improving quality of life in AIDS patients.

Since loss of GDF8 function is also associated with fat loss without diminution of nutrient intake (Zimmers et al., supra; McPherron and Lee, supra), the subject TGF-beta superfamily heteromultimer complexes may further be used as a therapeutic agent for slowing or preventing the development of obesity and type 2 diabetes.

Cancer anorexia-cachexia syndrome is among the most debilitating and life-threatening aspects of cancer. This syndrome is a common feature of many types of cancer—present in approximately 80% of cancer patients at death—and is responsible not only for a poor quality of life and poor response to chemotherapy but also a shorter survival time than is found in patients with comparable tumors but without weight loss. Cachexia is typically suspected in patients with cancer if an involuntary weight loss of greater than five percent of premorbid weight occurs within a six-month period. Associated with anorexia, wasting of fat and muscle tissue, and psychological distress, cachexia arises from a complex interaction between the cancer and the host. Cancer cachexia affects cytokine production, release of lipid-mobilizing and proteolysis-inducing factors, and alterations in intermediary metabolism. Although anorexia is common, a decreased food intake alone is unable to account for the changes in body composition seen in cancer patients, and increasing nutrient intake is unable to reverse the wasting syndrome. Currently, there is no treatment to control or reverse the cachexic process. Since systemic overexpression of GDF8 in adult mice was found to induce profound muscle and fat loss analogous to that seen in human cachexia syndromes (Zimmers et al., supra), the subject TGF-beta superfamily heteromultimer complex pharmaceutical compositions may be beneficially used to prevent, treat, or alleviate the symptoms of the cachexia syndrome, where muscle growth is desired. An example of a heteromeric complex useful for preventing, treating, or alleviating muscle loss as described above is ActRIIB-Fc:ALK4-Fc.

In certain embodiments, a TGF-beta superfamily heteromultimer complex, or combinations of TGF-beta superfamily heteromultimer complexes, of the present disclosure may be used in methods of inducing bone and/or cartilage formation, preventing bone loss, increasing bone mineralization, preventing the demineralization of bone, and/or increasing bone density. TGF-beta superfamily heteromultimer complexes may be useful in patients who are diagnosed with subclinical low bone density, as a protective measure against the development of osteoporosis.

In some embodiments, a TGF-beta superfamily heteromultimer complex, or combinations of TGF-beta superfamily heteromultimer complexes, of the present disclosure may find medical utility in the healing of bone fractures and cartilage defects in humans and other animals. The subject methods and compositions may also have prophylactic use in closed as well as open fracture reduction and also in the improved fixation of artificial joints. De novo bone formation induced by an osteogenic agent is useful for repair of craniofacial defects that are congenital, trauma-induced, or caused by oncologic resection, and is also useful in cosmetic plastic surgery. Further, methods and compositions of the invention may be used in the treatment of periodontal disease and in other tooth repair processes. In certain cases, a TGF-beta superfamily heteromultimer complex, or combinations of TGF-beta superfamily heteromultimer complexes, may provide an environment to attract bone-forming cells, stimulate growth of bone-forming cells, or induce differentiation of progenitors of bone-forming cells. TGF-beta superfamily heteromultimer complexes of the disclosure may also be useful in the treatment of osteoporosis. Further, TGF-beta superfamily heteromultimer complexes may be used in repair of cartilage defects and prevention/reversal of osteoarthritis. Examples of heteromeric complexes useful for inducing bone formation, preventing bone loss, increasing bone mineralization, preventing the demineralization of bone, and/or increasing bone density as described above are ActRIIB-Fc:ALK3-Fc and ActRIIB-Fc: ALK4-Fc.

Rosen et al. (ed) Primer on the Metabolic Bone Diseases and Disorders of Mineral Metabolism, $7^{th}$ ed. American Society for Bone and Mineral Research, Washington D.C. (incorporated herein by reference) provides an extensive discussion of bone disorders that may be subject to treatment with a TGF-beta superfamily heteromultimer complex or with combinations of TGF-beta superfamily heteromultimer complexes. A partial listing is provided herein. Methods and compositions of the invention can be applied to conditions characterized by or causing bone loss, such as osteoporosis (including secondary osteoporosis), hyperparathyroidism, chronic kidney disease mineral bone disorder, sex hormone deprivation or ablation (e.g. androgen and/or estrogen), glucocorticoid treatment, rheumatoid arthritis, severe burns, hyperparathyroidism, hypercalcemia, hypocalcemia, hypophosphatemia, osteomalacia (including tumor-induced osteomalacia), hyperphosphatemia, vitamin D deficiency, hyperparathyroidism (including familial hyperparathyroidism) and pseudohypoparathyroidism, tumor metastases to bone, bone loss as a consequence of a tumor or chemotherapy, tumors of the bone and bone marrow (e.g., multiple myeloma), ischemic bone disorders, periodontal disease and oral bone loss, Cushing's disease, Paget's disease, thyrotoxicosis, chronic diarrheal state or malabsorption, renal tubular acidosis, or anorexia nervosa. Methods and compositions of the invention may also be applied to conditions characterized by a failure of bone formation or healing, including non-union fractures, fractures that are otherwise slow to heal, fetal and neonatal bone dysplasias (e.g., hypocalcemia, hypercalcemia, calcium receptor defects and vitamin D deficiency), osteonecrosis (including osteonecrosis of the jaw) and osteogenesis imperfecta. Additionally, the anabolic effects will cause such antagonists to diminish bone pain associated with bone damage or erosion. As a consequence of the anti-resorptive effects, such antagonists may be useful to treat disorders of abnormal bone formation, such as osteoblastic tumor metastases (e.g., associated with primary prostate or breast cancer), osteogenic osteosarcoma, osteopetrosis, progressive diaphyseal dysplasia, endosteal hyperostosis, osteopoikilosis, and melorheostosis. Other disorders that may be treated include fibrous dysplasia and chondrodysplasias.

In another specific embodiment, the disclosure provides a therapeutic method and composition for repairing fractures and other conditions related to cartilage and/or bone defects or periodontal diseases. The invention further provides therapeutic methods and compositions for wound healing and tissue repair. The types of wounds include, but are not limited to, burns, incisions and ulcers. See, e.g., PCT Publication No. WO 84/01106. Such compositions comprise a therapeutically effective amount of at least one of the TGF-beta superfamily heteromultimer complexes of the disclosure in admixture with a pharmaceutically acceptable vehicle, carrier, or matrix.

In some embodiments, a TGF-beta superfamily heteromultimer complex, or combinations of TGF-beta superfamily heteromultimer complexes, of the disclosure can be applied to conditions causing bone loss such as osteoporosis, hyperparathyroidism, Cushing's disease, thyrotoxicosis, chronic diarrheal state or malabsorption, renal tubular acidosis, or anorexia nervosa. It is commonly appreciated that being female, having a low body weight, and leading a sedentary lifestyle are risk factors for osteoporosis (loss of bone mineral density, leading to fracture risk). However, osteoporosis can also result from the long-term use of certain medications. Osteoporosis resulting from drugs or another medical condition is known as secondary osteoporosis. In Cushing's disease, the excess amount of cortisol produced by the body results in osteoporosis and fractures. The most common medications associated with secondary osteoporosis are the corticosteroids, a class of drugs that act like cortisol, a hormone produced naturally by the adrenal glands. Although adequate levels of thyroid hormones are needed for the development of the skeleton, excess thyroid hormone can decrease bone mass over time. Antacids that contain aluminum can lead to bone loss when taken in high doses by people with kidney problems, particularly those undergoing dialysis. Other medications that can cause secondary osteoporosis include phenytoin (Dilantin) and barbiturates that are used to prevent seizures; methotrexate (Rheumatrex, Immunex, Folex PFS), a drug for some forms of arthritis, cancer, and immune disorders; cyclosporine (Sandimmune, Neoral), a drug used to treat some autoimmune diseases and to suppress the immune system in organ transplant patients; luteinizing hormone-releasing hormone agonists (Lupron, Zoladex), used to treat prostate cancer and endometriosis; heparin (Calciparine, Liquaemin), an anti-clotting medication; and cholestyramine (Questran) and colestipol (Colestid), used to treat high cholesterol. Bone loss resulting from cancer therapy is widely recognized and termed cancer therapy-induced bone loss (CTIBL). Bone metastases can create cavities in the bone that may be corrected by treatment with a TGF-beta superfamily heteromultimer complex. Bone loss can also be caused by gum disease, a chronic infection in which bacteria located in gum recesses produce toxins and harmful enzymes.

In a further embodiment, the present disclosure provides methods and therapeutic agents for treating diseases or disorders associated with abnormal or unwanted bone growth. For example, patients with the congenital disorder fibrodysplasia ossificans progressiva (FOP) are afflicted by progressive ectopic bone growth in soft tissues spontaneously or in response to tissue trauma, with a major impact on quality of life. Additionally, abnormal bone growth can occur after hip replacement surgery and thus ruin the surgical outcome. This is a more common example of pathological bone growth and a situation in which the subject methods and compositions may be therapeutically useful. The same methods and compositions may also be useful for treating other forms of abnormal bone growth (e.g., pathological growth of bone following trauma, burns or spinal cord injury), and for treating or preventing the undesirable conditions associated with the abnormal bone growth seen in connection with metastatic prostate cancer or osteosarcoma.

In certain embodiments, a TGF-beta superfamily heteromultimer complex, or combinations of TGF-beta superfamily heteromultimer complexes, of the disclosure may be used to promote bone formation in patients with cancer. Patients having certain tumors (e.g. prostate, breast, multiple myeloma or any tumor causing hyperparathyroidism) are at high risk for bone loss due to tumor-induced bone loss, bone metastases, and therapeutic agents. Such patients may be treated with a TGF-beta superfamily heteromultimer complex, or a combination of complexes, even in the absence of evidence of bone loss or bone metastases. Patients may also be monitored for evidence of bone loss or bone metastases, and may be treated with a TGF-beta superfamily heteromultimer complex in the event that indicators suggest an increased risk. Generally, DEXA scans are employed to assess changes in bone density, while indicators of bone remodeling may be used to assess the likelihood of bone metastases. Serum markers may be monitored. Bone specific alkaline phosphatase (BSAP) is an enzyme that is present in osteoblasts. Blood levels of BSAP are increased in patients with bone metastasis and other conditions that result in increased bone remodeling. Osteocalcin and procollagen peptides are also associated with bone formation and bone metastases. Increases in BSAP have been detected in patients with bone metastasis caused by prostate cancer, and to a lesser degree, in bone metastases from breast cancer. BMP7 levels are high in prostate cancer that has metastasized to bone, but not in bone metastases due to bladder, skin, liver, or lung cancer. Type I carboxy-terminal telopeptide (ICTP) is a crosslink found in collagen that is formed during to the resorption of bone. Since bone is constantly being broken down and reformed, ICTP will be found throughout the body. However, at the site of bone metastasis, the level will be significantly higher than in an area of normal bone. ICTP has been found in high levels in bone metastasis due to prostate, lung, and breast cancer. Another collagen crosslink, Type I N-terminal telopeptide (NTx), is produced along with ICTP during bone turnover. The amount of NTx is increased in bone metastasis caused by many different types of cancer including lung, prostate, and breast cancer. Also, the levels of NTx increase with the progression of the bone metastasis. Therefore, this marker can be used to both detect metastasis as well as measure the extent of the disease. Other markers of resorption include pyridinoline and deoxypyridinoline. Any increase in resorption markers or markers of bone metastases indicate the need for therapy with a TGF-beta superfamily heteromultimer complex, or combinations of TGF-beta superfamily heteromultimer complexes, in a patient.

A TGF-beta superfamily heteromultimer complex, or combinations of TGF-beta superfamily heteromultimer complexes, of the disclosure may be conjointly administered with other bone-active pharmaceutical agents. Conjoint administration may be accomplished by administration of a single co-formulation, by simultaneous administration, or by administration at separate times. TGF-beta superfamily heteromultimer complexes may be particularly advantageous if administered with other bone-active agents. A patient may benefit from conjointly receiving a TGF-beta superfamily heteromultimer complex and taking calcium supplements, vitamin D, appropriate exercise and/or, in some cases, other medication. Examples of other medications include, bisphosphonates (alendronate, ibandronate and risedronate), calcitonin, estrogens, parathyroid hormone and raloxifene. The bisphosphonates (alendronate, ibandronate and risedronate), calcitonin, estrogens and raloxifene affect the bone remodeling cycle and are classified as anti-resorptive medications. Bone remodeling consists of two distinct stages: bone resorption and bone formation. Anti-resorptive medications slow or stop the bone-resorbing portion of the bone-remodeling cycle but do not slow the bone-forming portion of the cycle. As a result, new formation continues at a greater rate than bone resorption, and bone density may increase over time. Teriparatide, a form of parathyroid hormone, increases the rate of bone formation in the bone remodeling cycle. Alendronate is approved for both the prevention (5 mg per day or 35 mg once a week) and treatment (10 mg per day or 70 mg once a week) of postmenopausal osteoporosis. Alendronate reduces bone loss, increases bone density and reduces the risk of spine, wrist and hip fractures. Alendronate also is approved for treatment of glucocorticoid-induced osteoporosis in men and women as a result of long-term use of these medications (i.e., prednisone and cortisone) and for the treatment of osteoporosis in men. Alendronate plus vitamin D is approved for the treatment of osteoporosis in postmenopausal women (70 mg once a week plus vitamin D), and for treatment to improve bone mass in men with osteoporosis. Ibandronate is approved for the prevention and treatment of postmenopausal osteoporosis. Taken as a once-a-month pill (150 mg), ibandronate should be taken on the same day each month. Ibandronate reduces bone loss, increases bone density and reduces the risk of spine fractures. Risedronate is approved for the prevention and treatment of postmenopausal osteoporosis. Taken daily (5 mg dose) or weekly (35 mg dose or 35 mg dose with calcium), risedronate slows bone loss, increases bone density and reduces the risk of spine and non-spine fractures. Risedronate also is approved for use by men and women to prevent and/or treat glucocorticoid-induced osteoporosis that results from long-term use of these medications (i.e., prednisone or cortisone). Calcitonin is a naturally occurring hormone involved in calcium regulation and bone metabolism. In women who are more than 5 years beyond menopause, calcitonin slows bone loss, increases spinal bone density, and may relieve the pain associated with bone fractures. Calcitonin reduces the risk of spinal fractures. Calcitonin is available as an injection (50-100 IU daily) or nasal spray (200 IU daily).

A patient may also benefit from conjointly receiving a TGF-beta superfamily heteromultimer complex, or combinations of TGF-beta superfamily heteromultimer complexes, and additional bone-active medications. Estrogen therapy (ET)/hormone therapy (HT) is approved for the prevention of osteoporosis. ET has been shown to reduce bone loss, increase bone density in both the spine and hip, and reduce the risk of hip and spinal fractures in postmenopausal women. ET is administered most commonly in the form of a pill or skin patch that delivers a low dose of approximately 0.3 mg daily or a standard dose of approximately 0.625 mg daily and is effective even when started after age 70. When estrogen is taken alone, it can increase a woman's risk of developing cancer of the uterine lining (endometrial cancer). To eliminate this risk, healthcare providers prescribe the hormone progestin in combination with estrogen (hormone replacement therapy or HT) for those women who have an intact uterus. ET/HT relieves menopause symptoms and has been shown to have a beneficial effect on bone health. Side effects may include vaginal bleeding, breast tenderness, mood disturbances and gallbladder disease. Raloxifene, 60 mg a day, is approved for the prevention and treatment of postmenopausal osteoporosis. It is from a class of drugs called Selective Estrogen Receptor Modulators (SERMs) that have been developed to provide the beneficial effects of estrogens without their potential disadvantages. Raloxifene increases bone mass and reduces the risk of spine fractures. Data are not yet available to demonstrate that raloxifene can reduce the risk of hip and other non-spine fractures. Teriparatide, a form of parathyroid hormone, is approved for the treatment of osteoporosis in postmenopausal women and men who are at high risk for a fracture. This medication stimulates new bone formation and significantly increases bone mineral density. In postmenopausal women, fracture reduction was noted in the spine, hip, foot, ribs and wrist. In men, fracture reduction was noted in the spine, but there were insufficient data to evaluate fracture reduction at other sites. Teriparatide is self-administered as a daily injection for up to 24 months.

In other embodiments, a TGF-beta superfamily heteromultimer complex, or combinations of TGF-beta superfamily heteromultimer complexes can be used for regulating body fat content in an animal and for treating or preventing conditions related thereto, and particularly, health-compromising conditions related thereto. According to the present invention, to regulate (control) body weight can refer to reducing or increasing body weight, reducing or increasing the rate of weight gain, or increasing or reducing the rate of weight loss, and also includes actively maintaining, or not significantly changing body weight (e.g., against external or internal influences which may otherwise increase or decrease body weight). One embodiment of the present disclosure relates to regulating body weight by administering to an animal (e.g., a human) in need thereof a TGF-beta superfamily heteromultimer complex, or combinations of TGF-beta superfamily heteromultimer complexese, of the disclosure.

In some embodiments, a TGF-beta superfamily heteromultimer complex, or combinations of TGF-beta superfamily heteromultimer complexes, of the present disclosure can be used for reducing body weight and/or reducing weight gain in an animal, and more particularly, for treating or ameliorating obesity in patients at risk for or suffering from obesity. In another specific embodiment, the present invention is directed to methods and compounds for treating an animal that is unable to gain or retain weight (e.g., an animal with a wasting syndrome). Such methods are effective to increase body weight and/or mass, or to reduce weight and/or mass loss, or to improve conditions associated with or caused by undesirably low (e.g., unhealthy) body weight and/or mass. In addition, disorders of high cholesterol (e.g., hypercholesterolemia or dislipidemia) may be treated with a TGF-beta superfamily heteromultimer complex, or combinations of TGF-beta superfamily heteromultimer complexes, of the disclosure.

In certain aspects, a TGF-beta superfamily heteromultimer complex, or a combination of TGF-beta superfamily heteromultimer complexes, of the present disclosure can be used to increase red blood cell levels, treat or prevent an anemia, and/or treat or prevent ineffective erythropoiesis in a subject in need thereof. In certain aspects, a TGF-beta superfamily heteromultimer complex, or a combination of TGF-beta superfamily heteromultimer complexes, of the present disclosure may be used in combination with conventional therapeutic approaches for increasing red blood cell levels, particularly those used to treat anemias of multifactorial origin. Conventional therapeutic approaches for increasing red blood cell levels include, for example, red blood cell transfusion, administration of one or more EPO receptor activators, hematopoietic stem cell transplantation, immunosuppressive biologics and drugs (e.g., corticosteroids). In certain embodiments, a TGF-beta superfamily heteromultimer complex, or a combination of TGF-beta superfamily heteromultimer complexes, of the present disclosure can be used to treat or prevent ineffective erythropoiesis and/or the disorders associated with ineffective erythropoiesis in a subject in need thereof. In certain aspects, a TGF-beta superfamily heteromultimer complex, or a combination of TGF-beta superfamily heteromultimer complexes, of the present disclosure can be used in combination with conventional therapeutic approaches for treating or preventing an anemia or ineffective erythropoiesis disorder, particularly those used to treat anemias of multifactorial origin.

In general, treatment or prevention of a disease or condition as described in the present disclosure is achieved by administering a TGF-beta superfamily heteromultimer complex, or a combination of TGF-beta superfamily heteromultimer complexes, of the present disclosure in an "effective amount". An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

In certain embodiments, a TGF-beta superfamily heteromultimer complex, or a combination of TGF-beta superfamily heteromultimer complexes, optionally combined with an EPO receptor activator, may be used to increase red blood cell, hemoglobin, or reticulocyte levels in healthy individuals and selected patient populations. Examples of appropriate patient populations include those with undesirably low red blood cell or hemoglobin levels, such as patients having an anemia, and those that are at risk for developing undesirably low red blood cell or hemoglobin levels, such as those patients who are about to undergo major surgery or other procedures that may result in substantial blood loss. In one embodiment, a patient with adequate red blood cell levels is treated with a TGF-beta superfamily heteromultimer complex, or a combination of TGF-beta superfamily heteromultimer complexes, to increase red blood cell levels, and then blood is drawn and stored for later use in transfusions.

One or more TGF-beta superfamily heteromultimer complexes of the disclosure, optionally combined with an EPO receptor activator, may be used to increase red blood cell levels, hemoglobin levels, and/or hematocrit levels in a patient having an anemia. When observing hemoglobin and/or hematocrit levels in humans, a level of less than normal for the appropriate age and gender category may be indicative of anemia, although individual variations are taken into account. For example, a hemoglobin level from 10-12.5 g/dl, and typically about 11.0 g/dl is considered to be within the normal range in health adults, although, in terms of therapy, a lower target level may cause fewer cardiovascular side effects [see, e.g., Jacobs et al. (2000) Nephrol Dial Transplant 15, 15-19]. Alternatively, hematocrit levels (percentage of the volume of a blood sample occupied by the cells) can be used as a measure for anemia. Hematocrit levels for healthy individuals range from about 41-51% for adult males and from 35-45% for adult females. In certain embodiments, a patient may be treated with a dosing regimen intended to restore the patient to a target level of red blood cells, hemoglobin, and/or hematocrit. As hemoglobin and hematocrit levels vary from person to person, optimally, the target hemoglobin and/or hematocrit level can be individualized for each patient.

Anemia is frequently observed in patients having a tissue injury, an infection, and/or a chronic disease, particularly cancer. In some subjects, anemia is distinguished by low erythropoietin levels and/or an inadequate response to erythropoietin in the bone marrow [see, e.g., Adamson (2008) Harrison's Principles of Internal Medicine, 17th ed.; McGraw Hill, New York, pp 628-634]. Potential causes of anemia include, for example, blood loss, nutritional deficits (e.g. reduced dietary intake of protein), medication reaction, various problems associated with the bone marrow, and many diseases. More particularly, anemia has been associated with a variety of disorders and conditions that include, for example, bone marrow transplantation; solid tumors (e.g., breast cancer, lung cancer, and colon cancer); tumors of the lymphatic system (e.g., chronic lymphocyte leukemia, non-Hodgkins lymphoma, and Hodgkins lymphoma); tumors of the hematopoietic system (e.g., leukemia, a myelodysplastic syndrome and multiple myeloma); radiation therapy; chemotherapy (e.g., platinum containing regimens); inflammatory and autoimmune diseases, including, but not limited to, rheumatoid arthritis, other inflammatory arthritides, systemic lupus erythematosis (SLE), acute or chronic skin diseases (e.g., psoriasis), inflammatory bowel disease (e.g., Crohn's disease and ulcerative colitis); acute or chronic renal disease or failure, including idiopathic or congenital conditions; acute or chronic liver disease; acute or chronic bleeding; situations where transfusion of red blood cells is not possible due to patient allo- or autoantibodies and/or for religious reasons (e.g., some Jehovah's Witnesses); infections (e.g., malaria and osteomyelitis); hemoglobinopathies including, for example, sickle cell disease (anemia), thalassemias; drug use or abuse (e.g., alcohol misuse); pediatric patients with anemia from any cause to avoid transfusion; and elderly patients or patients with underlying cardiopulmonary disease with anemia who cannot receive transfusions due to concerns about circulatory overload [see, e.g., Adamson (2008) Harrison's Principles of Internal Medicine, 17th ed.; McGraw Hill, New York, pp 628-634]. In some embodiments, one or more TGF-beta superfamily heteromultimer complexes of the disclosure could be used to treat or prevent anemia associated with one or more of the disorders or conditions disclosed herein.

Many factors can contribute to cancer-related anemia. Some are associated with the disease process itself and the generation of inflammatory cytokines such as interleukin-1, interferon-gamma, and tumor necrosis factor [Bron et al. (2001) Semin Oncol 28(Suppl 8):1-6]. Among its effects, inflammation induces the key iron-regulatory peptide hepcidin, thereby inhibiting iron export from macrophages and generally limiting iron availability for erythropoiesis [see, e.g., Ganz (2007) J Am Soc Nephrol 18:394-400]. Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality. In some embodiments, one or more TGF-beta superfamily heteromultimer complexes of the disclosure, optionally combined with an EPO receptor activator, could be used to treat a cancer-related anemia.

A hypoproliferative anemia can result from primary dysfunction or failure of the bone marrow. Hypoproliferative anemias include: anemia of chronic disease, anemia of kidney disease, anemia associated with hypometabolic states, and anemia associated with cancer. In each of these types, endogenous erythropoietin levels are inappropriately low for the degree of anemia observed. Other hypoproliferative anemias include: early-stage iron-deficient anemia, and anemia caused by damage to the bone marrow. In these types, endogenous erythropoietin levels are appropriately elevated for the degree of anemia observed. Prominent examples would be myelosuppression caused by cancer and/or chemotherapeutic drugs or cancer radiation therapy. A broad review of clinical trials found that mild anemia can occur in 100% of patients after chemotherapy, while more severe anemia can occur in up to 80% of such patients [see, e.g., Groopman et al. (1999) J Natl Cancer Inst 91:1616-1634]. Myelosuppressive drugs include, for example: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibiotics such as anthracyclines (e.g., doxorubicin); 4) kinase inhibitors (e.g., gefitinib); 5) mitotic inhibitors such as taxanes (e.g., paclitaxel) and vinca alkaloids (e.g., vinorelbine); 6) monoclonal antibodies (e.g., rituximab); and 7) topoisomerase inhibitors (e.g., topotecan and etoposide). In addition, conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. In some embodiments, one or more TGF-beta superfamily heteromultimer complexes of the disclosure, optionally combined with an EPO receptor activator, could be used to treat a hyperproliferative anemia.

Chronic kidney disease is sometimes associated with hypoproliferative anemia, and the degree of the anemia varies in severity with the level of renal impairment. Such anemia is primarily due to inadequate production of erythropoietin and reduced survival of red blood cells. Chronic kidney disease usually proceeds gradually over a period of years or decades to end-stage (Stage 5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function [see, e.g., Levin et al. (1999) Am J Kidney Dis 27:347-354; Nissenson (1992) Am J Kidney Dis 20(Suppl 1):21-24; Revicki et al. (1995) Am J Kidney Dis 25:548-554; Gafter et al., (1994) Kidney Int 45:224-231]. In some embodiments, one or more TGF-beta superfamily heteromultimer complexes of the disclosure, optionally combined with an EPO receptor activator, could be used to treat anemia associated with acute or chronic renal disease or failure.

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of RBCs along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. In some embodiments, one or more TGF-beta superfamily heteromultimer complexes of the disclosure, optionally combined with an EPO receptor activator, could be used to treat anemia resulting from acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs [see, e.g., Adamson (2008) Harrison's Principles of Internal Medicine, 17th ed.; McGraw Hill, New York, pp 628-634]. Appropriate therapy for iron-deficiency anemia depends on its cause and severity, with oral iron preparations, parenteral iron formulations, and RBC transfusion as major conventional options. In some embodiments, one or more TGF-beta superfamily heteromultimer complexes of the disclosure, optionally combined with an EPO receptor activator, could be used to treat a chronic iron-deficiency.

Myelodysplastic syndrome (MDS) is a diverse collection of hematological conditions characterized by ineffective production of myeloid blood cells and risk of transformation to acute myelogenous leukemia. In MDS patients, blood stem cells do not mature into healthy red blood cells, white blood cells, or platelets. MDS disorders include, for example, refractory anemia, refractory anemia with ringed sideroblasts, refractory anemia with excess blasts, refractory anemia with excess blasts in transformation, refractory cytopenia with multilineage dysplasia, and myelodysplastic syndrome associated with an isolated 5q chromosome abnormality. As these disorders manifest as irreversible defects in both quantity and quality of hematopoietic cells, most MDS patients are afflicted with chronic anemia. Therefore, MDS patients eventually require blood transfusions and/or treatment with growth factors (e.g., erythropoietin or G-CSF) to increase red blood cell levels. However, many MDS patients develop side-effects due to frequency of such therapies. For example, patients who receive frequent red blood cell transfusion can exhibit tissue and organ damage from the buildup of extra iron. Accordingly, one or more TGF-beta superfamily heteromultimer complexes of the disclosure, may be used to treat patients having MDS. In certain embodiments, patients suffering from MDS may be treated using one or more TGF-beta superfamily heteromultimer complexes of the disclosure, optionally in combination with an EPO receptor activator. In other embodiments, patients suffering from MDS may be treated using a combination of one or more TGF-beta superfamily heteromultimer complexes of the disclosure and one or more additional therapeutic agents for treating MDS including, for example, thalidomide, lenalidomide, azacitadine, decitabine, erythropoietins, deferoxamine, antithymocyte globulin, and filgrastrim (G-CSF).

Originally distinguished from aplastic anemia, hemorrhage, or peripheral hemolysis on the basis of ferrokinetic studies [see, e.g., Ricketts et al. (1978) Clin Nucl Med 3:159-164], ineffective erythropoiesis describes a diverse group of anemias in which production of mature RBCs is less than would be expected given the number of erythroid precursors (erythroblasts) present in the bone marrow [Tanno et al. (2010) Adv Hematol 2010:358283]. In such anemias, tissue hypoxia persists despite elevated erythropoietin levels due to ineffective production of mature RBCs. A vicious cycle eventually develops in which elevated erythropoietin levels drive massive expansion of erythroblasts, potentially leading to splenomegaly (spleen enlargement) due to extramedullary erythropoiesis [see, e.g., Aizawa et al. (2003) Am J Hematol 74:68-72], erythroblast-induced bone pathology [see, e.g., Di Matteo et al. (2008) J Biol Regul Homeost Agents 22:211-216], and tissue iron overload, even in the absence of therapeutic RBC transfusions [see, e.g., Pippard et al. (1979) Lancet 2:819-821]. Thus, by boosting erythropoietic effectiveness, one or more TGF-beta superfamily heteromultimer complexes of the present disclosure may break the aforementioned cycle and thus alleviate not only the underlying anemia but also the associated complications of elevated erythropoietin levels, splenomegaly, bone pathology, and tissue iron overload. In some embodiments, one or more TGF-beta superfamily heteromultimer complexes of the present disclosure can be used to treat or prevent ineffective erythropoiesis, including anemia and elevated EPO levels as well as complications such as splenomegaly, erythroblast-induced bone pathology, iron overload, and their attendant pathologies. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudotumors [see, e.g., Musallam et al. (2012) Cold Spring Harb Perspect Med 2:a013482]. With erythroblast-induced bone pathology, attendant pathologies include low bone mineral density, osteoporosis, and bone pain [see, e.g., Haidar et al. (2011) Bone 48:425-432]. With iron overload, attendant pathologies include hepcidin suppression and hyperabsorption of dietary iron [see, e.g., Musallam et al. (2012) Blood Rev 26(Suppl 1):S16-S19], multiple endocrinopathies and liver fibrosis/cirrhosis [see, e.g., Galanello et al. (2010) Orphanet J Rare Dis 5:11], and iron-overload cardiomyopathy [Lekawanvijit et al., 2009, Can J Cardiol 25:213-218].

The most common causes of ineffective erythropoiesis are the thalassemia syndromes, hereditary hemoglobinopathies in which imbalances in the production of intact alpha- and beta-hemoglobin chains lead to increased apoptosis during erythroblast maturation [see, e.g., Schrier (2002) Curr Opin Hematol 9:123-126]. Thalassemias are collectively among the most frequent genetic disorders worldwide, with changing epidemiologic patterns predicted to contribute to a growing public health problem in both the U.S. and globally [Vichinsky (2005) Ann NY Acad Sci 1054:18-24]. Thalassemia syndromes are named according to their severity. Thus, α-thalassemias include α-thalassemia minor (also known as α-thalassemia trait; two affected α-globin genes), hemoglobin H disease (three affected α-globin genes), and α-thalassemia major (also known as hydrops fetalis; four affected α-globin genes). β-Thalassemias include β-thalassemia minor (also known as β-thalassemia trait; one affected β-globin gene), β-thalassemia intermedia (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia [see, e.g., Rund et al. (2005) N Engl J Med 353:1135-1146]. In certain embodiments, one or more TGF-beta superfamily heteromultimer complexes of the disclosure, optionally combined with an EPO receptor activator, can be used to treat or prevent a thalassemia syndrome.

In some embodiments, one or more TGF-beta superfamily heteromultimer complexes of the disclosure, optionally combined with an EPO receptor activator, can be used for treating disorders of ineffective erythropoiesis besides thalassemia syndromes. Such disorders include siderblastic anemia (inherited or acquired); dyserythropoietic anemia (types I and II); sickle cell anemia; hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anemia, refractory megaloblastic anemia, or erythroleukemia); myelophthisic anemias including, for example, myelofibrosis (myeloid metaplasia) and myelophthisis; congenital erythropoietic porphyria; and lead poisoning.

In certain embodiments, one or more TGF-beta superfamily heteromultimer complexes of the disclosure may be used in combination with supportive therapies for ineffective erythropoiesis. Such therapies include transfusion with either red blood cells or whole blood to treat anemia. In chronic or hereditary anemias, normal mechanisms for iron homeostasis are overwhelmed by repeated transfusions, eventually leading to toxic and potentially fatal accumulation of iron in vital tissues such as heart, liver, and endocrine glands. Thus, supportive therapies for patients chronically afflicted with ineffective erythropoiesis also include treatment with one or more iron-chelating molecules to promote iron excretion in the urine and/or stool and thereby prevent, or reverse, tissue iron overload [see, e.g., Hershko (2006) Haematologica 91:1307-1312; Cao et al. (2011), Pediatr Rep 3(2):e17]. Effective iron-chelating agents should be able to selectively bind and neutralize ferric iron, the oxidized form of non-transferrin bound iron which likely accounts for most iron toxicity through catalytic production of hydroxyl radicals and oxidation products [see, e.g., Esposito et al. (2003) Blood 102:2670-2677]. These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) [Kalinowski et al. (2005) Pharmacol Rev 57:547-583]. In general, effective iron-chelating agents also are relatively low molecular weight (e.g., less than 700 daltons), with solubility in both water and lipids to enable access to affected tissues. Specific examples of iron-chelating molecules include deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone [Cao et al. (2011) Pediatr Rep 3(2):e17; Galanello et al. (2010) Ann NY Acad Sci 1202:79-86].

As used herein, "in combination with" or "conjoint administration" refers to any form of administration such that the second therapy is still effective in the body (e.g., the two compounds are simultaneously effective in the patient, which may include synergistic effects of the two compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more TGF-beta superfamily heteromultimer complexes of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired therapeutic effect to be achieved.

In certain embodiments, one or more TGF-beta superfamily heteromultimer complexes of the disclosure may be used in combination with hepcidin or a hepcidin agonist for ineffective erythropoiesis. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. Broadly speaking, hepcidin reduces availability of extracellular iron, so hepcidin agonists may be beneficial in the treatment of ineffective erythropoiesis [see, e.g., Nemeth (2010) Adv Hematol 2010:750643]. This view is supported by beneficial effects of increased hepcidin expression in a mouse model of β-thalassemia [Gardenghi et al. (2010) J Clin Invest 120:4466-4477].

One or more TGF-beta superfamily heteromultimer complexes of the disclosure, optionally combined with an EPO receptor activator, would also be appropriate for treating anemias of disordered RBC maturation, which are characterized in part by undersized (microcytic), oversized (macrocytic), misshapen, or abnormally colored (hypochromic) RBCs.

In certain embodiments, the present disclosure provides methods of treating or preventing anemia in an individual in need thereof by administering to the individual a therapeutically effective amount of one or more TGF-beta superfamily heteromultimer complexes of the disclosure and a EPO receptor activator. In certain embodiments, one or more TGF-beta superfamily heteromultimer complexes of the disclosure may be used in combination with EPO receptor activators to reduce the required dose of these activators in patients that are susceptible to adverse effects of EPO. These methods may be used for therapeutic and prophylactic treatments of a patient.

One or more TGF-beta superfamily heteromultimer complexes of the disclosure may be used in combination with EPO receptor activators to achieve an increase in red blood cells, particularly at lower dose ranges of EPO receptor activators. This may be beneficial in reducing the known off-target effects and risks associated with high doses of EPO receptor activators. The primary adverse effects of EPO include, for example, an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which relate to hypertension, are headaches, influenza-like syndrome, obstruction of shunts, myocardial infarctions and cerebral convulsions due to thrombosis, hypertensive encephalopathy, and red cell blood cell aplasia. See, e.g., Singibarti (1994) J. Clin Investig 72(suppl 6), S36-S43; Horl et al. (2000) Nephrol Dial Transplant 15(suppl 4), 51-56; Delanty et al. (1997) Neurology 49, 686-689; and Bunn (2002) N Engl J Med 346(7), 522-523).

Provided that TGF-beta superfamily heteromultimer complexes of the present disclosure act by a different mechanism than EPO, these antagonists may be useful for increasing red blood cell and hemoglobin levels in patients that do not respond well to EPO. For example, a TGF-beta superfamily heteromultimer complex of the present disclosure may be beneficial for a patient in which administration of a normal-to-increased dose of EPO (>300 IU/kg/week) does not result in the increase of hemoglobin level up to the target level. Patients with an inadequate EPO response are found in all types of anemia, but higher numbers of non-responders have been observed particularly frequently in patients with cancers and patients with end-stage renal disease. An inadequate response to EPO can be either constitutive (observed upon the first treatment with EPO) or acquired (observed upon repeated treatment with EPO).

In certain embodiments, the present disclosure provides methods for managing a patient that has been treated with, or is a candidate to be treated with, one or more TGF-beta superfamily heteromultimer complexes of the disclosure by measuring one or more hematologic parameters in the patient. The hematologic parameters may be used to evaluate appropriate dosing for a patient who is a candidate to be treated with the antagonist of the present disclosure, to monitor the hematologic parameters during treatment, to evaluate whether to adjust the dosage during treatment with one or more antagonist of the disclosure, and/or to evaluate an appropriate maintenance dose of one or more antagonists of the disclosure. If one or more of the hematologic parameters are outside the normal level, dosing with one or more TGF-beta superfamily heteromultimer complexes of the disclosure may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art-recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range or on the high side of normal in a patient who is a candidate to be treated with one or more TGF-beta superfamily heteromultimer complexes of the disclosure, then onset of administration of the one or more TGF-beta superfamily heteromultimer complexes of the disclosure may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the one or more TGF-beta superfamily heteromultimer complexes of the disclosure may be delayed until the levels have returned to a normal or acceptable level.

In certain embodiments, if one or more hematologic parameters are outside the normal range or on the high side of normal in a patient who is a candidate to be treated with one or more TGF-beta superfamily heteromultimer complexes of the disclosure, then the onset of administration may not be delayed. However, the dosage amount or frequency of dosing of the one or more TGF-beta superfamily heteromultimer complexes of the disclosure may be set at an amount that would reduce the risk of an unacceptable increase in the hematologic parameters arising upon administration of the one or more TGF-beta superfamily heteromultimer complexes of the disclosure. Alternatively, a therapeutic regimen may be developed for the patient that combines one or more TGF-beta superfamily heteromultimer complexes of the disclosure with a therapeutic agent that addresses the undesirable level of the hematologic parameter. For example, if the patient has elevated blood pressure, then a therapeutic regimen involving administration of one or more TGF-beta superfamily heteromultimer complexes of the disclosure and a blood pressure-lowering agent may be designed. For a patient having lower than desired iron stores, a therapeutic regimen of one or more TGF-beta superfamily heteromultimer complexes of the disclosure and iron supplementation may be developed.

In one embodiment, baseline parameter(s) for one or more hematologic parameters may be established for a patient who is a candidate to be treated with one or more TGF-beta superfamily heteromultimer complexes of the disclosure and an appropriate dosing regimen established for that patient based on the baseline value(s). Alternatively, established baseline parameters based on a patient's medical history could be used to inform an appropriate dosing regimen for a patient. For example, if a healthy patient has an established baseline blood pressure reading that is above the defined normal range it may not be necessary to bring the patient's blood pressure into the range that is considered normal for the general population prior to treatment with the one or more TGF-beta superfamily heteromultimer complexes of the disclosure. A patient's baseline values for one or more hematologic parameters prior to treatment with one or more TGF-beta superfamily heteromultimer complexes of the disclosure may also be used as the relevant comparative values for monitoring any changes to the hematologic parameters during treatment with the one or more TGF-beta superfamily heteromultimer complexes of the disclosure.

In certain embodiments, one or more hematologic parameters are measured in patients who are being treated with a one or more TGF-beta superfamily heteromultimer complexes of the disclosure. The hematologic parameters may be used to monitor the patient during treatment and permit adjustment or termination of the dosing with the one or more TGF-beta superfamily heteromultimer complexes of the disclosure or additional dosing with another therapeutic agent. For example, if administration of one or more TGF-beta superfamily heteromultimer complexes of the disclosure of the disclosure results in an increase in blood pressure, red blood cell level, or hemoglobin level, or a reduction in iron stores, then the dose of the one or more TGF-beta superfamily heteromultimer complexes of the disclosure may be reduced in amount or frequency in order to decrease the effects of the one or more TGF-beta superfamily heteromultimer complexes of the disclosure on the one or more hematologic parameters. If administration of one or more TGF-beta superfamily heteromultimer complexes of the disclosure results in a change in one or more hematologic parameters that is adverse to the patient, then the dosing of the one or more TGF-beta superfamily heteromultimer complexes of the disclosure may be terminated either temporarily, until the hematologic parameter(s) return to an acceptable level, or permanently. Similarly, if one or more hematologic parameters are not brought within an acceptable range after reducing the dose or frequency of administration of the one or more TGF-beta superfamily heteromultimer complexes of the disclosure, then the dosing may be terminated. As an alternative, or in addition to, reducing or terminating the dosing with the one or more TGF-beta superfamily heteromultimer complexes of the disclosure, the patient may be dosed with an additional therapeutic agent that addresses the undesirable level in the hematologic parameter(s), such as, for example, a blood pressure-lowering agent or an iron supplement. For example, if a patient being treated with one or more TGF-beta superfamily heteromultimer complexes of the disclosure has elevated blood pressure, then dosing with the one or more TGF-beta superfamily heteromultimer complexes of the disclosure may continue at the same level and a blood pressure-lowering agent is added to the treatment regimen, dosing with the one or more TGF-beta superfamily heteromultimer complexes of the disclosure may be reduced (e.g., in amount and/or frequency) and a blood pressure-lowering agent is added to the treatment regimen, or dosing with the one or more TGF-beta superfamily heteromultimer complexes of the disclosure may be terminated and the patient may be treated with a blood pressure-lowering agent.

6. Pharmaceutical Compositions

In certain aspects, TGF-beta superfamily heteromultimer complexes of the present disclosure can be administered alone or as a component of a pharmaceutical formulation (also referred to as a therapeutic composition or pharmaceutical composition). A pharmaceutical formation refers to a preparation which is in such form as to permit the biological activity of an active ingredient (e.g., an agent of the present disclosure) contained therein to be effective and which contains no additional components which are unacceptably toxic to a subject to which the formulation would be administered. The subject compounds may be formulated for administration in any convenient way for use in human or veterinary medicine. For example, one or more agents of the present disclosure may be formulated with a pharmaceutically acceptable carrier. A pharmaceutically acceptable carrier refers to an ingredient in a pharmaceutical formulation, other than an active ingredient, which is generally nontoxic to a subject. A pharmaceutically acceptable carrier includes, but is not limited to, a buffer, excipient, stabilizer, and/or preservative. In general, pharmaceutical formulations for use in the present disclosure are in a pyrogen-free, physiologically-acceptable form when administered to a subject. Therapeutically useful agents other than those described herein, which may optionally be included in the formulation as described above, may be administered in combination with the subject agents in the methods of the present disclosure.

In certain embodiments, compositions will be administered parenterally [e.g., by intravenous (I. V.) injection, intraarterial injection, intraosseous injection, intramuscular injection, intrathecal injection, subcutaneous injection, or intradermal injection]. Pharmaceutical compositions suitable for parenteral administration may comprise one or more agents of the disclosure in combination with one or more pharmaceutically acceptable sterile isotonic aqueous or nonaqueous solutions, dispersions, suspensions or emulsions, or sterile powders which may be reconstituted into sterile injectable solutions or dispersions just prior to use. Injectable solutions or dispersions may contain antioxidants, buffers, bacteriostats, suspending agents, thickening agents, or solutes which render the formulation isotonic with the blood of the intended recipient. Examples of suitable aqueous and nonaqueous carriers which may be employed in the pharmaceutical formulations of the present disclosure include water, ethanol, polyols (e.g., glycerol, propylene glycol, polyethylene glycol, etc.), vegetable oils (e.g., olive oil), injectable organic esters (e.g., ethyl oleate), and suitable mixtures thereof. Proper fluidity can be maintained, for example, by the use of coating materials (e.g., lecithin), by the maintenance of the required particle size in the case of dispersions, and by the use of surfactants.

In some embodiments, a therapeutic method of the present disclosure includes administering the pharmaceutical composition systemically, or locally, from an implant or device. Further, the pharmaceutical composition may be encapsulated or injected in a form for delivery to a target tissue site (e.g., bone marrow or muscle). In certain embodiments, compositions of the present disclosure may include a matrix capable of delivering one or more of the agents of the present disclosure to a target tissue site (e.g., bone marrow or muscle), providing a structure for the developing tissue and optimally capable of being resorbed into the body. For example, the matrix may provide slow release of one or more agents of the present disclosure. Such matrices may be formed of materials presently in use for other implanted medical applications.

The choice of matrix material may be based on one or more of: biocompatibility, biodegradability, mechanical properties, cosmetic appearance, and interface properties. The particular application of the subject compositions will define the appropriate formulation. Potential matrices for the compositions may be biodegradable and chemically defined calcium sulfate, tricalciumphosphate, hydroxyapatite, polylactic acid, and polyanhydrides. Other potential materials are biodegradable and biologically well-defined including, for example, bone or dermal collagen. Further matrices are comprised of pure proteins or extracellular matrix components. Other potential matrices are non-biodegradable and chemically defined including, for example, sintered hydroxyapatite, bioglass, aluminates, or other ceramics. Matrices may be comprised of combinations of any of the above mentioned types of material including, for example, polylactic acid and hydroxyapatite or collagen and tricalciumphosphate. The bioceramics may be altered in composition (e.g., calcium-aluminate-phosphate) and processing to alter one or more of pore size, particle size, particle shape, and biodegradability.

In certain embodiments, pharmaceutical compositions of present disclosure can be administered topically. "Topical application" or "topically" means contact of the pharmaceutical composition with body surfaces including, for example, the skin, wound sites, and mucous membranes. The topical pharmaceutical compositions can have various application forms and typically comprises a drug-containing layer, which is adapted to be placed near to or in direct contact with the tissue upon topically administering the composition. Pharmaceutical compositions suitable for topical administration may comprise one or more one or more TGFβ superfamily type I and/or type II receptor polypeptide complexes of the disclosure in combination formulated as a liquid, a gel, a cream, a lotion, an ointment, a foam, a paste, a putty, a semi-solid, or a solid. Compositions in the liquid, gel, cream, lotion, ointment, foam, paste, or putty form can be applied by spreading, spraying, smearing, dabbing or rolling the composition on the target tissue. The compositions also may be impregnated into sterile dressings, transdermal patches, plasters, and bandages. Compositions of the putty, semi-solid or solid forms may be deformable. They may be elastic or non-elastic (e.g., flexible or rigid). In certain aspects, the composition forms part of a composite and can include fibers, particulates, or multiple layers with the same or different compositions.

Topical compositions in the liquid form may include pharmaceutically acceptable solutions, emulsions, microemulsions, and suspensions. In addition to the active ingredient(s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof].

Topical gel, cream, lotion, ointment, semi-solid or solid compositions may include one or more thickening agents, such as a polysaccharide, synthetic polymer or protein-based polymer. In one embodiment of the invention, the gelling agent herein is one that is suitably nontoxic and gives the desired viscosity. The thickening agents may include polymers, copolymers, and monomers of: vinylpyrrolidones, methacrylamides, acrylamides N-vinylimidazoles, carboxy vinyls, vinyl esters, vinyl ethers, silicones, polyethyleneoxides, polyethyleneglycols, vinylalcohols, sodium acrylates, acrylates, maleic acids, NN-dimethylacrylamides, diacetone acrylamides, acrylamides, acryloyl morpholine, pluronic, collagens, polyacrylamides, polyacrylates, polyvinyl alcohols, polyvinylenes, polyvinyl silicates, polyacrylates substituted with a sugar (e.g., sucrose, glucose, glucosamines, galactose, trehalose, mannose, or lactose), acylamidopropane sulfonic acids, tetramethoxyorthosilicates, methyltrimethoxyorthosilicates, tetraalkoxyorthosilicates, trialkoxyorthosilicates, glycols, propylene glycol, glycerine, polysaccharides, alginates, dextrans, cyclodextrin, celluloses, modified celluloses, oxidized celluloses, chitosans, chitins, guars, carrageenans, hyaluronic acids, inulin, starches, modified starches, agarose, methylcelluloses, plant gums, hylaronans, hydrogels, gelatins, glycosaminoglycans, carboxymethyl celluloses, hydroxyethyl celluloses, hydroxy propyl methyl celluloses, pectins, low-methoxy pectins, cross-linked dextrans, starch-acrylonitrile graft copolymers, starch sodium polyacrylate, hydroxyethyl methacrylates, hydroxyl ethyl acrylates, polyvinylene, polyethylvinylethers, polymethyl methacrylates, polystyrenes, polyurethanes, polyalkanoates, polylactic acids, polylactates, poly (3-hydroxybutyrate), sulfonated hydrogels, AMPS (2-acrylamido-2-methyl-1-propanesulfonic acid), SEM (sulfoethylmethacrylate), SPM (sulfopropyl methacrylate), SPA (sulfopropyl acrylate), N,N-dimethyl-N-methacryloxyethyl-N-(3-sulfopropyl)ammonium betaine, methacrylic acid amidopropyl-dimethyl ammonium sulfobetaine, SPI (itaconic acid-bis(1-propyl sulfonizacid-3) ester di-potassium salt), itaconic acids, AMBC (3-acrylamido-3-methylbutanoic acid), beta-carboxyethyl acrylate (acrylic acid dimers), and maleic anhydride-methylvinyl ether polymers, derivatives thereof, salts thereof, acids thereof, and combinations thereof. In certain embodiments, pharmaceutical compositions of present disclosure can be administered orally, for example, in the form of capsules, cachets, pills, tablets, lozenges (using a flavored basis such as sucrose and acacia or tragacanth), powders, granules, a solution or a suspension in an aqueous or non-aqueous liquid, an oil-in-water or water-in-oil liquid emulsion, or an elixir or syrup, or pastille (using an inert base, such as gelatin and glycerin, or sucrose and acacia), and/or a mouth wash, each containing a predetermined amount of a compound of the present disclosure and optionally one or more other active ingredients. A compound of the present disclosure and optionally one or more other active ingredients may also be administered as a bolus, electuary, or paste.

In solid dosage forms for oral administration (e.g., capsules, tablets, pills, dragees, powders, and granules), one or more compounds of the present disclosure may be mixed with one or more pharmaceutically acceptable carriers including, for example, sodium citrate, dicalcium phosphate, a filler or extender (e.g., a starch, lactose, sucrose, glucose, mannitol, and silicic acid), a binder (e.g. carboxymethylcellulose, an alginate, gelatin, polyvinyl pyrrolidone, sucrose, and acacia), a humectant (e.g., glycerol), a disintegrating agent (e.g., agar-agar, calcium carbonate, potato or tapioca starch, alginic acid, a silicate, and sodium carbonate), a solution retarding agent (e.g. paraffin), an absorption accelerator (e.g. a quaternary ammonium compound), a wetting agent (e.g., cetyl alcohol and glycerol monostearate), an absorbent (e.g., kaolin and bentonite clay), a lubricant (e.g., a talc, calcium stearate, magnesium stearate, solid polyethylene glycols, sodium lauryl sulfate), a coloring agent, and mixtures thereof. In the case of capsules, tablets, and pills, the pharmaceutical formulation (composition) may also comprise a buffering agent. Solid compositions of a similar type may also be employed as fillers in soft and hard-filled gelatin capsules using one or more excipients including, e.g., lactose or a milk sugar as well as a high molecular-weight polyethylene glycol.

Liquid dosage forms for oral administration of the pharmaceutical composition may include pharmaceutically acceptable emulsions, microemulsions, solutions, suspensions, syrups, and elixirs. In addition to the active ingredient (s), the liquid dosage form may contain an inert diluent commonly used in the art including, for example, water or other solvent, a solubilizing agent and/or emulsifier [e.g., ethyl alcohol, isopropyl alcohol, ethyl carbonate, ethyl acetate, benzyl alcohol, benzyl benzoate, propylene glycol, or 1,3-butylene glycol, an oil (e.g., cottonseed, groundnut, corn, germ, olive, castor, and sesame oil), glycerol, tetrahydrofuryl alcohol, a polyethylene glycol, a fatty acid ester of sorbitan, and mixtures thereof]. Besides inert diluents, the oral formulation can also include an adjuvant including, for example, a wetting agent, an emulsifying and suspending agent, a sweetening agent, a flavoring agent, a coloring agent, a perfuming agent, a preservative agent, and combinations thereof.

Suspensions, in addition to the active compounds, may contain suspending agents including, for example, an ethoxylated isostearyl alcohol, polyoxyethylene sorbitol, a sorbitan ester, microcrystalline cellulose, aluminum metahydroxide, bentonite, agar-agar, tragacanth, and combinations thereof.

Prevention of the action and/or growth of microorganisms may be ensured by the inclusion of various antibacterial and antifungal agents including, for example, paraben, chlorobutanol, and phenol sorbic acid.

In certain embodiments, it may be desirable to include an isotonic agent including, for example, a sugar or sodium chloride into the compositions. In addition, prolonged absorption of an injectable pharmaceutical form may be brought about by the inclusion of an agent that delay absorption including, for example, aluminum monostearate and gelatin.

It is understood that the dosage regimen will be determined by the attending physician considering various factors which modify the action of the one or more of the agents of the present disclosure. In the case of a TGF-beta superfamily heteromultimer complex that promotes red blood cell formation, various factors may include, but are not limited to, the patient's red blood cell count, hemoglobin level, the desired target red blood cell count, the patient's age, the patient's sex, the patient's diet, the severity of any disease that may be contributing to a depressed red blood cell level, the time of administration, and other clinical factors. The addition of other known active agents to the final composition may also affect the dosage. Progress can be monitored by periodic assessment of one or more of red blood cell levels, hemoglobin levels, reticulocyte levels, and other indicators of the hematopoietic process.

In certain embodiments, the present disclosure also provides gene therapy for the in vivo production of one or more of the agents of the present disclosure. Such therapy would achieve its therapeutic effect by introduction of the agent sequences into cells or tissues having one or more of the disorders as listed above. Delivery of the agent sequences can be achieved, for example, by using a recombinant expression vector such as a chimeric virus or a colloidal dispersion system. Preferred therapeutic delivery of one or more of agent sequences of the disclosure is the use of targeted liposomes.

Various viral vectors which can be utilized for gene therapy as taught herein include adenovirus, herpes virus, vaccinia, or an RNA virus (e.g., a retrovirus). The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing one or more of the agents of the present disclosure.

Alternatively, tissue culture cells can be directly transfected with plasmids encoding the retroviral structural genes (gag, pol, and env), by conventional calcium phosphate transfection. These cells are then transfected with the vector plasmid containing the genes of interest. The resulting cells release the retroviral vector into the culture medium.

Another targeted delivery system for one or more of the agents of the present disclosure is a colloidal dispersion system. Colloidal dispersion systems include, for example, macromolecule complexes, nanocapsules, microspheres, beads, and lipid-based systems including oil-in-water emulsions, micelles, mixed micelles, and liposomes. In certain embodiments, the preferred colloidal system of this disclosure is a liposome. Liposomes are artificial membrane vesicles which are useful as delivery vehicles in vitro and in vivo. RNA, DNA, and intact virions can be encapsulated within the aqueous interior and be delivered to cells in a biologically active form. See, e.g., Fraley, et al. (1981) Trends Biochem. Sci., 6:77. Methods for efficient gene transfer using a liposome vehicle are known in the art. See, e.g., Mannino, et al. (1988) Biotechniques, 6:682, 1988.

The composition of the liposome is usually a combination of phospholipids, which may include a steroid (e.g. cholesterol). The physical characteristics of liposomes depend on pH, ionic strength, and the presence of divalent cations. Other phospholipids or other lipids may also be used including, for example a phosphatidyl compound (e.g., phosphatidylglycerol, phosphatidylcholine, phosphatidylserine, phosphatidylethanolamine, a sphingolipid, a cerebroside, and a ganglioside), egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

Example 1. Generation of an ActRIIB-Fc:ALK4-Fc Heterodimer

Applicants constructed a soluble ActRIIB-Fc:ALK4-Fc heteromeric complex comprising the extracellular domains of human ActRIIB and human ALK4, which are each separately fused to an Fc domain with a linker positioned between the extracellular domain and the Fc domain. The individual constructs are referred to as ActRIIB-Fc fusion polypeptide and ALK4-Fc fusion polypeptide, respectively, and the sequences for each are provided below.

A methodology for promoting formation of ActRIIB-Fc: ALK4-Fc heteromeric complexes, as opposed to the ActRIIB-Fc or ALK4-Fc homodimeric complexes, is to introduce alterations in the amino acid sequence of the Fc domains to guide the formation of asymmetric heteromeric complexes. Many different approaches to making asymmetric interaction pairs using Fc domains are described in this disclosure.

In one approach, illustrated in the ActRIIB-Fc and ALK4-Fc polypeptide sequences of SEQ ID NOs: 100-102 and 104-106, respectively, one Fc domain is altered to introduce cationic amino acids at the interaction face, while the other Fc domain is altered to introduce anionic amino acids at the interaction face. The ActRIIB-Fc fusion polypeptide and ALK4-Fc fusion polypeptide each employ the tissue plasminogen activator (TPA) leader:

(SEQ ID NO: 98)
MDAMKRGLCCVLLLCGAVFVSP.

The ActRIIB-Fc polypeptide sequence (SEQ ID NO: 100) is shown below:

```
                                                      (SEQ ID NO: 100)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSRKEMT KNQVSLTCLV KGFYPSDIAV

301 EWESNGQPEN NYKTTPPVLK SDGSFFLYSK LTVDKSRWQQ GNVFSCSVMH

351 EALHNHYTQK SLSLSPGK
```

The leader (signal) sequence and linker are underlined. To promote formation of the ActRIIB-Fc:ALK4-Fc heterodimer rather than either of the possible homodimeric complexes, two amino acid substitutions (replacing acidic amino acids with lysine) can be introduced into the Fc domain of the ActRIIB fusion protein as indicated by double underline above. The amino acid sequence of SEQ ID NO: 100 may optionally be provided with lysine (K) removed from the C-terminus.

This ActRIIB-Fc fusion protein is encoded by the following nucleic acid sequence (SEQ ID NO: 101):

```
                                                      (SEQ ID NO: 101)
   1 ATGGATGCAA TGAAGAGAGG GCTCTGCTGT GTGCTGCTGC TGTGTGGAGC

51 AGTCTTCGTT TCGCCCGGCG CCTCTGGGCG TGGGGAGGCT GAGACACGGG

101 AGTGCATCTA CTACAACGCC AACTGGGAGC TGGAGCGCAC CAACCAGAGC

151 GGCCTGGAGC GCTGCGAAGG CGAGCAGGAC AAGCGGCTGC ACTGCTACGC

201 CTCCTGGCGC AACAGCTCTG GCACCATCGA GCTCGTGAAG AAGGGCTGCT

251 GGCTAGATGA CTTCAACTGC TACGATAGGC AGGAGTGTGT GGCCACTGAG

301 GAGAACCCCC AGGTGTACTT CTGCTGCTGT GAAGGCAACT TCTGCAACGA

351 GCGCTTCACT CATTTGCCAG AGGCTGGGGG CCCGGAAGTC ACGTACGAGC

401 CACCCCCGAC AGCCCCCACC GGTGGTGGAA CTCACACATG CCCACCGTGC

451 CCAGCACCTG AACTCCTGGG GGGACCGTCA GTCTTCCTCT TCCCCCCAAA

501 ACCCAAGGAC ACCCTCATGA TCTCCCGGAC CCCTGAGGTC ACATGCGTGG

551 TGGTGGACGT GAGCCACGAA GACCCTGAGG TCAAGTTCAA CTGGTACGTG

601 GACGGCGTGG AGGTGCATAA TGCCAAGACA AAGCCGCGGG AGGAGCAGTA

651 CAACAGCACG TACCGTGTGG TCAGCGTCCT CACCGTCCTG CACCAGGACT

701 GGCTGAATGG CAAGGAGTAC AAGTGCAAGG TCTCCAACAA AGCCCTCCCA

751 GCCCCCATCG AGAAAACCAT CTCCAAAGCC AAAGGGCAGC CCCGAGAACC

801 ACAGGTGTAC ACCCTGCCCC CATCCCGGAA GGAGATGACC AAGAACCAGG

851 TCAGCCTGAC CTGCCTGGTC AAAGGCTTCT ATCCCAGCGA CATCGCCGTG

901 GAGTGGGAGA GCAATGGGCA GCCGGAGAAC AACTACAAGA CCACGCCTCC

951 CGTGCTGAAG TCCGACGGCT CCTTCTTCCT CTATAGCAAG CTCACCGTGG

1001 ACAAGAGCAG GTGGCAGCAG GGGAACGTCT TCTCATGCTC CGTGATGCAT

1051 GAGGCTCTGC ACAACCACTA CACGCAGAAG AGCCTCTCCC TGTCTCCGGG

1101 TAAA
```

The mature ActRIIB-Fc fusion polypeptide (SEQ ID NO: 102) is as follows, and may optionally be provided with lysine removed from the C-terminus.

```
                                                            (SEQ ID NO: 102)
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 RKEMTKNQVS LTCLVKGFYP SDIAVEWESN GQPENNYKTT PPVLKSDGSF

301 FLYSKLTVDK SRWQQGNVFS CSVMHEALHN HYTQKSLSLS PGK
```

The complementary form of ALK4-Fc fusion polypeptide (SEQ ID NO: 104) is as follows:

```
                                                            (SEQ ID NO: 104)
  1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSREEMTKN QVSLTCLVKG FYPSDIAVEW ESNGQPENNY

301 DTTPPVLDSD GSFFLYSDLT VDKSRWQQGN VFSCSVMHEA LHNHYTQKSL

351 SLSPG
```

The leader sequence and linker sequence are underlined. To guide heterodimer formation with the ActRIIB-Fc fusion polypeptide of SEQ ID NOs: 100 and 102 above, two amino acid substitutions (replacing lysines with aspartic acids) can be introduced into the Fc domain of the ALK4-Fc fusion polypeptide as indicated by double underline above. The amino acid sequence of SEQ ID NO: 104 may optionally be provided with lysine added at the C-terminus.

This ALK4-Fc fusion protein is encoded by the following nucleic acid (SEQ ID NO: 105):

```
                                                            (SEQ ID NO: 105)
  1 ATGGATGCAA TGAAGAGAGG GCTCTGCTGT GTGCTGCTGC TGTGTGGAGC

51 AGTCTTCGTT TCGCCCGGCG CCTCCGGGCC CCGGGGGGTC CAGGCTCTGC

101 TGTGTGCGTG CACCAGCTGC CTCCAGGCCA ACTACACGTG TGAGACAGAT

151 GGGGCCTGCA TGGTTTCCAT TTTCAATCTG GATGGGATGG AGCACCATGT

201 GCGCACCTGC ATCCCCAAAG TGGAGCTGGT CCCTGCCGGG AAGCCCTTCT

251 ACTGCCTGAG CTCGGAGGAC CTGCGCAACA CCCACTGCTG CTACACTGAC

301 TACTGCAACA GGATCGACTT GAGGGTGCCC AGTGGTCACC TCAAGGAGCC

351 TGAGCACCCG TCCATGTGGG GCCCGGTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAGGGG
```

-continued

```
 751 CAGCCCCGAG AACCACAGGT GTACACCCTG CCCCCATCCC GGGAGGAGAT
 801 GACCAAGAAC CAGGTCAGCC TGACCTGCCT GGTCAAAGGC TTCTATCCCA
 851 GCGACATCGC CGTGGAGTGG GAGAGCAATG GGCAGCCGGA GAACAACTAC
 901 GACACCACGC CTCCCGTGCT GGACTCCGAC GGCTCCTTCT TCCTCTATAG
 951 CGACCTCACC GTGGACAAGA GCAGGTGGCA GCAGGGGAAC GTCTTCTCAT
1001 GCTCCGTGAT GCATGAGGCT CTGCACAACC ACTACACGCA GAAGAGCCTC
1051 TCCCTGTCTC CGGGT
```

The mature ALK4-Fc fusion protein sequence (SEQ ID NO: 106) is as follows and may optionally be provided with lysine added at the C-terminus.

```
                                               (SEQ ID NO: 106)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPSR EEMTKNQVSL

251 TCLVKGFYPS DIAVEWESNG QPENNYDTTP PVLDSDGSFF LYSDLTVDKS

301 RWQQGNVFSC SVMHEALHNH YTQKSLSLSP G
```

The ActRIIB-Fc and ALK4-Fc proteins of SEQ ID NO: 102 and SEQ ID NO: 106, respectively, may be co-expressed and purified from a CHO cell line, to give rise to a heteromeric complex comprising ActRIIB-Fc:ALK4-Fc.

In another approach to promote the formation of heteromultimer complexes using asymmetric Fc fusion proteins the Fc domains are altered to introduce complementary hydrophobic interactions and an additional intermolecular disulfide bond as illustrated in the ActRIIB-Fc and ALK4-Fc polypeptide sequences of SEQ ID NOs: 401-402 and 403-404, respectively. The ActRIIB-Fc fusion polypeptide and ALK4-Fc fusion polypeptide each employ the tissue plasminogen activator (TPA) leader:

```
                    (SEQ ID NO: 98)
       MDAMKRGLCCVLLLCGAVFVSP.
```

The ActRIIB-Fc polypeptide sequence (SEQ ID NO: 401) is shown below:

```
                                               (SEQ ID NO: 401)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPCREEMT KNQVSLWCLV KGFYPSDIAV

301 EWESNGQPEN NYKTTPPVLD SDGSFFLYSK LTVDKSRWQQ GNVFSCSVMH

351 EALHNHYTQK SLSLSPGK
```

The leader (signal) sequence and linker sequence are underlined. To promote formation of the ActRIIB-Fc:ALK4-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 401 may optionally be provided with lysine removed from the C-terminus.

The mature ActRIIB-Fc fusion polypeptide is as follows:

```
                                                  (SEQ ID NO: 402)
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPC

251 REEMTKNQVS LWCLVKGFYP SDIAVEWESN GQPENNYKTT PPVLDSDGSF

301 FLYSKLTVDK SRWQQGNVFS CSVMHEALHN HYTQKSLSLS PGK
```

The complementary form of ALK4-Fc fusion polypeptide (SEQ ID NO: 403) is as follows and may optionally be provided with lysine removed from the C-terminus.

```
                                                  (SEQ ID NO: 403)
  1 MDAMKRGLCC VLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVCTL PPSREEMTKN QVSLSCAVKG FYPSDIAVEW ESNGQPENNY

301 KTTPPVLDSD GSFFLVSKLT VDKSRWQQGN VFSCSVMHEA LHNHYTQKSL

351 SLSPGK
```

The leader sequence and the linker are underlined. To guide heterodimer formation with the ActRIIB-Fc fusion polypeptide of SEQ ID NOs: 401 and 402 above, four amino acid substitutions can be introduced into the Fc domain of the ALK4 fusion polypeptide as indicated by double underline above. The amino acid sequence of SEQ ID NO: 403 may optionally be provided with lysine removed from the C-terminus.

The mature ALK4-Fc fusion protein sequence is as follows and may optionally be provided with lysine removed from the C-terminus.

```
                                                  (SEQ ID NO: 404)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL

251 SCAVKGFYPS DIAVEWESNG QPENNYKTTP PVLDSDGSFF LVSKLTVDKS

301 RWQQGNVFSC SVMHEALHNH YTQKSLSLSP GK
```

The ActRIIB-Fc and ALK4-Fc proteins of SEQ ID NO: 402 and SEQ ID NO: 404, respectively, may be co-expressed and purified from a CHO cell line, to give rise to a heteromeric complex comprising ActRIIB-Fc:ALK4-Fc.

Purification of various ActRIIB-Fc:ALK4-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

of inhibitor, however this can generate off-target effects that reduce tolerability and safety. A preferable approach is to use an inhibitor with a slower ligand off-rate (longer capture time) combined with ligand binding selectivity to achieve an effective level of ligand antagonism at a lower concentration of inhibitor.

| | Ligand binding profile of ActRIIB-Fc:ALK4-Fc heterodimer compared to ActRIIB-Fc homodimer and ALK4-Fc homodimer | | | | | | | | |
|---|---|---|---|---|---|---|---|---|---|
| | ActRIIB-Fc homodimer | | | ALK4-Fc homodimer | | | ActRIIB-Fc:ALK4-Fc heterodimer | | |
| Ligand | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.2 \times 10^7$ | 2.3 × 10−4 | 19 | $5.8 \times 10^5$ | $1.2 \times 10^2$ | 20000 | $1.3 \times 10^7$ | 1.5 × 10−4 | 12 |
| Activin B | $5.1 \times 10^6$ | 1.0 × 10−4 | 20 | | No binding | | $7.1 \times 10^6$ | 4.0 × 10−5 | 6 |
| BMP6 | $3.2 \times 10^7$ | $6.8 \times 10^{-3}$ | 190 | | — | | $2.0 \times 10^6$ | $5.5 \times 10^{-3}$ | 2700 |
| BMP9 | $1.4 \times 10^7$ | $1.1 \times 10^{-3}$ | 77 | | — | | Transient* | | 3400 |
| BMP10 | $2.3 \times 10^7$ | 2.6 × 10−4 | 11 | | — | | $5.6 \times 10^7$ | $4.1 \times 10^{-3}$ | 74 |
| GDF3 | $1.4 \times 10^6$ | $2.2 \times 10^{-3}$ | 1500 | | — | | $3.4 \times 10^6$ | $1.7 \times 10^{-2}$ | 4900 |
| GDF8 | $8.3 \times 10^5$ | 2.3 × 10−4 | 280 | $1.3 \times 10^5$ | $1.9 \times 10^{-3}$ | 15000† | $3.9 \times 10^5$ | 2.1 × 10−4 | 550 |
| GDF11 | $5.0 \times 10^7$ | 1.1 × 10−4 | 2 | $5.0 \times 10^6$ | $4.8 \times 10^{-3}$ | 270† | $3.8 \times 10^7$ | 1.1 × 10−4 | 3 |

*Indeterminate due to transient nature of interaction
†Very low signal
—Not tested

Example 2. Ligand Binding Profile of ActRIIB-Fc:ALK4-Fc Heterodimer Compared to ActRIIB-Fc Homodimer and ALK4-Fc Homodimer A Biacore™-based binding assay was used to compare ligand binding selectivity of the ActRIIB-Fc:ALK4-Fc heterodimeric complex described above with that of ActRIIB-Fc and ALK4-Fc homodimeric complexes. The ActRIIB-Fc:ALK4-Fc heterodimer, ActRIIB-Fc homodimer, and ALK4-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand off-rate is a particularly significant parameter to evaluate for ligand traps. Soluble receptor-Fc proteins administered in vivo are in constant competition with native receptors for ligands. When endogenous ligands of the TGFbeta superfamily typically bind to cognate receptors at the cell surface, a multi-step signal transduction process is triggered that is relatively slow on a molecular time scale. Native receptors dissociate from ligand slowly in part because significant time is required to generate an intracellular signal from a ligand binding event. For a soluble receptor-Fc protein to compete effectively for ligand, the off-rate for its complex with the ligand needs to be similar to, or slower than, the off-rate for a ligand complex with native receptor. Ligand binding is a dynamic process and some fraction of ligands will always be in unbound form, so it is important therapeutically for a dose of receptor-Fc protein to capture target ligand for as long as possible. One way to shift the binding equilibrium in favor of more captured ligand is to increase the concentration (dose level)

These comparative binding data demonstrate that the ActRIIB-Fc:ALK4-Fc heterodimer has an altered binding profile/selectivity relative to either the ActRIIB-Fc or ALK4-Fc homodimers. The ActRIIB-Fc:ALK4-Fc heterodimer displays enhanced binding to activin B compared with either homodimer, retains strong binding to activin A, GDF8, and GDF11 as observed with ActRIIB-Fc homodimer, and exhibits substantially reduced binding to BMP9, BMP10, and GDF3. In particular, BMP9 displays low or no observable affinity for the ActRIIB-Fc:ALK4-Fc heterodimer, whereas this ligand binds strongly to ActRIIB-Fc homodimer. Like ActRIIB-Fc homodimer, the heterodimer retains intermediate-level binding to BMP6. See FIG. 6.

These results therefore demonstrate that the ActRIIB-Fc:ALK4-Fc heterodimer is a more selective antagonist of activin A, activin B, GDF8, and GDF11 compared to a ActRIIB-Fc homodimer. Accordingly, an ActRIIB-Fc:ALK4-Fc heterodimer will be more useful than an ActRIIB-Fc homodimer in certain applications where such selective antagonism is advantageous. Examples include therapeutic applications where it is desirable to retain antagonism of one or more of activin A, activin B, activin AC, GDF8, and GDF11 but minimize antagonism of one or more of BMP9, BMP10, and BMP6.

Example 3. Activity Profile of ActRIIB-Fc:ALK4-Fc Heterodimer in Mice Compared to ActRIIB-Fc Homodimer Homodimeric and heterodimeric complexes were tested in mice to investigate differences in their activity profiles in vivo. Wild-type C57BL/6 mice were dosed subcutaneously with an ActRIIB-Fc homodimer (10 mg/kg), an ActRIIB-Fc:ALK4-Fc heterodimer (3 or 10 mg/kg), or vehicle (phosphate-buffered saline, PBS) twice per week for 4 weeks beginning at approximately 10 weeks of age (n=9 mice per group). ALK4-Fc homodimer was not tested in vivo due to its inability to bind ligands with high affinity under cell-free conditions as determined by surface plasmon resonance. Study endpoints included: body weight; total lean mass and total adipose mass as determined by nuclear magnetic resonance (NMR) at baseline and study completion (4 weeks); total bone mineral density as determined by dual energy x-ray absorptiometry (DEXA) at baseline and 4 weeks; and weights of the gastrocnemius, rectus femoris, and pectoralis muscles determined at 4 weeks.

Activity of ActRIIB-Fc and ALK4-Fc Complexes in Wild-Type Mice

| Endpoint (4 wk) | Vehicle | ActRIIB-Fc homodimer 10 mg/kg | ActRIIB-Fc:ALK4-Fc heterodimer 10 mg/kg | ActRIIB-Fc:ALK4-Fc heterodimer 3 mg/kg |
|---|---|---|---|---|
| Change in body weight from baseline | ↑ 15% | ↑ 38%  | ↑ 41%  | ↑ 33% ** |
| Change in total lean mass from baseline | ↓ 1% | ↑ 5%  | ↑ 5%  | ↑ 5% ** |
| Change in total adipose mass from baseline | ↑ 5% | ↓ 36%  | ↓ 35%  | ↓ 35% ** |
| Change in total bone mineral density from baseline | ↑ 8% | ↑ 14% * | ↑ 12% * | ↑ 11% |
| Gastrocnemius weight † | 23 | 36  | 35  | 30 ** |
| Femoris weight † | 11.5 | 17  | 16  | 14 ** |
| Pectoralis weight † | 15 | 23  | 28  | 23 ** |

\* $P < 0.05$ vs. vehicle
\*\* $P < 0.01$ vs. vehicle
† Combined left and right muscle weights normalized to femur length (mg/mm) to control for body size Study results are summarized in the table above. As expected, ActRIIB-Fc homodimer caused marked changes in body composition, many consistent with known effects of GDF8 and activin inhibition. Treatment of wild-type mice with ActRIIB-Fc homodimer more than doubled body weight gain over the course of the study compared to vehicle-treated controls. Accompanying this net weight gain were significant increases in total lean mass and total bone mineral density, as well as a significant reduction in total adipose mass, compared to vehicle. It should be recognized that normalized (percentage-based) changes in lean and adipose tissues differ in their correspondence to absolute changes because lean mass (typically about 70% of body weight in a mouse) is much larger than adipose mass (typically about 10% of body weight). Individual skeletal muscles examined, including the gastrocnemius, femoris, and pectoralis all increased significantly in weight compared to vehicle controls over the course of treatment with ActRIIB-Fc homodimer.

The ActRIIB-Fc:ALK4-Fc heterodimer produced certain effects strikingly similar to those of the ActRIIB-Fc homodimer despite differential ligand selectivity of the two complexes. As shown in the table above, treatment of mice with the ActRIIB-Fc:ALK4-Fc heterodimer at a dose level of 10 mg/kg matched, nearly matched, or exceeded the effects of ActRIIB-Fc homodimer at the same dose level for all endpoints listed. Effects of the ActRIIB-Fc:ALK4-Fc heterodimer at 3 mg/kg were mildly attenuated for several endpoints compared to 10 mg/kg, thus providing evidence for a dose-effect relationship.

Thus, an ActRIIB-Fc:ALK4-Fc heterodimer exerts beneficial anabolic effects on skeletal muscle and bone, and catabolic effects on adipose tissue, very similar to those of ActRIIB-Fc homodimer. However, unlike ActRIIB homodimer, an ActRIIB-Fc:ALK4-Fc heterodimer exhibits only low-affinity or transient binding to BMP9 and BMP10 and so will not concurrently inhibit processes mediated by those ligands, such as angiogenesis. This novel selectivity will be useful, for example, in treating patients in need of stimulatory effects on muscle and bone, and inhibitory effects on fat, but not in need of altered angiogenesis.

Example 4. Generation of an ActRIIB-Fc:ALK3-Fc Heterodimer

Applicants constructed a soluble ActRIIB-Fc:ALK3-Fc heteromeric complex comprising the extracellular domains of human ActRIIB and human ALK3, which are each fused to an Fc domain with a linker positioned between the extracellular domain and the Fc domain. The individual constructs are referred to as ActRIIB-Fc and ALK3-Fc, respectively.

Formation of heteromeric ActRIIB-Fc:ALK3-Fc may be guided by approaches similar to those described in Example 1.

In a first approach, the polypeptide sequence of the ActRIIB-Fc fusion protein and a nucleic acid sequence encoding it are provided above in Example 1 as SEQ ID NOs: 100-102.

The complementary ALK3-Fc fusion protein employs the TPA leader and is as follows:

```
                                                   (SEQ ID NO: 115)
  1 MDAMKRGLCC VLLLCGAVFV SPGAQNLDSM LHGTGMKSDS DQKKSENGVT

51 LAPEDTLPFL KCYCSGHCPD DAINNTCITN GHCFAIIEED DQGETTLASG

101 CMKYEGSDFQ CKDSPKAQLR RTIECCRTNL CNQYLQPTLP PVVIGPFFDG

151 SIRTGGGTHT CPPCPAPELL GGPSVFLFPP KPKDTLMISR TPEVTCVVVD

201 VSHEDPEVKF NWYVDGVEVH NAKTKPREEQ YNSTYRVVSV LTVLHQDWLN

251 GKEYKCKVSN KALPAPIEKT ISKAKGQPRE PQVYTLPPSR EEMTKNQVSL

301 TCLVKGFYPS DIAVEWESNG QPENNYDTTP PVLDSDGSFF LYSDLTVDKS

351 RWQQGNVFSC SVMHEALHNH YTQKSLSLSP G
```

The leader and linker sequences are underlined. To promote formation of the ActRIIB-Fc:ALK3-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 115 may optionally be provided with a lysine added at the C-terminus.

This ALK3-Fc fusion protein is encoded by the following nucleic acid (SEQ ID NO: 116).

```
                                                  (SEQ ID NO: 116)
   1  ATGGATGCAA TGAAGAGAGG GCTCTGCTGT GTGCTGCTGC TGTGTGGAGC

51  AGTCTTCGTT TCGCCCGGCG CCCAGAATCT GGATAGTATG CTTCATGGCA

101  CTGGGATGAA ATCAGACTCC GACCAGAAAA AGTCAGAAAA TGGAGTAACC

151  TTAGCACCAG AGGATACCTT GCCTTTTTTA AAGTGCTATT GCTCAGGGCA

201  CTGTCCAGAT GATGCTATTA ATAACACATG CATAACTAAT GGACATTGCT

251  TTGCCATCAT AGAAGAAGAT GACCAGGGAG AAACCACATT AGCTTCAGGG

301  TGTATGAAAT ATGAAGGATC TGATTTTCAG TGCAAAGATT CTCCAAAAGC

351  CCAGCTACGC CGGACAATAG AATGTTGTCG GACCAATTTA TGTAACCAGT

401  ATTTGCAACC CACACTGCCC CCTGTTGTCA TAGGTCCGTT TTTTGATGGC

451  AGCATTCGAA CCGGTGGTGG AACTCACACA TGCCCACCGT GCCCAGCACC

501  TGAACTCCTG GGGGGACCGT CAGTCTTCCT CTTCCCCCCA AAACCCAAGG

551  ACACCCTCAT GATCTCCCGG ACCCCTGAGG TCACATGCGT GGTGGTGGAC

601  GTGAGCCACG AAGACCCTGA GGTCAAGTTC AACTGGTACG TGGACGGCGT

651  GGAGGTGCAT AATGCCAAGA CAAAGCCGCG GGAGGAGCAG TACAACAGCA

701  CGTACCGTGT GGTCAGCGTC CTCACCGTCC TGCACCAGGA CTGGCTGAAT

751  GGCAAGGAGT ACAAGTGCAA GGTCTCCAAC AAAGCCCTCC CAGCCCCCAT

801  CGAGAAAACC ATCTCCAAAG CCAAAGGGCA GCCCCGAGAA CCACAGGTGT

851  ACACCCTGCC CCCATCCCGG GAGGAGATGA CCAAGAACCA GGTCAGCCTG

901  ACCTGCCTGG TCAAAGGCTT CTATCCCAGC GACATCGCCG TGGAGTGGGA

951  GAGCAATGGG CAGCCGGAGA ACAACTACGA CACCACGCCT CCCGTGCTGG

1001  ACTCCGACGG CTCCTTCTTC CTCTATAGCG ACCTCACCGT GGACAAGAGC

1051  AGGTGGCAGC AGGGGAACGT CTTCTCATGC TCCGTGATGC ATGAGGCTCT

1101  GCACAACCAC TACACGCAGA AGAGCCTCTC CCTGTCTCCG GGT
```

The mature ALK3-Fc fusion protein sequence is as follows (SEQ ID NO: 117) and may optionally be provided with a lysine added at the C-terminus.

```
                                                  (SEQ ID NO: 117)
   1  GAQNLDSMLH GTGMKSDSDQ KKSENGVTLA PEDTLPFLKC YCSGHCPDDA

51  INNTCITNGH CFAIIEEDDQ GETTLASGCM KYEGSDFQCK DSPKAQLRRT

101  IECCRTNLCN QYLQPTLPPV VIGPFFDGSI RTGGGTHTCP PCPAPELLGG

151  PSVFLFPPKP KDTLMISRTP EVTCVVVDVS HEDPEVKFNW YVDGVEVHNA

201  KTKPREEQYN STYRVVSVLT VLHQDWLNGK EYKCKVSNKA LPAPIEKTIS

251  KAKGQPREPQ VYTLPPSREE MTKNQVSLTC LVKGFYPSDI AVEWESNGQP

301  ENNYDTTPPV LDSDGSFFLY SDLTVDKSRW QQGNVFSCSV MHEALHNHYT

351  QKSLSLSPG
```

The ActRIIB-Fc and ALK3-Fc fusion proteins of SEQ ID NO: 102 and SEQ ID NO: 117, respectively, may be co-expressed and purified from a CHO cell line to give rise to a heteromeric complex comprising ActRIIB-Fc:ALK3-Fc.

In another approach to promoting the formation of heteromultimer complexes using asymmetric Fc fusion proteins, illustrated in the ActRIIB-Fc and ALK3-Fc polypeptide sequences of SEQ ID NOs: 401-402 and 407-408, respectively, the Fc domains are altered to introduce complementary hydrophobic interactions and an additional intermolecular disulfide bond. The ActRIIB-Fc fusion polypeptide sequences are discussed in Example 1.

The complementary form of ALK3-Fc fusion polypeptide (SEQ ID NO: 407) is as follows:

```
                                                    (SEQ ID NO: 407)
  1 MDAMKRGLCC VLLLCGAVFV SPGAQNLDSM LHGTGMKSDS DQKKSENGVT

51 LAPEDTLPFL KCYCSGHCPD DAINNTCITN GHCFAIIEED DQGETTLASG

101 CMKYEGSDFQ CKDSPKAQLR RTIECCRTNL CNQYLQPTLP PVVIGPFFDG

151 SIRTGGGTHT CPPCPAPELL GGPSVFLFPP KPKDTLMISR TPEVTCVVVD

201 VSHEDPEVKF NWYVDGVEVH NAKTKPREEQ YNSTYRVVSV LTVLHQDWLN

251 GKEYKCKVSN KALPAPIEKT ISKAKGQPRE PQVCTLPPSR EEMTKNQVSL

301 SCAVKGFYPS DIAVEWESNG QPENNYKTTP PVLDSDGSFF LVSKLTVDKS

351 RWQQGNVFSC SVMHEALHNH YTQKSLSLSP GK
```

The leader sequence and linker are underlined. To guide heterodimer formation with the ActRIIB-Fc fusion polypeptide of SEQ ID NOs 401 and 402 above, four amino acid substitutions can be introduced into the Fc domain of the ALK3 fusion polypeptide as indicated by double underline above. The amino acid sequence of SEQ ID NO: 407 may optionally be provided with the lysine removed from the C-terminus.

The mature ALK3-Fc fusion protein sequence (SEQ ID NO: 408) is as follows and may optionally be provided with the lysine (K) removed from the C-terminus.

```
                                                    (SEQ ID NO: 408)
  1 GAQNLDSMLH GTGMKSDSDQ KKSENGVTLA PEDTLPFLKC YCSGHCPDDA

51 INNTCITNGH CFAIIEEDDQ GETTLASGCM KYEGSDFQCK DSPKAQLRRT

101 IECCRTNLCN QYLQPTLPPV VIGPFFDGSI RTGGGTHTCP PCPAPELLGG

151 PSVFLFPPKP KDTLMISRTP EVTCVVVDVS HEDPEVKFNW YVDGVEVHNA

201 KTKPREEQYN STYRVVSVLT VLHQDWLNGK EYKCKVSNKA LPAPIEKTIS

251 KAKGQPREPQ VCTLPPSREE MTKNQVSLSC AVKGFYPSDI AVEWESNGQP

301 ENNYKTTPPV LDSDGSFFLV SKLTVDKSRW QQGNVFSCSV MHEALHNHYT

351 QKSLSLSPGK
```

The ActRIIB-Fc and ALK3-Fc proteins of SEQ ID NO: 402 and SEQ ID NO: 408, respectively, may be co-expressed and purified from a CHO cell line, to give rise to a heteromeric complex comprising ActRIIB-Fc:ALK3-Fc.

Purification of various ActRIIB-Fc:ALK3-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 5. Ligand Binding Profile of ActRIIB-Fc:ALK3-Fc Heterodimer Compared to ActRIIB-Fc Homodimer and ALK3-Fc Homodimer A Biacore™-based binding assay was used to compare ligand binding selectivity of the ActRIIB-Fc:ALK3-Fc heterodimeric complex described above with that of ActRIIB-Fc and ALK3-Fc homodimeric complexes. The ActRIIB-Fc:ALK3-Fc heterodimer, ActRIIB-Fc homodimer, and ALK3-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profile of ActRIIB-Fc:ALK3-Fc heterodimer compared to ActRIIB-Fc homodimer and ALK3-Fc homodimer

| Ligand | ActRIIB-Fc homodimer | | | ALK3-Fc homodimer | | | ActRIIB-Fc:ALK3-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.3 \times 10^7$ | $1.4 \times 10^{-4}$ | 11 | No binding | | | $3.4 \times 10^7$ | $5.0 \times 10^{-3}$ | 150 |
| Activin B | $5.1 \times 10^6$ | $1.0 \times 10^{-4}$ | 20 | No binding | | | $2.8 \times 10^6$ | $5.7 \times 10^{-4}$ | 200 |
| BMP2 | Transient* | | >66000 | $6.8 \times 10^5$ | $8.9 \times 10^{-5}$ | 130 | $8.0 \times 10^6$ | $1.1 \times 10^{-5}$ | 1 |
| BMP4 | — | | | $3.0 \times 10^5$ | $5.3 \times 10^{-5}$ | 180 | $2.6 \times 10^6$ | $6.5 \times 10^{-6}$ | 3 |
| BMP5 | $2.6 \times 10^7$ | $7.5 \times 10^{-2}$ | 2900 | $2.9 \times 10^4$ | $2.0 \times 10^{-3}$ | 70000 | $9.0 \times 10^5$ | $5.8 \times 10^{-4}$ | 640 |
| BMP6 | $3.5 \times 10^7$ | $6.8 \times 10^{-3}$ | 190 | $1.4 \times 10^5$ | $4.9 \times 10^{-3}$ | 35000 | $2.0 \times 10^7$ | $2.9 \times 10^{-4}$ | 15 |
| BMP7 | $8.8 \times 10^6$ | $1.4 \times 10^{-2}$ | 1600 | $1.2 \times 10^6$ | $1.8 \times 10^{-2}$ | 15000 | $8.2 \times 10^5$ | $1.5 \times 10^{-3}$ | 1900 |

-continued

Ligand binding profile of ActRIIB-Fc:ALK3-Fc heterodimer compared to
ActRIIB-Fc homodimer and ALK3-Fc homodimer

| | ActRIIB-Fc homodimer | | | ALK3-Fc homodimer | | | ActRIIB-Fc:ALK3-Fc heterodimer | | |
|---|---|---|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| BMP9 | $3.9 \times 10^7$ | $1.3 \times 10^{-3}$ | 34 | No binding | | | Transient* | | >33000 |
| BMP10 | $5.9 \times 10^7$ | $2.0 \times 10^{-4}$ | 4 | No binding | | | $3.0 \times 10^7$ | $9.4 \times 10^{-4}$ | 31 |
| GDF3 | $1.6 \times 10^6$ | $2.3 \times 10^{-3}$ | 1400 | No binding | | | $1.4 \times 10^7$ | $8.2 \times 10^{-2}$ | 5900 |
| GDF5 | Transient* | | >9600 | $4.8 \times 10^5$ | $1.1 \times 10^{-2}$ | 22000 | $1.2 \times 10^7$ | $8.3 \times 10^{-4}$ | 70 |
| GDF6 | — | | | $3.4 \times 10^4$ | $1.3 \times 10^{-3}$ | 40000 | $2.8 \times 10^5$ | $4.5 \times 10^{-2}$ | 1600 |
| GDF7 | Transient* | | >12000 | $2.2 \times 10^5$ | $2.7 \times 10^{-2}$ | 12000 | $7.5 \times 10^6$ | $4.0 \times 10^{-4}$ | 52 |
| GDF8 | $8.3 \times 10^5$ | $2.3 \times 10^{-4}$ | 280 | No binding | | | $3.0 \times 10^6$ | $9.2 \times 10^{-4}$ | 310 |
| GDF11 | $5.0 \times 10^7$ | $1.1 \times 10^{-4}$ | 2 | No binding | | | $1.6 \times 10^7$ | $1.1 \times 10^{-3}$ | 66 |

*Indeterminate due to transient nature of interaction
—Not tested

Figure 7:
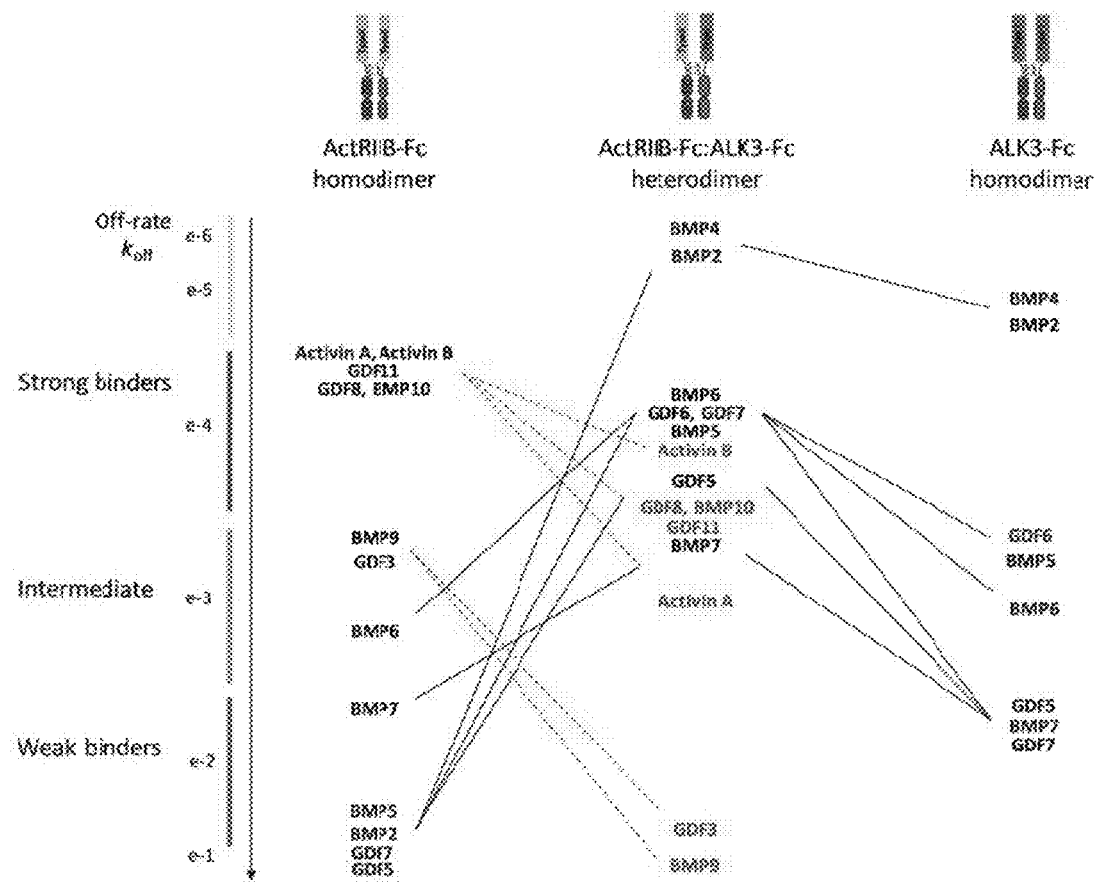
FIG. 7 shows ligand binding data for an ActRIIB-Fc:ALK3-Fc heterodimeric protein complex as compared to ActRIIB-Fc homodimer and ALK3-Fc homodimer. Format is the same as in FIG. 6. As shown, the ActRIIB-Fc:ALK3-Fc heterodimer binds BMP2 and BMP4 with exceptionally high affinity and displays greatly enhanced binding to BMP5, BMP6, BMP7, GDF5, GDF6, and GDF7 compared with either homodimer. Compared to ActRIIB homodimer, the ActRIIB-Fc:ALK3-Fc heterodimer displays reduced binding to activin A, activin B, BMP10, GDF8, and GDF11 and also discriminates among these ligands to a greater degree, particularly between activin A and activin B. In addition, the ability of ActRIIB-Fc homodimer to bind BMP9 and GDF3 with high affinity is absent for ActRIIB-Fc:ALK3-Fc heterodimer.

These comparative binding data demonstrate that the ActRIIB-Fc:ALK3-Fc heterodimer has an altered binding profile/selectivity relative to either the ActRIIB-Fc homodimer or ALK3-Fc homodimer. The ActRIIB-Fc:ALK3-Fc heterodimer binds BMP2 and BMP4 with exceptionally high affinity and displays greatly enhanced binding to BMP5, BMP6, BMP7, GDF5, GDF6, and GDF7 compared with either homodimer. Compared to ActRIIB homodimer, the ActRIIB-Fc:ALK3-Fc heterodimer displays reduced binding to activin A, activin B, BMP10, GDF8, and GDF11 and also discriminates among these ligands to a greater degree, particularly between activin A and activin B. In addition, the ability of ActRIIB-Fc homodimer to bind BMP9 and GDF3 with high affinity is absent for ActRIIB-Fc:ALK3-Fc heterodimer. See FIG. 7.

These results therefore demonstrate that the ActRIIB-Fc:ALK3-Fc heterodimer is a selective inhibitor of activin B, the GDF5/GDF6/GDF7 ligand subfamily, and several key BMP ligands excluding most notably BMP9. Accordingly, an ActRIIB-Fc:ALK3-Fc heterodimer will be more useful than either an ActRIIB-Fc homodimer or an ALK3-Fc homodimer in certain applications where such selective antagonism is advantageous. Examples include therapeutic applications where it is desirable to retain antagonism of BMP2, BMP4, BMP5, and BMP6 or activin B but minimize antagonism of one or more ligands with anabolic muscle effects (e.g., activin A and GDF8) or ligands with angiogenic effects (e.g., BMP9 and BMP10).

Example 6. Activity Profile of ActRIIB-Fc:ALK3-Fc Heterodimer in Mice Compared to ActRIIB-Fc Homodimer and ALK3-Fc Homodimer Homodimeric and heterodimeric complexes were tested in mice to investigate differences in their activity profiles in vivo. Wild-type C57BL/6 mice were dosed intraperitoneally with ActRIIB-Fc homodimer (10 mg/kg), ALK3-Fc homodimer (10 mg/kg), ActRIIB-Fc:ALK4-Fc heterodimer (3 or 10 mg/kg), or vehicle (phosphate-buffered saline, PBS) twice per week for 6.5 weeks (46 days) beginning at 10 weeks of age (n=5 mice per group). Study endpoints included body weight, total adipose mass as determined by nuclear magnetic resonance (NMR) at baseline and study completion (6.5 weeks), and total bone mineral density as determined by dual energy x-ray absorptiometry (DEXA) at baseline and 6.5 weeks.

Activity of ActRIIB-Fc and ALK3-Fc Complexes
in Wild-Type Mice Compared to Vehicle

| Endpoint | ActRIIB-Fc homodimer | ALK3-Fc homodimer | ActRIIB-Fc:ALK3-Fc heterodimer | |
|---|---|---|---|---|
| 6.5 wk | 10 mg/kg | 10 mg/kg | 10 mg/kg | 3 mg/kg |
| Body weight | ↑ 23% * | ↓ 3% | ↓ 0.5% | ↓ 1% |
| Total adipose mass | ↓ 41% * | ↓ 12% | ↓ 14% * | ↓ 18% * |
| Total bone mineral density | ↑ 8% * | ↑ 6% * | ↑ 9% * | ↑ 10% * |

* $P < 0.05$ vs. vehicle

Study results are summarized in the table above. As expected, the ActRIIB-Fc homodimer significantly increased body weight and total bone mineral density, and significantly reduced total adipose mass, all compared to vehicle. Also as expected, the ALK3-Fc homodimer significantly increased total bone mineral density compared to vehicle but unlike the ActRIIB-Fc homodimer did not significantly alter either body weight or total adipose mass. The ActRIIB-Fc:ALK3-Fc heterodimer notably displayed an activity profile different from either the ActRIIB-Fc homodimer or the ALK3-Fc homodimer. Treatment of mice with the ActRIIB-Fc:ALK4-Fc heterodimer at either dose level significantly increased bone mineral density at least as well either homodimer. However, unlike ALK3-Fc homodimer, the ActRIIB-Fc:ALK3-Fc heterodimer significantly reduced adipose mass, and unlike ActRIIB-Fc homodimer, the ActRIIB-Fc:ALK3-Fc heterodimer signficantly reduced adipose mass without altering body weight. Thus, an ActRIIB-Fc:ALK3-Fc heterodimer exerts beneficial effects on bone together with potentially beneficial effects on adipose tissue. This novel selectivity will be useful, for example, in treating patients in need of stimulatory effects on bone and inhibitory effects on fat but not in need of altered body weight.

Example 7. Generation of an ActRIIB-Fc:ALK7-Fc Heterodimer

Applicants constructed a soluble ActRIIB-Fc:ALK7-Fc heteromeric complex comprising the extracellular domains of human ActRIIB and human ALK7, which are each fused to an Fc domain with a linker positioned between the extracellular domain and the Fc domain. The individual constructs are referred to as ActRIIB-Fc and ALK7-Fc, respectively.

Formation of heteromeric ALK7-Fc:ActRIIB-Fc may be guided by approaches similar to those described in Example 1.

In a first approach, the polypeptide sequence of the ActRIIB-Fc fusion protein and a nucleic acid sequence encoding it are provided above in Example 1 as SEQ ID NOs: 100-102.

The complementary ALK7-Fc fusion protein employs the TPA leader and is as follows (SEQ ID NO: 112):

```
                                                      (SEQ ID NO: 112)
  1 MDAMKRGLCC VLLLCGAVFV SPGAGLKCVC LLCDSSNFTC QTEGACWASV

51 MLTNGKEQVI KSCVSLPELN AQVFCHSSNN VTKTECCFTD FCNNITLHLP

101 TASPNAPKLG PMETGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPSR

251 EEMTKNQVSL TCLVKGFYPS DIAVEWESNG QPENNYDTTP PVLDSDGSFF

301 LYSDLTVDKS RWQQGNVFSC SVMHEALHNH YTQKSLSLSP G
```

The signal sequence and linker sequence are underlined. To promote formation of the ActRIIB-Fc:ALK7-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 112 may optionally be provided with a lysine added at the C-terminus.

This ALK7-Fc fusion protein is encoded by the following nucleic acid (SEQ ID NO: 113):

```
                                                      (SEQ ID NO: 113)
   1 ATGGATGCAA TGAAGAGAGG GCTCTGCTGT GTGCTGCTGC TGTGTGGAGC

51 AGTCTTCGTT TCGCCCGGCG CCGGACTGAA GTGTGTATGT CTTTTGTGTG

101 ATTCTTCAAA CTTTACCTGC CAAACAGAAG GAGCATGTTG GGCATCAGTC

151 ATGCTAACCA ATGGAAAAGA GCAGGTGATC AAATCCTGTG TCTCCCTTCC

201 AGAACTGAAT GCTCAAGTCT TCTGTCATAG TTCCAACAAT GTTACCAAAA

251 CCGAATGCTG CTTCACAGAT TTTTGCAACA ACATAACACT GCACCTTCCA

301 ACAGCATCAC CAAATGCCCC AAAACTTGGA CCCATGGAGA CCGGTGGTGG

351 AACTCACACA TGCCCACCGT GCCCAGCACC TGAACTCCTG GGGGGACCGT

401 CAGTCTTCCT CTTCCCCCCA AAACCCAAGG ACACCCTCAT GATCTCCCGG

451 ACCCCTGAGG TCACATGCGT GGTGGTGGAC GTGAGCCACG AAGACCCTGA

501 GGTCAAGTTC AACTGGTACG TGGACGGCGT GGAGGTGCAT AATGCCAAGA

551 CAAAGCCGCG GGAGGAGCAG TACAACAGCA CGTACCGTGT GGTCAGCGTC

601 CTCACCGTCC TGCACCAGGA CTGGCTGAAT GGCAAGGAGT ACAAGTGCAA

651 GGTCTCCAAC AAAGCCCTCC CAGCCCCCAT CGAGAAAACC ATCTCCAAAG

701 CCAAAGGGCA GCCCCGAGAA CCACAGGTGT ACACCCTGCC CCCATCCCGG

751 GAGGAGATGA CCAAGAACCA GGTCAGCCTG ACCTGCCTGG TCAAAGGCTT

801 CTATCCCAGC GACATCGCCG TGGAGTGGGA GAGCAATGGG CAGCCGGAGA

851 ACAACTACGA CACCACGCCT CCCGTGCTGG ACTCCGACGG CTCCTTCTTC

901 CTCTATAGCG ACCTCACCGT GGACAAGAGC AGGTGGCAGC AGGGGAACGT

951 CTTCTCATGC TCCGTGATGC ATGAGGCTCT GCACAACCAC TACACGCAGA

1001 AGAGCCTCTC CCTGTCTCCG GGT
```

The mature ALK7-Fc fusion protein sequence (SEQ ID NO: 114) is expected to be as follows and may optionally be provided with a lysine added at the C-terminus.

```
                                                      (SEQ ID NO: 114)
  1 GLKCVCLLCD SSNFTCQTEG ACWASVMLTN GKEQVIKSCV SLPELNAQVF

51 CHSSNNVTKT ECCFTDFCNN ITLHLPTASP NAPKLGPMET GGGTHTCPPC

101 PAPELLGGPS VFLFPPKPKD TLMISRTPEV TCVVVDVSHE DPEVKFNWYV

151 DGVEVHNAKT KPREEQYNST YRVVSVLTVL HQDWLNGKEY KCKVSNKALP

201 APIEKTISKA KGQPREPQVY TLPPSREEMT KNQVSLTCLV KGFYPSDIAV

251 EWESNGQPEN NYDTTPPVLD SDGSFFLYSD LTVDKSRWQQ GNVFSCSVMH

301 EALHNHYTQK SLSLSPG
```

The ActRIIB-Fc and ALK7-Fc fusion proteins of SEQ ID NO: 102 and SEQ ID NO: 114, respectively, may be co-expressed and purified from a CHO cell line to give rise to a heteromeric complex comprising ActRIIB-Fc:ALK7-Fc.

In another approach to promoting the formation of heteromultimer complexes using asymmetric Fc fusion proteins, illustrated in the ActRIIB-Fc and ALK7-Fc polypeptide sequences of SEQ ID NOs: 401-402 and 405-406, respectively, the Fc domains are altered to introduce complementary hydrophobic interactions and an additional intermolecular disulfide bond. The ActRIIB-Fc fusion polypeptide sequences are discussed in Example 1.

The complementary form of ALK7-Fc fusion polypeptide (SEQ ID NO: 405) is as follows:

```
                                                      (SEQ ID NO: 405)
  1 MDAMKRGLCC VLLLCGAVFV SPGAGLKCVC LLCDSSNFTC QTEGACWASV

51 MLTNGKEQVI KSCVSLPELN AQVFCHSSNN VTKTECCFTD FCNNITLHLP

101 TASPNAPKLG PMETGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVCTLPPSR

251 EEMTKNQVSL SCAVKGFYPS DIAVEWESNG QPENNYKTTP PVLDSDGSFF

301 LVSKLTVDKS RWQQGNVFSC SVMHEALHNH YTQKSLSLSP GK
```

The leader sequence and linker sequence are underlined. To guide heterodimer formation with the ActRIIB-Fc fusion polypeptide of SEQ ID NOs 401 and 402 above, four amino acid substitutions can be introduced into the Fc domain of the ALK7 fusion polypeptide as indicated by double underline above. Furthermore, the C-terminal lysine residue of the Fc domain can be deleted. The amino acid sequence of SEQ ID NO: 405 may optionally be provided with the lysine removed from the C-terminus.

The mature ALK7-Fc fusion protein sequence (SEQ ID NO: 406) is expected to be as follows and may optionally be provided with the lysine removed from the C-terminus.

```
                                                      (SEQ ID NO: 406)
  1 GLKCVCLLCD SSNFTCQTEG ACWASVMLTN GKEQVIKSCV SLPELNAQVF

51 CHSSNNVTKT ECCFTDFCNN ITLHLPTASP NAPKLGPMET GGGTHTCPPC

101 PAPELLGGPS VFLFPPKPKD TLMISRTPEV TCVVVDVSHE DPEVKFNWYV

151 DGVEVHNAKT KPREEQYNST YRVVSVLTVL HQDWLNGKEY KCKVSNKALP

201 APIEKTISKA KGQPREPQVC TLPPSREEMT KNQVSLSCAV KGFYPSDIAV

251 EWESNGQPEN NYKTTPPVLD SDGSFFLVSK LTVDKSRWQQ GNVFSCSVMH

301 EALHNHYTQK SLSLSPGK
```

The ActRIIB-Fc and ALK7-Fc proteins of SEQ ID NO: 402 and SEQ ID NO: 406, respectively, may be co-expressed and purified from a CHO cell line, to give rise to a heteromeric complex comprising ActRIIB-Fc:ALK7-Fc.

Purification of various ActRIIB-Fc:ALK7-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 8. Ligand Binding Profile of ActRIIB-Fc:ALK7-Fc Heterodimer Compared to ActRIIB-Fc Homodimer and ALK7-Fc Homodimer A Biacore™-based binding assay was used to compare ligand binding selectivity of the ActRIIB-Fc:ALK7-Fc heterodimeric complex described above with that of ActRIIB-Fc and ALK7-Fc homodimeric complexes. The ActRIIB-Fc:ALK7-Fc heterodimer, ActRIIB-Fc homodimer, and ALK7-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profile of ActRIIB-Fc:ALK7-Fc heterodimer compared to ActRIIB-Fc homodimer and ALK7-Fc homodimer

| Ligand | ActRIIB-Fc homodimer | | | ALK7-Fc homodimer | | | ActRIIB-Fc:ALK7-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.3 \times 10^7$ | $1.4 \times 10{-4}$ | 11 | No binding | | | $4.4 \times 10^7$ | $1.9 \times 10^{-3}$ | 43 |
| Activin B | $1.5 \times 10^7$ | $1.6 \times 10{-4}$ | 8 | No binding | | | $1.2 \times 10^7$ | $2.0 \times 10{-4}$ | 17 |
| BMP5 | $2.6 \times 10^7$ | $7.5 \times 10^{-2}$ | 2900 | No binding | | | $1.5 \times 10^5$ | $8.5 \times 10^{-3}$ | 57000 |
| BMP6 | $2.4 \times 10^7$ | $3.9 \times 10^{-3}$ | 160 | No binding | | | $1.2 \times 10^6$ | $6.3 \times 10^{-3}$ | 5300 |
| BMP9 | $1.2 \times 10^8$ | $1.2 \times 10^{-3}$ | 10 | No binding | | | Transient* | | >1400 |
| BMP10 | $5.9 \times 10^6$ | $1.5 \times 10{-4}$ | 25 | No binding | | | $1.5 \times 10^7$ | $2.8 \times 10^{-3}$ | 190 |
| GDF3 | $1.4 \times 10^6$ | $2.2 \times 10^{-3}$ | 1500 | No binding | | | $2.3 \times 10^6$ | $1.0 \times 10^{-2}$ | 4500 |
| GDF8 | $3.5 \times 10^6$ | $2.4 \times 10{-4}$ | 69 | No binding | | | $3.7 \times 10^6$ | $1.0 \times 10^{-3}$ | 270 |
| GDF11 | $9.6 \times 10^7$ | $1.5 \times 10{-4}$ | 2 | No binding | | | $9.5 \times 10^7$ | $7.5 \times 10{-4}$ | 8 |

*Indeterminate due to transient nature of interaction

Figure 8:
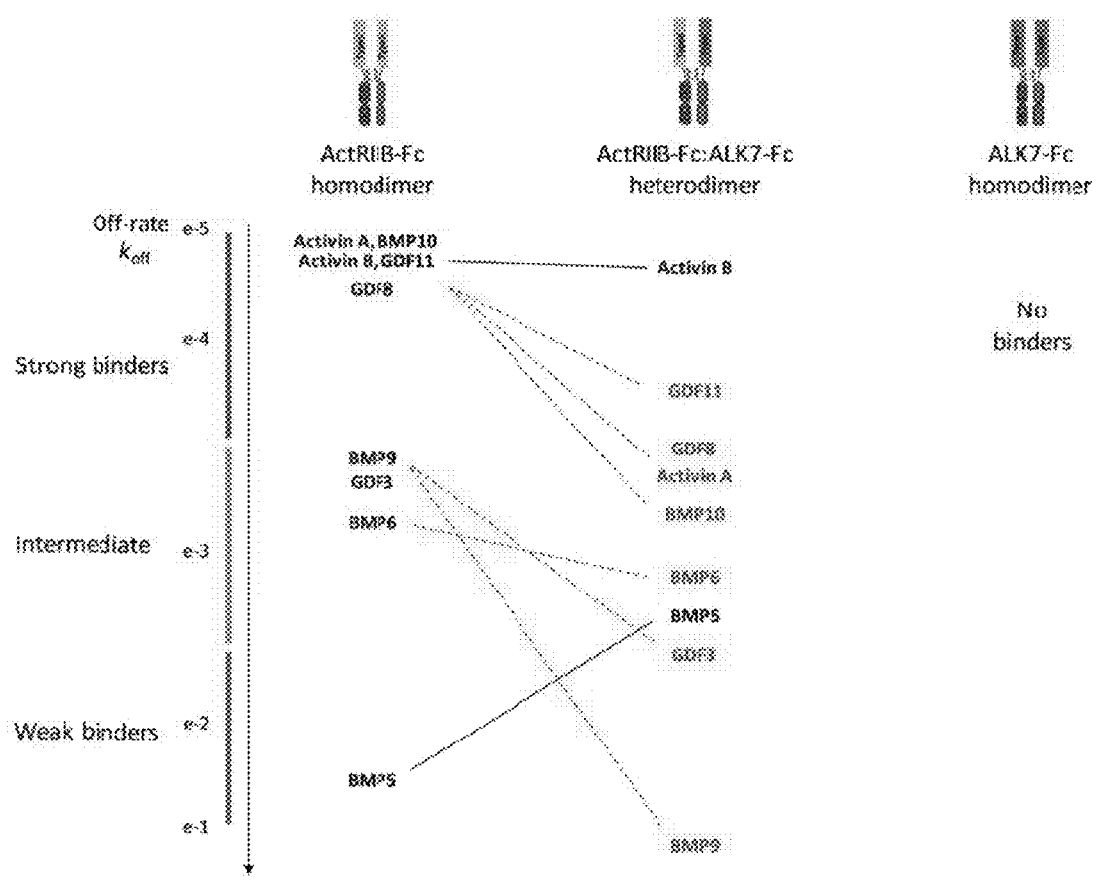
FIG. 8 shows ligand binding data for an ActRIIB-Fc:ALK7-Fc heterodimeric protein complex as compared to ActRIIB-Fc homodimer and ALK7-Fc homodimer. Format is the same as in FIG. 6. As shown, four of the five ligands with strong binding to ActRIIB-Fc homodimer (activin A, BMP10, GDF8, and GDF11) exhibit reduced binding to the ActRIIB-Fc:ALK7-Fc heterodimer, the exception being activin B which retains tight binding to the heterodimer. In addition, three ligands with intermediate binding to ActRIIB-Fc homodimer (GDF3, BMP6, and particularly BMP9) exhibit reduced binding to the ActRIIB-Fc:ALK7-Fc heterodimer. In contrast, BMP5 binds the ActRIIB-Fc:ALK7 heterodimer with intermediate strength despite only weak binding to ActRIIB-Fc homodimer. No ligands tested bind to ALK7-Fc homodimer.

These comparative binding data demonstrate that the ActRIIB-Fc:ALK7-Fc heterodimer has a different binding profile compared to either the ActRIIB-Fc homodimer or ALK7-Fc homodimer. Interestingly, four of the five ligands with strong binding to ActRIIB-Fc homodimer (activin A, BMP10, GDF8, and GDF11) exhibit reduced binding to the ActRIIB-Fc:ALK7-Fc heterodimer, the exception being activin B which retains tight binding to the heterodimer. In addition, three ligands with intermediate binding to ActRIIB-Fc homodimer (GDF3, BMP6, and particularly BMP9) exhibit reduced binding to the ActRIIB-Fc:ALK7-Fc heterodimer. In contrast, BMP5 binds the ActRIIB-Fc:ALK7 heterodimer with intermediate strength despite only weak binding to ActRIIB-Fc homodimer. No ligands tested bind to ALK7-Fc homodimer. See FIG. 8.

These results therefore demonstrate that the ActRIIB-Fc:ALK7-Fc heterodimer is a more selective antagonist of activin B in comparison to a ActRIIB-Fc homodimer. Accordingly, an ActRIIB-Fc:ALK7-Fc heterodimer will be more useful than an ActRIIB-Fc homodimer in certain applications where such selective antagonism is advantageous. Examples include therapeutic applications where it is desirable to retain antagonism of activin B but minimize antagonism of one or more of activin A, GDF3, GDF8, GDF11, BMP9, or BMP10.

Example 9. Generation of an ActRIIB-Fc:ALK2-Fc Heterodimer

Applicants constructed a soluble ActRIIB-Fc:ALK2-Fc heteromeric complex comprising the extracellular domains of human ActRIIB and human ALK2, which are each fused to an Fc domain with a linker positioned between the extracellular domain and the Fc domain. The individual constructs are referred to as ActRIIB-Fc and ALK2-Fc, respectively.

Formation of heteromeric ActRIIB-Fc:ALK2-Fc may be guided by approaches similar to those described in Example 1.

In a first approach, the polypeptide sequence of the ActRIIB-Fc fusion protein and a nucleic acid sequence encoding it are provided in Example 1 as SEQ ID NOs: 100-102.

The complementary ALK2-Fc fusion protein employs the TPA leader and is as follows (SEQ ID NO: 136):

```
                                                    (SEQ ID NO: 136)
  1 MDAMKRGLCC VLLLCGAVFV SPGAMEDEKP KVNPKLYMCV CEGLSCGNED

51 HCEGQQCFSS LSINDGFHVY QKGCFQVYEQ GKMTCKTPPS PGQAVECCQG

101 DWCNRNITAQ LPTKGKSFPG TQNFHLETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSREEMTKN QVSLTCLVKG FYPSDIAVEW ESNGQPENNY

301 DTTPPVLDSD GSFFLYSDLT VDKSRWQQGN VFSCSVMHEA LHNHYTQKSL

351 SLSPG
```

The signal sequence and linker sequence are underlined. To promote formation of the ActRIIB-Fc:ALK2-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 136 may optionally be provided with a lysine added at the C-terminus.

This ALK2-Fc fusion protein is encoded by the following nucleic acid (SEQ ID NO: 137):

```
                                                      (SEQ ID NO: 137)
   1 ATGGATGCAA TGAAGAGAGG GCTCTGCTGT GTGCTGCTGC TGTGTGGAGC

51 AGTCTTCGTT TCGCCCGGCG CCATGGAAGA TGAGAAGCCC AAGGTCAACC

101 CCAAACTCTA CATGTGTGTG TGTGAAGGTC TCTCCTGCGG TAATGAGGAC

151 CACTGTGAAG GCCAGCAGTG CTTTTCCTCA CTGAGCATCA ACGATGGCTT

201 CCACGTCTAC CAGAAAGGCT GCTTCCAGGT TTATGAGCAG GGAAAGATGA

251 CCTGTAAGAC CCCGCCGTCC CCTGGCCAAG CTGTGGAGTG CTGCCAAGGG

301 GACTGGTGTA ACAGGAACAT CACGGCCCAG CTGCCCACTA AGGAAAATC

351 CTTCCCTGGA ACACAGAATT TCCACTTGGA GACCGGTGGT GGAACTCACA

401 CATGCCCACC GTGCCCAGCA CCTGAACTCC TGGGGGGACC GTCAGTCTTC

451 CTCTTCCCCC CAAAACCCAA GGACACCCTC ATGATCTCCC GGACCCCTGA

501 GGTCACATGC GTGGTGGTGG ACGTGAGCCA CGAAGACCCT GAGGTCAAGT

551 TCAACTGGTA CGTGGACGGC GTGGAGGTGC ATAATGCCAA GACAAAGCCG

601 CGGGAGGAGC AGTACAACAG CACGTACCGT GTGGTCAGCG TCCTCACCGT

651 CCTGCACCAG GACTGGCTGA ATGGCAAGGA GTACAAGTGC AAGGTCTCCA

701 ACAAAGCCCT CCCAGCCCCC ATCGAGAAAA CCATCTCCAA AGCCAAAGGG

751 CAGCCCCGAG AACCACAGGT GTACACCCTG CCCCCATCCC GGGAGGAGAT

801 GACCAAGAAC CAGGTCAGCC TGACCTGCCT GGTCAAAGGC TTCTATCCCA

851 GCGACATCGC CGTGGAGTGG GAGAGCAATG GCAGCCGGA GAACAACTAC

901 GACACCACGC CTCCCGTGCT GGACTCCGAC GGCTCCTTCT TCCTCTATAG

951 CGACCTCACC GTGGACAAGA GCAGGTGGCA GCAGGGGAAC GTCTTCTCAT

1001 GCTCCGTGAT GCATGAGGCT CTGCACAACC ACTACACGCA GAAGAGCCTC

1051 TCCCTGTCTC CGGGT
```

The mature ALK2-Fc fusion protein sequence (SEQ ID NO: 138) is as follows and may optionally be provided with a lysine added at the C-terminus.

```
                                                          (SEQ ID NO: 138)
  1 MEDEKPKVNP KLYMCVCEGL SCGNEDHCEG QQCFSSLSIN DGFHVYQKGC

51 FQVYEQGKMT CKTPPSPGQA VECCQGDWCN RNITAQLPTK GKSFPGTQNF

101 HLETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPSR EEMTKNQVSL

251 TCLVKGFYPS DIAVEWESNG QPENNYDTTP PVLDSDGSFF LYSDLTVDKS

301 RWQQGNVFSC SVMHEALHNH YTQKSLSLSP G
```

The ActRIIB-Fc and ALK2-Fc fusion proteins of SEQ ID NO: 102 and SEQ ID NO: 138, respectively, may be co-expressed and purified from a CHO cell line to give rise to a heteromeric complex comprising ActRIIB-Fc:ALK2-Fc.

In another approach to promoting the formation of heteromultimer complexes using asymmetric Fc fusion proteins, illustrated in the ActRIIB-Fc and ALK2-Fc polypeptide sequences of SEQ ID NOs: 401-402 and 421-422, respectively, the Fc domains are altered to introduce complementary hydrophobic interactions and an additional intermolecular disulfide bond. The ActRIIB-Fc fusion polypeptide sequences are discussed in Example 1.

The complementary form of ALK2-Fc fusion polypeptide (SEQ ID NO: 421) is as follows:

```
                                                          (SEQ ID NO: 421)
  1 MDAMKRGLCC VLLLCGAVFV SPGAMEDEKP KVNPKLYMCV CEGLSCGNED

51 HCEGQQCFSS LSINDGFHVY QKGCFQVYEQ GKMTCKTPPS PGQAVECCQG

101 DWCNRNITAQ LPTKGKSFPG TQNFHLETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVCTL PPSREEMTKN QVSLSCAVKG FYPSDIAVEW ESNGQPENNY

301 KTTPPVLDSD GSFFLVSKLT VDKSRWQQGN VFSCSVMHEA LHNHYTQKSL

351 SLSPGK
```

The leader sequence and linker sequence are underlined. To guide heterodimer formation with the ActRIIB-Fc fusion polypeptide of SEQ ID NOs 401 and 402 above, four amino acid substitutions can be introduced into the Fc domain of the ALK2 fusion polypeptide as indicated by double underline above. Furthermore, the C-terminal lysine residue of the Fc domain can be deleted. The amino acid sequence of SEQ ID NO: 421 may optionally be provided with the lysine removed from the C-terminus.

The mature ALK2-Fc fusion protein sequence (SEQ ID NO: 422) is as follows and may optionally be provided with the lysine removed from the C-terminus.

```
                                                          (SEQ ID NO: 422)
  1 MEDEKPKVNP KLYMCVCEGL SCGNEDHCEG QQCFSSLSIN DGFHVYQKGC

51 FQVYEQGKMT CKTPPSPGQA VECCQGDWCN RNITAQLPTK GKSFPGTQNF

101 HLETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVCTLPPSR EEMTKNQVSL

251 SCAVKGFYPS DIAVEWESNG QPENNYKTTP PVLDSDGSFF LVSKLTVDKS

301 RWQQGNVFSC SVMHEALHNH YTQKSLSLSP GK
```

The ActRIIB-Fc and ALK2-Fc proteins of SEQ ID NO: 402 and SEQ ID NO: 422, respectively, may be co-expressed and purified from a CHO cell line, to give rise to a heteromeric complex comprising ActRIIB-Fc:ALK2-Fc.

Purification of various ActRIIB-Fc:ALK2-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Figure 9:
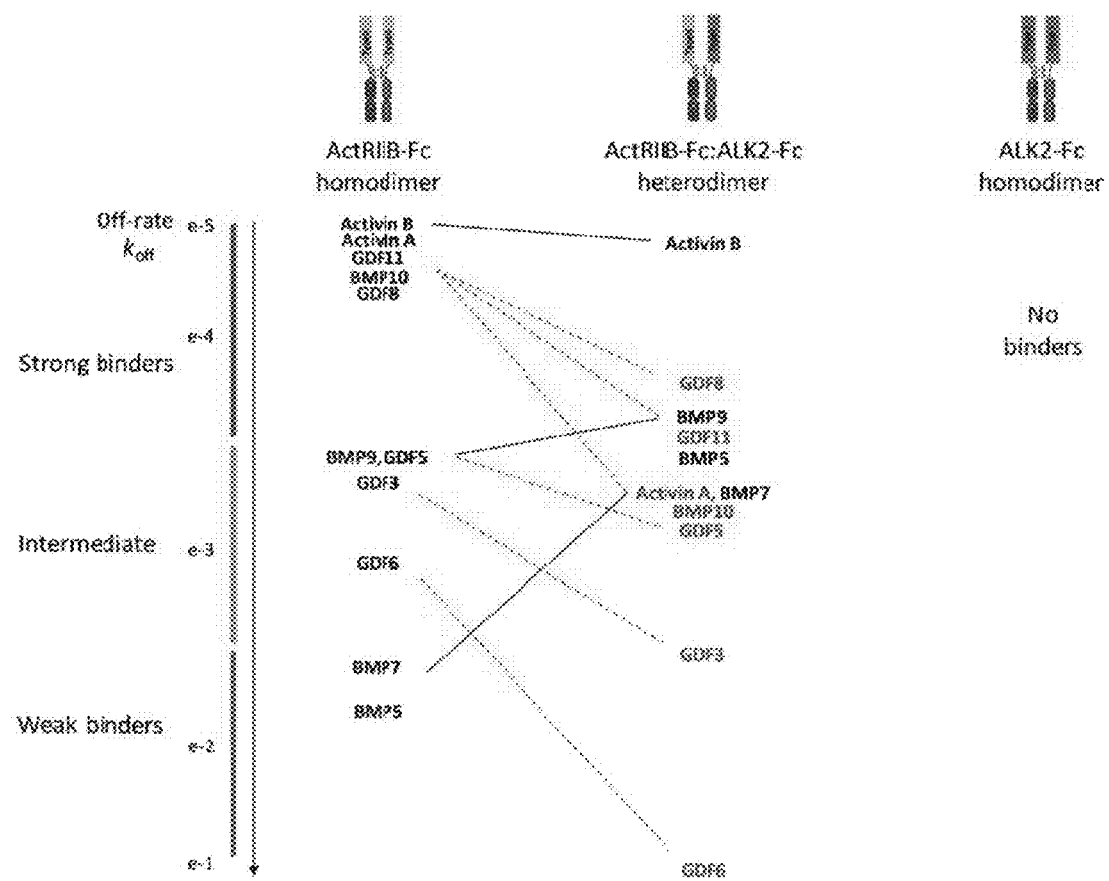
FIG. 9 shows ligand binding data for an ActRIIB-Fc:ALK2-Fc heterodimeric protein complex as compared to ActRIIB-Fc homodimer and ALK2-Fc homodimer. Format is the same as in FIG. 6. As shown, the ActRIIB-Fc:ALK2-Fc heterodimer exhibits preferential and strong binding to activin B, thus resembling ActRIIB-Fc:ALK7-Fc heterodimer (FIG. 8). However, ActRIIB-Fc:ALK2-Fc heterodimer differs from ActRIIB-Fc:ALK7-Fc in part by retaining the tight binding to BMP9 characteristic of ActRIIB-Fc homodimer. No ligands tested bind to ALK2-Fc homodimer.

Example 10. Ligand Binding Profile of ActRIIB-Fc:ALK2-Fc Heterodimer Compared to ActRIIB-Fc Homodimer and ALK2-Fc Homodimer A Biacore™-based binding assay was used to compare ligand binding selectivity of the ActRIIB-Fc:ALK2-Fc heterodimeric complex described above with that of ActRIIB-Fc and ALK2-Fc homodimeric complexes. The ActRIIB-Fc:ALK2-Fc heterodimer, ActRIIB-Fc homodimer, and ALK2-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

mer, whereas ActRIIB-Fc:ALK7-Fc binds BMP9 very weakly, if at all. No ligands tested bind to ALK2-Fc homodimer. See FIG. 9.

These results demonstrate that the ActRIIB-Fc:ALK2-Fc heterodimer is a more selective antagonist of activin B compared to ActRIIB-Fc homodimer. Accordingly, an ActRIIB-Fc:ALK2-Fc heterodimer will be useful in certain applications where such selective antagonism is advantageous. Examples include therapeutic applications where it is desirable to retain antagonism primarily of activin B and to supplement that with antagonism secondarily of BMP9, GDF8, and GDF11.

Example 11. Generation of an ActRIIB-Fc:ALK5-Fc Heterodimer

Applicants constructed a soluble ActRIIB-Fc:ALK5-Fc heteromeric complex comprising the extracellular domains of human ActRIIB and human ALK5, which are each fused to an Fc domain with a linker positioned between the extracellular domain and the Fc domain. The individual constructs are referred to as ActRIIB-Fc and ALK5-Fc, respectively.

Ligand binding profile of ActRIIB-Fc:ALK2-Fc heterodimer compared to ActRIIB-Fc homodimer and ALK2-Fc homodimer

| Ligand | ActRIIB-Fc Homodimer | | | ALK2-Fc Homodimer | | | ActRIIB-Fc:ALK2-Fc Heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.2 \times 10^7$ | $1.7 \times 10^{-4}$ | 15 | No binding | | | $3.4 \times 10^7$ | $2.6 \times 10^{-3}$ | 76 |
| Activin B | $3.8 \times 10^6$ | $1.1 \times 10^{-4}$ | 28 | No binding | | | $3.2 \times 10^6$ | $1.5 \times 10^{-4}$ | 47 |
| BMP5 | $3.8 \times 10^6$ | $3.7 \times 10^{-2}$ | 9700 | No binding | | | $1.2 \times 10^6$ | $1.4 \times 10^{-3}$ | 1200 |
| BMP7 | $8.8 \times 10^6$ | $1.4 \times 10^{-2}$ | 1600 | No binding | | | $1.5 \times 10^7$ | $2.6 \times 10^{-3}$ | 170 |
| BMP9 | $3.9 \times 10^7$ | $1.3 \times 10^{-3}$ | 34 | No binding | | | $3.2 \times 10^6$ | $8.9 \times 10^{-4}$ | 280 |
| BMP10 | $5.4 \times 10^7$ | $2.8 \times 10^{-4}$ | 5 | No binding | | | $5.5 \times 10^7$ | $2.9 \times 10^{-3}$ | 53 |
| GDF3 | $1.2 \times 10^6$ | $2.0 \times 10^{-3}$ | 1700 | No binding | | | $1.8 \times 10^6$ | $1.2 \times 10^{-2}$ | 6500 |
| GDF5 | $1.2 \times 10^6$ | $1.4 \times 10^{-3}$ | 1100 | No binding | | | $8.8 \times 10^5$ | $4.4 \times 10^{-3}$ | 5000 |
| GDF6 | $1.5 \times 10^5$ | $5.7 \times 10^{-3}$ | 39000 | No binding | | | Transient* | | >240000 |
| GDF8 | $2.5 \times 10^6$ | $3.2 \times 10^{-4}$ | 130 | No binding | | | $2.1 \times 10^6$ | $7.3 \times 10^{-4}$ | 360 |
| GDF11 | $2.0 \times 10^6$ | $2.2 \times 10^{-4}$ | 110 | No binding | | | $1.6 \times 10^6$ | $9.3 \times 10^{-4}$ | 600 |

*Indeterminate due to transient nature of interaction

These comparative binding data demonstrate that the ActRIIB-Fc:ALK2-Fc heterodimer exhibits a ligand binding profile different from either the ActRIIB-Fc homodimer or the ALK2-Fc homodimer. ActRIIB-Fc:ALK2-Fc heterodimer exhibits preferential and strong binding to activin B, thus resembling ActRIIB-Fc:ALK7-Fc heterodimer (see Example 8). However, ActRIIB-Fc:ALK2-Fc heterodimer differs from ActRIIB-Fc:ALK7-Fc in part by retaining the tight binding to BMP9 characteristic of ActRIIB-Fc homodi- Formation of heteromeric ActRIIB-Fc:ALK5-Fc may be guided by approaches similar to those described in Example 1.

In a first approach, the polypeptide sequence of the ActRIIB-Fc fusion protein and a nucleic acid sequence encoding it are provided in Example 1 as SEQ ID NOs: 100-102.

The complementary ALK5-Fc fusion protein employs the TPA leader and is as follows (SEQ ID NO: 139):

(SEQ ID NO: 139)
```
  1 MDAMKRGLCC VLLLCGAVFV SPGAALLPGA TALQCFCHLC TKDNFTCVTD

51 GLCFVSVTET TDKVIHNSMC IAEIDLIPRD RPFVCAPSSK TGSVTTTYCC

101 NQDHCNKIEL PTTVKSSPGL GPVETGGGTH TCPPCPAPEL LGGPSVFLFP

151 PKPKDTLMIS RTPEVTCVVV DVSHEDPEVK FNWYVDGVEV HNAKTKPREE

201 QYNSTYRVVS VLTVLHQDWL NGKEYKCKVS NKALPAPIEK TISKAKGQPR

251 EPQVYTLPPS REEMTKNQVS LTCLVKGFYP SDIAVEWESN GQPENNYDTT

301 PPVLDSDGSF FLYSDLTVDK SRWQQGNVFS CSVMHEALHN HYTQKSLSLS

351 PG
```

The signal sequence and linker sequence are underlined. To promote formation of the ActRIIB-Fc:ALK5-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 139 may optionally be provided with a lysine added at the C-terminus.

This ALK5-Fc fusion protein is encoded by the following nucleic acid (SEQ ID NO: 140):

(SEQ ID NO: 140)
```
   1 ATGGATGCAA TGAAGAGAGG GCTCTGCTGT GTGCTGCTGC TGTGTGGAGC

51 AGTCTTCGTT TCGCCCGGCG CCGCGCTGCT CCCGGGGGCG ACGGCGTTAC

101 AGTGTTTCTG CCACCTCTGT ACAAAAGACA ATTTTACTTG TGTGACAGAT

151 GGGCTCTGCT TTGTCTCTGT CACAGAGACC ACAGACAAAG TTATACACAA

201 CAGCATGTGT ATAGCTGAAA TTGACTTAAT TCCTCGAGAT AGGCCGTTTG

251 TATGTGCACC CTCTTCAAAA ACTGGGTCTG TGACTACAAC ATATTGCTGC

301 AATCAGGACC ATTGCAATAA AATAGAACTT CCAACTACTG TAAAGTCATC

351 ACCTGGCCTT GGTCCTGTGG AAACCGGTGG TGGAACTCAC ACATGCCCAC

401 CGTGCCCAGC ACCTGAACTC CTGGGGGGAC CGTCAGTCTT CCTCTTCCCC

451 CCAAAACCCA AGGACACCCT CATGATCTCC CGGACCCCTG AGGTCACATG

501 CGTGGTGGTG GACGTGAGCC ACGAAGACCC TGAGGTCAAG TTCAACTGGT

551 ACGTGGACGG CGTGGAGGTG CATAATGCCA AGACAAAGCC GCGGGAGGAG

601 CAGTACAACA GCACGTACCG TGTGGTCAGC GTCCTCACCG TCCTGCACCA

651 GGACTGGCTG AATGGCAAGG AGTACAAGTG CAAGGTCTCC AACAAAGCCC

701 TCCCAGCCCC CATCGAGAAA ACCATCTCCA AAGCCAAAGG GCAGCCCCGA

751 GAACCACAGG TGTACACCCT GCCCCCATCC CGGGAGGAGA TGACCAAGAA

801 CCAGGTCAGC CTGACCTGCC TGGTCAAAGG CTTCTATCCC AGCGACATCG

851 CCGTGGAGTG GGAGAGCAAT GGGCAGCCGG AGAACAACTA CGACACCACG

901 CCTCCCGTGC TGGACTCCGA CGGCTCCTTC TTCCTCTATA GCGACCTCAC

951 CGTGGACAAG AGCAGGTGGC AGCAGGGGAA CGTCTTCTCA TGCTCCGTGA

1001 TGCATGAGGC TCTGCACAAC CACTACACGC AGAAGAGCCT CTCCCTGTCT

1051 CCGGGT
```

The mature ALK5-Fc fusion protein sequence (SEQ ID NO: 141) is as follows and may optionally be provided with a lysine added at the C-terminus.

```
                                                    (SEQ ID NO: 141)
    1 ALLPGATALQ CFCHLCTKDN FTCVTDGLCF VSVTETTDKV IHNSMCIAEI

51 DLIPRDRPFV CAPSSKTGSV TTTYCCNQDH CNKIELPTTV KSSPGLGPVE

101 TGGGTHTCPP CPAPELLGGP SVFLFPPKPK DTLMISRTPE VTCVVVDVSH

151 EDPEVKFNWY VDGVEVHNAK TKPREEQYNS TYRVVSVLTV LHQDWLNGKE

201 YKCKVSNKAL PAPIEKTISK AKGQPREPQV YTLPPSREEM TKNQVSLTCL

251 VKGFYPSDIA VEWESNGQPE NNYDTTPPVL DSDGSFFLYS DLTVDKSRWQ

301 QGNVFSCSVM HEALHNHYTQ KSLSLSPG
```

The ActRIIB-Fc and ALK5-Fc fusion proteins of SEQ ID NO: 102 and SEQ ID NO: 141, respectively, may be co-expressed and purified from a CHO cell line to give rise to a heteromeric complex comprising ActRIIB-Fc:ALK5-Fc.

In another approach to promoting the formation of heteromultimer complexes using asymmetric Fc fusion proteins, illustrated in the ActRIIB-Fc and ALK5-Fc polypeptide sequences of SEQ ID NOs: 401-402 and 423-424, respectively, the Fc domains are altered to introduce complementary hydrophobic interactions and an additional intermolecular disulfide bond. The ActRIIB-Fc fusion polypeptide sequences are discussed in Example 1.

The complementary form of ALK5-Fc fusion polypeptide (SEQ ID NO: 423) is as follows:

```
                                                    (SEQ ID NO: 423)
    1 MDAMKRGLCC VLLLCGAVFV SPGAALLPGA TALQCFCHLC TKDNFTCVTD

51 GLCFVSVTET TDKVIHNSMC IAEIDLIPRD RPFVCAPSSK TGSVTTTYCC

101 NQDHCNKIEL PTTVKSSPGL GPVETGGGTH TCPPCPAPEL LGGPSVFLFP

151 PKPKDTLMIS RTPEVTCVVV DVSHEDPEVK FNWYVDGVEV HNAKTKPREE

201 QYNSTYRVVS VLTVLHQDWL NGKEYKCKVS NKALPAPIEK TISKAKGQPR

251 EPQVCTLPPS REEMTKNQVS LSCAVKGFYP SDIAVEWESN GQPENNYKTT

301 PPVLDSDGSF FLVSKLTVDK SRWQQGNVFS CSVMHEALHN HYTQKSLSLS

351 PGK
```

The leader sequence and linker sequence are underlined. To guide heterodimer formation with the ActRIIB-Fc fusion polypeptide of SEQ ID NOs 401 and 402 above, four amino acid substitutions can be introduced into the Fc domain of the ALK5 fusion polypeptide as indicated by double underline above. Furthermore, the C-terminal lysine residue of the Fc domain can be deleted. The amino acid sequence of SEQ ID NO: 423 may optionally be provided with the lysine removed from the C-terminus.

The mature ALK5-Fc fusion protein sequence (SEQ ID NO: 424) is as follows and may optionally be provided with the lysine removed from the C-terminus.

```
                                                    (SEQ ID NO: 424)
    1 ALLPGATALQ CFCHLCTKDN FTCVTDGLCF VSVTETTDKV IHNSMCIAEI

51 DLIPRDRPFV CAPSSKTGSV TTTYCCNQDH CNKIELPTTV KSSPGLGPVE

101 TGGGTHTCPP CPAPELLGGP SVFLFPPKPK DTLMISRTPE VTCVVVDVSH

151 EDPEVKFNWY VDGVEVHNAK TKPREEQYNS TYRVVSVLTV LHQDWLNGKE
```

```
201 YKCKVSNKAL PAPIEKTISK AKGQPREPQV CTLPPSREEM TKNQVSLSCA

251 VKGFYPSDIA VEWESNGQPE NNYKTTPPVL DSDGSFFLVS KLTVDKSRWQ

301 QGNVFSCSVM HEALHNHYTQ KSLSLSPGK
```

The ActRIIB-Fc and ALK5-Fc proteins of SEQ ID NO: 402 and SEQ ID NO: 424, respectively, may be co-expressed and purified from a CHO cell line, to give rise to a heteromeric complex comprising ActRIIB-Fc:ALK5-Fc.

Purification of various ActRIIB-Fc:ALK5-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 12. Ligand Binding Profile of ActRIIB-Fc:ALK5-Fc Heterodimer Compared to ActRIIB-Fc Homodimer and ALK5-Fc Homodimer A Biacore™-based binding assay was used to compare ligand binding selectivity of the ActRIIB-Fc:ALK5-Fc heterodimeric complex described above with that of ActRIIB-Fc and ALK5-Fc homodimeric complexes. The ActRIIB-Fc:ALK5-Fc heterodimer, ActRIIB-Fc homodimer, and ALK5-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profile of ActRIIB-Fc:ALK5-Fc heterodimer compared to ActRIIB-Fc homodimer and ALK5-Fc homodimer

| Ligand | ActRIIB-Fc Homodimer | | | ALK5-Fc Homodimer | | | ActRIIB-Fc:ALK5-Fc Heterodimer | | |
| --- | --- | --- | --- | --- | --- | --- | --- | --- | --- |
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.2 \times 10^7$ | $2.3 \times 10{-4}$ | 19 | No binding | | | $3.6 \times 10^7$ | $1.6 \times 10^{-3}$ | 46 |
| Activin B | $5.1 \times 10^6$ | $1.0 \times 10{-4}$ | 20 | No binding | | | $3.9 \times 10^6$ | $3.1 \times 10{-4}$ | 79 |
| BMP6 | $6.4 \times 10^6$ | $7.0 \times 10^{-3}$ | 1100 | No binding | | | $9.3 \times 10^6$ | $1.5 \times 10^{-2}$ | 1700 |
| BMP9 | $3.9 \times 10^7$ | $1.3 \times 10^{-3}$ | 34 | No binding | | | Transient* | | >6600 |
| BMP10 | $2.1 \times 10^7$ | $3.8 \times 10{-4}$ | 18 | No binding | | | $2.3 \times 10^7$ | $2.2 \times 10^{-3}$ | 150 |
| GDF3 | $4.7 \times 10^5$ | $1.8 \times 10^{-3}$ | 3900 | No binding | | | $1.1 \times 10^5$ | $9.7 \times 10^{-3}$ | 8500 |
| GDF8 | $1.2 \times 10^6$ | $1.9 \times 10{-4}$ | 160 | No binding | | | $1.1 \times 10^6$ | $5.2 \times 10{-4}$ | 490 |
| GDF11 | $1.9 \times 10^6$ | $1.4 \times 10{-4}$ | 74 | No binding | | | $2.3 \times 10^6$ | $4.6 \times 10{-4}$ | 600 |

*Indeterminate due to transient nature of interaction

Example 13. Generation of an ActRIIB-Fc:ALK6-Fc Heterodimer

A soluble ActRIIB-Fc:ALK6-Fc heteromeric complex can be generated comprising the extracellular domains of human ActRIIB and human ALK6, which can each be fused to an Fc domain with a linker positioned between the extracellular domain and the Fc domain. The individual constructs are referred to as ActRIIB-Fc and ALK6-Fc, respectively.

Formation of heteromeric ActRIIB-Fc: ALK6-Fc may be guided by approaches similar to those described in Example 1.

In a first approach, the polypeptide sequence of the ActRIIB-Fc fusion protein and a nucleic acid sequence encoding it are provided above in Example 1 as SEQ ID NOs: 100-102.

The complementary ALK6-Fc fusion protein employs the TPA leader and is as follows (SEQ ID NO: 142):

```
                                                      (SEQ ID NO: 142)
  1 MDAMKRGLCC VLLLCGAVFV SPGAKKEDGE STAPTPRPKV LRCKCHHHCP

51 EDSVNNICST DGYCFTMIEE DDSGLPVVTS GCLGLEGSDF QCRDTPIPHQ

101 RRSIECCTER NECNKDLHPT LPPLKNRDFV DGPIHHRTGG GTHTCPPCPA

151 PELLGGPSVF LFPPKPKDTL MISRTPEVTC VVVDVSHEDP EVKFNWYVDG
```

```
201 VEVHNAKTKP REEQYNSTYR VVSVLTVLHQ DWLNGKEYKC KVSNKALPAP

251 IEKTISKAKG QPREPQVYTL PPSREEMTKN QVSLTCLVKG FYPSDIAVEW

301 ESNGQPENNY DTTPPVLDSD GSFFLYSDLT VDKSRWQQGN VFSCSVMHEA

351 LHNHYTQKSL SLSPG
```

The signal sequence and linker sequence are underlined. To promote formation of the ActRIIB-Fc:ALK6-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 142 may optionally be provided with a lysine added at the C-terminus.

This ALK6-Fc fusion protein is encoded by the following nucleic acid (SEQ ID NO: 143):

```
                                                    (SEQ ID NO: 143)
   1 ATGGATGCAA TGAAGAGAGG GCTCTGCTGT GTGCTGCTGC TGTGTGGAGC

51 AGTCTTCGTT TCGCCCGGCG CCAAGAAAGA GGATGGTGAG AGTACAGCCC

101 CCACCCCCCG TCCAAAGGTC TTGCGTTGTA AATGCCACCA CCATTGTCCA

151 GAAGACTCAG TCAACAATAT TTGCAGCACA GACGGATATT GTTTCACGAT

201 GATAGAAGAG GATGACTCTG GGTTGCCTGT GGTCACTTCT GGTTGCCTAG

251 GACTAGAAGG CTCAGATTTT CAGTGTCGGG ACACTCCCAT TCCTCATCAA

301 AGAAGATCAA TTGAATGCTG CACAGAAAGG AACGAATGTA ATAAAGACCT

351 ACACCCTACA CTGCCTCCAT TGAAAAACAG AGATTTTGTT GATGGACCTA

401 TACACCACAG GACCGGTGGT GGAACTCACA CATGCCCACC GTGCCCAGCA

451 CCTGAACTCC TGGGGGGACC GTCAGTCTTC CTCTTCCCCC CAAAACCCAA

501 GGACACCCTC ATGATCTCCC GGACCCCTGA GGTCACATGC GTGGTGGTGG

551 ACGTGAGCCA CGAAGACCCT GAGGTCAAGT TCAACTGGTA CGTGGACGGC

601 GTGGAGGTGC ATAATGCCAA GACAAAGCCG CGGGAGGAGC AGTACAACAG

651 CACGTACCGT GTGGTCAGCG TCCTCACCGT CCTGCACCAG GACTGGCTGA

701 ATGGCAAGGA GTACAAGTGC AAGGTCTCCA ACAAAGCCCT CCCAGCCCCC

751 ATCGAGAAAA CCATCTCCAA AGCCAAAGGG CAGCCCCGAG AACCACAGGT

801 GTACACCCTG CCCCCATCCC GGGAGGAGAT GACCAAGAAC CAGGTCAGCC

851 TGACCTGCCT GGTCAAAGGC TTCTATCCCA GCGACATCGC CGTGGAGTGG

901 GAGAGCAATG GGCAGCCGGA GAACAACTAC GACACCACGC CTCCCGTGCT

951 GGACTCCGAC GGCTCCTTCT TCCTCTATAG CGACCTCACC GTGGACAAGA

1001 GCAGGTGGCA GCAGGGGAAC GTCTTCTCAT GCTCCGTGAT GCATGAGGCT

1051 CTGCACAACC ACTACACGCA GAAGAGCCTC TCCCTGTCTC CGGGT
```

The mature ALK6-Fc fusion protein sequence (SEQ ID NO: 144) is as follows and may optionally be provided with a lysine added at the C-terminus.

```
                                                    (SEQ ID NO: 144)
   1 KKEDGESTAP TPRPKVLRCK CHHHCPEDSV NNICSTDGYC FTMIEEDDSG

51 LPVVTSGCLG LEGSDFQCRD TPIPHQRRSI ECCTERNECN KDLHPTLPPL

101 KNRDFVDGPI HHRTGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPSR
```

```
-continued
251 EEMTKNQVSL TCLVKGFYPS DIAVEWESNG QPENNYDTTP PVLDSDGSFF

301 LYSDLTVDKS RWQQGNVFSC SVMHEALHNH YTQKSLSLSP G
```

The ActRIIB-Fc and ALK6-Fc fusion proteins of SEQ ID NO: 102 and SEQ ID NO: 144, respectively, may be co-expressed and purified from a CHO cell line to give rise to a heteromeric complex comprising ActRIIB-Fc:ALK6-Fc.

In another approach to promoting the formation of heteromultimer complexes using asymmetric Fc fusion proteins, illustrated in the ActRIIB-Fc and ALK6-Fc polypeptide sequences of SEQ ID NOs: 401-402 and 425-426, respectively, the Fc domains can be altered to introduce complementary hydrophobic interactions and an additional intermolecular disulfide bond. The ActRIIB-Fc fusion polypeptide sequences are discussed in Example 1.

The complementary form of ALK6-Fc fusion polypeptide (SEQ ID NO: 425) is as follows:

The ActRIIB-Fc and ALK6-Fc proteins of SEQ ID NO: 402 and SEQ ID NO: 426, respectively, may be co-expressed and purified from a CHO cell line, to give rise to a heteromeric complex comprising ActRIIB-Fc:ALK6-Fc.

Purification of various ActRIIB-Fc:ALK6-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

```
                                                         (SEQ ID NO: 425)
  1 MDAMKRGLCC VLLLCGAVFV SPGAKKEDGE STAPTPRPKV LRCKCHHHCP

51 EDSVNNICST DGYCFTMIEE DDSGLPVVTS GCLGLEGSDF QCRDTPIPHQ

101 RRSIECCTER NECNKDLHPT LPPLKNRDFV DGPIHHRTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVCTL PPSREEMTKN QVSLSCAVKG FYPSDIAVEW

301 ESNGQPENNY KTTPPVLDSD GSFFLVSKLT VDKSRWQQGN VFSCSVMHEA

351 LHNHYTQKSL SLSPGK
```

The leader sequence and linker sequence are underlined. To guide heterodimer formation with the ActRIIB-Fc fusion polypeptide of SEQ ID NOs 401 and 402 above, four amino acid substitutions can be introduced into the Fc domain of the ALK6 fusion polypeptide as indicated by double underline above. Furthermore, the C-terminal lysine residue of the Fc domain can be deleted. The amino acid sequence of SEQ ID NO: 425 may optionally be provided with the lysine removed from the C-terminus.

The mature ALK6-Fc fusion protein sequence (SEQ ID NO: 426) can be as follows and may optionally be provided with the lysine removed from the C-terminus.

Example 14. Generation of an ActRIIA-Fc:ALK4-Fc Heterodimer

Applicants constructed a soluble ActRIIA-Fc:ALK4-Fc heteromeric complex comprising the extracellular domains of human ActRIIA and human ALK4, which are each separately fused to an Fc domain with a linker positioned between the extracellular domain and the Fc domain. The individual constructs are referred to as ActRIIA-Fc fusion polypeptide and ALK4-Fc fusion polypeptide, respectively.

Formation of heteromeric ActRIIA-Fc:ALK4-Fc may be guided by approaches similar to those described in Example 1. In a first approach, one Fc domain is altered to introduce cationic amino acids at the interaction face, while the other Fc domain is altered to introduce anionic amino acids at the interaction face.

```
                                                         (SEQ ID NO: 426)
  1 KKEDGESTAP TPRPKVLRCK CHHHCPEDSV NNICSTDGYC FTMIEEDDSG

51 LPVVTSGCLG LEGSDFQCRD TPIPHQRRSI ECCTERNECN KDLHPTLPPL

101 KNRDFVDGPI HHRTGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVCTLPPSR

251 EEMTKNQVSL SCAVKGFYPS DIAVEWESNG QPENNYKTTP PVLDSDGSFF

301 LVSKLTVDKS RWQQGNVFSC SVMHEALHNH YTQKSLSLSP GK
```

The ActRIIA-Fc polypeptide sequence (SEQ ID NO: 118) is shown below:

```
                                                    (SEQ ID NO: 118)
  1 MDAMKRGLCC VLLLCGAVFV SPGAAILGRS ETQECLFFNA NWEKDRTNQT

51 GVEPCYGDKD KRRHCFATWK NISGSIEIVK QGCWLDDINC YDRTDCVEKK

101 DSPEVYFCCC EGNMCNEKFS YFPEMEVTQP TSNPVTPKPP TGGGTHTCPP

151 CPAPELLGGP SVFLFPPKPK DTLMISRTPE VTCVVVDVSH EDPEVKFNWY

201 VDGVEVHNAK TKPREEQYNS TYRVVSVLTV LHQDWLNGKE YKCKVSNKAL

251 PAPIEKTISK AKGQPREPQV YTLPPSRKEM TKNQVSLTCL VKGFYPSDIA

301 VEWESNGQPE NNYKTTPPVL KSDGSFFLYS KLTVDKSRWQ QGNVFSCSVM

351 HEALHNHYTQ KSLSLSPGK
```

The leader sequence and linker sequence are underlined. To promote formation of the ActRIIA-Fc:ALK4-Fc heterodimer rather than either of the possible homodimeric complexes, two amino acid substitutions (replacing acidic amino acids with lysine) can be introduced into the Fc domain of the ActRIIA fusion protein as indicated by double underline above. The amino acid sequence of SEQ ID NO: 118 may optionally be provided with the lysine removed from the C-terminus.

This ActRIIA-Fc fusion protein is encoded by the following nucleic acid sequence (SEQ ID NO: 119):

```
                                                       (SEQ ID NO: 119)
   1 ATGGATGCAA TGAAGAGAGG GCTCTGCTGT GTGCTGCTGC TGTGTGGAGC

51 AGTCTTCGTT TCGCCCGGCG CCGCTATACT TGGTAGATCA GAAACTCAGG

101 AGTGTCTTTT CTTTAATGCT AATTGGGAAA AGACAGAAC CAATCAAACT

151 GGTGTTGAAC CGTGTTATGG TGACAAAGAT AAACGGCGGC ATTGTTTTGC

201 TACCTGGAAG AATATTTCTG GTTCCATTGA ATAGTGAAA CAAGGTTGTT

251 GGCTGGATGA TATCAACTGC TATGACAGGA CTGATTGTGT AGAAAAAAAA

301 GACAGCCCTG AAGTATATTT CTGTTGCTGT GAGGGCAATA TGTGTAATGA

351 AAAGTTTTCT TATTTTCCGG AGATGGAAGT CACACAGCCC ACTTCAAATC

401 CAGTTACACC TAAGCCACCC ACCGGTGGTG GAACTCACAC ATGCCCACCG

451 TGCCCAGCAC CTGAACTCCT GGGGGGACCG TCAGTCTTCC TCTTCCCCCC

501 AAAACCCAAG GACACCCTCA TGATCTCCCG GACCCCTGAG GTCACATGCG

551 TGGTGGTGGA CGTGAGCCAC GAAGACCCTG AGGTCAAGTT CAACTGGTAC

601 GTGGACGGCG TGGAGGTGCA TAATGCCAAG ACAAAGCCGC GGGAGGAGCA

651 GTACAACAGC ACGTACCGTG TGGTCAGCGT CCTCACCGTC CTGCACCAGG

701 ACTGGCTGAA TGGCAAGGAG TACAAGTGCA AGGTCTCCAA CAAAGCCCTC

751 CCAGCCCCCA TCGAGAAAAC CATCTCCAAA GCCAAAGGGC AGCCCCGAGA

801 ACCACAGGTG TACACCCTGC CCCCATCCCG GAAGGAGATG ACCAAGAACC

851 AGGTCAGCCT GACCTGCCTG GTCAAAGGCT TCTATCCCAG CGACATCGCC

901 GTGGAGTGGG AGAGCAATGG GCAGCCGGAG AACAACTACA AGACCACGCC

951 TCCCGTGCTG AAGTCCGACG GCTCCTTCTT CCTCTATAGC AAGCTCACCG

1001 TGGACAAGAG CAGGTGGCAG CAGGGGAACG TCTTCTCATG CTCCGTGATG

1051 CATGAGGCTC TGCACAACCA CTACACGCAG AAGAGCCTCT CCCTGTCTCC

1101 GGGTAAA
```

The mature ActRIIA-Fc fusion polypeptide (SEQ ID NO: 120) is as follows and may optionally be provided with the lysine removed from the C-terminus.

```
                                                          (SEQ ID NO: 120)
  1 ILGRSETQEC LFFNANWEKD RTNQTGVEPC YGDKDKRRHC FATWKNISGS

51 IEIVKQGCWL DDINCYDRTD CVEKKDSPEV YFCCCEGNMC NEKFSYFPEM

101 EVTQPTSNPV TPKPPTGGGT HTCPPCPAPE LLGGPSVFLF PPKPKDTLMI

151 SRTPEVTCVV VDVSHEDPEV KFNWYVDGVE VHNAKTKPRE EQYNSTYRVV

201 SVLTVLHQDW LNGKEYKCKV SNKALPAPIE KTISKAKGQP REPQVYTLPP

251 SRKEMTKNQV SLTCLVKGFY PSDIAVEWES NGQPENNYKT TPPVLKSDGS

301 FFLYSKLTVD KSRWQQGNVF SCSVMHEALH NHYTQKSLSL SPGK
```

In this first approach, the polypeptide sequence of the complementary ALK4-Fc fusion protein and a nucleic acid sequence encoding it are provided above in Example 1 as SEQ ID NOs: 104-106.

The ActRIIA-Fc and ALK4-Fc proteins of SEQ ID NO: 120 and SEQ ID NO: 106, respectively, may be co-expressed and purified from a CHO cell line, to give rise to a heteromeric complex comprising ActRIIA-Fc:ALK4-Fc.

In a second approach to promote the formation of heteromultimer complexes using asymmetric Fc fusion proteins, the Fc domains are altered to introduce complementary hydrophobic interactions and an additional intermolecular disulfide bond.

The ActRIIA-Fc polypeptide sequence (SEQ ID NO: 409) is shown below:

```
                                                          (SEQ ID NO: 409)
  1 MDAMKRGLCC VLLLCGAVFV SPGAAILGRS ETQECLFFNA NWEKDRTNQT

51 GVEPCYGDKD KRRHCFATWK NISGSIEIVK QGCWLDDINC YDRTDCVEKK

101 DSPEVYFCCC EGNMCNEKFS YFPEMEVTQP TSNPVTPKPP TGGGTHTCPP

151 CPAPELLGGP SVFLFPPKPK DTLMISRTPE VTCVVVDVSH EDPEVKFNWY

201 VDGVEVHNAK TKPREEQYNS TYRVVSVLTV LHQDWLNGKE YKCKVSNKAL

251 PAPIEKTISK AKGQPREPQV YTLPPCREEM TKNQVSLWCL VKGFYPSDIA

301 VEWESNGQPE NNYKTTPPVL DSDGSFFLYS KLTVDKSRWQ QGNVFSCSVM

351 HEALHNHYTQ KSLSLSPGK
```

The leader sequence and linker sequence are underlined. To promote formation of the ActRIIA-Fc:ALK4-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 409 may optionally be provided with the lysine removed from the C-terminus.

The mature ActRIIA-Fc fusion polypeptide (SEQ ID NO: 410) is as follows and may optionally be provided with the lysine removed from the C-terminus.

```
                                                          (SEQ ID NO: 410)
  1 ILGRSETQEC LFFNANWEKD RTNQTGVEPC YGDKDKRRHC FATWKNISGS

51 IEIVKQGCWL DDINCYDRTD CVEKKDSPEV YFCCCEGNMC NEKFSYFPEM

101 EVTQPTSNPV TPKPPTGGGT HTCPPCPAPE LLGGPSVFLF PPKPKDTLMI

151 SRTPEVTCVV VDVSHEDPEV KFNWYVDGVE VHNAKTKPRE EQYNSTYRVV

201 SVLTVLHQDW LNGKEYKCKV SNKALPAPIE KTISKAKGQP REPQVYTLPP

251 CREEMTKNQV SLWCLVKGFY PSDIAVEWES NGQPENNYKT TPPVLDSDGS

301 FFLYSKLTVD KSRWQQGNVF SCSVMHEALH NHYTQKSLSL SPGK
```

In this second approach, the polypeptide sequence of the complementary ALK4-Fc fusion protein and a nucleic acid sequence encoding it are provided above in Example 1 as SEQ ID NOs: 403-404.

The ActRIIA-Fc and ALK4-Fc proteins of SEQ ID NO: 410 and SEQ ID NO: 404, respectively, may be co-expressed and purified from a CHO cell line, to give rise to a heteromeric complex comprising ActRIIA-Fc:ALK4-Fc.

Purification of various ActRIIA-Fc:ALK4-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 15. Ligand Binding Profile of ActRIIA-Fc:ALK4-Fc Heterodimer Compared to ActRIIA-Fc Homodimer and ALK4-Fc Homodimer A Biacore™-based binding assay was used to compare ligand binding selectivity of the ActRIIA-Fc:ALK4-Fc heterodimeric complex described above with that of ActRIIA-Fc and ALK4-Fc homodimeric complexes. The ActRIIA-Fc:ALK4-Fc heterodimer, ActRIIA-Fc homodimer, and ALK4-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Figure 10:
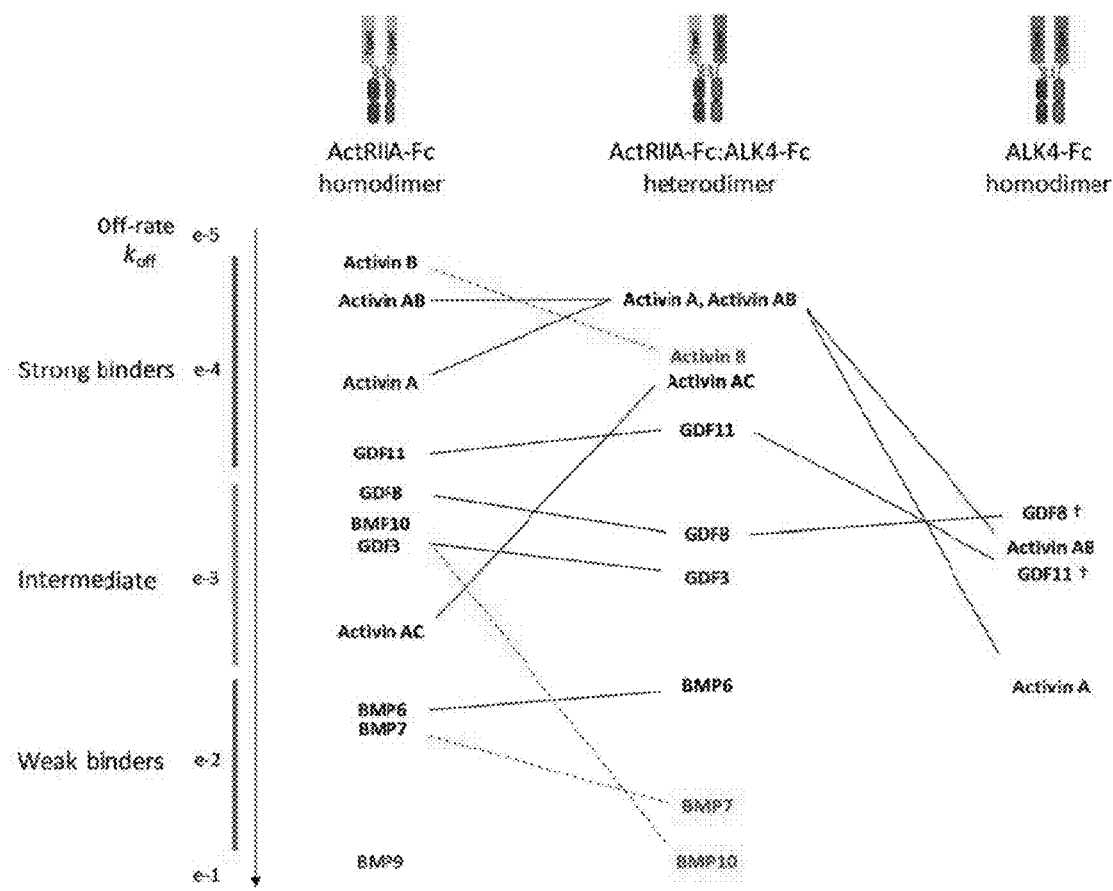
FIG. 10 shows ligand binding data for an ActRIIA-Fc:ALK4-Fc heterodimeric protein complex as compared to ActRIIA-Fc homodimer and ALK4-Fc homodimer. Format is the same as in FIG. 6. As shown, the ActRIIA-Fc:ALK4-Fc heterodimer exhibits enhanced binding to activin A, and particularly enhanced binding to activin AC, compared to ActRIIA-Fc homodimer, while retaining strong binding to activin AB and GDF11. In addition, the ligand with highest affinity for ActRIIA-Fc homodimer, activin B, displays reduced affinity (albeit still within the high-affinity range) for the ActRIIA-Fc:ALK4-Fc heterodimer. The ActRIIA-Fc:ALK4-Fc heterodimer also exhibits markedly reduced binding to BMP10 compared to ActRIIA-Fc homodimer.

ActRIIA-Fc:ALK4-Fc heterodimer also exhibits markedly reduced binding to BMP10 compared to ActRIIA-Fc homodimer. See FIG. 10.

These results demonstrate that the ActRIIA-Fc:ALK4-Fc heterodimer is a more selective antagonist of activin A and activin AB over activin B than is ActRIIA-Fc homodimer. In addition, the ActRIIA-Fc:ALK4-Fc heterodimer has substantially increased affinity for activin AC and greatly reduced affinity for BMP10 compared to ActRIIA-Fc homodimer. Accordingly, an ActRIIA-Fc:ALK4-Fc heterodimer will be more useful than ActRIIA-Fc homodimer in certain applications where such selective antagonism is advantageous. Examples include therapeutic applications where it is desirable to antagonize activin A and/or activin AB preferentially over activin B, and to obtain strong inhibition of activin AC, while avoiding inhibition of BMP10.

Example 16. Generation of a BMPRII-Fc:ALK1-Fc Heterodimer

Applicants constructed a soluble BMPRII-Fc:ALK1-Fc heteromeric complex comprising the extracellular domains of human BMPRII and human ALK1, which are each separately fused to an Fc domain with a linker positioned between the extracellular domain and the Fc domain. The Ligand binding profile of ActRIIA-Fc:ALK4-Fc heterodimer compared to ActRIIA-Fc homodimer and ALK4-Fc homodimer

| Ligand | ActRIIA-Fc homodimer | | | ALK4-Fc homodimer | | | ActRIIA-Fc:ALK4-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | $1.4 \times 10^7$ | $\mathbf{6.2 \times 10^{-4}}$ | 45 | $5.8 \times 10^5$ | $1.2 \times 10^{-2}$ | 20000 | $7.4 \times 10^6$ | $\mathbf{2.4 \times 10^{-4}}$ | 32 |
| Activin B | $1.1 \times 10^7$ | $\mathbf{1.1 \times 10^{-4}}$ | 10 | No binding | | | $9.5 \times 10^6$ | $\mathbf{4.8 \times 10^{-4}}$ | 50 |
| Activin AB | $2.8 \times 10^7$ | $\mathbf{2.6 \times 10^{-4}}$ | 9 | $1.8 \times 10^6$ | $3.6 \times 10^{-3}$ | 2000 | $1.8 \times 10^7$ | $\mathbf{2.3 \times 10^{-4}}$ | 13 |
| Activin AC | $2.2 \times 10^7$ | $7.9 \times 10^{-3}$ | 360 | No binding | | | $3.2 \times 10^6$ | $\mathbf{5.4 \times 10^{-4}}$ | 170 |
| BMP6 | $2.7 \times 10^8$ | $2.2 \times 10^{-2}$ | 800 | No binding | | | $5.4 \times 10^6$ | $1.2 \times 10^{-2}$ | 2200 |
| BMP7 | $8.9 \times 10^6$ | $3.3 \times 10^{-2}$ | 3700 | No binding | | | $2.0 \times 10^7$ | $7.2 \times 10^{-2}$ | 3500 |
| BMP9 | Transient* | | >10000 | — | | | No binding | | |
| BMP10 | $2.9 \times 10^7$ | $2.5 \times 10^{-3}$ | 85 | No binding | | | Transient* | | >6000 |
| GDF3 | $1.5 \times 10^6$ | $3.6 \times 10^{-3}$ | 2400 | — | | | $4.9 \times 10^7$ | $4.8 \times 10^{-3}$ | 9800 |
| GDF8 | $1.4 \times 10^6$ | $1.4 \times 10^{-3}$ | 99 | $1.3 \times 10^5$ | $1.9 \times 10^{-3}$ | 15000† | $1.8 \times 10^7$ | $2.8 \times 10^{-3}$ | 150 |
| GDF11 | $7.3 \times 10^7$ | $\mathbf{9.2 \times 10^{-4}}$ | 13 | $5.0 \times 10^6$ | $4.8 \times 10^{-3}$ | 970† | $3.0 \times 10^7$ | $\mathbf{6.5 \times 10^{-4}}$ | 22 |

*Indeterminate due to transient nature of interaction
†Very low signal
—Not tested These comparative binding data demonstrate that the ActRIIA-Fc:ALK4-Fc heterodimer has an altered binding profile/selectivity relative to either the ActRIIA-Fc or ALK4-Fc homodimers. For example, the ActRIIA-Fc:ALK4-Fc heterodimer exhibits enhanced binding to activin A, and particularly enhanced binding to activin AC, compared to ActRIIA-Fc homodimer, while retaining strong binding to activin AB and GDF11. In addition, the ligand with highest affinity for ActRIIA-Fc homodimer, activin B, displays reduced affinity (albeit still within the high-affinity range) for the ActRIIA-Fc:ALK4-Fc heterodimer. The individual constructs are referred to as BMPRII-Fc fusion polypeptide and ALK1-Fc fusion polypeptide, respectively, and the sequences for each are provided below.

Formation of heteromeric BMPRII-Fc:ALK1-Fc may be guided by approaches similar to those described in Example 1. In a first approach, one Fc domain is altered to introduce cationic amino acids at the interaction face, while the other Fc domain is altered to introduce anionic amino acids at the interaction face.

The BMPRII-Fc polypeptide sequence (SEQ ID NO: 121) is shown below:

(SEQ ID NO: 121)
```
  1 MDAMKRGLCC VLLLCGAVFV SPGASQNQER LCAFKDPYQQ DLGIGESRIS

51 HENGTILCSK GSTCYGLWEK SKGDINLVKQ GCWSHIGDPQ ECHYEECVVT

101 TTPPSIQNGT YRFCCCSTDL CNVNFTENFP PPDTTPLSPP HSFNRDETGG

151 GTHTCPPCPA PELLGGPSVF LFPPKPKDTL MISRTPEVTC VVVDVSHEDP

201 EVKFNWYVDG VEVHNAKTKP REEQYNSTYR VVSVLTVLHQ DWLNGKEYKC

251 KVSNKALPAP IEKTISKAKG QPREPQVYTL PPSRKEMTKN QVSLTCLVKG

301 FYPSDIAVEW ESNGQPENNY KTTPPVLKSD GSFFLYSKLT VDKSRWQQGN

351 VFSCSVMHEA LHNHYTQKSL SLSPGK
```

The leader sequence and linker sequence are underlined. To promote formation of the BMPRII-Fc:ALK1-Fc heterodimer rather than either of the possible homodimeric complexes, two amino acid substitutions (replacing acidic amino acids with lysine) can be introduced into the Fc domain of the BMPRII-Fc fusion protein as indicated by double underline above. The amino acid sequence of SEQ ID NO: 121 may optionally be provided with the lysine removed from the C-terminus.

This BMPRII-Fc fusion protein is encoded by the following nucleic acid sequence (SEQ ID NO: 122):

(SEQ ID NO: 122)
```
   1 ATGGATGCAA TGAAGAGAGG GCTCTGCTGT GTGCTGCTGC TGTGTGGAGC

51 AGTCTTCGTT TCGCCCGGCG CCTCGCAGAA TCAAGAACGC CTATGTGCGT

101 TTAAAGATCC GTATCAGCAA GACCTTGGGA TAGGTGAGAG TAGAATCTCT

151 CATGAAAATG GGACAATATT ATGCTCGAAA GGTAGCACCT GCTATGGCCT

201 TTGGGAGAAA TCAAAGGGG ACATAAATCT TGTAAAACAA GGATGTTGGT

251 CTCACATTGG AGATCCCCAA GAGTGTCACT ATGAAGAATG TGTAGTAACT

301 ACCACTCCTC CCTCAATTCA GAATGGAACA TACCGTTTCT GCTGTTGTAG

351 CACAGATTTA TGTAATGTCA ACTTTACTGA GAATTTTCCA CCTCCTGACA

401 CAACACCACT CAGTCCACCT CATTCATTTA ACCGAGATGA GACCGGTGGT

451 GGAACTCACA CATGCCCACC GTGCCCAGCA CCTGAACTCC TGGGGGGACC

501 GTCAGTCTTC CTCTTCCCCC CAAAACCCAA GGACACCCTC ATGATCTCCC

551 GGACCCCTGA GGTCACATGC GTGGTGGTGG ACGTGAGCCA CGAAGACCCT

601 GAGGTCAAGT TCAACTGGTA CGTGGACGGC GTGGAGGTGC ATAATGCCAA

651 GACAAAGCCG CGGGAGGAGC AGTACAACAG CACGTACCGT GTGGTCAGCG

701 TCCTCACCGT CCTGCACCAG GACTGGCTGA ATGGCAAGGA GTACAAGTGC

751 AAGGTCTCCA ACAAAGCCCT CCCAGCCCCC ATCGAGAAAA CCATCTCCAA

801 AGCCAAAGGG CAGCCCCGAG AACCACAGGT GTACACCCTG CCCCCATCCC

851 GGAAGGAGAT GACCAAGAAC CAGGTCAGCC TGACCTGCCT GGTCAAAGGC

901 TTCTATCCCA GCGACATCGC CGTGGAGTGG GAGAGCAATG GGCAGCCGGA

951 GAACAACTAC AAGACCACGC CTCCCGTGCT GAAGTCCGAC GGCTCCTTCT

1001 TCCTCTATAG CAAGCTCACC GTGGACAAGA GCAGGTGGCA GCAGGGGAAC

1051 GTCTTCTCAT GCTCCGTGAT GCATGAGGCT CTGCACAACC ACTACACGCA

1101 GAAGAGCCTC TCCCTGTCTC CGGGTAAA
```

The mature BMPRII-Fc fusion polypeptide (SEQ ID NO: 123) is as follows and may optionally be provided with the lysine removed from the C-terminus.

```
                                                        (SEQ ID NO: 123)
  1 SQNQERLCAF KDPYQQDLGI GESRISHENG TILCSKGSTC YGLWEKSKGD

51 INLVKQGCWS HIGDPQECHY EECVVTTTPP SIQNGTYRFC CCSTDLCNVN

101 FTENFPPPDT TPLSPPHSFN RDETGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPSR KEMTKNQVSL TCLVKGFYPS DIAVEWESNG QPENNYKTTP

301 PVLKSDGSFF LYSKLTVDKS RWQQGNVFSC SVMHEALHNH YTQKSLSLSP

351 GK
```

The complementary form of ALK1-Fc fusion polypeptide (SEQ ID NO: 124) is as follows:

```
                                                        (SEQ ID NO: 124)
  1 MDAMKRGLCC VLLLCGAVFV SPGADPVKPS RGPLVTCTCE SPHCKGPTCR

51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPSR EEMTKNQVSL TCLVKGFYPS DIAVEWESNG QPENNYDTTP

301 PVLDSDGSFF LYSDLTVDKS RWQQGNVFSC SVMHEALHNH YTQKSLSLSP

351 G
```

The leader sequence and linker sequence are underlined. To guide heterodimer formation with the BMPRII-Fc fusion polypeptide of SEQ ID NOs: 121 and 123 above, two amino acid substitutions (replacing lysines with aspartic acids) can be introduced into the Fc domain of the ALK1-Fc fusion polypeptide as indicated by double underline above. The amino acid sequence of SEQ ID NO: 124 may optionally be provided with a lysine added at the C-terminus.

This ALK1-Fc fusion protein is encoded by the following nucleic acid (SEQ ID NO: 125):

```
                                                        (SEQ ID NO: 125)
  1 ATGGATGCAA TGAAGAGAGG GCTCTGCTGT GTGCTGCTGC TGTGTGGAGC

51 AGTCTTCGTT TCGCCCGGCG CCGACCCTGT GAAGCCGTCT CGGGGCCCGC

101 TGGTGACCTG CACGTGTGAG AGCCCACATT GCAAGGGGCC TACCTGCCGG

151 GGGGCCTGGT GCACAGTAGT GCTGGTGCGG GAGGAGGGGA GGCACCCCCA

201 GGAACATCGG GGCTGCGGGA ACTTGCACAG GGAGCTCTGC AGGGGCCGCC

251 CCACCGAGTT CGTCAACCAC TACTGCTGCG ACAGCCACCT CTGCAACCAC

301 AACGTGTCCC TGGTGCTGGA GGCCACCCAA CCTCCTTCGG AGCAGCCGGG

351 AACAGATGGC CAGCTGGCCA CCGGTGGTGG AACTCACACA TGCCCACCGT

401 GCCCAGCACC TGAACTCCTG GGGGGACCGT CAGTCTTCCT CTTCCCCCCA

451 AAACCCAAGG ACACCCTCAT GATCTCCCGG ACCCCTGAGG TCACATGCGT

501 GGTGGTGGAC GTGAGCCACG AAGACCCTGA GGTCAAGTTC AACTGGTACG

551 TGGACGGCGT GGAGGTGCAT AATGCCAAGA CAAAGCCGCG GGAGGAGCAG

601 TACAACAGCA CGTACCGTGT GGTCAGCGTC CTCACCGTCC TGCACCAGGA

651 CTGGCTGAAT GGCAAGGAGT ACAAGTGCAA GGTCTCCAAC AAAGCCCTCC
```

-continued

```
 701 CAGCCCCCAT CGAGAAAACC ATCTCCAAAG CCAAAGGGCA GCCCCGAGAA
 751 CCACAGGTGT ACACCCTGCC CCCATCCCGG GAGGAGATGA CCAAGAACCA
 801 GGTCAGCCTG ACCTGCCTGG TCAAAGGCTT CTATCCCAGC GACATCGCCG
 851 TGGAGTGGGA GAGCAATGGG CAGCCGGAGA ACAACTACGA CACCACGCCT
 901 CCCGTGCTGG ACTCCGACGG CTCCTTCTTC CTCTATAGCG ACCTCACCGT
 951 GGACAAGAGC AGGTGGCAGC AGGGGAACGT CTTCTCATGC TCCGTGATGC
1001 ATGAGGCTCT GCACAACCAC TACACGCAGA AGAGCCTCTC CCTGTCTCCG
1051 GGT
```

The mature ALK1-Fc fusion protein sequence (SEQ ID NO: 126) is as follows and may optionally be provided with a lysine added at the C-terminus.

```
                                              (SEQ ID NO: 126)
  1 DPVKPSRGPL VTCTCESPHC KGPTCRGAWC TVVLVREEGR HPQEHRGCGN
 51 LHRELCRGRP TEFVNHYCCD SHLCNHNVSL VLEATQPPSE QPGTDGQLAT
101 GGGTHTCPPC PAPELLGGPS VFLFPPKPKD TLMISRTPEV TCVVVDVSHE
151 DPEVKFNWYV DGVEVHNAKT KPREEQYNST YRVVSVLTVL HQDWLNGKEY
201 KCKVSNKALP APIEKTISKA KGQPREPQVY TLPPSREEMT KNQVSLTCLV
251 KGFYPSDIAV EWESNGQPEN NYDTTPPVLD SDGSFFLYSD LTVDKSRWQQ
301 GNVFSCSVMH EALHNHYTQK SLSLSPG
```

The BMPRII-Fc and ALK1-Fc proteins of SEQ ID NO: 123 and SEQ ID NO: 126, respectively, may be co-expressed and purified from a CHO cell line, to give rise to a heteromeric complex comprising BMPRII-Fc:ALK1-Fc.

In a second approach to promote the formation of heteromultimer complexes using asymmetric Fc fusion proteins, the Fc domains are altered to introduce complementary hydrophobic interactions and an additional intermolecular disulfide bond.

The BMPRII-Fc polypeptide sequence (SEQ ID NO: 411) is shown below:

```
                                              (SEQ ID NO: 411)
  1 MDAMKRGLCC VLLLCGAVFV SPGASQNQER LCAFKDPYQQ DLGIGESRIS
 51 HENGTILCSK GSTCYGLWEK SKGDINLVKQ GCWSHIGDPQ ECHYEECVVT
101 TTPPSIQNGT YRFCCCSTDL CNVNFTENFP PPDTTPLSPP HSFNRDETGG
151 GTHTCPPCPA PELLGGPSVF LFPPKPKDTL MISRTPEVTC VVVDVSHEDP
201 EVKFNWYVDG VEVHNAKTKP REEQYNSTYR VVSVLTVLHQ DWLNGKEYKC
251 KVSNKALPAP IEKTISKAKG QPREPQVYTL PPCREEMTKN QVSLWCLVKG
301 FYPSDIAVEW ESNGQPENNY KTTPPVLDSD GSFFLYSKLT VDKSRWQQGN
351 VFSCSVMHEA LHNHYTQKSL SLSPGK
```

The leader sequence and linker sequence are underlined. To promote formation of the BMPRII-Fc:ALK1-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 411 may optionally be provided with the lysine removed from the C-terminus.

The mature BMPRII-Fc fusion polypeptide (SEQ ID NO: 412) is as follows and may optionally be provided with the lysine (K) removed from the C-terminus.

```
                                                    (SEQ ID NO: 412)
  1 SQNQERLCAF KDPYQQDLGI GESRISHENG TILCSKGSTC YGLWEKSKGD

51 INLVKQGCWS HIGDPQECHY EECVVTTTPP SIQNGTYRFC CCSTDLCNVN

101 FTENFPPPDT TPLSPPHSFN RDETGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPCR EEMTKNQVSL WCLVKGFYPS DIAVEWESNG QPENNYKTTP

301 PVLDSDGSFF LYSKLTVDKS RWQQGNVFSC SVMHEALHNH YTQKSLSLSP

351 GK
```

The complementary form of ALK1-Fc fusion polypeptide (SEQ ID NO: 413) is as follows:

```
                                                    (SEQ ID NO: 413)
  1 MDAMKRGLCC VLLLCGAVFV SPGADPVKPS RGPLVTCTCE SPHCKGPTCR

51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVCTLPPSR EEMTKNQVSL SCAVKGFYPS DIAVEWESNG QPENNYKTTP

301 PVLDSDGSFF LVSKLTVDKS RWQQGNVFSC SVMHEALHNH YTQKSLSLSP

351 GK
```

The leader sequence and linker sequence are underlined. To guide heterodimer formation with the BMPRII-Fc fusion polypeptide of SEQ ID NOs: 411 and 412 above, four amino acid substitutions can be introduced into the Fc domain of the ALK1 fusion polypeptide as indicated by double underline above. The amino acid sequence of SEQ ID NO: 413 may optionally be provided with the lysine removed from the C-terminus.

The mature ALK1-Fc fusion protein sequence (SEQ ID NO: 414) is as follows and may optionally be provided with the lysine removed from the C-terminus.

```
                                                    (SEQ ID NO: 414)
  1 DPVKPSRGPL VTCTCESPHC KGPTCRGAWC TVVLVREEGR HPQEHRGCGN

51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY

201 KCKVSNKALP APIEKTISKA KGQPREPQVC TLPPSREEMT KNQVSLSCAV

251 KGFYPSDIAV EWESNGQPEN NYKTTPPVLD SDGSFFLVSK LTVDKSRWQQ

301 GNVFSCSVMH EALHNHYTQK SLSLSPGK
```

The BMPRII-Fc and ALK1-Fc proteins of SEQ ID NO: 412 and SEQ ID NO: 414, respectively, may be co-expressed and purified from a CHO cell line, to give rise to a heteromeric complex comprising BMPRII-Fc:ALK1-Fc.

Purification of various BMPRII-Fc:ALK1-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 17. Ligand Binding Profile of BMPRII-Fc:ALK1-Fc Heterodimer Compared to BMPRII-Fc Homodimer and ALK1-Fc Homodimer A Biacore™-based binding assay was used to compare ligand binding selectivity of the BMPRII-Fc:ALK1-Fc heterodimeric complex described above with that of BMPRII-Fc and ALK1-Fc homodimeric complexes. The BMPRII-Fc:ALK1-Fc heterodimer, BMPRII-Fc homodimer, and ALK1-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profile of BMPRII-Fc:ALK1-Fc heterodimer compared to BMPRII-Fc homodimer and ALK1-Fc homodimer

| Ligand | BMPRII-Fc homodimer | | | ALK1-Fc homodimer | | | BMPRII-Fc:ALK1-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| BMP9 | $1.2 \times 10^7$ | $2.6 \times 10^{-2}$ | 2100 | $7.8 \times 10^6$ | $1.3 \times 10^{-4}$ | 16 | $1.2 \times 10^6$ | $4.1 \times 10^{-4}$ | 360 |
| BMP10 | $2.6 \times 10^7$ | $2.5 \times 10^{-3}$ | 100 | $4.1 \times 10^6$ | $1.6 \times 10^{-4}$ | 38 | $1.5 \times 10^7$ | $3.5 \times 10^{-4}$ | 23 |
| BMP15 | $9.9 \times 10^6$ | $2.8 \times 10^{-3}$ | 290 | No binding | | | $1.2 \times 10^7$ | $4.2 \times 10^{-2}$ | 3500 |

Figure 11:
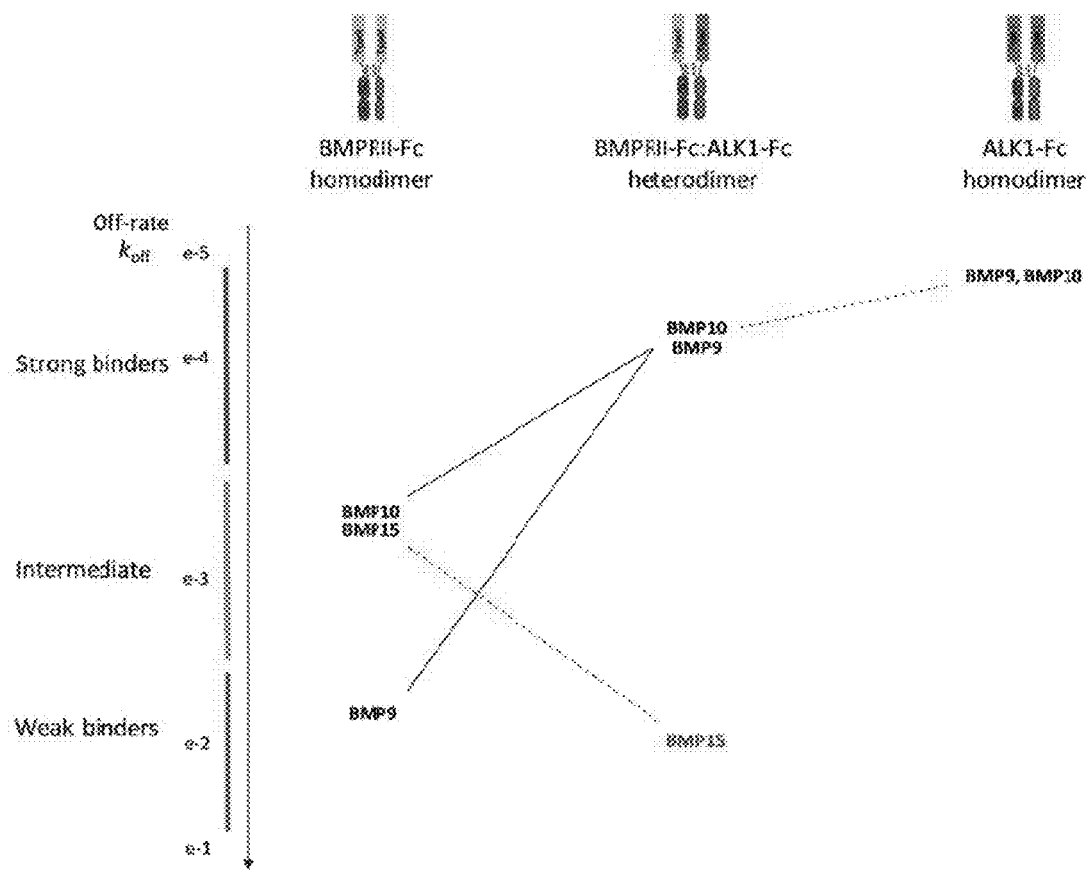
FIG. 11 shows ligand binding data for a BMPRII-Fc:ALK1-Fc heterodimeric protein complex as compared to ActRIIB-Fc homodimer and ALK1-Fc homodimer. Format is the same as in FIG. 6. As shown, the BMPRII-Fc:ALK1-Fc heterodimer largely retains the strong binding to BMP9 and BMP10 characteristic of ALK1-Fc homodimer; however, the heterodimer displays modest selectivity for BMP10 over BMP9 not present with the homodimer. Also unlike ALK1-Fc homodimer, the BMPRII-Fc:ALK1-Fc heterodimer binds to BMP15, albeit with an off-rate approximately ten times faster than that of BMPRII-Fc homodimer.

These comparative binding data demonstrate that the BMPRII-Fc:ALK1-Fc heterodimer has a binding profile/selectivity which differs from that of BMPRII-Fc homodimer but is similar to that of ALK1-Fc homodimer. For example, the BMPRII-Fc:ALK1-Fc heterodimer largely retains the strong binding to BMP9 and BMP10 characteristic of ALK1-Fc homodimer; however, the heterodimer displays modest selectivity for BMP10 over BMP9 not present with the homodimer. Also unlike ALK1-Fc homodimer, the BMPRII-Fc:ALK1-Fc heterodimer binds to BMP15, albeit with an affinity approximately an order of magnitude weaker than that of BMPRII-Fc homodimer. See FIG. 11. Accordingly, a BMPRII-Fc:ALK1-Fc heterodimer will be unexpectedly useful in certain therapeutic applications where selective antagonism of BMP9 and particularly BMP10 is advantageous, e.g., for inhibition of angiogenesis, or in applications where antagonism of BMP15 is also advantageous.

Example 18. Generation of a BMPRII-Fc:ALK2-Fc Heterodimer

Applicants constructed a soluble BMPRII-Fc:ALK2-Fc heteromeric complex comprising the extracellular domains of human BMPRII and human ALK2, which are each separately fused to an Fc domain with a linker positioned between the extracellular domain and the Fc domain. The individual constructs are referred to as BMPRII-Fc fusion polypeptide and ALK2-Fc fusion polypeptide, respectively, and the sequences for each are provided herein.

Formation of heteromeric BMPRII-Fc:ALK2-Fc may be guided by approaches similar to those described in Example 1. In a first approach, one Fc domain is altered to introduce cationic amino acids at the interaction face, while the other Fc domain is altered to introduce anionic amino acids at the interaction face. The polypeptide sequence of the BMPRII-Fc fusion polypeptide and a nucleic acid sequence encoding it are provided above in Example 16 as SEQ ID NOs: 121-123. To promote formation of the BMPRII-Fc:ALK2-Fc heterodimer rather than either of the possible homodimeric complexes, two amino acid substitutions (replacing acidic amino acids with lysine) can be introduced into the Fc domain of the BMPRII-Fc fusion protein as indicated in Example 16. The amino acid sequences of SEQ ID NOs: 121 and 123 may optionally be provided with the lysine removed from the C-terminus.

The polypeptide sequence of the complementary ALK2-Fc fusion polypeptide and a nucleic acid sequence encoding it are provided in Example 9 as SEQ ID NOs: 136-138. To guide heterodimer formation with the BMPRII-Fc fusion polypeptide of SEQ ID NOs: 121 and 123, two amino acid substitutions (replacing lysines with aspartic acids) can be introduced into the Fc domain of the ALK2-Fc fusion polypeptide as indicated in Example 9. The amino acid sequences of SEQ ID NOs: 136 and 138 may optionally be provided with a lysine added at the C-terminus.

The BMPRII-Fc and ALK2-Fc fusion polypeptides of SEQ ID NO: 123 and SEQ ID NO: 138, respectively, may be co-expressed and purified from a CHO cell line, to give rise to a heteromeric complex comprising BMPRII-Fc:ALK2-Fc.

In a second approach to promote the formation of heteromultimer complexes using asymmetric Fc fusion proteins, the Fc domains are altered to introduce complementary hydrophobic interactions and an additional intermolecular disulfide bond. BMPRII-Fc fusion polypeptide sequences (SEQ ID NOs: 411-412) are discussed in Example 16. To promote formation of the BMPRII-Fc:ALK2-Fc heterodimer rather than either of the possible homodimeric complexes, two amino acid substitutions (replacing a serine with a cysteine and a threonine with a trytophan) can be introduced into the Fc domain of the BMPRII-Fc polypeptide as indicated in Example 16. The amino acid sequences of SEQ ID NOs: 411 and 412 may optionally be provided with the lysine removed from the C-terminus.

Polypeptide sequences of the complementary ALK2-Fc fusion polypeptide (SEQ ID NOs: 421-422) are discussed in Example 9. To guide heterodimer formation with the BMPRII-Fc fusion polypeptide of SEQ ID NOs: 411-412, four amino acid substitutions can be introduced into the Fc domain of the ALK2 fusion polypeptide as indicated in Example 9. The amino acid sequences of SEQ ID NOs: 421-422 may optionally be provided with the lysine removed from the C-terminus.

The BMPRII-Fc and ALK2-Fc fusion polypeptides of SEQ ID NO: 412 and SEQ ID NO: 422, respectively, may be co-expressed and purified from a CHO cell line, to give rise to a heteromeric complex comprising BMPRII-Fc:ALK2-Fc.

Purification of various BMPRII-Fc:ALK2-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 19. Ligand Binding Profile of BMPRII-Fc:ALK2-Fc Heterodimer Compared to BMPRII-Fc Homodimer and ALK2-Fc Homodimer A Biacore™-based binding assay was used to compare ligand binding selectivity of the BMPRII-Fc:ALK2-Fc heterodimeric complex described above with that of BMPRII-Fc and ALK2-Fc homodimeric complexes. The BMPRII-Fc:ALK2-Fc heterodimer, BMPRII-Fc homodimer, and ALK2-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted by gray shading.

Ligand binding profile of BMPRII-Fc:ALK2-Fc heterodimer compared to BMPRII-Fc homodimer and ALK2-Fc homodimer

| Ligand | BMPRII-Fc homodimer | | | ALK2-Fc homodimer | | | BMPRII-Fc:ALK2-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin B | $1.9 \times 10^6$ | $4.9 \times 10^{-3}$ | 2600 | No binding | | | $5.9 \times 10^5$ | $3.1 \times 10^{-3}$ | 5200 |
| BMP5 | $1.9 \times 10^6$ | $1.9 \times 10^{-2}$ | 9900 | No binding | | | $1.8 \times 10^6$ | $5.0 \times 10^{-3}$ | 2800 |
| BMP7 | Transient* | | >93000 | No binding | | | $1.5 \times 10^7$ | $1.2 \times 10^{-2}$ | 760 |
| BMP9 | $4.5 \times 10^7$ | $7.3 \times 10^{-2}$ | 1600 | No binding | | | $1.0 \times 10^7$ | $5.1 \times 10^{-3}$ | 500 |
| BMP10 | $3.8 \times 10^7$ | $5.0 \times 10^{-3}$ | 130 | No binding | | | $1.1 \times 10^8$ | $3.4 \times 10^{-2}$ | 300 |
| BMP15 | $5.8 \times 10^6$ | $4.2 \times 10^{-3}$ | 720 | No binding | | | $9.6 \times 10^6$ | $1.1 \times 10^{-2}$ | 1100 |

*Indeterminate due to transient nature of interaction

Example 20. Generation of a BMPRII-Fc:ALK3-Fc Heterodimer

Applicants constructed a soluble BMPRII-Fc:ALK3-Fc heteromeric complex comprising the extracellular domains of human BMPRII and human ALK3, which are each separately fused to an Fc domain with a linker positioned between the extracellular domain and the Fc domain. The individual constructs are referred to as BMPRII-Fc fusion polypeptide and ALK3-Fc fusion polypeptide, respectively, and the sequences for each are provided herein.

Formation of heteromeric BMPRII-Fc:ALK3-Fc may be guided by approaches similar to those described in Example 1. In a first approach, one Fc domain is altered to introduce cationic amino acids at the interaction face, while the other Fc domain is altered to introduce anionic amino acids at the interaction face. The polypeptide sequence of the BMPRII-Fc fusion polypeptide and a nucleic acid sequence encoding it are provided above in Example 16 as SEQ ID NOs: 121-123. To promote formation of the BMPRII-Fc:ALK3-Fc heterodimer rather than either of the possible homodimeric complexes, two amino acid substitutions (replacing acidic amino acids with lysine) can be introduced into the Fc domain of the BMPRII-Fc fusion protein as indicated in Example 16. The amino acid sequences of SEQ ID NOs: 121 and 123 may optionally be provided with the lysine removed from the C-terminus.

The polypeptide sequence of the complementary ALK3-Fc fusion polypeptide and a nucleic acid sequence encoding it are provided in Example 4 as SEQ ID NOs: 115-117. To guide heterodimer formation with the BMPRII-Fc fusion polypeptide of SEQ ID NOs: 121 and 123, two amino acid substitutions (replacing lysines with aspartic acids) can be introduced into the Fc domain of the ALK3-Fc fusion polypeptide as indicated in Example 4. The amino acid sequences of SEQ ID NOs: 115 and 117 may optionally be provided with a lysine added at the C-terminus.

The BMPRII-Fc and ALK3-Fc fusion polypeptides of SEQ ID NO: 123 and SEQ ID NO: 117, respectively, may be co-expressed and purified from a CHO cell line, to give rise to a heteromeric complex comprising BMPRII-Fc:ALK3-Fc.

In a second approach to promote the formation of heteromultimer complexes using asymmetric Fc fusion proteins, the Fc domains are altered to introduce complementary hydrophobic interactions and an additional intermolecular disulfide bond. BMPRII-Fc fusion polypeptide sequences (SEQ ID NOs: 411-412) are discussed in Example 16. To promote formation of the BMPRII-Fc:ALK3-Fc heterodimer rather than either of the possible homodimeric complexes, two amino acid substitutions (replacing a serine with a cysteine and a threonine with a trytophan) can be introduced into the Fc domain of the BMPRII-Fc polypeptide as indicated in Example 16. The amino acid sequences of SEQ ID NOs: 411 and 412 may optionally be provided with the lysine removed from the C-terminus.

Polypeptide sequences of the complementary ALK3-Fc fusion polypeptide (SEQ ID NOs: 407-408) are discussed in Example 4. To guide heterodimer formation with the BMPRII-Fc fusion polypeptide of SEQ ID NOs: 411-412, four amino acid substitutions can be introduced into the Fc domain of the ALK3 fusion polypeptide as indicated in Example 4. The amino acid sequences of SEQ ID NOs: 407 and 408 may optionally be provided with the lysine removed from the C-terminus.

The BMPRII-Fc and ALK3-Fc fusion polypeptides of SEQ ID NO: 412 and SEQ ID NO: 408, respectively, may be co-expressed and purified from a CHO cell line, to give rise to a heteromeric complex comprising BMPRII-Fc:ALK3-Fc.

Purification of various BMPRII-Fc:ALK3-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 21. Ligand Binding Profile of BMPRII-Fc:ALK3-Fc Heterodimer Compared to BMPRII-Fc Homodimer and ALK3-Fc Homodimer A Biacore™-based binding assay was used to compare ligand binding selectivity of the BMPRII-Fc:ALK3-Fc heterodimeric complex described above with that of BMPRII-Fc and ALK3-Fc homodimeric complexes. The BMPRII-Fc:ALK3-Fc heterodimer, BMPRII-Fc homodimer, and ALK3-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profile of BMPRII-Fc:ALK3-Fc heterodimer compared to BMPRII-Fc homodimer and ALK3-Fc homodimer

| Ligand | BMPRII-Fc homodimer | | | ALK3-Fc homodimer | | | BMPRII-Fc:ALK3-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin B | $2.0 \times 10^7$ | $7.5 \times 10^{-2}$ | 3800 | No binding | | | Minimal binding | | |
| BMP2 | Transient* | | $>2 \times 10^6$ | $6.2 \times 10^5$ | $1.4 \times 10{-4}$ | 230 | $2.9 \times 10^6$ | $1.5 \times 10{-4}$ | 51 |
| BMP4 | — | | | $2.6 \times 10^5$ | $5.5 \times 10{-5}$ | 210 | $9.1 \times 10^5$ | $9.1 \times 10{-5}$ | 100 |
| BMP5 | — | | | $2.9 \times 10^4$ | $2.3 \times 10^{-3}$ | 70000 | $4.3 \times 10^5$ | $1.4 \times 10^{-3}$ | 3200 |
| BMP6 | Transient* | | $>8900$ | $1.4 \times 10^5$ | $4.9 \times 10^{-3}$ | 35000 | $3.6 \times 10^5$ | $5.9 \times 10{-4}$ | 1600 |
| BMP7 | Transient* | | $>38000$ | $1.2 \times 10^6$ | $1.8 \times 10^{-2}$ | 15000 | $1.2 \times 10^7$ | $1.2 \times 10^{-2}$ | 1000 |
| BMP9 | $1.2 \times 10^7$ | $2.6 \times 10^{-2}$ | 2100 | No binding | | | No binding | | |
| BMP10 | $2.6 \times 10^7$ | $2.5 \times 10^{-3}$ | 100 | — | | | $6.8 \times 10^5$ | $1.6 \times 10^{-3}$ | 2400 |
| BMP15 | $9.9 \times 10^6$ | $2.8 \times 10^{-3}$ | 290 | — | | | $9.1 \times 10^5$ | $5.5 \times 10^{-3}$ | 6000 |
| GDF5 | No binding | | | $4.3 \times 10^5$ | $1.1 \times 10^{-2}$ | 22000 | Minimal binding | | |
| GDF6 | Transient* | | $>88000$ | $3.4 \times 10^4$ | $1.3 \times 10^{-3}$ | 40000 | $1.4 \times 10^6$ | $1.9 \times 10^{-3}$ | 1400 |

*Indeterminate due to transient nature of interaction
—Not tested

These comparative binding data demonstrate that the BMPRII-Fc:ALK3-Fc heterodimer has ligand binding selectivity which is clearly unlike that of BMPRII-Fc homodimer but also differs from that of ALK3-Fc homodimer. BMPRII-Fc:ALK3-Fc heterodimer binds much more strongly to BMP6 than does ALK3-Fc homodimer, reflecting an off-rate nearly ten-fold slower. With its largely unchanged binding to BMP2 and BMP4, the BMPRII-Fc:ALK3 heterodimer can therefore be considered a joint inhibitor of BMP2, BMP4, and BMP6. This binding profile contrasts with that of ALK3-Fc homodimer, whose exceptionally strongly binding to BMP4 and BMP2 identifies it as highly selective for this ligand pair compared to four ligands with intermediate-level binding, including BMP6. See FIG. 12. Accordingly, a BMPRII-Fc:ALK3-Fc heterodimer will be unexpectedly useful in certain therapeutic applications where joint antagonism of BMP2, BMP4, and BMP6 is advantageous.

Example 22. Generation of a BMPRII-Fc:ALK4-Fc Heterodimer

Applicants constructed a soluble BMPRII-Fc:ALK4-Fc heteromeric complex comprising the extracellular domains of human BMPRII and human ALK4, which are each separately fused to an Fc domain with a linker positioned between the extracellular domain and the Fc domain. The individual constructs are referred to as BMPRII-Fc fusion polypeptide and ALK4-Fc fusion polypeptide, respectively, and the sequences for each are provided herein.

Formation of heteromeric BMPRII-Fc:ALK4-Fc may be guided by approaches similar to those described in Example 1. In a first approach, one Fc domain is altered to introduce cationic amino acids at the interaction face, while the other Fc domain is altered to introduce anionic amino acids at the interaction face. The polypeptide sequence of the BMPRII-Fc fusion polypeptide and a nucleic acid sequence encoding it are provided above in Example 16 as SEQ ID NOs: 121-123. To promote formation of the BMPRII-Fc:ALK4-Fc heterodimer rather than either of the possible homodimeric complexes, two amino acid substitutions (replacing acidic amino acids with lysine) can be introduced into the Fc domain of the BMPRII-Fc fusion protein as indicated in Example 16. The amino acid sequences of SEQ ID NOs: 121 and 123 may optionally be provided with the lysine removed from the C-terminus.

The polypeptide sequence of the complementary ALK4-Fc fusion polypeptide and a nucleic acid sequence encoding it are provided in Example 1 as SEQ ID NOs: 104-106. To guide heterodimer formation with the BMPRII-Fc fusion polypeptide of SEQ ID NOs: 121 and 123, two amino acid substitutions (replacing lysines with aspartic acids) can be introduced into the Fc domain of the ALK4-Fc fusion polypeptide as indicated in Example 1. The amino acid sequences of SEQ ID NOs: 104 and 106 may optionally be provided with a lysine added at the C-terminus.

The BMPRII-Fc and ALK4-Fc fusion polypeptides of SEQ ID NO: 123 and SEQ ID NO: 106, respectively, may be co-expressed and purified from a CHO cell line, to give rise to a heteromeric complex comprising BMPRII-Fc:ALK4-Fc.

In a second approach to promote the formation of heteromultimer complexes using asymmetric Fc fusion proteins, the Fc domains are altered to introduce complementary hydrophobic interactions and an additional intermolecular disulfide bond. BMPRII-Fc fusion polypeptide sequences (SEQ ID NOs: 411 and 412) are discussed in Example 16. To promote formation of the BMPRII-Fc:ALK4-Fc heterodimer rather than either of the possible homodimeric complexes, two amino acid substitutions (replacing a serine with a cysteine and a threonine with a trytophan) can be introduced into the Fc domain of the BMPRII-Fc polypeptide as indicated in Example 16. The amino acid sequences of SEQ ID NOs: 411 and 412 may optionally be provided with the lysine removed from the C-terminus.

Polypeptide sequences of the complementary ALK4-Fc fusion polypeptide (SEQ ID NOs: 403 and 404) are discussed in Example 1. To guide heterodimer formation with the BMPRII-Fc fusion polypeptide of SEQ ID NOs: 411 and 412, four amino acid substitutions can be introduced into the Fc domain of the ALK4 fusion polypeptide as indicated in Example 1. The amino acid sequences of SEQ ID NOs: 403 and 404 may optionally be provided with the lysine removed from the C-terminus.

The BMPRII-Fc and ALK4-Fc fusion polypeptides of SEQ ID NO: 412 and SEQ ID NO: 404, respectively, may be co-expressed and purified from a CHO cell line, to give rise to a heteromeric complex comprising BMPRII-Fc:ALK4-Fc.

Purification of various BMPRII-Fc:ALK4-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 23. Ligand Binding Profile of BMPRII-Fc:ALK4-Fc Heterodimer Compared to BMPRII-Fc Homodimer and ALK4-Fc Homodimer A Biacore™-based binding assay was used to compare ligand binding selectivity of the BMPRII-Fc:ALK4-Fc heterodimeric complex described above with that of BMPRII-Fc and ALK4-Fc homodimeric complexes. The BMPRII-Fc:ALK4-Fc heterodimer, BMPRII-Fc homodimer, and ALK4-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

activin AB. See FIG. 13. Accordingly, a BMPRII-Fc:ALK4-Fc heterodimer will be unexpectedly useful in certain therapeutic applications where antagonism of activin A, activin B, and particularly activin AB are advantageous and where antagonism of BMP15 (which is heavily implicated in ovulation) is to be avoided.

Example 24. Generation of a TGFβRII-Fc:ALK1-Fc Heterodimer

Applicants constructed a soluble TGFβRII-Fc:ALK1-Fc heteromeric complex comprising the extracellular domains of the short (canonical) isoform of human TGFβRII and human ALK1, which are each separately fused to an Fc domain with a linker positioned between the extracellular domain and the Fc domain. The individual constructs are referred to as TGFβRII$_{SHORT}$-Fc fusion polypeptide and ALK1-Fc fusion polypeptide, respectively, and the sequences for each are provided herein.

Ligand binding profile of BMPRII-Fc:ALK4-Fc heterodimer compared to BMPRII-Fc homodimer and ALK4-Fc homodimer

| Ligand | BMPRII-Fc homodimer | | | ALK4-Fc homodimer | | | BMPRII-Fc:ALK4-Fc heterodimer | | |
|---|---|---|---|---|---|---|---|---|---|
| | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| Activin A | Transient* | | >43000 | $5.8 \times 10^5$ | $1.2 \times 10^{-2}$ | 20000 | $2.0 \times 10^6$ | $2.2 \times 10^{-3}$ | 1100 |
| Activin B | $2.0 \times 10^7$ | $7.5 \times 10^{-2}$ | 3800 | No binding | | | $1.6 \times 10^6$ | $2.6 \times 10^{-3}$ | 1700 |
| Activin AB | — | — | — | $4.4 \times 10^6$ | $6.4 \times 10^{-3}$ | 1500 | $3.6 \times 10^6$ | $5.0 \times 10^{-4}$ | 140 |
| BMP9 | $1.2 \times 10^7$ | $2.6 \times 10^{-2}$ | 2100 | No binding | | | Transient* | | >140000 |
| BMP10 | $2.6 \times 10^7$ | $2.5 \times 10^{-3}$ | 100 | No binding | | | $8.0 \times 10^5$ | $1.8 \times 10^{-3}$ | 2200 |
| BMP15 | $9.9 \times 10^6$ | $2.8 \times 10^{-3}$ | 290 | No binding | | | $2.8 \times 10^7$ | $4.8 \times 10^{-2}$ | 1700 |

*Indeterminate due to transient nature of interaction
— Not tested

These comparative binding data demonstrate that the BMPRII-Fc:ALK4-Fc heterodimer has ligand binding selectivity which is unlike that of either BMPRII-Fc homodimer or ALK4-Fc homodimer. BMPRII-Fc:ALK4-Fc heterodimer differs from both homodimers by binding several activin ligands with high or intermediate strength and differs from BMPRII-Fc homodimer by binding BMP15 only weakly. Most notably, BMPRII-Fc:ALK4-Fc heterodimer binds strongly and preferentially to the heterodimeric ligand Formation of heteromeric TGFβRII$_{SHORT}$-Fc:ALK1-Fc may be guided by approaches similar to those described in Example 1. In a first approach, one Fc domain is altered to introduce cationic amino acids at the interaction face, while the other Fc domain is altered to introduce anionic amino acids at the interaction face.

The TGFβRII$_{SHORT}$-Fc polypeptide sequence (SEQ ID NO: 127) is shown below:

(SEQ ID NO: 127)

```
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYNTSNP DTGGGTHTCP PCPAPELLGG PSVFLFPPKP KDTLMISRTP

201 EVTCVVVDVS HEDPEVKFNW YVDGVEVHNA KTKPREEQYN STYRVVSVLT

251 VLHQDWLNGK EYKCKVSNKA LPAPIEKTIS KAKGQPREPQ VYTLPPSRKE

301 MTKNQVSLTC LVKGFYPSDI AVEWESNGQP ENNYKTTPPV LKSDGSFFLY

351 SKLTVDKSRW QQGNVFSCSV MHEALHNHYT QKSLSLSPGK
```

The leader sequence and linker sequence are underlined. To promote formation of the TGFβRII$_{SHORT}$-Fc:ALK1-Fc heterodimer rather than either of the possible homodimeric complexes, two amino acid substitutions (replacing acidic amino acids with lysine) can be introduced into the Fc domain of the TGFβRII$_{SHORT}$-Fc fusion protein as indicated by double underline above. The amino acid sequence of SEQ ID NO: 127 may optionally be provided with the lysine removed from the C-terminus.

This TGFβRII$_{SHORT}$-Fc fusion protein is encoded by the following nucleic acid sequence (SEQ ID NO: 128):

```
                                                    (SEQ ID NO: 128)
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 TTAATAACGA CATGATAGTC ACTGACAACA ACGGTGCAGT CAAGTTTCCA

151 CAACTGTGTA AATTTTGTGA TGTGAGATTT TCCACCTGTG ACAACCAGAA

201 ATCCTGCATG AGCAACTGCA GCATCACCTC CATCTGTGAG AAGCCACAGG

251 AAGTCTGTGT GGCTGTATGG AGAAAGAATG ACGAGAACAT AACACTAGAG

301 ACAGTTTGCC ATGACCCCAA GCTCCCCTAC CATGACTTTA TTCTGGAAGA

351 TGCTGCTTCT CCAAAGTGCA TTATGAAGGA AAAAAAAAAG CCTGGTGAGA

401 CTTTCTTCAT GTGTTCCTGT AGCTCTGATG AGTGCAATGA CAACATCATC

451 TTCTCAGAAG AATATAACAC CAGCAATCCT GACACCGGTG GTGGAACTCA

501 CACATGCCCA CCGTGCCCAG CACCTGAACT CCTGGGGGGA CCGTCAGTCT

551 TCCTCTTCCC CCCAAAACCC AAGGACACCC TCATGATCTC CCGGACCCCT

601 GAGGTCACAT GCGTGGTGGT GGACGTGAGC CACGAAGACC CTGAGGTCAA

651 GTTCAACTGG TACGTGGACG GCGTGGAGGT GCATAATGCC AAGACAAAGC

701 CGCGGGAGGA GCAGTACAAC AGCACGTACC GTGTGGTCAG CGTCCTCACC

751 GTCCTGCACC AGGACTGGCT GAATGGCAAG GAGTACAAGT GCAAGGTCTC

801 CAACAAAGCC CTCCCAGCCC CCATCGAGAA AACCATCTCC AAAGCCAAAG

851 GGCAGCCCCG AGAACCACAG GTGTACACCC TGCCCCCATC CCGGAAGGAG

901 ATGACCAAGA ACCAGGTCAG CCTGACCTGC CTGGTCAAAG GCTTCTATCC

951 CAGCGACATC GCCGTGGAGT GGGAGAGCAA TGGGCAGCCG GAGAACAACT

1001 ACAAGACCAC GCCTCCCGTG CTGAAGTCCG ACGGCTCCTT CTTCCTCTAT

1051 AGCAAGCTCA CCGTGGACAA GAGCAGGTGG CAGCAGGGGA ACGTCTTCTC

1101 ATGCTCCGTG ATGCATGAGG CTCTGCACAA CCACTACACG CAGAAGAGCC

1151 TCTCCCTGTC TCCGGGTAAA
```

The mature TGFβRII$_{SHORT}$-Fc fusion polypeptide (SEQ ID NO: 129) is as follows and may optionally be provided with the lysine removed from the C-terminus.

```
                                                    (SEQ ID NO: 129)
   1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPDTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPSRKEMTKN QVSLTCLVKG FYPSDIAVEW

301 ESNGQPENNY KTTPPVLKSD GSFFLYSKLT VDKSRWQQGN VFSCSVMHEA

351 LHNHYTQKSL SLSPGK
```

The polypeptide sequence of the complementary ALK1-Fc fusion polypeptide and a nucleic acid sequence encoding it are provided in Example 16 as SEQ ID NOs: 124-126. To guide heterodimer formation with the TGFβRII$_{SHORT}$-Fc fusion polypeptide of SEQ ID NOs: 127 and 129, two amino acid substitutions (replacing lysines with aspartic acids) can be introduced into the Fc domain of the ALK1-Fc fusion polypeptide as indicated in Example 16. The amino acid sequences of SEQ ID NOs: 124 and 126 may optionally be provided with a lysine added at the C-terminus.

The TGFβRII$_{SHORT}$-Fc and ALK1-Fc proteins of SEQ ID NO: 129 and SEQ ID NO: 126, respectively, may be co-expressed and purified from a CHO cell line, to give rise to a heteromeric complex comprising TGFβRII$_{SHORT}$-Fc: ALK1-Fc.

A variant TGFβRII-Fc:ALK1-Fc heteromeric complex may be generated in which the ALK1-Fc polypeptide described above (SEQ ID NO: 126) is paired with an Fc fusion protein comprising the extracellular domain of the long (A) isoform of TGFβRII (TGFβRII$_{LONG}$) in place of the extracellular domain of the short isoform.

The TGFβRII$_{LONG}$-Fc polypeptide sequence (SEQ ID NO: 130) is shown below:

```
                                                    (SEQ ID NO: 130)
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG THTCPPCPAP

201 ELLGGPSVFL FPPKPKDTLM ISRTPEVTCV VVDVSHEDPE VKFNWYVDGV

251 EVHNAKTKPR EEQYNSTYRV VSVLTVLHQD WLNGKEYKCK VSNKALPAPI

301 EKTISKAKGQ PREPQVYTLP PSRKEMTKNQ VSLTCLVKGF YPSDIAVEWE

351 SNGQPENNYK TTPPVLKSDG SFFLYSKLTV DKSRWQQGNV FSCSVMHEAL

401 HNHYTQKSLS LSPGK
```

The leader sequence and linker sequence are underlined. To promote formation of the TGFβRII$_{LONG}$-Fc:ALK1-Fc heterodimer rather than either of the possible homodimeric complexes, two amino acid substitutions (replacing acidic amino acids with lysine) can be introduced into the Fc domain of the TGFβRII$_{LONG}$-Fc fusion protein as indicated by double underline above. The amino acid sequence of SEQ ID NO: 130 may optionally be provided with the lysine removed from the C-terminus.

This TGFβRII$_{LONG}$-Fc fusion protein is encoded by the following nucleic acid sequence (SEQ ID NO: 131):

```
                                                    (SEQ ID NO: 131)
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA ACTCACACAT GCCCACCGTG CCCAGCACCT

601 GAACTCCTGG GGGGACCGTC AGTCTTCCTC TTCCCCCCAA AACCCAAGGA

651 CACCCTCATG ATCTCCCGGA CCCCTGAGGT CACATGCGTG GTGGTGGACG

701 TGAGCCACGA AGACCCTGAG GTCAAGTTCA ACTGGTACGT GGACGGCGTG
```

```
 751 GAGGTGCATA ATGCCAAGAC AAAGCCGCGG GAGGAGCAGT ACAACAGCAC

801 GTACCGTGTG GTCAGCGTCC TCACCGTCCT GCACCAGGAC TGGCTGAATG

851 GCAAGGAGTA CAAGTGCAAG GTCTCCAACA AAGCCCTCCC AGCCCCCATC

901 GAGAAAACCA TCTCCAAAGC CAAAGGGCAG CCCCGAGAAC CACAGGTGTA

951 CACCCTGCCC CCATCCCGGA AGGAGATGAC CAAGAACCAG GTCAGCCTGA

1001 CCTGCCTGGT CAAAGGCTTC TATCCCAGCG ACATCGCCGT GGAGTGGGAG

1051 AGCAATGGGC AGCCGGAGAA CAACTACAAG ACCACGCCTC CCGTGCTGAA

1101 GTCCGACGGC TCCTTCTTCC TCTATAGCAA GCTCACCGTG GACAAGAGCA

1151 GGTGGCAGCA GGGGAACGTC TTCTCATGCT CCGTGATGCA TGAGGCTCTG

1201 CACAACCACT ACACGCAGAA GAGCCTCTCC CTGTCTCCGG GTAAA
```

The mature TGFβRII$_{LONG}$-Fc fusion polypeptide (SEQ ID NO: 132) is as follows and may optionally be provided with the lysine removed from the C-terminus.

The leader sequence and linker sequence are underlined. To promote formation of the TGFβRII$_{SHORT}$-Fc:ALK1-Fc heterodimer rather than either of the possible homodimeric

```
                                                  (SEQ ID NO: 132)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PDTGGGTHTC PPCPAPELLG GPSVFLFPPK PKDTLMISRT

201 PEVTCVVVDV SHEDPEVKFN WYVDGVEVHN AKTKPREEQY NSTYRVVSVL

251 TVLHQDWLNG KEYKCKVSNK ALPAPIEKTI SKAKGQPREP QVYTLPPSRK

301 EMTKNQVSLT CLVKGFYPSD IAVEWESNGQ PENNYKTTPP VLKSDGSFFL

351 YSKLTVDKSR WQQGNVFSCS VMHEALHNHY TQKSLSLSPG K
```

In a second approach to promote the formation of heteromultimer complexes using asymmetric Fc fusion proteins, the Fc domains are altered to introduce complementary hydrophobic interactions and an additional intermolecular disulfide bond.

The TGFβRII$_{SHORT}$-Fc polypeptide sequence (SEQ ID NO: 415) is shown below:

complexes, two amino acid substitutions (replacing a serine with a cysteine and a threonine with a trytophan) can be introduced into the Fc domain of the fusion protein as indicated by double underline above. The amino acid sequence of SEQ ID NO: 415 may optionally be provided with the lysine removed from the C-terminus.

```
                                                  (SEQ ID NO: 415)
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYNTSNP DTGGGTHTCP PCPAPELLGG PSVFLFPPKP KDTLMISRTP

201 EVTCVVVDVS HEDPEVKFNW YVDGVEVHNA KTKPREEQYN STYRVVSVLT

251 VLHQDWLNGK EYKCKVSNKA LPAPIEKTIS KAKGQPREPQ VYTLPPCREE

301 MTKNQVSLWC LVKGFYPSDI AVEWESNGQP ENNYKTTPPV LDSDGSFFLY

351 SKLTVDKSRW QQGNVFSCSV MHEALHNHYT QKSLSLSPGK
```

The mature TGFβRII$_{SHORT}$-Fc fusion polypeptide (SEQ ID NO: 416) is as follows and may optionally be provided with the lysine removed from the C-terminus.

```
                                                            (SEQ ID NO: 416)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPDTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPCREEMTKN QVSLWCLVKG FYPSDIAVEW

301 ESNGQPENNY KTTPPVLDSD GSFFLYSKLT VDKSRWQQGN VFSCSVMHEA

351 LHNHYTQKSL SLSPGK
```

Polypeptide sequences of the complementary ALK1-Fc fusion polypeptide (SEQ ID NOs: 413 and 414) are discussed in Example 16. To guide heterodimer formation with the TGFβ$_{SHORT}$-Fc fusion polypeptide of SEQ ID NOs: 415 and 416, four amino acid substitutions can be introduced into the Fc domain of the ALK1 fusion polypeptide as indicated in Example 16. The amino acid sequences of SEQ ID NOs: 413 and 414 may optionally be provided with the lysine removed from the C-terminus.

The TGFβRII$_{SHORT}$-Fc and ALK1-Fc proteins of SEQ ID NO: 416 and SEQ ID NO: 414, respectively, may be co-expressed and purified from a CHO cell line, to give rise to a heteromeric complex comprising TGFBRII-Fc:ALK1-Fc.

A variant TGFβRII-Fc:ALK1-Fc heteromeric complex may be generated in which the ALK1-Fc polypeptide described above (SEQ ID NO: 414) is paired with an Fc fusion protein comprising the extracellular domain of the long (A) isoform of TGFβRII (TGFβRII$_{LONG}$) in place of the extracellular domain of the short isoform.

The TGFβRII$_{LONG}$-Fc polypeptide sequence (SEQ ID NO: 417) is shown below:

```
                                                            (SEQ ID NO: 417)
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG THTCPPCPAP

201 ELLGGPSVFL FPPKPKDTLM ISRTPEVTCV VVDVSHEDPE VKFNWYVDGV

251 EVHNAKTKPR EEQYNSTYRV VSVLTVLHQD WLNGKEYKCK VSNKALPAPI

301 EKTISKAKGQ PREPQVYTLP PCREEMTKNQ VSLWCLVKGF YPSDIAVEWE

351 SNGQPENNYK TTPPVLDSDG SFFLYSKLTV DKSRWQQGNV FSCSVMHEAL

401 HNHYTQKSLS LSPGK
```

The leader sequence and linker sequence are underlined. To promote formation of the TGFβRII$_{LONG}$-Fc:ALK1-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 417 may optionally be provided with the lysine removed from the C-terminus.

The mature TGFβRII$_{LONG}$-Fc fusion polypeptide (SEQ ID NO: 418) is as follows and may optionally be provided with the lysine removed from the C-terminus.

```
                                                            (SEQ ID NO: 418)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PDTGGGTHTC PPCPAPELLG GPSVFLFPPK PKDTLMISRT
```

```
201 PEVTCVVVDV SHEDPEVKFN WYVDGVEVHN AKTKPREEQY NSTYRVVSVL

251 TVLHQDWLNG KEYKCKVSNK ALPAPIEKTI SKAKGQPREP QVYTLPPCRE

301 EMTKNQVSLW CLVKGFYPSD IAVEWESNGQ PENNYKTTPP VLDSDGSFFL

351 YSKLTVDKSR WQQGNVFSCS VMHEALHNHY TQKSLSLSPG K
```

The TGFβRII$_{LONG}$-Fc and ALK1-Fc proteins of SEQ ID NO: 418 and SEQ ID NO: 414, respectively, may be co-expressed and purified from a CHO cell line, to give rise to a heteromeric complex comprising TGFβRII$_{LONG}$-Fc:ALK1-Fc.

Purification of various TGFβRII-Fc:ALK1-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 25. Ligand Binding Profile of TGFβRII-Fc:ALK1-Fc Heterodimer Compared to TGFβRII-Fc Homodimer and ALK1-Fc Homodimer A Biacore™-based binding assay was used to compare ligand binding selectivity of the TGFβRII$_{SHORT}$-Fc:ALK1-Fc heterodimeric complex described above with that of TGFβRII$_{SHORT}$-Fc and ALK1-Fc homodimeric complexes. The TGFβRII$_{SHORT}$-Fc:ALK1-Fc heterodimer, TGFβRII$_{SHORT}$-Fc homodimer, and ALK1-Fc homodimer were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Formation of heteromeric TGFβRII$_{SHORT}$-Fc:ALK5-Fc may be guided by approaches similar to those described in Example 1. In a first approach, one Fc domain is altered to introduce cationic amino acids at the interaction face, while the other Fc domain is altered to introduce anionic amino acids at the interaction face. The polypeptide sequence of the TGFβRII$_{SHORT}$-Fc fusion polypeptide and a nucleic acid sequence encoding it are provided above in Example 24 as SEQ ID NOs: 127-129. To promote formation of the TGFβRII$_{SHORT}$-Fc:ALK5-Fc heterodimer rather than either of the possible homodimeric complexes, two amino acid substitutions (replacing acidic amino acids with lysine) can be introduced into the Fc domain of the TGFβRII$_{SHORT}$-Fc fusion protein as indicated in Example 24. The amino acid sequences of SEQ ID NOs: 127 and 129 may optionally be provided with the lysine removed from the C-terminus.

The polypeptide sequence of the complementary ALK5-Fc fusion polypeptide and a nucleic acid sequence encoding it are provided in Example 11 as SEQ ID NOs: 139-141. To guide heterodimer formation with the TGFβRII$_{SHORT}$-Fc fusion polypeptide of SEQ ID NOs: 127 and 129, two amino acid substitutions (replacing lysines with aspartic acids) can be introduced into the Fc domain of the ALK5-Fc fusion polypeptide as indicated in Example 11. The amino acid sequences of SEQ ID NOs: 139 and 141 may optionally be provided with a lysine added at the C-terminus.

The TGFβRII$_{SHORT}$-Fc and ALK5-Fc fusion polypeptides of SEQ ID NO: 129 and SEQ ID NO: 141, respectively, may be co-expressed and purified from a CHO cell line, to give rise to a heteromeric complex comprising TGFβRII$_{SHORT}$-Fc:ALK5-Fc.

Ligand binding profile of TGFBRII$_{SHORT}$-Fc:ALK1-Fc heterodimer compared to TGFBRII$_{SHORT}$-Fc homodimer and ALK1-Fc homodimer

| | TGFBRII$_{SHORT}$-Fc homodimer | | | ALK1-Fc homodimer | | | TGFBRII$_{SHORT}$-Fc:ALK1-Fc heterodimer | | |
|---|---|---|---|---|---|---|---|---|---|
| Ligand | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| BMP9 | No binding | | | $7.9 \times 10^6$ | $1.3 \times 10^{-4}$ | 16 | $2.1 \times 10^7$ | $2.2 \times 10^{-3}$ | 110 |
| BMP10 | No binding | | | $1.7 \times 10^7$ | $1.1 \times 10^{-4}$ | 6 | $1.2 \times 10^7$ | $9.6 \times 10^{-4}$ | 78 |
| TGFβ1 | $4.2 \times 10^7$ | $1.1 \times 10^{-3}$ | 25 | No binding | | | Transient* | | >5300 |
| TGFβ2 | Transient* | | >44000 | No binding | | | No binding | | |
| TGFβ3 | $5.9 \times 10^7$ | $5.9 \times 10^{-3}$ | 99 | No binding | | | Transient* | | >4700 |

*Indeterminate due to transient nature of interaction

Example 26. Generation of a TGFβRII$_{SHORT}$-Fc:ALK5-Fc Heterodimer

Applicants constructed a soluble TGFβRII$_{SHORT}$-Fc:ALK5-Fc heteromeric complex comprising the extracellular domains of the human TGFβRII short (canonical) isoform and human ALK5, which are each separately fused to an Fc domain with a linker positioned between the extracellular domain and the Fc domain. The individual constructs are referred to as TGFβRII$_{SHORT}$-Fc fusion polypeptide and ALK5-Fc fusion polypeptide, respectively, and the sequences for each are provided herein.

In a second approach to promote the formation of heteromultimer complexes using asymmetric Fc fusion proteins, the Fc domains are altered to introduce complementary hydrophobic interactions and an additional intermolecular disulfide bond. TGFβRII$_{SHORT}$-Fc fusion polypeptide sequences (SEQ ID NOs: 415-416) are discussed in Example 24. To promote formation of the TGFβRII$_{SHORT}$-Fc:ALK5-Fc heterodimer rather than either of the possible homodimeric complexes, two amino acid substitutions (replacing a serine with a cysteine and a threonine with a trytophan) can be introduced into the Fc domain of the TGFβRII$_{SHORT}$-Fc polypeptide as indicated in Example 24. The amino acid sequences of SEQ ID NOs:

415-416 may optionally be provided with the lysine removed from the C-terminus.

Polypeptide sequences of the complementary ALK5-Fc fusion polypeptide (SEQ ID NOs: 423-424) are discussed in Example 11. To guide heterodimer formation with the TGFβRII$_{SHORT}$-Fc fusion polypeptide of SEQ ID NOs: 415-416, four amino acid substitutions can be introduced into the Fc domain of the ALK5 fusion polypeptide as indicated in Example 11. The amino acid sequences of SEQ ID NOs: 423-424 may optionally be provided with the lysine removed from the C-terminus.

The TGFβRII$_{SHORT}$-Fc and ALK5-Fc fusion polypeptides of SEQ ID NO: 416 and SEQ ID NO: 424, respectively, may be co-expressed and purified from a CHO cell line, to give rise to a heteromeric complex comprising TGFβRII$_{SHORT}$-Fc:ALK5-Fc.

Purification of various TGFβRII$_{SHORT}$-Fc:ALK5-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 27. Generation of a TGFβRII$_{LONG}$-Fc:ALK5-Fc Heterodimer

Applicants constructed a soluble TGFβRII$_{LONG}$-Fc:ALK5-Fc heteromeric complex comprising the extracellular domain of the long (A) isoform of human TGFβRII and the extracellular domain of human ALK5, which are each separately fused to an Fc domain with a linker positioned between the extracellular domain and the Fc domain. The individual constructs are referred to as TGFβRII$_{LONG}$-Fc fusion polypeptide and ALK5-Fc fusion polypeptide, respectively, and the sequences for each are provided herein.

Formation of heteromeric TGFβRII$_{LONG}$-Fc:ALK5-Fc may be guided by approaches similar to those described in Example 1. In a first approach, one Fc domain is altered to introduce cationic amino acids at the interaction face, while the other Fc domain is altered to introduce anionic amino acids at the interaction face. The polypeptide sequence of the TGFβRII$_{LONG}$-Fc fusion polypeptide and a nucleic acid sequence encoding it are provided above in Example 24 as SEQ ID NOs: 130-132. To promote formation of the TGFβRII$_{LONG}$-Fc:ALK5-Fc heterodimer rather than either of the possible homodimeric complexes, two amino acid substitutions (replacing acidic amino acids with lysine) can be introduced into the Fc domain of the TGFβRII$_{LONG}$-Fc fusion protein as indicated in Example 24. The amino acid sequences of SEQ ID NOs: 130 and 132 may optionally be provided with the lysine removed from the C-terminus.

The polypeptide sequence of the complementary ALK5-Fc fusion polypeptide and a nucleic acid sequence encoding it are provided in Example 11 as SEQ ID NOs: 139-141. To guide heterodimer formation with the TGFβRII$_{LONG}$-Fc fusion polypeptide of SEQ ID NOs: 130 and 132, two amino acid substitutions (replacing lysines with aspartic acids) can be introduced into the Fc domain of the ALK5-Fc fusion polypeptide as indicated in Example 11. The amino acid sequences of SEQ ID NOs: 139 and 142 may optionally be provided with a lysine added at the C-terminus.

The TGFβRII$_{LONG}$-Fc and ALK5-Fc fusion polypeptides of SEQ ID NO: 132 and SEQ ID NO: 141, respectively, may be co-expressed and purified from a CHO cell line, to give rise to a heteromeric complex comprising TGFβRII$_{LONG}$-Fc:ALK5-Fc.

In a second approach to promote the formation of heteromultimer complexes using asymmetric Fc fusion proteins, the Fc domains are altered to introduce complementary hydrophobic interactions and an additional intermolecular disulfide bond. TGFβRII$_{LONG}$-Fc fusion polypeptide sequences (SEQ ID NOs: 417-418) are discussed in Example 24. To promote formation of the TGFβRII$_{LONG}$-Fc:ALK5-Fc heterodimer rather than either of the possible homodimeric complexes, two amino acid substitutions (replacing a serine with a cysteine and a threonine with a trytophan) can be introduced into the Fc domain of the TGFβRII$_{LONG}$-Fc polypeptide as indicated in Example 24. The amino acid sequences of SEQ ID NOs: 417-418 may optionally be provided with the lysine removed from the C-terminus.

Polypeptide sequences of the complementary ALK5-Fc fusion polypeptide (SEQ ID NOs: 423-424) are discussed in Example 11. To guide heterodimer formation with the TGFβRII$_{LONG}$-Fc fusion polypeptide of SEQ ID NOs: 417-418, four amino acid substitutions can be introduced into the Fc domain of the ALK5 fusion polypeptide as indicated in Example 11. The amino acid sequences of SEQ ID NOs: 423-424 may optionally be provided with the lysine removed from the C-terminus.

The TGFβRII$_{LONG}$-Fc and ALK5-Fc fusion polypeptides of SEQ ID NO: 418 and SEQ ID NO: 424, respectively, may be co-expressed and purified from a CHO cell line, to give rise to a heteromeric complex comprising TGFβRII$_{LONG}$-Fc:ALK5-Fc.

Purification of various TGFβRII$_{LONG}$-Fc:ALK5-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 28. Activity Profiles of TGFβRII-Fc:ALK5-Fc Heterodimers Compared to TGFβRII-Fc Homodimer and ALK5-Fc Homodimer A Biacore™-based binding assay was used to compare ligand binding selectivity of the TGFβRII$_{SHORT}$-Fc:ALK5-Fc and TGFβRII$_{LONG}$-Fc:ALK5-Fc heterodimeric complexes described in Examples 26-27 with that of TGFβRII$_{SHORT}$-Fc and ALK5-Fc homodimeric complexes. The heteromeric or homomeric protein complexes were independently captured onto the system using an anti-Fc antibody. Ligands were injected and allowed to flow over the captured receptor protein. Results are summarized in the table below, in which ligand off-rates ($k_d$) most indicative of effective ligand traps are denoted in bold.

Ligand binding profiles of TGFβRII-Fc:ALK5-Fc heterodimers compared to TGFβRII-Fc homodimer and ALK5-Fc homodimer

| | ALK5-Fc Homodimer | | | TGFβRII$_{SHORT}$-Fc Homodimer | | | TGFβRII$_{SHORT}$-Fc:ALK5-Fc Heterodimer | | | TGFβRII$_{SHORT}$-Fc:ALK5-Fc Heterodimer | | |
|---|---|---|---|---|---|---|---|---|---|---|---|---|
| Ligand | $k_a$ | $k_d$ | $K_D$ | $k_a$ (1/Ms) | $k_d$ (1/s) | $K_D$ (pM) | $k_a$ (1/Ms) | $k_d$ (1/s) | $K_D$ (pM) | $k_a$ (1/Ms) | $k_d$ (1/s) | $K_D$ (pM) |
| TGFβ1 | No binding | | | $5.6 \times 10^7$ | $1.1 \times 10^{-3}$ | 20 | $1.4 \times 10^8$ | $1.7 \times 10^{-3}$ | 12 | $6.6 \times 10^7$ | $9.2 \times 10^{-1}$ | 14 |
| TGFβ2 | No binding | | | $2.1 \times 10^5$ | $2.2 \times 10^{-3}$ | 11000 | $6.6 \times 10^6$ | $2.9 \times 10^{-6}$ | 0.4 | $4.2 \times 10^6$ | $2.8 \times 10^{-7}$ | 0.07 |
| TGFβ3 | No binding | | | $1.9 \times 10^7$ | $1.4 \times 10^{-3}$ | 71 | $2.7 \times 10^7$ | $1.0 \times 10^{-3}$ | 38 | $2.7 \times 10^7$ | $1.0 \times 10^{-3}$ | 38 |

*Low signal which suggests that a substantial fraction of the protein is inactive These comparative binding data indicate that the ligand binding profiles of TGFBRII-Fc:ALK5-Fc heterodimers are markedly different from that of TGFBRII-Fc homodimer and from ALK5-Fc homodimer, which did not bind any ligands. Based on the equilibrium dissociation constant ($K_D$), TGFβRII-Fc homodimer bound TGFβ1 and TGFβ3 with much higher affinity than TGFβ1, even though off-rates for the three TGFβ ligands were similar. In contrast, TGF-BRII-Fc:ALK5-Fc heterodimers displayed high selectivity for TGFβ2 over TGFβ1/TGFβ3. In particular, TGFβRII$_{LONG}$-Fc:ALK5-Fc heterodimer bound TGFβ2 with an affinity approximately five orders of magnitude higher and an off-rate approximately four orders of magnitude slower than did TGFβRII-Fc homodimer. TGFβRII$_{LONG}$-Fc:ALK5-Fc heterodimer also bound TGFβ2 more strongly than did heterodimer containing the short isoform. See FIG. 14. Neither of the TGFβRII-Fc:ALK5-Fc heterodimers was able to bind BMP9 or BMP10 (data not shown), which distinguishes these TGFβRII-Fc:ALK5-Fc heterodimers from TGFβRII-Fc:ALK1-Fc heterodimer (see Example 25). Sensograms for the two TGFβRII-Fc:ALK5-Fc heterodimers exhibited low signal amplitude which suggests that a substantial fraction of each protein was inactive.

To better interpret these data obtained by surface plasmon resonance, a reporter gene assay in A549 cells was used to determine the ability of TGFβRII fusion proteins to inhibit activity of TGFβ1, TGFβ2, and TGFβ3. This assay is based on a human lung carcinoma cell line transfected with reporter plasmids pGL3(CAGA)12-firefly luciferase (Dennler et al, 1998, EMBO 17: 3091-3100) and pRLCMV-renilla luciferase, the latter to control for transfection efficiency. The CAGA motif is present in the promoters of TGFβ-responsive genes (for example, PAI-1), so this vector is of general use for factors signaling through SMAD2 and SMAD3.

On the first day of the assay, A549 cells (ATCC®: CCL-185™) were distributed in 48-well plates at 6.5×10⁴ cells per well and incubated overnight. All incubations were at 37° C. and 5% $CO_2$ in a tissue culture incubator unless otherwise indicated. On the second day, a solution containing 10 µg pGL3(CAGA)12-firefly luciferase, 100 ng pRL-CMV-renilla luciferase, 30 µL X-tremeGENE 9 (Roche Applied Science), and 970 µL OptiMEM (Invitrogen) was preincubated for 30 min at room temperature, then added to 24 mL Eagle's minimum essential medium (EMEM, ATCC®) supplemented with 0.1% BSA. Medium was removed from the plated cells and this transfection mixture was applied to the cells (500 µl/well) for an overnight incubation. On the third day, medium was removed, and cells were incubated overnight with a mixture of ligands and inhibitors prepared as described below.

Serial dilutions of test articles were made in a 48-well plate in a 200 µL volume of assay buffer (EMEM+0.1% BSA). An equal volume of assay buffer containing the test ligand was added to obtain a final ligand concentration equal to the $EC_{50}$ determined previously. Human TGFβ1, TGFβ2, and TGFβ3 were obtained from PeproTech. Test solutions were incubated for 30 minutes, then 250 µL of the mixture was added to the transfected cells. Each concentration of test article was determined in duplicate. After incubation with test solutions overnight, cells were rinsed with phosphate-buffered saline, then lysed with passive lysis buffer (Promega E1941) and stored overnight at −70° C. On the fourth and final day, plates were warmed to room temperature with gentle shaking. Cell lysates were transferred to a chemiluminescence plate (96-well) and analyzed in a luminometer with reagents from a Dual-Luciferase Reporter Assay system (Promega E1980) to determine normalized luciferase activity.

This assay was used to compare the ability of TGFβRII fusion protein variants to inhibit cell signaling by TGFβRII ligands. Results are shown in the table below.

| | Inhibitory Activity of TGFβRII Fusion Proteins in A549 Cells | | |
|---|---|---|---|
| | $IC_{50}$ (pM) | | |
| Construct | TGFβ1 (640 pg/mL) | TGFβ2 (480 pg/mL) | TGFβ3 (270 pg/mL) |
| TGFβRII$_{SHORT}$-Fc homodimer | 90 | — | 9 |
| TGFβRII$_{SHORT}$-Fc:ALK5-Fc heterodimer* | <350* | ~200* | <90* |
| TGFβRII$_{LONG}$-Fc:ALK5-Fc heterodimer | 204 | 154 | 35 |

— No inhibition (tested at concentrations up to 10 nM)
*Value imprecise due to range of concentrations tested Results with TGFβRII-Fc homodimer were consistent with previous reports concerning wild-type TGFβRII$_{SHORT}$-Fc and TGFβRII$_{LONG}$-Fc homodimers (del Re et al., J Biol Chem 279:22765, 2004). In this experiment, TGFβRII$_{SHORT}$-Fc homodimer potently inhibited TGFβ1 and TGFβ3 but was unable to inhibit TGFβ2 at homodimer concentrations up to 10 nM. This finding is consistent with the low affinity of TGFβ2 binding to TGFβRII-Fc homodimer but oddly inconsistent with its slow off-rate (see binding results above). In contrast, TGFβRII-Fc:ALK5-Fc heterodimers potently inhibited all three TGFβ ligands in a cellular environment. Accordingly, a TGFβRII-Fc:ALK5-Fc heterodimer will be unexpectedly useful in certain therapeutic applications where preferential antagonism of TGFβ2—or combined antagonism of TGFβ1, TGFβ2, and TGFβ3—are advantageous.

Example 29. Generation of MISRII-Fc:ALK3-Fc Heterodimers

A soluble MISRII-Fc:ALK3-Fc heteromeric complex can be generated comprising the extracellular domains of human MISRII and human ALK3, which can each be separately fused to an Fc domain with a linker positioned between the extracellular domain and the Fc domain. The individual constructs are referred to as MISRII-Fc fusion polypeptide and ALK3-Fc fusion polypeptide, respectively.

Formation of heteromeric MISRII-Fc:ALK3-Fc may be guided by approaches similar to those described in Example 1. In a first approach, one Fc domain is altered to introduce cationic amino acids at the interaction face, while the other Fc domain is altered to introduce anionic amino acids at the interaction face.

The MISRII-Fc polypeptide sequence (SEQ ID NO: 133) is shown below:

```
                                                   (SEQ ID NO: 133)
  1 MDAMKRGLCC VLLLCGAVFV SPGAPPNRRT CVFFEAPGVR GSTKTLGELL

51 DTGTELPRAI RCLYSRCCFG IWNLTQDRAQ VEMQGCRDSD EPGCESLHCD

101 PSPRAHPSPG STLFTCSCGT DFCNANYSHL PPPGSPGTPG SQGPQAAPGE

151 SIWMALTGGG THTCPPCPAP ELLGGPSVFL FPPKPKDTLM ISRTPEVTCV

201 VVDVSHEDPE VKFNWYVDGV EVHNAKTKPR EEQYNSTYRV VSVLTVLHQD

251 WLNGKEYKCK VSNKALPAPI EKTISKAKGQ PREPQVYTLP PSRKEMTKNQ

301 VSLTCLVKGF YPSDIAVEWE SNGQPENNYK TTPPVLKSDG SFFLYSKLTV

351 DKSRWQQGNV FSCSVMHEAL HNHYTQKSLS LSPGK
```

The leader sequence and linker sequence are underlined. To promote formation of the MISRII-Fc:ALK3-Fc heterodimer rather than either of the possible homodimeric complexes, two amino acid substitutions (replacing acidic amino acids with lysine) can be introduced into the Fc domain of the MISRII fusion protein as indicated by double underline above. The amino acid sequence of SEQ ID NO: 133 may optionally be provided with the lysine removed from the C-terminus.

The mature MISRII-Fc fusion polypeptide (SEQ ID NO: 135) is as follows and may optionally be provided with the lysine removed from the C-terminus.

```
                                                   (SEQ ID NO: 135)
  1 PPNRRTCVFF EAPGVRGSTK TLGELLDTGT ELPRAIRCLY SRCCFGIWNL

51 TQDRAQVEMQ GCRDSDEPGC ESLHCDPSPR AHPSPGSTLF TCSCGTDFCN

101 ANYSHLPPPG SPGTPGSQGP QAAPGESIWM ALTGGGTHTC PPCPAPELLG

151 GPSVFLFPPK PKDTLMISRT PEVTCVVVDV SHEDPEVKFN WYVDGVEVHN

201 AKTKPREEQY NSTYRVVSVL TVLHQDWLNG KEYKCKVSNK ALPAPIEKTI

251 SKAKGQPREP QVYTLPPSRK EMTKNQVSLT CLVKGFYPSD IAVEWESNGQ

301 PENNYKTTPP VLKSDGSFFL YSKLTVDKSR WQQGNVFSCS VMHEALHNHY

351 TQKSLSLSPG K
```

In this first approach, the polypeptide sequence of the complementary ALK3-Fc fusion protein and a nucleic acid sequence encoding it are provided above in Example 4 as SEQ ID NOs: 115-117.

The MISRII-Fc and ALK3-Fc proteins of SEQ ID NO: 135 and SEQ ID NO: 117, respectively, may be co-expressed and purified from a CHO cell line, to give rise to a heteromeric complex comprising MISRII-Fc:ALK3-Fc. Similar heteromeric complexes may generated by pairing the ALK3-Fc protein described above (SEQ ID NO: 117) with an Fc fusion protein comprising the extracellular domain of MISRII isoform 2 or the extracellular domain of MISRII isoform 3 in place of the extracellular domain of MISRII isoform 1.

In a second approach to promote the formation of heteromultimer complexes using asymmetric Fc fusion proteins, the Fc domains can be altered to introduce complementary hydrophobic interactions and an additional intermolecular disulfide bond.

The MISRII-Fc polypeptide sequence (SEQ ID NO: 419) is shown below:

In this second approach, the polypeptide sequence of the complementary ALK3-Fc fusion protein and a nucleic acid sequence encoding it are provided above in Example 4 as SEQ ID NOs: 407-408.

The MISRII-Fc and ALK3-Fc proteins of SEQ ID NO: 420 and SEQ ID NO: 408, respectively, may be co-expressed and purified from a CHO cell line, to give rise to a heteromeric complex comprising MISRII-Fc:ALK3-Fc. Similar heteromeric complexes may be generated by pairing the ALK3-Fc protein described above (SEQ ID NO: 408) with an Fc fusion protein comprising the extracellular domain of MISRII isoform 2 or the extracellular domain of MISRII isoform 3 in place of the extracellular domain of MISRII isoform 1 described above.

Purification of various MISRII-Fc:ALK3-Fc complexes could be achieved by a series of column chromatography steps, including, for example, three or more of the following, in any order: protein A chromatography, Q sepharose chromatography, phenylsepharose chromatography, size exclu-

```
                                                    (SEQ ID NO: 419)
  1 MDAMKRGLCC VLLLCGAVFV SPGAPPNRRT CVFFEAPGVR GSTKTLGELL

51 DTGTELPRAI RCLYSRCCFG IWNLTQDRAQ VEMQGCRDSD EPGCESLHCD

101 PSPRAHPSPG STLFTCSCGT DFCNANYSHL PPPGSPGTPG SQGPQAAPGE

151 SIWMALTGGG THTCPPCPAP ELLGGPSVFL FPPKPKDTLM ISRTPEVTCV

201 VVDVSHEDPE VKFNWYVDGV EVHNAKTKPR EEQYNSTYRV VSVLTVLHQD

251 WLNGKEYKCK VSNKALPAPI EKTISKAKGQ PREPQVYTLP PCREEMTKNQ

301 VSLWCLVKGF YPSDIAVEWE SNGQPENNYK TTPPVLDSDG SFFLYSKLTV

351 DKSRWQQGNV FSCSVMHEAL HNHYTQKSLS LSPGK
```

The leader sequence and linker sequence are underlined. To promote formation of the MISRII-Fc:ALK3-Fc heterodimer rather than either of the possible homodimeric complexes, two amino acid substitutions (replacing a serine with a cysteine and a threonine with a trytophan) can be introduced into the Fc domain of the fusion protein as indicated by double underline above. The amino acid sequence of SEQ ID NO: 419 may optionally be provided with the lysine removed from the C-terminus.

The mature MISRII-Fc fusion polypeptide (SEQ ID NO: 420) is as follows and may optionally be provided with the lysine removed from the C-terminus.

sion chromatography, and cation exchange chromatography. The purification could be completed with viral filtration and buffer exchange.

Example 30. Generation of an ActRIIA-Fc:ActRIIB-Fc Heterodimer

A soluble ActRIIA-Fc:ActRIIB-Fc heteromeric complex can be generated comprising the extracellular domains of human ActRIIA and human ActRIIB, which are each fused to an Fc domain with a linker positioned between the

```
                                                    (SEQ ID NO: 420)
  1 PPNRRTCVFF EAPGVRGSTK TLGELLDTGT ELPRAIRCLY SRCCFGIWNL

51 TQDRAQVEMQ GCRDSDEPGC ESLHCDPSPR AHPSPGSTLF TCSCGTDFCN

101 ANYSHLPPPG SPGTPGSQGP QAAPGESIWM ALTGGGTHTC PPCPAPELLG

151 GPSVFLFPPK PKDTLMISRT PEVTCVVVDV SHEDPEVKFN WYVDGVEVHN

201 AKTKPREEQY NSTYRVVSVL TVLHQDWLNG KEYKCKVSNK ALPAPIEKTI

251 SKAKGQPREP QVYTLPPCRE EMTKNQVSLW CLVKGFYPSD IAVEWESNGQ

301 PENNYKTTPP VLDSDGSFFL YSKLTVDKSR WQQGNVFSCS VMHEALHNHY

351 TQKSLSLSPG K
``` extracellular domain and the Fc domain. The individual constructs are referred to as ActRIIA-Fc and ActRIIB-Fc fusion proteins, respectively.

Formation of heteromeric ActRIIA-Fc:ActRIIB-Fc may be guided by approaches similar to those described in Example 1.

Electrostatic Approach

In a first approach, the polypeptide sequence of the ActRIIA-Fc fusion protein and a nucleic acid sequence encoding it are provided above in Example 14 as SEQ ID NOs: 118-120.

The polypeptide sequence of the complementary ActRIIB-Fc fusion protein (SEQ ID NO: 153) employs the TPA leader and is as follows:

```
                                                    (SEQ ID NO: 153)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVY TLPPSREEMT KNQVSLTCLV KGFYPSDIAV

301 EWESNGQPEN NYDTTPPVLD SDGSFFLYSD LTVDKSRWQQ GNVFSCSVMH

351 EALHNHYTQK SLSLSPGK
```

The leader and linker sequences are underlined. To promote formation of the ActRIIA-Fc:ActRIIB-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 153 may optionally be provided with the lysine removed from the C-terminus.

The mature ActRIIB-Fc fusion protein sequence is as follows (SEQ ID NO: 154) and may optionally be provided with the lysine removed from the C-terminus.

```
                                                    (SEQ ID NO: 154)
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVYTLPPS

251 REEMTKNQVS LTCLVKGFYP SDIAVEWESN GQPENNYDTT PPVLDSDGSF

301 FLYSDLTVDK SRWQQGNVFS CSVMHEALHN HYTQKSLSLS PGK
```

The ActRIIA-Fc and ActRIIB-Fc fusion proteins of SEQ ID NO: 120 and SEQ ID NO: 154, respectively, may be co-expressed and purified from a CHO cell line to give rise to a heteromeric complex comprising ActRIIA-Fc:ActRIIB-Fc.

Reverse Electrostatic Approach

In a reverse approach, receptor extracellular domains are both linked to the opposite member of the Fc interaction pair compared to the first approach described above. In this example, an alternative polypeptide sequence of the ActRIIA-Fc fusion protein (SEQ ID NO: 151) employs the TPA leader and is as follows.

```
                                                    (SEQ ID NO: 151)
  1 MDAMKRGLCC VLLLCGAVFV SPGAAILGRS ETQECLFFNA NWEKDRTNQT

51 GVEPCYGDKD KRRHCFATWK NISGSIEIVK QGCWLDDINC YDRTDCVEKK
```

```
-continued
101 DSPEVYFCCC EGNMCNEKFS YFPEMEVTQP TSNPVTPKPP TGGGTHTCPP

151 CPAPELLGGP SVFLFPPKPK DTLMISRTPE VTCVVVDVSH EDPEVKFNWY

201 VDGVEVHNAK TKPREEQYNS TYRVVSVLTV LHQDWLNGKE YKCKVSNKAL

251 PAPIEKTISK AKGQPREPQV YTLPPSREEM TKNQVSLTCL VKGFYPSDIA

301 VEWESNGQPE NNYDTTPPVL DSDGSFFLYS DLTVDKSRWQ QGNVFSCSVM

351 HEALHNHYTQ KSLSLSPGK
```

The leader and linker sequences are underlined. To promote formation of the ActRIIA-Fc:ActRIIB-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 151 may optionally be provided with the lysine removed from the C-terminus.

The mature ActRIIA-Fc fusion protein sequence is as follows (SEQ ID NO: 152) and may optionally be provided with the lysine removed from the C-terminus.

```
                                              (SEQ ID NO: 152)
  1 ILGRSETQEC LFFNANWEKD RTNQTGVEPC YGDKDKRRHC FATWKNISGS

51 IEIVKQGCWL DDINCYDRTD CVEKKDSPEV YFCCCEGNMC NEKFSYFPEM

101 EVTQPTSNPV TPKPPTGGGT HTCPPCPAPE LLGGPSVFLF PPKPKDTLMI

151 SRTPEVTCVV VDVSHEDPEV KFNWYVDGVE VHNAKTKPRE EQYNSTYRVV

201 SVLTVLHQDW LNGKEYKCKV SNKALPAPIE KTISKAKGQP REPQVYTLPP

251 SREEMTKNQV SLTCLVKGFY PSDIAVEWES NGQPENNYDT TPPVLDSDGS

301 FFLYSDLTVD KSRWQQGNVF SCSVMHEALH NHYTQKSLSL SPGK
```

The polypeptide sequence of the ActRIIB-Fc fusion protein and a nucleic acid sequence encoding it are provided in Example 1 as SEQ ID NOs: 100-102.

The ActRIIA-Fc and ActRIIB-Fc fusion proteins of SEQ ID NO: 152 and SEQ ID NO: 102, respectively, may be co-expressed and purified from a CHO cell line to give rise to a variant heteromeric complex comprising ActRIIA-Fc:ActRIIB-Fc.

Hydrophobic Approach

In another approach to promoting the formation of heteromultimer complexes using asymmetric Fc fusion proteins, the Fc domains are altered to introduce complementary hydrophobic interactions and an additional intermolecular disulfide bond. The polypeptide sequence of the ActRIIA-Fc fusion protein is provided in Example 14 as SEQ ID NOs: 409-410.

The complementary form of ActRIIB-Fc fusion polypeptide (SEQ ID NO: 453) is as follows:

```
                                              (SEQ ID NO: 453)
  1 MDAMKRGLCC VLLLCGAVFV SPGASGRGEA ETRECIYYNA NWELERTNQS

51 GLERCEGEQD KRLHCYASWR NSSGTIELVK KGCWLDDFNC YDRQECVATE

101 ENPQVYFCCC EGNFCNERFT HLPEAGGPEV TYEPPPTAPT GGGTHTCPPC

151 PAPELLGGPS VFLFPPKPKD TLMISRTPEV TCVVVDVSHE DPEVKFNWYV

201 DGVEVHNAKT KPREEQYNST YRVVSVLTVL HQDWLNGKEY KCKVSNKALP

251 APIEKTISKA KGQPREPQVC TLPPSREEMT KNQVSLSCAV KGFYPSDIAV

301 EWESNGQPEN NYKTTPPVLD SDGSFFLVSK LTVDKSRWQQ GNVFSCSVMH

351 EALHNHYTQK SLSLSPGK
```

The leader and linker sequences are underlined. To guide heterodimer formation with the ActRIIA-Fc fusion polypeptide of SEQ ID NOs: 409-410, four amino acid substitutions can be introduced into the Fc domain of the ActRIIB-Fc fusion polypeptide as indicated by double underline above.

The amino acid sequence of SEQ ID NO: 453 may optionally be provided with a lysine removed from the C-terminus.

The mature ActRIIB-Fc fusion protein sequence (SEQ ID NO: 454) is as follows and may optionally be provided with a lysine removed from the C-terminus.

```
                                                       (SEQ ID NO: 454)
  1 GRGEAETREC IYYNANWELE RTNQSGLERC EGEQDKRLHC YASWRNSSGT

51 IELVKKGCWL DDFNCYDRQE CVATEENPQV YFCCCEGNFC NERFTHLPEA

101 GGPEVTYEPP PTAPTGGGTH TCPPCPAPEL LGGPSVFLFP PKPKDTLMIS

151 RTPEVTCVVV DVSHEDPEVK FNWYVDGVEV HNAKTKPREE QYNSTYRVVS

201 VLTVLHQDWL NGKEYKCKVS NKALPAPIEK TISKAKGQPR EPQVCTLPPS

251 REEMTKNQVS LSCAVKGFYP SDIAVEWESN GQPENNYKTT PPVLDSDGSF

301 FLVSKLTVDK SRWQQGNVFS CSVMHEALHN HYTQKSLSLS PGK
```

The ActRIIA-Fc and ActRIIB-Fc proteins of SEQ ID NO: 410 and SEQ ID NO: 454, respectively, may be co-expressed and purified from a CHO cell line, to give rise to a variant heteromeric complex comprising ActRIIA-Fc:ActRIIB-Fc.

Reverse Hydrophobic Approach

In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, an alternative polypeptide sequence of the ActRIIA-Fc fusion protein (SEQ ID NO: 451) employs the TPA leader and is as follows.

```
                                                       (SEQ ID NO: 451)
  1 MDAMKRGLCC VLLLCGAVFV SPGAAILGRS ETQECLFFNA NWEKDRTNQT

51 GVEPCYGDKD KRRHCFATWK NISGSIEIVK QGCWLDDINC YDRTDCVEKK

101 DSPEVYFCCC EGNMCNEKFS YFPEMEVTQP TSNPVTPKPP TGGGTHTCPP

151 CPAPELLGGP SVFLFPPKPK DTLMISRTPE VTCVVVDVSH EDPEVKFNWY

201 VDGVEVHNAK TKPREEQYNS TYRVVSVLTV LHQDWLNGKE YKCKVSNKAL

251 PAPIEKTISK AKGQPREPQV CTLPPSREEM TKNQVSLSCA VKGFYPSDIA

301 VEWESNGQPE NNYKTTPPVL DSDGSFFLVS KLTVDKSRWQ QGNVFSCSVM

351 HEALHNHYTQ KSLSLSPGK
```

The leader and linker sequences are underlined. To guide heterodimer formation with the ActRIIB-Fc fusion polypeptide of SEQ ID NOs 401-402, four amino acid substitutions can be introduced into the Fc domain of the ActRIIA-Fc fusion polypeptide as indicated by double underline above. The amino acid sequence of SEQ ID NO: 451 may optionally be provided with the lysine removed from the C-terminus.

The mature ActRIIA-Fc fusion protein sequence is as follows (SEQ ID NO: 452) and may optionally be provided with the lysine removed from the C-terminus.

```
                                                       (SEQ ID NO: 452)
  1 ILGRSETQEC LFFNANWEKD RTNQTGVEPC YGDKDKRRHC FATWKNISGS

51 IEIVKQGCWL DDINCYDRTD CVEKKDSPEV YFCCCEGNMC NEKFSYFPEM
```

```
101 EVTQPTSNPV TPKPPTGGGT HTCPPCPAPE LLGGPSVFLF PPKPKDTLMI

151 SRTPEVTCVV VDVSHEDPEV KFNWYVDGVE VHNAKTKPRE EQYNSTYRVV

201 SVLTVLHQDW LNGKEYKCKV SNKALPAPIE KTISKAKGQP REPQVCTLPP

251 SREEMTKNQV SLSCAVKGFY PSDIAVEWES NGQPENNYKT TPPVLDSDGS

301 FFLVSKLTVD KSRWQQGNVF SCSVMHEALH NHYTQKSLSL SPGK
```

The polypeptide sequence of the ActRIIB-Fc fusion protein is provided in Example 1 as SEQ ID NOs: 401-402.

The ActRIIA-Fc and ActRIIB-Fc proteins of SEQ ID NO: 452 and SEQ ID NO: 402, respectively, may be co-expressed and purified from a CHO cell line, to give rise to a variant heteromeric complex comprising ActRIIA-Fc:ActRIIB-Fc.

Purification of various ActRIIA-Fc:ActRIIB-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 31. Generation of an ActRIIA-Fc:BMPRII-Fc Heterodimer

A soluble ActRIIA-Fc:BMPRII-Fc heteromeric complex can be generated comprising the extracellular domains of human ActRIIA and human BMPRII, which are each fused to an Fc domain with a linker positioned between the extracellular domain and the Fc domain. The individual constructs are referred to as ActRIIA-Fc and BMPRII-Fc fusion proteins, respectively.

Formation of heteromeric ActRIIA-Fc:BMPRII-Fc may be guided by approaches similar to those described in Example 30.

Electrostatic Approach

In a first approach, the polypeptide sequence of the ActRIIA-Fc fusion protein and a nucleic acid sequence encoding it are provided in Example 14 as SEQ ID NOs: 118-120.

The polypeptide sequence of the complementary BMPRII-Fc fusion protein (SEQ ID NO: 155) employs the TPA leader and is as follows:

```
                                                  (SEQ ID NO: 155)
  1 MDAMKRGLCC VLLLCGAVFV SPGASQNQER LCAFKDPYQQ DLGIGESRIS

51 HENGTILCSK GSTCYGLWEK SKGDINLVKQ GCWSHIGDPQ ECHYEECVVT

101 TTPPSIQNGT YRFCCCSTDL CNVNFTENFP PPDTTPLSPP HSFNRDETGG

151 GTHTCPPCPA PELLGGPSVF LFPPKPKDTL MISRTPEVTC VVVDVSHEDP

201 EVKFNWYVDG VEVHNAKTKP REEQYNSTYR VVSVLTVLHQ DWLNGKEYKC

251 KVSNKALPAP IEKTISKAKG QPREPQVYTL PPSREEMTKN QVSLTCLVKG

301 FYPSDIAVEW ESNGQPENNY DTTPPVLDSD GSFFLYSDLT VDKSRWQQGN

351 VFSCSVMHEA LHNHYTQKSL SLSPGK
```

The leader and linker sequences are underlined. To promote formation of the ActRIIA-Fc:BMPRII-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 155 may optionally be provided with the lysine removed from the C-terminus.

The mature BMPRII-Fc fusion protein sequence is as follows (SEQ ID NO: 156) and may optionally be provided with the lysine removed from the C-terminus.

```
                                                  (SEQ ID NO: 156)
  1 SQNQERLCAF KDPYQQDLGI GESRISHENG TILCSKGSTC YGLWEKSKGD

51 INLVKQGCWS HIGDPQECHY EECVVTTTPP SIQNGTYRFC CCSTDLCNVN

101 FTENFPPPDT TPLSPPHSFN RDETGGGTHT CPPCPAPELL GGPSVFLFPP

151 KPKDTLMISR TPEVTCVVVD VSHEDPEVKF NWYVDGVEVH NAKTKPREEQ
```

```
-continued
201 YNSTYRVVSV LTVLHQDWLN GKEYKCKVSN KALPAPIEKT ISKAKGQPRE

251 PQVYTLPPSR EEMTKNQVSL TCLVKGFYPS DIAVEWESNG QPENNYDTTP

301 PVLDSDGSFF LYSDLTVDKS RWQQGNVFSC SVMHEALHNH YTQKSLSLSP

351 GK
```

The ActRIIA-Fc and BMPRII-Fc fusion proteins of SEQ ID NO: 120 and SEQ ID NO: 156, respectively, may be co-expressed and purified from a CHO cell line to give rise to a heteromeric complex comprising ActRIIA-Fc:BMPRII-Fc.

Reverse Electrostatic Approach

In a reverse approach, receptor extracellular domains are linked to the opposite member of the Fc interaction pair compared to the first approach described above. In this example, the alternative polypeptide sequence of the ActRIIA-Fc fusion protein is provided in Example 30 as SEQ ID NOs: 151-152.

The polypeptide sequence of the BMPRII-Fc fusion protein and a nucleic acid sequence encoding it are provided in Example 16 as SEQ ID NOs: 121-123.

The ActRIIA-Fc and BMPRII-Fc fusion proteins of SEQ ID NO: 152 and SEQ ID NO: 123, respectively, may be co-expressed and purified from a CHO cell line to give rise to a variant heteromeric complex comprising ActRIIA-Fc:BMPRII-Fc.

Hydrophobic Approach

In another approach to promoting the formation of heteromultimer complexes using asymmetric Fc fusion proteins, the Fc domains are altered to introduce complementary hydrophobic interactions and an additional intermolecular disulfide bond. The polypeptide sequence of the ActRIIA-Fc fusion protein is provided in Example 14 as SEQ ID NOs 409-410.

The complementary form of BMPRII-Fc fusion polypeptide (SEQ ID NO: 455) is as follows:

```
                                              (SEQ ID NO: 455)
  1 MDAMKRGLCC VLLLCGAVFV SPGASQNQER LCAFKDPYQQ DLGIGESRIS

51 HENGTILCSK GSTCYGLWEK SKGDINLVKQ GCWSHIGDPQ ECHYEECVVT

101 TTPPSIQNGT YRFCCCSTDL CNVNFTENFP PPDTTPLSPP HSFNRDETGG

151 GTHTCPPCPA PELLGGPSVF LFPPKPKDTL MISRTPEVTC VVVDVSHEDP

201 EVKFNWYVDG VEVHNAKTKP REEQYNSTYR VVSVLTVLHQ DWLNGKEYKC

251 KVSNKALPAP IEKTISKAKG QPREPQVCTL PPSREEMTKN QVSLSCAVKG

301 FYPSDIAVEW ESNGQPENNY KTTPPVLDSD GSFFLVSKLT VDKSRWQQGN

351 VFSCSVMHEA LHNHYTQKSL SLSPGK
```

The leader and linker sequences are underlined. To guide heterodimer formation with the ActRIIA-Fc fusion polypeptide of SEQ ID NOs: 409-410, four amino acid substitutions can be introduced into the Fc domain of the BMPRII-Fc fusion polypeptide as indicated by double underline above. The amino acid sequence of SEQ ID NO: 455 may optionally be provided with a lysine removed from the C-terminus.

The mature BMPRII-Fc fusion protein sequence (SEQ ID NO: 456) is as follows and may optionally be provided with a lysine removed from the C-terminus.

```
                                              (SEQ ID NO: 456)
  1 SQNQERLCAF KDPYQQDLGI GESRISHENG TILCSKGSTC YGLWEKSKGD

51 INLVKQGCWS HIGDPQECHY EECVVTTTPP SIQNGTYRFC CCSTDLCNVN

101 FTENFPPPDT TPLSPPHSFN RDETGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVCTLPPSR EEMTKNQVSL SCAVKGFYPS DIAVEWESNG QPENNYKTTP

301 PVLDSDGSFF LVSKLTVDKS RWQQGNVFSC SVMHEALHNH YTQKSLSLSP

351 GK
```

The ActRIIA-Fc and BMPRII-Fc proteins of SEQ ID NO: 410 and SEQ ID NO: 456, respectively, may be co-expressed and purified from a CHO cell line, to give rise to a variant heteromeric complex comprising ActRIIA-Fc:BMPRII-Fc.

Reverse Hydrophobic Approach

In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, the alternative polypeptide sequence of the ActRIIA-Fc fusion protein is provided in Example 30 as SEQ ID NOs: 451-452.

The polypeptide sequence of the BMPRII-Fc fusion protein is provided in Example 16 as SEQ ID NOs: 411-412.

The ActRIIA-Fc and BMPRII-Fc proteins of SEQ ID NO: 452 and SEQ ID NO: 412, respectively, may be co-expressed and purified from a CHO cell line, to give rise to a variant heteromeric complex comprising ActRIIA-Fc:BMPRII-Fc.

Purification of various ActRIIA-Fc:BMPRII-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 32. Generation of an ActRIIA-Fc:MISRII-Fc Heterodimer

A soluble ActRIIA-Fc:MISRII-Fc heteromeric complex can be generated comprising the extracellular domains of human ActRIIA and human MISRII, which are each fused to an Fc domain with a linker positioned between the extracellular domain and the Fc domain. The individual constructs are referred to as ActRIIA-Fc and MISRII-Fc fusion proteins, respectively.

Formation of heteromeric ActRIIA-Fc:MISRII-Fc may be guided by approaches similar to those described in Example 30.

Electrostatic Approach

In a first approach, the polypeptide sequence of the ActRIIA-Fc fusion protein and a nucleic acid sequence encoding it are provided in Example 14 as SEQ ID NOs: 118-120.

The polypeptide sequence of the complementary MISRII-Fc fusion protein (SEQ ID NO: 161) employs the TPA leader and is as follows:

```
                                                        (SEQ ID NO: 161)
  1 MDAMKRGLCC VLLLCGAVFV SPGAPPNRRT CVFFEAPGVR GSTKTLGELL

51 DTGTELPRAI RCLYSRCCFG IWNLTQDRAQ VEMQGCRDSD EPGCESLHCD

101 PSPRAHPSPG STLFTCSCGT DFCNANYSHL PPPGSPGTPG SQGPQAAPGE

151 SIWMALTGGG THTCPPCPAP ELLGGPSVFL FPPKPKDTLM ISRTPEVTCV

201 VVDVSHEDPE VKFNWYVDGV EVHNAKTKPR EEQYNSTYRV VSVLTVLHQD

251 WLNGKEYKCK VSNKALPAPI EKTISKAKGQ PREPQVYTLP PSREEMTKNQ

301 VSLTCLVKGF YPSDIAVEWE SNGQPENNYD TTPPVLDSDG SFFLYSDLTV

351 DKSRWQQGNV FSCSVMHEAL HNHYTQKSLS LSPGK
```

The leader and linker sequences are underlined. To promote formation of the ActRIIA-Fc:MISRII-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 161 may optionally be provided with the lysine removed from the C-terminus.

The mature MISRII-Fc fusion protein sequence is as follows (SEQ ID NO: 162) and may optionally be provided with the lysine removed from the C-terminus.

```
                                                        (SEQ ID NO: 162)
  1 PPNRRTCVFF EAPGVRGSTK TLGELLDTGT ELPRAIRCLY SRCCFGIWNL

51 TQDRAQVEMQ GCRDSDEPGC ESLHCDPSPR AHPSPGSTLF TCSCGTDFCN

101 ANYSHLPPPG SPGTPGSQGP QAAPGESIWM ALTGGGTHTC PPCPAPELLG

151 GPSVFLFPPK PKDTLMISRT PEVTCVVVDV SHEDPEVKFN WYVDGVEVHN

201 AKTKPREEQY NSTYRVVSVL TVLHQDWLNG KEYKCKVSNK ALPAPIEKTI

251 SKAKGQPREP QVYTLPPSRE EMTKNQVSLT CLVKGFYPSD IAVEWESNGQ

301 PENNYDTTPP VLDSDGSFFL YSDLTVDKSR WQQGNVFSCS VMHEALHNHY

351 TQKSLSLSPG K
```

The ActRIIA-Fc and MISRII-Fc fusion proteins of SEQ ID NO: 120 and SEQ ID NO: 162, respectively, may be co-expressed and purified from a CHO cell line to give rise to a heteromeric complex comprising ActRIIA-Fc:MISRII-Fc.

Reverse Electrostatic Approach

In a reverse approach, receptor extracellular domains are linked to the opposite member of the Fc interaction pair compared to the first approach described above. In this example, the alternative polypeptide sequence of the ActRIIA-Fc fusion protein is provided in Example 30 as SEQ ID NOs: 151 and 152.

The polypeptide sequence of the MISRII-Fc fusion protein is provided in Example 29 as SEQ ID NOs: 133 and 135.

The ActRIIA-Fc and MISRII-Fc fusion proteins of SEQ ID NO: 152 and SEQ ID NO: 135, respectively, may be co-expressed and purified from a CHO cell line to give rise to a variant heteromeric complex comprising ActRIIA-Fc:MISRII-Fc.

Hydrophobic Approach

In another approach to promoting the formation of heteromultimer complexes using asymmetric Fc fusion proteins, the Fc domains are altered to introduce complementary hydrophobic interactions and an additional intermolecular disulfide bond. The polypeptide sequence of the ActRIIA-Fc fusion protein is provided in Example 14 as SEQ ID NOs 409-410.

The complementary form of MISRII-Fc fusion polypeptide (SEQ ID NO: 457) is as follows:

```
                                                           (SEQ ID NO: 457)
  1 MDAMKRGLCC VLLLCGAVFV SPGAPPNRRT CVFFEAPGVR GSTKTLGELL

51 DTGTELPRAI RCLYSRCCFG IWNLTQDRAQ VEMQGCRDSD EPGCESLHCD

101 PSPRAHPSPG STLFTCSCGT DFCNANYSHL PPPGSPGTPG SQGPQAAPGE

151 SIWMALTGGG THTCPPCPAP ELLGGPSVFL FPPKPKDTLM ISRTPEVTCV

201 VVDVSHEDPE VKFNWYVDGV EVHNAKTKPR EEQYNSTYRV VSVLTVLHQD

251 WLNGKEYKCK VSNKALPAPI EKTISKAKGQ PREPQVCTLP PSREEMTKNQ

301 VSLSCAVKGF YPSDIAVEWE SNGQPENNYK TTPPVLDSDG SFFLVSKLTV

351 DKSRWQQGNV FSCSVMHEAL HNHYTQKSLS LSPGK
```

The leader and linker sequences are underlined. To guide heterodimer formation with the ActRIIA-Fc fusion polypeptide of SEQ ID NOs: 409-410, four amino acid substitutions can be introduced into the Fc domain of the MISRII-Fc fusion polypeptide as indicated by double underline above. The amino acid sequence of SEQ ID NO: 457 may optionally be provided with a lysine removed from the C-terminus.

The mature MISRII-Fc fusion protein sequence (SEQ ID NO: 458) is as follows and may optionally be provided with a lysine removed from the C-terminus.

```
                                                           (SEQ ID NO: 458)
  1 PPNRRTCVFF EAPGVRGSTK TLGELLDTGT ELPRAIRCLY SRCCFGIWNL

51 TQDRAQVEMQ GCRDSDEPGC ESLHCDPSPR AHPSPGSTLF TCSCGTDFCN

101 ANYSHLPPPG SPGTPGSQGP QAAPGESIWM ALTGGGTHTC PPCPAPELLG

151 GPSVFLFPPK PKDTLMISRT PEVTCVVVDV SHEDPEVKFN WYVDGVEVHN

201 AKTKPREEQY NSTYRVVSVL TVLHQDWLNG KEYKCKVSNK ALPAPIEKTI

251 SKAKGQPREP QVCTLPPSRE EMTKNQVSLS CAVKGFYPSD IAVEWESNGQ

301 PENNYKTTPP VLDSDGSFFL VSKLTVDKSR WQQGNVFSCS VMHEALHNHY

351 TQKSLSLSPG K
```

The ActRIIA-Fc and MISRII-Fc proteins of SEQ ID NO: 410 and SEQ ID NO: 458, respectively, may be co-expressed and purified from a CHO cell line, to give rise to a variant heteromeric complex comprising ActRIIA-Fc:MIS-RII-Fc.

Reverse Hydrophobic Approach

In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, the alternative polypeptide sequence of the ActRIIA-Fc fusion protein is provided in Example 30 as SEQ ID NOs: 451-452.

The polypeptide sequence of the MISRII-Fc fusion protein is provided in Example 29 as SEQ ID NOs: 419-420.

The ActRIIA-Fc and MISRII-Fc proteins of SEQ ID NO: 452 and SEQ ID NO: 420, respectively, may be co-expressed and purified from a CHO cell line, to give rise to a variant heteromeric complex comprising ActRIIA-Fc:MIS-RII-Fc.

Purification of various ActRIIA-Fc:MISRII-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 33. Generation of an ActRIIA-Fc: TGFβRII$_{SHORT}$-Fc Heterodimer

A soluble ActRIIA-Fc:TGFβRII$_{SHORT}$-Fc heteromeric complex can be generated comprising the extracellular domains of human ActRIIA and human TGFβRII$_{SHORT}$, which are each fused to an Fc domain with a linker positioned between the extracellular domain and the Fc domain. The individual constructs are referred to as ActRIIA-Fc and TGFβRII$_{SHORT}$-Fc fusion proteins, respectively.

Formation of heteromeric ActRIIA-Fc:TGFβRII$_{SHORT}$-Fc may be guided by approaches similar to those described in Example 30.

Electrostatic Approach

In a first approach, the polypeptide sequence of the ActRIIA-Fc fusion protein and a nucleic acid sequence encoding it are provided in Example 14 as SEQ ID NOs: 118-120.

The polypeptide sequence of the complementary TGFβRII$_{SHORT}$-Fc fusion protein (SEQ ID NO: 157) employs the TPA leader and is as follows:

(SEQ ID NO: 157)

```
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYNTSNP DTGGGTHTCP PCPAPELLGG PSVFLFPPKP KDTLMISRTP

201 EVTCVVVDVS HEDPEVKFNW YVDGVEVHNA KTKPREEQYN STYRVVSVLT

251 VLHQDWLNGK EYKCKVSNKA LPAPIEKTIS KAKGQPREPQ VYTLPPSREE

301 MTKNQVSLTC LVKGFYPSDI AVEWESNGQP ENNYDTTPPV LDSDGSFFLY

351 SDLTVDKSRW QQGNVFSCSV MHEALHNHYT QKSLSLSPGK
```

The leader and linker sequences are underlined. To promote formation of the ActRIIA-Fc: TGFβRII$_{SHORT}$-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 157 may optionally be provided with the lysine removed from the C-terminus.

The mature TGFβRII$_{SHORT}$-Fc fusion protein sequence is as follows (SEQ ID NO: 158) and may optionally be provided with the lysine removed from the C-terminus.

```
                                                         (SEQ ID NO: 158)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPDTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPSREEMTKN QVSLTCLVKG FYPSDIAVEW

301 ESNGQPENNY DTTPPVLDSD GSFFLYSDLT VDKSRWQQGN VFSCSVMHEA

351 LHNHYTQKSL SLSPGK
```

The ActRIIA-Fc and TGFβRII$_{SHORT}$-Fc fusion proteins of SEQ ID NO: 120 and SEQ ID NO: 158, respectively, may be co-expressed and purified from a CHO cell line to give rise to a heteromeric complex comprising ActRIIA-Fc:TGFβRII$_{SHORT}$-Fc.

Reverse Electrostatic Approach

In a reverse approach, receptor extracellular domains are linked to the opposite member of the Fc interaction pair compared to the first approach described above. In this example, the alternative polypeptide sequence of the ActRIIA-Fc fusion protein is provided in Example 30 as SEQ ID NOs: 151-152.

The polypeptide sequence of the TGFβRII$_{SHORT}$-Fc fusion protein and a nucleic acid sequence encoding it are provided in Example 24 as SEQ ID NOs: 127-129.

The ActRIIA-Fc and TGFβRII$_{SHORT}$-Fc fusion proteins of SEQ ID NO: 152 and SEQ ID NO: 129, respectively, may be co-expressed and purified from a CHO cell line to give rise to a variant heteromeric complex comprising ActRIIA-Fc:TGFβRII$_{SHORT}$-Fc.

Hydrophobic Approach

In another approach to promoting the formation of heteromultimer complexes using asymmetric Fc fusion proteins, the Fc domains are altered to introduce complementary hydrophobic interactions and an additional intermolecular disulfide bond. The polypeptide sequence of the ActRIIA-Fc fusion protein is provided in Example 14 as SEQ ID NOs 409-410.

The complementary form of TGFβRII$_{SHORT}$-Fc fusion polypeptide (SEQ ID NO: 459) is as follows:

```
                                                         (SEQ ID NO: 459)
  1 MDAMKRGLCC VLLLCGAVFV SPGATIPPHV QKSVNNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYNTSNP DTGGGTHTCP PCPAPELLGG PSVFLFPPKP KDTLMISRTP

201 EVTCVVVDVS HEDPEVKFNW YVDGVEVHNA KTKPREEQYN STYRVVSVLT

251 VLHQDWLNGK EYKCKVSNKA LPAPIEKTIS KAKGQPREPQ VCTLPPSREE

301 MTKNQVSLSC AVKGFYPSDI AVEWESNGQP ENNYKTTPPV LDSDGSFFLV

351 SKLTVDKSRW QQGNVFSCSV MHEALHNHYT QKSLSLSPGK
```

The leader and linker sequences are underlined. To guide heterodimer formation with the ActRIIA-Fc fusion polypeptide of SEQ ID NOs: 409-410, four amino acid substitutions can be introduced into the Fc domain of the TGFβRII$_{SHORT}$-Fc fusion polypeptide as indicated by double underline above. The amino acid sequence of SEQ ID NO: 459 may optionally be provided with a lysine removed from the C-terminus.

The mature TGFβRII$_{SHORT}$-Fc fusion protein sequence (SEQ ID NO: 460) is as follows and may optionally be provided with a lysine removed from the C-terminus.

```
                                                         (SEQ ID NO: 460)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE YNTSNPDTGG GTHTCPPCPA

151 PELLGGPSVF LFPPKPKDTL MISRTPEVTC VVVDVSHEDP EVKFNWYVDG
```

```
-continued
201 VEVHNAKTKP REEQYNSTYR VVSVLTVLHQ DWLNGKEYKC KVSNKALPAP

251 IEKTISKAKG QPREPQVCTL PPSREEMTKN QVSLSCAVKG FYPSDIAVEW

301 ESNGQPENNY KTTPPVLDSD GSFFLVSKLT VDKSRWQQGN VFSCSVMHEA

351 LHNHYTQKSL SLSPGK
```

The ActRIIA-Fc and TGFβRII$_{SHORT}$-Fc proteins of SEQ ID NO: 410 and SEQ ID NO: 460, respectively, may be co-expressed and purified from a CHO cell line, to give rise to a variant heteromeric complex comprising ActRIIA-Fc:TGFβRII$_{SHORT}$-Fc.

Reverse Hydrophobic Approach

In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, the alternative polypeptide sequence of the ActRIIA-Fc fusion protein is provided in Example 30 as SEQ ID NOs: 451-452.

The polypeptide sequence of the TGFβRII$_{SHORT}$-Fc fusion protein is provided in Example 24 as SEQ ID NOs: 415-416.

The ActRIIA-Fc and TGFβRII$_{SHORT}$-Fc proteins of SEQ ID NO: 452 and SEQ ID NO: 416, respectively, may be co-expressed and purified from a CHO cell line, to give rise to a variant heteromeric complex comprising ActRIIA-Fc:TGFβRII$_{SHORT}$-Fc.

Purification of various ActRIIA-Fc:TGFβRII$_{SHORT}$-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 34. Generation of an ActRIIA-Fc: TGFβRII$_{LONG}$-Fc Heterodimer

A soluble ActRIIA-Fc:TGFβRII$_{LONG}$-Fc heteromeric complex can be generated comprising the extracellular domains of human ActRIIA and human TGFβRII$_{LONG}$, which are each fused to an Fc domain with a linker positioned between the extracellular domain and the Fc domain. The individual constructs are referred to as ActRIIA-Fc and TGFβRII$_{LONG}$-Fc fusion proteins, respectively.

Formation of heteromeric ActRIIA-Fc:TGFβRII$_{LONG}$-Fc may be guided by approaches similar to those described in Example 30.

Electrostatic Approach

In a first approach, the polypeptide sequence of the ActRIIA-Fc fusion protein and a nucleic acid sequence encoding it are provided in Example 14 as SEQ ID NOs: 118-120.

The polypeptide sequence of the complementary TGFβRII$_{LONG}$-Fc fusion protein (SEQ ID NO: 159) employs the TPA leader and is as follows:

```
                                                    (SEQ ID NO: 159)
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG THTCPPCPAP

201 ELLGGPSVFL FPPKPKDTLM ISRTPEVTCV VVDVSHEDPE VKFNWYVDGV

251 EVHNAKTKPR EEQYNSTYRV VSVLTVLHQD WLNGKEYKCK VSNKALPAPI

301 EKTISKAKGQ PREPQVYTLP PSREEMTKNQ VSLTCLVKGF YPSDIAVEWE

351 SNGQPENNYD TTPPVLDSDG SFFLYSDLTV DKSRWQQGNV FSCSVMHEAL

401 HNHYTQKSLS LSPGK
```

The leader and linker sequences are underlined. To promote formation of the ActRIIA-Fc:TGFβRII$_{LONG}$-Fc heterodimer rather than either of the possible homodimeric complexes, two amino acid substitutions (replacing lysines with aspartic acids) can be introduced into the Fc domain of the fusion protein as indicated by double underline above. The amino acid sequence of SEQ ID NO: 159 may optionally be provided with the lysine removed from the C-terminus.

The mature TGFβRII$_{LONG}$-Fc fusion protein sequence is as follows (SEQ ID NO: 160) and may optionally be provided with the lysine removed from the C-terminus.

```
                                                  (SEQ ID NO: 160)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PDTGGGTHTC PPCPAPELLG GPSVFLFPPK PKDTLMISRT

201 PEVTCVVVDV SHEDPEVKFN WYVDGVEVHN AKTKPREEQY NSTYRVVSVL

251 TVLHQDWLNG KEYKCKVSNK ALPAPIEKTI SKAKGQPREP QVYTLPPSRE

301 EMTKNQVSLT CLVKGFYPSD IAVEWESNGQ PENNYDTTPP VLDSDGSFFL

351 YSDLTVDKSR WQQGNVFSCS VMHEALHNHY TQKSLSLSPG K
```

The ActRIIA-Fc and TGFβRII$_{LONG}$-Fc fusion proteins of SEQ ID NO: 120 and SEQ ID NO: 160, respectively, may be co-expressed and purified from a CHO cell line to give rise to a heteromeric complex comprising ActRIIA-Fc:TGFβRII$_{LONG}$-Fc.

Reverse Electrostatic Approach

In a reverse approach, receptor extracellular domains are linked to the opposite member of the Fc interaction pair compared to the first approach described above. In this example, the alternative polypeptide sequence of the ActRIIA-Fc fusion protein is provided in Example 30 as SEQ ID NOs: 151-152.

The polypeptide sequence of the TGFβRII$_{LONG}$-Fc fusion protein and a nucleic acid sequence encoding it are provided in Example 24 as SEQ ID NOs: 130-132.

The ActRIIA-Fc and TGFβRII$_{LONG}$-Fc fusion proteins of SEQ ID NO: 152 and SEQ ID NO: 132, respectively, may be co-expressed and purified from a CHO cell line to give rise to a variant heteromeric complex comprising ActRIIA-Fc:TGFβRII$_{LONG}$-Fc.

Hydrophobic Approach

In another approach to promoting the formation of heteromultimer complexes using asymmetric Fc fusion proteins, the Fc domains are altered to introduce complementary hydrophobic interactions and an additional intermolecular disulfide bond. The polypeptide sequence of the ActRIIA-Fc fusion protein is provided in Example 14 as SEQ ID NOs 409-410.

The complementary form of TGFβRII$_{LONG}$-Fc fusion polypeptide (SEQ ID NO: 461) is as follows:

```
                                                  (SEQ ID NO: 461)
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG THTCPPCPAP

201 ELLGGPSVFL FPPKPKDTLM ISRTPEVTCV VVDVSHEDPE VKFNWYVDGV

251 EVHNAKTKPR EEQYNSTYRV VSVLTVLHQD WLNGKEYKCK VSNKALPAPI

301 EKTISKAKGQ PREPQVCTLP PSREEMTKNQ VSLSCAVKGF YPSDIAVEWE

351 SNGQPENNYK TTPPVLDSDG SFFLVSKLTV DKSRWQQGNV FSCSVMHEAL

401 HNHYTQKSLS LSPGK
```

The leader and linker sequences are underlined. To guide heterodimer formation with the ActRIIA-Fc fusion polypeptide of SEQ ID NOs: 409-410, four amino acid substitutions can be introduced into the Fc domain of the ActRIIB-Fc fusion polypeptide as indicated by double underline above. The amino acid sequence of SEQ ID NO: 461 may optionally be provided with the lysine removed from the C-terminus.

The mature TGFβRII$_{LONG}$-Fc fusion protein sequence (SEQ ID NO: 462) is as follows and may optionally be provided with the lysine removed from the C-terminus.

```
                                                  (SEQ ID NO: 462)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI
```

```
151 IFSEEYNTSN PDTGGGTHTC PPCPAPELLG GPSVFLFPPK PKDTLMISRT

201 PEVTCVVVDV SHEDPEVKFN WYVDGVEVHN AKTKPREEQY NSTYRVVSVL

251 TVLHQDWLNG KEYKCKVSNK ALPAPIEKTI SKAKGQPREP QVCTLPPSRE

301 EMTKNQVSLS CAVKGFYPSD IAVEWESNGQ PENNYKTTPP VLDSDGSFFL

351 VSKLTVDKSR WQQGNVFSCS VMHEALHNHY TQKSLSLSPG K
```

The ActRIIA-Fc and TGFβRII$_{LONG}$-Fc proteins of SEQ ID NO: 410 and SEQ ID NO: 462, respectively, may be co-expressed and purified from a CHO cell line, to give rise to a variant heteromeric complex comprising ActRIIA-Fc:TGFβRII$_{LONG}$-Fc.

Reverse Hydrophobic Approach

In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, the alternative polypeptide sequence of the ActRIIA-Fc fusion protein is provided in Example 30 as SEQ ID NOs: 451-452.

The polypeptide sequence of the TGFβRII$_{LONG}$-Fc fusion protein is provided in Example 24 as SEQ ID NOs: 417-418.

The ActRIIA-Fc and TGFβRII$_{LONG}$-Fc proteins of SEQ ID NO: 452 and SEQ ID NO: 418, respectively, may be co-expressed and purified from a CHO cell line, to give rise to a variant heteromeric complex comprising ActRIIA-Fc:TGFβRII$_{LONG}$-Fc.

Purification of various ActRIIA-Fc:TGFβRII$_{LONG}$-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 35. Generation of Additional Heterodimers Comprising Two Type II Receptors Formation of additional heterdimeric protein complexes comprising extracellular domains of two type II receptors may be guided by approaches similar to those described in Example 30. Amino acid SEQ ID NOs for these variant heterodimers are disclosed in the following table, which for completeness also includes the heterodimers already discussed that comprise two type II receptors (Examples 30-34). As disclosed in Examples 30-34, the C-terminal lysine of each receptor-Fc fusion protein may optionally be included or omitted.

In each case, a soluble heteromeric complex can be generated comprising the extracellular domains (ECD) of two different type II receptors, which are each fused to an Fc domain with a linker positioned between the extracellular domain and the Fc domain. In each case, the fusion proteins may be co-expressed and purified from a CHO cell line to give rise to a variant heteromeric protein complex. In each case, purification of various heteromeric complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

TABLE

"Type II:Type II Receptor Heterodimers"
Amino Acid SEQ ID NOs for Type II:Type II Receptor Heterodimers

| Heteromeric Fusion Protein Complex | Fc Pair Type | Correspondence to Fc Pair | Receptor-Fc Fusion Protein | Amino Acid SEQ ID NO With Leader | Amino Acid SEQ ID NO Mature |
|---|---|---|---|---|---|
| ActRIIA-Fc:ActRIIB-Fc | Electrostatic | A | ActRIIA-Fc | 118 | 120 |
| | | | ActRIIB-Fc | 153 | 154 |
| | | B | ActRIIA-Fc | 151 | 152 |
| | | | ActRIIB-Fc | 100 | 102 |
| | Hydrophobic | A | ActRIIA-Fc | 409 | 410 |
| | | | ActRIIB-Fc | 453 | 454 |
| | | B | ActRIIA-Fc | 451 | 452 |
| | | | ActRIIB-Fc | 401 | 402 |
| ActRIIA-Fc:BMPRII-Fc | Electrostatic | A | ActRIIA-Fc | 118 | 120 |
| | | | BMPRII-Fc | 155 | 156 |
| | | B | ActRIIA-Fc | 151 | 152 |
| | | | BMPRII-Fc | 121 | 123 |
| | Hydrophobic | A | ActRIIA-Fc | 409 | 410 |
| | | | BMPRII-Fc | 455 | 456 |
| | | B | ActRIIA-Fc | 451 | 452 |
| | | | BMPRII-Fc | 411 | 412 |
| ActRIIA-Fc:MISRII-Fc | Electrostatic | A | ActRIIA-Fc | 118 | 120 |
| | | | MISRII-Fc | 161 | 162 |
| | | B | ActRIIA-Fc | 151 | 152 |
| | | | MISRII-Fc | 133 | 135 |

TABLE-continued

"Type II:Type II Receptor Heterodimers"
Amino Acid SEQ ID NOs for Type II:Type II Receptor Heterodimers

| Heteromeric Fusion Protein Complex | Fc Pair Type | Correspondence to Fc Pair | Receptor-Fc Fusion Protein | Amino Acid SEQ ID NO With Leader | Mature |
|---|---|---|---|---|---|
| | Hydrophobic | A | ActRIIA-Fc | 409 | 410 |
| | | | MISRII-Fc | 457 | 458 |
| | | B | ActRIIA-Fc | 451 | 452 |
| | | | MISRII-Fc | 419 | 420 |
| ActRIIA-Fc:TGFβRII$_{SHORT}$-Fc | Electrostatic | A | ActRIIA-Fc | 118 | 120 |
| | | | TGFβRII$_{SHORT}$-Fc | 157 | 158 |
| | | B | ActRIIA-Fc | 151 | 152 |
| | | | TGFβRII$_{SHORT}$-Fc | 127 | 129 |
| | Hydrophobic | A | ActRIIA-Fc | 409 | 410 |
| | | | TGFβRII$_{SHORT}$-Fc | 459 | 460 |
| | | B | ActRIIA-Fc | 451 | 452 |
| | | | TGFβRII$_{SHORT}$-Fc | 415 | 416 |
| ActRIIA-Fc:TGFβRIILONG-Fc | Electrostatic | A | ActRIIA-Fc | 118 | 120 |
| | | | TGFβRIILONG-Fc | 159 | 160 |
| | | B | ActRIIA-Fc | 151 | 152 |
| | | | TGFβRIILONG-Fc | 130 | 132 |
| | Hydrophobic | A | ActRIIA-Fc | 409 | 410 |
| | | | TGFβRIILONG-Fc | 461 | 462 |
| | | B | ActRIIA-Fc | 451 | 452 |
| | | | TGFβRIILONG-Fc | 417 | 418 |
| ActRIIB-Fc:BMPRII-Fc | Electrostatic | A | ActRIIB-Fc | 100 | 102 |
| | | | BMPRII-Fc | 155 | 156 |
| | | B | ActRIIB-Fc | 153 | 154 |
| | | | BMPRII-Fc | 121 | 123 |
| | Hydrophobic | A | ActRIIB-Fc | 401 | 402 |
| | | | BMPRII-Fc | 455 | 456 |
| | | B | ActRIIB-Fc | 453 | 454 |
| | | | BMPRII-Fc | 411 | 412 |
| ActRIIB-Fc:MISRII-Fc | Electrostatic | A | ActRIIB-Fc | 100 | 102 |
| | | | MISRII-Fc | 161 | 162 |
| | | B | ActRIIB-Fc | 153 | 154 |
| | | | MISRII-Fc | 133 | 135 |
| | Hydrophobic | A | ActRIIB-Fc | 401 | 402 |
| | | | MISRII-Fc | 457 | 458 |
| | | B | ActRIIB-Fc | 453 | 454 |
| | | | MISRII-Fc | 419 | 420 |
| ActRIIB-Fc:TGFβRII$_{SHORT}$-Fc | Electrostatic | A | ActRIIB-Fc | 100 | 102 |
| | | | TGFβRII$_{SHORT}$-Fc | 157 | 158 |
| | | B | ActRIIB-Fc | 153 | 154 |
| | | | TGFβRII$_{SHORT}$-Fc | 127 | 129 |
| | Hydrophobic | A | ActRIIB-Fc | 401 | 402 |
| | | | TGFβRII$_{SHORT}$-Fc | 459 | 460 |
| | | B | ActRIIB-Fc | 453 | 454 |
| | | | TGFβRII$_{SHORT}$-Fc | 415 | 416 |
| ActRIIB-Fc:TGFβRIILONG-Fc | Electrostatic | A | ActRIIB-Fc | 100 | 102 |
| | | | TGFβRIILONG-Fc | 159 | 160 |
| | | B | ActRIIB-Fc | 153 | 154 |
| | | | TGFβRIILONG-Fc | 130 | 132 |
| | Hydrophobic | A | ActRIIB-Fc | 401 | 402 |
| | | | TGFβRIILONG-Fc | 461 | 462 |
| | | B | ActRIIB-Fc | 453 | 454 |
| | | | TGFβRIILONG-Fc | 417 | 418 |
| BMPRII-Fc:MISRII-Fc | Electrostatic | A | BMPRII-Fc | 121 | 123 |
| | | | MISRII-Fc | 161 | 162 |
| | | B | BMPRII-Fc | 155 | 156 |
| | | | MISRII-Fc | 133 | 135 |
| | Hydrophobic | A | BMPRII-Fc | 411 | 412 |
| | | | MISRII-Fc | 457 | 458 |
| | | B | BMPRII-Fc | 455 | 456 |
| | | | MISRII-Fc | 419 | 420 |
| BMPRII-Fc:TGFβRIISHORT-Fc | Electrostatic | A | BMPRII-Fc | 121 | 123 |
| | | | TGFβRIISHORT-Fc | 157 | 158 |
| | | B | BMPRII-Fc | 155 | 156 |
| | | | TGFβRIISHORT-Fc | 127 | 129 |
| | Hydrophobic | A | BMPRII-Fc | 411 | 412 |
| | | | TGFβRIISHORT-Fc | 459 | 460 |
| | | B | BMPRII-Fc | 455 | 456 |
| | | | TGFβRIISHORT-Fc | 415 | 416 |

TABLE-continued

"Type II:Type II Receptor Heterodimers"
Amino Acid SEQ ID NOs for Type II:Type II Receptor Heterodimers

| Heteromeric Fusion Protein Complex | Fc Pair Type | ECD Correspondence to Fc Pair | Receptor-Fc Fusion Protein | Amino Acid SEQ ID NO With Leader | Mature |
|---|---|---|---|---|---|
| BMPRII-Fc:TGFβRII$_{LONG}$-Fc | Electrostatic | A | BMPRII-Fc | 121 | 123 |
| | | | TGFβRII$_{LONG}$-Fc | 159 | 160 |
| | | B | BMPRII-Fc | 155 | 156 |
| | | | TGFβRII$_{LONG}$-Fc | 130 | 132 |
| | Hydrophobic | A | BMPRII-Fc | 411 | 412 |
| | | | TGFβRII$_{LONG}$-Fc | 461 | 462 |
| | | B | BMPRII-Fc | 455 | 456 |
| | | | TGFβRII$_{LONG}$-Fc | 417 | 418 |
| MISRII-Fc:TGFβRIISHORT-Fc | Electrostatic | A | MISRII-Fc | 133 | 135 |
| | | | TGFβRIISHORT-Fc | 157 | 158 |
| | | B | MISRII-Fc | 161 | 162 |
| | | | TGFβRIISHORT-Fc | 127 | 129 |
| | Hydrophobic | A | MISRII-Fc | 419 | 420 |
| | | | TGFβRIISHORT-Fc | 459 | 460 |
| | | B | MISRII-Fc | 457 | 458 |
| | | | TGFβRIISHORT-Fc | 415 | 416 |
| MISRII-Fc:TGFβRII$_{LONG}$-Fc | Electrostatic | A | MISRII-Fc | 133 | 135 |
| | | | TGFβRII$_{LONG}$-Fc | 159 | 160 |
| | | B | MISRII-Fc | 161 | 162 |
| | | | TGFβRII$_{LONG}$-Fc | 130 | 132 |
| | Hydrophobic | A | MISRII-Fc | 419 | 420 |
| | | | TGFβRII$_{LONG}$-Fc | 461 | 462 |
| | | B | MISRII-Fc | 457 | 458 |
| | | | TGFβRII$_{LONG}$-Fc | 417 | 418 |
| TGFβRIISHORT-Fc: TGFβRIILONG-Fc | Electrostatic | A | TGFβRIISHORT-Fc | 127 | 129 |
| | | | TGFβRIILONG-Fc | 159 | 160 |
| | | B | TGFβRIISHORT-Fc | 157 | 158 |
| | | | TGFβRIILONG-Fc | 130 | 132 |
| | Hydrophobic | A | TGFβRIISHORT-Fc | 415 | 416 |
| | | | TGFβRIILONG-Fc | 461 | 462 |
| | | B | TGFβRIISHORT-Fc | 459 | 460 |
| | | | TGFβRIILONG-Fc | 417 | 418 |

Example 36. Generation of an ALK1-Fc:ALK2-Fc Heterodimer

A soluble ALK1-Fc:ALK2-Fc heteromeric complex can be generated comprising the extracellular domains of human ALK1 and human ALK2, which are each fused to an Fc domain with a linker positioned between the extracellular domain and the Fc domain. The individual constructs are referred to as ALK1-Fc and ALK2-Fc fusion proteins, respectively.

Formation of heteromeric ALK1-Fc:ALK2-Fc may be guided by approaches similar to those described in Example 1.

Electrostatic Approach

In a first approach, the polypeptide sequence of the ALK1-Fc fusion protein and a nucleic acid sequence encoding it are provided above in Example 16 as SEQ ID NOs: 124-126.

The polypeptide sequence of the complementary ALK2-Fc fusion protein (SEQ ID NO: 173) employs the TPA leader and is as follows:

(SEQ ID NO: 173)

```
  1 MDAMKRGLCC VLLLCGAVFV SPGAMEDEKP KVNPKLYMCV CEGLSCGNED

51 HCEGQQCFSS LSINDGFHVY QKGCFQVYEQ GKMTCKTPPS PGQAVECCQG

101 DWCNRNITAQ LPTKGKSFPG TQNFHLETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSRKEMTKN QVSLTCLVKG FYPSDIAVEW ESNGQPENNY

301 KTTPPVLKSD GSFFLYSKLT VDKSRWQQGN VFSCSVMHEA LHNHYTQKSL

351 SLSPG
```

The leader and linker sequences are underlined. To promote formation of the ALK1-Fc:ALK2-Fc heterodimer rather than either of the possible homodimeric complexes, two amino acid substitutions (replacing acidic amino acids with lysines) can be introduced into the Fc domain of the fusion protein as indicated by double underline above. The amino acid sequence of SEQ ID NO: 173 may optionally be provided with a lysine added to the C-terminus.

The mature ALK2-Fc fusion protein sequence is as follows (SEQ ID NO: 174) and may optionally be provided with a lysine added to the C-terminus.

```
                                                  (SEQ ID NO: 174)
  1 MEDEKPKVNP KLYMCVCEGL SCGNEDHCEG QQCFSSLSIN DGFHVYQKGC

51 FQVYEQGKMT CKTPPSPGQA VECCQGDWCN RNITAQLPTK GKSFPGTQNF

101 HLETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPSR KEMTKNQVSL

251 TCLVKGFYPS DIAVEWESNG QPENNYKTTP PVLKSDGSFF LYSKLTVDKS

301 RWQQGNVFSC SVMHEALHNH YTQKSLSLSP G
```

The ALK1-Fc and ALK2-Fc fusion proteins of SEQ ID NO: 126 and SEQ ID NO: 174, respectively, may be co-expressed and purified from a CHO cell line to give rise to a heteromeric complex comprising ALK1-Fc:ALK2-Fc.

Reverse Electrostatic Approach

In a reverse approach, receptor extracellular domains are both linked to the opposite member of the Fc interaction pair compared to the first approach described above. In this example, an alternative polypeptide sequence of the ALK1-Fc fusion protein (SEQ ID NO: 171) employs the TPA leader and is as follows.

```
                                                  (SEQ ID NO: 171)
  1 MDAMKRGLCC VLLLCGAVFV SPGADPVKPS RGPLVTCTCE SPHCKGPTCR

51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPSR KEMTKNQVSL TCLVKGFYPS DIAVEWESNG QPENNYKTTP

301 PVLKSDGSFF LYSKLTVDKS RWQQGNVFSC SVMHEALHNH YTQKSLSLSP

351 G
```

The leader and linker sequences are underlined. To promote formation of the ALK1-Fc:ALK2-Fc heterodimer rather than either of the possible homodimeric complexes, two amino acid substitutions (replacing acidic amino acids with lysines) can be introduced into the Fc domain of the fusion protein as indicated by double underline above. The amino acid sequence of SEQ ID NO: 171 may optionally be provided with a lysine added to the C-terminus.

The mature ALK1-Fc fusion protein sequence is as follows (SEQ ID NO: 172) and may optionally be provided with a lysine added to the C-terminus.

```
                                                  (SEQ ID NO: 172)
  1 DPVKPSRGPL VTCTCESPHC KGPTCRGAWC TVVLVREEGR HPQEHRGCGN

51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY
```

```
201 KCKVSNKALP APIEKTISKA KGQPREPQVY TLPPSRKEMT KNQVSLTCLV

251 KGFYPSDIAV EWESNGQPEN NYKTTPPVLK SDGSFFLYSK LTVDKSRWQQ

301 GNVFSCSVMH EALHNHYTQK SLSLSPG
```

The polypeptide sequence of the ALK2-Fc fusion protein and a nucleic acid sequence encoding it are provided in Example 9 as SEQ ID NOs: 136-138.

The ALK1-Fc and ALK2-Fc fusion proteins of SEQ ID NO: 172 and SEQ ID NO: 138, respectively, may be co-expressed and purified from a CHO cell line to give rise to a variant heteromeric complex comprising ALK1-Fc:ALK2-Fc.

Hydrophobic Approach

In another approach to promoting the formation of heteromultimer complexes using asymmetric Fc fusion proteins, the Fc domains are altered to introduce complementary hydrophobic interactions and an additional intermolecular disulfide bond. The polypeptide sequence of the ALK1-Fc fusion protein is provided in Example 16 as SEQ ID NOs: 413-414.

The complementary form of ALK2-Fc fusion polypeptide (SEQ ID NO: 465) is as follows:

```
                                                      (SEQ ID NO: 465)
  1 MDAMKRGLCC VLLLCGAVFV SPGAMEDEKP KVNPKLYMCV CEGLSCGNED

51 HCEGQQCFSS LSINDGFHVY QKGCFQVYEQ GKMTCKTPPS PGQAVECCQG

101 DWCNRNITAQ LPTKGKSFPG TQNFHLETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPCREEMTKN QVSLWCLVKG FYPSDIAVEW ESNGQPENNY

301 KTTPPVLDSD GSFFLYSKLT VDKSRWQQGN VFSCSVMHEA LHNHYTQKSL

351 SLSPGK
```

The leader and linker sequences are underlined. To guide heterodimer formation with the ALK1-Fc fusion polypeptide of SEQ ID NOs: 413-414, two amino acid substitutions (replacing a serine with a cysteine and a threonine with a tryptophan) can be introduced into the Fc domain of the ALK2-Fc fusion polypeptide as indicated by double underline above. The amino acid sequence of SEQ ID NO: 465 may optionally be provided with the lysine removed from the C-terminus.

The mature ALK2-Fc fusion protein sequence (SEQ ID NO: 466) is as follows and may optionally be provided with the lysine removed from the C-terminus.

```
                                                      (SEQ ID NO: 466)
  1 MEDEKPKVNP KLYMCVCEGL SCGNEDHCEG QQCFSSLSIN DGFHVYQKGC

51 FQVYEQGKMT CKTPPSPGQA VECCQGDWCN RNITAQLPTK GKSFPGTQNF

101 HLETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPCR EEMTKNQVSL

251 WCLVKGFYPS DIAVEWESNG QPENNYKTTP PVLDSDGSFF LYSKLTVDKS

301 RWQQGNVFSC SVMHEALHNH YTQKSLSLSP GK
```

The ALK1-Fc and ALK2-Fc proteins of SEQ ID NO: 414 and SEQ ID NO: 466, respectively, may be co-expressed and purified from a CHO cell line, to give rise to a variant heteromeric complex comprising ALK1-Fc:ALK2-Fc.

Reverse Hydrophobic Approach

In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, an alternative polypeptide sequence of the ALK1-Fc fusion protein (SEQ ID NO: 463) employs the TPA leader and is as follows.

```
                                              (SEQ ID NO: 463)
  1 MDAMKRGLCC VLLLCGAVFV SPGADPVKPS RGPLVTCTCE SPHCKGPTCR

51 GAWCTVVLVR EEGRHPQEHR GCGNLHRELC RGRPTEFVNH YCCDSHLCNH

101 NVSLVLEATQ PPSEQPGTDG QLATGGGTHT CPPCPAPELL GGPSVFLFPP

151 KPKDTLMISR TPEVTCVVVD VSHEDPEVKF NWYVDGVEVH NAKTKPREEQ

201 YNSTYRVVSV LTVLHQDWLN GKEYKCKVSN KALPAPIEKT ISKAKGQPRE

251 PQVYTLPPCR EEMTKNQVSL WCLVKGFYPS DIAVEWESNG QPENNYKTTP

301 PVLDSDGSFF LYSKLTVDKS RWQQGNVFSC SVMHEALHNH YTQKSLSLSP

351 GK
```

The leader and linker sequences are underlined. To guide heterodimer formation with the ALK2-Fc fusion polypeptide of SEQ ID NOs 421-422, two amino acid substitutions (replacing a serine with a cysteine and a threonine with a tryptophan) can be introduced into the Fc domain of the ALK1-Fc fusion polypeptide as indicated by double underline above. The amino acid sequence of SEQ ID NO: 463 may optionally be provided with the lysine removed from the C-terminus.

The mature ALK1-Fc fusion protein sequence is as follows (SEQ ID NO: 464) and may optionally be provided with the lysine removed from the C-terminus.

```
                                              (SEQ ID NO: 464)
  1 DPVKPSRGPL VTCTCESPHC KGPTCRGAWC TVVLVREEGR HPQEHRGCGN

51 LHRELCRGRP TEFVNHYCCD SHLCNHNVSL VLEATQPPSE QPGTDGQLAT

101 GGGTHTCPPC PAPELLGGPS VFLFPPKPKD TLMISRTPEV TCVVVDVSHE

151 DPEVKFNWYV DGVEVHNAKT KPREEQYNST YRVVSVLTVL HQDWLNGKEY

201 KCKVSNKALP APIEKTISKA KGQPREPQVY TLPPCREEMT KNQVSLWCLV

251 KGFYPSDIAV EWESNGQPEN NYKTTPPVLD SDGSFFLYSK LTVDKSRWQQ

301 GNVFSCSVMH EALHNHYTQK SLSLSPGK
```

The polypeptide sequence of the ALK2-Fc fusion protein is provided in Example 9 as SEQ ID NOs: 421-422.

The ALK1-Fc and ALK2-Fc proteins of SEQ ID NO: 464 and SEQ ID NO: 422, respectively, may be co-expressed and purified from a CHO cell line, to give rise to a variant heteromeric complex comprising ALK1-Fc:ALK2-Fc.

Purification of various ALK1-Fc:ALK2-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 37. Generation of an ALK1-Fc:ALK3-Fc Heterodimer

A soluble ALK1-Fc:ALK3-Fc heteromeric complex can be generated comprising the extracellular domains of human ALK1 and human ALK3, which are each fused to an Fc domain with a linker positioned between the extracellular domain and the Fc domain. The individual constructs are referred to as ALK1-Fc and ALK3-Fc fusion proteins, respectively.

Formation of heteromeric ALK1-Fc:ALK3-Fc may be guided by approaches similar to those described in Example 36.

Electrostatic Approach

In a first approach, the polypeptide sequence of the ALK1-Fc fusion protein and a nucleic acid sequence encoding it are provided in Example 16 as SEQ ID NOs: 124-126.

The polypeptide sequence of the complementary ALK3-Fc fusion protein (SEQ ID NO: 175) employs the TPA leader and is as follows:

```
                                                         (SEQ ID NO: 175)
  1  MDAMKRGLCC VLLLCGAVFV SPGAQNLDSM LHGTGMKSDS DQKKSENGVT

51  LAPEDTLPFL KCYCSGHCPD DAINNTCITN GHCFAIIEED DQGETTLASG

101  CMKYEGSDFQ CKDSPKAQLR RTIECCRTNL CNQYLQPTLP PVVIGPFFDG

151  SIRTGGGTHT CPPCPAPELL GGPSVFLFPP KPKDTLMISR TPEVTCVVVD

201  VSHEDPEVKF NWYVDGVEVH NAKTKPREEQ YNSTYRVVSV LTVLHQDWLN

251  GKEYKCKVSN KALPAPIEKT ISKAKGQPRE PQVYTLPPSR KEMTKNQVSL

301  TCLVKGFYPS DIAVEWESNG QPENNYKTTP PVLKSDGSFF LYSKLTVDKS

351  RWQQGNVFSC SVMHEALHNH YTQKSLSLSP G
```

The leader and linker sequences are underlined. To promote formation of the ALK1-Fc:ALK3-Fc heterodimer rather than either of the possible homodimeric complexes, two amino acid substitutions (replacing acidic amino acids with lysines) can be introduced into the Fc domain of the fusion protein as indicated by double underline above. The amino acid sequence of SEQ ID NO: 175 may optionally be provided with a lysine added to the C-terminus.

The mature ALK3-Fc fusion protein sequence is as follows (SEQ ID NO: 176) and may optionally be provided with a lysine added to the C-terminus.

The ALK1-Fc and ALK3-Fc fusion proteins of SEQ ID NO: 126 and SEQ ID NO: 176, respectively, may be co-expressed and purified from a CHO cell line to give rise to a heteromeric complex comprising ALK1-Fc:ALK3-Fc.

Reverse Electrostatic Approach

In a reverse approach, receptor extracellular domains are linked to the opposite member of the Fc interaction pair compared to the first approach described above. In this example, the alternative polypeptide sequence of the ALK1-Fc fusion protein is provided in Example 36 as SEQ ID NOs: 171-172.

The polypeptide sequence of the ALK3-Fc fusion protein and a nucleic acid sequence encoding it are provided in Example 4 as SEQ ID NOs: 115-117.

The ALK1-Fc and ALK3-Fc fusion proteins of SEQ ID NO: 172 and SEQ ID NO: 117, respectively, may be co-expressed and purified from a CHO cell line to give rise to a variant heteromeric complex comprising ALK1-Fc:ALK3-Fc.

Hydrophobic Approach

In another approach to promoting the formation of heteromultimer complexes using asymmetric Fc fusion proteins, the Fc domains are altered to introduce complementary hydrophobic interactions and an additional intermolecular disulfide bond. The polypeptide sequence of the ALK1-Fc fusion protein is provided in Example 16 as SEQ ID NOs 413-414.

The complementary form of ALK3-Fc fusion polypeptide (SEQ ID NO: 467) is as follows:

```
                                                         (SEQ ID NO: 176)
  1  GAQNLDSMLH GTGMKSDSDQ KKSENGVTLA PEDTLPFLKC YCSGHCPDDA

51  INNTCITNGH CFAIIEEDDQ GETTLASGCM KYEGSDFQCK DSPKAQLRRT

101  IECCRTNLCN QYLQPTLPPV VIGPFFDGSI RTGGGTHTCP PCPAPELLGG

151  PSVFLFPPKP KDTLMISRTP EVTCVVVDVS HEDPEVKFNW YVDGVEVHNA

201  KTKPREEQYN STYRVVSVLT VLHQDWLNGK EYKCKVSNKA LPAPIEKTIS

251  KAKGQPREPQ VYTLPPSRKE MTKNQVSLTC LVKGFYPSDI AVEWESNGQP

301  ENNYKTTPPV LKSDGSFFLY SKLTVDKSRW QQGNVFSCSV MHEALHNHYT

351  QKSLSLSPG
```

```
                                                          (SEQ ID NO: 467)
  1 MDAMKRGLCC VLLLCGAVFV SPGAQNLDSM LHGTGMKSDS DQKKSENGVT

51 LAPEDTLPFL KCYCSGHCPD DAINNTCITN GHCFAIIEED DQGETTLASG

101 CMKYEGSDFQ CKDSPKAQLR RTIECCRTNL CNQYLQPTLP PVVIGPFFDG

151 SIRTGGGTHT CPPCPAPELL GGPSVFLFPP KPKDTLMISR TPEVTCVVVD

201 VSHEDPEVKF NWYVDGVEVH NAKTKPREEQ YNSTYRVVSV LTVLHQDWLN

251 GKEYKCKVSN KALPAPIEKT ISKAKGQPRE PQVYTLPPCR EEMTKNQVSL

301 WCLVKGFYPS DIAVEWESNG QPENNYKTTP PVLDSDGSFF LYSKLTVDKS

351 RWQQGNVFSC SVMHEALHNH YTQKSLSLSP GK
```

The leader and linker sequences are underlined. To guide heterodimer formation with the ALK1-Fc fusion polypeptide of SEQ ID NOs: 413-414, two amino acid substitutions (replacing a serine with a cysteine and a threonine with a tryptophan) can be introduced into the Fc domain of the ALK3-Fc fusion polypeptide as indicated by double underline above. The amino acid sequence of SEQ ID NO: 467 may optionally be provided with the lysine removed from the C-terminus.

The mature ALK3-Fc fusion protein sequence (SEQ ID NO: 468) is as follows and may optionally be provided with the lysine removed from the C-terminus.

```
                                                          (SEQ ID NO: 468)
  1 GAQNLDSMLH GTGMKSDSDQ KKSENGVTLA PEDTLPFLKC YCSGHCPDDA

51 INNTCITNGH CFAIIEEDDQ GETTLASGCM KYEGSDFQCK DSPKAQLRRT

101 IECCRTNLCN QYLQPTLPPV VIGPFFDGSI RTGGGTHTCP PCPAPELLGG

151 PSVFLFPPKP KDTLMISRTP EVTCVVVDVS HEDPEVKFNW YVDGVEVHNA

201 KTKPREEQYN STYRVVSVLT VLHQDWLNGK EYKCKVSNKA LPAPIEKTIS

251 KAKGQPREPQ VYTLPPCREE MTKNQVSLWC LVKGFYPSDI AVEWESNGQP

301 ENNYKTTPPV LDSDGSFFLY SKLTVDKSRW QQGNVFSCSV MHEALHNHYT

351 QKSLSLSPGK
```

The ALK1-Fc and ALK3-Fc proteins of SEQ ID NO: 414 and SEQ ID NO: 468, respectively, may be co-expressed and purified from a CHO cell line, to give rise to a variant heteromeric complex comprising ALK1-Fc:ALK3-Fc.

Reverse Hydrophobic Approach

In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, the alternative polypeptide sequence of the ALK1-Fc fusion protein is provided in Example 36 as SEQ ID NOs: 463-464.

The polypeptide sequence of the ALK3-Fc fusion protein is provided in Example 4 as SEQ ID NOs: 407-408.

The ALK1-Fc and ALK3-Fc proteins of SEQ ID NO: 464 and SEQ ID NO: 408, respectively, may be co-expressed and purified from a CHO cell line, to give rise to a variant heteromeric complex comprising ALK1-Fc:ALK3-Fc.

Purification of various ALK1-Fc:ALK3-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 38. Generation of an ALK1-Fc:ALK4-Fc Heterodimer

A soluble ALK1-Fc:ALK4-Fc heteromeric complex can be generated comprising the extracellular domains of human ALK1 and human ALK4, which are each fused to an Fc domain with a linker positioned between the extracellular domain and the Fc domain. The individual constructs are referred to as ALK1-Fc and ALK4-Fc fusion proteins, respectively.

Formation of heteromeric ALK1-Fc:ALK4-Fc may be guided by approaches similar to those described in Example 36.

Electrostatic Approach

In a first approach, the polypeptide sequence of the ALK1-Fc fusion protein and a nucleic acid sequence encoding it are provided in Example 16 as SEQ ID NOs: 124-126.

The polypeptide sequence of the complementary ALK4-Fc fusion protein (SEQ ID NO: 177) employs the TPA leader and is as follows:

```
                                                            (SEQ ID NO: 177)
  1 MDAMKRGLCC VLLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPSRKEMTKN QVSLTCLVKG FYPSDIAVEW ESNGQPENNY

301 KTTPPVLKSD GSFFLYSKLT VDKSRWQQGN VFSCSVMHEA LHNHYTQKSL

351 SLSPG
```

The leader and linker sequences are underlined. To promote formation of the ALK1-Fc:ALK4-Fc heterodimer rather than either of the possible homodimeric complexes, two amino acid substitutions (replacing acidic amino acids with lysines) can be introduced into the Fc domain of the fusion protein as indicated by double underline above. The amino acid sequence of SEQ ID NO: 177 may optionally be provided with a lysine added to the C-terminus.

The mature ALK4-Fc fusion protein sequence is as follows (SEQ ID NO: 178) and may optionally be provided with a lysine added to the C-terminus.

The polypeptide sequence of the ALK4-Fc fusion protein and a nucleic acid sequence encoding it are provided in Example 1 as SEQ ID NOs: 104-106.

The ALK1-Fc and ALK4-Fc fusion proteins of SEQ ID NO: 172 and SEQ ID NO: 106, respectively, may be co-expressed and purified from a CHO cell line to give rise to a variant heteromeric complex comprising ALK1-Fc:ALK4-Fc.

Hydrophobic Approach

In another approach to promoting the formation of heteromultimer complexes using asymmetric Fc fusion pro-

```
                                                            (SEQ ID NO: 178)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPSR KEMTKNQVSL

251 TCLVKGFYPS DIAVEWESNG QPENNYKTTP PVLKSDGSFF LYSKLTVDKS

301 RWQQGNVFSC SVMHEALHNH YTQKSLSLSP G
```

The ALK1-Fc and ALK4-Fc fusion proteins of SEQ ID NO: 126 and SEQ ID NO: 178, respectively, may be co-expressed and purified from a CHO cell line to give rise to a heteromeric complex comprising ALK1-Fc:ALK4-Fc.

Reverse Electrostatic Approach

In a reverse approach, receptor extracellular domains are linked to the opposite member of the Fc interaction pair compared to the first approach described above. In this example, the alternative polypeptide sequence of the ALK1-Fc fusion protein is provided in Example 36 as SEQ ID NOs: 171-172.

teins, the Fc domains are altered to introduce complementary hydrophobic interactions and an additional intermolecular disulfide bond. The polypeptide sequence of the ALK1-Fc fusion protein is provided in Example 16 as SEQ ID NOs 413-414.

The complementary form of ALK4-Fc fusion polypeptide (SEQ ID NO: 469) is as follows:

```
                                                            (SEQ ID NO: 469)
  1 MDAMKRGLCC VLLLLCGAVFV SPGASGPRGV QALLCACTSC LQANYTCETD

51 GACMVSIFNL DGMEHHVRTC IPKVELVPAG KPFYCLSSED LRNTHCCYTD

101 YCNRIDLRVP SGHLKEPEHP SMWGPVETGG GTHTCPPCPA PELLGGPSVF

151 LFPPKPKDTL MISRTPEVTC VVVDVSHEDP EVKFNWYVDG VEVHNAKTKP

201 REEQYNSTYR VVSVLTVLHQ DWLNGKEYKC KVSNKALPAP IEKTISKAKG

251 QPREPQVYTL PPCREEMTKN QVSLWCLVKG FYPSDIAVEW ESNGQPENNY

301 KTTPPVLDSD GSFFLYSKLT VDKSRWQQGN VFSCSVMHEA LHNHYTQKSL

351 SLSPGK
```

The leader and linker sequences are underlined. To guide heterodimer formation with the ALK1-Fc fusion polypeptide of SEQ ID NOs: 413-414, two amino acid substitutions (replacing a serine with a cysteine and a threonine with a tryptophan) can be introduced into the Fc domain of the ALK4-Fc fusion polypeptide as indicated by double underline above. The amino acid sequence of SEQ ID NO: 469 may optionally be provided with the lysine removed from the C-terminus.

The mature ALK4-Fc fusion protein sequence (SEQ ID NO: 470) is as follows and may optionally be provided with the lysine removed from the C-terminus.

in any order: protein A chromatography, Q sepharose chromatography, phenylsepharose chromatography, size exclusion chromatography, and cation exchange chromatography. The purification could be completed with viral filtration and buffer exchange.

Example 39. Generation of an ALK1-Fc:ALK5-Fc Heterodimer

A soluble ALK1-Fc:ALK5-Fc heteromeric complex can be generated comprising the extracellular domains of human ALK1 and human ALK5, which are each fused to an Fc

```
                                                               (SEQ ID NO: 470)
  1 SGPRGVQALL CACTSCLQAN YTCETDGACM VSIFNLDGME HHVRTCIPKV

51 ELVPAGKPFY CLSSEDLRNT HCCYTDYCNR IDLRVPSGHL KEPEHPSMWG

101 PVETGGGTHT CPPCPAPELL GGPSVFLFPP KPKDTLMISR TPEVTCVVVD

151 VSHEDPEVKF NWYVDGVEVH NAKTKPREEQ YNSTYRVVSV LTVLHQDWLN

201 GKEYKCKVSN KALPAPIEKT ISKAKGQPRE PQVYTLPPCR EEMTKNQVSL

251 WCLVKGFYPS DIAVEWESNG QPENNYKTTP PVLDSDGSFF LYSKLTVDKS

301 RWQQGNVFSC SVMHEALHNH YTQKSLSLSP GK
```

The ALK1-Fc and ALK4-Fc proteins of SEQ ID NO: 414 and SEQ ID NO: 470, respectively, may be co-expressed and purified from a CHO cell line, to give rise to a variant heteromeric complex comprising ALK1-Fc:ALK4-Fc.
Reverse Hydrophobic Approach In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, the alternative polypeptide sequence of the ALK1-Fc fusion protein is provided in Example 36 as SEQ ID NOs: 463-464.

domain with a linker positioned between the extracellular domain and the Fc domain. The individual constructs are referred to as ALK1-Fc and ALK5-Fc fusion proteins, respectively.

Formation of heteromeric ALK1-Fc:ALK5-Fc may be guided by approaches similar to those described in Example 36.

Electrostatic Approach

In a first approach, the polypeptide sequence of the ALK1-Fc fusion protein and a nucleic acid sequence encoding it are provided in Example 16 as SEQ ID NOs: 124-126.

The polypeptide sequence of the complementary ALK5-Fc fusion protein (SEQ ID NO: 179) employs the TPA leader and is as follows:

```
                                                               (SEQ ID NO: 179)
  1 MDAMKRGLCC VLLLCGAVFV SPGAALLPGA TALQCFCHLC TKDNFTCVTD

51 GLCFVSVTET TDKVIHNSMC IAEIDLIPRD RPFVCAPSSK TGSVTTTYCC

101 NQDHCNKIEL PTTVKSSPGL GPVETGGGTH TCPPCPAPEL LGGPSVFLFP

151 PKPKDTLMIS RTPEVTCVVV DVSHEDPEVK FNWYVDGVEV HNAKTKPREE

201 QYNSTYRVVS VLTVLHQDWL NGKEYKCKVS NKALPAPIEK TISKAKGQPR

251 EPQVYTLPPS RKEMTKNQVS LTCLVKGFYP SDIAVEWESN GQPENNYKTT

301 PPVLKSDGSF FLYSKLTVDK SRWQQGNVFS CSVMHEALHN HYTQKSLSLS

351 PG
```

The polypeptide sequence of the ALK4-Fc fusion protein is provided in Example 1 as SEQ ID NOs: 403-404.

The ALK1-Fc and ALK4-Fc proteins of SEQ ID NO: 464 and SEQ ID NO: 404, respectively, may be co-expressed and purified from a CHO cell line, to give rise to a variant heteromeric complex comprising ALK1-Fc:ALK4-Fc.

Purification of various ALK1-Fc:ALK4-Fc complexes could be achieved by a series of column chromatography steps, including, for example, three or more of the following, The leader and linker sequences are underlined. To promote formation of the ALK1-Fc:ALK5-Fc heterodimer rather than either of the possible homodimeric complexes, two amino acid substitutions (replacing acidic amino acids with lysines) can be introduced into the Fc domain of the fusion protein as indicated by double underline above. The amino acid sequence of SEQ ID NO: 179 may optionally be provided with a lysine added to the C-terminus.

The mature ALK5-Fc fusion protein sequence is as follows (SEQ ID NO: 180) and may optionally be provided with a lysine added to the C-terminus.

```
                                                    (SEQ ID NO: 180)
  1 ALLPGATALQ CFCHLCTKDN FTCVTDGLCF VSVTETTDKV IHNSMCIAEI

51 DLIPRDRPFV CAPSSKTGSV TTTYCCNQDH CNKIELPTTV KSSPGLGPVE

101 TGGGTHTCPP CPAPELLGGP SVFLFPPKPK DTLMISRTPE VTCVVVDVSH

151 EDPEVKFNWY VDGVEVHNAK TKPREEQYNS TYRVVSVLTV LHQDWLNGKE

201 YKCKVSNKAL PAPIEKTISK AKGQPREPQV YTLPPSRKEM TKNQVSLTCL

251 VKGFYPSDIA VEWESNGQPE NNYKTTPPVL KSDGSFFLYS KLTVDKSRWQ

301 QGNVFSCSVM HEALHNHYTQ KSLSLSPG
```

The ALK1-Fc and ALK5-Fc fusion proteins of SEQ ID NO: 126 and SEQ ID NO: 180, respectively, may be co-expressed and purified from a CHO cell line to give rise to a heteromeric complex comprising ALK1-Fc:ALK5-Fc.
Reverse Electrostatic Approach In a reverse approach, receptor extracellular domains are linked to the opposite member of the Fc interaction pair compared to the first approach described above. In this example, the alternative polypeptide sequence of the ALK1-Fc fusion protein is provided in Example 36 as SEQ ID NOs: 171-172.

The polypeptide sequence of the ALK5-Fc fusion protein and a nucleic acid sequence encoding it are provided in Example 11 as SEQ ID NOs: 139-141.

The ALK1-Fc and ALK5-Fc fusion proteins of SEQ ID NO: 172 and SEQ ID NO: 141, respectively, may be co-expressed and purified from a CHO cell line to give rise to a variant heteromeric complex comprising ALK1-Fc:ALK5-Fc.
Hydrophobic Approach In another approach to promoting the formation of heteromultimer complexes using asymmetric Fc fusion proteins, the Fc domains are altered to introduce complementary hydrophobic interactions and an additional intermolecular disulfide bond. The polypeptide sequence of the ALK1-Fc fusion protein is provided in Example 16 as SEQ ID NOs 413-414.

The complementary form of ALK5-Fc fusion polypeptide (SEQ ID NO: 471) is as follows:

```
                                                    (SEQ ID NO: 471)
  1 MDAMKRGLCC VLLLCGAVFV SPGAALLPGA TALQCFCHLC TKDNFTCVTD

51 GLCFVSVTET TDKVIHNSMC IAEIDLIPRD RPFVCAPSSK TGSVTTTYCC

101 NQDHCNKIEL PTTVKSSPGL GPVETGGGTH TCPPCPAPEL LGGPSVFLFP

151 PKPKDTLMIS RTPEVTCVVV DVSHEDPEVK FNWYVDGVEV HNAKTKPREE

201 QYNSTYRVVS VLTVLHQDWL NGKEYKCKVS NKALPAPIEK TISKAKGQPR

251 EPQVYTLPPC REEMTKNQVS LWCLVKGFYP SDIAVEWESN GQPENNYKTT

301 PPVLDSDGSF FLYSKLTVDK SRWQQGNVFS CSVMHEALHN HYTQKSLSLS

351 PGK
```

The leader and linker sequences are underlined. To guide heterodimer formation with the ALK1-Fc fusion polypeptide of SEQ ID NOs: 413-414, two amino acid substitutions (replacing a serine with a cysteine and a threonine with a tryptophan) can be introduced into the Fc domain of the ALK5-Fc fusion polypeptide as indicated by double underline above. The amino acid sequence of SEQ ID NO: 471 may optionally be provided with the lysine removed from the C-terminus.

The mature ALK5-Fc fusion protein sequence (SEQ ID NO: 472) is as follows and may optionally be provided with the lysine removed from the C-terminus.

```
                                                    (SEQ ID NO: 472)
  1 ALLPGATALQ CFCHLCTKDN FTCVTDGLCF VSVTETTDKV IHNSMCIAEI

51 DLIPRDRPFV CAPSSKTGSV TTTYCCNQDH CNKIELPTTV KSSPGLGPVE

101 TGGGTHTCPP CPAPELLGGP SVFLFPPKPK DTLMISRTPE VTCVVVDVSH
```

-continued

```
151 EDPEVKFNWY VDGVEVHNAK TKPREEQYNS TYRVVSVLTV LHQDWLNGKE

201 YKCKVSNKAL PAPIEKTISK AKGQPREPQV YTLPPCREEM TKNQVSLWCL

251 VKGFYPSDIA VEWESNGQPE NNYKTTPPVL DSDGSFFLYS KLTVDKSRWQ

301 QGNVFSCSVM HEALHNHYTQ KSLSLSPGK
```

The ALK1-Fc and ALK5-Fc proteins of SEQ ID NO: 414 and SEQ ID NO: 472, respectively, may be co-expressed and purified from a CHO cell line, to give rise to a variant heteromeric complex comprising ALK1-Fc:ALK5-Fc.

Reverse Hydrophobic Approach

In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, the alternative polypeptide sequence of the ALK1-Fc fusion protein is provided in Example 36 as SEQ ID NOs: 463-464.

The polypeptide sequence of the ALK5-Fc fusion protein is provided in Example 16 as SEQ ID NOs: 423-424.

The ALK1-Fc and ALK5-Fc proteins of SEQ ID NO: 464 and SEQ ID NO: 424, respectively, may be co-expressed and purified from a CHO cell line, to give rise to a variant heteromeric complex comprising ALK1-Fc:ALK5-Fc.

Purification of various ALK1-Fc:ALK5-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 40. Generation of an ALK1-Fc:ALK6-Fc Heterodimer

A soluble ALK1-Fc:ALK6-Fc heteromeric complex can be generated comprising the extracellular domains of human ALK1 and human ALK6, which are each fused to an Fc domain with a linker positioned between the extracellular domain and the Fc domain. The individual constructs are referred to as ALK1-Fc and ALK6-Fc fusion proteins, respectively.

Formation of heteromeric ALK1-Fc:ALK6-Fc may be guided by approaches similar to those described in Example 36.

Electrostatic Approach

In a first approach, the polypeptide sequence of the ALK1-Fc fusion protein and a nucleic acid sequence encoding it are provided in Example 16 as SEQ ID NOs: 124-126.

The polypeptide sequence of the complementary ALK6-Fc fusion protein (SEQ ID NO: 181) employs the TPA leader and is as follows:

```
                                              (SEQ ID NO: 181)
  1 MDAMKRGLCC VLLLCGAVFV SPGAKKEDGE STAPTPRPKV LRCKCHHHCP

51 EDSVNNICST DGYCFTMIEE DDSGLPVVTS GCLGLEGSDF QCRDTPIPHQ

101 RRSIECCTER NECNKDLHPT LPPLKNRDFV DGPIHHRTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPSRKEMTKN QVSLTCLVKG FYPSDIAVEW

301 ESNGQPENNY KTTPPVLKSD GSFFLYSKLT VDKSRWQQGN VFSCSVMHEA

351 LHNHYTQKSL SLSPG
```

The leader and linker sequences are underlined. To promote formation of the ALK1-Fc:ALK6-Fc heterodimer rather than either of the possible homodimeric complexes, two amino acid substitutions (replacing acidic amino acids with lysines) can be introduced into the Fc domain of the fusion protein as indicated by double underline above. The amino acid sequence of SEQ ID NO: 181 may optionally be provided with a lysine added to the C-terminus.

The mature ALK6-Fc fusion protein sequence is as follows (SEQ ID NO: 182) and may optionally be provided with a lysine added to the C-terminus.

```
                                              (SEQ ID NO: 182)
  1 KKEDGESTAP TPRPKVLRCK CHHHCPEDSV NNICSTDGYC FTMIEEDDSG

51 LPVVTSGCLG LEGSDFQCRD TPIPHQRRSI ECCTERNECN KDLHPTLPPL
```

```
101 KNRDFVDGPI HHRTGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPSR

251 KEMTKNQVSL TCLVKGFYPS DIAVEWESNG QPENNYKTTP PVLKSDGSFF

301 LYSKLTVDKS RWQQGNVFSC SVMHEALHNH YTQKSLSLSP G
```

The ALK1-Fc and ALK6-Fc fusion proteins of SEQ ID NO: 126 and SEQ ID NO: 182, respectively, may be co-expressed and purified from a CHO cell line to give rise to a heteromeric complex comprising ALK1-Fc:ALK6-Fc.

Reverse Electrostatic Approach

In a reverse approach, receptor extracellular domains are linked to the opposite member of the Fc interaction pair compared to the first approach described above. In this example, the alternative polypeptide sequence of the ALK1-Fc fusion protein is provided in Example 36 as SEQ ID NOs: 171-172.

The polypeptide sequence of the ALK6-Fc fusion protein and a nucleic acid sequence encoding it are provided in Example 13 as SEQ ID NOs: 142-144.

The ALK1-Fc and ALK6-Fc fusion proteins of SEQ ID NO: 172 and SEQ ID NO: 144, respectively, may be co-expressed and purified from a CHO cell line to give rise to a variant heteromeric complex comprising ALK1-Fc: ALK6-Fc.

Hydrophobic Approach

In another approach to promoting the formation of heteromultimer complexes using asymmetric Fc fusion proteins, the Fc domains are altered to introduce complementary hydrophobic interactions and an additional intermolecular disulfide bond. The polypeptide sequence of the ALK1-Fc fusion protein is provided in Example 16 as SEQ ID NOs 413-414.

The complementary form of ALK6-Fc fusion polypeptide (SEQ ID NO: 473) is as follows:

```
                                                    (SEQ ID NO: 473)
  1 MDAMKRGLCC VLLLCGAVFV SPGAKKEDGE STAPTPRPKV LRCKCHHHCP

51 EDSVNNICST DGYCFTMIEE DDSGLPVVTS GCLGLEGSDF QCRDTPIPHQ

101 RRSIECCTER NECNKDLHPT LPPLKNRDFV DGPIHHRTGG GTHTCPPCPA

151 PELLGGPSVF LFPPKPKDTL MISRTPEVTC VVVDVSHEDP EVKFNWYVDG

201 VEVHNAKTKP REEQYNSTYR VVSVLTVLHQ DWLNGKEYKC KVSNKALPAP

251 IEKTISKAKG QPREPQVYTL PPCREEMTKN QVSLWCLVKG FYPSDIAVEW

301 ESNGQPENNY KTTPPVLDSD GSFFLYSKLT VDKSRWQQGN VFSCSVMHEA

351 LHNHYTQKSL SLSPGK
```

The leader and linker sequences are underlined. To guide heterodimer formation with the ALK1-Fc fusion polypeptide of SEQ ID NOs: 413-414, two amino acid substitutions (replacing a serine with a cysteine and a threonine with a tryptophan) can be introduced into the Fc domain of the ALK6-Fc fusion polypeptide as indicated by double underline above. The amino acid sequence of SEQ ID NO: 473 may optionally be provided with the lysine removed from the C-terminus.

The mature ALK6-Fc fusion protein sequence (SEQ ID NO: 474) is as follows and may optionally be provided with the lysine removed from the C-terminus.

```
                                                    (SEQ ID NO: 474)
  1 KKEDGESTAP TPRPKVLRCK CHHHCPEDSV NNICSTDGYC FTMIEEDDSG

51 LPVVTSGCLG LEGSDFQCRD TPIPHQRRSI ECCTERNECN KDLHPTLPPL

101 KNRDFVDGPI HHRTGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPCR

251 EEMTKNQVSL WCLVKGFYPS DIAVEWESNG QPENNYKTTP PVLDSDGSFF

301 LYSKLTVDKS RWQQGNVFSC SVMHEALHNH YTQKSLSLSP GK
```

The ALK1-Fc and ALK6-Fc proteins of SEQ ID NO: 414 and SEQ ID NO: 474, respectively, may be co-expressed and purified from a CHO cell line, to give rise to a variant heteromeric complex comprising ALK1-Fc:ALK6-Fc.

Reverse Hydrophobic Approach

In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, the alternative polypeptide sequence of the ALK1-Fc fusion protein is provided in Example 36 as SEQ ID NOs: 463-464.

The polypeptide sequence of the ALK6-Fc fusion protein is provided in Example 13 as SEQ ID NOs: 425-426.

The ALK1-Fc and ALK6-Fc proteins of SEQ ID NO: 464 and SEQ ID NO: 426, respectively, may be co-expressed and purified from a CHO cell line, to give rise to a variant heteromeric complex comprising ALK1-Fc:ALK6-Fc.

Purification of various ALK1-Fc:ALK6-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 41. Generation of an ALK1-Fc:ALK7-Fc Heterodimer

A soluble ALK1-Fc:ALK7-Fc heteromeric complex can be generated comprising the extracellular domains of human ALK1 and human ALK7, which are each fused to an Fc domain with a linker positioned between the extracellular domain and the Fc domain. The individual constructs are referred to as ALK1-Fc and ALK7-Fc fusion proteins, respectively.

Formation of heteromeric ALK1-Fc:ALK7-Fc may be guided by approaches similar to those described in Example 36.

Electrostatic Approach

In a first approach, the polypeptide sequence of the ALK1-Fc fusion protein and a nucleic acid sequence encoding it are provided in Example 16 as SEQ ID NOs: 124-126.

The polypeptide sequence of the complementary ALK7-Fc fusion protein (SEQ ID NO: 183) employs the TPA leader and is as follows:

```
                                                    (SEQ ID NO: 183)
  1 MDAMKRGLCC VLLLCGAVFV SPGAGLKCVC LLCDSSNFTC QTEGACWASV

51 MLTNGKEQVI KSCVSLPELN AQVFCHSSNN VTKTECCFTD FCNNITLHLP

101 TASPNAPKLG PMETGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPSR

251 KEMTKNQVSL TCLVKGFYPS DIAVEWESNG QPENNYKTTP PVLKSDGSFF

301 LYSKLTVDKS RWQQGNVFSC SVMHEALHNH YTQKSLSLSP G
```

The leader and linker sequences are underlined. To promote formation of the ALK1-Fc:ALK7-Fc heterodimer rather than either of the possible homodimeric complexes, two amino acid substitutions (replacing acidic amino acids with lysines) can be introduced into the Fc domain of the fusion protein as indicated by double underline above. The amino acid sequence of SEQ ID NO: 183 may optionally be provided with a lysine added to the C-terminus.

The mature ALK7-Fc fusion protein sequence is expected to be as follows (SEQ ID NO: 184) and may optionally be provided with a lysine added to the C-terminus.

```
                                                    (SEQ ID NO: 184)
  1 GLKCVCLLCD SSNFTCQTEG ACWASVMLTN GKEQVIKSCV SLPELNAQVF

51 CHSSNNVTKT ECCFTDFCNN ITLHLPTASP NAPKLGPMET GGGTHTCPPC

101 PAPELLGGPS VFLFPPKPKD TLMISRTPEV TCVVVDVSHE DPEVKFNWYV

151 DGVEVHNAKT KPREEQYNST YRVVSVLTVL HQDWLNGKEY KCKVSNKALP

201 APIEKTISKA KGQPREPQVY TLPPSRKEMT KNQVSLTCLV KGFYPSDIAV

251 EWESNGQPEN NYKTTPPVLK SDGSFFLYSK LTVDKSRWQQ GNVFSCSVMH

301 EALHNHYTQK SLSLSPG
```

The ALK1-Fc and ALK7-Fc fusion proteins of SEQ ID NO: 126 and SEQ ID NO: 184, respectively, may be co-expressed and purified from a CHO cell line to give rise to a heteromeric complex comprising ALK1-Fc:ALK7-Fc.

Reverse Electrostatic Approach

In a reverse approach, receptor extracellular domains are linked to the opposite member of the Fc interaction pair compared to the first approach described above. In this example, the alternative polypeptide sequence of the ALK1-Fc fusion protein is provided in Example 36 as SEQ ID NOs: 171-172.

The polypeptide sequence of the ALK7-Fc fusion protein and a nucleic acid sequence encoding it are provided in Example 7 as SEQ ID NOs: 112-114.

The ALK1-Fc and ALK7-Fc fusion proteins of SEQ ID NO: 172 and SEQ ID NO: 114, respectively, may be co-expressed and purified from a CHO cell line to give rise to a variant heteromeric complex comprising ALK1-Fc:ALK7-Fc.

Hydrophobic Approach

In another approach to promoting the formation of heteromultimer complexes using asymmetric Fc fusion proteins, the Fc domains are altered to introduce complementary hydrophobic interactions and an additional intermolecular disulfide bond. The polypeptide sequence of the ALK1-Fc fusion protein is provided in Example 16 as SEQ ID NOs 413-414.

The complementary form of ALK7-Fc fusion polypeptide (SEQ ID NO: 475) is as follows:

```
                                                        (SEQ ID NO: 475)
  1 MDAMKRGLCC VLLLCGAVFV SPGAGLKCVC LLCDSSNFTC QTEGACWASV

51 MLTNGKEQVI KSCVSLPELN AQVFCHSSNN VTKTECCFTD FCNNITLHLP

101 TASPNAPKLG PMETGGGTHT CPPCPAPELL GGPSVFLFPP KPKDTLMISR

151 TPEVTCVVVD VSHEDPEVKF NWYVDGVEVH NAKTKPREEQ YNSTYRVVSV

201 LTVLHQDWLN GKEYKCKVSN KALPAPIEKT ISKAKGQPRE PQVYTLPPCR

251 EEMTKNQVSL WCLVKGFYPS DIAVEWESNG QPENNYKTTP PVLDSDGSFF

301 LYSKLTVDKS RWQQGNVFSC SVMHEALHNH YTQKSLSLSP GK
```

The leader and linker sequences are underlined. To guide heterodimer formation with the ALK1-Fc fusion polypeptide of SEQ ID NOs: 413-414, two amino acid substitutions (replacing a serine with a cysteine and a threonine with a tryptophan) can be introduced into the Fc domain of the ALK7-Fc fusion polypeptide as indicated by double underline above. The amino acid sequence of SEQ ID NO: 475 may optionally be provided with the lysine removed from the C-terminus.

The mature ALK7-Fc fusion protein sequence (SEQ ID NO: 476) is expected to be as follows and may optionally be provided with the lysine removed from the C-terminus.

```
                                                        (SEQ ID NO: 476)
  1 GLKCVCLLCD SSNFTCQTEG ACWASVMLTN GKEQVIKSCV SLPELNAQVF

51 CHSSNNVTKT ECCFTDFCNN ITLHLPTASP NAPKLGPMET GGGTHTCPPC

101 PAPELLGGPS VFLFPPKPKD TLMISRTPEV TCVVVDVSHE DPEVKFNWYV

151 DGVEVHNAKT KPREEQYNST YRVVSVLTVL HQDWLNGKEY KCKVSNKALP

201 APIEKTISKA KGQPREPQVY TLPPCREEMT KNQVSLWCLV KGFYPSDIAV

251 EWESNGQPEN NYKTTPPVLD SDGSFFLYSK LTVDKSRWQQ GNVFSCSVMH

301 EALHNHYTQK SLSLSPGK
```

The ALK1-Fc and ALK7-Fc proteins of SEQ ID NO: 414 and SEQ ID NO: 476, respectively, may be co-expressed and purified from a CHO cell line, to give rise to a variant heteromeric complex comprising ALK1-Fc:ALK7-Fc.

Reverse Hydrophobic Approach

In another approach to promoting the formation of heteromultimer complexes using asymmetric Fc fusion proteins, the Fc domains are altered to introduce complementary hydrophobic interactions and an additional intermolecular disulfide bond as described immediately above. However, receptor extracellular domains in this approach are linked to the opposite member of the Fc interaction pair compared to the above approach. In this example, the alternative polypeptide sequence of the ALK1-Fc fusion protein is provided in Example 36 as SEQ ID NOs: 463-464.

The polypeptide sequence of the ALK7-Fc fusion protein is provided in Example 7 as SEQ ID NOs: 405-406.

The ALK1-Fc and ALK7-Fc proteins of SEQ ID NO: 464 and SEQ ID NO: 406, respectively, may be co-expressed and purified from a CHO cell line, to give rise to a variant heteromeric complex comprising ALK1-Fc:ALK7-Fc.

Purification of various ALK1-Fc:ALK7-Fc complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

Example 42. Generation of Additional Heterodimers Comprising Two Type I Receptors Formation of additional heterdimeric protein complexes comprising extracellular domains of two type I receptors may be guided by approaches similar to those described in Example 36. Amino acid SEQ ID NOs for these variant heterodimers are disclosed in the following table, which for completeness also includes the heterodimers already discussed that comprise two type I receptors (Examples 36-41). As disclosed in Examples 36-41, the C-terminal lysine of each receptor-Fc fusion protein may optionally be included or omitted.

In each case, a soluble heteromeric complex can be generated comprising the extracellular domains of two different type I receptors, which are each fused to an Fc domain with a linker positioned between the extracellular domain and the Fc domain. In each case, the fusion proteins may be co-expressed and purified from a CHO cell line to give rise to a variant heteromeric protein complex. In each case, purification of various heteromeric protein complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

TABLE

"Type I:Type I Receptor Heterodimers"
Amino Acid SEQ ID NOs for Type I:Type I Receptor Heterodimers

| Heteromeric Fusion Protein Complex | Fc Pair Type | Correspondence to Fc Pair | Receptor-Fc Fusion Protein | Amino Acid SEQ ID NO With Leader | Mature |
|---|---|---|---|---|---|
| ALK1-Fc:ALK2-Fc | Electrostatic | A | ALK1-Fc | 124 | 126 |
| | | | ALK2-Fc | 173 | 174 |
| | | B | ALK1-Fc | 171 | 172 |
| | | | ALK2-Fc | 136 | 138 |
| | Hydrophobic | A | ALK1-Fc | 413 | 414 |
| | | | ALK2-Fc | 465 | 466 |
| | | B | ALK1-Fc | 463 | 464 |
| | | | ALK2-Fc | 421 | 422 |
| ALK1-Fc:ALK3-Fc | Electrostatic | A | ALK1-Fc | 124 | 126 |
| | | | ALK3-Fc | 175 | 176 |
| | | B | ALK1-Fc | 171 | 172 |
| | | | ALK3-Fc | 115 | 117 |
| | Hydrophobic | A | ALK1-Fc | 413 | 414 |
| | | | ALK3-Fc | 467 | 468 |
| | | B | ALK1-Fc | 463 | 464 |
| | | | ALK3-Fc | 407 | 408 |
| ALK1-Fc:ALK4-Fc | Electrostatic | A | ALK1-Fc | 124 | 126 |
| | | | ALK4-Fc | 177 | 178 |
| | | B | ALK1-Fc | 171 | 172 |
| | | | ALK4-Fc | 104 | 106 |
| | Hydrophobic | A | ALK1-Fc | 413 | 414 |
| | | | ALK4-Fc | 469 | 470 |
| | | B | ALK1-Fc | 463 | 464 |
| | | | ALK4-Fc | 403 | 404 |
| ALK1-Fc:ALK5-Fc | Electrostatic | A | ALK1-Fc | 124 | 126 |
| | | | ALK5-Fc | 179 | 180 |
| | | B | ALK1-Fc | 171 | 172 |
| | | | ALK5-Fc | 139 | 141 |
| | Hydrophobic | A | ALK1-Fc | 413 | 414 |
| | | | ALK5-Fc | 471 | 472 |
| | | B | ALK1-Fc | 463 | 464 |
| | | | ALK5-Fc | 423 | 424 |

TABLE-continued

"Type I:Type I Receptor Heterodimers"
Amino Acid SEQ ID NOs for Type I:Type I Receptor Heterodimers

| Heteromeric Fusion Protein Complex | Fc Pair Type | ECD Correspondence to Fc Pair | Receptor-Fc Fusion Protein | Amino Acid SEQ ID NO With Leader | Mature |
|---|---|---|---|---|---|
| ALK1-Fc:ALK6-Fc | Electrostatic | A | ALK1-Fc | 124 | 126 |
| | | | ALK6-Fc | 181 | 182 |
| | | B | ALK1-Fc | 171 | 172 |
| | | | ALK6-Fc | 142 | 144 |
| | Hydrophobic | A | ALK1-Fc | 413 | 414 |
| | | | ALK6-Fc | 473 | 474 |
| | | B | ALK1-Fc | 463 | 464 |
| | | | ALK6-Fc | 425 | 426 |
| ALK1-Fc:ALK7-Fc | Electrostatic | A | ALK1-Fc | 124 | 126 |
| | | | ALK7-Fc | 183 | 184 |
| | | B | ALK1-Fc | 171 | 172 |
| | | | ALK7-Fc | 112 | 114 |
| | Hydrophobic | A | ALK1-Fc | 413 | 414 |
| | | | ALK7-Fc | 475 | 476 |
| | | B | ALK1-Fc | 463 | 464 |
| | | | ALK7-Fc | 405 | 406 |
| ALK2-Fc:ALK3-Fc | Electrostatic | A | ALK2-Fc | 136 | 138 |
| | | | ALK3-Fc | 175 | 176 |
| | | B | ALK2-Fc | 173 | 174 |
| | | | ALK3-Fc | 115 | 117 |
| | Hydrophobic | A | ALK2-Fc | 421 | 422 |
| | | | ALK3-Fc | 467 | 468 |
| | | B | ALK2-Fc | 465 | 466 |
| | | | ALK3-Fc | 407 | 408 |
| ALK2-Fc:ALK4-Fc | Electrostatic | A | ALK2-Fc | 136 | 138 |
| | | | ALK4-Fc | 177 | 178 |
| | | B | ALK2-Fc | 173 | 174 |
| | | | ALK4-Fc | 104 | 106 |
| | Hydrophobic | A | ALK2-Fc | 421 | 422 |
| | | | ALK4-Fc | 469 | 470 |
| | | B | ALK2-Fc | 465 | 466 |
| | | | ALK4-Fc | 403 | 404 |
| ALK2-Fc:ALK5-Fc | Electrostatic | A | ALK2-Fc | 136 | 138 |
| | | | ALK5-Fc | 179 | 180 |
| | | B | ALK2-Fc | 173 | 174 |
| | | | ALK5-Fc | 139 | 141 |
| | Hydrophobic | A | ALK2-Fc | 421 | 422 |
| | | | ALK5-Fc | 471 | 472 |
| | | B | ALK2-Fc | 465 | 466 |
| | | | ALK5-Fc | 423 | 424 |
| ALK2-Fc:ALK6-Fc | Electrostatic | A | ALK2-Fc | 136 | 138 |
| | | | ALK6-Fc | 181 | 182 |
| | | B | ALK2-Fc | 173 | 174 |
| | | | ALK6-Fc | 142 | 144 |
| | Hydrophobic | A | ALK2-Fc | 421 | 422 |
| | | | ALK6-Fc | 473 | 474 |
| | | B | ALK2-Fc | 465 | 466 |
| | | | ALK6-Fc | 425 | 426 |
| ALK2-Fc:ALK7-Fc | Electrostatic | A | ALK2-Fc | 136 | 138 |
| | | | ALK7-Fc | 183 | 184 |
| | | B | ALK2-Fc | 173 | 174 |
| | | | ALK7-Fc | 112 | 114 |
| | Hydrophobic | A | ALK2-Fc | 421 | 422 |
| | | | ALK7-Fc | 475 | 476 |
| | | B | ALK2-Fc | 465 | 466 |
| | | | ALK7-Fc | 405 | 406 |
| ALK3-Fc:ALK4-Fc | Electrostatic | A | ALK3-Fc | 115 | 117 |
| | | | ALK4-Fc | 177 | 178 |
| | | B | ALK3-Fc | 175 | 176 |
| | | | ALK4-Fc | 104 | 106 |
| | Hydrophobic | A | ALK3-Fc | 407 | 408 |
| | | | ALK4-Fc | 469 | 470 |
| | | B | ALK3-Fc | 467 | 468 |
| | | | ALK4-Fc | 403 | 404 |
| ALK3-Fc:ALK5-Fc | Electrostatic | A | ALK3-Fc | 115 | 117 |
| | | | ALK5-Fc | 179 | 180 |
| | | B | ALK3-Fc | 175 | 176 |
| | | | ALK5-Fc | 139 | 141 |

TABLE-continued

"Type I:Type I Receptor Heterodimers"
Amino Acid SEQ ID NOs for Type I:Type I Receptor Heterodimers

| Heteromeric Fusion Protein Complex | Fc Pair Type | ECD Correspondence to Fc Pair | Receptor-Fc Fusion Protein | Amino Acid SEQ ID NO With Leader | Mature |
|---|---|---|---|---|---|
| | Hydrophobic | A | ALK3-Fc | 407 | 408 |
| | | | ALK5-Fc | 471 | 472 |
| | | B | ALK3-Fc | 467 | 468 |
| | | | ALK5-Fc | 423 | 424 |
| ALK3-Fc:ALK6-Fc | Electrostatic | A | ALK3-Fc | 115 | 117 |
| | | | ALK6-Fc | 181 | 182 |
| | | B | ALK3-Fc | 175 | 176 |
| | | | ALK6-Fc | 142 | 144 |
| | Hydrophobic | A | ALK3-Fc | 407 | 408 |
| | | | ALK6-Fc | 473 | 474 |
| | | B | ALK3-Fc | 467 | 468 |
| | | | ALK6-Fc | 425 | 426 |
| ALK3-Fc:ALK7-Fc | Electrostatic | A | ALK3-Fc | 115 | 117 |
| | | | ALK7-Fc | 183 | 184 |
| | | B | ALK3-Fc | 175 | 176 |
| | | | ALK7-Fc | 112 | 114 |
| | Hydrophobic | A | ALK3-Fc | 407 | 408 |
| | | | ALK7-Fc | 475 | 476 |
| | | B | ALK3-Fc | 467 | 468 |
| | | | ALK7-Fc | 405 | 406 |
| ALK4-Fc:ALK5-Fc | Electrostatic | A | ALK4-Fc | 104 | 106 |
| | | | ALK5-Fc | 179 | 180 |
| | | B | ALK4-Fc | 177 | 178 |
| | | | ALK5-Fc | 139 | 141 |
| | Hydrophobic | A | ALK4-Fc | 403 | 404 |
| | | | ALK5-Fc | 471 | 472 |
| | | B | ALK4-Fc | 469 | 470 |
| | | | ALK5-Fc | 423 | 424 |
| ALK4-Fc:ALK6-Fc | Electrostatic | A | ALK4-Fc | 104 | 106 |
| | | | ALK6-Fc | 181 | 182 |
| | | B | ALK4-Fc | 177 | 178 |
| | | | ALK6-Fc | 142 | 144 |
| | Hydrophobic | A | ALK4-Fc | 403 | 404 |
| | | | ALK6-Fc | 473 | 474 |
| | | B | ALK4-Fc | 469 | 470 |
| | | | ALK6-Fc | 425 | 426 |
| ALK4-Fc:ALK7-Fc | Electrostatic | A | ALK4-Fc | 104 | 106 |
| | | | ALK7-Fc | 183 | 184 |
| | | B | ALK4-Fc | 177 | 178 |
| | | | ALK7-Fc | 112 | 114 |
| | Hydrophobic | A | ALK4-Fc | 403 | 404 |
| | | | ALK7-Fc | 475 | 476 |
| | | B | ALK4-Fc | 469 | 470 |
| | | | ALK7-Fc | 405 | 406 |
| ALK5-Fc:ALK6-Fc | Electrostatic | A | ALK5-Fc | 139 | 141 |
| | | | ALK6-Fc | 181 | 182 |
| | | B | ALK5-Fc | 179 | 180 |
| | | | ALK6-Fc | 142 | 144 |
| | Hydrophobic | A | ALK5-Fc | 423 | 424 |
| | | | ALK6-Fc | 473 | 474 |
| | | B | ALK5-Fc | 471 | 472 |
| | | | ALK6-Fc | 425 | 426 |
| ALK5-Fc:ALK7-Fc | Electrostatic | A | ALK5-Fc | 139 | 141 |
| | | | ALK7-Fc | 183 | 184 |
| | | B | ALK5-Fc | 179 | 180 |
| | | | ALK7-Fc | 112 | 114 |
| | Hydrophobic | A | ALK5-Fc | 423 | 424 |
| | | | ALK7-Fc | 475 | 476 |
| | | B | ALK5-Fc | 471 | 472 |
| | | | ALK7-Fc | 405 | 406 |
| ALK6-Fc:ALK7-Fc | Electrostatic | A | ALK6-Fc | 142 | 144 |
| | | | ALK7-Fc | 183 | 184 |
| | | B | ALK6-Fc | 181 | 182 |
| | | | ALK7-Fc | 112 | 114 |
| | Hydrophobic | A | ALK6-Fc | 425 | 426 |
| | | | ALK7-Fc | 475 | 476 |
| | | B | ALK6-Fc | 473 | 474 |
| | | | ALK7-Fc | 405 | 406 |

Example 43. Generation of Additional Heterodimers Comprising a Type I Receptor and a Type II Receptor Formation of additional heterdimeric protein complexes comprising extracellular domains of a type I receptor and a type II receptor may be guided by approaches similar to those described in Example 1. Amino acid SEQ ID NOs for these variant heterodimers are disclosed in the following table, which for completeness also includes the heterodimers already discussed that comprise a type I receptor and a type II receptor (Examples 1-29). As disclosed in Examples 1-29, the C-terminal lysine of each receptor-Fc fusion protein may optionally be included or omitted.

In each case, a soluble heteromeric complex can be generated comprising the extracellular domains of a type I receptor and a type II receptor, which are each fused to an Fc domain with a linker positioned between the extracellular domain and the Fc domain. In each case, the fusion proteins may be co-expressed and purified from a CHO cell line to give rise to a variant heteromeric protein complex. In each case, purification of various heteromeric protein complexes could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

TABLE

"Type I:Type II Receptor Heterodimers"
Amino Acid SEQ ID NOs for Type I:Type II Receptor Heterodimers

| Heteromeric Fusion Protein Complex | Fc Pair Type | ECD Correspondence to Fc Pair | Receptor-Fc Fusion Protein | Amino Acid SEQ ID NO With Leader | Mature |
|---|---|---|---|---|---|
| ActRIIA-Fc:ALK1-Fc | Electrostatic | A | ActRIIA-Fc | 118 | 120 |
| | | | ALK1-Fc | 124 | 126 |
| | | B | ActRIIA-Fc | 151 | 152 |
| | | | ALK1-Fc | 171 | 172 |
| | Hydrophobic | A | ActRIIA-Fc | 409 | 410 |
| | | | ALK1-Fc | 413 | 414 |
| | | B | ActRIIA-Fc | 451 | 452 |
| | | | ALK1-Fc | 463 | 464 |
| ActRIIA-Fc:ALK2-Fc | Electrostatic | A | ActRIIA-Fc | 118 | 120 |
| | | | ALK2-Fc | 136 | 138 |
| | | B | ActRIIA-Fc | 151 | 152 |
| | | | ALK2-Fc | 173 | 174 |
| | Hydrophobic | A | ActRIIA-Fc | 409 | 410 |
| | | | ALK2-Fc | 421 | 422 |
| | | B | ActRIIA-Fc | 451 | 452 |
| | | | ALK2-Fc | 465 | 466 |
| ActRIIA-Fc:ALK3-Fc | Electrostatic | A | ActRIIA-Fc | 118 | 120 |
| | | | ALK3-Fc | 115 | 117 |
| | | B | ActRIIA-Fc | 151 | 152 |
| | | | ALK3-Fc | 175 | 176 |
| | Hydrophobic | A | ActRIIA-Fc | 409 | 410 |
| | | | ALK3-Fc | 407 | 408 |
| | | B | ActRIIA-Fc | 451 | 452 |
| | | | ALK3-Fc | 467 | 468 |
| ActRIIA-Fc:ALK4-Fc | Electrostatic | A | ActRIIA-Fc | 118 | 120 |
| | | | ALK4-Fc | 104 | 106 |
| | | B | ActRIIA-Fc | 151 | 152 |
| | | | ALK4-Fc | 177 | 178 |
| | Hydrophobic | A | ActRIIA-Fc | 409 | 410 |
| | | | ALK4-Fc | 403 | 404 |
| | | B | ActRIIA-Fc | 451 | 452 |
| | | | ALK4-Fc | 469 | 470 |
| ActRIIA-Fc:ALK5-Fc | Electrostatic | A | ActRIIA-Fc | 118 | 120 |
| | | | ALK5-Fc | 139 | 141 |
| | | B | ActRIIA-Fc | 151 | 152 |
| | | | ALK5-Fc | 179 | 180 |
| | Hydrophobic | A | ActRIIA-Fc | 409 | 410 |
| | | | ALK5-Fc | 423 | 424 |
| | | B | ActRIIA-Fc | 451 | 452 |
| | | | ALK5-Fc | 471 | 472 |
| ActRIIA-Fc:ALK6-Fc | Electrostatic | A | ActRIIA-Fc | 118 | 120 |
| | | | ALK6-Fc | 142 | 144 |
| | | B | ActRIIA-Fc | 151 | 152 |
| | | | ALK6-Fc | 181 | 182 |
| | Hydrophobic | A | ActRIIA-Fc | 409 | 410 |
| | | | ALK6-Fc | 425 | 426 |
| | | B | ActRIIA-Fc | 451 | 452 |
| | | | ALK6-Fc | 473 | 474 |
| ActRIIA-Fc:ALK7-Fc | Electrostatic | A | ActRIIA-Fc | 112 | 120 |
| | | | ALK7-Fc | 112 | 114 |
| | | B | ActRIIA-Fc | 151 | 152 |
| | | | ALK7-Fc | 183 | 184 |

TABLE-continued

"Type I:Type II Receptor Heterodimers"
Amino Acid SEQ ID NOs for Type I:Type II Receptor Heterodimers

| Heteromeric Fusion Protein Complex | ECD Fc Pair Type | Correspondence to Fc Pair | Receptor-Fc Fusion Protein | Amino Acid SEQ ID NO With Leader | Mature |
|---|---|---|---|---|---|
| | Hydrophobic | A | ActRIIA-Fc | 409 | 410 |
| | | | ALK7-Fc | 405 | 406 |
| | | B | ActRIIA-Fc | 451 | 452 |
| | | | ALK7-Fc | 475 | 476 |
| ActRIIB-Fc:ALK1-Fc | Electrostatic | A | ActRIIB-Fc | 100 | 102 |
| | | | ALK1-Fc | 124 | 126 |
| | | B | ActRIIB-Fc | 153 | 154 |
| | | | ALK1-Fc | 171 | 172 |
| | Hydrophobic | A | ActRIIB-Fc | 401 | 402 |
| | | | ALK1-Fc | 413 | 414 |
| | | B | ActRIIB-Fc | 453 | 454 |
| | | | ALK1-Fc | 463 | 464 |
| ActRIIB-Fc:ALK2-Fc | Electrostatic | A | ActRIIB-Fc | 100 | 102 |
| | | | ALK2-Fc | 136 | 138 |
| | | B | ActRIIB-Fc | 153 | 154 |
| | | | ALK2-Fc | 173 | 174 |
| | Hydrophobic | A | ActRIIB-Fc | 401 | 402 |
| | | | ALK2-Fc | 421 | 422 |
| | | B | ActRIIB-Fc | 453 | 454 |
| | | | ALK2-Fc | 465 | 466 |
| ActRIIB-Fc:ALK3-Fc | Electrostatic | A | ActRIIB-Fc | 100 | 102 |
| | | | ALK3-Fc | 115 | 117 |
| | | B | ActRIIB-Fc | 153 | 154 |
| | | | ALK3-Fc | 175 | 176 |
| | Hydrophobic | A | ActRIIB-Fc | 401 | 402 |
| | | | ALK3-Fc | 407 | 408 |
| | | B | ActRIIB-Fc | 453 | 454 |
| | | | ALK3-Fc | 467 | 468 |
| ActRIIB-Fc:ALK4-Fc | Electrostatic | A | ActRIIB-Fc | 100 | 102 |
| | | | ALK4-Fc | 104 | 106 |
| | | B | ActRIIB-Fc | 153 | 154 |
| | | | ALK4-Fc | 177 | 178 |
| | Hydrophobic | A | ActRIIB-Fc | 401 | 402 |
| | | | ALK4-Fc | 403 | 404 |
| | | B | ActRIIB-Fc | 453 | 454 |
| | | | ALK4-Fc | 469 | 470 |
| ActRIIB-Fc:ALK5-Fc | Electrostatic | A | ActRIIB-Fc | 100 | 102 |
| | | | ALK5-Fc | 139 | 141 |
| | | B | ActRIIB-Fc | 153 | 154 |
| | | | ALK5-Fc | 179 | 180 |
| | Hydrophobic | A | ActRIIB-Fc | 401 | 402 |
| | | | ALK5-Fc | 423 | 424 |
| | | B | ActRIIB-Fc | 453 | 454 |
| | | | ALK5-Fc | 471 | 472 |
| ActRIIB-Fc:ALK6-Fc | Electrostatic | A | ActRIIB-Fc | 100 | 102 |
| | | | ALK6-Fc | 142 | 144 |
| | | B | ActRIIB-Fc | 153 | 154 |
| | | | ALK6-Fc | 181 | 182 |
| | Hydrophobic | A | ActRIIB-Fc | 401 | 402 |
| | | | ALK6-Fc | 425 | 426 |
| | | B | ActRIIB-Fc | 453 | 454 |
| | | | ALK6-Fc | 473 | 474 |
| ActRIIB-Fc:ALK7-Fc | Electrostatic | A | ActRIIB-Fc | 100 | 102 |
| | | | ALK7-Fc | 112 | 114 |
| | | B | ActRIIB-Fc | 153 | 154 |
| | | | ALK7-Fc | 183 | 184 |
| | Hydrophobic | A | ActRIIB-Fc | 401 | 402 |
| | | | ALK7-Fc | 405 | 406 |
| | | B | ActRIIB-Fc | 453 | 454 |
| | | | ALK7-Fc | 475 | 476 |
| BMPRII-Fc:ALK1-Fc | Electrostatic | A | BMPRII-Fc | 121 | 123 |
| | | | ALK1-Fc | 124 | 126 |
| | | B | BMPRII-Fc | 155 | 156 |
| | | | ALK1-Fc | 171 | 172 |
| | Hydrophobic | A | BMPRII-Fc | 411 | 412 |
| | | | ALK1-Fc | 413 | 414 |
| | | B | BMPRII-Fc | 455 | 456 |
| | | | ALK1-Fc | 463 | 464 |

TABLE-continued

"Type I:Type II Receptor Heterodimers"
Amino Acid SEQ ID NOs for Type I:Type II Receptor Heterodimers

| Heteromeric Fusion Protein Complex | Fc Pair Type | ECD Correspondence to Fc Pair | Receptor-Fc Fusion Protein | Amino Acid SEQ ID NO With Leader | Mature |
|---|---|---|---|---|---|
| BMPRII-Fc:ALK2-Fc | Electrostatic | A | BMPRII-Fc | 121 | 123 |
| | | | ALK2-Fc | 136 | 138 |
| | | B | BMPRII-Fc | 155 | 156 |
| | | | ALK2-Fc | 173 | 174 |
| | Hydrophobic | A | BMPRII-Fc | 411 | 412 |
| | | | ALK2-Fc | 421 | 422 |
| | | B | BMPRII-Fc | 455 | 456 |
| | | | ALK2-Fc | 465 | 466 |
| BMPRII-Fc:ALK3-Fc | Electrostatic | A | BMPRII-Fc | 121 | 123 |
| | | | ALK3-Fc | 115 | 117 |
| | | B | BMPRII-Fc | 155 | 156 |
| | | | ALK3-Fc | 175 | 176 |
| | Hydrophobic | A | BMPRII-Fc | 411 | 412 |
| | | | ALK3-Fc | 407 | 408 |
| | | B | BMPRII-Fc | 455 | 456 |
| | | | ALK3-Fc | 467 | 468 |
| BMPRII-Fc:ALK4-Fc | Electrostatic | A | BMPRII-Fc | 121 | 123 |
| | | | ALK4-Fc | 104 | 106 |
| | | B | BMPRII-Fc | 155 | 156 |
| | | | ALK4-Fc | 177 | 178 |
| | Hydrophobic | A | BMPRII-Fc | 411 | 412 |
| | | | ALK4-Fc | 403 | 404 |
| | | B | BMPRII-Fc | 455 | 456 |
| | | | ALK4-Fc | 469 | 470 |
| BMPRII-Fc:ALK5-Fc | Electrostatic | A | BMPRII-Fc | 121 | 123 |
| | | | ALK5-Fc | 139 | 141 |
| | | B | BMPRII-Fc | 155 | 156 |
| | | | ALK5-Fc | 179 | 180 |
| | Hydrophobic | A | BMPRII-Fc | 411 | 412 |
| | | | ALK5-Fc | 423 | 424 |
| | | B | BMPRII-Fc | 455 | 456 |
| | | | ALK5-Fc | 471 | 472 |
| BMPRII-Fc:ALK6-Fc | Electrostatic | A | BMPRII-Fc | 121 | 123 |
| | | | ALK6-Fc | 142 | 144 |
| | | B | BMPRII-Fc | 155 | 156 |
| | | | ALK6-Fc | 181 | 182 |
| | Hydrophobic | A | BMPRII-Fc | 411 | 412 |
| | | | ALK6-Fc | 425 | 426 |
| | | B | BMPRII-Fc | 455 | 456 |
| | | | ALK6-Fc | 473 | 474 |
| BMPRII-Fc:ALK7-Fc | Electrostatic | A | BMPRII-Fc | 121 | 123 |
| | | | ALK7-Fc | 112 | 114 |
| | | B | BMPRII-Fc | 155 | 156 |
| | | | ALK7-Fc | 183 | 184 |
| | Hydrophobic | A | BMPRII-Fc | 411 | 412 |
| | | | ALK7-Fc | 405 | 406 |
| | | B | BMPRII-Fc | 455 | 456 |
| | | | ALK7-Fc | 475 | 476 |
| MISRII-Fc:ALK1-Fc | Electrostatic | A | MISRII-Fc | 133 | 135 |
| | | | ALK1-Fc | 124 | 126 |
| | | B | MISRII-Fc | 161 | 162 |
| | | | ALK1-Fc | 171 | 172 |
| | Hydrophobic | A | MISRII-Fc | 419 | 420 |
| | | | ALK1-Fc | 413 | 414 |
| | | B | MISRII-Fc | 457 | 458 |
| | | | ALK1-Fc | 463 | 464 |
| MISRII-Fc:ALK2-Fc | Electrostatic | A | MISRII-Fc | 133 | 135 |
| | | | ALK2-Fc | 136 | 138 |
| | | B | MISRII-Fc | 161 | 162 |
| | | | ALK2-Fc | 173 | 174 |
| | Hydrophobic | A | MISRII-Fc | 419 | 420 |
| | | | ALK2-Fc | 421 | 422 |
| | | B | MISRII-Fc | 457 | 458 |
| | | | ALK2-Fc | 465 | 466 |
| MISRII-Fc:ALK3-Fc | Electrostatic | A | MISRII-Fc | 133 | 135 |
| | | | ALK3-Fc | 115 | 117 |
| | | B | MISRII-Fc | 161 | 162 |
| | | | ALK3-Fc | 175 | 176 |
| | Hydrophobic | A | MISRII-Fc | 419 | 420 |
| | | | ALK3-Fc | 407 | 408 |

TABLE-continued

"Type I:Type II Receptor Heterodimers"
Amino Acid SEQ ID NOs for Type I:Type II Receptor Heterodimers

| Heteromeric Fusion Protein Complex | Fc Pair Type | ECD Correspondence to Fc Pair | Receptor-Fc Fusion Protein | Amino Acid SEQ ID NO With Leader | Mature |
|---|---|---|---|---|---|
| | | B | MISRII-Fc | 457 | 458 |
| | | | ALK3-Fc | 467 | 468 |
| MISRII-Fc:ALK4-Fc | Electrostatic | A | MISRII-Fc | 133 | 135 |
| | | | ALK4-Fc | 104 | 106 |
| | | B | MISRII-Fc | 161 | 162 |
| | | | ALK4-Fc | 177 | 178 |
| | Hydrophobic | A | MISRII-Fc | 419 | 420 |
| | | | ALK4-Fc | 403 | 404 |
| | | B | MISRII-Fc | 457 | 458 |
| | | | ALK4-Fc | 469 | 470 |
| MISRII-Fc:ALK5-Fc | Electrostatic | A | MISRII-Fc | 133 | 135 |
| | | | ALK5-Fc | 139 | 141 |
| | | B | MISRII-Fc | 161 | 162 |
| | | | ALK5-Fc | 179 | 180 |
| | Hydrophobic | A | MISRII-Fc | 419 | 420 |
| | | | ALK5-Fc | 423 | 424 |
| | | B | MISRII-Fc | 457 | 458 |
| | | | ALK5-Fc | 471 | 472 |
| MISRII-Fc:ALK6-Fc | Electrostatic | A | MISRII-Fc | 133 | 135 |
| | | | ALK6-Fc | 142 | 144 |
| | | B | MISRII-Fc | 161 | 162 |
| | | | ALK6-Fc | 181 | 182 |
| | Hydrophobic | A | MISRII-Fc | 419 | 420 |
| | | | ALK6-Fc | 425 | 426 |
| | | B | MISRII-Fc | 457 | 458 |
| | | | ALK6-Fc | 473 | 474 |
| MISRII-Fc:ALK7-Fc | Electrostatic | A | MISRII-Fc | 133 | 135 |
| | | | ALK7-Fc | 112 | 114 |
| | | B | MISRII-Fc | 161 | 162 |
| | | | ALK7-Fc | 183 | 184 |
| | Hydrophobic | A | MISRII-Fc | 419 | 420 |
| | | | ALK7-Fc | 405 | 406 |
| | | B | MISRII-Fc | 457 | 458 |
| | | | ALK7-Fc | 475 | 476 |
| TGFβRIISHORT-Fc:ALK1-Fc | Electrostatic | A | TGFβRIISHORT-Fc | 127 | 129 |
| | | | ALK1-Fc | 124 | 126 |
| | | B | TGFβRIISHORT-Fc | 157 | 158 |
| | | | ALK1-Fc | 171 | 172 |
| | Hydrophobic | A | TGFβRIISHORT-Fc | 415 | 416 |
| | | | ALK1-Fc | 413 | 414 |
| | | B | TGFβRIISHORT-Fc | 459 | 460 |
| | | | ALK1-Fc | 463 | 464 |
| TGFβRII$_{SHORT}$-Fc:ALK2-Fc | Electrostatic | A | TGFβRII$_{SHORT}$-Fc | 127 | 129 |
| | | | ALK2-Fc | 136 | 138 |
| | | B | TGFβRII$_{SHORT}$-Fc | 157 | 158 |
| | | | ALK2-Fc | 173 | 174 |
| | Hydrophobic | A | TGFβRII$_{SHORT}$-Fc | 415 | 416 |
| | | | ALK2-Fc | 421 | 422 |
| | | B | TGFβRII$_{SHORT}$-Fc | 459 | 460 |
| | | | ALK2-Fc | 465 | 466 |
| TGFβRIISHORT-Fc:ALK3-Fc | Electrostatic | A | TGFβRIISHORT-Fc | 127 | 129 |
| | | | ALK3-Fc | 115 | 117 |
| | | B | TGFβRIISHORT-Fc | 157 | 158 |
| | | | ALK3-Fc | 175 | 176 |
| | Hydrophobic | A | TGFβRIISHORT-Fc | 415 | 416 |
| | | | ALK3-Fc | 407 | 408 |
| | | B | TGFβRIISHORT-Fc | 459 | 460 |
| | | | ALK3-Fc | 467 | 468 |
| TGFβRII$_{SHORT}$-Fc:ALK4-Fc | Electrostatic | A | TGFβRII$_{SHORT}$-Fc | 127 | 129 |
| | | | ALK4-Fc | 104 | 106 |
| | | B | TGFβRII$_{SHORT}$-Fc | 157 | 158 |
| | | | ALK4-Fc | 177 | 178 |
| | Hydrophobic | A | TGFβRII$_{SHORT}$-Fc | 415 | 416 |
| | | | ALK4-Fc | 403 | 404 |
| | | B | TGFβRII$_{SHORT}$-Fc | 459 | 460 |
| | | | ALK4-Fc | 469 | 470 |

TABLE-continued

"Type I:Type II Receptor Heterodimers"
Amino Acid SEQ ID NOs for Type I:Type II Receptor Heterodimers

| Heteromeric Fusion Protein Complex | Fc Pair Type | ECD Correspondence to Fc Pair | Receptor-Fc Fusion Protein | Amino Acid SEQ ID NO With Leader | Mature |
|---|---|---|---|---|---|
| TGFβRIISHORT-Fc:ALK5-Fc | Electrostatic | A | TGFβRIISHORT-Fc | 127 | 129 |
| | | | ALK5-Fc | 139 | 141 |
| | | B | TGFβRIISHORT-Fc | 157 | 158 |
| | | | ALK5-Fc | 179 | 180 |
| | Hydrophobic | A | TGFβRIISHORT-Fc | 415 | 416 |
| | | | ALK5-Fc | 423 | 424 |
| | | B | TGFβRIISHORT-Fc | 459 | 460 |
| | | | ALK5-Fc | 471 | 472 |
| TGFβRII$_{SHORT}$-Fc:ALK6-Fc | Electrostatic | A | TGFβRII$_{SHORT}$-Fc | 127 | 129 |
| | | | ALK6-Fc | 142 | 144 |
| | | B | TGFβRII$_{SHORT}$-Fc | 157 | 158 |
| | | | ALK6-Fc | 181 | 182 |
| | Hydrophobic | A | TGFβRII$_{SHORT}$-Fc | 415 | 416 |
| | | | ALK6-Fc | 425 | 426 |
| | | B | TGFβRII$_{SHORT}$-Fc | 459 | 460 |
| | | | ALK6-Fc | 473 | 474 |
| TGFβRIISHORT-Fc:ALK7-Fc | Electrostatic | A | TGFβRIISHORT-Fc | 127 | 129 |
| | | | ALK7-Fc | 112 | 114 |
| | | B | TGFβRIISHORT-Fc | 157 | 158 |
| | | | ALK7-Fc | 183 | 184 |
| | Hydrophobic | A | TGFβRIISHORT-Fc | 415 | 416 |
| | | | ALK7-Fc | 405 | 406 |
| | | B | TGFβRIISHORT-Fc | 459 | 460 |
| | | | ALK7-Fc | 475 | 476 |
| TGFβRII$_{LONG}$-Fc:ALK1-Fc | Electrostatic | A | TGFβRII$_{LONG}$-Fc | 130 | 132 |
| | | | ALK1-Fc | 124 | 126 |
| | | B | TGFβRII$_{LONG}$-Fc | 159 | 160 |
| | | | ALK1-Fc | 171 | 172 |
| | Hydrophobic | A | TGFβRII$_{LONG}$-Fc | 417 | 418 |
| | | | ALK1-Fc | 413 | 414 |
| | | B | TGFβRII$_{LONG}$-Fc | 461 | 462 |
| | | | ALK1-Fc | 463 | 464 |
| TGFβRIILONG-Fc:ALK2-Fc | Electrostatic | A | TGFβRIILONG-Fc | 130 | 132 |
| | | | ALK2-Fc | 136 | 138 |
| | | B | TGFβRIILONG-Fc | 159 | 160 |
| | | | ALK2-Fc | 173 | 174 |
| | Hydrophobic | A | TGFβRIILONG-Fc | 417 | 418 |
| | | | ALK2-Fc | 421 | 422 |
| | | B | TGFβRIILONG-Fc | 461 | 462 |
| | | | ALK2-Fc | 465 | 466 |
| TGFβRII$_{LONG}$-Fc:ALK3-Fc | Electrostatic | A | TGFβRII$_{LONG}$-Fc | 130 | 132 |
| | | | ALK3-Fc | 115 | 117 |
| | | B | TGFβRII$_{LONG}$-Fc | 159 | 160 |
| | | | ALK3-Fc | 175 | 176 |
| | Hydrophobic | A | TGFβRII$_{LONG}$-Fc | 417 | 418 |
| | | | ALK3-Fc | 407 | 408 |
| | | B | TGFβRII$_{LONG}$-Fc | 461 | 462 |
| | | | ALK3-Fc | 467 | 468 |
| TGFβRIILONG-Fc:ALK4-Fc | Electrostatic | A | TGFβRIILONG-Fc | 130 | 132 |
| | | | ALK4-Fc | 104 | 106 |
| | | B | TGFβRIILONG-Fc | 159 | 160 |
| | | | ALK4-Fc | 177 | 178 |
| | Hydrophobic | A | TGFβRIILONG-Fc | 417 | 418 |
| | | | ALK4-Fc | 403 | 404 |
| | | B | TGFβRIILONG-Fc | 461 | 462 |
| | | | ALK4-Fc | 469 | 470 |
| TGFβRII$_{LONG}$-Fc:ALK5-Fc | Electrostatic | A | TGFβRII$_{LONG}$-Fc | 130 | 132 |
| | | | ALK5-Fc | 139 | 141 |
| | | B | TGFβRII$_{LONG}$-Fc | 159 | 160 |
| | | | ALK5-Fc | 179 | 180 |
| | Hydrophobic | A | TGFβRII$_{LONG}$-Fc | 417 | 418 |
| | | | ALK5-Fc | 423 | 424 |
| | | B | TGFβRII$_{LONG}$-Fc | 461 | 462 |
| | | | ALK5-Fc | 471 | 472 |
| TGFβRIILONG-Fc:ALK6-Fc | Electrostatic | A | TGFβRIILONG-Fc | 130 | 132 |
| | | | ALK6-Fc | 142 | 144 |
| | | B | TGFβRIILONG-Fc | 159 | 160 |
| | | | ALK6-Fc | 181 | 182 |

TABLE-continued

"Type I:Type II Receptor Heterodimers"
Amino Acid SEQ ID NOs for Type I:Type II Receptor Heterodimers

| Heteromeric Fusion Protein Complex | Fc Pair Type | ECD Correspondence to Fc Pair | Receptor-Fc Fusion Protein | Amino Acid SEQ ID NO With Leader | Mature |
|---|---|---|---|---|---|
| | Hydrophobic | A | TGFβRIILONG-Fc | 417 | 418 |
| | | | ALK6-Fc | 425 | 426 |
| | | B | TGFβRIILONG-Fc | 461 | 462 |
| | | | ALK6-Fc | 473 | 474 |
| TGFβRII$_{LONG}$-Fc:ALK7-Fc | Electrostatic | A | TGFβRII$_{LONG}$-Fc | 130 | 132 |
| | | | ALK7-Fc | 112 | 114 |
| | | B | TGFβRII$_{LONG}$-Fc | 159 | 160 |
| | | | ALK7-Fc | 183 | 184 |
| | Hydrophobic | A | TGFβRII$_{LONG}$-Fc | 417 | 418 |
| | | | ALK7-Fc | 405 | 406 |
| | | B | TGFβRII$_{LONG}$-Fc | 461 | 462 |
| | | | ALK7-Fc | 475 | 476 |

In their entirety, these examples demonstrate that type I and type II receptor polypeptides, when placed in the context of a heteromeric complex, form novel binding pockets that exhibit altered selectivity relative to either type of homomeric complex, allowing the formation of novel protein agents for possible use as therapeutic agents.

```

We claim:

1. A soluble recombinant heteromultimer comprising an ALK3 polypeptide and an ActRIIB polypeptide, wherein the ALK3 polypeptide is a fusion protein comprising an ALK3 domain and a heterologous domain, wherein the ALK3 domain comprises an amino acid sequence that is at least 90% identical to amino acids 61-130 of SEQ ID NO: 22, and wherein the ActRIIB polypeptide is a fusion protein comprising an ActRIIB domain and a heterologous domain, wherein the ActRIIB domain comprises an amino acid sequence that is at least 90% identical to amino acids 29-109 of SEQ ID NO: 1, wherein the amino acid position in the ActRIIB polypeptide corresponding to L79 of SEQ ID NO: 1 is not an aspartic acid (D); and wherein the heteromultimer binds to BMP2 and/or BMP4.

2. The heteromultimer of claim 1, wherein the heteromultimer is an ALK3:ActRIIB heterodimer.

3. The heteromultimer of claim 1, wherein the heterologous domain of the ALK3 polypeptide comprises a constant region from an IgG heavy chain, and wherein the heterologous domain of the ActRIIB polypeptide comprises a constant region from an IgG heavy chain.

4. The heteromultimer of claim 3, wherein one or both of the constant regions from the IgG heavy chain is an immunoglobulin Fc domain of IgG1 immunoglobulin.

5. The heteromultimer of claim 4, wherein the immunoglobulin Fc domain comprises one or more amino acid mutations that promote heterodimer formation.

6. The heteromultimer of claim 4, wherein the immunoglobulin Fc domain comprises one or more amino acid mutations that inhibit homodimer formation.

7. The heteromultimer of claim 1, wherein the ALK3 polypeptide and/or ActRIIB polypeptide comprises one or more modified amino acid residues selected from the group consisting of: a glycosylated amino acid, a PEGylated amino acid, a farnesylated amino acid, an acetylated amino acid, a biotinylated amino acid, and an amino acid conjugated to a lipid moiety.

8. The heteromultimer of claim 7, wherein the ALK3 polypeptide and/or ActRIIB polypeptide is glycosylated and has a glycosylation pattern obtainable from expression of the type I receptor polypeptide in a CHO cell.

9. A pharmaceutical preparation comprising the heteromultimer of claim 1 and a pharmaceutically acceptable carrier.

10. The heteromultimer of claim 1, wherein the ALK3 polypeptide comprises an amino acid sequence that is at least 90% identical to amino acids 24-152 of SEQ ID NO: 22.

11. The heteromultimer of claim 1, wherein the ALK3 polypeptide comprises an amino acid sequence that is at least 90% identical to a polypeptide that:
   a) begins at any one of amino acids 24-61 of SEQ ID NO: 22, and
   b) ends at any one of amino acids 130-152 of SEQ ID NO: 22.

12. The heteromultimer of claim 1, wherein the ALK3 polypeptide comprises an amino acid sequence that is at least 90% identical to any one of SEQ ID Nos: 22, 23, 115, 117, 175, 176, 407, 408, 467, and 468.

13. The heteromultimer of claim 1, wherein the ActRIIB polypeptide comprises an amino acid sequence that is at least 90% identical to a polypeptide that:
   a) begins at any one of amino acids 20-29 of SEQ ID NO: 1, and
   b) ends at any one of amino acids 109-134 of SEQ ID NO: 1.

14. The heteromultimer of claim 1, wherein the ActRIIB polypeptide comprises an amino acid sequence that is at least 90% identical to any one of SEQ ID Nos: 1, 2, 3, 4, 5, 6, 100, 102, 153, 154, 401, 402, 453, and 454.

15. The heteromultimer of claim 1, wherein the ALK3 polypeptide comprises an amino acid sequence that is at least 95% identical to amino acids 61-130 of SEQ ID NO: 22, and wherein the ActRIIB polypeptide comprises an amino acid sequence that is at least 95% identical to amino acids 29-109 of SEQ ID NO: 1.

16. The heteromultimer of claim 1, wherein the ALK3 polypeptide comprises the amino acid sequence corresponding to amino acids 61-130 of SEQ ID NO: 22, and wherein the ActRIIB polypeptide comprises the amino acid sequence corresponding to amino acids 29-109 of SEQ ID NO: 1.

17. The heteromultimer of claim 1, wherein the ALK3 polypeptide comprises an amino acid sequence that is at least 90% identical to the amino acid sequence of SEQ ID NO: 23, and wherein the ActRIIB polypeptide comprises an amino acid sequence that is at least 90% identical to the amino acid sequence of SEQ ID NO: 2.

18. The heteromultimer of claim 1, wherein the ALK3 polypeptide comprises an amino acid sequence that is at least 95% identical to the amino acid sequence of SEQ ID NO: 23, and wherein the ActRIIB polypeptide comprises an amino acid sequence that is at least 95% identical to the amino acid sequence of SEQ ID NO: 2.

19. The heteromultimer of claim 1, wherein the ALK3 polypeptide comprises the amino acid sequence of SEQ ID NO: 23, and wherein the ActRIIB polypeptide comprises the amino acid sequence of SEQ ID NO: 2.

20. The heteromultimer of claim 15, wherein the heterologous domain of the ALK3 polypeptide and the heterologous domain of the ActRIIB polypeptide each comprises an Fc immunoglobulin domain, wherein the Fc immunoglobulin domain is an IgG1 immunoglobulin domain.

21. The heteromultimer of claim 16, wherein the heterologous domain of the ALK3 polypeptide and the heterologous domain of the ActRIIB polypeptide each comprises an Fc immunoglobulin domain, wherein the Fc immunoglobulin domain is an IgG1 immunoglobulin domain.

22. The heteromultimer of claim 18, wherein the heterologous domain of the ALK3 polypeptide and the heterologous domain of the ActRIIB polypeptide each comprises an Fc immunoglobulin domain, wherein the Fc immunoglobulin domain is an IgG1 immunoglobulin domain.

23. The heteromultimer of claim 19, wherein the heterologous domain of the ALK3 polypeptide and the heterologous domain of the ActRIIB polypeptide each comprises an Fc immunoglobulin domain, wherein the Fc immunoglobulin domain is an IgG1 immunoglobulin domain.

24. The heteromultimer of claim 15, wherein a linker domain is positioned between the ALK3 domain and the heterologous domain and/or a linker domain is positioned between the ActRIIB domain and the heterologous domain.

25. The heteromultimer of claim 16, wherein a linker domain is positioned between the ALK3 domain and the heterologous domain and/or a linker domain is positioned between the ActRIIB domain and the heterologous domain.

26. The heteromultimer of claim 18, wherein a linker domain is positioned between the ALK3 domain and the heterologous domain and/or a linker domain is positioned between the ActRIIB domain and the heterologous domain.

27. The heteromultimer of claim 19, wherein a linker domain is positioned between the ALK3 domain and the heterologous domain and/or a linker domain is positioned between the ActRIIB domain and the heterologous domain.

* * * * *

                       SEQUENCE LISTING

<160> NUMBER OF SEQ ID NOS: 509

<210

```
Leu Met Asn Asp Phe Val Ala Val Lys Ile Phe Pro Leu Gln Asp Lys
        210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 2
<211> LENGTH: 115
<212> TYPE: PRT
<213> ORGANISM: Homo sapiens

<400> SEQUENCE: 2

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
```

```
                65                  70                  75                  80
Tyr Phe Cys Cys Cys Glu Gly Asn Phe Cys Asn Glu Arg Phe Thr His
                    85                  90                  95

Leu Pro Glu Ala Gly Gly Pro Glu Val Thr Tyr Glu Pro Pro Pro Thr
                100                 105                 110

Ala Pro Thr
        115

<210> SEQ ID NO 3
<211> LENGTH: 100
<212> TYPE: PRT
<213> ORGANISM: Homo sapiens

<400> SEQUENCE: 3

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Leu Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100

<210> SEQ ID NO 4
<211> LENGTH: 512
<212> TYPE: PRT
<213> ORGANISM: Homo sapiens

<400> SEQUENCE: 4

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
                35                  40                  45

Cys Glu Gly Glu Gln Asp Lys Arg Leu His Cys Tyr Ala Ser Trp Ala
        50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
                100                 105                 110

Phe Thr His Leu Pro Glu Ala Gly Gly Pro Glu Val Thr Tyr Glu Pro
            115                 120                 125

Pro Pro Thr Ala Pro Thr Leu Leu Thr Val Leu Ala Tyr Ser Leu Leu
        130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
```

```
                165                 170                 175
Gly Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
            195                 200                 205

Leu Met Asn Asp Phe Val Ala Val Lys Ile Phe Pro Leu Gln Asp Lys
        210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
            260                 265                 270

Leu Thr Asp Tyr Leu Lys Gly Asn Ile Ile Thr Trp Asn Glu Leu Cys
        275                 280                 285

His Val Ala Glu Thr Met Ser Arg Gly Leu Ser Tyr Leu His Glu Asp
    290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
            340                 345                 350

Gly Asp Thr His Gly Gln Val Gly Thr Arg Arg Tyr Met Ala Pro Glu
        355                 360                 365

Val Leu Glu Gly Ala Ile Asn Phe Gln Arg Asp Ala Phe Leu Arg Ile
    370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
            420                 425                 430

His Lys Lys Met Arg Pro Thr Ile Lys Asp His Trp Leu Lys His Pro
        435                 440                 445

Gly Leu Ala Gln Leu Cys Val Thr Ile Glu Glu Cys Trp Asp His Asp
    450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
            500                 505                 510

<210> SEQ ID NO 5
<211> LENGTH: 115
<212> TYPE: PRT
<213> ORGANISM: Homo sapiens

<400> SEQUENCE: 5

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30
```

Glu Gln Asp Lys Arg Leu His Cys Tyr Ala Ser Trp Ala Asn Ser Ser
            35                  40                  45

Gly Thr Ile Glu Leu Val Lys Lys Gly Cys Trp Leu Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
                100                 105                 110

Ala Pro Thr
        115

<210> SEQ ID NO 6
<211> LENGTH: 100
<212> TYPE: PRT
<213> ORGANISM: Homo sapiens

<400> SEQUENCE: 6

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Ala Asn Ser Ser
            35                  40                  45

Gly Thr Ile Glu Leu Val Lys Lys Gly Cys Trp Leu Asp Asp Phe Asn
        50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala
            100

<210> SEQ ID NO 7
<211> LENGTH: 1536
<212> TYPE: DNA
<213> ORGANISM: Homo sapiens

<400> SEQUENCE: 7
atgacggcgc cctgggtggc cctcgccctc ctctggggat cgctgtgcgc cggctctggg      60
cgtggggagg ctgagacacg ggagtgcatc tactacaacg ccaactggga gctggagcgc     120
accaaccaga gcggcctgga gcgctgcgaa ggcgagcagg acaagcggct gcactgctac     180
gcctcctggc gcaacagctc tggcaccatc gagctcgtga agaagggctg ctggctagat     240
gacttcaact gctacgatag gcaggagtgt gtggccactg aggagaaccc ccaggtgtac     300
ttctgctgct gtgaaggcaa cttctgcaac gaacgcttca ctcatttgcc agaggctggg     360
ggcccggaag tcacgtacga gccaccccg acagccccca ccctgctcac ggtgctggcc     420
tactcactgc tgcccatcgg ggccttttcc ctcatcgtcc tgctggcctt ttggatgtac     480
cggcatcgca agcccccta cggtcatgtg gacatccatg aggaccctgg gcctccacca     540
ccatcccctc tggtgggcct gaagccactg cagctgctgg agatcaaggc tcggggcgc     600 tttggctgtg tctggaaggc ccagctcatg aatgactttg tagctgtcaa gatcttccca     660
ctccaggaca gcagtcgtg gcagagtgaa cgggagatct cagcacacc tggcatgaag     720

```
cacgagaacc tgctacagtt cattgctgcc gagaagcgag gctccaacct cgaagtagag    780
ctgtggctca tcacggcctt ccatgacaag ggctccctca cggattacct caagggggaac   840 atcatcacat ggaacgaact gtgtcatgta gcagagacga tgtcacgagg cctctcatac    900
ctgcatgagg atgtgccctg gtgccgtggc gagggccaca agccgtctat tgcccacagg    960
gactttaaaa gtaagaatgt attgctgaag agcgacctca cagccgtgct ggctgacttt   1020
ggcttggctg ttcgatttga gccagggaaa cctccagggg acacccacgg acaggtaggc   1080
acgagacggt acatggctcc tgaggtgctc gagggagcca tcaacttcca gagagatgcc   1140
ttcctgcgca ttgacatgta tgccatgggg ttggtgctgt gggagcttgt gtctcgctgc   1200
aaggctgcag acggacccgt ggatgagtac atgctgccct tgaggaaga gattggccag    1260 cacccttcgt tggaggagct gcaggaggtg gtggtgcaca agaagatgag gcccaccatt   1320
aaagatcact ggttgaaaca cccgggcctg gcccagcttt gtgtgaccat cgaggagtgc   1380
tgggaccatg atgcagaggc tcgcttgtcc gcgggctgtg tggaggagcg ggtgtccctg   1440
attcggaggt cggtcaacgg cactacctcg gactgtctcg tttccctggt gacctctgtc   1500
accaatgtgg acctgccccc taaagagtca agcatc                             1536
```

<210> SEQ ID NO 8
<211> LENGTH: 345
<212> TYPE: DNA
<213> ORGANISM: Homo sapiens

<400> SEQUENCE: 8

```
gggcgtgggg aggctgagac acgggagtgc atctactaca acgccaactg ggagctggag     60
cgcaccaacc agagcggcct ggagcgctgc gaaggcgagc aggacaagcg gctgcactgc    120
tacgcctcct ggcgcaacag ctctggcacc atcgagctcg tgaagaaggg ctgctggcta    180
gatgacttca actgctacga taggcaggag tgtgtggcca ctgaggagaa ccccaggtg     240 tacttctgct gctgtgaagg caacttctgc aacgaacgct tcactcattt gccagaggct    300
gggggcccgg aagtcacgta cgagccaccc ccgacagccc ccacc                    345
```

<210> SEQ ID NO 9
<211> LENGTH: 513
<212> TYPE: PRT
<213> ORGANISM: Homo sapiens

<400> SEQUENCE: 9

```
Met Gly Ala Ala Ala Lys Leu Ala Phe Ala Val Phe Leu Ile Ser Cys
 1               5                  10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125
```

Pro Val Thr Pro Lys Pro Pro Tyr Tyr Asn Ile Leu Leu Tyr Ser Leu
130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
                180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
                260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
                340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
                420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
                500                 505                 510

Leu

<210> SEQ ID NO 10
<211> LENGTH: 115
<212> TYPE: PRT

<213> ORGANISM: Homo sapiens

<400> SEQUENCE: 10

Ile Leu Gly Arg Ser Glu Thr Gln Glu Cys Leu Phe Phe Asn Ala Asn
1               5                   10                  15
Trp Glu Lys Asp Arg Thr Asn Gln Thr Gly Val Glu Pro Cys Tyr Gly
            20                  25                  30
Asp Lys Asp Lys Arg Arg His Cys Phe Ala Thr Trp Lys Asn Ile Ser
        35                  40                  45
Gly Ser Ile Glu Ile Val Lys Gln Gly Cys Trp Leu Asp Asp Ile Asn
    50                  55                  60
Cys Tyr Asp Arg Thr Asp Cys Val Glu Lys Lys Asp Ser Pro Glu Val
65                  70                  75                  80
Tyr Phe Cys Cys Cys Glu Gly Asn Met Cys Asn Glu Lys Phe Ser Tyr
                85                  90                  95
Phe Pro Glu Met Glu Val Thr Gln Pro Thr Ser Asn Pro Val Thr Pro
                100                 105                 110
Lys Pro Pro
        115

<210> SEQ ID NO 11
<211> LENGTH: 100
<212> TYPE: PRT
<213> ORGANISM: Homo sapiens

<400> SEQUENCE: 11

Ile Leu Gly Arg Ser Glu Thr Gln Glu Cys Leu Phe Phe Asn Ala Asn
1               5                   10                  15
Trp Glu Lys Asp Arg Thr Asn Gln Thr Gly Val Glu Pro Cys Tyr Gly
            20                  25                  30
Asp Lys Asp Lys Arg Arg His Cys Phe Ala Thr Trp Lys Asn Ile Ser
        35                  40                  45
Gly Ser Ile Glu Ile Val Lys Gln Gly Cys Trp Leu Asp Asp Ile Asn
    50                  55                  60
Cys Tyr Asp Arg Thr Asp Cys Val Glu Lys Lys Asp Ser Pro Glu Val
65                  70                  75                  80
Tyr Phe Cys Cys Cys Glu Gly Asn Met Cys Asn Glu Lys Phe Ser Tyr
                85                  90                  95
Phe Pro Glu Met
            100

<210> SEQ ID NO 12
<211> LENGTH: 1539
<212> TYPE: DNA
<213> ORGANISM: Homo sapiens

<400> SEQUENCE: 12
atgggagctg ctgcaaagtt ggcgtttgcc gtctttctta tctcctgttc ttcaggtgct    60
atacttggta gatcagaaac tcaggagtgt ctttttctta atgctaattg ggaaaaagac   120
agaaccaatc aaactggtgt tgaaccgtgt tatggtgaca agataaaacg gcggcattgt   180
tttgctacct ggaagaatat ttctggttcc attgaaatag tgaaacaagg ttgttggctg   240
gatgatatca actgctatga caggactgat tgtgtagaaa aaaagacag ccctgaagta   300 tattttttgtt gctgtgaggg caatatgtgt aatgaaaagt tttcttattt tccggagatg   360
gaagtcacac agcccacttc aaatccagtt acacctaagc cacctattaa caacatcctg   420

```
ctctattcct tggtgccact tatgttaatt gcggggattg tcatttgtgc attttgggtg      480
tacaggcatc acaagatggc ctaccctcct gtacttgttc caactcaaga cccaggacca      540
cccccacctt ctccattact aggtttgaaa ccactgcagt tattagaagt gaaagcaagg      600
ggaagatttg gttgtgtctg gaaagcccag ttgcttaacg aatatgtggc tgtcaaaata      660
tttccaatac aggacaaaca gtcatggcaa aatgaatacg aagtctacag tttgcctgga      720
atgaagcatg agaacatatt acagttcatt ggtgcagaaa aacgaggcac cagtgttgat      780
gtggatcttt ggctgatcac agcatttcat gaaaagggtt cactatcaga ctttcttaag      840
gctaatgtgg tctcttggaa tgaactgtgt catattgcag aaaccatggc tagaggattg      900
gcatatttac atgaggatat acctggccta aaagatggcc acaaacctgc catatctcac      960
agggacatca aaagtaaaaa tgtgctgttg aaaaacaacc tgacagcttg cattgctgac     1020
tttgggttgg ccttaaaatt tgaggctggc aagtctgcag gcgataccca tggacaggtt     1080
ggtacccgga ggtacatggc tccagaggta ttagagggtg ctataaactt ccaaagggat     1140 gcattttga ggatagatat gtatgccatg ggattagtcc tatgggaact ggcttctcgc      1200
tgtactgctg cagatggacc tgtagatgaa tacatgttgc catttgagga ggaaattggc      1260
cagcatccat ctcttgaaga catgcaggaa gttgttgtgc ataaaaaaaa gaggcctgtt     1320
ttaagagatt attggcagaa acatgctgga atggcaatgc tctgtgaaac cattgaagaa     1380
tgttgggatc acgacgcaga agccaggtta tcagctggat gtgtaggtga agaattacc      1440 cagatgcaga gactaacaaa tattattacc acagaggaca ttgtaacagt ggtcacaatg     1500
gtgacaaatg ttgactttcc tcccaaagaa tctagtcta                           1539
```

<210> SEQ ID NO 13
<211> LENGTH: 345
<212> TYPE: DNA
<213> ORGANISM: Homo sapiens

<400> SEQUENCE: 13

```
atacttggta gatcagaaac tcaggagtgt cttttctta atgctaattg ggaaaaagac       60
agaaccaatc aaactggtgt tgaaccgtgt tatggtgaca agataaacg gcggcattgt      120 tttgctacct ggaagaatat ttctggttcc attgaaatag tgaaacaagg ttgttggctg     180
gatgatatca actgctatga caggactgat tgtgtagaaa aaaagacag ccctgaagta     240 tattttgtt gctgtgaggg caatatgtgt aatgaaaagt tttcttattt tccggagatg      300
gaagtcacac agcccacttc aaatccagtt acacctaagc caccc                     345
```

<210> SEQ ID NO 14
<211> LENGTH: 503
<212> TYPE: PRT
<213> ORGANISM: Homo sapiens

<400> SEQUENCE: 14

Met Thr Leu Gly Ser Pro Arg Lys Gly Leu Leu Met Leu Met Ala
1               5                   10                  15

Leu Val Thr Gln Gly Asp Pro Val Lys Pro Ser Arg Gly Pro Leu Val
                20                  25                  30

Thr Cys Thr Cys Glu Ser Pro His Cys Lys Gly Pro Thr Cys Arg Gly
            35                  40                  45

Ala Trp Cys Thr Val Val Leu Val Arg Glu Glu Gly Arg His Pro Gln
        50                  55                  60

Glu His Arg Gly Cys Gly Asn Leu His Arg Glu Leu Cys Arg Gly Arg

```
                65                  70                  75                  80

Pro Thr Glu Phe Val Asn His Tyr Cys Cys Asp Ser His Leu Cys Asn
                    85                  90                  95

His Asn Val Ser Leu Val Leu Glu Ala Thr Gln Pro Pro Ser Glu Gln
                100                 105                 110

Pro Gly Thr Asp Gly Gln Leu Ala Leu Ile Leu Gly Pro Val Leu Ala
                115                 120                 125

Leu Leu Ala Leu Val Ala Leu Gly Val Leu Gly Leu Trp His Val Arg
            130                 135                 140

Arg Arg Gln Glu Lys Gln Arg Gly Leu His Ser Glu Leu Gly Glu Ser
145                 150                 155                 160

Ser Leu Ile Leu Lys Ala Ser Glu Gln Gly Asp Ser Met Leu Gly Asp
                165                 170                 175

Leu Leu Asp Ser Asp Cys Thr Thr Gly Ser Gly Ser Gly Leu Pro Phe
                180                 185                 190

Leu Val Gln Arg Thr Val Ala Arg Gln Val Ala Leu Val Glu Cys Val
            195                 200                 205

Gly Lys Gly Arg Tyr Gly Glu Val Trp Arg Gly Leu Trp His Gly Glu
210                 215                 220

Ser Val Ala Val Lys Ile Phe Ser Ser Arg Asp Glu Gln Ser Trp Phe
225                 230                 235                 240

Arg Glu Thr Glu Ile Tyr Asn Thr Val Leu Leu Arg His Asp Asn Ile
                245                 250                 255

Leu Gly Phe Ile Ala Ser Asp Met Thr Ser Arg Asn Ser Ser Thr Gln
                260                 265                 270

Leu Trp Leu Ile Thr His Tyr His Glu His Gly Ser Leu Tyr Asp Phe
            275                 280                 285

Leu Gln Arg Gln Thr Leu Glu Pro His Leu Ala Leu Arg Leu Ala Val
            290                 295                 300

Ser Ala Ala Cys Gly Leu Ala His Leu His Val Glu Ile Phe Gly Thr
305                 310                 315                 320

Gln Gly Lys Pro Ala Ile Ala His Arg Asp Phe Lys Ser Arg Asn Val
                325                 330                 335

Leu Val Lys Ser Asn Leu Gln Cys Cys Ile Ala Asp Leu Gly Leu Ala
                340                 345                 350

Val Met His Ser Gln Gly Ser Asp Tyr Leu Asp Ile Gly Asn Asn Pro
            355                 360                 365

Arg Val Gly Thr Lys Arg Tyr Met Ala Pro Glu Val Leu Asp Glu Gln
            370                 375                 380

Ile Arg Thr Asp Cys Phe Glu Ser Tyr Lys Trp Thr Asp Ile Trp Ala
385                 390                 395                 400

Phe Gly Leu Val Leu Trp Glu Ile Ala Arg Arg Thr Ile Val Asn Gly
                405                 410                 415

Ile Val Glu Asp Tyr Arg Pro Pro Phe Tyr Asp Val Val Pro Asn Asp
                420                 425                 430

Pro Ser Phe Glu Asp Met Lys Lys Val Val Cys Val Asp Gln Gln Thr
            435                 440                 445

Pro Thr Ile Pro Asn Arg Leu Ala Ala Asp Pro Val Leu Ser Gly Leu
            450                 455                 460

Ala Gln Met Met Arg Glu Cys Trp Tyr Pro Asn Pro Ser Ala Arg Leu
465                 470                 475                 480

Thr Ala Leu Arg Ile Lys Lys Thr Leu Gln Lys Ile Ser Asn Ser Pro
                485                 490                 495
```

```
Glu Lys Pro Lys Val Ile Gln
            500

<210> SEQ ID NO 15
<211> LENGTH: 97
<212> TYPE: PRT
<213> ORGANISM: Homo sapiens

<400> SEQUENCE: 15

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
        35                  40                  45

Gly Asn Leu His Arg Glu Leu Cys Arg Gly Arg Pro Thr Glu Phe Val
    50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln

<210> SEQ ID NO 16
<211> LENGTH: 1509
<212> TYPE: DNA
<213> ORGANISM: Homo sapiens

<400> SEQUENCE: 16
atgaccttgg gctcccccag gaaaggcctt ctgatgctgc tgatggcctt ggtgacccag      60
ggagaccctg tgaagccgtc tcggggcccg ctggtgacct gcacgtgtga gagcccacat     120
tgcaaggggc ctacctgccg gggggcctgg tgcacagtag tgctggtgcg gaggagggg      180 aggcaccccc aggaacatcg gggctgcggg aacttgcaca gggagctctg caggggcgc      240 cccaccgagt tcgtcaacca ctactgctgc gacagccacc tctgcaacca caacgtgtcc     300
ctggtgctgg aggccaccca acctccttcg gagcagccgg aacagatgg ccagctggcc      360 ctgatcctgg gccccgtgct ggccttgctg gccctggtgg ccctgggtgt cctgggcctg     420
tggcatgtcc gacggaggca ggagaagcag cgtggcctgc acagcgagct gggagagtcc     480
agtctcatcc tgaaagcatc tgagcagggc gacagcatgt tggggacct cctggacagt      540 gactgcacca cagggagtgg ctcagggctc cccttcctgg tgcagaggac agtggcacgg     600
caggttgcct tggtggagtg tgtgggaaaa ggccgctatg gcgaagtgtg gcggggcttg     660
tggcacggtg agagtgtggc cgtcaagatc ttctcctcga gggatgaaca gtcctggttc     720
cgggagactg agatctataa cacagtgttg ctcagacacg acaacatcct aggcttcatc     780
gcctcagaca tgacctcccg caactcgagc acgcagctgt ggctcatcac gcactaccac     840
gagcacggct ccctctacga ctttctgcag agacagacgc tggagcccca tctggctctg     900
aggctagctg tgtccgcggc atgcggcctg cgcacctgc acgtggagat cttcggtaca     960
cagggcaaac cagccattgc ccaccgcgac ttcaagagcc gcaatgtgct ggtcaagagc    1020
aacctgcagt gttgcatcgc cgacctgggc ctggctgtga tgcactcaca gggcagcgat    1080
tacctggaca tcggcaacaa cccgagagtg ggcaccaagc ggtacatggc acccgaggtg    1140
ctggacgagc agatccgcac ggactgcttt gagtcctaca gtggactga catctgggcc    1200
```

```
tttggcctgg tgctgtggga gattgcccgc cggaccatcg tgaatggcat cgtggaggac    1260
tatagaccac ccttctatga tgtggtgccc aatgacccca gctttgagga catgaagaag    1320
gtggtgtgtg tggatcagca gacccccacc atccctaacc ggctggctgc agacccggtc    1380
ctctcaggcc tagctcagat gatgcgggag tgctggtacc caaacccctc tgcccgactc    1440
accgcgctgc ggatcaagaa gacactacaa aaaattagca acagtccaga gaagcctaaa    1500
gtgattcaa                                                            1509

<210> SEQ ID NO 17
<211> LENGTH: 291
<212> TYPE: DNA
<213> ORGANISM: Homo sapiens

<400> SEQUENCE: 17
gaccctgtga agccgtctcg gggcccgctg gtgacctgca cgtgtgagag cccacattgc      60
aaggggccta cctgccgggg ggcctggtgc acagtagtgc tggtgcggga ggaggggagg     120
cacccccagg aacatcgggg ctgcgggaac ttgcacaggg agctctgcag ggggcgcccc     180
accgagttcg tcaaccacta ctgctgcgac agccacctct gcaaccacaa cgtgtccctg     240
gtgctggagg ccacccaacc tccttcggag cagccgggaa cagatggcca g              291

<210> SEQ ID NO 18
<211> LENGTH: 509
<212> TYPE: PRT
<213> ORGANISM: Homo sapiens

<400> SEQUENCE: 18

Met Val Asp Gly Val Met Ile Leu Pro Val Leu Ile Met Ile Ala Leu
1               5                   10                  15

Pro Ser Pro Ser Met Glu Asp Glu Lys Pro Lys Val Asn Pro Lys Leu
            20                  25                  30

Tyr Met Cys Val Cys Glu Gly Leu Ser Cys Gly Asn Glu Asp His Cys
        35                  40                  45

Glu Gly Gln Gln Cys Phe Ser Ser Leu Ser Ile Asn Asp Gly Phe His
    50                  55                  60

Val Tyr Gln Lys Gly Cys Phe Gln Val Tyr Glu Gln Gly Lys Met Thr
65                  70                  75                  80

Cys Lys Thr Pro Pro Ser Pro Gly Gln Ala Val Glu Cys Cys Gln Gly
                85                  90                  95

Asp Trp Cys Asn Arg Asn Ile Thr Ala Gln Leu Pro Thr Lys Gly Lys
            100                 105                 110

Ser Phe Pro Gly Thr Gln Asn Phe His Leu Glu Val Gly Leu Ile Ile
        115                 120                 125

Leu Ser Val Val Phe Ala Val Cys Leu Leu Ala Cys Leu Leu Gly Val
    130                 135                 140

Ala Leu Arg Lys Phe Lys Arg Arg Asn Gln Glu Arg Leu Asn Pro Arg
145                 150                 155                 160

Asp Val Glu Tyr Gly Thr Ile Glu Gly Leu Ile Thr Thr Asn Val Gly
                165                 170                 175

Asp Ser Thr Leu Ala Asp Leu Leu Asp His Ser Cys Thr Ser Gly Ser
            180                 185                 190

Gly Ser Gly Leu Pro Phe Leu Val Gln Arg Thr Val Ala Arg Gln Ile
        195                 200                 205

Thr Leu Leu Glu Cys Val Gly Lys Gly Arg Tyr Gly Glu Val Trp Arg
```

```
                210                 215                 220
Gly Ser Trp Gln Gly Glu Asn Val Ala Val Lys Ile Phe Ser Arg
225                 230                 235                 240

Asp Glu Lys Ser Trp Phe Arg Glu Thr Glu Leu Tyr Asn Thr Val Met
                245                 250                 255

Leu Arg His Glu Asn Ile Leu Gly Phe Ile Ala Ser Asp Met Thr Ser
                260                 265                 270

Arg His Ser Ser Thr Gln Leu Trp Leu Ile Thr His Tyr His Glu Met
                275                 280                 285

Gly Ser Leu Tyr Asp Tyr Leu Gln Leu Thr Thr Leu Asp Thr Val Ser
                290                 295                 300

Cys Leu Arg Ile Val Leu Ser Ile Ala Ser Gly Leu Ala His Leu His
305                 310                 315                 320

Ile Glu Ile Phe Gly Thr Gln Gly Lys Pro Ala Ile Ala His Arg Asp
                325                 330                 335

Leu Lys Ser Lys Asn Ile Leu Val Lys Lys Asn Gly Gln Cys Cys Ile
                340                 345                 350

Ala Asp Leu Gly Leu Ala Val Met His Ser Gln Ser Thr Asn Gln Leu
                355                 360                 365

Asp Val Gly Asn Asn Pro Arg Val Gly Thr Lys Arg Tyr Met Ala Pro
                370                 375                 380

Glu Val Leu Asp Glu Thr Ile Gln Val Asp Cys Phe Asp Ser Tyr Lys
385                 390                 395                 400

Arg Val Asp Ile Trp Ala Phe Gly Leu Val Leu Trp Glu Val Ala Arg
                405                 410                 415

Arg Met Val Ser Asn Gly Ile Val Glu Asp Tyr Lys Pro Pro Phe Tyr
                420                 425                 430

Asp Val Val Pro Asn Asp Pro Ser Phe Glu Asp Met Arg Lys Val Val
                435                 440                 445

Cys Val Asp Gln Gln Arg Pro Asn Ile Pro Asn Arg Trp Phe Ser Asp
450                 455                 460

Pro Thr Leu Thr Ser Leu Ala Lys Leu Met Lys Glu Cys Trp Tyr Gln
465                 470                 475                 480

Asn Pro Ser Ala Arg Leu Thr Ala Leu Arg Ile Lys Lys Thr Leu Thr
                485                 490                 495

Lys Ile Asp Asn Ser Leu Asp Lys Leu Lys Thr Asp Cys
                500                 505

<210> SEQ ID NO 19
<211> LENGTH: 103
<212> TYPE: PRT
<213> ORGANISM: Homo sapiens

<400> SEQUENCE: 19

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
                20                  25                  30

Cys Phe Ser Ser Leu Ser Ile Asn Asp Gly Phe His Val Tyr Gln Lys
                35                  40                  45

Gly Cys Phe Gln Val Tyr Glu Gln Gly Lys Met Thr Cys Lys Thr Pro
            50                  55                  60

Pro Ser Pro Gly Gln Ala Val Glu Cys Cys Gln Gly Asp Trp Cys Asn
65                  70                  75                  80
```

Arg Asn Ile Thr Ala Gln Leu Pro Thr Lys Gly Lys Ser Phe Pro Gly
            85                  90                  95

Thr Gln Asn Phe His Leu Glu
            100

<210> SEQ ID NO 20
<211> LENGTH: 1527
<212> TYPE: DNA
<213> ORGANISM: Homo sapiens

<400> SEQUENCE: 20

| | | | | | |
|---|---|---|---|---|---|
| atggtagatg | gagtgatgat | tcttcctgtg | cttatcatga | ttgctctccc | ctcccctagt | 60 |
| atggaagatg | agaagcccaa | ggtcaacccc | aaactctaca | tgtgtgtgtg | tgaaggtctc | 120 |
| tcctgcggta | atgaggacca | ctgtgaaggc | cagcagtgct | tttcctcact | gagcatcaac | 180 |
| gatggcttcc | acgtctacca | gaaaggctgc | ttccaggttt | atgagcaggg | aaagatgacc | 240 |
| tgtaagaccc | cgccgtcccc | tggccaagcc | gtggagtgct | gccaagggga | ctggtgtaac | 300 |
| aggaacatca | cggcccagct | gcccactaaa | ggaaaatcct | tccctggaac | acagaatttc | 360 |
| cacttggagg | ttggcctcat | tattctctct | gtagtgttcg | cagtatgtct | tttagcctgc | 420 |
| ctgctgggag | ttgctctccg | aaaatttaaa | aggcgcaacc | aagaacgcct | caatccccga | 480 |
| gacgtggagt | atggcactat | cgaagggctc | atcaccacca | atgttggaga | cagcacttta | 540 |
| gcagatttat | tggatcattc | gtgtacatca | ggaagtggcc | tggtcttcc | ttttctggta | 600 |
| caaagaacag | tggctcgcca | gattacactg | ttggagtgtg | tcgggaaagg | caggtatggt | 660 |
| gaggtgtgga | ggggcagctg | gcaagggggag | aatgttgccg | tgaagatctt | ctcctcccgt | 720 |
| gatgagaagt | catggttcag | ggaaacggaa | ttgtacaaca | ctgtgatgct | gaggcatgaa | 780 |
| aatatcttag | gtttcattgc | ttcagacatg | acatcaagac | actccagtac | ccagctgtgg | 840 |
| ttaattacac | attatcatga | atgggatcg | ttgtacgact | atcttcagct | tactactctg | 900 |
| gatacagtta | gctgccttcg | aatagtgctg | tccatagcta | gtggtcttgc | acatttgcac | 960 |
| atagagatat | ttgggaccca | agggaaacca | gccattgccc | atcgagattt | aaagagcaaa | 1020 |
| aatattctgg | ttaagaagaa | tggacagtgt | tgcatagcag | atttgggcct | ggcagtcatg | 1080 |
| cattcccaga | gcaccaatca | gcttgatgtg | gggaacaatc | cccgtgtggg | caccaagcgc | 1140 |
| tacatggccc | ccgaagttct | agatgaaacc | atccaggtgg | attgtttcga | ttcttataaa | 1200 |
| agggtcgata | tttgggcctt | tggacttgtt | ttgtgggaag | tggccaggcg | gatggtgagc | 1260 |
| aatggtatag | tggaggatta | caagccaccg | ttctacgatg | tggttcccaa | tgacccaagt | 1320 |
| tttgaagata | tgaggaaggt | agtctgtgtg | gatcaacaaa | ggccaaacat | acccaacaga | 1380 |
| tggttctcag | acccgacatt | aacctctctg | gccaagctaa | tgaaagaatg | ctggtatcaa | 1440 |
| aatccatccg | caagactcac | agcactgcgt | atcaaaaaga | ctttgaccaa | aattgataat | 1500 |
| tccctcgaca | aattgaaaac | tgactgt | | | | 1527 |

<210> SEQ ID NO 21
<211> LENGTH: 309
<212> TYPE: DNA
<213> ORGANISM: Homo sapiens

<400> SEQUENCE: 21

| | | | | | |
|---|---|---|---|---|---|
| atggaagatg | agaagcccaa | ggtcaacccc | aaactctaca | tgtgtgtgtg | tgaaggtctc | 60 |
| tcctgcggta | atgaggacca | ctgtgaaggc | cagcagtgct | tttcctcact | gagcatcaac | 120 |
| gatggcttcc | acgtctacca | gaaaggctgc | ttccaggttt | atgagcaggg | aaagatgacc | 180 |

```
tgtaagaccc cgccgtcccc tggccaagcc gtggagtgct gccaagggga ctggtgtaac    240
aggaacatca cggcccagct gcccactaaa ggaaaatcct tccctggaac acagaatttc    300
cacttggag                                                            309
```

<210> SEQ ID NO 22
<211> LENGTH: 532
<212> TYPE: PRT
<213> ORGANISM: Homo sapiens

<400> SEQUENCE: 22

```
Met Pro Gln Leu Tyr Ile Tyr Ile Arg Leu Leu Gly Ala Tyr Leu Phe
1               5                   10                  15

Ile Ile Ser Arg Val Gln Gly Gln Asn Leu Asp Ser Met Leu His Gly
            20                  25                  30

Thr Gly Met Lys Ser Asp Ser Asp Gln Lys Ser Glu Asn Gly Val
        35                  40                  45

Thr Leu Ala Pro Glu Asp Thr Leu Pro Phe Leu Lys Cys Tyr Cys Ser
50                  55                  60

Gly His Cys Pro Asp Asp Ala Ile Asn Asn Thr Cys Ile Thr Asn Gly
65                  70                  75                  80

His Cys Phe Ala Ile Ile Glu Glu Asp Asp Gln Gly Glu Thr Thr Leu
                85                  90                  95

Ala Ser Gly Cys Met Lys Tyr Glu Gly Ser Asp Phe Gln Cys Lys Asp
            100                 105                 110

Ser Pro Lys Ala Gln Leu Arg Arg Thr Ile Glu Cys Cys Arg Thr Asn
        115                 120                 125

Leu Cys Asn Gln Tyr Leu Gln Pro Thr Leu Pro Pro Val Val Ile Gly
130                 135                 140

Pro Phe Phe Asp Gly Ser Ile Arg Trp Leu Val Leu Leu Ile Ser Met
145                 150                 155                 160

Ala Val Cys Ile Ile Ala Met Ile Ile Phe Ser Ser Cys Phe Cys Tyr
                165                 170                 175

Lys His Tyr Cys Lys Ser Ile Ser Ser Arg Arg Arg Tyr Asn Arg Asp
            180                 185                 190

Leu Glu Gln Asp Glu Ala Phe Ile Pro Val Gly Glu Ser Leu Lys Asp
        195                 200                 205

Leu Ile Asp Gln Ser Gln Ser Ser Gly Ser Gly Ser Gly Leu Pro Leu
210                 215                 220

Leu Val Gln Arg Thr Ile Ala Lys Gln Ile Gln Met Val Arg Gln Val
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
290                 295                 300

Leu Tyr Leu Ile Thr Asp Tyr His Glu Asn Gly Ser Leu Tyr Asp Phe
305                 310                 315                 320

Leu Lys Cys Ala Thr Leu Asp Thr Arg Ala Leu Leu Lys Leu Ala Tyr
                325                 330                 335

Ser Ala Ala Cys Gly Leu Cys His Leu His Thr Glu Ile Tyr Gly Thr
```

```
            340                 345                 350
Gln Gly Lys Pro Ala Ile Ala His Arg Asp Leu Lys Ser Lys Asn Ile
            355                 360                 365

Leu Ile Lys Lys Asn Gly Ser Cys Cys Ile Ala Asp Leu Gly Leu Ala
            370                 375                 380

Val Lys Phe Asn Ser Asp Thr Asn Glu Val Asp Val Pro Leu Asn Thr
385                 390                 395                 400

Arg Val Gly Thr Lys Arg Tyr Met Ala Pro Glu Val Leu Asp Glu Ser
                405                 410                 415

Leu Asn Lys Asn His Phe Gln Pro Tyr Ile Met Ala Asp Ile Tyr Ser
            420                 425                 430

Phe Gly Leu Ile Ile Trp Glu Met Ala Arg Arg Cys Ile Thr Gly Gly
            435                 440                 445

Ile Val Glu Glu Tyr Gln Leu Pro Tyr Tyr Asn Met Val Pro Ser Asp
            450                 455                 460

Pro Ser Tyr Glu Asp Met Arg Glu Val Val Cys Val Lys Arg Leu Arg
465                 470                 475                 480

Pro Ile Val Ser Asn Arg Trp Asn Ser Asp Glu Cys Leu Arg Ala Val
                485                 490                 495

Leu Lys Leu Met Ser Glu Cys Trp Ala His Asn Pro Ala Ser Arg Leu
            500                 505                 510

Thr Ala Leu Arg Ile Lys Lys Thr Leu Ala Lys Met Val Glu Ser Gln
            515                 520                 525

Asp Val Lys Ile
            530

<210> SEQ ID NO 23
<211> LENGTH: 129
<212> TYPE: PRT
<213> ORGANISM: Homo sapiens

<400> SEQUENCE: 23

Gln Asn Leu Asp Ser Met Leu His Gly Thr Gly Met Lys Ser Asp Ser
1               5                   10                  15

Asp Gln Lys Lys Ser Glu Asn Gly Val Thr Leu Ala Pro Glu Asp Thr
            20                  25                  30

Leu Pro Phe Leu Lys Cys Tyr Cys Ser Gly His Cys Pro Asp Asp Ala
            35                  40                  45

Ile Asn Asn Thr Cys Ile Thr Asn Gly His Cys Phe Ala Ile Ile Glu
        50                  55                  60

Glu Asp Asp Gln Gly Glu Thr Thr Leu Ala Ser Gly Cys Met Lys Tyr
65                  70                  75                  80

Glu Gly Ser Asp Phe Gln Cys Lys Asp Ser Pro Lys Ala Gln Leu Arg
                85                  90                  95

Arg Thr Ile Glu Cys Cys Arg Thr Asn Leu Cys Asn Gln Tyr Leu Gln
            100                 105                 110

Pro Thr Leu Pro Pro Val Val Ile Gly Pro Phe Phe Asp Gly Ser Ile
            115                 120                 125

Arg

<210> SEQ ID NO 24
<211> LENGTH: 1596
<212> TYPE: DNA
<213> ORGANISM: Homo sapiens

<400> SEQUENCE: 24
```

```
atgcctcagc tatacattta catcagatta ttgggagcct atttgttcat catttctcgt      60
gttcaaggac agaatctgga tagtatgctt catggcactg ggatgaaatc agactccgac     120
cagaaaaagt cagaaaatgg agtaaccttg gcaccagagg ataccttgcc ttttttaaag    180
tgctattgct cagggcactg tccagatgat gctattaata acacatgcat aactaatgga    240
cattgctttg ccatcataga agaagatgac cagggagaaa ccacattagc ttcagggtgt    300
atgaaatatg aaggatctga ttttcagtgc aaagattctc caaaagccca gctacgccgg    360
acaatagaat gttgtcggac caatttatgt aaccagtatt tgcaacccac actgccccct    420
gttgtcatag gtccgttttt tgatggcagc attcgatggc tggttttgct catttctatg    480
gctgtctgca taattgctat gatcatcttc tccagctgct tttgttacaa acattattgc    540
aagagcatct caagcagacg tcgttacaat cgtgatttgg aacaggatga agcatttatt    600
ccagttggag aatcactaaa agaccttatt gaccagtcac aaagttctgg tagtgggtct    660
ggactacctt tattggttca gcgaactatt gccaaacaga ttcagatggt ccggcaagtt    720
ggtaaaggcc gatatggaga agtatggatg gcaaatggc gtggcgaaaa agtggcggtg    780
aaagtattct ttaccactga agaagccagc tggtttcgag aaacagaaat ctaccaaact    840
gtgctaatgc gccatgaaaa catacttggt ttcatagcgg cagacattaa aggtacaggt    900
tcctggactc agctctattt gattactgat taccatgaaa atggatctct ctatgacttc    960
ctgaaatgtg ctacactgga caccagagcc ctgcttaaat tggcttattc agctgcctgt   1020
ggtctgtgcc acctgcacac agaaatttat ggcacccaag aaagcccgc aattgctcat   1080
cgagacctaa agagcaaaaa catcctcatc aagaaaaatg ggagttgctg cattgctgac   1140
ctgggccttg ctgttaaatt caacagtgac acaaatgaag ttgatgtgcc cttgaatacc   1200
agggtgggca ccaaacgcta catggctccc gaagtgctgg acgaaagcct gaacaaaaac   1260
cacttccagc cctacatcat ggctgacatc tacagcttcg gcctaatcat tgggagatg   1320
gctcgtcgtt gtatcacagg agggatcgtg aagaatacc aattgccata ttacaacatg   1380
gtaccgagtg atccgtcata cgaagatatg cgtgaggttg tgtgtgtcaa acgtttgcgg   1440
ccaattgtgt ctaatcggtg gaacagtgat gaatgtctac gagcagtttt gaagctaatg   1500
tcagaatgct gggcccacaa tccagcctcc agactcacag cattgagaat taagaagacg   1560
cttgccaaga tggttgaatc ccaagatgta aaaatc                             1596
```

<210> SEQ ID NO 25
<211> LENGTH: 387
<212> TYPE: DNA
<213> ORGANISM: Homo sapiens

<400> SEQUENCE: 25

```
cagaatctgg atagtatgct tcatggcact gggatgaaat cagactccga ccagaaaaag     60
tcagaaaatg gagtaaccttt agcaccagag gataccttgc cttttttaaa gtgctattgc    120
tcagggcact gtccagatga tgctattaat aacacatgca taactaatgg acattgcttt    180
gccatcatag aagaagatga ccagggagaa accacattag cttcagggtg tatgaaatat    240
gaaggatctg attttcagtg caaagattct ccaaaagccc agctacgccg gacaatagaa    300
tgttgtcgga ccaatttatg taaccagtat ttgcaaccca cactgccccc tgttgtcata    360
ggtccgtttt ttgatggcag cattcga                                        387
```

<210> SEQ ID NO 26

```
<211> LENGTH: 505
<212> TYPE: PRT
<213> ORGANISM: Homo sapiens

<400> SEQUENCE: 26

Met Ala Glu Ser Ala Gly Ala Ser Ser Phe Phe Pro Leu Val Val Leu
1               5                   10                  15

Leu Leu Ala Gly Ser Gly Ser Gly Pro Arg Gly Val Gln Ala Leu
            20                  25                  30

Leu Cys Ala Cys Thr Ser Cys Leu Gln Ala Asn Tyr Thr Cys Glu Thr
        35                  40                  45

Asp Gly Ala Cys Met Val Ser Ile Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
            100                 105                 110

Leu Lys Glu Pro Glu His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
                165                 170                 175

Lys Thr Leu Gln Asp Leu Val Tyr Asp Leu Ser Thr Ser Gly Ser Gly
            180                 185                 190

Ser Gly Leu Pro Leu Phe Val Gln Arg Thr Val Ala Arg Thr Ile Val
        195                 200                 205

Leu Gln Glu Ile Ile Gly Lys Gly Arg Phe Gly Glu Val Trp Arg Gly
    210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Asp Asn
            260                 265                 270

Gly Thr Trp Thr Gln Leu Trp Leu Val Ser Asp Tyr His Glu His Gly
        275                 280                 285

Ser Leu Phe Asp Tyr Leu Asn Arg Tyr Thr Val Thr Ile Glu Gly Met
    290                 295                 300

Ile Lys Leu Ala Leu Ser Ala Ala Ser Gly Leu Ala His Leu His Met
305                 310                 315                 320

Glu Ile Val Gly Thr Gln Gly Lys Pro Gly Ile Ala His Arg Asp Leu
                325                 330                 335

Lys Ser Lys Asn Ile Leu Val Lys Lys Asn Gly Met Cys Ala Ile Ala
            340                 345                 350

Asp Leu Gly Leu Ala Val Arg His Asp Ala Val Thr Asp Thr Ile Asp
        355                 360                 365

Ile Ala Pro Asn Gln Arg Val Gly Thr Lys Arg Tyr Met Ala Pro Glu
    370                 375                 380

Val Leu Asp Glu Thr Ile Asn Met Lys His Phe Asp Ser Phe Lys Cys
```

```
                385                 390                 395                 400
Ala Asp Ile Tyr Ala Leu Gly Leu Val Tyr Trp Glu Ile Ala Arg Arg
                            405                 410                 415

Cys Asn Ser Gly Gly Val His Glu Glu Tyr Gln Leu Pro Tyr Tyr Asp
                420                 425                 430

Leu Val Pro Ser Asp Pro Ser Ile Glu Glu Met Arg Lys Val Val Cys
            435                 440                 445

Asp Gln Lys Leu Arg Pro Asn Ile Pro Asn Trp Trp Gln Ser Tyr Glu
        450                 455                 460

Ala Leu Arg Val Met Gly Lys Met Met Arg Glu Cys Trp Tyr Ala Asn
465                 470                 475                 480

Gly Ala Ala Arg Leu Thr Ala Leu Arg Ile Lys Lys Thr Leu Ser Gln
                485                 490                 495

Leu Ser Val Gln Glu Asp Val Lys Ile
                500                 505

<210> SEQ ID NO 27
<211> LENGTH: 103
<212> TYPE: PRT
<213> ORGANISM: Homo sapiens

<400> SEQUENCE: 27

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100

<210> SEQ ID NO 28
<211> LENGTH: 1515
<212> TYPE: DNA
<213> ORGANISM: Homo sapiens

<400> SEQUENCE: 28
atggcggagt cggccggagc ctcctccttc ttccccttg ttgtcctcct gctcgccggc      60
agcggcgggt ccgggccccg gggggtccag gctctgctgt gtgcgtgcac cagctgcctc    120
caggccaact acacgtgtga gacagatggg gcctgcatgg tttccatttt caatctggat    180
gggatggagc accatgtgcg cacctgcatc cccaaagtgg agctggtccc tgccgggaag    240
cccttctact gcctgagctc ggaggacctg cgcaacaccc actgctgcta cactgactac    300
tgcaacagga tcgacttgag ggtgccagt ggtcacctca aggagcctga gcacccgtcc    360
atgtggggcc cggtggagct ggtaggcatc atcgccggcc cggtgttcct cctgttcctc    420
atcatcatca ttgttttcct tgtcattaac tatcatcagc gtgtctatca aaccgccag    480 agactggaca tggaagatcc ctcatgtgag atgtgtctct ccaaagacaa gacgctccag    540
gatcttgtct acgatctctc cacctcaggg tctggctcag ggttacccct ctttgtccag    600
```

```
cgcacagtgg cccgaaccat cgttttacaa gagattattg caagggtcg gtttggggaa    660 gtatggcggg gccgctggag gggtggtgat gtggctgtga aaatattctc ttctcgtgaa    720
gaacggtctt ggttcaggga agcagagata taccagacgg tcatgctgcg ccatgaaaac    780
atccttggat ttattgctgc tgacaataaa gataatggca cctggacaca gctgtggctt    840
gtttctgact atcatgagca cgggtccctg tttgattatc tgaaccggta cacagtgaca    900
attgagggga tgattaagct ggccttgtct gctgctagtg ggctggcaca cctgcacatg    960
gagatcgtgg gcacccaagg gaagcctgga attgctcatc gagacttaaa gtcaaagaac   1020
attctggtga agaaaaatgg catgtgtgcc atagcagacc tgggcctggc tgtccgtcat   1080
gatgcagtca ctgacaccat tgacattgcc ccgaatcaga gggtggggac caaacgatac   1140
atggcccctg aagtacttga tgaaaccatt aatatgaaac actttgactc ctttaaatgt   1200
gctgatattt atgccctcgg gcttgtatat tgggagattg ctcgaagatg caattctgga   1260
ggagtccatg aagaatatca gctgccatat tacgacttag tgccctctga cccttccatt   1320
gaggaaatgc gaaaggttgt atgtgatcag aagctgcgtc ccaacatccc caactggtgg   1380
cagagttatg aggcactgcg ggtgatgggg aagatgatgc gagagtgttg gtatgccaac   1440
ggcgcagccc gcctgacggc cctgcgcatc aagaagaccc tctcccagct cagcgtgcag   1500
gaagacgtga agatc                                                   1515

<210> SEQ ID NO 29
<211> LENGTH: 309
<212> TYPE: DNA
<213> ORGANISM: Homo sapiens

<400> SEQUENCE: 29
tccgggcccc gggggtcca ggctctgctg tgtgcgtgca ccagctgcct ccaggccaac     60
tacacgtgtg agacagatgg ggcctgcatg gtttccattt tcaatctgga tgggatggag    120
caccatgtgc gcacctgcat ccccaaagtg gagctggtcc ctgccgggaa gcccttctac    180
tgcctgagct cggaggacct gcgcaacacc cactgctgct acactgacta ctgcaacagg    240
atcgacttga gggtgcccag tggtcacctc aaggagcctg agcacccgtc catgtggggc    300
ccggtggag                                                           309

<210> SEQ ID NO 30
<211> LENGTH: 503
<212> TYPE: PRT
<213> ORGANISM: Homo sapiens

<400> SEQUENCE: 30

Met Glu Ala Ala Val Ala Ala Pro Arg Pro Arg Leu Leu Leu Val
1               5                   10                  15

Leu Ala Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95
```

```
Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
            115                 120                 125

Val Ile Ala Gly Pro Val Cys Phe Val Cys Ile Ser Leu Met Leu Met
130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
                180                 185                 190

Leu Pro Leu Leu Val Gln Arg Thr Ile Ala Arg Thr Ile Val Leu Gln
                195                 200                 205

Glu Ser Ile Gly Lys Gly Arg Phe Gly Glu Val Trp Arg Gly Lys Trp
            210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
            275                 280                 285

Phe Asp Tyr Leu Asn Arg Tyr Thr Val Thr Val Glu Gly Met Ile Lys
290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
            355                 360                 365

Pro Asn His Arg Val Gly Thr Lys Arg Tyr Met Ala Pro Glu Val Leu
370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
            420                 425                 430

Pro Ser Asp Pro Ser Val Glu Glu Met Arg Lys Val Val Cys Glu Gln
                435                 440                 445

Lys Leu Arg Pro Asn Ile Pro Asn Arg Trp Gln Ser Cys Glu Ala Leu
450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
                485                 490                 495

Gln Gln Glu Gly Ile Lys Met
                500
```

<210> SEQ ID NO 31
<211> LENGTH: 102
<212> TYPE: PRT
<213> ORGANISM: Homo sapiens

<400> SEQUENCE: 31

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Val Lys Ser Ser Pro Gly
                85                  90                  95

Leu Gly Pro Val Glu Leu
            100

<210> SEQ ID NO 32
<211> LENGTH: 1509
<212> TYPE: DNA
<213> ORGANISM: Homo sapiens

<400> SEQUENCE: 32
atggaggcgg cggtcgctgc tccgcgtccc cggctgctcc tcctcgtgct ggcggcggcg      60
gcggcggcgg cggcggcgct gctcccgggg gcgacggcgt acagtgtttt ctgccacctc     120
tgtacaaaag acaattttac ttgtgtgaca gatgggctct gctttgtctc tgtcacagag     180
accacagaca agttatacaa cagcatgtgt atagctgaaa ttgacttaat tcctcga        240 gataggccgt ttgtatgtgc accctcttca aaaactgggt ctgtgactac aacatattgc     300
tgcaatcagg accattgcaa taaaatagaa cttccaacta ctgtaaagtc atcacctggc     360
cttggtcctg tggaactggc agctgtcatt gctggaccag tgtgcttcgt ctgcatctca     420
ctcatgttga tggtctatat ctgccacaac cgcactgtca ttcaccatcg agtgccaaat     480
gaagaggacc cttcattaga tcgcccttt atttcagagg gtactacgtt gaaagactta     540
atttatgata tgacaacgtc aggttctggc tcaggtttac cattgcttgt tcagagaaca     600
attgcgagaa ctattgtgtt acaagaaagc attggcaaag tcgatttgg agaagtttgg     660 agaggaaagt ggcggggaga agaagttgct gttaagatat tctcctctag aagaacgt       720 tcgtggttcc gtgaggcaga gatttatcaa actgtaatgt tacgtcatga aaacatcctg     780
ggatttatag cagcagacaa taaagacaat ggtacttgga ctcagctctg gttggtgtca     840
gattatcatg agcatggatc ccttttgat tacttaaaca gatacacagt tactgtggaa      900
ggaatgataa aacttgctct gtccacggcg agcggtcttg cccatcttca catggagatt     960
gttggtaccc caggaaagcc agccattgct catagagatt gaaatcaaa gaatatcttg     1020 gtaaagaaga atggaacttg ctgtattgca gacttaggac tggcagtaag acatgattca    1080
gccacagata ccattgatat tgctccaaac cacagagtgg aacaaaaag gtacatggcc     1140 cctgaagttc tcgatgattc cataaatatg aaacattttg aatccttcaa acgtgctgac    1200
atctatgcaa tgggcttagt attctgggaa attgctcgac gatgttccat ggtggaatt    1260 catgaagatt accaactgcc ttattatgat cttgtacctt ctgacccatc agttgaagaa   1320

```
atgagaaaag ttgtttgtga acagaagtta aggccaaata tcccaaacag atggcagagc   1380
tgtgaagcct tgagagtaat ggctaaaatt atgagagaat gttggtatgc caatggagca   1440
gctaggctta cagcattgcg gattaagaaa acattatcgc aactcagtca acaggaaggc   1500
atcaaaatg                                                           1509
```

<210> SEQ ID NO 33
<211> LENGTH: 306
<212> TYPE: DNA
<213> ORGANISM: Homo sapiens

<400> SEQUENCE: 33

```
gcggcgctgc tcccgggggc gacggcgtta cagtgtttct gccacctctg tacaaaagac    60
aattttactt gtgtgacaga tgggctctgc tttgtctctg tcacagagac cacagacaaa   120
gttatacaca acagcatgtg tatagctgaa attgacttaa ttcctcgaga taggccgttt   180
gtatgtgcac cctcttcaaa aactgggtct gtgactacaa catattgctg caatcaggac   240
cattgcaata aaatagaact tccaactact gtaaagtcat cacctggcct tggtcctgtg   300
gaactg                                                              306
```

<210> SEQ ID NO 34
<211> LENGTH: 502
<212> TYPE: PRT
<213> ORGANISM: Homo sapiens

<400> SEQUENCE: 34

```
Met Leu Leu Arg Ser Ala Gly Lys Leu Asn Val Gly Thr Lys Lys Glu
1               5                   10                  15

Asp Gly Glu Ser Thr Ala Pro Thr Pro Arg Pro Lys Val Leu Arg Cys
            20                  25                  30

Lys Cys His His His Cys Pro Glu Asp Ser Val Asn Asn Ile Cys Ser
        35                  40                  45

Thr Asp Gly Tyr Cys Phe Thr Met Ile Glu Glu Asp Asp Ser Gly Leu
    50                  55                  60

Pro Val Val Thr Ser Gly Cys Leu Gly Leu Glu Gly Ser Asp Phe Gln
65                  70                  75                  80

Cys Arg Asp Thr Pro Ile Pro His Gln Arg Arg Ser Ile Glu Cys Cys
                85                  90                  95

Thr Glu Arg Asn Glu Cys Asn Lys Asp Leu His Pro Thr Leu Pro Pro
            100                 105                 110

Leu Lys Asn Arg Asp Phe Val Asp Gly Pro Ile His His Arg Ala Leu
        115                 120                 125

Leu Ile Ser Val Thr Val Cys Ser Leu Leu Leu Val Leu Ile Ile Leu
    130                 135                 140

Phe Cys Tyr Phe Arg Tyr Lys Arg Gln Glu Thr Arg Pro Arg Tyr Ser
145                 150                 155                 160

Ile Gly Leu Glu Gln Asp Glu Thr Tyr Ile Pro Pro Gly Glu Ser Leu
                165                 170                 175

Arg Asp Leu Ile Glu Gln Ser Gln Ser Ser Gly Ser Gly Ser Gly Leu
            180                 185                 190

Pro Leu Leu Val Gln Arg Thr Ile Ala Lys Gln Ile Gln Met Val Lys
        195                 200                 205

Gln Ile Gly Lys Gly Arg Tyr Gly Glu Val Trp Met Gly Lys Trp Arg
    210                 215                 220
```

```
Gly Glu Lys Val Ala Val Lys Val Phe Phe Thr Glu Glu Ala Ser
225                 230                 235                 240

Trp Phe Arg Glu Thr Glu Ile Tyr Gln Thr Val Leu Met Arg His Glu
                245                 250                 255

Asn Ile Leu Gly Phe Ile Ala Ala Asp Ile Lys Gly Thr Gly Ser Trp
                260                 265                 270

Thr Gln Leu Tyr Leu Ile Thr Asp Tyr His Glu Asn Gly Ser Leu Tyr
            275                 280                 285

Asp Tyr Leu Lys Ser Thr Thr Leu Asp Ala Lys Ser Met Leu Lys Leu
            290                 295                 300

Ala Tyr Ser Ser Val Ser Gly Leu Cys His Leu His Thr Glu Ile Phe
305                 310                 315                 320

Ser Thr Gln Gly Lys Pro Ala Ile Ala His Arg Asp Leu Lys Ser Lys
                325                 330                 335

Asn Ile Leu Val Lys Lys Asn Gly Thr Cys Cys Ile Ala Asp Leu Gly
                340                 345                 350

Leu Ala Val Lys Phe Ile Ser Asp Thr Asn Glu Val Asp Ile Pro Pro
            355                 360                 365

Asn Thr Arg Val Gly Thr Lys Arg Tyr Met Pro Pro Glu Val Leu Asp
370                 375                 380

Glu Ser Leu Asn Arg Asn His Phe Gln Ser Tyr Ile Met Ala Asp Met
385                 390                 395                 400

Tyr Ser Phe Gly Leu Ile Leu Trp Glu Val Ala Arg Arg Cys Val Ser
                405                 410                 415

Gly Gly Ile Val Glu Glu Tyr Gln Leu Pro Tyr His Asp Leu Val Pro
                420                 425                 430

Ser Asp Pro Ser Tyr Glu Asp Met Arg Glu Ile Val Cys Ile Lys Lys
            435                 440                 445

Leu Arg Pro Ser Phe Pro Asn Arg Trp Ser Ser Asp Glu Cys Leu Arg
            450                 455                 460

Gln Met Gly Lys Leu Met Thr Glu Cys Trp Ala His Asn Pro Ala Ser
465                 470                 475                 480

Arg Leu Thr Ala Leu Arg Val Lys Lys Thr Leu Ala Lys Met Ser Glu
                485                 490                 495

Ser Gln Asp Ile Lys Leu
            500

<210> SEQ ID NO 35
<211> LENGTH: 113
<212> TYPE: PRT
<213> ORGANISM: Homo sapiens

<400> SEQUENCE: 35

Lys Lys Glu Asp Gly Glu Ser Thr Ala Pro Thr Pro Arg Pro Lys Val
1               5                   10                  15

Leu Arg Cys Lys Cys His His His Cys Pro Glu Asp Ser Val Asn Asn
                20                  25                  30

Ile Cys Ser Thr Asp Gly Tyr Cys Phe Thr Met Ile Glu Glu Asp Asp
            35                  40                  45

Ser Gly Leu Pro Val Val Thr Ser Gly Cys Leu Gly Leu Glu Gly Ser
        50                  55                  60

Asp Phe Gln Cys Arg Asp Thr Pro Ile Pro His Gln Arg Arg Ser Ile
65                  70                  75                  80

Glu Cys Cys Thr Glu Arg Asn Glu Cys Asn Lys Asp Leu His Pro Thr
                85                  90                  95
```

Leu Pro Pro Leu Lys Asn Arg Asp Phe Val Asp Gly Pro Ile His His
            100                 105                 110
Arg

<210> SEQ ID NO 36
<211> LENGTH: 1506
<212> TYPE: DNA
<213> ORGANISM: Homo sapiens

<400> SEQUENCE: 36

| | | | | | |
|---|---|---|---|---|---|
| atgcttttgc | gaagtgcagg | aaaattaaat | gtgggcacca | agaaagagga | tggtgagagt | 60 |
| acagccccca | ccccccgtcc | aaaggtcttg | cgttgtaaat | gccaccacca | ttgtccagaa | 120 |
| gactcagtca | acaatatttg | cagcacagac | ggatattgtt | tcacgatgat | agaagaggat | 180 |
| gactctgggt | tgcctgtggt | cacttctggt | tgcctaggac | tagaaggctc | agattttcag | 240 |
| tgtcgggaca | ctcccattcc | tcatcaaaga | agatcaattg | aatgctgcac | agaaaggaac | 300 |
| gaatgtaata | aagacctaca | ccctacactg | cctccattga | aaaacagaga | ttttgttgat | 360 |
| ggacctatac | accacagggc | tttacttata | tctgtgactg | tctgtagttt | gctcttggtc | 420 |
| cttatcatat | tattttgtta | cttccggtat | aaaagacaag | aaaccagacc | tcgatacagc | 480 |
| attgggttag | aacaggatga | aacttacatt | cctcctggag | aatccctgag | agacttaatt | 540 |
| gagcagtctc | agagctcagg | aagtggatca | ggcctccctc | tgctggtcca | aaggactata | 600 |
| gctaagcaga | ttcagatggt | gaaacagatt | ggaaaaggtc | gctatgggga | agtttggatg | 660 |
| ggaaagtggc | gtggcgaaaa | ggtagctgtg | aaagtgttct | tcaccacaga | ggaagccagc | 720 |
| tggttcagag | agacagaaat | atatcagaca | gtgttgatga | ggcatgaaaa | catttttggt | 780 |
| ttcattgctg | cagatatcaa | agggacaggg | tcctggaccc | agttgtacct | aatcacagac | 840 |
| tatcatgaaa | atggttccct | ttatgattat | ctgaagtcca | ccaccctaga | cgctaaatca | 900 |
| atgctgaagt | tagcctactc | ttctgtcagt | ggcttatgtc | atttacacac | agaaatcttt | 960 |
| agtactcaag | gcaaaccagc | aattgcccat | cgagatctga | aaagtaaaaa | cattctggtg | 1020 |
| aagaaaaatg | gaacttgctg | tattgctgac | ctgggcctgg | ctgttaaatt | tattagtgat | 1080 |
| acaaatgaag | ttgacatacc | acctaacact | cgagttggca | ccaaacgcta | tatgcctcca | 1140 |
| gaagtgttgg | acgagagctt | gaacagaaat | cacttccagt | cttacatcat | ggctgacatg | 1200 |
| tatagttttg | gcctcatcct | ttgggaggtt | gctaggagat | gtgtatcagg | aggtatagtg | 1260 |
| gaagaatacc | agcttcctta | tcatgaccta | gtgcccagtg | acccctctta | tgaggacatg | 1320 |
| agggagattg | tgtgcatcaa | gaagttacgc | ccctcattcc | caaaccggtg | gagcagtgat | 1380 |
| gagtgtctaa | gcagatggg | aaaactcatg | acagaatgct | gggctcacaa | tcctgcatca | 1440 |
| aggctgacag | ccctgcgggt | taagaaaaca | cttgccaaaa | tgtcagagtc | ccaggacatt | 1500 |
| aaactc | | | | | | 1506 |

<210> SEQ ID NO 37
<211> LENGTH: 339
<212> TYPE: DNA
<213> ORGANISM: Homo sapiens

<400> SEQUENCE: 37

| | | | | | |
|---|---|---|---|---|---|
| aagaaagagg | atggtgagag | tacagccccc | accccccgtc | caaaggtctt | gcgttgtaaa | 60 |
| tgccaccacc | attgtccaga | agactcagtc | aacaatattt | gcagcacaga | cggatattgt | 120 |
| ttcacgatga | tagaagagga | tgactctggg | ttgcctgtgg | tcacttctgg | ttgcctagga | 180 |

```
ctagaaggct cagattttca gtgtcgggac actcccattc ctcatcaaag aagatcaatt    240
gaatgctgca cagaaaggaa cgaatgtaat aaagacctac accctacact gcctccattg    300
aaaaacagag attttgttga tggacctata caccacagg                          339
```

```
<210> SEQ ID NO 38
<211> LENGTH: 493
<212> TYPE: PRT
<213> ORGANISM: Homo sapiens

<400> SEQUENCE: 38
```

| | | | | | | | | | | | | | | |
|---|---|---|---|---|---|---|---|---|---|---|---|---|---|---|
|Met|Thr|Arg|Ala|Leu|Cys|Ser|Ala|Leu|Arg|Gln|Ala|Leu|Leu|Leu|
|1| | |5| | | | |10| | | | |15| |
|Ala|Ala|Ala|Ala|Glu|Leu|Ser|Pro|Gly|Leu|Lys|Cys|Val|Cys|Leu|Leu|
| | | |20| | | |25| | | |30| | | |
|Cys|Asp|Ser|Ser|Asn|Phe|Thr|Cys|Gln|Thr|Glu|Gly|Ala|Cys|Trp|Ala|
| | |35| | | |40| | | |45| | | | |
|Ser|Val|Met|Leu|Thr|Asn|Gly|Lys|Glu|Gln|Val|Ile|Lys|Ser|Cys|Val|
| |50| | | |55| | | |60| | | | | |
|Ser|Leu|Pro|Glu|Leu|Asn|Ala|Gln|Val|Phe|Cys|His|Ser|Ser|Asn|Asn|
|65| | | |70| | | |75| | | | |80| |
|Val|Thr|Lys|Thr|Glu|Cys|Cys|Phe|Thr|Asp|Phe|Cys|Asn|Asn|Ile|Thr|
| | | |85| | | |90| | | |95| | | |
|Leu|His|Leu|Pro|Thr|Ala|Ser|Pro|Asn|Ala|Pro|Lys|Leu|Gly|Pro|Met|
| | |100| | | |105| | | |110| | | | |
|Glu|Leu|Ala|Ile|Ile|Ile|Thr|Val|Pro|Val|Cys|Leu|Leu|Ser|Ile|Ala|
| |115| | | |120| | | |125| | | | | |
|Ala|Met|Leu|Thr|Val|Trp|Ala|Cys|Gln|Gly|Arg|Gln|Cys|Ser|Tyr|Arg|
|130| | | |135| | | |140| | | | | | |
|Lys|Lys|Lys|Arg|Pro|Asn|Val|Glu|Glu|Pro|Leu|Ser|Glu|Cys|Asn|Leu|
|145| | | |150| | | |155| | | |160| | |
|Val|Asn|Ala|Gly|Lys|Thr|Leu|Lys|Asp|Leu|Ile|Tyr|Asp|Val|Thr|Ala|
| | | |165| | | |170| | | |175| | | |
|Ser|Gly|Ser|Gly|Ser|Gly|Leu|Pro|Leu|Leu|Val|Gln|Arg|Thr|Ile|Ala|
| | |180| | | |185| | | |190| | | | |
|Arg|Thr|Ile|Val|Leu|Gln|Glu|Ile|Val|Gly|Lys|Gly|Arg|Phe|Gly|Glu|
| |195| | | |200| | | |205| | | | | |
|Val|Trp|His|Gly|Arg|Trp|Cys|Gly|Glu|Asp|Val|Ala|Val|Lys|Ile|Phe|
| |210| | | |215| | | |220| | | | | |
|Ser|Ser|Arg|Asp|Glu|Arg|Ser|Trp|Phe|Arg|Glu|Ala|Glu|Ile|Tyr|Gln|
|225| | | |230| | | |235| | | |240| | |
|Thr|Val|Met|Leu|Arg|His|Glu|Asn|Ile|Leu|Gly|Phe|Ile|Ala|Ala|Asp|
| | | |245| | | |250| | | |255| | | |
|Asn|Lys|Asp|Asn|Gly|Thr|Trp|Thr|Gln|Leu|Trp|Leu|Val|Ser|Glu|Tyr|
| | |260| | | |265| | | |270| | | | |
|His|Glu|Gln|Gly|Ser|Leu|Tyr|Asp|Tyr|Leu|Asn|Arg|Asn|Ile|Val|Thr|
| |275| | | |280| | | |285| | | | | |
|Val|Ala|Gly|Met|Ile|Lys|Leu|Ala|Leu|Ser|Ile|Ala|Ser|Gly|Leu|Ala|
| |290| | | |295| | | |300| | | | | |
|His|Leu|His|Met|Glu|Ile|Val|Gly|Thr|Gln|Gly|Lys|Pro|Ala|Ile|Ala|
|305| | | |310| | | |315| | | | | |320|
|His|Arg|Asp|Ile|Lys|Ser|Lys|Asn|Ile|Leu|Val|Lys|Lys|Cys|Glu|Thr|
| | | |325| | | |330| | | |335| | | |
|Cys|Ala|Ile|Ala|Asp|Leu|Gly|Leu|Ala|Val|Lys|His|Asp|Ser|Ile|Leu|

```
            340                 345                 350
Asn Thr Ile Asp Ile Pro Gln Asn Pro Lys Val Gly Thr Lys Arg Tyr
        355                 360                 365

Met Ala Pro Glu Met Leu Asp Asp Thr Met Asn Val Asn Ile Phe Glu
        370                 375                 380

Ser Phe Lys Arg Ala Asp Ile Tyr Ser Val Gly Leu Val Tyr Trp Glu
385                 390                 395                 400

Ile Ala Arg Arg Cys Ser Val Gly Ile Val Glu Glu Tyr Gln Leu
                405                 410                 415

Pro Tyr Tyr Asp Met Val Pro Ser Asp Pro Ser Ile Glu Glu Met Arg
                420                 425                 430

Lys Val Val Cys Asp Gln Lys Phe Arg Pro Ser Ile Pro Asn Gln Trp
            435                 440                 445

Gln Ser Cys Glu Ala Leu Arg Val Met Gly Arg Ile Met Arg Glu Cys
        450                 455                 460

Trp Tyr Ala Asn Gly Ala Ala Arg Leu Thr Ala Leu Arg Ile Lys Lys
465                 470                 475                 480

Thr Ile Ser Gln Leu Cys Val Lys Glu Asp Cys Lys Ala
                485                 490

<210> SEQ ID NO 39
<211> LENGTH: 93
<212> TYPE: PRT
<213> ORGANISM: Homo sapiens

<400> SEQUENCE: 39

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
                20                  25                  30

Thr Asn Gly Lys Glu Gln Val Ile Lys Ser Cys Val Ser Leu Pro Glu
            35                  40                  45

Leu Asn Ala Gln Val Phe Cys His Ser Ser Asn Asn Val Thr Lys Thr
        50                  55                  60

Glu Cys Cys Phe Thr Asp Phe Cys Asn Asn Ile Thr Leu His Leu Pro
65                  70                  75                  80

Thr Ala Ser Pro Asn Ala Pro Lys Leu Gly Pro Met Glu
                85                  90

<210> SEQ ID NO 40
<211> LENGTH: 1479
<212> TYPE: DNA
<213> ORGANISM: Homo sapiens

<400> SEQUENCE: 40
atgacccggg cgctctgctc agcgctccgc caggctctcc tgctgctcgc agcggccgcc      60
gagctctcgc caggactgaa gtgtgtatgt cttttgtgtg attcttcaaa ctttacctgc     120
caaacagaag gagcatgttg ggcatcagtc atgctaacca atggaaaaga gcaggtgatc     180
aaatcctgtg tctcccttcc agaactgaat gctcaagtct tctgtcatag ttccaacaat     240
gttaccaaaa ccgaatgctg cttcacagat ttttgcaaca acataacact gcaccttcca     300
acagcatcac caaatgcccc aaaacttgga cccatggagc tggccatcat tattactgtg     360
cctgtttgcc tcctgtccat agctgcgatg ctgacagtat gggcatgcca gggtcgacag     420
tgctcctaca ggaagaaaaa gagaccaaat gtggaggaac cactctctga gtgcaatctg     480
```

```
gtaaatgctg gaaaaactct gaaagatctg atttatgatg tgaccgcctc tggatctggc    540
tctggtctac ctctgttggt tcaaaggaca attgcaagga cgattgtgct tcaggaaata    600
gtaggaaaag gtagatttgg tgaggtgtgg catggaagat ggtgtgggga agatgtggct    660
gtgaaaatat tctcctccag agatgaaaga tcttggtttc gtgaggcaga aatttaccag    720
acggtcatgc tgcgacatga aacatccttg gtttcattg ctgctgacaa caaagataat    780
ggaacttgga ctcaactttg ctggtatct gaatatcatg aacagggctc cttatatgac    840
tatttgaata gaaatatagt gaccgtggct ggaatgatca agctggcgct ctcaattgct    900
agtggtctgg cacaccttca tatggagatt gttggtacac aaggtaaacc tgctattgct    960
catcgagaca taaaatcaaa gaatatctta gtgaaaaagt gtgaaacttg tgccatagcg   1020
gacttagggt tggctgtgaa gcatgattca atactgaaca ctatcgacat acctcagaat   1080
cctaaagtgg gaaccaagag gtatatggct cctgaaatgc ttgatgatac aatgaatgtg   1140
aatatctttg agtccttcaa cgagctgac atctattctg ttggtctggt ttactgggaa    1200
atagcccgga ggtgttcagt cggaggaatt gttgaggagt accaattgcc ttattatgac   1260
atggtgcctt cagatccctc gatagaggaa atgagaaagg ttgtttgtga ccagaagttt   1320
cgaccaagta tcccaaacca gtggcaaagt tgtgaagcac tccgagtcat ggggagaata   1380
atgcgtgagt gttggtatgc caacggagcg gcccgcctaa ctgctcttcg tattaagaag   1440
actatatctc aactttgtgt caaagaagac tgcaaagcc                           1479

<210> SEQ ID NO 41
<211> LENGTH: 279
<212> TYPE: DNA
<213> ORGANISM: Homo sapiens

<400> SEQUENCE: 41
gagctctcgc caggactgaa gtgtgtatgt cttttgtgtg attcttcaaa ctttacctgc     60
caaacagaag gagcatgttg ggcatcagtc atgctaacca atggaaaaga gcaggtgatc    120
aaatcctgtg tctcccttcc agaactgaat gctcaagtct tctgtcatag ttccaacaat    180
gttaccaaaa ccgaatgctg cttcacagat ttttgcaaca acataacact gcaccttcca    240
acagcatcac caaatgcccc aaaacttgga cccatggag                           279

<210> SEQ ID NO 42
<211> LENGTH: 567
<212> TYPE: PRT
<213> ORGANISM: Homo sapiens

<400> SEQUENCE: 42
```

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
        50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile

```
                100             105             110
Leu Glu Asp Ala Ala Ser Pro Lys Cys Ile Met Lys Glu Lys Lys
            115                 120             125

Pro Gly Glu Thr Phe Phe Met Cys Ser Cys Ser Ser Asp Glu Cys Asn
        130                 135             140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Phe Tyr Cys Tyr Arg Val Asn
            180                 185             190

Arg Gln Gln Lys Leu Ser Ser Thr Trp Glu Thr Gly Lys Thr Arg Lys
            195                 200             205

Leu Met Glu Phe Ser Glu His Cys Ala Ile Ile Leu Glu Asp Asp Arg
        210                 215             220

Ser Asp Ile Ser Ser Thr Cys Ala Asn Asn Ile Asn His Asn Thr Glu
225                 230                 235             240

Leu Leu Pro Ile Glu Leu Asp Thr Leu Val Gly Lys Gly Arg Phe Ala
                245                 250             255

Glu Val Tyr Lys Ala Lys Leu Lys Gln Asn Thr Ser Glu Gln Phe Glu
            260                 265             270

Thr Val Ala Val Lys Ile Phe Pro Tyr Glu Tyr Ala Ser Trp Lys
            275                 280             285

Thr Glu Lys Asp Ile Phe Ser Asp Ile Asn Leu Lys His Glu Asn Ile
        290                 295             300

Leu Gln Phe Leu Thr Ala Glu Glu Arg Lys Thr Glu Leu Gly Lys Gln
305                 310                 315             320

Tyr Trp Leu Ile Thr Ala Phe His Ala Lys Gly Asn Leu Gln Glu Tyr
                325                 330             335

Leu Thr Arg His Val Ile Ser Trp Glu Asp Leu Arg Lys Leu Gly Ser
            340                 345             350

Ser Leu Ala Arg Gly Ile Ala His Leu His Ser Asp His Thr Pro Cys
        355                 360             365

Gly Arg Pro Lys Met Pro Ile Val His Arg Asp Leu Lys Ser Ser Asn
        370                 375             380

Ile Leu Val Lys Asn Asp Leu Thr Cys Cys Leu Cys Asp Phe Gly Leu
385                 390                 395             400

Ser Leu Arg Leu Asp Pro Thr Leu Ser Val Asp Asp Leu Ala Asn Ser
            405                 410             415

Gly Gln Val Gly Thr Ala Arg Tyr Met Ala Pro Glu Val Leu Glu Ser
            420                 425             430

Arg Met Asn Leu Glu Asn Val Glu Ser Phe Lys Gln Thr Asp Val Tyr
        435                 440             445

Ser Met Ala Leu Val Leu Trp Glu Met Thr Ser Arg Cys Asn Ala Val
        450                 455             460

Gly Glu Val Lys Asp Tyr Glu Pro Pro Phe Gly Ser Lys Val Arg Glu
465                 470                 475             480

His Pro Cys Val Glu Ser Met Lys Asp Asn Val Leu Arg Asp Arg Gly
                485                 490             495

Arg Pro Glu Ile Pro Ser Phe Trp Leu Asn His Gln Gly Ile Gln Met
            500                 505             510

Val Cys Glu Thr Leu Thr Glu Cys Trp Asp His Asp Pro Glu Ala Arg
            515                 520             525
```

Leu Thr Ala Gln Cys Val Ala Glu Arg Phe Ser Glu Leu Glu His Leu
        530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 43
<211> LENGTH: 144
<212> TYPE: PRT
<213> ORGANISM: Homo sapiens

<400> SEQUENCE: 43

Thr Ile Pro Pro His Val Gln Lys Ser Val Asn Asn Asp Met Ile Val
1               5                  10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Leu Leu Leu Val Ile Phe Gln
    130                 135                 140

<210> SEQ ID NO 44
<211> LENGTH: 1701
<212> TYPE: DNA
<213> ORGANISM: Homo sapiens

<400> SEQUENCE: 44
atgggtcggg ggctgctcag gggcctgtgg ccgctgcaca tcgtcctgtg gacgcgtatc      60
gccagcacga tcccaccgca cgttcagaag tcggttaata cgacatgat agtcactgac     120 aacaacggtg cagtcaagtt tccacaactg tgtaaatttt gtgatgtgag attttccacc    180
tgtgacaacc agaaatcctg catgagcaac tgcagcatca cctccatctg tgagaagcca    240
caggaagtct gtgtggctgt atggagaaag aatgacgaga acataacact agagacagtt    300
tgccatgacc ccaagctccc ctaccatgac tttattctgg aagatgctgc ttctccaaag    360
tgcattatga ggaaaaaaa aaagcctggt gagactttct tcatgtgttc ctgtagctct    420
gatgagtgca atgacaacat catcttctca gaagaatata caccagcaa tcctgacttg    480 ttgctagtca tatttcaagt gacaggcatc agcctcctgc caccactggg agttgccata    540
tctgtcatca tcatcttcta ctgctaccgc gttaaccggc agcagaagct gagttcaacc    600
tgggaaaccg gcaagacgcg gaagctcatg gagttcagcg agcactgtgc catcatcctg    660
gaagatgacc gctctgacat cagctccacg tgtgccaaca acatcaacca caacacagag    720
ctgctgccca ttgagctgga caccctggtg gggaaaggtc gctttgctga ggtctataag    780

```
gccaagctga agcagaacac ttcagagcag tttgagacag tggcagtcaa gatctttccc      840
tatgaggagt atgcctcttg gaagacagag aaggacatct tctcagacat caatctgaag      900
catgagaaca tactccagtt cctgacggct gaggagcgga agacggagtt ggggaaacaa      960
tactggctga tcaccgcctt ccacgccaag ggcaacctac aggagtacct gacgcggcat     1020
gtcatcagct gggaggacct gcgcaagctg ggcagctccc tcgcccgggg gattgctcac     1080
ctccacagtg atcacactcc atgtgggagg cccaagatgc ccatcgtgca cagggacctc     1140
aagagctcca atatcctcgt gaagaacgac ctaacctgct gcctgtgtga ctttgggctt     1200
tccctgcgtc tggaccctac tctgtctgtg atgacctgg ctaacagtgg gcaggtggga      1260
actgcaagat acatggctcc agaagtccta gaatccagga tgaatttgga gaatgttgag     1320
tccttcaagc agaccgatgt ctactccatg gctctggtgc tctgggaaat gacatctcgc     1380
tgtaatgcag tgggagaagt aaaagattat gagcctccat ttggttccaa ggtgcgggag     1440 caccctgtg tcgaaagcat gaaggacaac gtgttgagag atcgagggcg accagaaatt      1500
cccagcttct ggctcaacca ccagggcatc cagatggtgt gtgagacgtt gactgagtgc     1560
tgggaccacg acccagaggc ccgtctcaca gcccagtgtg tggcagaacg cttcagtgag     1620
ctggagcatc tggacaggct ctcggggagg agctgctcgg aggagaagat tcctgaagac     1680
ggctccctaa acactaccaa a                                               1701

<210> SEQ ID NO 45
<211> LENGTH: 432
<212> TYPE: DNA
<213> ORGANISM: Homo sapiens

<400> SEQUENCE: 45
acgatcccac cgcacgttca gaagtcggtt aataacgaca tgatagtcac tgacaacaac       60
ggtgcagtca agtttccaca actgtgtaaa ttttgtgatg tgagatttc cacctgtgac       120 aaccagaaat cctgcatgag caactgcagc atcacctcca tctgtgagaa gccacaggaa      180
gtctgtgtgg ctgtatggag aaagaatgac gagaacataa cactagagac agtttgccat      240
gaccccaagc tcccctacca tgactttatt ctggaagatg ctgcttctcc aaagtgcatt      300
atgaaggaaa aaaaaaagcc tggtgagact ttcttcatgt gttcctgtag ctctgatgag      360
tgcaatgaca catcatctt ctcagaagaa tataacacca gcaatcctga cttgttgcta       420
gtcatatttc aa                                                         432

<210> SEQ ID NO 46
<211> LENGTH: 1038
<212> TYPE: PRT
<213> ORGANISM: Homo sapiens

<400> SEQUENCE: 46

Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80
```

-continued

```
Lys Gln Gly Cys Trp Ser His Ile Gly Asp Pro Gln Glu Cys His Tyr
                 85                  90                  95
Glu Glu Cys Val Val Thr Thr Thr Pro Pro Ser Ile Gln Asn Gly Thr
            100                 105                 110
Tyr Arg Phe Cys Cys Cys Ser Thr Asp Leu Cys Asn Val Asn Phe Thr
        115                 120                 125
Glu Asn Phe Pro Pro Pro Asp Thr Thr Pro Leu Ser Pro Pro His Ser
130                 135                 140
Phe Asn Arg Asp Glu Thr Ile Ile Ile Ala Leu Ala Ser Val Ser Val
145                 150                 155                 160
Leu Ala Val Leu Ile Val Ala Leu Cys Phe Gly Tyr Arg Met Leu Thr
                165                 170                 175
Gly Asp Arg Lys Gln Gly Leu His Ser Met Asn Met Met Glu Ala Ala
            180                 185                 190
Ala Ser Glu Pro Ser Leu Asp Leu Asp Asn Leu Lys Leu Leu Glu Leu
        195                 200                 205
Ile Gly Arg Gly Arg Tyr Gly Ala Val Tyr Lys Gly Ser Leu Asp Glu
210                 215                 220
Arg Pro Val Ala Val Lys Val Phe Ser Phe Ala Asn Arg Gln Asn Phe
225                 230                 235                 240
Ile Asn Glu Lys Asn Ile Tyr Arg Val Pro Leu Met Glu His Asp Asn
                245                 250                 255
Ile Ala Arg Phe Ile Val Gly Asp Glu Arg Val Thr Ala Asp Gly Arg
            260                 265                 270
Met Glu Tyr Leu Leu Val Met Glu Tyr Tyr Pro Asn Gly Ser Leu Cys
        275                 280                 285
Lys Tyr Leu Ser Leu His Thr Ser Asp Trp Val Ser Ser Cys Arg Leu
290                 295                 300
Ala His Ser Val Thr Arg Gly Leu Ala Tyr Leu His Thr Glu Leu Pro
305                 310                 315                 320
Arg Gly Asp His Tyr Lys Pro Ala Ile Ser His Arg Asp Leu Asn Ser
                325                 330                 335
Arg Asn Val Leu Val Lys Asn Asp Gly Thr Cys Val Ile Ser Asp Phe
            340                 345                 350
Gly Leu Ser Met Arg Leu Thr Gly Asn Arg Leu Val Arg Pro Gly Glu
        355                 360                 365
Glu Asp Asn Ala Ala Ile Ser Glu Val Gly Thr Ile Arg Tyr Met Ala
370                 375                 380
Pro Glu Val Leu Glu Gly Ala Val Asn Leu Arg Asp Cys Glu Ser Ala
385                 390                 395                 400
Leu Lys Gln Val Asp Met Tyr Ala Leu Gly Leu Ile Tyr Trp Glu Ile
                405                 410                 415
Phe Met Arg Cys Thr Asp Leu Phe Pro Gly Glu Ser Val Pro Glu Tyr
            420                 425                 430
Gln Met Ala Phe Gln Thr Glu Val Gly Asn His Pro Thr Phe Glu Asp
        435                 440                 445
Met Gln Val Leu Val Ser Arg Glu Lys Gln Arg Pro Lys Phe Pro Glu
450                 455                 460
Ala Trp Lys Glu Asn Ser Leu Ala Val Arg Ser Leu Lys Glu Thr Ile
465                 470                 475                 480
Glu Asp Cys Trp Asp Gln Asp Ala Glu Ala Arg Leu Thr Ala Gln Cys
                485                 490                 495
Ala Glu Glu Arg Met Ala Glu Leu Met Met Ile Trp Glu Arg Asn Lys
```

```
                500             505              510
Ser Val Ser Pro Thr Val Asn Pro Met Ser Thr Ala Met Gln Asn Glu
        515                 520                 525

Arg Asn Leu Ser His Asn Arg Arg Val Pro Lys Ile Gly Pro Tyr Pro
        530                 535             540

Asp Tyr Ser Ser Ser Ser Tyr Ile Glu Asp Ser Ile His His Thr Asp
545                 550                 555                 560

Ser Ile Val Lys Asn Ile Ser Ser Glu His Ser Met Ser Ser Thr Pro
                565                 570                 575

Leu Thr Ile Gly Glu Lys Asn Arg Asn Ser Ile Asn Tyr Glu Arg Gln
                580                 585                 590

Gln Ala Gln Ala Arg Ile Pro Ser Pro Glu Thr Ser Val Thr Ser Leu
        595                 600                 605

Ser Thr Asn Thr Thr Thr Thr Asn Thr Thr Gly Leu Thr Pro Ser Thr
        610                 615                 620

Gly Met Thr Thr Ile Ser Glu Met Pro Tyr Pro Asp Glu Thr Asn Leu
625                 630                 635                 640

His Thr Thr Asn Val Ala Gln Ser Ile Gly Pro Thr Pro Val Cys Leu
                645                 650                 655

Gln Leu Thr Glu Glu Asp Leu Glu Thr Asn Lys Leu Asp Pro Lys Glu
                660                 665                 670

Val Asp Lys Asn Leu Lys Glu Ser Ser Asp Glu Asn Leu Met Glu His
        675                 680                 685

Ser Leu Lys Gln Phe Ser Gly Pro Asp Pro Leu Ser Ser Thr Ser Ser
        690                 695                 700

Ser Leu Leu Tyr Pro Leu Ile Lys Leu Ala Val Glu Ala Thr Gly Gln
705                 710                 715                 720

Gln Asp Phe Thr Gln Thr Ala Asn Gly Gln Ala Cys Leu Ile Pro Asp
                725                 730                 735

Val Leu Pro Thr Gln Ile Tyr Pro Leu Pro Lys Gln Gln Asn Leu Pro
                740                 745                 750

Lys Arg Pro Thr Ser Leu Pro Leu Asn Thr Lys Asn Ser Thr Lys Glu
        755                 760                 765

Pro Arg Leu Lys Phe Gly Ser Lys His Lys Ser Asn Leu Lys Gln Val
        770                 775             780

Glu Thr Gly Val Ala Lys Met Asn Thr Ile Asn Ala Ala Glu Pro His
785                 790                 795                 800

Val Val Thr Val Thr Met Asn Gly Val Ala Gly Arg Asn His Ser Val
                805                 810                 815

Asn Ser His Ala Ala Thr Thr Gln Tyr Ala Asn Gly Thr Val Leu Ser
                820                 825                 830

Gly Gln Thr Thr Asn Ile Val Thr His Arg Ala Gln Glu Met Leu Gln
                835                 840                 845

Asn Gln Phe Ile Gly Glu Asp Thr Arg Leu Asn Ile Asn Ser Ser Pro
        850                 855                 860

Asp Glu His Glu Pro Leu Leu Arg Arg Glu Gln Gln Ala Gly His Asp
865                 870                 875                 880

Glu Gly Val Leu Asp Arg Leu Val Asp Arg Arg Glu Arg Pro Leu Glu
                885                 890                 895

Gly Gly Arg Thr Asn Ser Asn Asn Asn Ser Asn Pro Cys Ser Glu
        900                 905                 910

Gln Asp Val Leu Ala Gln Gly Val Pro Ser Thr Ala Ala Asp Pro Gly
        915                 920                 925
```

Pro Ser Lys Pro Arg Arg Ala Gln Arg Pro Asn Ser Leu Asp Leu Ser
    930                 935                 940

Ala Thr Asn Val Leu Asp Gly Ser Ser Ile Gln Ile Gly Glu Ser Thr
945                 950                 955                 960

Gln Asp Gly Lys Ser Gly Ser Gly Glu Lys Ile Lys Lys Arg Val Lys
                965                 970                 975

Thr Pro Tyr Ser Leu Lys Arg Trp Arg Pro Ser Thr Trp Val Ile Ser
            980                 985                 990

Thr Glu Ser Leu Asp Cys Glu Val Asn Asn Asn Gly Ser Asn Arg Ala
        995                 1000                1005

Val His Ser Lys Ser Ser Thr Ala Val Tyr Leu Ala Glu Gly Gly
    1010                1015                1020

Thr Ala Thr Thr Met Val Ser Lys Asp Ile Gly Met Asn Cys Leu
    1025                1030                1035

<210> SEQ ID NO 47
<211> LENGTH: 124
<212> TYPE: PRT
<213> ORGANISM: Homo sapiens

<400> SEQUENCE: 47

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Cys Ser Thr Asp Leu
                85                  90                  95

Cys Asn Val Asn Phe Thr Glu Asn Phe Pro Pro Pro Asp Thr Thr Pro
            100                 105                 110

Leu Ser Pro Pro His Ser Phe Asn Arg Asp Glu Thr
        115                 120

<210> SEQ ID NO 48
<211> LENGTH: 3114
<212> TYPE: DNA
<213> ORGANISM: Homo sapiens

<400> SEQUENCE: 48
atgacttcct cgctgcagcg gccctggcgg gtgccctggc taccatggac catcctgctg        60
gtcagcactg cggctgcttc gcagaatcaa gaacggctat gtgcgtttaa agatccgtat       120
cagcaagacc ttgggatagg tgagagtaga atctctcatg aaaatgggac aatattatgc       180
tcgaaaggta gcacctgcta tggccttttgg gagaaatcaa aaggggacat aaatcttgta      240
aaacaaggat gttggtctca cattggagat ccccaagagt gtcactatga agaatgtgta       300
gtaactacca ctcctccctc aattcagaat ggaacatacc gtttctgctg ttgtagcaca       360
gatttatgta atgtcaactt tactgagaat tttccacctc ctgacacaac accactcagt       420
ccacctcatt catttaaccg agatgagaca ataatcattg ctttggcatc agtctctgta       480
ttagctgttt tgatagttgc cttatgcttt ggatacagaa tgttgacagg agaccgtaaa       540

-continued

```
caaggtcttc acagtatgaa catgatggag gcagcagcat ccgaaccctc tcttgatcta    600
gataatctga aactgttgga gctgattggc cgaggtcgat atggagcagt atataaaggc    660
tccttggatg agcgtccagt tgctgtaaaa gtgttttcct ttgcaaaccg tcagaatttt    720
atcaacgaaa agaacattta cagagtgcct ttgatggaac atgacaacat tgcccgcttt    780
atagttggag atgagagagt cactgcagat ggacgcatgg aatatttgct tgtgatggag    840
tactatccca atggatcttt atgcaagtat ttaagtctcc acacaagtga ctgggtaagc    900
tcttgccgtc ttgctcattc tgttactaga ggactggctt atcttcacac agaattacca    960
cgaggagatc attataaacc tgcaatttcc catcgagatt aaacagcag aaatgtccta   1020
gtgaaaaatg atggaacctg tgttattagt gactttggac tgtccatgag gctgactgga   1080
aatagactgg tgcgcccagg ggaggaagat aatgcagcca taagcgaggt tggcactatc   1140
agatatatgg caccagaagt gctagaagga gctgtgaact tgagggactg tgaatcagct   1200
ttgaaacaag tagacatgta tgctcttgga ctaatctatt gggagatatt tatgagatgt   1260
acagacctct tcccagggga atccgtacca gagtaccaga tggcttttca gacagaggtt   1320
ggaaaccatc ccacttttga ggatatgcag gttctcgtgt ctagggaaaa acagagaccc   1380
aagttcccag aagcctggaa agaaaatagc ctggcagtga ggtcactcaa ggagacaatc   1440
gaagactgtt gggaccagga tgcagaggct cggcttactg cacagtgtgc tgaggaaagg   1500
atggctgaac ttatgatgat ttgggaaaga aacaaatctg tgagcccaac agtcaatcca   1560
atgtctactg ctatgcagaa tgaacgcaac ctgtcacata ataggcgtgt gccaaaaatt   1620
ggtccttatc cagattattc ttcctcctca tacattgaag actctatcca tcatactgac   1680
agcatcgtga agaatatttc ctctgagcat tctatgtcca gcacaccttt gactataggg   1740
gaaaaaaacc gaaattcaat taactatgaa cgacagcaag cacaagctcg aatccccagc   1800
cctgaaacaa gtgtcaccag cctctccacc aacacaacaa ccacaaacac cacaggactc   1860
acgccaagta ctggcatgac tactatatct gagatgccat acccagatga aacaaatctg   1920
cataccacaa atgttgcaca gtcaattggg ccaacccctg tctgcttaca gctgacagaa   1980
gaagacttgg aaaccaacaa gctagaccca aaagaagttg ataagaacct caaggaaagc   2040
tctgatgaga atctcatgga gcactctctt aaacagttca gtggcccaga cccactgagc   2100
agtactagtt ctagcttgct ttacccactc ataaaacttg cagtagaagc aactggacag   2160
caggacttca cacagactgc aaatggccaa gcatgtttga ttcctgatgt tctgcctact   2220
cagatctatc ctctccccaa gcagcagaac cttcccaaga gacctactag tttgcctttg   2280
aacaccaaaa attcaacaaa agagccccgg ctaaaatttg gcagcaagca caatcaaac    2340
ttgaaacaag tcgaaactgg agttgccaag atgaatacaa tcaatgcagc agaacctcat   2400
gtggtgacag tcaccatgaa tggtgtggca ggtagaaacc acagtgttaa ctcccatgct   2460
gccacaaccc aatatgccaa tgggacagta ctatctggcc aaacaaccaa catagtgaca   2520
catagggccc aagaaatgtt gcagaatcag tttattggtg aggacacccg gctgaatatt   2580
aattccagtc ctgatgagca tgagcctttt actgagacgag agcaacaagc tggccatgat   2640
gaaggtgttc tggatcgtct tgtggacagg agggaacggc cactagaagg tggccgaact   2700
aattccaata caacaacag caatccatgt tcagaacaag atgttcttgc acagggtgtt    2760
ccaagcacag cagcagatcc tgggccatca aagcccagaa gagcacagag gcctaattct   2820
ctggatcttt cagccacaaa tgtcctggat ggcagcagta tacagatagg tgagtcaaca   2880
```

```
caagatggca aatcaggatc aggtgaaaag atcaagaaac gtgtgaaaac tccctattct    2940
cttaagcggt ggcgcccctc cacctgggtc atctccactg aatcgctgga ctgtgaagtc    3000
aacaataatg gcagtaacag ggcagttcat tccaaatcca gcactgctgt ttaccttgca    3060
gaaggaggca ctgctacaac catggtgtct aaagatatag gaatgaactg tctg          3114
```

<210> SEQ ID NO 49  
<211> LENGTH: 372  
<212> TYPE: DNA  
<213> ORGANISM: Homo sapiens

<400> SEQUENCE: 49

```
tcgcagaatc aagaacggct atgtgcgttt aaagatccgt atcagcaaga ccttgggata     60
ggtgagagta gaatctctca tgaaaatggg acaatattat gctcgaaagg tagcaccctgc   120 tatggccttt gggagaaatc aaaagggac ataaatcttg taaaacaagg atgttggtct    180
cacattggag atccccaaga gtgtcactat gaagaatgtg tagtaactac cactcctccc    240
tcaattcaga atgaacata ccgtttctgc tgttgtagca cagatttatg taatgtcaac     300
tttactgaga attttccacc tcctgacaca acaccactca gtccacctca ttcatttaac    360
cgagatgaga ca                                                         372
```

<210> SEQ ID NO 50  
<211> LENGTH: 573  
<212> TYPE: PRT  
<213> ORGANISM: Homo sapiens

<400> SEQUENCE: 50

```
Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Pro Gly Glu Ser
    130                 135                 140

Ile Trp Met Ala Leu Val Leu Leu Gly Leu Phe Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220
```

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
            245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
            275                 280                 285

His Tyr Leu Thr Gln Tyr Thr Ser Asp Trp Gly Ser Ser Leu Arg Met
            290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
            325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
            355                 360                 365

Pro Thr Gln Pro Gln Gly Pro Ala Ala Ile Met Glu Ala Gly Thr Gln
370                 375                 380

Arg Tyr Met Ala Pro Glu Leu Leu Asp Lys Thr Leu Asp Leu Gln Asp
385                 390                 395                 400

Trp Gly Met Ala Leu Arg Arg Ala Asp Ile Tyr Ser Leu Ala Leu Leu
            405                 410                 415

Leu Trp Glu Ile Leu Ser Arg Cys Pro Asp Leu Arg Pro Asp Ser Ser
            420                 425                 430

Pro Pro Pro Phe Gln Leu Ala Tyr Glu Ala Glu Leu Gly Asn Thr Pro
            435                 440                 445

Thr Ser Asp Glu Leu Trp Ala Leu Ala Val Gln Glu Arg Arg Arg Pro
450                 455                 460

Tyr Ile Pro Ser Thr Trp Arg Cys Phe Ala Thr Asp Pro Asp Gly Leu
465                 470                 475                 480

Arg Glu Leu Leu Glu Asp Cys Trp Asp Ala Asp Pro Glu Ala Arg Leu
            485                 490                 495

Thr Ala Glu Cys Val Gln Gln Arg Leu Ala Ala Leu Ala His Pro Gln
            500                 505                 510

Glu Ser His Pro Phe Pro Glu Ser Cys Pro Arg Gly Cys Pro Pro Leu
            515                 520                 525

Cys Pro Glu Asp Cys Thr Ser Ile Pro Ala Pro Thr Ile Leu Pro Cys
            530                 535                 540

Arg Pro Gln Arg Ser Ala Cys His Phe Ser Val Gln Gln Gly Pro Cys
545                 550                 555                 560

Ser Arg Asn Pro Gln Pro Ala Cys Thr Leu Ser Pro Val
            565                 570

<210> SEQ ID NO 51
<211> LENGTH: 132
<212> TYPE: PRT
<213> ORGANISM: Homo sapiens

<400> SEQUENCE: 51

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu

```
            20                  25                  30
Pro Arg Ala Ile Arg Cys Leu Tyr Ser Arg Cys Cys Phe Gly Ile Trp
         35                  40                  45

Asn Leu Thr Gln Asp Arg Ala Gln Val Glu Met Gln Gly Cys Arg Asp
 50                  55                  60

Ser Asp Glu Pro Gly Cys Glu Ser Leu His Cys Asp Pro Ser Pro Arg
 65                  70                  75                  80

Ala His Pro Ser Pro Gly Ser Thr Leu Phe Thr Cys Ser Cys Gly Thr
                 85                  90                  95

Asp Phe Cys Asn Ala Asn Tyr Ser His Leu Pro Pro Pro Gly Ser Pro
             100                 105                 110

Gly Thr Pro Gly Ser Gln Gly Pro Gln Ala Ala Pro Gly Glu Ser Ile
         115                 120                 125

Trp Met Ala Leu
    130

<210> SEQ ID NO 52
<211> LENGTH: 1719
<212> TYPE: DNA
<213> ORGANISM: Homo sapiens

<400> SEQUENCE: 52
atgctagggt cttgggggct ttgggcatta cttcccacag ctgtggaagc accccaaac       60 aggcgaacct gtgtgttctt tgaggcccct ggagtgcggg gaagcacaaa gacactggga     120
gagctgctag atacaggcac agagctcccc agagctatcc gctgcctcta cagccgctgc     180
tgctttggga tctggaacct gacccaagac cgggcacagg tggaaatgca aggatgccga     240
gacagtgatg agccaggctg tgagtccctc cactgtgacc caagtccccg agcccacccc     300
agccctggct ccactctctt cacctgctcc tgtggcactg acttctgcaa tgccaattac     360
agccatctgc ctcctccagg gagccctggg actcctggct cccagggtcc caggctgcc    420 ccaggtgagt ccatctggat ggcactggtg ctgctggggc tgttcctcct cctcctgctg     480
ctgctgggca gcatcatctt ggccctgcta cagcgaaaga actacagagt gcgaggtgag     540
ccagtgccag agccaaggcc agactcaggc agggactgga gtgtggagct gcaggagctg     600
cctgagctgt gtttctccca ggtaatccgg gaaggaggtc atgcagtggt ttgggccggg     660
cagctgcaag gaaaactggt tgccatcaag gccttccac cgaggtctgt ggctcagttc     720
caagctgaga gagcattgta cgaacttcca ggcctacagc acgaccacat tgtccgattt     780
atcactgcca gccggggggg tcctggccgc tgctctctg ggcccctgct ggtactggaa     840
ctgcatccca agggctccct gtgccactac ttgacccagt acaccagtga ctggggaagt     900
tccctgcgga tggcactgtc cctggcccag ggcctgcat ttctccatga ggagcgctgg     960
cagaatggcc aatataaacc aggtattgcc caccgagatc tgagcagcca gaatgtgctc    1020
attcgggaag atgatcgtg tgccattgga gacctgggcc ttgccttggt gctccctggc    1080
ctcactcagc cccctgcctg gacccctact caaccacaag gcccagctgc catcatggaa    1140
gctggcaccc agaggtacat ggcaccgaga ctcttggaca agactctgga cctacaggat    1200
tggggcatgg ccctccgacg agctgatatt tactcttttgg ctctgctcct gtgggagata    1260
ctgagccgct gcccagattt gaggcctgac agcagtccac cacccttcca actggcctat    1320
gaggcagaac tggcaatac ccctacctct gatgagctat ggcccttggc agtgcaggag    1380
aggaggcgtc cctacatccc atccacctgg cgctgctttg ccacagaccc tgatgggctg    1440
```

```
agggagctcc tagaagactg ttgggatgca gacccagaag cacggctgac agctgagtgt    1500
gtacagcagc gcctggctgc cttggcccat cctcaagaga gccacccctt tccagagagc    1560
tgtccacgtg gctgcccacc tctctgccca gaagactgta cttcaattcc tgccctacc     1620 atcctcccct gtaggcctca gcggagtgcc tgccacttca gcgttcagca aggcccttgt    1680
tccaggaatc ctcagcctgc ctgtacccctt tctcctgtg                          1719
```

<210> SEQ ID NO 53
<211> LENGTH: 396
<212> TYPE: DNA
<213> ORGANISM: Homo sapiens

<400> SEQUENCE: 53

```
cccccaaaca ggcgaacctg tgtgttcttt gaggcccctg gagtgcgggg aagcacaaag     60
acactgggag agctgctaga tacaggcaca gagctcccca gagctatccg ctgcctctac    120
agccgctgct gctttgggat ctggaacctg acccaagacc gggcacaggt ggaaatgcaa    180
ggatgccgag acagtgatga gccaggctgt gagtccctcc actgtgaccc aagtccccga    240
gcccacccca gccctggctc cactctcttc acctgctcct gtggcactga cttctgcaat    300
gccaattaca gccatctgcc tcctccaggg agccctggga ctcctggctc ccagggtccc    360
caggctgccc caggtgagtc catctggatg gcactg                              396
```

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Gly
1

<210> SEQ ID NO 59
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 59

Gly Gly Gly Gly
1

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Thr Gly Gly Gly Gly
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Gly Gly Gly Gly
1               5

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Gly Gly Gly
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Gly Gly Gly
1

<210> SEQ ID NO 64

<400> SEQUENCE: 64

000

<210> SEQ ID NO 65

<400> SEQUENCE: 65

000
```

<210> SEQ ID NO 66

<400> SEQUENCE: 66

000

<210> SEQ ID NO 67
<211> LENGTH: 592
<212> TYPE: PRT
<213> ORGANISM: Homo sapiens

<400> SEQUENCE: 67

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
            100                 105                 110

Trp Arg Lys Asn Asp Glu Asn Ile Thr Leu Glu Thr Val Cys His Asp
        115                 120                 125

Pro Lys Leu Pro Tyr His Asp Phe Ile Leu Glu Asp Ala Ala Ser Pro
    130                 135                 140

Lys Cys Ile Met Lys Glu Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
            180                 185                 190

Thr Gly Ile Ser Leu Leu Pro Pro Leu Gly Val Ala Ile Ser Val Ile
        195                 200                 205

Ile Ile Phe Tyr Cys Tyr Arg Val Asn Arg Gln Gln Lys Leu Ser Ser
    210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
            260                 265                 270

Thr Leu Val Gly Lys Gly Arg Phe Ala Glu Val Tyr Lys Ala Lys Leu
        275                 280                 285

Lys Gln Asn Thr Ser Glu Gln Phe Glu Thr Val Ala Val Lys Ile Phe
    290                 295                 300

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
                325                 330                 335

Glu Arg Lys Thr Glu Leu Gly Lys Gln Tyr Trp Leu Ile Thr Ala Phe
```

```
            340                 345                 350
His Ala Lys Gly Asn Leu Gln Glu Tyr Leu Thr Arg His Val Ile Ser
        355                 360                 365

Trp Glu Asp Leu Arg Lys Leu Gly Ser Ser Leu Ala Arg Gly Ile Ala
370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
                405                 410                 415

Thr Cys Cys Leu Cys Asp Phe Gly Leu Ser Leu Arg Leu Asp Pro Thr
            420                 425                 430

Leu Ser Val Asp Asp Leu Ala Asn Ser Gly Gln Val Gly Thr Ala Arg
        435                 440                 445

Tyr Met Ala Pro Glu Val Leu Glu Ser Arg Met Asn Leu Glu Asn Val
    450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
                485                 490                 495

Pro Pro Phe Gly Ser Lys Val Arg Glu His Pro Cys Val Glu Ser Met
            500                 505                 510

Lys Asp Asn Val Leu Arg Asp Arg Gly Arg Pro Glu Ile Pro Ser Phe
        515                 520                 525

Trp Leu Asn His Gln Gly Ile Gln Met Val Cys Glu Thr Leu Thr Glu
    530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
                565                 570                 575

Cys Ser Glu Glu Lys Ile Pro Glu Asp Gly Ser Leu Asn Thr Thr Lys
            580                 585                 590

<210> SEQ ID NO 68
<211> LENGTH: 169
<212> TYPE: PRT
<213> ORGANISM: Homo sapiens

<400> SEQUENCE: 68

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
                20                  25                  30

Arg His Ile Asn Asn Asp Met Ile Val Thr Asp Asn Asn Gly Ala Val
            35                  40                  45

Lys Phe Pro Gln Leu Cys Lys Phe Cys Asp Val Arg Phe Ser Thr Cys
        50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125
```

```
Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp Leu Leu Leu Val Ile Phe Gln
            165
```

<210> SEQ ID NO 69
<211> LENGTH: 1776
<212> TYPE: DNA
<213> ORGANISM: Homo sapiens

<400> SEQUENCE: 69

```
atgggtcggg ggctgctcag gggcctgtgg ccgctgcaca tcgtcctgtg gacgcgtatc     60
gccagcacga tcccaccgca cgttcagaag tcggatgtgg aaatggaggc cagaaaagat    120
gaaatcatct gccccagctg taataggact gcccatccac tgagacatat taataacgac    180
atgatagtca ctgacaacaa cggtgcagtc aagtttccac aactgtgtaa attttgtgat    240
gtgagatttt ccacctgtga caaccagaaa tcctgcatga gcaactgcag catcacctcc    300
atctgtgaga agccacagga agtctgtgtg gctgtatgga gaaagaatga cgagaacata    360
acactagaga cagtttgcca tgaccccaag ctcccctacc atgactttat tctggaagat    420
gctgcttctc caaagtgcat tatgaaggaa aaaaaaaagc tggtgagac tttcttcatg    480
tgttcctgta gctctgatga gtgcaatgac aacatcatct tctcagaaga atataacacc    540
agcaatcctg acttgttgct agtcatattt caagtgacag gcatcagcct cctgccacca    600
ctgggagttg ccatatctgt catcatcatc ttctactgct accgcgttaa ccggcagcag    660
aagctgagtt caactgggga aaccggcaag acgcggaagc tcatggagtt cagcgagcac    720
tgtgccatca tcctggaaga tgaccgctct gacatcagct ccacgtgtgc caacaacatc    780
aaccacaaca cagagctgct gcccattgag ctggacaccc tggtggggaa aggtcgcttt    840
gctgaggtct ataaggccaa gctgaagcag aacacttcag agcagtttga acagtggca    900
gtcaagatct ttccctatga ggagtatgcc tcttggaaga cagagaagga catcttctca    960
gacatcaatc tgaagcatga aacatactc cagttcctga cggctgagga gcggaagacg   1020
gagttgggga acaatactgc tgatcacc gccttccacg ccaagggcaa cctacaggag   1080
tacctgacgc ggcatgtcat cagctgggag gacctgcgca agctgggcag ctccctcgcc   1140
cgggggattg ctcacctcca cagtgatcac actccatgtg ggaggcccaa gatgcccatc   1200
gtgcacaggg acctcaagag ctccaatatc ctcgtgaaga cgacctaac ctgctgcctg   1260
tgtgactttg gcttttccct gcgtctggac cctactctgt ctgtggatga cctggctaac   1320
agtgggcagt gggaactgc aagatacatg gctccagaag tcctagaatc caggatgaat   1380
ttggagaatg ttgagtcctt caagcagacc gatgtctact ccatggctct ggtgctctgg   1440
gaaatgacat ctcgctgtaa tgcagtggga gaagtaaaag attatgagcc tccatttggt   1500
tccaaggtgc gggagcaccc ctgtgtcgaa agcatgaagg acaacgtgtt gagagatcga   1560
gggcgaccag aaattcccag cttctggctc aaccaccagg gcatccagat ggtgtgtgag   1620
acgttgactg agtgctggga ccacgaccca gaggcccgtc tcacagccca gtgtgtggca   1680
gaacgcttca gtgagctgga gcatctggac aggctctcgg ggaggagctg ctcggaggag   1740
aagattcctg aagacggctc cctaaacact accaaa                             1776
```

<210> SEQ ID NO 70

<211> LENGTH: 507
<212> TYPE: DNA
<213> ORGANISM: Homo sapiens

<400> SEQUENCE: 70

```
acgatcccac cgcacgttca gaagtcggat gtggaaatgg aggcccagaa agatgaaatc      60
atctgcccca gctgtaatag gactgcccat ccactgagac atattaataa cgacatgata     120
gtcactgaca caacggtgc agtcaagttt ccacaactgt gtaaattttg tgatgtgaga      180
ttttccacct gtgacaacca gaaatcctgc atgagcaact gcagcatcac ctccatctgt     240
gagaagccac aggaagtctg tgtggctgta tggagaaaga tgacgagaa cataacacta      300
gagacagttt gccatgaccc caagctcccc taccatgact ttattctgga agatgctgct     360
tctccaaagt gcattatgaa ggaaaaaaaa aagcctggtg agactttctt catgtgttcc     420
tgtagctctg atgagtgcaa tgacaacatc atcttctcag aagaatataa caccagcaat     480
cctgacttgt tgctagtcat atttcaa                                        507
```

<210> SEQ ID NO 71
<211> LENGTH: 530
<212> TYPE: PRT
<213> ORGANISM: Homo sapiens

<400> SEQUENCE: 71

```
Met Thr Ser Ser Leu Gln Arg Pro Trp Arg Val Pro Trp Leu Pro Trp
1               5                   10                  15

Thr Ile Leu Leu Val Ser Thr Ala Ala Ala Ser Gln Asn Gln Glu Arg
            20                  25                  30

Leu Cys Ala Phe Lys Asp Pro Tyr Gln Gln Asp Leu Gly Ile Gly Glu
        35                  40                  45

Ser Arg Ile Ser His Glu Asn Gly Thr Ile Leu Cys Ser Lys Gly Ser
    50                  55                  60

Thr Cys Tyr Gly Leu Trp Glu Lys Ser Lys Gly Asp Ile Asn Leu Val
65                  70                  75                  80

Lys Gln Gly Cys Trp Ser His Ile Gly Asp Pro Gln Glu Cys His Tyr
                85                  90                  95

Glu Glu Cys Val Val Thr Thr Pro Pro Ser Ile Gln Asn Gly Thr
            100                 105                 110

Tyr Arg Phe Cys Cys Cys Ser Thr Asp Leu Cys Asn Val Asn Phe Thr
        115                 120                 125

Glu Asn Phe Pro Pro Pro Asp Thr Thr Pro Leu Ser Pro Pro His Ser
    130                 135                 140

Phe Asn Arg Asp Glu Thr Ile Ile Ile Ala Leu Ala Ser Val Ser Val
145                 150                 155                 160

Leu Ala Val Leu Ile Val Ala Leu Cys Phe Gly Tyr Arg Met Leu Thr
                165                 170                 175

Gly Asp Arg Lys Gln Gly Leu His Ser Met Asn Met Met Glu Ala Ala
            180                 185                 190

Ala Ser Glu Pro Ser Leu Asp Leu Asp Asn Leu Lys Leu Leu Glu Leu
        195                 200                 205

Ile Gly Arg Gly Arg Tyr Gly Ala Val Tyr Lys Gly Ser Leu Asp Glu
    210                 215                 220

Arg Pro Val Ala Val Lys Val Phe Ser Phe Ala Asn Arg Gln Asn Phe
225                 230                 235                 240

Ile Asn Glu Lys Asn Ile Tyr Arg Val Pro Leu Met Glu His Asp Asn
                245                 250                 255
```

-continued

```
Ile Ala Arg Phe Ile Val Gly Asp Glu Arg Val Thr Ala Asp Gly Arg
            260                 265                 270

Met Glu Tyr Leu Leu Val Met Glu Tyr Tyr Pro Asn Gly Ser Leu Cys
            275                 280                 285

Lys Tyr Leu Ser Leu His Thr Ser Asp Trp Val Ser Ser Cys Arg Leu
            290                 295                 300

Ala His Ser Val Thr Arg Gly Leu Ala Tyr Leu His Thr Glu Leu Pro
305                 310                 315                 320

Arg Gly Asp His Tyr Lys Pro Ala Ile Ser His Arg Asp Leu Asn Ser
            325                 330                 335

Arg Asn Val Leu Val Lys Asn Asp Gly Thr Cys Val Ile Ser Asp Phe
            340                 345                 350

Gly Leu Ser Met Arg Leu Thr Gly Asn Arg Leu Val Arg Pro Gly Glu
            355                 360                 365

Glu Asp Asn Ala Ala Ile Ser Glu Val Gly Thr Ile Arg Tyr Met Ala
            370                 375                 380

Pro Glu Val Leu Glu Gly Ala Val Asn Leu Arg Asp Cys Glu Ser Ala
385                 390                 395                 400

Leu Lys Gln Val Asp Met Tyr Ala Leu Gly Leu Ile Tyr Trp Glu Ile
            405                 410                 415

Phe Met Arg Cys Thr Asp Leu Phe Pro Gly Glu Ser Val Pro Glu Tyr
            420                 425                 430

Gln Met Ala Phe Gln Thr Glu Val Gly Asn His Pro Thr Phe Glu Asp
            435                 440                 445

Met Gln Val Leu Val Ser Arg Glu Lys Gln Arg Pro Lys Phe Pro Glu
            450                 455                 460

Ala Trp Lys Glu Asn Ser Leu Ala Val Arg Ser Leu Lys Glu Thr Ile
465                 470                 475                 480

Glu Asp Cys Trp Asp Gln Asp Ala Glu Ala Arg Leu Thr Ala Gln Cys
            485                 490                 495

Ala Glu Glu Arg Met Ala Glu Leu Met Met Ile Trp Glu Arg Asn Lys
            500                 505                 510

Ser Val Ser Pro Thr Val Asn Pro Met Ser Thr Ala Met Gln Asn Glu
            515                 520                 525

Arg Arg
    530

<210> SEQ ID NO 72
<211> LENGTH: 124
<212> TYPE: PRT
<213> ORGANISM: Homo sapiens

<400> SEQUENCE: 72

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
            35                  40                  45

Gly Asp Ile Asn Leu Val Lys Gln Gly Cys Trp Ser His Ile Gly Asp
            50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Cys Ser Thr Asp Leu
```

```
                     85                  90                  95
Cys Asn Val Asn Phe Thr Glu Asn Phe Pro Pro Pro Asp Thr Thr Pro
            100                 105                 110

Leu Ser Pro Pro His Ser Phe Asn Arg Asp Glu Thr
            115                 120

<210> SEQ ID NO 73
<211> LENGTH: 1590
<212> TYPE: DNA
<213> ORGANISM: Homo sapiens

<400> SEQUENCE: 73
atgacttcct cgctgcagcg gccctggcgg gtgccctggc taccatggac catcctgctg      60
gtcagcactg cggctgcttc gcagaatcaa gaacggctat gtgcgtttaa agatccgtat     120
cagcaagacc ttgggatagg tgagagtaga atctctcatg aaaatgggac aatattatgc     180
tcgaaaggta gcacctgcta tggcctttgg gagaaatcaa aaggggacat aaatcttgta     240
aaacaaggat gttggtctca cattggagat ccccaagagt gtcactatga agaatgtgta     300
gtaactacca ctcctccctc aattcagaat ggaacatacc gtttctgctg ttgtagcaca     360
gatttatgta atgtcaactt tactgagaat tttccacctc ctgacacaac accactcagt     420
ccacctcatt catttaaccg agatgagaca ataatcattg ctttggcatc agtctctgta     480
ttagctgttt tgatagttgc cttatgcttt ggatacagaa tgttgacagg agaccgtaaa     540
caaggtcttc acagtatgaa catgatggag gcagcagcat ccgaaccctc tcttgatcta     600
gataatctga aactgttgga gctgattggc cgaggtcgat atggagcagt atataaaggc     660
tccttggatg agcgtccagt tgctgtaaaa gtgttttcct ttgcaaaccg tcagaatttt     720
atcaacgaaa agaacattta cagagtgcct tgatggaac atgacaacat tgcccgcttt     780
atagttggag atgagagagt cactgcagat ggacgcatgg aatatttgct tgtgatggag     840
tactatccca tggatctttt atgcaagtat ttaagtctcc acacaagtga ctgggtaagc     900
tcttgccgtc ttgctcattc tgttactaga ggactggctt atcttcacac agaattacca     960
cgaggagatc attataaacc tgcaatttcc catcgagatt taaacagcag aaatgtccta    1020
gtgaaaaatg atggaaacctg tgttattagt gactttggac tgtccatgag gctgactgga    1080
aatagactgg tgcgcccagg ggaggaagat aatgcagcca taagcgaggt tggcactatc    1140
agatatatgg caccagaagt gctagaagga gctgtgaact tgagggactg tgaatcagct    1200
ttgaaacaag tagacatgta tgctcttgga ctaatctatt gggagatatt tatgagatgt    1260
acagacctct tcccagggga atccgtacca gagtaccaga tggcttttca gacagaggtt    1320
ggaaaccatc ccacttttga ggatatgcag gttctcgtgt ctagggaaaa acagagaccc    1380
aagttcccag aagcctggaa agaaaatagc ctggcagtga ggtcactcaa ggagacaatc    1440
gaagactgtt gggaccagga tgcagaggct cggcttactg cacagtgtgc tgaggaaagg    1500
atggctgaac ttatgatgat ttgggaaaga aacaaatctg tgagcccaac agtcaatcca    1560
atgtctactg ctatgcagaa tgaacgtagg                                      1590

<210> SEQ ID NO 74
<211> LENGTH: 372
<212> TYPE: DNA
<213> ORGANISM: Homo sapiens

<400> SEQUENCE: 74
tcgcagaatc aagaacggct atgtgcgttt aaagatccgt atcagcaaga ccttgggata      60
```

-continued

```
ggtgagagta gaatctctca tgaaaatggg acaatattat gctcgaaagg tagcacctgc    120
tatggccttt gggagaaatc aaagggac   ataaatcttg taaaacaagg atgttggtct    180
cacattggag atccccaaga gtgtcactat gaagaatgtg tagtaactac cactcctccc    240
tcaattcaga atgaacata  ccgtttctgc tgttgtagca cagatttatg taatgtcaac    300
tttactgaga attttccacc tcctgacaca acaccactca gtccacctca ttcatttaac    360
cgagatgaga ca                                                         372
```

<210> SEQ ID NO 75
<211> LENGTH: 478
<212> TYPE: PRT
<213> ORGANISM: Homo sapiens

<400> SEQUENCE: 75

```
Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
            20                  25                  30

Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Pro Gly Ser
        115                 120                 125

Pro Gly Thr Pro Gly Ser Gln Gly Pro Gln Ala Ala Pro Gly Glu Ser
    130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
```

```
              305                 310                 315                 320
        Gln Asn Gly Gln Tyr Lys Pro Gly Ile Ala His Arg Asp Leu Ser Ser
                        325                 330                 335

Gln Asn Val Leu Ile Arg Glu Asp Gly Ser Cys Ala Ile Gly Asp Leu
                        340                 345                 350

Gly Leu Ala Leu Val Leu Pro Gly Leu Thr Gln Pro Pro Ala Trp Thr
                        355                 360                 365

Pro Thr Gln Pro Gln Gly Pro Ala Ala Ile Met Glu Ala Gly Thr Gln
                        370                 375                 380

Arg Tyr Met Ala Pro Glu Leu Leu Asp Lys Thr Leu Asp Leu Gln Asp
        385                 390                 395                 400

Trp Gly Met Ala Leu Arg Arg Ala Asp Ile Tyr Ser Leu Ala Leu Leu
                            405                 410                 415

Leu Trp Glu Ile Leu Ser Arg Cys Pro Asp Leu Arg Pro Ala Val His
                        420                 425                 430

His Pro Ser Asn Trp Pro Met Arg Gln Asn Trp Ala Ile Pro Leu Pro
                        435                 440                 445

Leu Met Ser Tyr Gly Pro Trp Gln Cys Arg Arg Gly Gly Val Pro Thr
                        450                 455                 460

Ser His Pro Pro Gly Ala Ala Leu Pro Gln Thr Leu Met Gly
        465                 470                 475

<210> SEQ ID NO 76
<211> LENGTH: 132
<212> TYPE: PRT
<213> ORGANISM: Homo sapiens

<400> SEQUENCE: 76

Pro Pro Asn Arg Arg Thr Cys Val Phe Phe Glu Ala Pro Gly Val Arg
        1               5                   10                  15

Gly Ser Thr Lys Thr Leu Gly Glu Leu Leu Asp Thr Gly Thr Glu Leu
                        20                  25                  30

Pro Arg Ala Ile Arg Cys Leu Tyr Ser Arg Cys Cys Phe Gly Ile Trp
                        35                  40                  45

Asn Leu Thr Gln Asp Arg Ala Gln Val Glu Met Gln Gly Cys Arg Asp
                    50                  55                  60

Ser Asp Glu Pro Gly Cys Glu Ser Leu His Cys Asp Pro Ser Pro Arg
        65                  70                  75                  80

Ala His Pro Ser Pro Gly Ser Thr Leu Phe Thr Cys Ser Cys Gly Thr
                        85                  90                  95

Asp Phe Cys Asn Ala Asn Tyr Ser His Leu Pro Pro Gly Ser Pro
                        100                 105                 110

Gly Thr Pro Gly Ser Gln Gly Pro Gln Ala Ala Pro Gly Glu Ser Ile
                        115                 120                 125

Trp Met Ala Leu
                130

<210> SEQ ID NO 77
<211> LENGTH: 1434
<212> TYPE: DNA
<213> ORGANISM: Homo sapiens

<400> SEQUENCE: 77
atgctagggt ctttggggct ttggcatta cttcccacag ctgtggaagc accccaaac     60 aggcgaacct gtgtgttctt tgaggcccct ggagtgcggg aagcacaaa gacactggga   120
```

```
gagctgctag atacaggcac agagctcccc agagctatcc gctgcctcta cagccgctgc    180
tgctttggga tctggaacct gacccaagac cgggcacagg tggaaatgca aggatgccga    240
gacagtgatg agccaggctg tgagtccctc cactgtgacc caagtccccg agcccacccc    300
agccctggct ccactctctt cacctgctcc tgtggcactg acttctgcaa tgccaattac    360
agccatctgc ctcctccagg gagccctggg actcctggct cccagggtcc ccaggctgcc    420
ccaggtgagt ccatctggat ggcactggtg ctgctgggc tgttcctcct cctcctgctg    480
ctgctgggca gcatcatctt ggccctgcta cagcgaaaga actacagagt gcgaggtgag    540
ccagtgccag agccaaggcc agactcaggc agggactgga gtgtggagct gcaggagctg    600
cctgagctgt gtttctccca ggtaatccgg gaaggaggtc atgcagtggt ttgggccggg    660
cagctgcaag gaaaactggt tgccatcaag gccttccac cgaggtctgt ggctcagttc     720
caagctgaga gagcattgta cgaacttcca ggcctacagc acgaccacat tgtccgattt    780
atcactgcca gccgggggg tcctggccgc ctgctctctg gcccctgct ggtactggaa      840 ctgcatccca agggctccct gtgccactac ttgacccagt acaccagtga ctggggaagt    900
tccctgcgga tggcactgtc cctggcccag ggcctggcat ttctccatga ggagcgctgg    960
cagaatggcc aatataaacc aggtattgcc accgagatc tgagcagcca gaatgtgctc      1020
attcgggaag atggatcgtg tgccattgga gacctgggcc ttgccttggt gctccctggc    1080
ctcactcagc cccctgcctg gacccctact caaccacaag gcccagctgc catcatggaa    1140
gctggcaccc agaggtacat ggaccagag ctcttggaca agactctgga cctacaggat     1200
tggggcatgg ccctccgacg agctgatatt tactcttttgg ctctgctcct gtgggagata   1260
ctgagccgct gcccagattt gaggcctgca gtccaccacc cttccaactg gcctatgagg    1320
cagaactggg caatacccct acctctgatg agctatgggc cttggcagtg caggagagga    1380
ggcgtcccta catcccatcc acctggcgct gctttgccac agaccctgat gggc           1434

<210> SEQ ID NO 78
<211> LENGTH: 396
<212> TYPE: DNA
<213> ORGANISM: Homo sapiens

<400> SEQUENCE: 78
cccccaaaca ggcgaacctg tgtgttcttt gaggcccctg gagtgcgggg aagcacaaag     60
acactgggag agctgctaga tacaggcaca gagctcccca gagctatccg ctgcctctac    120
agccgctgct gctttgggat ctggaacctg acccaagacc gggcacaggt ggaaatgcaa    180
ggatgccgag acagtgatga gccaggctgt gagtccctcc actgtgaccc aagtccccga    240
gcccacccca gccctggctc cactctcttc acctgctcct gtggcactga cttctgcaat    300
gccaattaca gccatctgcc tcctccaggg agccctggga ctcctggctc ccagggtccc    360
caggctgccc caggtgagtc catctggatg cactg                              396

<210> SEQ ID NO 79
<211> LENGTH: 478
<212> TYPE: PRT
<213> ORGANISM: Homo sapiens

<400> SEQUENCE: 79

Met Leu Gly Ser Leu Gly Leu Trp Ala Leu Leu Pro Thr Ala Val Glu
1               5                   10                  15

Ala Pro Pro Asn Arg Arg Thr Cys Val Phe Phe Glu Ala Pro Gly Val
            20                  25                  30
```

```
Arg Gly Ser Thr Lys Thr Leu Gly Glu Leu Leu Asp Thr Gly Thr Glu
        35                  40                  45

Leu Pro Arg Ala Ile Arg Cys Leu Tyr Ser Arg Cys Cys Phe Gly Ile
    50                  55                  60

Trp Asn Leu Thr Gln Asp Arg Ala Gln Val Glu Met Gln Gly Cys Arg
65                  70                  75                  80

Asp Ser Asp Glu Pro Gly Cys Glu Ser Leu His Cys Asp Pro Ser Pro
                85                  90                  95

Arg Ala His Pro Ser Pro Gly Ser Thr Leu Phe Thr Cys Ser Cys Gly
            100                 105                 110

Thr Asp Phe Cys Asn Ala Asn Tyr Ser His Leu Pro Pro Gly Ser
            115                 120                 125

Pro Gly Thr Pro Gly Ser Gln Gly Pro Gln Ala Ala Pro Gly Glu Ser
        130                 135                 140

Ile Trp Met Ala Leu Val Leu Leu Gly Leu Phe Leu Leu Leu Leu Leu
145                 150                 155                 160

Leu Leu Gly Ser Ile Ile Leu Ala Leu Leu Gln Arg Lys Asn Tyr Arg
                165                 170                 175

Val Arg Gly Glu Pro Val Pro Glu Pro Arg Pro Asp Ser Gly Arg Asp
            180                 185                 190

Trp Ser Val Glu Leu Gln Glu Leu Pro Glu Leu Cys Phe Ser Gln Val
        195                 200                 205

Ile Arg Glu Gly Gly His Ala Val Val Trp Ala Gly Gln Leu Gln Gly
    210                 215                 220

Lys Leu Val Ala Ile Lys Ala Phe Pro Pro Arg Ser Val Ala Gln Phe
225                 230                 235                 240

Gln Ala Glu Arg Ala Leu Tyr Glu Leu Pro Gly Leu Gln His Asp His
                245                 250                 255

Ile Val Arg Phe Ile Thr Ala Ser Arg Gly Gly Pro Gly Arg Leu Leu
            260                 265                 270

Ser Gly Pro Leu Leu Val Leu Glu Leu His Pro Lys Gly Ser Leu Cys
        275                 280                 285

His Tyr Leu Thr Gln Tyr Thr Ser Asp Trp Gly Ser Ser Leu Arg Met
    290                 295                 300

Ala Leu Ser Leu Ala Gln Gly Leu Ala Phe Leu His Glu Glu Arg Trp
305                 310                 315                 320

Gln Asn Gly Gln Tyr Lys Pro Gly Ile Ala His Arg Asp Leu Ser Ser
                325                 330                 335

Gln Asn Val Leu Ile Arg Glu Asp Gly Ser Cys Ala Ile Gly Asp Leu
            340                 345                 350

Gly Leu Ala Leu Val Leu Pro Gly Leu Thr Gln Pro Pro Ala Trp Thr
        355                 360                 365

Pro Thr Gln Pro Gln Gly Pro Ala Ala Ile Met Glu Asp Pro Asp Gly
    370                 375                 380

Leu Arg Glu Leu Leu Glu Asp Cys Trp Asp Ala Asp Pro Glu Ala Arg
385                 390                 395                 400

Leu Thr Ala Glu Cys Val Gln Gln Arg Leu Ala Ala Leu Ala His Pro
                405                 410                 415

Gln Glu Ser His Pro Phe Pro Glu Ser Cys Pro Arg Gly Cys Pro Pro
            420                 425                 430

Leu Cys Pro Glu Asp Cys Thr Ser Ile Pro Ala Pro Thr Ile Leu Pro
        435                 440                 445
```

Cys Arg Pro Gln Arg Ser Ala Cys His Phe Ser Val Gln Gln Gly Pro
    450                 455                 460

Cys Ser Arg Asn Pro Gln Pro Ala Cys Thr Leu Ser Pro Val
465                 470                 475

<210> SEQ ID NO 80
<211> LENGTH: 132
<212> TYPE: PRT
<213> ORGANISM: Homo sapiens

<400> SEQUENCE: 80

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu
    130

<210> SEQ ID NO 81
<211> LENGTH: 1434
<212> TYPE: DNA
<213> ORGANISM: Homo sapiens

<400> SEQUENCE: 81
atgctagggt ctttggggct ttgggcatta cttcccacag ctgtggaagc acccccaaac        60
aggcgaacct gtgtgttctt tgaggcccct ggagtgcggg gaagcacaaa gacactggga       120
gagctgctag atacaggcac agagctcccc agagctatcc gctgcctcta cagccgctgc       180
tgctttggga tctggaacct gacccaagac cgggcacagg tggaaatgca aggatgccga       240
gacagtgatg agccaggctg tgagtccctc cactgtgacc caagtccccg agcccacccc       300
agccctggct ccactctctt cacctgctcc tgtggcactg acttctgcaa tgccaattac       360
agccatctgc ctcctccagg gagccctggg actcctggct cccagggtcc ccaggctgcc       420
ccaggtgagt ccatctggat ggcactggtg ctgctggggc tgttcctcct cctcctgctg       480
ctgctgggca gcatcatctt ggccctgcta cagcgaaaga actacagagt gcgaggtgag       540
ccagtgccag agccaaggcc agactcaggc agggactgga gtgtggagct gcaggagctg       600
cctgagctgt gtttctccca ggtaatccgg aaggaggtc atgcagtggt ttgggccggg       660
cagctgcaag gaaaactggt tgccatcaag gccttccac cgaggtctgt ggctcagttc       720
caagctgaga gagcattgta cgaacttcca ggcctacagc acgaccacat tgtccgattt       780
atcactgcca gccggggggg tcctggccgc ctgctctctg gcccctgct ggtactggaa       840 ctgcatccca agggctccct gtgccactac ttgacccagt acaccagtga ctggggaagt       900

```
tccctgcgga tggcactgtc cctggcccag ggcctggcat ttctccatga ggagcgctgg      960
cagaatggcc aatataaacc aggtattgcc caccgagatc tgagcagcca gaatgtgctc     1020
attcgggaag atggatcgtg tgccattgga gacctgggcc ttgccttggt gctccctggc     1080
ctcactcagc ccctgcctg  acccctact  caaccacaag gcccagctgc catcatggaa     1140
gaccctgatg ggctgaggga gctcctagaa gactgttggg atgcagaccc agaagcacgg     1200
ctgacagctg agtgtgtaca gcagcgcctg gctgccttgg cccatcctca agagagccac     1260 cccttccag  agagctgtcc acgtggctgc ccacctctct gcccagaaga ctgtacttca     1320
attcctgccc ctaccatcct ccctgtagg  cctcagcgga gtgcctgcca cttcagcgtt     1380
cagcaaggcc cttgttccag gaatcctcag cctgcctgta cccttctcc  tgtg           1434
```

<210> SEQ ID NO 82
<211> LENGTH: 396
<212> TYPE: DNA
<213> ORGANISM: Homo sapiens

<400> SEQUENCE: 82

```
cccccaaaca ggcgaacctg tgtgttcttt gaggcccctg gagtgcgggg aagcacaaag       60
acactgggag agctgctaga tacaggcaca gagctcccca gagctatccg ctgcctctac      120
agccgctgct gctttgggat ctggaacctg acccaagacc gggcacaggt ggaaatgcaa      180
ggatgccgag acagtgatga gccaggctgt gagtccctcc actgtgaccc aagtccccga      240
gcccacccca gcctggctc  cactctcttc acctgctcct gtggcactga cttctgcaat      300
gccaattaca gccatctgcc tcctccaggg agccctggga ctcctggctc ccagggtccc      360
caggctgccc caggtgagtc catctggatg gcactg                                396
```

<210> SEQ ID NO 83
<211> LENGTH: 546
<212> TYPE: PRT
<213> ORGANISM: Homo sapiens

<400> SEQUENCE: 83

```
Met Ala Glu Ser Ala Gly Ala Ser Ser Phe Phe Pro Leu Val Val Leu
1               5                   10                  15

Leu Leu Ala Gly Ser Gly Gly Ser Gly Pro Arg Gly Val Gln Ala Leu
            20                  25                  30

Leu Cys Ala Cys Thr Ser Cys Leu Gln Ala Asn Tyr Thr Cys Glu Thr
        35                  40                  45

Asp Gly Ala Cys Met Val Ser Ile Phe Asn Leu Asp Gly Met Glu His
    50                  55                  60

His Val Arg Thr Cys Ile Pro Lys Val Glu Leu Val Pro Ala Gly Lys
65                  70                  75                  80

Pro Phe Tyr Cys Leu Ser Ser Glu Asp Leu Arg Asn Thr His Cys Cys
                85                  90                  95

Tyr Thr Asp Tyr Cys Asn Arg Ile Asp Leu Arg Val Pro Ser Gly His
            100                 105                 110

Leu Lys Glu Pro Glu His Pro Ser Met Trp Gly Pro Val Glu Leu Val
        115                 120                 125

Gly Ile Ile Ala Gly Pro Val Phe Leu Leu Phe Leu Ile Ile Ile Ile
    130                 135                 140

Val Phe Leu Val Ile Asn Tyr His Gln Arg Val Tyr His Asn Arg Gln
145                 150                 155                 160

Arg Leu Asp Met Glu Asp Pro Ser Cys Glu Met Cys Leu Ser Lys Asp
```

```
                165                 170                 175
Lys Thr Leu Gln Asp Leu Val Tyr Asp Leu Ser Thr Gly Ser Gly
                180                 185                 190

Ser Gly Leu Pro Leu Phe Val Gln Arg Thr Val Ala Arg Thr Ile Val
            195                 200                 205

Leu Gln Glu Ile Ile Gly Lys Gly Arg Phe Gly Glu Val Trp Arg Gly
        210                 215                 220

Arg Trp Arg Gly Gly Asp Val Ala Val Lys Ile Phe Ser Ser Arg Glu
225                 230                 235                 240

Glu Arg Ser Trp Phe Arg Glu Ala Glu Ile Tyr Gln Thr Val Met Leu
                245                 250                 255

Arg His Glu Asn Ile Leu Gly Phe Ile Ala Ala Asp Asn Lys Ala Asp
                260                 265                 270

Cys Ser Phe Leu Thr Leu Pro Trp Glu Val Val Met Val Ser Ala Ala
                275                 280                 285

Pro Lys Leu Arg Ser Leu Arg Leu Gln Tyr Lys Gly Gly Arg Gly Arg
            290                 295                 300

Ala Arg Phe Leu Phe Pro Leu Asn Asn Gly Thr Trp Thr Gln Leu Trp
305                 310                 315                 320

Leu Val Ser Asp Tyr His Glu His Gly Ser Leu Phe Asp Tyr Leu Asn
                325                 330                 335

Arg Tyr Thr Val Thr Ile Glu Gly Met Ile Lys Leu Ala Leu Ser Ala
                340                 345                 350

Ala Ser Gly Leu Ala His Leu His Met Glu Ile Val Gly Thr Gln Gly
            355                 360                 365

Lys Pro Gly Ile Ala His Arg Asp Leu Lys Ser Lys Asn Ile Leu Val
            370                 375                 380

Lys Lys Asn Gly Met Cys Ala Ile Ala Asp Leu Gly Leu Ala Val Arg
385                 390                 395                 400

His Asp Ala Val Thr Asp Thr Ile Asp Ile Ala Pro Asn Gln Arg Val
                405                 410                 415

Gly Thr Lys Arg Tyr Met Ala Pro Glu Val Leu Asp Glu Thr Ile Asn
                420                 425                 430

Met Lys His Phe Asp Ser Phe Lys Cys Ala Asp Ile Tyr Ala Leu Gly
            435                 440                 445

Leu Val Tyr Trp Glu Ile Ala Arg Arg Cys Asn Ser Gly Gly Val His
        450                 455                 460

Glu Glu Tyr Gln Leu Pro Tyr Tyr Asp Leu Val Pro Ser Asp Pro Ser
465                 470                 475                 480

Ile Glu Glu Met Arg Lys Val Val Cys Asp Gln Lys Leu Arg Pro Asn
                485                 490                 495

Ile Pro Asn Trp Trp Gln Ser Tyr Glu Ala Leu Arg Val Met Gly Lys
                500                 505                 510

Met Met Arg Glu Cys Trp Tyr Ala Asn Gly Ala Ala Arg Leu Thr Ala
            515                 520                 525

Leu Arg Ile Lys Lys Thr Leu Ser Gln Leu Ser Val Gln Glu Asp Val
        530                 535                 540

Lys Ile
545

<210> SEQ ID NO 84
<211> LENGTH: 103
<212> TYPE: PRT
<213> ORGANISM: Homo sapiens
```

<400> SEQUENCE: 84

```
Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu
            100
```

<210> SEQ ID NO 85
<211> LENGTH: 1638
<212> TYPE: DNA
<213> ORGANISM: Homo sapiens

<400> SEQUENCE: 85

| | |
|---|---:|
| atggcggagt cggccggagc ctcctccttc ttcccccttg ttgtcctcct gctcgccggc | 60 |
| agcggcgggt ccgggccccg gggggtccag gctctgctgt gtgcgtgcac cagctgcctc | 120 |
| caggccaact acacgtgtga cacagatggg gcctgcatgg tttccatttt caatctggat | 180 |
| gggatggagc accatgtgcg cacctgcatc cccaaagtgg agctggtccc tgccgggaag | 240 |
| cccttctact gcctgagctc ggaggacctg cgcaacaccc actgctgcta cactgactac | 300 |
| tgcaacagga tcgacttgag ggtgcccagt ggtcacctca aggagcctga gcacccgtcc | 360 |
| atgtggggcc cggtggagct ggtaggcatc atcgccggcc cggtgttcct cctgttcctc | 420 |
| atcatcatca ttgttttcct tgtcattaac tatcatcagc gtgtctatca aaccgccag | 480 |
| agactggaca tggaagatcc ctcatgtgag atgtgtctct ccaaagacaa gacgctccag | 540 |
| gatcttgtct acgatctctc cacctcaggg tctggctcag ggttacccct ctttgtccag | 600 |
| cgcacagtgg cccgaaccat cgttttacaa gagattattg caagggtcg gtttggggaa | 660 |
| gtatggcggg ccgctggag gggtggtgat gtggctgtga aatattctc ttctcgtgaa | 720 |
| gaacggtctt ggttcaggga agcagagata taccagacgg tcatgctgcg ccatgaaaac | 780 |
| atccttggat ttattgctgc tgacaataaa gcagactgct cattcctcac attgccatgg | 840 |
| gaagttgtaa tggtctctgc tgcccccaag ctgaggagcc ttagactcca atacaaggga | 900 |
| ggaaggggaa gagcaagatt tttattccca ctgaataatg gcacctggac acagctgtgg | 960 |
| cttgtttctg actatcatga gcacgggtcc ctgtttgatt atctgaaccg gtacacagtg | 1020 |
| acaattgagg ggatgattaa gctggccttg tctgctgcta gtgggctggc acacctgcac | 1080 |
| atggagatcg tgggcacccca aggaagcct ggaattgctc atcgagactt aaagtcaaag | 1140 |
| aacattctgg tgaagaaaaa tggcatgtgt gccatagcag acctgggcct ggctgtccgt | 1200 |
| catgatgcag tcactgacac cattgacatt gccccgaatc agagggtggg gaccaaacga | 1260 |
| tacatggccc ctgaagtact tgatgaaacc attaatatga acactttga ctcctttaaa | 1320 |
| tgtgctgata tttatgccct cgggcttgta tattgggaga ttgctcgaag atgcaattct | 1380 |
| ggaggagtcc atgaagaata tcagctgcca tattacgact tagtgccctc tgacccttcc | 1440 |

```
attgaggaaa tgcgaaaggt tgtatgtgat cagaagctgc gtcccaacat ccccaactgg    1500
tggcagagtt atgaggcact gcgggtgatg gggaagatga tgcgagagtg ttggtatgcc    1560
aacggcgcag cccgcctgac ggccctgcgc atcaagaaga ccctctccca gctcagcgtg    1620
caggaagacg tgaagatc                                                  1638

<210> SEQ ID NO 86
<211> LENGTH: 309
<212> TYPE: DNA
<213> ORGANISM: Homo sapiens

<400> SEQUENCE: 86
tccgggcccc gggggtgtcca ggctctgctg tgtgcgtgca ccagctgcct ccaggccaac     60
tacacgtgtg agacagatgg ggcctgcatg gtttccattt tcaatctgga tgggatggag    120
caccatgtgc gcacctgcat ccccaaagtg gagctggtcc ctgccgggaa gcccttctac    180
tgcctgagct cggaggacct gcgcaacacc cactgctgct acactgacta ctgcaacagg    240
atcgacttga gggtgcccag tggtcacctc aaggagcctg agcacccgtc catgtggggc    300
ccggtggag                                                            309

<210> SEQ ID NO 87
<211> LENGTH: 507
<212> TYPE: PRT
<213> ORGANISM: Homo sapiens

<400> SEQUENCE: 87

Met Glu Ala Ala Val Ala Ala Pro Arg Pro Arg Leu Leu Leu Leu Val
 1               5                  10                  15

Leu Ala Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Gly Pro Phe Ser Val Lys Ser Ser Pro Gly Leu Gly Pro Val
        115                 120                 125

Glu Leu Ala Ala Val Ile Ala Gly Pro Val Cys Phe Val Cys Ile Ser
    130                 135                 140

Leu Met Leu Met Val Tyr Ile Cys His Asn Arg Thr Val Ile His His
145                 150                 155                 160

Arg Val Pro Asn Glu Glu Asp Pro Ser Leu Asp Arg Pro Phe Ile Ser
                165                 170                 175

Glu Gly Thr Thr Leu Lys Asp Leu Ile Tyr Asp Met Thr Thr Ser Gly
            180                 185                 190

Ser Gly Ser Gly Leu Pro Leu Leu Val Gln Arg Thr Ile Ala Arg Thr
        195                 200                 205

Ile Val Leu Gln Glu Ser Ile Gly Lys Gly Arg Phe Gly Glu Val Trp
    210                 215                 220
```

Arg Gly Lys Trp Arg Gly Glu Glu Val Ala Val Lys Ile Phe Ser Ser
225                 230                 235                 240

Arg Glu Glu Arg Ser Trp Phe Arg Glu Ala Glu Ile Tyr Gln Thr Val
            245                 250                 255

Met Leu Arg His Glu Asn Ile Leu Gly Phe Ile Ala Ala Asp Asn Lys
        260                 265                 270

Asp Asn Gly Thr Trp Thr Gln Leu Trp Leu Val Ser Asp Tyr His Glu
            275                 280                 285

His Gly Ser Leu Phe Asp Tyr Leu Asn Arg Tyr Thr Val Thr Val Glu
    290                 295                 300

Gly Met Ile Lys Leu Ala Leu Ser Thr Ala Ser Gly Leu Ala His Leu
305                 310                 315                 320

His Met Glu Ile Val Gly Thr Gln Gly Lys Pro Ala Ile Ala His Arg
                325                 330                 335

Asp Leu Lys Ser Lys Asn Ile Leu Val Lys Lys Asn Gly Thr Cys Cys
                340                 345                 350

Ile Ala Asp Leu Gly Leu Ala Val Arg His Asp Ser Ala Thr Asp Thr
            355                 360                 365

Ile Asp Ile Ala Pro Asn His Arg Val Gly Thr Lys Arg Tyr Met Ala
370                 375                 380

Pro Glu Val Leu Asp Asp Ser Ile Asn Met Lys His Phe Glu Ser Phe
385                 390                 395                 400

Lys Arg Ala Asp Ile Tyr Ala Met Gly Leu Val Phe Trp Glu Ile Ala
                405                 410                 415

Arg Arg Cys Ser Ile Gly Gly Ile His Glu Asp Tyr Gln Leu Pro Tyr
            420                 425                 430

Tyr Asp Leu Val Pro Ser Asp Pro Ser Val Glu Glu Met Arg Lys Val
            435                 440                 445

Val Cys Glu Gln Lys Leu Arg Pro Asn Ile Pro Asn Arg Trp Gln Ser
    450                 455                 460

Cys Glu Ala Leu Arg Val Met Ala Lys Ile Met Arg Glu Cys Trp Tyr
465                 470                 475                 480

Ala Asn Gly Ala Ala Arg Leu Thr Ala Leu Arg Ile Lys Lys Thr Leu
            485                 490                 495

Ser Gln Leu Ser Gln Gln Glu Gly Ile Lys Met
            500                 505

<210> SEQ ID NO 88
<211> LENGTH: 106
<212> TYPE: PRT
<213> ORGANISM: Homo sapiens

<400> SEQUENCE: 88

Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
    50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Gly Pro Phe Ser Val Lys
                85                  90                  95

Ser Ser Pro Gly Leu Gly Pro Val Glu Leu
        100                 105

<210> SEQ ID NO 89
<211> LENGTH: 1521
<212> TYPE: DNA
<213> ORGANISM: Homo sapiens

<400> SEQUENCE: 89

| | | |
|---|---|---|
| atggaggcgg cggtcgctgc tccgcgtccc cggctgctcc tcctcgtgct ggcggcggcg | 60 |
| gcggcggcgg cggcggcgct gctcccgggg gcgacggcgt tacagtgttt ctgccacctc | 120 |
| tgtacaaaag acaattttac ttgtgtgaca gatgggctct gctttgtctc tgtcacagag | 180 |
| accacagaca agttataca caacagcatg tgtatagctg aaattgactt aattcctcga | 240 |
| gataggccgt ttgtatgtgc accctcttca aaaactgggt ctgtgactac aacatattgc | 300 |
| tgcaatcagg accattgcaa taaaatagaa cttccaacta ctggcccttt ttcagtaaag | 360 |
| tcatcacctg gccttggtcc tgtggaactg gcagctgtca ttgctggacc agtgtgcttc | 420 |
| gtctgcatct cactcatgtt gatggtctat atctgccaca accgcactgt cattcaccat | 480 |
| cgagtgccaa atgaagagga cccttcatta gatcgccctt ttatttcaga gggtactacg | 540 |
| ttgaaagact taatttatga tatgacaacg tcaggttctg gctcaggttt accattgctt | 600 |
| gttcagagaa caattgcgag aactattgtg ttacaagaaa gcattggcaa aggtcgattt | 660 |
| ggagaagttt ggagaggaaa gtggcgggga aagaagttg ctgttaagat attctcctct | 720 |
| agagaagaac gttcgtggtt ccgtgaggca gagatttatc aaactgtaat gttacgtcat | 780 |
| gaaaacatcc tgggatttat agcagcagac aataaagaca atggtacttg gactcagctc | 840 |
| tggttggtgt cagattatca tgagcatgga tccctttttg attacttaaa cagatacaca | 900 |
| gttactgtgg aaggaatgat aaaacttgct ctgtccacgg cgagcggtct tgcccatctt | 960 |
| cacatggaga ttgttggtac ccaaggaaag ccagccattg ctcatagaga tttgaaatca | 1020 |
| aagaatatct tggtaaagaa gaatggaact tgctgtattg cagacttagg actggcagta | 1080 |
| agacatgatt cagccacaga taccattgat attgctccaa accacagagt gggaacaaaa | 1140 |
| aggtacatgg cccctgaagt tctcgatgat tccataaata tgaaacattt tgaatccttc | 1200 |
| aaacgtgctg acatctatgc aatgggctta gtattctggg aaattgctcg acgatgttcc | 1260 |
| attggtggaa ttcatgaaga ttaccaactg ccttattatg atcttgtacc ttctgaccca | 1320 |
| tcagttgaag aaatgagaaa agttgtttgt gaacagaagt taaggccaaa tatcccaaac | 1380 |
| agatggcaga gctgtgaagc cttgagagta atggctaaaa ttatgagaga atgttggtat | 1440 |
| gccaatggag cagctaggct tacagcattg cggattaaga aaacattatc gcaactcagt | 1500 |
| caacaggaag gcatcaaaat g | 1521 |

<210> SEQ ID NO 90
<211> LENGTH: 318
<212> TYPE: DNA
<213> ORGANISM: Homo sapiens

<400> SEQUENCE: 90

| | | |
|---|---|---|
| gcggcgctgc tcccgggggc gacggcgtta cagtgtttct gccacctctg tacaaaagac | 60 |
| aattttactt gtgtgacaga tgggctctgc tttgtctctg tcacagagac cacagacaaa | 120 |
| gttatacaca acagcatgtg tatagctgaa attgacttaa ttcctcgaga taggccgttt | 180 |
| gtatgtgcac cctcttcaaa aactgggtct gtgactacaa catattgctg caatcaggac | 240 |

```
cattgcaata aaatagaact tccaactact ggcccttttt cagtaaagtc atcacctggc    300
cttggtcctg tggaactg                                                  318
```

<210> SEQ ID NO 91
<211> LENGTH: 532
<212> TYPE: PRT
<213> ORGANISM: Homo sapiens

<400> SEQUENCE: 91

```
Met Gly Trp Leu Glu Glu Leu Asn Trp Gln Leu His Ile Phe Leu Leu
1               5                   10                  15

Ile Leu Leu Ser Met His Thr Arg Ala Asn Phe Leu Asp Asn Met Leu
            20                  25                  30

Leu Arg Ser Ala Gly Lys Leu Asn Val Gly Thr Lys Lys Glu Asp Gly
        35                  40                  45

Glu Ser Thr Ala Pro Thr Pro Arg Pro Lys Val Leu Arg Cys Lys Cys
    50                  55                  60

His His His Cys Pro Glu Asp Ser Val Asn Asn Ile Cys Ser Thr Asp
65                  70                  75                  80

Gly Tyr Cys Phe Thr Met Ile Glu Glu Asp Asp Ser Gly Leu Pro Val
                85                  90                  95

Val Thr Ser Gly Cys Leu Gly Leu Glu Gly Ser Asp Phe Gln Cys Arg
            100                 105                 110

Asp Thr Pro Ile Pro His Gln Arg Arg Ser Ile Glu Cys Cys Thr Glu
        115                 120                 125

Arg Asn Glu Cys Asn Lys Asp Leu His Pro Thr Leu Pro Pro Leu Lys
130                 135                 140

Asn Arg Asp Phe Val Asp Gly Pro Ile His His Arg Ala Leu Leu Ile
145                 150                 155                 160

Ser Val Thr Val Cys Ser Leu Leu Val Leu Ile Ile Leu Phe Cys Tyr
                165                 170                 175

Tyr Phe Arg Tyr Lys Arg Gln Glu Thr Arg Pro Arg Tyr Ser Ile Gly
            180                 185                 190

Leu Glu Gln Asp Glu Thr Tyr Ile Pro Pro Gly Glu Ser Leu Arg Asp
        195                 200                 205

Leu Ile Glu Gln Ser Gln Ser Ser Gly Ser Gly Ser Gly Leu Pro Leu
210                 215                 220

Leu Val Gln Arg Thr Ile Ala Lys Gln Ile Gln Met Val Lys Gln Ile
225                 230                 235                 240

Gly Lys Gly Arg Tyr Gly Glu Val Trp Met Gly Lys Trp Arg Gly Glu
                245                 250                 255

Lys Val Ala Val Lys Val Phe Phe Thr Thr Glu Glu Ala Ser Trp Phe
            260                 265                 270

Arg Glu Thr Glu Ile Tyr Gln Thr Val Leu Met Arg His Glu Asn Ile
        275                 280                 285

Leu Gly Phe Ile Ala Ala Asp Ile Lys Gly Thr Gly Ser Trp Thr Gln
290                 295                 300

Leu Tyr Leu Ile Thr Asp Tyr His Glu Asn Gly Ser Leu Tyr Asp Tyr
305                 310                 315                 320

Leu Lys Ser Thr Thr Leu Asp Ala Lys Ser Met Leu Lys Leu Ala Tyr
                325                 330                 335

Ser Ser Val Ser Gly Leu Cys His Leu His Thr Glu Ile Phe Ser Thr
            340                 345                 350
```

```
Gln Gly Lys Pro Ala Ile Ala His Arg Asp Leu Lys Ser Lys Asn Ile
            355                 360                 365

Leu Val Lys Lys Asn Gly Thr Cys Cys Ile Ala Asp Leu Gly Leu Ala
    370                 375                 380

Val Lys Phe Ile Ser Asp Thr Asn Glu Val Asp Ile Pro Pro Asn Thr
385                 390                 395                 400

Arg Val Gly Thr Lys Arg Tyr Met Pro Pro Glu Val Leu Asp Glu Ser
                405                 410                 415

Leu Asn Arg Asn His Phe Gln Ser Tyr Ile Met Ala Asp Met Tyr Ser
                420                 425                 430

Phe Gly Leu Ile Leu Trp Glu Val Ala Arg Arg Cys Val Ser Gly Gly
            435                 440                 445

Ile Val Glu Glu Tyr Gln Leu Pro Tyr His Asp Leu Val Pro Ser Asp
    450                 455                 460

Pro Ser Tyr Glu Asp Met Arg Glu Ile Val Cys Ile Lys Lys Leu Arg
465                 470                 475                 480

Pro Ser Phe Pro Asn Arg Trp Ser Ser Asp Glu Cys Leu Arg Gln Met
                485                 490                 495

Gly Lys Leu Met Thr Glu Cys Trp Ala His Asn Pro Ala Ser Arg Leu
            500                 505                 510

Thr Ala Leu Arg Val Lys Lys Thr Leu Ala Lys Met Ser Glu Ser Gln
    515                 520                 525

Asp Ile Lys Leu
    530

<210> SEQ ID NO 92
<211> LENGTH: 131
<212> TYPE: PRT
<213> ORGANISM: Homo sapiens

<400> SEQUENCE: 92

Asn Phe Leu Asp Asn Met Leu Leu Arg Ser Ala Gly Lys Leu Asn Val
1               5                   10                  15

Gly Thr Lys Lys Glu Asp Gly Glu Ser Thr Ala Pro Thr Pro Arg Pro
            20                  25                  30

Lys Val Leu Arg Cys Lys Cys His His His Cys Pro Glu Asp Ser Val
        35                  40                  45

Asn Asn Ile Cys Ser Thr Asp Gly Tyr Cys Phe Thr Met Ile Glu Glu
    50                  55                  60

Asp Asp Ser Gly Leu Pro Val Val Thr Ser Gly Cys Leu Gly Leu Glu
65                  70                  75                  80

Gly Ser Asp Phe Gln Cys Arg Asp Thr Pro Ile Pro His Gln Arg Arg
                85                  90                  95

Ser Ile Glu Cys Cys Thr Glu Arg Asn Glu Cys Asn Lys Asp Leu His
            100                 105                 110

Pro Thr Leu Pro Pro Leu Lys Asn Arg Asp Phe Val Asp Gly Pro Ile
        115                 120                 125

His His Arg
    130

<210> SEQ ID NO 93
<211> LENGTH: 1596
<212> TYPE: DNA
<213> ORGANISM: Homo sapiens

<400> SEQUENCE: 93
```

| | |
|---|---|
| atgggttggc tggaagaact aaactggcag cttcacattt tcttgctcat tcttctctct | 60 |
| atgcacacaa gggcaaactt ccttgataac atgcttttgc gaagtgcagg aaaattaaat | 120 |
| gtgggcacca agaaagagga tggtgagagt acagccccca cccccgtcc aaaggtcttg | 180 |
| cgttgtaaat gccaccacca ttgtccagaa gactcagtca acaatatttg cagcacagac | 240 |
| ggatattgtt tcacgatgat agaagaggat gactctgggt tgcctgtggt cacttctggt | 300 |
| tgcctaggac tagaaggctc agattttcag tgtcgggaca ctcccattcc tcatcaaaga | 360 |
| agatcaattg aatgctgcac agaaaggaac gaatgtaata aagacctaca ccctacactg | 420 |
| cctccattga aaacagaga ttttgttgat ggacctatac accacagggc tttacttata | 480 |
| tctgtgactg tctgtagttt gctcttggtc cttatcatat tattttgtta cttccggtat | 540 |
| aaaagacaag aaaccagacc tcgatacagc attgggttag aacaggatga aacttacatt | 600 |
| cctcctggag aatccctgag agacttaatt gagcagtctc agagctcagg aagtggatca | 660 |
| ggcctccctc tgctggtcca aaggactata gctaagcaga ttcagatggt gaaacagatt | 720 |
| ggaaaaggtc gctatgggga gtttggatgg gaaagtggg gtggcgaaaa ggtagctgtg | 780 |
| aaagtgttct tcaccacaga ggaagccagc tggttcagag agacagaaat atatcagaca | 840 |
| gtgttgatga ggcatgaaaa cattttgggt ttcattgctg cagatatcaa agggacaggg | 900 |
| tcctggaccc agttgtacct aatcacagac tatcatgaaa atggttccct ttatgattat | 960 |
| ctgaagtcca ccaccctaga cgctaaatca atgctgaagt tagcctactc ttctgtcagt | 1020 |
| ggcttatgtc atttacacac agaaatcttt agtactcaag gcaaaccagc aattgcccat | 1080 |
| cgagatctga aagtaaaaa cattctggtg aagaaaaatg gaacttgctg tattgctgac | 1140 |
| ctgggcctgg ctgttaaatt tattagtgat acaaatgaag ttgacatacc acctaacact | 1200 |
| cgagttggca ccaaacgcta tatgcctcca gaagtgttgg acgagagctt gaacagaaat | 1260 |
| cacttccagt cttacatcat ggctgacatg tatagttttg gcctcatcct ttgggaggtt | 1320 |
| gctaggagat gtgtatcagg aggtatagtg gaagaatacc agcttcctta tcatgaccta | 1380 |
| gtgcccagtg acccctctta tgaggacatg agggagattg tgtgcatcaa gaagttacgc | 1440 |
| ccctcattcc caaccggtg gagcagtgat gagtgtctaa ggcagatggg aaaactcatg | 1500 |
| acagaatgct gggctcacaa tcctgcatca aggctgacag ccctgcgggt taagaaaaca | 1560 |
| cttgccaaaa tgtcagagtc ccaggacatt aaactc | 1596 |

<210> SEQ ID NO 94
<211> LENGTH: 393
<212> TYPE: DNA
<213> ORGANISM: Homo sapiens

<400> SEQUENCE: 94

| | |
|---|---|
| aacttccttg ataacatgct tttgcgaagt gcaggaaaat taaatgtggg caccaagaaa | 60 |
| gaggatggtg agagtacagc ccccaccccc cgtccaaagg tcttgcgttg taaatgccac | 120 |
| caccattgtc cagaagactc agtcaacaat atttgcagca cagacggata ttgtttcacg | 180 |
| atgatagaag aggatgactc tgggttgcct gtggtcactt ctggttgcct aggactagaa | 240 |
| ggctcagatt ttcagtgtcg ggacactccc attcctcatc aaagaagatc aattgaatgc | 300 |
| tgcacagaaa ggaacgaatg taataaagac ctacacccta cactgcctcc attgaaaaac | 360 |
| agagattttg ttgatggacc tatacaccac agg | 393 |

<210> SEQ ID NO 95
<211> LENGTH: 36

```
<212> TYPE: PRT
<213> ORGANISM: Homo sapiens

<400> SEQUENCE: 95

Gly Arg Cys Lys Ile Arg His Ile Gly Ser Asn Asn Arg Leu Gln Arg
1               5                   10                  15

Ser Thr Cys Gln Asn Thr Gly Trp Glu Ser Ala His Val Met Lys Thr
            20                  25                  30

Pro Gly Phe Arg
        35

<210> SEQ ID NO 96

<400> SEQUENCE: 96

000

<210> SEQ ID NO 97

<400> SEQUENCE: 97

000

<210> SEQ ID NO 98
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Met Asp Ala Met Lys Arg Gly Leu Cys Cys Val Leu Leu Leu Cys Gly
1               5                   10                  15

Ala Val Phe Val Ser Pro
            20

<210> SEQ ID NO 99

<400> SEQUENCE: 99

000

<210> SEQ ID NO 100
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
```

85                  90                  95
Val Ala Thr Glu Glu Asn Pro Gln Val Tyr Phe Cys Cys Glu Gly
            100                 105                 110

Asn Phe Cys Asn Glu Arg Phe Thr His Leu Pro Glu Ala Gly Gly Pro
            115                 120                 125

Glu Val Thr Tyr Glu Pro Pro Thr Ala Pro Thr Gly Gly Gly Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Lys Glu Met Thr Lys Asn Gln Val Ser Leu Thr Cys
        275                 280                 285

Leu Val Lys Gly Phe Tyr Pro Ser Asp Ile Ala Val Glu Trp Glu Ser
290                 295                 300

Asn Gly Gln Pro Glu Asn Asn Tyr Lys Thr Thr Pro Pro Val Leu Lys
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 101
<211> LENGTH: 1104
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
atggatgcaa tgaagagagg gctctgctgt gtgctgctgc tgtgtggagc agtcttcgtt      60
tcgcccggcg cctctgggcg tgggaggct gagacacggg agtgcatcta ctacaacgcc     120
aactgggagc tggagcgcac caaccagagc ggcctggagc gctgcgaagg cgagcaggac    180
aagcggctgc actgctacgc ctcctggcgc aacagctctg gcaccatcga gctcgtgaag    240
aagggctgct ggctagatga cttcaactgc tacgataggc aggagtgtgt ggccactgag    300
gagaaccccc aggtgtactt ctgctgctgt gaaggcaact tctgcaacga gcgcttcact    360
catttgccag aggctggggg cccggaagtc acgtacgagc cacccccgac agcccccacc    420
ggtggtggaa ctcacacatg cccaccgtgc ccagcacctg aactcctggg ggaccgtca    480

```
gtcttcctct tccccccaaa acccaaggac accctcatga tctcccggac ccctgaggtc    540
acatgcgtgg tggtggacgt gagccacgaa gaccctgagg tcaagttcaa ctggtacgtg    600
gacggcgtgg aggtgcataa tgccaagaca aagccgcggg aggagcagta caacagcacg    660
taccgtgtgg tcagcgtcct caccgtcctg caccaggact ggctgaatgg caaggagtac    720
aagtgcaagg tctccaacaa agccctccca gcccccatcg agaaaaccat ctccaaagcc    780
aaagggcagc cccgagaacc acaggtgtac accctgcccc catcccggaa ggagatgacc    840
aagaaccagg tcagcctgac ctgcctggtc aaaggcttct atcccagcga catcgccgtg    900
gagtgggaga gcaatgggca gccggagaac aactacaaga ccacgcctcc cgtgctgaag    960
tccgacggct ccttcttcct ctatagcaag ctcaccgtgg acaagagcag gtggcagcag   1020
gggaacgtct tctcatgctc cgtgatgcat gaggctctgc acaaccacta cacgcagaag   1080
agcctctccc tgtctccggg taaa                                          1104
```

<210> SEQ ID NO 102
<211> LENGTH: 343
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 102

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240
```

```
Glu Pro Gln Val Tyr Thr Leu Pro Pro Ser Arg Lys Glu Met Thr Lys
                245                 250                 255

Asn Gln Val Ser Leu Thr Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Lys Ser Asp Gly Ser Phe Phe Leu Tyr Ser
290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
                340

<210> SEQ ID NO 103

<400> SEQUENCE: 103

000

<210> SEQ ID NO 104
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
                20                  25                  30

Leu Leu Cys Ala Cys Thr Ser Cys Leu Gln Ala Asn Tyr Thr Cys Glu
            35                  40                  45

Thr Asp Gly Ala Cys Met Val Ser Ile Phe Asn Leu Asp Gly Met Glu
        50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
                100                 105                 110

His Leu Lys Glu Pro Glu His Pro Ser Met Trp Gly Pro Val Glu Thr
            115                 120                 125

Gly Gly Gly Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
```

```
                     210                 215                 220
Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Asp Thr Thr Pro
    290                 295                 300

Pro Val Leu Asp Ser Asp Gly Ser Phe Phe Leu Tyr Ser Asp Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly
        355

<210> SEQ ID NO 105
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
atggatgcaa tgaagagagg gctctgctgt gtgctgctgc tgtgtggagc agtcttcgtt      60
tcgcccggcg cctccgggcc cggggggtc  caggctctgc tgtgtgcgtg caccagctgc     120
ctccaggcca actacgtg  tgagacagat ggggcctgca tggtttccat tttcaatctg     180
gatgggatgg agcaccatgt gcgcacctgc atccccaaag tggagctggt ccctgccggg     240 aagccct tct actgcctgag ctcggaggac ctgcgcaaca cccactgctg ctacactgac     300
tactgcaaca ggatcgactt gagggtgccc agtggtcacc tcaaggagcc tgagcacccg     360
tccatgtggg gccggtgga  gaccggtggt ggaactcaca catgcccacc gtgcccagca     420
cctgaactcc tggggggacc gtcagtcttc ctcttccccc caaaacccaa ggacaccctc     480
atgatctccc ggacccctga ggtcacatgc gtggtggtgg acgtgagcca cgaagaccct     540
gaggtcaagt tcaactggta cgtggacggc gtggaggtgc ataatgccaa gacaaagccg     600
cgggaggagc agtacaacag cacgtaccgt gtggtcagcg tcctcaccgt cctgcaccag     660
gactggctga atggcaagga gtacaagtgc aaggtctcca acaaagccct cccagccccc     720
atcgagaaaa ccatctccaa agccaaaggg cagccccgag aaccacaggt gtacaccctg     780
cccccatccc gggaggagat gaccaagaac caggtcagcc tgacctgcct ggtcaaaggc     840
ttctatccca gcgacatcgc cgtggagtgg gagagcaatg ggcagccgga gaacaactac     900
gacaccacgc ctcccgtgct ggactccgac ggctccttct tcctctatag cgacctcacc     960
gtggacaaga gcaggtggca gcaggggaac gtcttctcat gctccgtgat gcatgaggct    1020
ctgcacaacc actacacgca gaagagcctc tccctgtctc cgggt               1065

<210> SEQ ID NO 106
<211> LENGTH: 331
```

<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 106

```
Ser Gly Pro Arg Gly Val Gln Ala Leu Leu Cys Ala Cys Thr Ser Cys
1               5                   10                  15
Leu Gln Ala Asn Tyr Thr Cys Glu Thr Asp Gly Ala Cys Met Val Ser
            20                  25                  30
Ile Phe Asn Leu Asp Gly Met Glu His His Val Arg Thr Cys Ile Pro
        35                  40                  45
Lys Val Glu Leu Val Pro Ala Gly Lys Pro Phe Tyr Cys Leu Ser Ser
    50                  55                  60
Glu Asp Leu Arg Asn Thr His Cys Cys Tyr Thr Asp Tyr Cys Asn Arg
65                  70                  75                  80
Ile Asp Leu Arg Val Pro Ser Gly His Leu Lys Glu Pro Glu His Pro
                85                  90                  95
Ser Met Trp Gly Pro Val Glu Thr Gly Gly Thr His Thr Cys Pro
            100                 105                 110
Pro Cys Pro Ala Pro Glu Leu Leu Gly Gly Pro Ser Val Phe Leu Phe
        115                 120                 125
Pro Pro Lys Pro Lys Asp Thr Leu Met Ile Ser Arg Thr Pro Glu Val
    130                 135                 140
Thr Cys Val Val Val Asp Val Ser His Glu Asp Pro Glu Val Lys Phe
145                 150                 155                 160
Asn Trp Tyr Val Asp Gly Val Glu Val His Asn Ala Lys Thr Lys Pro
                165                 170                 175
Arg Glu Glu Gln Tyr Asn Ser Thr Tyr Arg Val Val Ser Val Leu Thr
            180                 185                 190
Val Leu His Gln Asp Trp Leu Asn Gly Lys Glu Tyr Lys Cys Lys Val
        195                 200                 205
Ser Asn Lys Ala Leu Pro Ala Pro Ile Glu Lys Thr Ile Ser Lys Ala
    210                 215                 220
Lys Gly Gln Pro Arg Glu Pro Gln Val Tyr Thr Leu Pro Pro Ser Arg
225                 230                 235                 240
Glu Glu Met Thr Lys Asn Gln Val Ser Leu Thr Cys Leu Val Lys Gly
                245                 250                 255
Phe Tyr Pro Ser Asp Ile Ala Val Glu Trp Glu Ser Asn Gly Gln Pro
            260                 265                 270
Glu Asn Asn Tyr Asp Thr Thr Pro Pro Val Leu Asp Ser Asp Gly Ser
        275                 280                 285
Phe Phe Leu Tyr Ser Asp Leu Thr Val Asp Lys Ser Arg Trp Gln Gln
    290                 295                 300
Gly Asn Val Phe Ser Cys Ser Val Met His Glu Ala Leu His Asn His
305                 310                 315                 320
Tyr Thr Gln Lys Ser Leu Ser Leu Ser Pro Gly
                325                 330
```

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111

<400> SEQUENCE: 111

000

<210> SEQ ID NO 112
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

```
Met Asp Ala Met Lys Arg Gly Leu Cys Cys Val Leu Leu Leu Cys Gly
1               5                   10                  15

Ala Val Phe Val Ser Pro Gly Ala Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220
```

| Ala | Pro | Ile | Glu | Lys | Thr | Ile | Ser | Lys | Ala | Lys | Gly | Gln | Pro | Arg | Glu |
| --- | --- | --- | --- | --- | --- | --- | --- | --- | --- | --- | --- | --- | --- | --- | --- |
| 225 | | | | 230 | | | | | 235 | | | | | 240 | |

| Pro | Gln | Val | Tyr | Thr | Leu | Pro | Pro | Ser | Arg | Glu | Glu | Met | Thr | Lys | Asn |
| --- | --- | --- | --- | --- | --- | --- | --- | --- | --- | --- | --- | --- | --- | --- | --- |
| | | | | 245 | | | | | 250 | | | | | 255 | |

| Gln | Val | Ser | Leu | Thr | Cys | Leu | Val | Lys | Gly | Phe | Tyr | Pro | Ser | Asp | Ile |
| --- | --- | --- | --- | --- | --- | --- | --- | --- | --- | --- | --- | --- | --- | --- | --- |
| | | | 260 | | | | | 265 | | | | | 270 | | |

| Ala | Val | Glu | Trp | Glu | Ser | Asn | Gly | Gln | Pro | Glu | Asn | Asn | Tyr | Asp | Thr |
| --- | --- | --- | --- | --- | --- | --- | --- | --- | --- | --- | --- | --- | --- | --- | --- |
| | | | 275 | | | | 280 | | | | | 285 | | | |

| Thr | Pro | Pro | Val | Leu | Asp | Ser | Asp | Gly | Ser | Phe | Phe | Leu | Tyr | Ser | Asp |
| --- | --- | --- | --- | --- | --- | --- | --- | --- | --- | --- | --- | --- | --- | --- | --- |
| | 290 | | | | | 295 | | | | 300 | | | | | |

| Leu | Thr | Val | Asp | Lys | Ser | Arg | Trp | Gln | Gln | Gly | Asn | Val | Phe | Ser | Cys |
| --- | --- | --- | --- | --- | --- | --- | --- | --- | --- | --- | --- | --- | --- | --- | --- |
| 305 | | | | | 310 | | | | | 315 | | | | | 320 |

| Ser | Val | Met | His | Glu | Ala | Leu | His | Asn | His | Tyr | Thr | Gln | Lys | Ser | Leu |
| --- | --- | --- | --- | --- | --- | --- | --- | --- | --- | --- | --- | --- | --- | --- | --- |
| | | | | 325 | | | | | 330 | | | | | 335 | |

| Ser | Leu | Ser | Pro | Gly |
| --- | --- | --- | --- | --- |
| | | | | 340 |

<210> SEQ ID NO 113
<211> LENGTH: 1023
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 113

```
atggatgcaa tgaagagagg gctctgctgt gtgctgctgc tgtgtggagc agtcttcgtt      60
tcgcccggcg ccggactgaa gtgtgtatgt cttttgtgtg attcttcaaa ctttacctgc     120
caaacagaag gagcatgttg gcatcagtc atgctaacca atggaaaaga gcaggtgatc      180
aaatcctgtg tctcccttcc agaactgaat gctcaagtct tctgtcatag ttccaacaat     240
gttaccaaaa ccgaatgctg cttcacagat ttttgcaaca cataacact gcaccttcca      300 acagcatcac caaatgcccc aaaacttgga cccatggaga ccggtggtgg aactcacaca     360
tgcccaccgt gcccagcacc tgaactcctg ggggaccgt cagtcttcct cttccccccca     420 aaacccaagg acaccctcat gatctcccgg acccctgagg tcacatgcgt ggtggtggac     480
gtgagccacg aagaccctga ggtcaagttc aactggtacg tggacggcgt ggaggtgcat     540
aatgccaaga caaagccgcg ggaggagcag tacaacagca cgtaccgtgt ggtcagcgtc     600
ctcaccgtcc tgcaccagga ctggctgaat ggcaaggagt acaagtgcaa ggtctccaac     660
aaagccctcc cagcccccat cgagaaaacc atctccaaag ccaagggca gccccgagaa      720 ccacaggtgt acaccctgcc cccatcccgg gaggagatga ccaagaacca ggtcagcctg     780
acctgcctgg tcaaaggctt ctatcccagc gacatcgccg tggagtggga gagcaatggg     840
cagccggaga acaactacga caccacgcct cccgtgctgg actccgacgg ctccttcttc     900
ctctatagcg acctcaccgt ggacaagagc aggtggcagc aggggaacgt cttctcatgc     960
tccgtgatgc atgaggctct gcacaaccac tacacgcaga gagcctctc cctgtctccg    1020 ggt                                                                  1023
```

<210> SEQ ID NO 114
<211> LENGTH: 317
<212> TYPE: PRT
<213> ORGANISM: Artificial Sequence
<220> FEATURE:
<223> OTHER INFORMATION: Description of Artificial Sequence: Synthetic

<400> SEQUENCE: 114

Gly Leu Lys Cys Val Cys Leu Leu Cys Asp Ser Ser Asn Phe Thr Cys
1               5                   10                  15

Gln Thr Glu Gly Ala Cys Trp Ala Ser Val Met Leu Thr Asn Gly Lys
            20                  25                  30

Glu Gln Val Ile Lys Ser Cys Val Ser Leu Pro Glu Leu Asn Ala Gln
        35                  40                  45

Val Phe Cys His Ser Ser Asn Asn Val Thr Lys Thr Glu Cys Cys Phe
    50                  55                  60

Thr Asp Phe Cys Asn Asn Ile Thr Leu His Leu Pro Thr Ala Ser Pro
65                  70                  75                  80

Asn Ala Pro Lys Leu Gly Pro Met Glu Thr Gly Gly Thr His Thr
                85                  90                  95

Cys Pro Pro Cys Pro Ala Pro Glu Leu Leu Gly Gly Pro Ser Val Phe
                100                 105                 110

Leu Phe Pro Pro Lys Pro Lys Asp Thr Leu Met Ile Ser Arg Thr Pro
            115                 120                 125

Glu Val Thr Cys Val Val Val Asp Val Ser His Glu Asp Pro Glu Val
130                 135                 140

Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Tyr Thr Leu Pro Pro
210                 215                 220

Ser Arg Glu Glu Met Thr Lys Asn Gln Val Ser Leu Thr Cys Leu Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Asp Thr Thr Pro Pro Val Leu Asp Ser Asp
            260                 265                 270

Gly Ser Phe Phe Leu Tyr Ser Asp Leu Thr Val Asp Lys Ser Arg Trp
        275                 280                 285

Gln Gln Gly Asn Val Phe Ser Cys Ser Val Met His Glu Ala Leu His
    290                 295                 300

Asn His Tyr Thr Gln Lys Ser Leu Ser Leu Ser Pro Gly
305                 310                 315

<210> SEQ ID NO 115
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Met Asp Ala Met Lys Arg Gly Leu Cys Cys Val Leu Leu Leu Cys Gly
1               5                   10                  15

Ala Val Phe Val Ser Pro Gly Ala Gln Asn Leu Asp Ser Met Leu His

```
             20                  25                  30
Gly Thr Gly Met Lys Ser Asp Ser Asp Gln Lys Lys Ser Glu Asn Gly
         35                  40                  45

Val Thr Leu Ala Pro Glu Asp Thr Leu Pro Phe Leu Lys Cys Tyr Cys
 50                  55                  60

Ser Gly His Cys Pro Asp Asp Ala Ile Asn Asn Thr Cys Ile Thr Asn
 65                  70                  75                  80

Gly His Cys Phe Ala Ile Ile Glu Glu Asp Asp Gln Gly Glu Thr Thr
                 85                  90                  95

Leu Ala Ser Gly Cys Met Lys Tyr Glu Gly Ser Asp Phe Gln Cys Lys
                100                 105                 110

Asp Ser Pro Lys Ala Gln Leu Arg Arg Thr Ile Glu Cys Cys Arg Thr
                115                 120                 125

Asn Leu Cys Asn Gln Tyr Leu Gln Pro Thr Leu Pro Pro Val Val Ile
130                 135                 140

Gly Pro Phe Phe Asp Gly Ser Ile Arg Thr Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
                180                 185                 190

Glu Val Thr Cys Val Val Val Asp Val Ser His Glu Asp Pro Glu Val
                195                 200                 205

Lys Phe Asn Trp Tyr Val Asp Gly Val Glu Val His Asn Ala Lys Thr
            210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
                260                 265                 270

Lys Ala Lys Gly Gln Pro Arg Glu Pro Gln Val Tyr Thr Leu Pro Pro
            275                 280                 285

Ser Arg Glu Glu Met Thr Lys Asn Gln Val Ser Leu Thr Cys Leu Val
290                 295                 300

Lys Gly Phe Tyr Pro Ser Asp Ile Ala Val Glu Trp Glu Ser Asn Gly
305                 310                 315                 320

Gln Pro Glu Asn Asn Tyr Asp Thr Thr Pro Pro Val Leu Asp Ser Asp
                325                 330                 335

Gly Ser Phe Phe Leu Tyr Ser Asp Leu Thr Val Asp Lys Ser Arg Trp
                340                 345                 350

Gln Gln Gly Asn Val Phe Ser Cys Ser Val Met His Glu Ala Leu His
            355                 360                 365

Asn His Tyr Thr Gln Lys Ser Leu Ser Leu Ser Pro Gly
370                 375                 380

<210> SEQ ID NO 116
<211> LENGTH: 1143
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 116
```

-continued

```
atggatgcaa tgaagagagg ctctgctgt gtgctgctgc tgtgtggagc agtcttcgtt      60
tcgcccggcg cccagaatct ggatagtatg cttcatggca ctgggatgaa atcagactcc    120
gaccagaaaa agtcagaaaa tggagtaacc ttagcaccag aggataccttt gccttttta    180
aagtgctatt gctcagggca ctgtccagat gatgctatta ataacacatg cataactaat    240
ggacattgct ttgccatcat agaagaagat gaccagggag aaaccacatt agcttcaggg    300
tgtatgaaat atgaaggatc tgattttcag tgcaaagatt ctccaaaagc ccagctacgc    360
cggacaatag aatgttgtcg gaccaattta tgtaaccagt atttgcaacc cacactgccc    420
cctgttgtca taggtccgtt ttttgatggc agcattcgaa ccggtggtgg aactcacaca    480
tgcccaccgt gcccagcacc tgaactcctg ggggaccgt cagtcttcct cttccccca    540
aaacccaagg acaccctcat gatctcccgg acccctgagg tcacatgcgt ggtggtggac    600
gtgagccacg aagaccctga ggtcaagttc aactggtacg tggacggcgt ggaggtgcat    660
aatgccaaga caaagccgcg ggaggagcag tacaacagca cgtaccgtgt ggtcagcgtc    720
ctcaccgtcc tgcaccagga ctggctgaat ggcaaggagt acaagtgcaa ggtctccaac    780
aaagccctcc cagcccccat cgagaaaacc atctccaaag ccaaagggca gccccgagaa    840
ccacaggtgt acaccctgcc cccatcccgg gaggagatga ccaagaacca ggtcagcctg    900
acctgcctgg tcaaaggctt ctatcccagc gacatcgccg tggagtggga gagcaatggg    960
cagccggaga caactacga caccacgcct cccgtgctgg actccgacgg ctccttcttc   1020
ctctatagcg acctcaccgt ggacaagagc aggtggcagc aggggaacgt cttctcatgc   1080
tccgtgatgc atgaggctct gcacaaccac tacacgcaga gagcctctc cctgtctccg   1140
ggt                                                                 1143
```

<210> SEQ ID NO 117
<211> LENGTH: 359
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 117

```
Gly Ala Gln Asn Leu Asp Ser Met Leu His Gly Thr Gly Met Lys Ser
1               5                   10                  15

Asp Ser Asp Gln Lys Lys Ser Glu Asn Gly Val Thr Leu Ala Pro Glu
                20                  25                  30

Asp Thr Leu Pro Phe Leu Lys Cys Tyr Cys Ser Gly His Cys Pro Asp
            35                  40                  45

Asp Ala Ile Asn Asn Thr Cys Ile Thr Asn Gly His Cys Phe Ala Ile
        50                  55                  60

Ile Glu Glu Asp Asp Gln Gly Glu Thr Thr Leu Ala Ser Gly Cys Met
65                  70                  75                  80

Lys Tyr Glu Gly Ser Asp Phe Gln Cys Lys Asp Ser Pro Lys Ala Gln
                85                  90                  95

Leu Arg Arg Thr Ile Glu Cys Cys Arg Thr Asn Leu Cys Asn Gln Tyr
            100                 105                 110

Leu Gln Pro Thr Leu Pro Val Val Ile Gly Pro Phe Phe Asp Gly
        115                 120                 125

Ser Ile Arg Thr Gly Gly Gly Thr His Thr Cys Pro Pro Cys Pro Ala
    130                 135                 140

Pro Glu Leu Leu Gly Gly Pro Ser Val Phe Leu Phe Pro Pro Lys Pro
```

```
                145                 150                 155                 160
Lys Asp Thr Leu Met Ile Ser Arg Thr Pro Glu Val Thr Cys Val Val
                    165                 170                 175

Val Asp Val Ser His Glu Asp Pro Glu Val Lys Phe Asn Trp Tyr Val
                    180                 185                 190

Asp Gly Val Glu Val His Asn Ala Lys Thr Lys Pro Arg Glu Glu Gln
                    195                 200                 205

Tyr Asn Ser Thr Tyr Arg Val Val Ser Val Leu Thr Val Leu His Gln
                    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                    245                 250                 255

Arg Glu Pro Gln Val Tyr Thr Leu Pro Pro Ser Arg Glu Glu Met Thr
                    260                 265                 270

Lys Asn Gln Val Ser Leu Thr Cys Leu Val Lys Gly Phe Tyr Pro Ser
                    275                 280                 285

Asp Ile Ala Val Glu Trp Glu Ser Asn Gly Gln Pro Glu Asn Asn Tyr
                    290                 295                 300

Asp Thr Thr Pro Pro Val Leu Asp Ser Asp Gly Ser Phe Phe Leu Tyr
305                 310                 315                 320

Ser Asp Leu Thr Val Asp Lys Ser Arg Trp Gln Gln Gly Asn Val Phe
                    325                 330                 335

Ser Cys Ser Val Met His Glu Ala Leu His Asn His Tyr Thr Gln Lys
                    340                 345                 350

Ser Leu Ser Leu Ser Pro Gly
                355

<210> SEQ ID NO 118
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
                20                  25                  30

Gln Glu Cys Leu Phe Phe Asn Ala Asn Trp Glu Lys Asp Arg Thr Asn
                35                  40                  45

Gln Thr Gly Val Glu Pro Cys Tyr Gly Asp Lys Asp Lys Arg Arg His
                50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                    85                  90                  95

Val Glu Lys Lys Asp Ser Pro Glu Val Tyr Phe Cys Cys Cys Glu Gly
                    100                 105                 110

Asn Met Cys Asn Glu Lys Phe Ser Tyr Phe Pro Glu Met Glu Val Thr
                    115                 120                 125

Gln Pro Thr Ser Asn Pro Val Thr Pro Lys Pro Pro Thr Gly Gly Gly
                    130                 135                 140
```

```
Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
            165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
            245                 250                 255

Thr Ile Ser Lys Ala Lys Gly Gln Pro Arg Glu Pro Gln Val Tyr Thr
            260                 265                 270

Leu Pro Pro Ser Arg Lys Glu Met Thr Lys Asn Gln Val Ser Leu Thr
            275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Val Leu
305                 310                 315                 320

Lys Ser Asp Gly Ser Phe Phe Leu Tyr Ser Lys Leu Thr Val Asp Lys
            325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys

<210> SEQ ID NO 119
<211> LENGTH: 1107
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 119
atggatgcaa tgaagagagg gctctgctgt gtgctgctgc tgtgtggagc agtcttcgtt      60
tcgcccggcg ccgctatact tggtagatca gaaactcagg agtgtctttt ctttaatgct     120
aattgggaaa agacagaacc aatcaaact ggtgttgaac cgtgttatgg tgacaaagat      180
aaacggcggc attgttttgc tacctggaag aatatttctg gttccattga atagtgaaa      240 caaggttgtt ggctggatga tatcaactgc tatgacagga ctgattgtgt agaaaaaaaa     300
gacagccctg aagtatattt ctgttgctgt gagggcaata tgtgtaatga aaagttttct     360
tattttccgg agatggaagt cacacagccc acttcaaatc cagttacacc taagccaccc     420
accggtggtg gaactcacac atgcccaccg tgcccagcac ctgaactcct ggggggaccg     480
tcagtcttcc tcttcccccc aaaacccaag gacaccctca tgatctcccg gacccctgag     540
gtcacatgcg tggtggtgga cgtgagccac gaagaccctg aggtcaagtt caactggtac     600
gtggacggcg tggaggtgca taatgccaag acaaagccgc gggaggagca gtacaacagc     660
acgtaccgtg tggtcagcgt cctcaccgtc ctgcaccagg actggctgaa tggcaaggag     720
```

```
tacaagtgca aggtctccaa caaagccctc ccagccccca tcgagaaaac catctccaaa    780
gccaaagggc agccccgaga accacaggtg tacaccctgc ccccatcccg gaaggagatg    840
accaagaacc aggtcagcct gacctgcctg gtcaaaggct tctatcccag cgacatcgcc    900
gtggagtggg agagcaatgg gcagccggag aacaactaca agaccacgcc tcccgtgctg    960
aagtccgacg gctccttctt cctctatagc aagctcaccg tggacaagag caggtggcag   1020
caggggaacg tcttctcatg ctccgtgatg catgaggctc tgcacaacca ctacacgcag   1080
aagagcctct ccctgtctcc gggtaaa                                        1107
```

<210> SEQ ID NO 120
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Ser Arg Lys Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285
```

```
Lys Thr Thr Pro Pro Val Leu Lys Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
                340

<210> SEQ ID NO 121
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Met Asp Ala Met Lys Arg Gly Leu Cys Cys Val Leu Leu Leu Cys Gly
1               5                   10                  15

Ala Val Phe Val Ser Pro Gly Ala Ser Gln Asn Gln Glu Arg Leu Cys
                20                  25                  30

Ala Phe Lys Asp Pro Tyr Gln Gln Asp Leu Gly Ile Gly Glu Ser Arg
            35                  40                  45

Ile Ser His Glu Asn Gly Thr Ile Leu Cys Ser Lys Gly Ser Thr Cys
50                  55                  60

Tyr Gly Leu Trp Glu Lys Ser Lys Gly Asp Ile Asn Leu Val Lys Gln
65                  70                  75                  80

Gly Cys Trp Ser His Ile Gly Asp Pro Gln Glu Cys His Tyr Glu Glu
                85                  90                  95

Cys Val Val Thr Thr Thr Pro Pro Ser Ile Gln Asn Gly Thr Tyr Arg
                100                 105                 110

Phe Cys Cys Cys Ser Thr Asp Leu Cys Asn Val Asn Phe Thr Glu Asn
            115                 120                 125

Phe Pro Pro Pro Asp Thr Thr Pro Leu Ser Pro His Ser Phe Asn
130                 135                 140

Arg Asp Glu Thr Gly Gly Gly Thr His Thr Cys Pro Pro Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Ser Arg Lys Glu Met Thr
        275                 280                 285

Lys Asn Gln Val Ser Leu Thr Cys Leu Val Lys Gly Phe Tyr Pro Ser
    290                 295                 300
```

Asp Ile Ala Val Glu Trp Glu Ser Asn Gly Gln Pro Glu Asn Asn Tyr
305                 310                 315                 320

Lys Thr Thr Pro Pro Val Leu Lys Ser Asp Gly Ser Phe Phe Leu Tyr
            325                 330                 335

Ser Lys Leu Thr Val Asp Lys Ser Arg Trp Gln Gln Gly Asn Val Phe
        340                 345                 350

Ser Cys Ser Val Met His Glu Ala Leu His Asn His Tyr Thr Gln Lys
    355                 360                 365

Ser Leu Ser Leu Ser Pro Gly Lys
    370                 375

<210> SEQ ID NO 122
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 122
atggatgcaa tgaagagagg gctctgctgt gtgctgctgc tgtgtggagc agtcttcgtt      60
tcgcccggcg cctcgcagaa tcaagaacgc ctatgtgcgt ttaaagatcc gtatcagcaa     120
gaccttggga taggtgagag tagaatctct catgaaaatg ggacaatatt atgctcgaaa     180
ggtagcacct gctatggcct tgggagaaaa tcaaaggggg acataaatct tgtaaaacaa     240
ggatgttggt ctcacattgg agatccccaa gagtgtcact atgaagaatg tgtagtaact     300
accactcctc cctcaattca gaatggaaca taccgtttct gctgttgtag cacagattta     360
tgtaatgtca actttactga aattttccca cctcctgaca caacaccact cagtccacct     420
cattcattta accgagatga gaccggtggt ggaactcaca tgcccaccgt gcccagca     480
cctgaactcc tggggggacc gtcagtcttc ctcttccccc caaaacccaa ggacaccctc     540
atgatctccc ggacccctga ggtcacatgc gtggtggtgg acgtgagcca cgaagaccct     600
gaggtcaagt tcaactggta cgtggacggc gtggaggtgc ataatgccaa gacaaagccg     660
cgggaggagc agtacaacag cacgtaccgt gtggtcagcg tcctcaccgt cctgcaccag     720
gactggctga atggcaagga gtacaagtgc aaggtctcca acaaagccct cccagccccc     780
atcgagaaaa ccatctccaa agccaaaggg cagccccgag aaccacaggt gtacaccctg     840
cccccatccc ggaaggagat gaccaagaac caggtcagcc tgacctgcct ggtcaaaggc     900
ttctatccca gcgacatcgc cgtggagtgg gagagcaatg ggcagccgga gaacaactac     960
aagaccacgc ctcccgtgct gaagtccgac ggctccttct tcctctatag caagctcacc    1020
gtggacaaga gcaggtggca gcaggggaac gtcttctcat gctccgtgat gcatgaggct    1080
ctgcacaacc actacacgca gaagagcctc tccctgtctc cgggtaaa             1128

<210> SEQ ID NO 123
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Ser Gln Asn Gln Glu Arg Leu Cys Ala Phe Lys Asp Pro Tyr Gln Gln
1               5                   10                  15

```
Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Ser Thr Asp Leu
                85                  90                  95

Cys Asn Val Asn Phe Thr Glu Asn Phe Pro Pro Asp Thr Thr Pro
            100                 105                 110

Leu Ser Pro Pro His Ser Phe Asn Arg Asp Glu Thr Gly Gly Gly Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Lys Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Lys
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 124
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
            20                  25                  30
```

```
Pro Leu Val Thr Cys Thr Cys Glu Ser Pro His Cys Lys Gly Pro Thr
            35                  40                  45
Cys Arg Gly Ala Trp Cys Thr Val Val Leu Val Arg Glu Glu Gly Arg
        50                  55                  60
His Pro Gln Glu His Arg Gly Cys Gly Asn Leu His Arg Glu Leu Cys
65                  70                  75                  80
Arg Gly Arg Pro Thr Glu Phe Val Asn His Tyr Cys Cys Asp Ser His
                85                  90                  95
Leu Cys Asn His Asn Val Ser Leu Val Leu Glu Ala Thr Gln Pro Pro
            100                 105                 110
Ser Glu Gln Pro Gly Thr Asp Gly Gln Leu Ala Thr Gly Gly Gly Thr
            115                 120                 125
His Thr Cys Pro Pro Cys Pro Ala Pro Glu Leu Leu Gly Gly Pro Ser
        130                 135                 140
Val Phe Leu Phe Pro Pro Lys Pro Lys Asp Thr Leu Met Ile Ser Arg
145                 150                 155                 160
Thr Pro Glu Val Thr Cys Val Val Val Asp Val Ser His Glu Asp Pro
                165                 170                 175
Glu Val Lys Phe Asn Trp Tyr Val Asp Gly Val Glu Val His Asn Ala
            180                 185                 190
Lys Thr Lys Pro Arg Glu Glu Gln Tyr Asn Ser Thr Tyr Arg Val Val
            195                 200                 205
Ser Val Leu Thr Val Leu His Gln Asp Trp Leu Asn Gly Lys Glu Tyr
        210                 215                 220
Lys Cys Lys Val Ser Asn Lys Ala Leu Pro Ala Pro Ile Glu Lys Thr
225                 230                 235                 240
Ile Ser Lys Ala Lys Gly Gln Pro Arg Glu Pro Gln Val Tyr Thr Leu
                245                 250                 255
Pro Pro Ser Arg Glu Glu Met Thr Lys Asn Gln Val Ser Leu Thr Cys
            260                 265                 270
Leu Val Lys Gly Phe Tyr Pro Ser Asp Ile Ala Val Glu Trp Glu Ser
        275                 280                 285
Asn Gly Gln Pro Glu Asn Asn Tyr Asp Thr Thr Pro Pro Val Leu Asp
    290                 295                 300
Ser Asp Gly Ser Phe Phe Leu Tyr Ser Asp Leu Thr Val Asp Lys Ser
305                 310                 315                 320
Arg Trp Gln Gln Gly Asn Val Phe Ser Cys Ser Val Met His Glu Ala
                325                 330                 335
Leu His Asn His Tyr Thr Gln Lys Ser Leu Ser Leu Ser Pro Gly
            340                 345                 350
```

<210> SEQ ID NO 125
<211> LENGTH: 1053
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 125

```
atggatgcaa tgaagagagg ctctgctgtg tgctgctgc tgtgtggagc agtcttcgtt      60
tcgcccggcg ccgaccctgt gaagccgtct cggggcccgc tggtgacctg cacgtgtgag     120
agcccacatt gcaaggggcc tacctgccgg ggggcctggt gcacagtagt gctggtgcgg    180
gaggagggga ggcacccca ggaacatcgg ggctgcggga acttgcacag ggagctctgc     240
```

```
aggggccgcc ccaccgagtt cgtcaaccac tactgctgcg acagccacct ctgcaaccac      300
aacgtgtccc tggtgctgga ggccacccaa cctccttcgg agcagccggg aacagatggc      360
cagctggcca ccggtggtgg aactcacaca tgcccaccgt gcccagcacc tgaactcctg      420
gggggaccgt cagtcttcct cttccccccca aaacccaagg acaccctcat gatctcccgg      480 accccctgagg tcacatgcgt ggtggtggac gtgagccacg aagaccctga ggtcaagttc      540
aactggtacg tggacggcgt ggaggtgcat aatgccaaga caaagccgcg ggaggagcag      600
tacaacagca cgtaccgtgt ggtcagcgtc ctcaccgtcc tgcaccagga ctggctgaat      660
ggcaaggagt acaagtgcaa ggtctccaac aaagcccctcc cagcccccat cgagaaaacc      720
atctccaaag ccaaagggca gccccgagaa ccacaggtgt acaccctgcc cccatcccgg      780
gaggagatga ccaagaacca ggtcagcctg acctgcctgg tcaaaggctt ctatcccagc      840
gacatcgccg tggagtggga gagcaatggg cagccggaga caactacga caccacgcct      900 cccgtgctgg actccgacgg ctccttcttc ctctatagcg acctcaccgt ggacaagagc      960
aggtggcagc aggggaacgt cttctcatgc tccgtgatgc atgaggctct gcacaaccac     1020
tacacgcaga agagcctctc cctgtctccg ggt                                 1053
```

<210> SEQ ID NO 126  
<211> LENGTH: 327  
<212> TYPE: PRT  
<213> ORGANISM: Artificial Sequence  
<220> FEATURE:  
<223> OTHER INFORMATION: Description of Artificial Sequence: Synthetic polypeptide

<400> SEQUENCE: 126

```
Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
        35                  40                  45

Gly Asn Leu His Arg Glu Leu Cys Arg Gly Arg Pro Thr Glu Phe Val
    50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
            85                  90                  95

Gln Leu Ala Thr Gly Gly Gly Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
            165                 170                 175

Tyr Asn Ser Thr Tyr Arg Val Val Ser Val Leu Thr Val Leu His Gln
        180                 185                 190

Asp Trp Leu Asn Gly Lys Glu Tyr Lys Cys Lys Val Ser Asn Lys Ala
    195                 200                 205
```

```
Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Glu Glu Met Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
                260                 265                 270

Asp Thr Thr Pro Pro Val Leu Asp Ser Asp Gly Ser Phe Phe Leu Tyr
            275                 280                 285

Ser Asp Leu Thr Val Asp Lys Ser Arg Trp Gln Gln Gly Asn Val Phe
290                 295                 300

Ser Cys Ser Val Met His Glu Ala Leu His Asn His Tyr Thr Gln Lys
305                 310                 315                 320

Ser Leu Ser Leu Ser Pro Gly
                325

<210> SEQ ID NO 127
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
                20                  25                  30

Ser Val Asn Asn Asp Met Ile Val Thr Asp Asn Asn Gly Ala Val Lys
            35                  40                  45

Phe Pro Gln Leu Cys Lys Phe Cys Asp Val Arg Phe Ser Thr Cys Asp
50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Asn Thr Ser Asn Pro
145                 150                 155                 160

Asp Thr Gly Gly Gly Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
210                 215                 220

Val Glu Val His Asn Ala Lys Thr Lys Pro Arg Glu Glu Gln Tyr Asn
225                 230                 235                 240
```

```
Ser Thr Tyr Arg Val Ser Val Leu Thr Val Leu His Gln Asp Trp
            245                 250                 255

Leu Asn Gly Lys Glu Tyr Lys Cys Lys Val Ser Asn Lys Ala Leu Pro
        260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Ser Arg Lys Glu Met Thr Lys Asn
    290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Lys Ser Asp Gly Ser Phe Phe Leu Tyr Ser Lys
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
370                 375                 380

Ser Leu Ser Pro Gly Lys
385             390

<210> SEQ ID NO 128
<211> LENGTH: 1170
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 128
atggatgcaa tgaagagagg gctctgctgt gtgctgctgc tgtgtggagc agtcttcgtt      60
tcgcccggcg ccacgatccc accgcacgtt cagaagtcgg ttaataacga catgatagtc     120
actgacaaca acggtgcagt caagtttcca caactgtgta aattttgtga tgtgagattt     180
tccacctgtg acaaccagaa atcctgcatg agcaactgca gcatcacctc catctgtgag     240
aagccacagg aagtctgtgt ggctgtatgg agaaagaatg acgagaacat aacactagag     300
acagtttgcc atgaccccaa gctcccctac catgacttta ttctggaaga tgctgcttct     360
ccaaagtgca ttatgaagga aaaaaaaaag cctggtgaga ctttcttcat gtgttcctgt     420
agctctgatg agtgcaatga caacatcatc ttctcagaag aatataacac cagcaatcct     480
gacaccggtg gtggaactca cacatgccca ccgtgcccag cacctgaact cctgggggga     540
ccgtcagtct tcctcttccc cccaaaaccc aaggacaccc tcatgatctc ccggaccect     600 gaggtcacat gcgtggtggt ggacgtgagc cacgaagacc ctgaggtcaa gttcaactgg     660
tacgtggacg gcgtggaggt gcataatgcc aagacaaagc cgcgggagga gcagtacaac     720
agcacgtacc gtgtggtcag cgtcctcacc gtcctgcacc aggactggct gaatggcaag     780
gagtacaagt gcaaggtctc caacaaagcc ctcccagccc ccatcgagaa aaccatctcc     840
aaagccaaag gcagccccg agaaccacag gtgtacaccc tgcccccatc ccggaaggag     900
atgaccaaga accaggtcag cctgacctgc ctggtcaaag gcttctatcc cagcgacatc     960
gccgtggagt gggagagcaa tgggcagccg gagaacaact acaagaccac gcctcccgtg    1020
ctgaagtccg acggctcctt cttcctctat agcaagctca ccgtggacaa gagcaggtgg    1080
cagcagggga acgtcttctc atgctccgtg atgcatgagg ctctgcacaa ccactacacg    1140
```
cagaagagcc tctccctgtc tccgggtaaa       1170

<210> SEQ ID NO 129
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

```
Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Thr Gly Gly Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Lys Glu Met Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Lys Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350
```

Asn His Tyr Thr Gln Lys Ser Leu Ser Leu Ser Pro Gly Lys
         355                 360                 365

<210> SEQ ID NO 130
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Thr His
            180                 185                 190

Thr Cys Pro Pro Cys Pro Ala Pro Glu Leu Leu Gly Gly Pro Ser Val
    195                 200                 205

Phe Leu Phe Pro Pro Lys Pro Lys Asp Thr Leu Met Ile Ser Arg Thr
210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Ala Leu Pro Ala Pro Ile Glu Lys Thr Ile
    290                 295                 300

Ser Lys Ala Lys Gly Gln Pro Arg Glu Pro Gln Val Tyr Thr Leu Pro
305                 310                 315                 320

Pro Ser Arg Lys Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn

```
                340             345             350
Gly Gln Pro Glu Asn Asn Tyr Lys Thr Thr Pro Val Leu Lys Ser
            355             360             365

Asp Gly Ser Phe Phe Leu Tyr Ser Lys Leu Thr Val Asp Lys Ser Arg
        370             375             380

Trp Gln Gln Gly Asn Val Phe Ser Cys Ser Val Met His Glu Ala Leu
385             390             395             400

His Asn His Tyr Thr Gln Lys Ser Leu Ser Leu Ser Pro Gly Lys
            405             410             415

<210> SEQ ID NO 131
<211> LENGTH: 1245
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 131
atggatgcaa tgaagagagg gctctgctgt gtgctgctgc tgtgtggagc agtcttcgtt     60
tcgcccggcg ccacgatccc accgcacgtt cagaagtcgg atgtggaaat ggaggcccag    120
aaagatgaaa tcatctgccc cagctgtaat aggactgccc atccactgag acatattaat    180
aacgacatga tagtcactga caacaacggt gcagtcaagt tccacaact gtgtaaattt    240 tgtgatgtga gattttccac ctgtgacaac cagaaatcct gcatgagcaa ctgcagcatc    300
acctccatct gtgagaagcc acaggaagtc tgtgtggctg tatggagaaa gaatgacgag    360
aacataacac tagagacagt ttgccatgac cccaagctcc cctaccatga ctttattctg    420
gaagatgctg cttctccaaa gtgcattatg aaggaaaaaa aaaagcctgg tgagactttc    480
ttcatgtgtt cctgtagctc tgatgagtgc aatgacaaca tcatcttctc agaagaatat    540
aacaccagca atcctgacac cggtggtgga actcacacat gcccaccgtg cccagcacct    600
gaactcctgg ggggaccgtc agtcttcctc ttccccccaa aacccaagga caccctcatg    660
atctcccgga cccctgaggt cacatgcgtg gtggtggacg tgagccacga agaccctgag    720
gtcaagttca actggtacgt ggacggcgtg gaggtgcata atgccaagac aaagccgcgg    780
gaggagcagt acaacagcac gtaccgtgtg gtcagcgtcc tcaccgtcct gcaccaggac    840
tggctgaatg gcaaggagta caagtgcaag gtctccaaca aagcccctcc cagccccatc    900
gagaaaacca tctccaaagc caagggcag ccccgagaac acaggtgta caccctgccc    960 ccatcccgga aggagatgac caagaaccag gtcagcctga cctgcctggt caaaggcttc   1020
tatcccagcg acatcgccgt ggagtgggag agcaatgggc agccggagaa caactacaag   1080
accacgcctc ccgtgctgga gtccgacggc tccttcttcc tctatagcaa gctcaccgtg   1140
gacaagagca ggtggcagca ggggaacgtc ttctcatgct ccgtgatgca tgaggctctg   1200
cacaaccact acacgcagaa gagcctctcc ctgtctccgg gtaaa                   1245

<210> SEQ ID NO 132
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Thr Ile Pro Pro His Val Gln Lys Ser Asp Val Glu Met Glu Ala Gln
```

```
                1               5                    10                   15
              Lys  Asp  Glu  Ile  Ile  Cys  Pro  Ser  Cys  Asn  Arg  Thr  Ala  His  Pro  Leu
                               20                   25                   30
              Arg  His  Ile  Asn  Asn  Asp  Met  Ile  Val  Thr  Asp  Asn  Asn  Gly  Ala  Val
                               35                   40                   45
              Lys  Phe  Pro  Gln  Leu  Cys  Lys  Phe  Cys  Asp  Val  Arg  Phe  Ser  Thr  Cys
                    50                        55                   60
              Asp  Asn  Gln  Lys  Ser  Cys  Met  Ser  Asn  Cys  Ser  Ile  Thr  Ser  Ile  Cys
               65                        70                   75                        80
              Glu  Lys  Pro  Gln  Glu  Val  Cys  Val  Ala  Val  Trp  Arg  Lys  Asn  Asp  Glu
                                    85                   90                   95
              Asn  Ile  Thr  Leu  Glu  Thr  Val  Cys  His  Asp  Pro  Lys  Leu  Pro  Tyr  His
                              100                  105                  110
              Asp  Phe  Ile  Leu  Glu  Asp  Ala  Ala  Ser  Pro  Lys  Cys  Ile  Met  Lys  Glu
                              115                  120                  125
              Lys  Lys  Lys  Pro  Gly  Glu  Thr  Phe  Phe  Met  Cys  Ser  Cys  Ser  Ser  Asp
                    130                       135                  140
              Glu  Cys  Asn  Asp  Asn  Ile  Ile  Phe  Ser  Glu  Glu  Tyr  Asn  Thr  Ser  Asn
              145                       150                  155                       160
              Pro  Asp  Thr  Gly  Gly  Thr  His  Thr  Cys  Pro  Pro  Cys  Pro  Ala  Pro
                                   165                  170                  175
              Glu  Leu  Leu  Gly  Gly  Pro  Ser  Val  Phe  Leu  Phe  Pro  Pro  Lys  Pro  Lys
                              180                  185                  190
              Asp  Thr  Leu  Met  Ile  Ser  Arg  Thr  Pro  Glu  Val  Thr  Cys  Val  Val  Val
                              195                  200                  205
              Asp  Val  Ser  His  Glu  Asp  Pro  Glu  Val  Lys  Phe  Asn  Trp  Tyr  Val  Asp
                              210                  215                  220
              Gly  Val  Glu  Val  His  Asn  Ala  Lys  Thr  Lys  Pro  Arg  Glu  Glu  Gln  Tyr
              225                       230                  235                       240
              Asn  Ser  Thr  Tyr  Arg  Val  Val  Ser  Val  Leu  Thr  Val  Leu  His  Gln  Asp
                                   245                  250                       255
              Trp  Leu  Asn  Gly  Lys  Glu  Tyr  Lys  Cys  Lys  Val  Ser  Asn  Lys  Ala  Leu
                              260                       265                  270
              Pro  Ala  Pro  Ile  Glu  Lys  Thr  Ile  Ser  Lys  Ala  Lys  Gly  Gln  Pro  Arg
                         275                       280                  285
              Glu  Pro  Gln  Val  Tyr  Thr  Leu  Pro  Pro  Ser  Arg  Lys  Glu  Met  Thr  Lys
                         290                       295                  300
              Asn  Gln  Val  Ser  Leu  Thr  Cys  Leu  Val  Lys  Gly  Phe  Tyr  Pro  Ser  Asp
              305                       310                       315                       320
              Ile  Ala  Val  Glu  Trp  Glu  Ser  Asn  Gly  Gln  Pro  Glu  Asn  Asn  Tyr  Lys
                                        325                  330                  335
              Thr  Thr  Pro  Pro  Val  Leu  Lys  Ser  Asp  Gly  Ser  Phe  Phe  Leu  Tyr  Ser
                              340                       345                  350
              Lys  Leu  Thr  Val  Asp  Lys  Ser  Arg  Trp  Gln  Gln  Gly  Asn  Val  Phe  Ser
                              355                       360                  365
              Cys  Ser  Val  Met  His  Glu  Ala  Leu  His  Asn  His  Tyr  Thr  Gln  Lys  Ser
                    370                       375                  380
              Leu  Ser  Leu  Ser  Pro  Gly  Lys
              385                       390

<210> SEQ ID NO 133
<211> LENGTH: 385
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 133

Met Asp Ala Met Lys Arg Gly Leu Cys Cys Val Leu Leu Leu Cys Gly
1               5                   10                  15

Ala Val Phe Val Ser Pro Gly Ala Pro Asn Arg Arg Thr Cys Val
            20                  25                  30

Phe Phe Glu Ala Pro Gly Val Arg Gly Ser Thr Lys Thr Leu Gly Glu
        35                  40                  45

Leu Leu Asp Thr Gly Thr Glu Leu Pro Arg Ala Ile Arg Cys Leu Tyr
    50                  55                  60

Ser Arg Cys Cys Phe Gly Ile Trp Asn Leu Thr Gln Asp Arg Ala Gln
65                  70                  75                  80

Val Glu Met Gln Gly Cys Arg Asp Ser Asp Glu Pro Gly Cys Glu Ser
                85                  90                  95

Leu His Cys Asp Pro Ser Pro Arg Ala His Pro Ser Pro Gly Ser Thr
            100                 105                 110

Leu Phe Thr Cys Ser Cys Gly Thr Asp Phe Cys Asn Ala Asn Tyr Ser
        115                 120                 125

His Leu Pro Pro Gly Ser Pro Gly Thr Pro Gly Ser Gln Gly Pro
    130                 135                 140

Gln Ala Ala Pro Gly Glu Ser Ile Trp Met Ala Leu Thr Gly Gly Gly
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Ser Arg Lys Glu Met Thr Lys Asn Gln Val Ser Leu Thr
    290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Lys Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

Lys
```

<210> SEQ ID NO 134

<400> SEQUENCE: 134

000

<210> SEQ ID NO 135
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu Thr Gly Gly Thr His Thr Cys Pro Pro Cys Pro
130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Lys Glu Met
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Lys Ser Asp Gly Ser Phe Phe Leu
305                 310                 315                 320
```

Tyr Ser Lys Leu Thr Val Asp Lys Ser Arg Trp Gln Gln Gly Asn Val
            325                 330                 335

Phe Ser Cys Ser Val Met His Glu Ala Leu His Asn His Tyr Thr Gln
        340                 345                 350

Lys Ser Leu Ser Leu Ser Pro Gly Lys
        355                 360

<210> SEQ ID NO 136
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Met Asp Ala Met Lys Arg Gly Leu Cys Cys Val Leu Leu Leu Cys Gly
1               5                   10                  15

Ala Val Phe Val Ser Pro Gly Ala Met Glu Asp Glu Lys Pro Lys Val
            20                  25                  30

Asn Pro Lys Leu Tyr Met Cys Val Cys Glu Gly Leu Ser Cys Gly Asn
        35                  40                  45

Glu Asp His Cys Glu Gly Gln Gln Cys Phe Ser Ser Leu Ser Ile Asn
    50                  55                  60

Asp Gly Phe His Val Tyr Gln Lys Gly Cys Phe Gln Val Tyr Glu Gln
65                  70                  75                  80

Gly Lys Met Thr Cys Lys Thr Pro Pro Ser Pro Gly Gln Ala Val Glu
                85                  90                  95

Cys Cys Gln Gly Asp Trp Cys Asn Arg Asn Ile Thr Ala Gln Leu Pro
            100                 105                 110

Thr Lys Gly Lys Ser Phe Pro Gly Thr Gln Asn Phe His Leu Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Asp Thr Thr Pro
    290                 295                 300

Pro Val Leu Asp Ser Asp Gly Ser Phe Phe Leu Tyr Ser Asp Leu Thr

```
                305                 310                 315                 320
Val Asp Lys Ser Arg Trp Gln Gln Gly Asn Val Phe Ser Cys Ser Val
                    325                 330                 335
Met His Glu Ala Leu His Asn His Tyr Thr Gln Lys Ser Leu Ser Leu
                340                 345                 350
Ser Pro Gly
        355

<210> SEQ ID NO 137
<211> LENGTH: 1065
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
atggatgcaa tgaagagagg gctctgctgt gtgctgctgc tgtgtggagc agtcttcgtt      60
tcgcccggcg ccatggaaga tgagaagccc aaggtcaacc ccaaactcta catgtgtgtg     120
tgtgaaggtc tctcctgcgg taatgaggac cactgtgaag ccagcagtg ctttcctca      180 ctgagcatca acgatggctt ccacgtctac cagaaaggct gcttccaggt ttatgagcag     240
ggaaagatga cctgtaagac cccgccgtcc cctggccaag ctgtggagtg ctgccaaggg     300
gactggtgta caggaacat cacggcccag ctgcccacta aggaaaatc cttccctgga      360 acacagaatt ccacttgga gaccggtggt ggaactcaca catgcccacc gtgcccagca     420
cctgaactcc tggggggacc gtcagtcttc ctcttccccc caaaacccaa ggacaccctc     480
atgatctccc ggacccctga ggtcacatgc gtggtggtgg acgtgagcca cgaagaccct     540
gaggtcaagt tcaactggta cgtggacggc gtggaggtgc ataatgccaa gacaaagccg     600
cgggaggagc agtacaacag cacgtaccgt gtggtcagcg tcctcaccgt cctgcaccag     660
gactggctga atggcaagga gtacaagtgc aaggtctcca acaaagccct cccagccccc     720
atcgagaaaa ccatctccaa agccaaaggg cagccccgag aaccacaggt gtacaccctg     780
cccccatccc gggaggagat gaccaagaac caggtcagcc tgacctgcct ggtcaaaggc     840
ttctatccca gcgacatcgc cgtggagtgg gagagcaatg ggcagccgga gaacaactac     900
aagaccacgc ctcccgtgct ggactccgac ggctccttct tcctctatag cgacctcacc     960
gtggacaaga gcaggtggca gcaggggaac gtcttctcat gctccgtgat gcatgaggct    1020
ctgcacaacc actacacgca gaagagcctc tccctgtctc cgggt                    1065

<210> SEQ ID NO 138
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
```

```
                    50                  55                  60
Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                    85                  90                  95

Thr Gln Asn Phe His Leu Glu Thr Gly Gly Thr His Thr Cys Pro
                100                 105                 110

Pro Cys Pro Ala Pro Glu Leu Leu Gly Gly Pro Ser Val Phe Leu Phe
                115                 120                 125

Pro Pro Lys Pro Lys Asp Thr Leu Met Ile Ser Arg Thr Pro Glu Val
            130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
                180                 185                 190

Val Leu His Gln Asp Trp Leu Asn Gly Lys Glu Tyr Lys Cys Lys Val
            195                 200                 205

Ser Asn Lys Ala Leu Pro Ala Pro Ile Glu Lys Thr Ile Ser Lys Ala
            210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
                260                 265                 270

Glu Asn Asn Tyr Asp Thr Thr Pro Pro Val Leu Asp Ser Asp Gly Ser
            275                 280                 285

Phe Phe Leu Tyr Ser Asp Leu Thr Val Asp Lys Ser Arg Trp Gln Gln
            290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly
                325                 330

<210> SEQ ID NO 139
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Met Asp Ala Met Lys Arg Gly Leu Cys Cys Val Leu Leu Leu Cys Gly
1               5                   10                  15

Ala Val Phe Val Ser Pro Gly Ala Ala Leu Leu Pro Gly Ala Thr Ala
                20                  25                  30

Leu Gln Cys Phe Cys His Leu Cys Thr Lys Asp Asn Phe Thr Cys Val
            35                  40                  45

Thr Asp Gly Leu Cys Phe Val Ser Val Thr Glu Thr Thr Asp Lys Val
        50                  55                  60

Ile His Asn Ser Met Cys Ile Ala Glu Ile Asp Leu Ile Pro Arg Asp
65                  70                  75                  80
```

```
Arg Pro Phe Val Cys Ala Pro Ser Ser Lys Thr Gly Ser Val Thr Thr
                 85                  90                  95
Thr Tyr Cys Cys Asn Gln Asp His Cys Asn Lys Ile Glu Leu Pro Thr
            100                 105                 110
Thr Val Lys Ser Ser Pro Gly Leu Gly Pro Val Glu Thr Gly Gly Gly
        115                 120                 125
Thr His Thr Cys Pro Pro Cys Pro Ala Pro Glu Leu Leu Gly Gly Pro
    130                 135                 140
Ser Val Phe Leu Phe Pro Pro Lys Pro Lys Asp Thr Leu Met Ile Ser
145                 150                 155                 160
Arg Thr Pro Glu Val Thr Cys Val Val Val Asp Val Ser His Glu Asp
                165                 170                 175
Pro Glu Val Lys Phe Asn Trp Tyr Val Asp Gly Val Glu Val His Asn
            180                 185                 190
Ala Lys Thr Lys Pro Arg Glu Glu Gln Tyr Asn Ser Thr Tyr Arg Val
        195                 200                 205
Val Ser Val Leu Thr Val Leu His Gln Asp Trp Leu Asn Gly Lys Glu
    210                 215                 220
Tyr Lys Cys Lys Val Ser Asn Lys Ala Leu Pro Ala Pro Ile Glu Lys
225                 230                 235                 240
Thr Ile Ser Lys Ala Lys Gly Gln Pro Arg Glu Pro Gln Val Tyr Thr
                245                 250                 255
Leu Pro Pro Ser Arg Glu Glu Met Thr Lys Asn Gln Val Ser Leu Thr
            260                 265                 270
Cys Leu Val Lys Gly Phe Tyr Pro Ser Asp Ile Ala Val Glu Trp Glu
        275                 280                 285
Ser Asn Gly Gln Pro Glu Asn Asn Tyr Asp Thr Thr Pro Pro Val Leu
    290                 295                 300
Asp Ser Asp Gly Ser Phe Phe Leu Tyr Ser Asp Leu Thr Val Asp Lys
305                 310                 315                 320
Ser Arg Trp Gln Gln Gly Asn Val Phe Ser Cys Ser Val Met His Glu
                325                 330                 335
Ala Leu His Asn His Tyr Thr Gln Lys Ser Leu Ser Leu Ser Pro Gly
            340                 345                 350

<210> SEQ ID NO 140
<211> LENGTH: 1056
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 140
atggatgcaa tgaagagagg gctctgctgt gtgctgctgc tgtgtggagc agtcttcgtt    60
tcgcccggcg ccgcgctgct cccgggggcg acggcgttac agtgtttctg ccacctctgt   120
acaaaagaca attttacttg tgtgacagat gggctctgct tgtctctgt cacagagacc    180 acagacaaag ttatacacaa cagcatgtgt atagctgaaa ttgacttaat tcctcgagat   240
aggccgtttg tatgtgcacc ctcttcaaaa actgggtctg tgactacaac atattgctgc   300
aatcaggacc attgcaataa aatagaactt ccaactactg taaagtcatc acctggcctt   360
ggtcctgtgg aaaccggtgg tggaactcac acatgcccac cgtgcccagc acctgaactc   420
ctggggggac cgtcagtctt cctcttcccc ccaaaaccca aggacaccct catgatctcc   480
cggacccctg aggtcacatg cgtggtggtg gacgtgagcc acgaagaccc tgaggtcaag   540
```

```
ttcaactggt acgtggacgg cgtggaggtg cataatgcca agacaaagcc gcgggaggag    600
cagtacaaca gcacgtaccg tgtggtcagc gtcctcaccg tcctgcacca ggactggctg    660
aatggcaagg agtacaagtg caaggtctcc aacaaagccc tcccagcccc catcgagaaa    720
accatctcca aagccaaagg gcagccccga gaaccacagg tgtacaccct gcccccatcc    780
cgggaggaga tgaccaagaa ccaggtcagc ctgacctgcc tggtcaaagg cttctatccc    840
agcgacatcg ccgtggagtg ggagagcaat gggcagccgg agaacaacta cgacaccacg    900
cctcccgtgc tggactccga cggctccttc ttcctctata gcgacctcac cgtggacaag    960
agcaggtggc agcaggggaa cgtcttctca tgctccgtga tgcatgaggc tctgcacaac   1020
cactacacgc agaagagcct ctccctgtct ccgggt                             1056
```

<210> SEQ ID NO 141
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

```
Ala Leu Leu Pro Gly Ala Thr Ala Leu Gln Cys Phe Cys His Leu Cys
1               5                   10                  15

Thr Lys Asp Asn Phe Thr Cys Val Thr Asp Gly Leu Cys Phe Val Ser
            20                  25                  30

Val Thr Glu Thr Thr Asp Lys Val Ile His Asn Ser Met Cys Ile Ala
        35                  40                  45

Glu Ile Asp Leu Ile Pro Arg Asp Arg Pro Phe Val Cys Ala Pro Ser
    50                  55                  60

Ser Lys Thr Gly Ser Val Thr Thr Thr Tyr Cys Cys Asn Gln Asp His
65                  70                  75                  80

Cys Asn Lys Ile Glu Leu Pro Thr Thr Val Lys Ser Ser Pro Gly Leu
                85                  90                  95

Gly Pro Val Glu Thr Gly Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
```

```
                 260                 265                 270
Tyr Asp Thr Thr Pro Val Leu Asp Ser Asp Gly Ser Phe Phe Leu
                275                 280                 285

Tyr Ser Asp Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 142
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Met Asp Ala Met Lys Arg Gly Leu Cys Cys Val Leu Leu Leu Cys Gly
1               5                   10                  15

Ala Val Phe Val Ser Pro Gly Ala Lys Lys Glu Asp Gly Glu Ser Thr
            20                  25                  30

Ala Pro Thr Pro Arg Pro Lys Val Leu Arg Cys Lys Cys His His His
        35                  40                  45

Cys Pro Glu Asp Ser Val Asn Asn Ile Cys Ser Thr Asp Gly Tyr Cys
    50                  55                  60

Phe Thr Met Ile Glu Glu Asp Ser Gly Leu Pro Val Val Thr Ser
65                  70                  75                  80

Gly Cys Leu Gly Leu Glu Gly Ser Asp Phe Gln Cys Arg Asp Thr Pro
                85                  90                  95

Ile Pro His Gln Arg Arg Ser Ile Glu Cys Cys Thr Glu Arg Asn Glu
            100                 105                 110

Cys Asn Lys Asp Leu His Pro Thr Leu Pro Pro Leu Lys Asn Arg Asp
        115                 120                 125

Phe Val Asp Gly Pro Ile His His Arg Thr Gly Gly Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Glu Glu Met Thr Lys Asn Gln Val Ser Leu Thr Cys Leu Val
        275                 280                 285
```

```
Lys Gly Phe Tyr Pro Ser Asp Ile Ala Val Glu Trp Glu Ser Asn Gly
        290                 295                 300

Gln Pro Glu Asn Asn Tyr Asp Thr Thr Pro Pro Val Leu Asp Ser Asp
305                 310                 315                 320

Gly Ser Phe Phe Leu Tyr Ser Asp Leu Thr Val Asp Lys Ser Arg Trp
            325                 330                 335

Gln Gln Gly Asn Val Phe Ser Cys Ser Val Met His Glu Ala Leu His
        340                 345                 350

Asn His Tyr Thr Gln Lys Ser Leu Ser Leu Ser Pro Gly
        355                 360                 365

<210> SEQ ID NO 143
<211> LENGTH: 1095
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 143
atggatgcaa tgaagagagg gctctgctgt gtgctgctgc tgtgtggagc agtcttcgtt      60
tcgcccggcg ccaagaaaga ggatggtgag agtacagccc ccaccccccg tccaaaggtc     120
ttgcgttgta aatgccacca ccattgtcca gaagactcag tcaacaatat ttgcagcaca     180
gacggatatt gtttcacgat gatagaagag gatgactctg ggttgcctgt ggtcacttct     240
ggttgcctag gactagaagg ctcagatttt cagtgtcggg acactcccat tcctcatcaa     300
agaagatcaa ttgaatgctg cacagaaagg aacgaatgta taaagaccct acaccctaca     360
ctgcctccat tgaaaaacag agattttgtt gatggaccta caccacagga ccggtggt      420 ggaactcaca catgcccacc gtgcccagca cctgaactcc tggggggacc gtcagtcttc     480
ctcttccccc caaaacccaa ggacaccctc atgatctccc ggacccctga ggtcacatgc     540
gtggtggtgg acgtgagcca cgaagaccct gaggtcaagt tcaactggta cgtggacggc     600
gtggaggtgc ataatgccaa gacaaagccg cgggaggagc agtacaacag cacgtaccgt     660
gtggtcagcg tcctcaccgt cctgcaccag gactggctga atggcaagga gtacaagtgc     720
aaggtctcca acaaagccct cccagccccc atcgagaaaa ccatctccaa agccaaaggg     780
cagccccgag aaccacaggt gtacaccctg cccccatccc gggaggagat gaccaagaac     840
caggtcagcc tgacctgcct ggtcaaaggc ttctatccca gcgacatcgc cgtggagtgg     900
gagagcaatg ggcagccgga gaacaactac gacaccacgc ctcccgtgct ggactccgac     960
ggctccttct tcctctatag cgacctcacc gtggacaaga gcaggtggca gcaggggaac    1020
gtcttctcat gctccgtgat gcatgaggct ctgcacaacc actacacgca gaagagcctc    1080
tccctgtctc cgggt                                                    1095

<210> SEQ ID NO 144
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Lys Lys Glu Asp Gly Glu Ser Thr Ala Pro Thr Pro Arg Pro Lys Val
1               5                   10                  15

Leu Arg Cys Lys Cys His His His Cys Pro Glu Asp Ser Val Asn Asn
```

```
                  20                  25                  30
Ile Cys Ser Thr Asp Gly Tyr Cys Phe Thr Met Ile Glu Glu Asp
             35                  40                  45
Ser Gly Leu Pro Val Val Thr Ser Gly Cys Leu Gly Leu Glu Gly Ser
 50                  55                  60
Asp Phe Gln Cys Arg Asp Thr Pro Ile Pro His Gln Arg Arg Ser Ile
 65                  70                  75                  80
Glu Cys Cys Thr Glu Arg Asn Glu Cys Asn Lys Asp Leu His Pro Thr
                 85                  90                  95
Leu Pro Pro Leu Lys Asn Arg Asp Phe Val Asp Gly Pro Ile His His
                100                 105                 110
Arg Thr Gly Gly Thr His Thr Cys Pro Pro Cys Pro Ala Pro Glu
                115                 120                 125
Leu Leu Gly Gly Pro Ser Val Phe Leu Phe Pro Pro Lys Pro Lys Asp
                130                 135                 140
Thr Leu Met Ile Ser Arg Thr Pro Glu Val Thr Cys Val Val Val Asp
145                 150                 155                 160
Val Ser His Glu Asp Pro Glu Val Lys Phe Asn Trp Tyr Val Asp Gly
                165                 170                 175
Val Glu Val His Asn Ala Lys Thr Lys Pro Arg Glu Glu Gln Tyr Asn
                180                 185                 190
Ser Thr Tyr Arg Val Val Ser Val Leu Thr Val Leu His Gln Asp Trp
                195                 200                 205
Leu Asn Gly Lys Glu Tyr Lys Cys Lys Val Ser Asn Lys Ala Leu Pro
                210                 215                 220
Ala Pro Ile Glu Lys Thr Ile Ser Lys Ala Lys Gly Gln Pro Arg Glu
225                 230                 235                 240
Pro Gln Val Tyr Thr Leu Pro Pro Ser Arg Glu Glu Met Thr Lys Asn
                245                 250                 255
Gln Val Ser Leu Thr Cys Leu Val Lys Gly Phe Tyr Pro Ser Asp Ile
                260                 265                 270
Ala Val Glu Trp Glu Ser Asn Gly Gln Pro Glu Asn Asn Tyr Asp Thr
                275                 280                 285
Thr Pro Pro Val Leu Asp Ser Asp Gly Ser Phe Phe Leu Tyr Ser Asp
                290                 295                 300
Leu Thr Val Asp Lys Ser Arg Trp Gln Gln Gly Asn Val Phe Ser Cys
305                 310                 315                 320
Ser Val Met His Glu Ala Leu His Asn His Tyr Thr Gln Lys Ser Leu
                325                 330                 335
Ser Leu Ser Pro Gly
                340

<210> SEQ ID NO 145

<400> SEQUENCE: 145

000

<210> SEQ ID NO 146

<400> SEQUENCE: 146

000

<210> SEQ ID NO 147
```

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

<210> SEQ ID NO 151
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

```
Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
```

```
                225                 230                 235                 240
Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Asp Thr Thr Pro Pro Val Leu
305                 310                 315                 320

Asp Ser Asp Gly Ser Phe Phe Leu Tyr Ser Asp Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
        355                 360                 365

Lys

<210> SEQ ID NO 152
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
```

```
                210                 215                 220
Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
                260                 265                 270

Asp Ile Ala Val Glu Trp Glu Ser Asn Gly Gln Pro Glu Asn Asn Tyr
            275                 280                 285

Asp Thr Thr Pro Pro Val Leu Asp Ser Asp Gly Ser Phe Phe Leu Tyr
        290                 295                 300

Ser Asp Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 153
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
                20                  25                  30

Arg Glu Cys Ile Tyr Tyr Asn Ala Asn Trp Glu Leu Glu Arg Thr Asn
            35                  40                  45

Gln Ser Gly Leu Glu Arg Cys Glu Gly Glu Gln Asp Lys Arg Leu His
        50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
                100                 105                 110

Asn Phe Cys Asn Glu Arg Phe Thr His Leu Pro Glu Ala Gly Gly Pro
            115                 120                 125

Glu Val Thr Tyr Glu Pro Pro Pro Thr Ala Pro Thr Gly Gly Gly Thr
        130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
                180                 185                 190

Glu Val Lys Phe Asn Trp Tyr Val Asp Gly Val Glu Val His Asn Ala
            195                 200                 205

Lys Thr Lys Pro Arg Glu Glu Gln Tyr Asn Ser Thr Tyr Arg Val Val
        210                 215                 220
```

-continued

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Arg Glu Glu Met Thr Lys Asn Gln Val Ser Leu Thr Cys
        275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Asp Thr Thr Pro Pro Val Leu Asp
305                 310                 315                 320

Ser Asp Gly Ser Phe Phe Leu Tyr Ser Asp Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
        355                 360                 365

<210> SEQ ID NO 154
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

```
Pro Ala Pro Ile Glu Lys Thr Ile Ser Lys Ala Lys Gly Gln Pro Arg
225                 230                 235                 240

Glu Pro Gln Val Tyr Thr Leu Pro Pro Ser Arg Glu Glu Met Thr Lys
            245                 250                 255

Asn Gln Val Ser Leu Thr Cys Leu Val Lys Gly Phe Tyr Pro Ser Asp
        260                 265                 270

Ile Ala Val Glu Trp Glu Ser Asn Gly Gln Pro Glu Asn Asn Tyr Asp
    275                 280                 285

Thr Thr Pro Pro Val Leu Asp Ser Asp Gly Ser Phe Phe Leu Tyr Ser
290                 295                 300

Asp Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 155
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Met Asp Ala Met Lys Arg Gly Leu Cys Cys Val Leu Leu Leu Cys Gly
1               5                   10                  15

Ala Val Phe Val Ser Pro Gly Ala Ser Gln Asn Gln Glu Arg Leu Cys
            20                  25                  30

Ala Phe Lys Asp Pro Tyr Gln Gln Asp Leu Gly Ile Gly Glu Ser Arg
        35                  40                  45

Ile Ser His Glu Asn Gly Thr Ile Leu Cys Ser Lys Gly Ser Thr Cys
    50                  55                  60

Tyr Gly Leu Trp Glu Lys Ser Lys Gly Asp Ile Asn Leu Val Lys Gln
65                  70                  75                  80

Gly Cys Trp Ser His Ile Gly Asp Pro Gln Glu Cys His Tyr Glu Glu
                85                  90                  95

Cys Val Val Thr Thr Thr Pro Pro Ser Ile Gln Asn Gly Thr Tyr Arg
            100                 105                 110

Phe Cys Cys Cys Ser Thr Asp Leu Cys Asn Val Asn Phe Thr Glu Asn
        115                 120                 125

Phe Pro Pro Pro Asp Thr Thr Pro Leu Ser Pro His Ser Phe Asn
130                 135                 140

Arg Asp Glu Thr Gly Gly Gly Thr His Thr Cys Pro Pro Cys Pro Ala
145                 150                 155                 160

Pro Glu Leu Leu Gly Gly Pro Ser Val Phe Leu Phe Pro Pro Lys Pro
            165                 170                 175

Lys Asp Thr Leu Met Ile Ser Arg Thr Pro Glu Val Thr Cys Val Val
        180                 185                 190

Val Asp Val Ser His Glu Asp Pro Glu Val Lys Phe Asn Trp Tyr Val
    195                 200                 205

Asp Gly Val Glu Val His Asn Ala Lys Thr Lys Pro Arg Glu Glu Gln
210                 215                 220

Tyr Asn Ser Thr Tyr Arg Val Val Ser Val Leu Thr Val Leu His Gln
```

```
                225                 230                 235                 240
Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
                260                 265                 270

Arg Glu Pro Gln Val Tyr Thr Leu Pro Pro Ser Arg Glu Glu Met Thr
                275                 280                 285

Lys Asn Gln Val Ser Leu Thr Cys Leu Val Lys Gly Phe Tyr Pro Ser
            290                 295                 300

Asp Ile Ala Val Glu Trp Glu Ser Asn Gly Gln Pro Glu Asn Asn Tyr
305                 310                 315                 320

Asp Thr Thr Pro Pro Val Leu Asp Ser Asp Gly Ser Phe Phe Leu Tyr
                325                 330                 335

Ser Asp Leu Thr Val Asp Lys Ser Arg Trp Gln Gln Gly Asn Val Phe
                340                 345                 350

Ser Cys Ser Val Met His Glu Ala Leu His Asn His Tyr Thr Gln Lys
                355                 360                 365

Ser Leu Ser Leu Ser Pro Gly Lys
                370                 375

<210> SEQ ID NO 156
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 156

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Ser Thr Asp Leu
                85                  90                  95

Cys Asn Val Asn Phe Thr Glu Asn Phe Pro Pro Pro Asp Thr Thr Pro
                100                 105                 110

Leu Ser Pro Pro His Ser Phe Asn Arg Asp Glu Thr Gly Gly Gly Thr
            115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
                180                 185                 190

Lys Thr Lys Pro Arg Glu Glu Gln Tyr Asn Ser Thr Tyr Arg Val Val
            195                 200                 205
```

```
Ser Val Leu Thr Val Leu His Gln Asp Trp Leu Asn Gly Lys Glu Tyr
    210                 215                 220
Lys Cys Lys Val Ser Asn Lys Ala Leu Pro Ala Pro Ile Glu Lys Thr
225                 230                 235                 240
Ile Ser Lys Ala Lys Gly Gln Pro Arg Glu Pro Gln Val Tyr Thr Leu
                245                 250                 255
Pro Pro Ser Arg Glu Glu Met Thr Lys Asn Gln Val Ser Leu Thr Cys
            260                 265                 270
Leu Val Lys Gly Phe Tyr Pro Ser Asp Ile Ala Val Glu Trp Glu Ser
        275                 280                 285
Asn Gly Gln Pro Glu Asn Asn Tyr Asp Thr Thr Pro Pro Val Leu Asp
290                 295                 300
Ser Asp Gly Ser Phe Phe Leu Tyr Ser Asp Leu Thr Val Asp Lys Ser
305                 310                 315                 320
Arg Trp Gln Gln Gly Asn Val Phe Ser Cys Ser Val Met His Glu Ala
                325                 330                 335
Leu His Asn His Tyr Thr Gln Lys Ser Leu Ser Leu Ser Pro Gly Lys
            340                 345                 350

<210> SEQ ID NO 157
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 157

Met Asp Ala Met Lys Arg Gly Leu Cys Cys Val Leu Leu Leu Cys Gly
1               5                   10                  15
Ala Val Phe Val Ser Pro Gly Ala Thr Ile Pro His Val Gln Lys
                20                  25                  30
Ser Val Asn Asn Asp Met Ile Val Thr Asp Asn Asn Gly Ala Val Lys
            35                  40                  45
Phe Pro Gln Leu Cys Lys Phe Cys Asp Val Arg Phe Ser Thr Cys Asp
    50                  55                  60
Asn Gln Lys Ser Cys Met Ser Asn Cys Ser Ile Thr Ser Ile Cys Glu
65                  70                  75                  80
Lys Pro Gln Glu Val Cys Val Ala Val Trp Arg Lys Asn Asp Glu Asn
                85                  90                  95
Ile Thr Leu Glu Thr Val Cys His Asp Pro Lys Leu Pro Tyr His Asp
            100                 105                 110
Phe Ile Leu Glu Asp Ala Ala Ser Pro Lys Cys Ile Met Lys Glu Lys
        115                 120                 125
Lys Lys Pro Gly Glu Thr Phe Phe Met Cys Ser Cys Ser Ser Asp Glu
    130                 135                 140
Cys Asn Asp Asn Ile Ile Phe Ser Glu Glu Tyr Asn Thr Ser Asn Pro
145                 150                 155                 160
Asp Thr Gly Gly Gly Thr His Thr Cys Pro Pro Cys Pro Ala Pro Glu
                165                 170                 175
Leu Leu Gly Gly Pro Ser Val Phe Leu Phe Pro Pro Lys Pro Lys Asp
            180                 185                 190
Thr Leu Met Ile Ser Arg Thr Pro Glu Val Thr Cys Val Val Val Asp
        195                 200                 205
Val Ser His Glu Asp Pro Glu Val Lys Phe Asn Trp Tyr Val Asp Gly
    210                 215                 220
```

Val Glu Val His Asn Ala Lys Thr Lys Pro Arg Glu Gln Tyr Asn
225                 230                 235                 240

Ser Thr Tyr Arg Val Ser Val Leu Thr Val Leu His Gln Asp Trp
            245                 250                 255

Leu Asn Gly Lys Glu Tyr Lys Cys Lys Val Ser Asn Lys Ala Leu Pro
                260                 265                 270

Ala Pro Ile Glu Lys Thr Ile Ser Lys Ala Lys Gly Gln Pro Arg Glu
            275                 280                 285

Pro Gln Val Tyr Thr Leu Pro Pro Ser Arg Glu Glu Met Thr Lys Asn
        290                 295                 300

Gln Val Ser Leu Thr Cys Leu Val Lys Gly Phe Tyr Pro Ser Asp Ile
305                 310                 315                 320

Ala Val Glu Trp Glu Ser Asn Gly Gln Pro Glu Asn Asn Tyr Asp Thr
                325                 330                 335

Thr Pro Pro Val Leu Asp Ser Asp Gly Ser Phe Phe Leu Tyr Ser Asp
            340                 345                 350

Leu Thr Val Asp Lys Ser Arg Trp Gln Gln Gly Asn Val Phe Ser Cys
        355                 360                 365

Ser Val Met His Glu Ala Leu His Asn His Tyr Thr Gln Lys Ser Leu
    370                 375                 380

Ser Leu Ser Pro Gly Lys
385                 390

<210> SEQ ID NO 158
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp Thr Gly Gly Gly Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val

```
                180             185             190
Lys Phe Asn Trp Tyr Val Asp Gly Val Glu Val His Asn Ala Lys Thr
            195                 200                 205
Lys Pro Arg Glu Glu Gln Tyr Asn Ser Thr Tyr Arg Val Val Ser Val
        210                 215                 220
Leu Thr Val Leu His Gln Asp Trp Leu Asn Gly Lys Glu Tyr Lys Cys
225                 230                 235                 240
Lys Val Ser Asn Lys Ala Leu Pro Ala Pro Ile Glu Lys Thr Ile Ser
                245                 250                 255
Lys Ala Lys Gly Gln Pro Arg Glu Pro Gln Val Tyr Thr Leu Pro Pro
            260                 265                 270
Ser Arg Glu Glu Met Thr Lys Asn Gln Val Ser Leu Thr Cys Leu Val
        275                 280                 285
Lys Gly Phe Tyr Pro Ser Asp Ile Ala Val Glu Trp Glu Ser Asn Gly
        290                 295                 300
Gln Pro Glu Asn Asn Tyr Asp Thr Thr Pro Val Leu Asp Ser Asp
305                 310                 315                 320
Gly Ser Phe Phe Leu Tyr Ser Asp Leu Thr Val Asp Lys Ser Arg Trp
                325                 330                 335
Gln Gln Gly Asn Val Phe Ser Cys Ser Val Met His Glu Ala Leu His
            340                 345                 350
Asn His Tyr Thr Gln Lys Ser Leu Ser Leu Ser Pro Gly Lys
            355                 360                 365

<210> SEQ ID NO 159
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Met Asp Ala Met Lys Arg Gly Leu Cys Cys Val Leu Leu Leu Cys Gly
1               5                   10                  15
Ala Val Phe Val Ser Pro Gly Ala Thr Ile Pro Pro His Val Gln Lys
                20                  25                  30
Ser Asp Val Glu Met Glu Ala Gln Lys Asp Glu Ile Ile Cys Pro Ser
            35                  40                  45
Cys Asn Arg Thr Ala His Pro Leu Arg His Ile Asn Asn Asp Met Ile
        50                  55                  60
Val Thr Asp Asn Asn Gly Ala Val Lys Phe Pro Gln Leu Cys Lys Phe
65                  70                  75                  80
Cys Asp Val Arg Phe Ser Thr Cys Asp Asn Gln Lys Ser Cys Met Ser
                85                  90                  95
Asn Cys Ser Ile Thr Ser Ile Cys Glu Lys Pro Gln Glu Val Cys Val
            100                 105                 110
Ala Val Trp Arg Lys Asn Asp Glu Asn Ile Thr Leu Glu Thr Val Cys
        115                 120                 125
His Asp Pro Lys Leu Pro Tyr His Asp Phe Ile Leu Glu Asp Ala Ala
    130                 135                 140
Ser Pro Lys Cys Ile Met Lys Glu Lys Lys Pro Gly Glu Thr Phe
145                 150                 155                 160
Phe Met Cys Ser Cys Ser Ser Asp Glu Cys Asn Asp Asn Ile Ile Phe
                165                 170                 175
```

```
Ser Glu Glu Tyr Asn Thr Ser Asn Pro Asp Thr Gly Gly Thr His
            180                 185                 190

Thr Cys Pro Pro Cys Pro Ala Pro Glu Leu Leu Gly Gly Pro Ser Val
        195                 200                 205

Phe Leu Phe Pro Pro Lys Pro Lys Asp Thr Leu Met Ile Ser Arg Thr
    210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
        275                 280                 285

Cys Lys Val Ser Asn Lys Ala Leu Pro Ala Pro Ile Glu Lys Thr Ile
    290                 295                 300

Ser Lys Ala Lys Gly Gln Pro Arg Glu Pro Gln Val Tyr Thr Leu Pro
305                 310                 315                 320

Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
            340                 345                 350

Gly Gln Pro Glu Asn Asn Tyr Asp Thr Thr Pro Pro Val Leu Asp Ser
        355                 360                 365

Asp Gly Ser Phe Phe Leu Tyr Ser Asp Leu Thr Val Asp Lys Ser Arg
370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415

<210> SEQ ID NO 160
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
                20                  25                  30

Arg His Ile Asn Asn Asp Met Ile Val Thr Asp Asn Asn Gly Ala Val
            35                  40                  45

Lys Phe Pro Gln Leu Cys Lys Phe Cys Asp Val Arg Phe Ser Thr Cys
        50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125
```

Lys Lys Lys Pro Gly Glu Thr Phe Phe Met Cys Ser Cys Ser Ser Asp
130                 135                 140

Glu Cys Asn Asp Asn Ile Ile Phe Ser Glu Glu Tyr Asn Thr Ser Asn
145                 150                 155                 160

Pro Asp Thr Gly Gly Thr His Thr Cys Pro Pro Cys Pro Ala Pro
            165                 170                 175

Glu Leu Leu Gly Gly Pro Ser Val Phe Leu Phe Pro Pro Lys Pro Lys
            180                 185                 190

Asp Thr Leu Met Ile Ser Arg Thr Pro Glu Val Thr Cys Val Val Val
            195                 200                 205

Asp Val Ser His Glu Asp Pro Glu Val Lys Phe Asn Trp Tyr Val Asp
210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
            275                 280                 285

Glu Pro Gln Val Tyr Thr Leu Pro Pro Ser Arg Glu Glu Met Thr Lys
290                 295                 300

Asn Gln Val Ser Leu Thr Cys Leu Val Lys Gly Phe Tyr Pro Ser Asp
305                 310                 315                 320

Ile Ala Val Glu Trp Glu Ser Asn Gly Gln Pro Glu Asn Asn Tyr Asp
                325                 330                 335

Thr Thr Pro Pro Val Leu Asp Ser Asp Gly Ser Phe Phe Leu Tyr Ser
            340                 345                 350

Asp Leu Thr Val Asp Lys Ser Arg Trp Gln Gln Gly Asn Val Phe Ser
            355                 360                 365

Cys Ser Val Met His Glu Ala Leu His Asn His Tyr Thr Gln Lys Ser
370                 375                 380

Leu Ser Leu Ser Pro Gly Lys
385                 390

<210> SEQ ID NO 161
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Met Asp Ala Met Lys Arg Gly Leu Cys Cys Val Leu Leu Leu Cys Gly
1               5                   10                  15

Ala Val Phe Val Ser Pro Gly Ala Pro Pro Asn Arg Arg Thr Cys Val
                20                  25                  30

Phe Phe Glu Ala Pro Gly Val Arg Gly Ser Thr Lys Thr Leu Gly Glu
            35                  40                  45

Leu Leu Asp Thr Gly Thr Glu Leu Pro Arg Ala Ile Arg Cys Leu Tyr
            50                  55                  60

Ser Arg Cys Cys Phe Gly Ile Trp Asn Leu Thr Gln Asp Arg Ala Gln
65                  70                  75                  80

Val Glu Met Gln Gly Cys Arg Asp Ser Asp Glu Pro Gly Cys Glu Ser

```
                   85                  90                  95

Leu His Cys Asp Pro Ser Pro Arg Ala His Pro Ser Pro Gly Ser Thr
                100                 105                 110

Leu Phe Thr Cys Ser Cys Gly Thr Asp Phe Cys Asn Ala Asn Tyr Ser
                115                 120                 125

His Leu Pro Pro Pro Gly Ser Pro Gly Thr Pro Gly Ser Gln Gly Pro
            130                 135                 140

Gln Ala Ala Pro Gly Glu Ser Ile Trp Met Ala Leu Thr Gly Gly Gly
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
                180                 185                 190

Arg Thr Pro Glu Val Thr Cys Val Val Val Asp Val Ser His Glu Asp
                195                 200                 205

Pro Glu Val Lys Phe Asn Trp Tyr Val Asp Gly Val Glu Val His Asn
            210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
                260                 265                 270

Thr Ile Ser Lys Ala Lys Gly Gln Pro Arg Glu Pro Gln Val Tyr Thr
                275                 280                 285

Leu Pro Pro Ser Arg Glu Glu Met Thr Lys Asn Gln Val Ser Leu Thr
            290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Asp Thr Thr Pro Pro Val Leu
                325                 330                 335

Asp Ser Asp Gly Ser Phe Phe Leu Tyr Ser Asp Leu Thr Val Asp Lys
                340                 345                 350

Ser Arg Trp Gln Gln Gly Asn Val Phe Ser Cys Ser Val Met His Glu
            355                 360                 365

Ala Leu His Asn His Tyr Thr Gln Lys Ser Leu Ser Leu Ser Pro Gly
        370                 375                 380

Lys
385

<210> SEQ ID NO 162
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
                20                  25                  30

Pro Arg Ala Ile Arg Cys Leu Tyr Ser Arg Cys Cys Phe Gly Ile Trp
            35                  40                  45
```

```
Asn Leu Thr Gln Asp Arg Ala Gln Val Glu Met Gln Gly Cys Arg Asp
 50                  55                  60

Ser Asp Glu Pro Gly Cys Glu Ser Leu His Cys Asp Pro Ser Pro Arg
 65                  70                  75                  80

Ala His Pro Ser Pro Gly Ser Thr Leu Phe Thr Cys Ser Cys Gly Thr
                 85                  90                  95

Asp Phe Cys Asn Ala Asn Tyr Ser His Leu Pro Pro Gly Ser Pro
                100                 105                 110

Gly Thr Pro Gly Ser Gln Gly Pro Gln Ala Ala Pro Gly Glu Ser Ile
            115                 120                 125

Trp Met Ala Leu Thr Gly Gly Thr His Thr Cys Pro Pro Cys Pro
130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
            195                 200                 205

Gln Tyr Asn Ser Thr Tyr Arg Val Val Ser Val Leu Thr Val Leu His
210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Glu Glu Met
            260                 265                 270

Thr Lys Asn Gln Val Ser Leu Thr Cys Leu Val Lys Gly Phe Tyr Pro
            275                 280                 285

Ser Asp Ile Ala Val Glu Trp Glu Ser Asn Gly Gln Pro Glu Asn Asn
290                 295                 300

Tyr Asp Thr Thr Pro Pro Val Leu Asp Ser Asp Gly Ser Phe Phe Leu
305                 310                 315                 320

Tyr Ser Asp Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
            355                 360

<210> SEQ ID NO 163

<400> SEQUENCE: 163

000

<210> SEQ ID NO 164

<400> SEQUENCE: 164

000

<210> SEQ ID NO 165

<400> SEQUENCE: 165
```

-continued

000

<210> SEQ ID NO 166
<400> SEQUENCE: 166

000

<210> SEQ ID NO 167
<400> SEQUENCE: 167

000

<210> SEQ ID NO 168
<400> SEQUENCE: 168

000

<210> SEQ ID NO 169
<400> SEQUENCE: 169

000

<210> SEQ ID NO 170
<400> SEQUENCE: 170

000

<210> SEQ ID NO 171
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

```
Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
                20                  25                  30

Pro Leu Val Thr Cys Thr Cys Glu Ser Pro His Cys Lys Gly Pro Thr
            35                  40                  45

Cys Arg Gly Ala Trp Cys Thr Val Val Leu Val Arg Glu Glu Gly Arg
        50                  55                  60

His Pro Gln Glu His Arg Gly Cys Gly Asn Leu His Arg Glu Leu Cys
65                  70                  75                  80

Arg Gly Arg Pro Thr Glu Phe Val Asn His Tyr Cys Cys Asp Ser His
                85                  90                  95

Leu Cys Asn His Asn Val Ser Leu Val Leu Glu Ala Thr Gln Pro Pro
                100                 105                 110

Ser Glu Gln Pro Gly Thr Asp Gly Gln Leu Ala Thr Gly Gly Gly Thr
            115                 120                 125

His Thr Cys Pro Pro Cys Pro Ala Pro Glu Leu Leu Gly Gly Pro Ser
        130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
```

```
                       165                 170                 175
Glu Val Lys Phe Asn Trp Tyr Val Asp Gly Val Glu Val His Asn Ala
                180                 185                 190

Lys Thr Lys Pro Arg Glu Glu Gln Tyr Asn Ser Thr Tyr Arg Val Val
            195                 200                 205

Ser Val Leu Thr Val Leu His Gln Asp Trp Leu Asn Gly Lys Glu Tyr
        210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Lys Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Lys
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
            340                 345                 350

<210> SEQ ID NO 172
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
                20                  25                  30

Val Leu Val Arg Glu Glu Gly Arg His Pro Gln Glu His Arg Gly Cys
            35                  40                  45

Gly Asn Leu His Arg Glu Leu Cys Arg Gly Arg Pro Thr Glu Phe Val
        50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln Leu Ala Thr Gly Gly Gly Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175
```

```
Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Lys Glu Met Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Lys Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly
                325

<210> SEQ ID NO 173
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Met Asp Ala Met Lys Arg Gly Leu Cys Cys Val Leu Leu Leu Cys Gly
1               5                   10                  15

Ala Val Phe Val Ser Pro Gly Ala Met Glu Asp Glu Lys Pro Lys Val
            20                  25                  30

Asn Pro Lys Leu Tyr Met Cys Val Cys Glu Gly Leu Ser Cys Gly Asn
        35                  40                  45

Glu Asp His Cys Glu Gly Gln Gln Cys Phe Ser Ser Leu Ser Ile Asn
    50                  55                  60

Asp Gly Phe His Val Tyr Gln Lys Gly Cys Phe Gln Val Tyr Glu Gln
65                  70                  75                  80

Gly Lys Met Thr Cys Lys Thr Pro Pro Ser Pro Gly Gln Ala Val Glu
                85                  90                  95

Cys Cys Gln Gly Asp Trp Cys Asn Arg Asn Ile Thr Ala Gln Leu Pro
            100                 105                 110

Thr Lys Gly Lys Ser Phe Pro Gly Thr Gln Asn Phe His Leu Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205
```

```
Tyr Arg Val Val Ser Val Leu Thr Val Leu His Gln Asp Trp Leu Asn
            210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
            245                 250                 255

Val Tyr Thr Leu Pro Pro Ser Arg Lys Glu Met Thr Lys Asn Gln Val
            260                 265                 270

Ser Leu Thr Cys Leu Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
            290                 295                 300

Pro Val Leu Lys Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
            325                 330                 335

Met His Glu Ala Leu His Asn His Tyr Thr Gln Lys Ser Leu Ser Leu
            340                 345                 350

Ser Pro Gly
        355

<210> SEQ ID NO 174
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
        35                  40                  45

Gly Cys Phe Gln Val Tyr Glu Gln Gly Lys Met Thr Cys Lys Thr Pro
    50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Thr Gly Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
```

```
                195                 200                 205
Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Lys Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Lys Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly
                325                 330
```

<210> SEQ ID NO 175
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

```
Met Asp Ala Met Lys Arg Gly Leu Cys Cys Val Leu Leu Leu Cys Gly
1               5                   10                  15

Ala Val Phe Val Ser Pro Gly Ala Gln Asn Leu Asp Ser Met Leu His
                20                  25                  30

Gly Thr Gly Met Lys Ser Asp Ser Asp Gln Lys Lys Ser Glu Asn Gly
            35                  40                  45

Val Thr Leu Ala Pro Glu Asp Thr Leu Pro Phe Leu Lys Cys Tyr Cys
    50                  55                  60

Ser Gly His Cys Pro Asp Asp Ala Ile Asn Asn Thr Cys Ile Thr Asn
65                  70                  75                  80

Gly His Cys Phe Ala Ile Ile Glu Glu Asp Asp Gln Gly Glu Thr Thr
                85                  90                  95

Leu Ala Ser Gly Cys Met Lys Tyr Glu Gly Ser Asp Phe Gln Cys Lys
            100                 105                 110

Asp Ser Pro Lys Ala Gln Leu Arg Arg Thr Ile Glu Cys Cys Arg Thr
        115                 120                 125

Asn Leu Cys Asn Gln Tyr Leu Gln Pro Thr Leu Pro Pro Val Val Ile
    130                 135                 140

Gly Pro Phe Phe Asp Gly Ser Ile Arg Thr Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
        195                 200                 205

Lys Phe Asn Trp Tyr Val Asp Gly Val Glu Val His Asn Ala Lys Thr
    210                 215                 220
```

```
Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
            245                 250                 255

Lys Val Ser Asn Lys Ala Leu Pro Ala Pro Ile Glu Lys Thr Ile Ser
        260                 265                 270

Lys Ala Lys Gly Gln Pro Arg Glu Pro Gln Val Tyr Thr Leu Pro Pro
    275                 280                 285

Ser Arg Lys Glu Met Thr Lys Asn Gln Val Ser Leu Thr Cys Leu Val
290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Lys Ser Asp
            325                 330                 335

Gly Ser Phe Phe Leu Tyr Ser Lys Leu Thr Val Asp Lys Ser Arg Trp
        340                 345                 350

Gln Gln Gly Asn Val Phe Ser Cys Ser Val Met His Glu Ala Leu His
    355                 360                 365

Asn His Tyr Thr Gln Lys Ser Leu Ser Leu Ser Pro Gly
370                 375                 380

<210> SEQ ID NO 176
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Gly Ala Gln Asn Leu Asp Ser Met Leu His Gly Thr Gly Met Lys Ser
1               5                   10                  15

Asp Ser Asp Gln Lys Lys Ser Glu Asn Gly Val Thr Leu Ala Pro Glu
            20                  25                  30

Asp Thr Leu Pro Phe Leu Lys Cys Tyr Cys Ser Gly His Cys Pro Asp
        35                  40                  45

Asp Ala Ile Asn Asn Thr Cys Ile Thr Asn Gly His Cys Phe Ala Ile
    50                  55                  60

Ile Glu Glu Asp Asp Gln Gly Glu Thr Thr Leu Ala Ser Gly Cys Met
65                  70                  75                  80

Lys Tyr Glu Gly Ser Asp Phe Gln Cys Lys Asp Ser Pro Lys Ala Gln
                85                  90                  95

Leu Arg Arg Thr Ile Glu Cys Cys Arg Thr Asn Leu Cys Asn Gln Tyr
            100                 105                 110

Leu Gln Pro Thr Leu Pro Pro Val Val Ile Gly Pro Phe Phe Asp Gly
        115                 120                 125

Ser Ile Arg Thr Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205
```

```
Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Lys Glu Met Thr
                260                 265                 270

Lys Asn Gln Val Ser Leu Thr Cys Leu Val Lys Gly Phe Tyr Pro Ser
            275                 280                 285

Asp Ile Ala Val Glu Trp Glu Ser Asn Gly Gln Pro Glu Asn Asn Tyr
290                 295                 300

Lys Thr Thr Pro Pro Val Leu Lys Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335

Ser Cys Ser Val Met His Glu Ala Leu His Asn His Tyr Thr Gln Lys
            340                 345                 350

Ser Leu Ser Leu Ser Pro Gly
            355

<210> SEQ ID NO 177
<211> LENGTH: 355
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
```

```
                195                 200                 205
Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Lys Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Lys Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly
        355

<210> SEQ ID NO 178
<211> LENGTH: 331
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190
```

```
Val Leu His Gln Asp Trp Leu Asn Gly Lys Glu Tyr Lys Cys Lys Val
            195                 200                 205

Ser Asn Lys Ala Leu Pro Ala Pro Ile Glu Lys Thr Ile Ser Lys Ala
210                 215                 220

Lys Gly Gln Pro Arg Glu Pro Gln Val Tyr Thr Leu Pro Pro Ser Arg
225                 230                 235                 240

Lys Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Lys Ser Asp Gly Ser
        275                 280                 285

Phe Phe Leu Tyr Ser Lys Leu Thr Val Asp Lys Ser Arg Trp Gln Gln
290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly
                325                 330

<210> SEQ ID NO 179
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Met Asp Ala Met Lys Arg Gly Leu Cys Cys Val Leu Leu Leu Cys Gly
1               5                   10                  15

Ala Val Phe Val Ser Pro Gly Ala Ala Leu Leu Pro Gly Ala Thr Ala
            20                  25                  30

Leu Gln Cys Phe Cys His Leu Cys Thr Lys Asp Asn Phe Thr Cys Val
        35                  40                  45

Thr Asp Gly Leu Cys Phe Val Ser Val Thr Glu Thr Thr Asp Lys Val
50                  55                  60

Ile His Asn Ser Met Cys Ile Ala Glu Ile Asp Leu Ile Pro Arg Asp
65                  70                  75                  80

Arg Pro Phe Val Cys Ala Pro Ser Ser Lys Thr Gly Ser Val Thr Thr
                85                  90                  95

Thr Tyr Cys Cys Asn Gln Asp His Cys Asn Lys Ile Glu Leu Pro Thr
            100                 105                 110

Thr Val Lys Ser Ser Pro Gly Leu Gly Pro Val Glu Thr Gly Gly Gly
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220
```

```
Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Lys Glu Met Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Lys Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

<210> SEQ ID NO 180
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Ala Leu Leu Pro Gly Ala Thr Ala Leu Gln Cys Phe Cys His Leu Cys
1               5                   10                  15

Thr Lys Asp Asn Phe Thr Cys Val Thr Asp Gly Leu Cys Phe Val Ser
                20                  25                  30

Val Thr Glu Thr Thr Asp Lys Val Ile His Asn Ser Met Cys Ile Ala
            35                  40                  45

Glu Ile Asp Leu Ile Pro Arg Asp Arg Pro Phe Val Cys Ala Pro Ser
    50                  55                  60

Ser Lys Thr Gly Ser Val Thr Thr Thr Tyr Cys Cys Asn Gln Asp His
65                  70                  75                  80

Cys Asn Lys Ile Glu Leu Pro Thr Thr Val Lys Ser Ser Pro Gly Leu
                85                  90                  95

Gly Pro Val Glu Thr Gly Gly Gly Thr His Thr Cys Pro Pro Cys Pro
            100                 105                 110

Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Lys Glu Met
```

```
            225                 230                 235                 240
Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Lys Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 181
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Met Asp Ala Met Lys Arg Gly Leu Cys Cys Val Leu Leu Leu Cys Gly
1               5                   10                  15

Ala Val Phe Val Ser Pro Gly Ala Lys Lys Glu Asp Gly Glu Ser Thr
            20                  25                  30

Ala Pro Thr Pro Arg Pro Lys Val Leu Arg Cys Lys Cys His His
        35                  40                  45

Cys Pro Glu Asp Ser Val Asn Asn Ile Cys Ser Thr Asp Gly Tyr Cys
    50                  55                  60

Phe Thr Met Ile Glu Glu Asp Ser Gly Leu Pro Val Val Thr Ser
65                  70                  75                  80

Gly Cys Leu Gly Leu Glu Gly Ser Asp Phe Gln Cys Arg Asp Thr Pro
                85                  90                  95

Ile Pro His Gln Arg Arg Ser Ile Glu Cys Cys Thr Glu Arg Asn Glu
            100                 105                 110

Cys Asn Lys Asp Leu His Pro Thr Leu Pro Pro Leu Lys Asn Arg Asp
        115                 120                 125

Phe Val Asp Gly Pro Ile His His Arg Thr Gly Gly Thr His Thr
130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255
```

```
Lys Ala Lys Gly Gln Pro Arg Glu Pro Gln Val Tyr Thr Leu Pro Pro
                260                 265                 270

Ser Arg Lys Glu Met Thr Lys Asn Gln Val Ser Leu Thr Cys Leu Val
            275                 280                 285

Lys Gly Phe Tyr Pro Ser Asp Ile Ala Val Glu Trp Glu Ser Asn Gly
        290                 295                 300

Gln Pro Glu Asn Asn Tyr Lys Thr Thr Pro Pro Val Leu Lys Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly
        355                 360                 365

<210> SEQ ID NO 182
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Lys Lys Glu Asp Gly Glu Ser Thr Ala Pro Thr Pro Arg Pro Lys Val
1               5                   10                  15

Leu Arg Cys Lys Cys His His His Cys Pro Glu Asp Ser Val Asn Asn
            20                  25                  30

Ile Cys Ser Thr Asp Gly Tyr Cys Phe Thr Met Ile Glu Glu Asp Asp
        35                  40                  45

Ser Gly Leu Pro Val Val Thr Ser Gly Cys Leu Gly Leu Glu Gly Ser
    50                  55                  60

Asp Phe Gln Cys Arg Asp Thr Pro Ile Pro His Gln Arg Arg Ser Ile
65                  70                  75                  80

Glu Cys Cys Thr Glu Arg Asn Glu Cys Asn Lys Asp Leu His Pro Thr
                85                  90                  95

Leu Pro Pro Leu Lys Asn Arg Asp Phe Val Asp Gly Pro Ile His His
            100                 105                 110

Arg Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Lys Glu Met Thr Lys Asn
                245                 250                 255
```

```
Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
            275                 280                 285

Thr Pro Pro Val Leu Lys Ser Asp Gly Ser Phe Phe Leu Tyr Ser Lys
290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly
            340

<210> SEQ ID NO 183
<211> LENGTH: 341
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Met Asp Ala Met Lys Arg Gly Leu Cys Cys Val Leu Leu Leu Cys Gly
1               5                   10                  15

Ala Val Phe Val Ser Pro Gly Ala Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Lys Glu Met Thr Lys Asn
                245                 250                 255

Gln Val Ser Leu Thr Cys Leu Val Lys Gly Phe Tyr Pro Ser Asp Ile
```

```
                260                 265                 270
Ala Val Glu Trp Glu Ser Asn Gly Gln Pro Glu Asn Tyr Lys Thr
            275                 280                 285

Thr Pro Pro Val Leu Lys Ser Asp Gly Ser Phe Phe Leu Tyr Ser Lys
        290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly
            340

<210> SEQ ID NO 184
<211> LENGTH: 317
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gly Leu Lys Cys Val Cys Leu Leu Cys Asp Ser Ser Asn Phe Thr Cys
1               5                   10                  15

Gln Thr Glu Gly Ala Cys Trp Ala Ser Val Met Leu Thr Asn Gly Lys
            20                  25                  30

Glu Gln Val Ile Lys Ser Cys Val Ser Leu Pro Glu Leu Asn Ala Gln
        35                  40                  45

Val Phe Cys His Ser Ser Asn Asn Val Thr Lys Thr Glu Cys Cys Phe
    50                  55                  60

Thr Asp Phe Cys Asn Asn Ile Thr Leu His Leu Pro Thr Ala Ser Pro
65                  70                  75                  80

Asn Ala Pro Lys Leu Gly Pro Met Glu Thr Gly Gly Thr His Thr
                85                  90                  95

Cys Pro Pro Cys Pro Ala Pro Glu Leu Leu Gly Gly Pro Ser Val Phe
            100                 105                 110

Leu Phe Pro Pro Lys Pro Lys Asp Thr Leu Met Ile Ser Arg Thr Pro
        115                 120                 125

Glu Val Thr Cys Val Val Val Asp Val Ser His Glu Asp Pro Glu Val
130                 135                 140

Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Tyr Thr Leu Pro Pro
    210                 215                 220

Ser Arg Lys Glu Met Thr Lys Asn Gln Val Ser Leu Thr Cys Leu Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Lys Thr Thr Pro Pro Val Leu Lys Ser Asp
            260                 265                 270
```

```
Gly Ser Phe Phe Leu Tyr Ser Lys Leu Thr Val Asp Lys Ser Arg Trp
            275                 280                 285
Gln Gln Gly Asn Val Phe Ser Cys Ser Val Met His Glu Ala Leu His
        290                 295                 300
Asn His Tyr Thr Gln Lys Ser Leu Ser Leu Ser Pro Gly
305                 310                 315
```

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Lys Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175
```

```
Lys Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 201
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Asp Thr Thr Pro Pro Val Leu
                165                 170                 175

Asp Ser Asp Gly Ser Phe Phe Leu Tyr Ser Asp Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 202
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202
```

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
                35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
                115                 120                 125

Leu Pro Pro Ser Arg Glu Glu Met Thr Lys Asn Gln Val Ser Leu Tyr
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 203
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
                35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
                115                 120                 125

```
Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Thr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 204
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Cys Arg Glu Glu Met Thr Lys Asn Gln Val Ser Leu Trp
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225
```

```
<210> SEQ ID NO 205
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205
```

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Cys Thr
        115                 120                 125

Leu Pro Pro Ser Arg Glu Glu Met Thr Lys Asn Gln Val Ser Leu Ser
    130                 135                 140

Cys Ala Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Val Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

```
<210> SEQ ID NO 206
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206
```

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val

```
            65                  70                  75                  80
Val Ser Val Leu Thr Val Leu His Gln Asp Trp Leu Asn Gly Lys Glu
                    85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Phe Arg Pro Glu Val His Leu
            115                 120                 125

Leu Pro Pro Ser Arg Glu Glu Met Thr Lys Asn Gln Val Ser Leu Thr
        130                 135                 140

Cys Leu Ala Arg Gly Phe Tyr Pro Lys Asp Ile Ala Val Glu Trp Glu
145                 150                 155                 160

Ser Asn Gly Gln Pro Glu Asn Asn Tyr Lys Thr Thr Pro Ser Arg Gln
                165                 170                 175

Glu Pro Ser Gln Gly Thr Thr Thr Phe Ala Val Thr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Thr Ile Ser Leu
    210                 215                 220

Ser Pro Gly Lys
225

<210> SEQ ID NO 207
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
                100                 105                 110

Thr Ile Ser Lys Ala Lys Gly Gln Pro Arg Glu Pro Gln Val Tyr Thr
            115                 120                 125

Leu Pro Pro Ser Glu Glu Leu Ala Leu Asn Glu Leu Val Thr Leu
        130                 135                 140

Thr Cys Leu Val Lys Gly Phe Tyr Pro Ser Asp Ile Ala Val Glu Trp
145                 150                 155                 160

Glu Ser Asn Gly Gln Glu Leu Pro Arg Glu Lys Tyr Leu Thr Trp Ala
                165                 170                 175

Pro Val Leu Asp Ser Asp Gly Ser Phe Phe Leu Tyr Ser Ile Leu Arg
            180                 185                 190
```

Val Ala Ala Glu Asp Trp Lys Lys Gly Asp Thr Phe Ser Cys Ser Val
              195                 200                 205

Met His Glu Ala Leu His Asn His Tyr Thr Gln Lys Ser Leu Asp Arg
    210                 215                 220

Ser Pro Gly Lys
225

<210> SEQ ID NO 208
<211> LENGTH: 225
<212> TYPE: PRT
<213> ORGANISM: Homo sapiens

<400> SEQUENCE: 208

Thr His Thr Cys Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 209
<211> LENGTH: 223
<212> TYPE: PRT
<213> ORGANISM: Homo sapiens

<400> SEQUENCE: 209

Val Glu Cys Pro Pro Cys Pro Ala Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
                    85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
            195                 200                 205

His Asn His Tyr Thr Gln Lys Ser Leu Ser Leu Ser Pro Gly Lys
210                 215                 220

<210> SEQ ID NO 210
<211> LENGTH: 232
<212> TYPE: PRT
<213> ORGANISM: Homo sapiens

<400> SEQUENCE: 210

Glu Pro Lys Ser Cys Asp Thr Pro Pro Pro Cys Pro Arg Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Gln Phe Lys Trp Tyr Val
    50                  55                  60

Asp Gly Val Glu Val His Asn Ala Lys Thr Lys Pro Arg Glu Glu Gln
65                  70                  75                  80

Tyr Asn Ser Thr Phe Arg Val Val Ser Val Leu Thr Val Leu His Gln
                85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Thr Lys Gly Gln Pro
            115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
            195                 200                 205

```
Ser Cys Ser Val Met His Glu Ala Leu His Asn Arg Phe Thr Gln Lys
    210                 215                 220

Ser Leu Ser Leu Ser Pro Gly Lys
225                 230

<210> SEQ ID NO 211
<211> LENGTH: 279
<212> TYPE: PRT
<213> ORGANISM: Homo sapiens

<400> SEQUENCE: 211

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
            100                 105                 110

Gly Val Glu Val His Asn Ala Lys Thr Lys Pro Arg Glu Glu Gln Tyr
        115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 212
<211> LENGTH: 229
<212> TYPE: PRT
<213> ORGANISM: Homo sapiens

<400> SEQUENCE: 212

Glu Ser Lys Tyr Gly Pro Pro Cys Pro Ser Cys Pro Ala Pro Glu Phe
1               5                   10                  15
```

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
65                   70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 213
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Asp Val Ser His Glu Asp
        35                  40                  45

Pro Glu Val Lys Phe Asn Trp Tyr Val Asp Gly Val Glu Val His Asn
 50                  55                  60

Ala Lys Thr Lys Pro Arg Glu Glu Gln Tyr Asn Ser Thr Tyr Arg Val
65                   70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr

```
            130                 135                 140
Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
        210                 215                 220

Lys Gly Gly Ser Ala Gln Leu Glu Lys Glu Leu Gln Ala Leu Glu Lys
225                 230                 235                 240

Glu Asn Ala Gln Leu Glu Trp Glu Leu Gln Ala Leu Glu Lys Glu Leu
                245                 250                 255

Ala Gln Gly Ala Thr
            260

<210> SEQ ID NO 214
<211> LENGTH: 261
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
        100                 105                 110

Thr Ile Ser Lys Ala Lys Gly Gln Pro Arg Glu Pro Gln Val Tyr Thr
    115                 120                 125

Leu Pro Pro Ser Arg Glu Glu Met Thr Lys Asn Gln Val Ser Leu Thr
130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
        210                 215                 220
```

```
Lys Gly Gly Ser Ala Gln Leu Lys Lys Leu Gln Ala Leu Lys Lys
225                 230                 235                 240

Lys Asn Ala Gln Leu Lys Trp Lys Leu Gln Ala Leu Lys Lys Lys Leu
                245                 250                 255

Ala Gln Gly Ala Thr
            260

<210> SEQ ID NO 215

<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000
```

<210> SEQ ID NO 225

<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

```
<210> SEQ ID NO 270
<400> SEQUENCE: 270
000

<210> SEQ ID NO 271
<400> SEQUENCE: 271
000

<210> SEQ ID NO 272
<400> SEQUENCE: 272
000

<210> SEQ ID NO 273
<400> SEQUENCE: 273
000

<210> SEQ ID NO 274
<400> SEQUENCE: 274
000

<210> SEQ ID NO 275
<400> SEQUENCE: 275
000

<210> SEQ ID NO 276
<400> SEQUENCE: 276
000

<210> SEQ ID NO 277
<400> SEQUENCE: 277
000

<210> SEQ ID NO 278
<400> SEQUENCE: 278
000

<210> SEQ ID NO 279
<400> SEQUENCE: 279
000

<210> SEQ ID NO 280
<400> SEQUENCE: 280
000

<210> SEQ ID NO 281
```

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301
<211> LENGTH: 443
<212> TYPE: PRT
<213> ORGANISM: Homo sapiens

<400> SEQUENCE: 301

```
Met Leu Thr Asn Gly Lys Glu Gln Val Ile Lys Ser Cys Val Ser Leu
1               5                   10                  15

Pro Glu Leu Asn Ala Gln Val Phe Cys His Ser Ser Asn Asn Val Thr
            20                  25                  30

Lys Thr Glu Cys Cys Phe Thr Asp Phe Cys Asn Asn Ile Thr Leu His
        35                  40                  45

Leu Pro Thr Ala Ser Pro Asn Ala Pro Lys Leu Gly Pro Met Glu Leu
    50                  55                  60

Ala Ile Ile Ile Thr Val Pro Val Cys Leu Leu Ser Ile Ala Ala Met
```

```
            65                  70                  75                  80
Leu Thr Val Trp Ala Cys Gln Gly Arg Gln Cys Ser Tyr Arg Lys Lys
                    85                  90                  95

Lys Arg Pro Asn Val Glu Glu Pro Leu Ser Glu Cys Asn Leu Val Asn
                100                 105                 110

Ala Gly Lys Thr Leu Lys Asp Leu Ile Tyr Asp Val Thr Ala Ser Gly
                115                 120                 125

Ser Gly Ser Gly Leu Pro Leu Leu Val Gln Arg Thr Ile Ala Arg Thr
130                 135                 140

Ile Val Leu Gln Glu Ile Val Gly Lys Gly Arg Phe Gly Glu Val Trp
145                 150                 155                 160

His Gly Arg Trp Cys Gly Glu Asp Val Ala Val Lys Ile Phe Ser Ser
                165                 170                 175

Arg Asp Glu Arg Ser Trp Phe Arg Glu Ala Glu Ile Tyr Gln Thr Val
                180                 185                 190

Met Leu Arg His Glu Asn Ile Leu Gly Phe Ile Ala Ala Asp Asn Lys
                195                 200                 205

Asp Asn Gly Thr Trp Thr Gln Leu Trp Leu Val Ser Glu Tyr His Glu
210                 215                 220

Gln Gly Ser Leu Tyr Asp Tyr Leu Asn Arg Asn Ile Val Thr Val Ala
225                 230                 235                 240

Gly Met Ile Lys Leu Ala Leu Ser Ile Ala Ser Gly Leu Ala His Leu
                245                 250                 255

His Met Glu Ile Val Gly Thr Gln Gly Lys Pro Ala Ile Ala His Arg
                260                 265                 270

Asp Ile Lys Ser Lys Asn Ile Leu Val Lys Lys Cys Glu Thr Cys Ala
                275                 280                 285

Ile Ala Asp Leu Gly Leu Ala Val Lys His Asp Ser Ile Leu Asn Thr
290                 295                 300

Ile Asp Ile Pro Gln Asn Pro Lys Val Gly Thr Lys Arg Tyr Met Ala
305                 310                 315                 320

Pro Glu Met Leu Asp Asp Thr Met Asn Val Asn Ile Phe Glu Ser Phe
                325                 330                 335

Lys Arg Ala Asp Ile Tyr Ser Val Gly Leu Val Tyr Trp Glu Ile Ala
                340                 345                 350

Arg Arg Cys Ser Val Gly Gly Ile Val Glu Glu Tyr Gln Leu Pro Tyr
                355                 360                 365

Tyr Asp Met Val Pro Ser Asp Pro Ser Ile Glu Glu Met Arg Lys Val
                370                 375                 380

Val Cys Asp Gln Lys Phe Arg Pro Ser Ile Pro Asn Gln Trp Gln Ser
385                 390                 395                 400

Cys Glu Ala Leu Arg Val Met Gly Arg Ile Met Arg Glu Cys Trp Tyr
                405                 410                 415

Ala Asn Gly Ala Ala Arg Leu Thr Ala Leu Arg Ile Lys Lys Thr Ile
                420                 425                 430

Ser Gln Leu Cys Val Lys Glu Asp Cys Lys Ala
                435                 440

<210> SEQ ID NO 302
<211> LENGTH: 63
<212> TYPE: PRT
<213> ORGANISM: Homo sapiens

<400> SEQUENCE: 302
```

| Met | Leu | Thr | Asn | Gly | Lys | Glu | Gln | Val | Ile | Lys | Ser | Cys | Val | Ser | Leu |
| 1 | | | | 5 | | | | | 10 | | | | | 15 | |

| Pro | Glu | Leu | Asn | Ala | Gln | Val | Phe | Cys | His | Ser | Ser | Asn | Asn | Val | Thr |
| | | | 20 | | | | | 25 | | | | | 30 | | |

| Lys | Thr | Glu | Cys | Cys | Phe | Thr | Asp | Phe | Cys | Asn | Asn | Ile | Thr | Leu | His |
| | | 35 | | | | | 40 | | | | | 45 | | | |

| Leu | Pro | Thr | Ala | Ser | Pro | Asn | Ala | Pro | Lys | Leu | Gly | Pro | Met | Glu | |
| | 50 | | | | | 55 | | | | | 60 | | | | |

<210> SEQ ID NO 303
<211> LENGTH: 1329
<212> TYPE: DNA
<213> ORGANISM: Homo sapiens

<400> SEQUENCE: 303

| | | |
|---|---|---|
| atgctaacca atggaaaaga gcaggtgatc aaatcctgtg tctcccttcc agaactgaat | 60 |
| gctcaagtct tctgtcatag ttccaacaat gttaccaaaa ccgaatgctg cttcacagat | 120 |
| ttttgcaaca acataaacact gcaccttcca acagcatcac caaatgcccc aaaacttgga | 180 |
| cccatggagc tggccatcat tattactgtg cctgtttgcc tcctgtccat agctgcgatg | 240 |
| ctgacagtat gggcatgcca gggtcgacag tgctcctaca ggaagaaaaa gagaccaaat | 300 |
| gtggaggaac cactctctga gtgcaatctg gtaaatgctg gaaaaactct gaaagatctg | 360 |
| atttatgatg tgaccgcctc tggatctggc tctggtctac ctctgttggt tcaaaggaca | 420 |
| attgcaagga cgattgtgct tcaggaaata gtaggaaaag gtagatttgg tgaggtgtgg | 480 |
| catgaagat ggtgtgggga agatgtggct gtgaaaatat tctcctccag agatgaaaga | 540 |
| tcttggtttc gtgaggcaga aatttaccag acggtcatgc tgcgacatga aaacatcctt | 600 |
| ggtttcattg ctgctgacaa caaagataat ggaacttgga ctcaactttg gctggtatct | 660 |
| gaatatcatg aacagggctc cttatatgac tatttgaata gaaatatagt gaccgtggct | 720 |
| ggaatgatca gctggcgct ctcaattgct agtggtctgg cacaccttca tatggagatt | 780 |
| gttggtacac aaggtaaacc tgctattgct catcgagaca taaaatcaaa gaatatctta | 840 |
| gtgaaaaagt gtgaaacttg tgccatagcg gacttagggt tggctgtgaa gcatgattca | 900 |
| atactgaaca ctatcgacat acctcagaat cctaaagtgg gaaccaagag gtatatggct | 960 |
| cctgaaatgc ttgatgatac aatgaatgtg aatatctttg agtccttcaa acgagctgac | 1020 |
| atctattctg ttggtctggt ttactgggaa atagcccgga ggtgttcagt cggaggaatt | 1080 |
| gttgaggagt accaattgcc ttattatgac atggtgcctt cagatccctc gatagaggaa | 1140 |
| atgagaaagg ttgtttgtga ccagaagttt cgaccaagta tcccaaacca gtggcaaagt | 1200 |
| tgtgaagcac tccgagtcat ggggagaata atgcgtgagt gttggtatgc caacggagcg | 1260 |
| gcccgcctaa ctgctcttcg tattaagaag actatatctc aactttgtgt caaagaagac | 1320 |
| tgcaaagcc | 1329 |

<210> SEQ ID NO 304
<211> LENGTH: 189
<212> TYPE: DNA
<213> ORGANISM: Homo sapiens

<400> SEQUENCE: 304

| | | |
|---|---|---|
| atgctaacca atggaaaaga gcaggtgatc aaatcctgtg tctcccttcc agaactgaat | 60 |
| gctcaagtct tctgtcatag ttccaacaat gttaccaaaa ccgaatgctg cttcacagat | 120 |
| ttttgcaaca acataaacact gcaccttcca acagcatcac caaatgcccc aaaacttgga | 180 | cccatggag                                                                  189

<210> SEQ ID NO 305
<211> LENGTH: 413
<212> TYPE: PRT
<213> ORGANISM: Homo sapiens

<400> SEQUENCE: 305

Met Thr Arg Ala Leu Cys Ser Ala Leu Arg Gln Ala Leu Leu Leu
1               5                   10                  15

Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
                35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Gly Leu Pro Leu Leu Val Gln Arg Thr Ile Ala
                100                 105                 110

Arg Thr Ile Val Leu Gln Glu Ile Val Gly Lys Gly Arg Phe Gly Glu
            115                 120                 125

Val Trp His Gly Arg Trp Cys Gly Glu Asp Val Ala Val Lys Ile Phe
    130                 135                 140

Ser Ser Arg Asp Glu Arg Ser Trp Phe Arg Glu Ala Glu Ile Tyr Gln
145                 150                 155                 160

Thr Val Met Leu Arg His Glu Asn Ile Leu Gly Phe Ile Ala Ala Asp
                165                 170                 175

Asn Lys Asp Asn Gly Thr Trp Thr Gln Leu Trp Leu Val Ser Glu Tyr
            180                 185                 190

His Glu Gln Gly Ser Leu Tyr Asp Tyr Leu Asn Arg Asn Ile Val Thr
        195                 200                 205

Val Ala Gly Met Ile Lys Leu Ala Leu Ser Ile Ala Ser Gly Leu Ala
    210                 215                 220

His Leu His Met Glu Ile Val Gly Thr Gln Gly Lys Pro Ala Ile Ala
225                 230                 235                 240

His Arg Asp Ile Lys Ser Lys Asn Ile Leu Val Lys Lys Cys Glu Thr
                245                 250                 255

Cys Ala Ile Ala Asp Leu Gly Leu Ala Val Lys His Asp Ser Ile Leu
            260                 265                 270

Asn Thr Ile Asp Ile Pro Gln Asn Pro Lys Val Gly Thr Lys Arg Tyr
        275                 280                 285

Met Ala Pro Glu Met Leu Asp Asp Thr Met Asn Val Asn Ile Phe Glu
    290                 295                 300

Ser Phe Lys Arg Ala Asp Ile Tyr Ser Val Gly Leu Val Tyr Trp Glu
305                 310                 315                 320

Ile Ala Arg Arg Cys Ser Val Gly Gly Ile Val Glu Glu Tyr Gln Leu
                325                 330                 335

Pro Tyr Tyr Asp Met Val Pro Ser Asp Pro Ser Ile Glu Glu Met Arg
            340                 345                 350

Lys Val Val Cys Asp Gln Lys Phe Arg Pro Ser Ile Pro Asn Gln Trp
        355                 360                 365

```
Gln Ser Cys Glu Ala Leu Arg Val Met Gly Arg Ile Met Arg Glu Cys
        370                 375                 380

Trp Tyr Ala Asn Gly Ala Ala Arg Leu Thr Ala Leu Arg Ile Lys Lys
385                 390                 395                 400

Thr Ile Ser Gln Leu Cys Val Lys Glu Asp Cys Lys Ala
                405                 410

<210> SEQ ID NO 306
<211> LENGTH: 393
<212> TYPE: PRT
<213> ORGANISM: Homo sapiens

<400> SEQUENCE: 306

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
            20                  25                  30

Thr Asn Gly Lys Glu Gln Val Ile Lys Ser Cys Val Ser Leu Pro Glu
        35                  40                  45

Leu Asn Ala Gln Val Phe Cys His Ser Ser Asn Asn Val Thr Lys Thr
    50                  55                  60

Glu Cys Cys Phe Thr Asp Phe Cys Asn Asn Ile Thr Leu His Leu Pro
65                  70                  75                  80

Thr Gly Leu Pro Leu Leu Val Gln Arg Thr Ile Ala Arg Thr Ile Val
                85                  90                  95

Leu Gln Glu Ile Val Gly Lys Gly Arg Phe Gly Glu Val Trp His Gly
            100                 105                 110

Arg Trp Cys Gly Glu Asp Val Ala Val Lys Ile Phe Ser Ser Arg Asp
        115                 120                 125

Glu Arg Ser Trp Phe Arg Glu Ala Glu Ile Tyr Gln Thr Val Met Leu
    130                 135                 140

Arg His Glu Asn Ile Leu Gly Phe Ile Ala Ala Asp Asn Lys Asp Asn
145                 150                 155                 160

Gly Thr Trp Thr Gln Leu Trp Leu Val Ser Glu Tyr His Glu Gln Gly
                165                 170                 175

Ser Leu Tyr Asp Tyr Leu Asn Arg Asn Ile Val Thr Val Ala Gly Met
            180                 185                 190

Ile Lys Leu Ala Leu Ser Ile Ala Ser Gly Leu Ala His Leu His Met
        195                 200                 205

Glu Ile Val Gly Thr Gln Gly Lys Pro Ala Ile Ala His Arg Asp Ile
    210                 215                 220

Lys Ser Lys Asn Ile Leu Val Lys Lys Cys Glu Thr Cys Ala Ile Ala
225                 230                 235                 240

Asp Leu Gly Leu Ala Val Lys His Asp Ser Ile Leu Asn Thr Ile Asp
                245                 250                 255

Ile Pro Gln Asn Pro Lys Val Gly Thr Lys Arg Tyr Met Ala Pro Glu
            260                 265                 270

Met Leu Asp Asp Thr Met Asn Val Asn Ile Phe Glu Ser Phe Lys Arg
        275                 280                 285

Ala Asp Ile Tyr Ser Val Gly Leu Val Tyr Trp Glu Ile Ala Arg Arg
    290                 295                 300

Cys Ser Val Gly Gly Ile Val Glu Glu Tyr Gln Leu Pro Tyr Tyr Asp
305                 310                 315                 320

Met Val Pro Ser Asp Pro Ser Ile Glu Glu Met Arg Lys Val Val Cys
```

|     |     |     |     | 325 |     |     |     |     | 330 |     |     |     |     | 335 |
| --- | --- | --- | --- | --- | --- | --- | --- | --- | --- | --- | --- | --- | --- | --- |
| Asp | Gln | Lys | Phe | Arg | Pro | Ser | Ile | Pro | Asn | Gln | Trp | Gln | Ser | Cys | Glu |
|     |     |     | 340 |     |     |     |     | 345 |     |     |     |     | 350 |     |     |

Ala Leu Arg Val Met Gly Arg Ile Met Arg Glu Cys Trp Tyr Ala Asn
        355                      360                    365

Gly Ala Ala Arg Leu Thr Ala Leu Arg Ile Lys Lys Thr Ile Ser Gln
 370                   375                    380

Leu Cys Val Lys Glu Asp Cys Lys Ala
385               390

<210> SEQ ID NO 307
<211> LENGTH: 1239
<212> TYPE: DNA
<213> ORGANISM: Homo sapiens

<400> SEQUENCE: 307

| | | | | | |
|---|---|---|---|---|---|
| atgacccggg | cgctctgctc | agcgctccgc | caggctctcc | tgctgctcgc | agcggccgcc | 60 |
| gagctctcgc | caggactgaa | gtgtgtatgt | cttttgtgtg | attcttcaaa | ctttacctgc | 120 |
| caaacagaag | gagcatgttg | ggcatcagtc | atgctaacca | atggaaaaga | gcaggtgatc | 180 |
| aaatcctgtg | tctcccttcc | agaactgaat | gctcaagtct | tctgtcatag | ttccaacaat | 240 |
| gttaccaaaa | ccgaatgctg | cttcacagat | ttttgcaaca | acataacact | gcaccttcca | 300 |
| acaggtctac | ctctgttggt | tcaaaggaca | attgcaagga | cgattgtgct | tcaggaaata | 360 |
| gtaggaaaag | gtagatttgg | tgaggtgtgg | catggaagat | ggtgtgggga | agatgtggct | 420 |
| gtgaaaatat | tctcctccag | agatgaaaga | tcttggtttc | gtgaggcaga | aatttaccag | 480 |
| acggtcatgc | tgcgacatga | aaacatcctt | ggtttcattg | ctgctgacaa | caaagataat | 540 |
| ggaacttgga | ctcaactttg | gctggtatct | gaatatcatg | aacagggctc | cttatatgac | 600 |
| tatttgaata | gaaatatagt | gaccgtggct | ggaatgatca | agctggcgct | ctcaattgct | 660 |
| agtggtctgg | cacaccttca | tatggagatt | gttggtacac | aagtaaaacc | tgctattgct | 720 |
| catcgagaca | taaaatcaaa | gaatatctta | gtgaaaaagt | gtgaaacttg | tgccatagcg | 780 |
| gacttagggt | tggctgtgaa | gcatgattca | atactgaaca | ctatcgacat | acctcagaat | 840 |
| cctaaagtgg | gaaccaagag | gtatatggct | cctgaaatgc | ttgatgatac | aatgaatgtg | 900 |
| aatatctttg | agtccttcaa | acgagctgac | atctattctg | ttggtctggt | ttactgggaa | 960 |
| atagcccgga | ggtgttcagt | cggaggaatt | gttgaggagt | accaattgcc | ttattatgac | 1020 |
| atggtgcctt | cagatccctc | gatagaggaa | atgagaaagg | ttgtttgtga | ccagaagttt | 1080 |
| cgaccaagta | tcccaaacca | gtggcaaagt | tgtgaagcac | tccgagtcat | ggggagaata | 1140 |
| atgcgtgagt | gttggtatgc | caacggagcg | gcccgcctaa | ctgctcttcg | tattaagaag | 1200 |
| actatatctc | aactttgtgt | caaagaagac | tgcaaagcc | | | 1239 |

<210> SEQ ID NO 308
<211> LENGTH: 1179
<212> TYPE: DNA
<213> ORGANISM: Homo sapiens

<400> SEQUENCE: 308

| | | | | | |
|---|---|---|---|---|---|
| gagctctcgc | caggactgaa | gtgtgtatgt | cttttgtgtg | attcttcaaa | ctttacctgc | 60 |
| caaacagaag | gagcatgttg | ggcatcagtc | atgctaacca | atggaaaaga | gcaggtgatc | 120 |
| aaatcctgtg | tctcccttcc | agaactgaat | gctcaagtct | tctgtcatag | ttccaacaat | 180 |
| gttaccaaaa | ccgaatgctg | cttcacagat | ttttgcaaca | acataacact | gcaccttcca | 240 |

-continued

```
acaggtctac ctctgttggt tcaaaggaca attgcaagga cgattgtgct tcaggaaata      300
gtaggaaaag gtagatttgg tgaggtgtgg catggaagat ggtgtgggga agatgtggct      360
gtgaaaatat tctcctccag agatgaaaga tcttggtttc gtgaggcaga aatttaccag      420
acggtcatgc tgcgacatga aacatccttg gtttcattg ctgctgacaa caaagataat       480
ggaacttgga ctcaactttg ctggtatct gaatatcatg aacagggctc cttatatgac       540
tatttgaata gaaatatagt gaccgtggct ggaatgatca agctggcgct ctcaattgct      600
agtggtctgg cacaccttca tatggagatt gttggtacac aaggtaaacc tgctattgct      660
catcgagaca taaaatcaaa gaatatctta gtgaaaaagt gtgaaacttg tgccatagcg      720
gacttagggt tggctgtgaa gcatgattca atactgaaca ctatcgacat acctcagaat      780
cctaaagtgg gaaccaagag gtatatggct cctgaaatgc ttgatgatac aatgaatgtg      840
aatatctttg agtccttcaa acgagctgac atctattctg ttggtctggt ttactgggaa      900
atagcccgga ggtgttcagt cggaggaatt gttgaggagt accaattgcc ttattatgac      960
atggtgcctt cagatccctc gatagaggaa atgagaaagg ttgtttgtga ccagaagttt     1020
cgaccaagta tcccaaacca gtggcaaagt tgtgaagcac tccgagtcat ggggagaata     1080
atgcgtgagt gttggtatgc caacggagcg gcccgcctaa ctgctcttcg tattaagaag     1140
actatatctc aactttgtgt caaagaagac tgcaaagcc                             1179
```

<210> SEQ ID NO 309
<211> LENGTH: 336
<212> TYPE: PRT
<213> ORGANISM: Homo sapiens

<400> SEQUENCE: 309

```
Met Thr Arg Ala Leu Cys Ser Ala Leu Arg Gln Ala Leu Leu Leu Leu
1               5                   10                  15

Ala Ala Ala Glu Leu Ser Pro Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Asp Asn Gly Thr Trp Thr Gln Leu Trp Leu Val
            100                 105                 110

Ser Glu Tyr His Glu Gln Gly Ser Leu Tyr Asp Tyr Leu Asn Arg Asn
        115                 120                 125

Ile Val Thr Val Ala Gly Met Ile Lys Leu Ala Leu Ser Ile Ala Ser
    130                 135                 140

Gly Leu Ala His Leu His Met Glu Ile Val Gly Thr Gln Gly Lys Pro
145                 150                 155                 160

Ala Ile Ala His Arg Asp Ile Lys Ser Lys Asn Ile Leu Val Lys Lys
                165                 170                 175

Cys Glu Thr Cys Ala Ile Ala Asp Leu Gly Leu Ala Val Lys His Asp
            180                 185                 190

Ser Ile Leu Asn Thr Ile Asp Ile Pro Gln Asn Pro Lys Val Gly Thr
        195                 200                 205
```

Lys Arg Tyr Met Ala Pro Glu Met Leu Asp Asp Thr Met Asn Val Asn
              210                 215                 220

Ile Phe Glu Ser Phe Lys Arg Ala Asp Ile Tyr Ser Val Gly Leu Val
225                 230                 235                 240

Tyr Trp Glu Ile Ala Arg Arg Cys Ser Val Gly Ile Val Glu Glu
                    245                 250                 255

Tyr Gln Leu Pro Tyr Tyr Asp Met Val Pro Ser Asp Pro Ser Ile Glu
                260                 265                 270

Glu Met Arg Lys Val Val Cys Asp Gln Lys Phe Arg Pro Ser Ile Pro
                275                 280                 285

Asn Gln Trp Gln Ser Cys Glu Ala Leu Arg Val Met Gly Arg Ile Met
290                 295                 300

Arg Glu Cys Trp Tyr Ala Asn Gly Ala Ala Arg Leu Thr Ala Leu Arg
305                 310                 315                 320

Ile Lys Lys Thr Ile Ser Gln Leu Cys Val Lys Glu Asp Cys Lys Ala
                325                 330                 335

<210> SEQ ID NO 310
<211> LENGTH: 316
<212> TYPE: PRT
<213> ORGANISM: Homo sapiens

<400> SEQUENCE: 310

Glu Leu Ser Pro Gly Leu Lys Cys Val Cys Leu Leu Cys Asp Ser Ser
1               5                   10                  15

Asn Phe Thr Cys Gln Thr Glu Gly Ala Cys Trp Ala Ser Val Met Leu
                20                  25                  30

Thr Asn Gly Lys Glu Gln Val Ile Lys Ser Cys Val Ser Leu Pro Glu
            35                  40                  45

Leu Asn Ala Gln Val Phe Cys His Ser Ser Asn Asn Val Thr Lys Thr
        50                  55                  60

Glu Cys Cys Phe Thr Asp Phe Cys Asn Asn Ile Thr Leu His Leu Pro
65                  70                  75                  80

Thr Asp Asn Gly Thr Trp Thr Gln Leu Trp Leu Val Ser Glu Tyr His
                85                  90                  95

Glu Gln Gly Ser Leu Tyr Asp Tyr Leu Asn Arg Asn Ile Val Thr Val
            100                 105                 110

Ala Gly Met Ile Lys Leu Ala Leu Ser Ile Ala Ser Gly Leu Ala His
        115                 120                 125

Leu His Met Glu Ile Val Gly Thr Gln Gly Lys Pro Ala Ile Ala His
    130                 135                 140

Arg Asp Ile Lys Ser Lys Asn Ile Leu Val Lys Lys Cys Glu Thr Cys
145                 150                 155                 160

Ala Ile Ala Asp Leu Gly Leu Ala Val Lys His Asp Ser Ile Leu Asn
                165                 170                 175

Thr Ile Asp Ile Pro Gln Asn Pro Lys Val Gly Thr Lys Arg Tyr Met
            180                 185                 190

Ala Pro Glu Met Leu Asp Asp Thr Met Asn Val Asn Ile Phe Glu Ser
        195                 200                 205

Phe Lys Arg Ala Asp Ile Tyr Ser Val Gly Leu Val Tyr Trp Glu Ile
    210                 215                 220

Ala Arg Arg Cys Ser Val Gly Gly Ile Val Glu Glu Tyr Gln Leu Pro
225                 230                 235                 240

Tyr Tyr Asp Met Val Pro Ser Asp Pro Ser Ile Glu Glu Met Arg Lys

|       |       |       |       | 245   |       |       |       |       | 250   |       |       |       |       | 255   |       |
|-------|-------|-------|-------|-------|-------|-------|-------|-------|-------|-------|-------|-------|-------|-------|-------|
| Val   | Val   | Cys   | Asp   | Gln   | Lys   | Phe   | Arg   | Pro   | Ser   | Ile   | Pro   | Asn   | Gln   | Trp   | Gln   |
|       |       |       |       | 260   |       |       |       |       | 265   |       |       |       |       | 270   |       |
| Ser   | Cys   | Glu   | Ala   | Leu   | Arg   | Val   | Met   | Gly   | Arg   | Ile   | Met   | Arg   | Glu   | Cys   | Trp   |
|       |       |       |       | 275   |       |       |       |       | 280   |       |       |       |       | 285   |       |
| Tyr   | Ala   | Asn   | Gly   | Ala   | Ala   | Arg   | Leu   | Thr   | Ala   | Leu   | Arg   | Ile   | Lys   | Lys   | Thr   |
|       |       |       |       | 290   |       |       |       |       | 295   |       |       |       |       | 300   |       |
| Ile   | Ser   | Gln   | Leu   | Cys   | Val   | Lys   | Glu   | Asp   | Cys   | Lys   | Ala   |       |       |       |       |
| 305   |       |       |       |       | 310   |       |       |       |       | 315   |       |       |       |       |       |

<210> SEQ ID NO 311
<211> LENGTH: 1011
<212> TYPE: DNA
<213> ORGANISM: Homo sapiens

<400> SEQUENCE: 311

| atgacccggg cgctctgctc agcgctccgc caggctctcc tgctgctcgc agcggccgcc | 60 |
|---|---|
| gagctctcgc caggactgaa gtgtgtatgt cttttgtgtg attcttcaaa ctttacctgc | 120 |
| caaacagaag gagcatgttg ggcatcagtc atgctaacca atggaaaaga gcaggtgatc | 180 |
| aaatcctgtg tctcccttcc agaactgaat gctcaagtct tctgtcatag ttccaacaat | 240 |
| gttaccaaaa ccgaatgctg cttcacagat ttttgcaaca acataacact gcaccttcca | 300 |
| acagataatg gaacttggac tcaactttgg ctggtatctg aatatcatga cagggctcc | 360 |
| ttatatgact atttgaatag aaatatagtg accgtggctg aatgatcaa gctggcgctc | 420 |
| tcaattgcta gtggtctggc acaccttcat atggagattt tggtacaca aggtaaacct | 480 |
| gctattgctc atcgagacat aaaatcaaag aatatcttag tgaaaaagtg tgaaacttgt | 540 |
| gccatagcgg acttagggtt ggctgtgaag catgattcaa tactgaacac tatcgacata | 600 |
| cctcagaatc ctaaagtggg aaccaagagg tatatggctc ctgaaatgct tgatgataca | 660 |
| atgaatgtga atatctttga gtccttcaaa cgagctgaca tctattctgt tggtctggtt | 720 |
| tactgggaaa tagcccggag gtgttcagtc ggaggaattg ttgaggagta ccaattgcct | 780 |
| tattatgaca tggtgccttc agatccctcg atagaggaaa tgagaaaggt tgtttgtgac | 840 |
| cagaagtttc gaccaagtat cccaaaccag tggcaaagtt gtgaagcact ccgagtcatg | 900 |
| gggagaataa tgcgtgagtg ttggtatgcc aacggagcgg cccgcctaac tgctcttcgt | 960 |
| attaagaaga ctatatctca actttgtgtc aaagaagact gcaaagccta a | 1011 |

<210> SEQ ID NO 312
<211> LENGTH: 951
<212> TYPE: DNA
<213> ORGANISM: Homo sapiens

<400> SEQUENCE: 312

| gagctctcgc caggactgaa gtgtgtatgt cttttgtgtg attcttcaaa ctttacctgc | 60 |
|---|---|
| caaacagaag gagcatgttg ggcatcagtc atgctaacca atggaaaaga gcaggtgatc | 120 |
| aaatcctgtg tctcccttcc agaactgaat gctcaagtct tctgtcatag ttccaacaat | 180 |
| gttaccaaaa ccgaatgctg cttcacagat ttttgcaaca acataacact gcaccttcca | 240 |
| acagataatg gaacttggac tcaactttgg ctggtatctg aatatcatga cagggctcc | 300 |
| ttatatgact atttgaatag aaatatagtg accgtggctg aatgatcaa gctggcgctc | 360 |
| tcaattgcta gtggtctggc acaccttcat atggagattt tggtacaca aggtaaacct | 420 |
| gctattgctc atcgagacat aaaatcaaag aatatcttag tgaaaaagtg tgaaacttgt | 480 |

```
gccatagcgg acttagggtt ggctgtgaag catgattcaa tactgaacac tatcgacata      540
cctcagaatc ctaaagtggg aaccaagagg tatatggctc ctgaaatgct tgatgataca      600
atgaatgtga atatctttga gtccttcaaa cgagctgaca tctattctgt tggtctggtt      660
tactgggaaa tagcccggag gtgttcagtc ggaggaattg ttgaggagta ccaattgcct      720
tattatgaca tggtgccttc agatccctcg atagaggaaa tgagaaaggt tgtttgtgac      780
cagaagtttc gaccaagtat cccaaaccag tggcaaagtt gtgaagcact ccgagtcatg      840
gggagaataa tgcgtgagtg ttggtatgcc aacggagcgg cccgcctaac tgctcttcgt      900
attaagaaga ctatatctca actttgtgtc aaagaagact gcaaagccta a              951
```

<210> SEQ ID NO 313
<211> LENGTH: 88
<212> TYPE: PRT
<213> ORGANISM: Homo sapiens

<400> SEQUENCE: 313

```
Leu Lys Cys Val Cys Leu Leu Cys Asp Ser Ser Asn Phe Thr Cys Gln
1               5                   10                  15

Thr Glu Gly Ala Cys Trp Ala Ser Val Met Leu Thr Asn Gly Lys Glu
            20                  25                  30

Gln Val Ile Lys Ser Cys Val Ser Leu Pro Glu Leu Asn Ala Gln Val
        35                  40                  45

Phe Cys His Ser Ser Asn Asn Val Thr Lys Thr Glu Cys Cys Phe Thr
    50                  55                  60

Asp Phe Cys Asn Asn Ile Thr Leu His Leu Pro Thr Ala Ser Pro Asn
65                  70                  75                  80

Ala Pro Lys Leu Gly Pro Met Glu
                85
```

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

```
<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340

<400> SEQUENCE: 340

000

<210> SEQ ID NO 341

<400> SEQUENCE: 341
```

000

<210> SEQ ID NO 342
<400> SEQUENCE: 342
000

<210> SEQ ID NO 343
<400> SEQUENCE: 343
000

<210> SEQ ID NO 344
<400> SEQUENCE: 344
000

<210> SEQ ID NO 345
<400> SEQUENCE: 345
000

<210> SEQ ID NO 346
<400> SEQUENCE: 346
000

<210> SEQ ID NO 347
<400> SEQUENCE: 347
000

<210> SEQ ID NO 348
<400> SEQUENCE: 348
000

<210> SEQ ID NO 349
<400> SEQUENCE: 349
000

<210> SEQ ID NO 350
<400> SEQUENCE: 350
000

<210> SEQ ID NO 351
<400> SEQUENCE: 351
000

<210> SEQ ID NO 352
<400> SEQUENCE: 352
000

-continued

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

```
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371
<400> SEQUENCE: 371
000

<210> SEQ ID NO 372
<400> SEQUENCE: 372
000

<210> SEQ ID NO 373
<400> SEQUENCE: 373
000

<210> SEQ ID NO 374
<400> SEQUENCE: 374
000

<210> SEQ ID NO 375
<400> SEQUENCE: 375
```

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

```
Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Thr Ala Pro Thr Gly Gly Gly Thr
    130                 135                 140

His Thr Cys Pro Pro Cys Pro Ala Pro Glu Leu Leu Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser His Glu Asp Pro
            180                 185                 190

Glu Val Lys Phe Asn Trp Tyr Val Asp Gly Val Glu Val His Asn Ala
        195                 200                 205

Lys Thr Lys Pro Arg Glu Glu Gln Tyr Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255
```

Ile Ser Lys Ala Lys Gly Gln Pro Arg Glu Pro Gln Val Tyr Thr Leu
            260                 265                 270

Pro Pro Cys Arg Glu Glu Met Thr Lys Asn Gln Val Ser Leu Trp Cys
    275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Lys Leu Thr Val Asp Lys Ser
                325                 330                 335

Arg Trp Gln Gln Gly Asn Val Phe Ser Cys Ser Val Met His Glu Ala
            340                 345                 350

Leu His Asn His Tyr Thr Gln Lys Ser Leu Ser Leu Ser Pro Gly Lys
            355                 360                 365

<210> SEQ ID NO 402
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140

Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Tyr Thr Leu Pro Pro Cys Arg Glu Glu Met Thr Lys
                245                 250                 255

```
Asn Gln Val Ser Leu Trp Cys Leu Val Lys Gly Phe Tyr Pro Ser Asp
            260                 265                 270

Ile Ala Val Glu Trp Glu Ser Asn Gly Gln Pro Glu Asn Asn Tyr Lys
            275                 280                 285

Thr Thr Pro Pro Val Leu Asp Ser Asp Gly Ser Phe Phe Leu Tyr Ser
            290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 403
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Cys Thr Leu Pro Pro Ser Arg Glu Glu Met Thr Lys Asn Gln Val
```

```
            260                 265                 270
Ser Leu Ser Cys Ala Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
        290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 404
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Cys Thr Leu Pro Pro Ser Arg
225                 230                 235                 240

Glu Glu Met Thr Lys Asn Gln Val Ser Leu Ser Cys Ala Val Lys Gly
                245                 250                 255
```

```
Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
            275                 280                 285

Phe Phe Leu Val Ser Lys Leu Thr Val Asp Lys Ser Arg Trp Gln Gln
            290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330
```

<210> SEQ ID NO 405
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

```
Met Asp Ala Met Lys Arg Gly Leu Cys Cys Val Leu Leu Leu Cys Gly
1               5                   10                  15

Ala Val Phe Val Ser Pro Gly Ala Gly Leu Lys Cys Val Cys Leu Leu
            20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val
    50                  55                  60

Ser Leu Pro Glu Leu Asn Ala Gln Val Phe Cys His Ser Ser Asn Asn
65                  70                  75                  80

Val Thr Lys Thr Glu Cys Cys Phe Thr Asp Phe Cys Asn Asn Ile Thr
                85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

Pro Gln Val Cys Thr Leu Pro Pro Ser Arg Glu Glu Met Thr Lys Asn
                245                 250                 255

Gln Val Ser Leu Ser Cys Ala Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285
```

Thr Pro Pro Val Leu Asp Ser Asp Gly Ser Phe Phe Leu Val Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 406
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Gly Leu Lys Cys Val Cys Leu Leu Cys Asp Ser Ser Asn Phe Thr Cys
1               5                   10                  15

Gln Thr Glu Gly Ala Cys Trp Ala Ser Val Met Leu Thr Asn Gly Lys
            20                  25                  30

Glu Gln Val Ile Lys Ser Cys Val Ser Leu Pro Glu Leu Asn Ala Gln
        35                  40                  45

Val Phe Cys His Ser Ser Asn Asn Val Thr Lys Thr Glu Cys Cys Phe
    50                  55                  60

Thr Asp Phe Cys Asn Asn Ile Thr Leu His Leu Pro Thr Ala Ser Pro
65                  70                  75                  80

Asn Ala Pro Lys Leu Gly Pro Met Glu Thr Gly Gly Gly Thr His Thr
                85                  90                  95

Cys Pro Pro Cys Pro Ala Pro Glu Leu Leu Gly Gly Pro Ser Val Phe
            100                 105                 110

Leu Phe Pro Pro Lys Pro Lys Asp Thr Leu Met Ile Ser Arg Thr Pro
        115                 120                 125

Glu Val Thr Cys Val Val Val Asp Val Ser His Glu Asp Pro Glu Val
    130                 135                 140

Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Cys Thr Leu Pro Pro
    210                 215                 220

Ser Arg Glu Glu Met Thr Lys Asn Gln Val Ser Leu Ser Cys Ala Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Lys Thr Thr Pro Pro Val Leu Asp Ser Asp
            260                 265                 270

Gly Ser Phe Phe Leu Val Ser Lys Leu Thr Val Asp Lys Ser Arg Trp
        275                 280                 285

Gln Gln Gly Asn Val Phe Ser Cys Ser Val Met His Glu Ala Leu His 290                 295                 300
Asn His Tyr Thr Gln Lys Ser Leu Ser Leu Ser Pro Gly Lys
305                 310                 315

<210> SEQ ID NO 407
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Met Asp Ala Met Lys Arg Gly Leu Cys Cys Val Leu Leu Cys Gly
1               5                   10                  15

Ala Val Phe Val Ser Pro Gly Ala Gln Asn Leu Asp Ser Met Leu His
                20                  25                  30

Gly Thr Gly Met Lys Ser Asp Ser Asp Gln Lys Lys Ser Glu Asn Gly
                35                  40                  45

Val Thr Leu Ala Pro Glu Asp Thr Leu Pro Phe Leu Lys Cys Tyr Cys
            50                  55                  60

Ser Gly His Cys Pro Asp Asp Ala Ile Asn Asn Thr Cys Ile Thr Asn
65                  70                  75                  80

Gly His Cys Phe Ala Ile Ile Glu Glu Asp Asp Gln Gly Glu Thr Thr
                85                  90                  95

Leu Ala Ser Gly Cys Met Lys Tyr Glu Gly Ser Asp Phe Gln Cys Lys
                100                 105                 110

Asp Ser Pro Lys Ala Gln Leu Arg Arg Thr Ile Glu Cys Cys Arg Thr
                115                 120                 125

Asn Leu Cys Asn Gln Tyr Leu Gln Pro Thr Leu Pro Pro Val Val Ile
130                 135                 140

Gly Pro Phe Phe Asp Gly Ser Ile Arg Thr Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
                180                 185                 190

Glu Val Thr Cys Val Val Val Asp Val Ser His Glu Asp Pro Glu Val
                195                 200                 205

Lys Phe Asn Trp Tyr Val Asp Gly Val Glu Val His Asn Ala Lys Thr
            210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
                260                 265                 270

Lys Ala Lys Gly Gln Pro Arg Glu Pro Gln Val Cys Thr Leu Pro Pro
                275                 280                 285

Ser Arg Glu Glu Met Thr Lys Asn Gln Val Ser Leu Ser Cys Ala Val
                290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Val Ser Lys Leu Thr Val Asp Lys Ser Arg Trp
            340                 345                 350

Gln Gln Gly Asn Val Phe Ser Cys Ser Val Met His Glu Ala Leu His
        355                 360                 365

Asn His Tyr Thr Gln Lys Ser Leu Ser Leu Ser Pro Gly Lys
    370                 375                 380

<210> SEQ ID NO 408
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Gly Ala Gln Asn Leu Asp Ser Met Leu His Gly Thr Gly Met Lys Ser
1               5                   10                  15

Asp Ser Asp Gln Lys Lys Ser Glu Asn Gly Val Thr Leu Ala Pro Glu
            20                  25                  30

Asp Thr Leu Pro Phe Leu Lys Cys Tyr Cys Ser Gly His Cys Pro Asp
        35                  40                  45

Asp Ala Ile Asn Asn Thr Cys Ile Thr Asn Gly His Cys Phe Ala Ile
    50                  55                  60

Ile Glu Glu Asp Asp Gln Gly Glu Thr Thr Leu Ala Ser Gly Cys Met
65                  70                  75                  80

Lys Tyr Glu Gly Ser Asp Phe Gln Cys Lys Asp Ser Pro Lys Ala Gln
                85                  90                  95

Leu Arg Arg Thr Ile Glu Cys Cys Arg Thr Asn Leu Cys Asn Gln Tyr
            100                 105                 110

Leu Gln Pro Thr Leu Pro Pro Val Val Ile Gly Pro Phe Phe Asp Gly
        115                 120                 125

Ser Ile Arg Thr Gly Gly Thr His Thr Cys Pro Pro Cys Pro Ala
    130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
            180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
    210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Cys Thr Leu Pro Pro Ser Arg Glu Glu Met Thr
            260                 265                 270

Lys Asn Gln Val Ser Leu Ser Cys Ala Val Lys Gly Phe Tyr Pro Ser
        275                 280                 285

Asp Ile Ala Val Glu Trp Glu Ser Asn Gly Gln Pro Glu Asn Asn Tyr
    290                 295                 300

Lys Thr Thr Pro Pro Val Leu Asp Ser Asp Gly Ser Phe Phe Leu Val
305                 310                 315                 320

```
Ser Lys Leu Thr Val Asp Lys Ser Arg Trp Gln Gln Gly Asn Val Phe
            325                 330                 335

Ser Cys Ser Val Met His Glu Ala Leu His Asn His Tyr Thr Gln Lys
            340                 345                 350

Ser Leu Ser Leu Ser Pro Gly Lys
        355                 360

<210> SEQ ID NO 409
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Thr Gly Gly Gly
    130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
        195                 200                 205

Ala Lys Thr Lys Pro Arg Glu Glu Gln Tyr Asn Ser Thr Tyr Arg Val
    210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Cys Arg Glu Glu Met Thr Lys Asn Gln Val Ser Leu Trp
        275                 280                 285

Cys Leu Val Lys Gly Phe Tyr Pro Ser Asp Ile Ala Val Glu Trp Glu
    290                 295                 300

Ser Asn Gly Gln Pro Glu Asn Asn Tyr Lys Thr Thr Pro Pro Val Leu
```

Asp Ser Asp Gly Ser Phe Phe Leu Tyr Ser Lys Leu Thr Val Asp Lys
            325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys

<210> SEQ ID NO 410
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
        50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
            115                 120                 125

Pro Glu Leu Leu Gly Gly Pro Ser Val Phe Leu Phe Pro Pro Lys Pro
            130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
            195                 200                 205

Asp Trp Leu Asn Gly Lys Glu Tyr Lys Cys Lys Val Ser Asn Lys Ala
        210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Cys Arg Glu Glu Met Thr
                245                 250                 255

Lys Asn Gln Val Ser Leu Trp Cys Leu Val Lys Gly Phe Tyr Pro Ser
            260                 265                 270

Asp Ile Ala Val Glu Trp Glu Ser Asn Gly Gln Pro Glu Asn Asn Tyr
            275                 280                 285

Lys Thr Thr Pro Pro Val Leu Asp Ser Asp Gly Ser Phe Phe Leu Tyr

```
                290                 295                 300
Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
                340

<210> SEQ ID NO 411
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Met Asp Ala Met Lys Arg Gly Leu Cys Cys Val Leu Leu Leu Cys Gly
1               5                   10                  15

Ala Val Phe Val Ser Pro Gly Ala Ser Gln Asn Gln Glu Arg Leu Cys
                20                  25                  30

Ala Phe Lys Asp Pro Tyr Gln Gln Asp Leu Gly Ile Gly Glu Ser Arg
            35                  40                  45

Ile Ser His Glu Asn Gly Thr Ile Leu Cys Ser Lys Gly Ser Thr Cys
50                  55                  60

Tyr Gly Leu Trp Glu Lys Ser Lys Gly Asp Ile Asn Leu Val Lys Gln
65                  70                  75                  80

Gly Cys Trp Ser His Ile Gly Asp Pro Gln Glu Cys His Tyr Glu Glu
                85                  90                  95

Cys Val Val Thr Thr Thr Pro Pro Ser Ile Gln Asn Gly Thr Tyr Arg
            100                 105                 110

Phe Cys Cys Cys Ser Thr Asp Leu Cys Asn Val Asn Phe Thr Glu Asn
        115                 120                 125

Phe Pro Pro Pro Asp Thr Thr Pro Leu Ser Pro Pro His Ser Phe Asn
130                 135                 140

Arg Asp Glu Thr Gly Gly Gly Thr His Thr Cys Pro Pro Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Cys Arg Glu Glu Met Thr
        275                 280                 285

Lys Asn Gln Val Ser Leu Trp Cys Leu Val Lys Gly Phe Tyr Pro Ser
    290                 295                 300
```

```
Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
            325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365

Ser Leu Ser Leu Ser Pro Gly Lys
    370                 375

<210> SEQ ID NO 412
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Cys Ser Thr Asp Leu
                85                  90                  95

Cys Asn Val Asn Phe Thr Glu Asn Phe Pro Pro Pro Asp Thr Thr Pro
            100                 105                 110

Leu Ser Pro Pro His Ser Phe Asn Arg Asp Glu Thr Gly Gly Gly Thr
        115                 120                 125

His Thr Cys Pro Pro Cys Pro Ala Pro Glu Leu Leu Gly Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Cys Arg Glu Glu Met Thr Lys Asn Gln Val Ser Leu Trp Cys
            260                 265                 270

Leu Val Lys Gly Phe Tyr Pro Ser Asp Ile Ala Val Glu Trp Glu Ser
        275                 280                 285
```

Asn Gly Gln Pro Glu Asn Asn Tyr Lys Thr Thr Pro Pro Val Leu Asp
            290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 413
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
            20                  25                  30

Pro Leu Val Thr Cys Thr Cys Glu Ser Pro His Cys Lys Gly Pro Thr
        35                  40                  45

Cys Arg Gly Ala Trp Cys Thr Val Val Leu Val Arg Glu Glu Gly Arg
50                  55                  60

His Pro Gln Glu His Arg Gly Cys Gly Asn Leu His Arg Glu Leu Cys
65                  70                  75                  80

Arg Gly Arg Pro Thr Glu Phe Val Asn His Tyr Cys Cys Asp Ser His
                85                  90                  95

Leu Cys Asn His Asn Val Ser Leu Val Leu Glu Ala Thr Gln Pro Pro
            100                 105                 110

Ser Glu Gln Pro Gly Thr Asp Gly Gln Leu Ala Thr Gly Gly Gly Thr
        115                 120                 125

His Thr Cys Pro Pro Cys Pro Ala Pro Glu Leu Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Cys Thr Leu
                245                 250                 255

Pro Pro Ser Arg Glu Glu Met Thr Lys Asn Gln Val Ser Leu Ser Cys
            260                 265                 270

Ala Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp

```
              290                 295                 300
Ser Asp Gly Ser Phe Phe Leu Val Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 414
<211> LENGTH: 328
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
                20                  25                  30

Val Leu Val Arg Glu Glu Gly Arg His Pro Gln Glu His Arg Gly Cys
            35                  40                  45

Gly Asn Leu His Arg Glu Leu Cys Arg Gly Arg Pro Thr Glu Phe Val
50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln Leu Ala Thr Gly Gly Gly Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
210                 215                 220

Arg Glu Pro Gln Val Cys Thr Leu Pro Pro Ser Arg Glu Glu Met Thr
225                 230                 235                 240

Lys Asn Gln Val Ser Leu Ser Cys Ala Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Val
        275                 280                 285

Ser Lys Leu Thr Val Asp Lys Ser Arg Trp Gln Gln Gly Asn Val Phe
290                 295                 300
```

Ser Cys Ser Val Met His Glu Ala Leu His Asn His Tyr Thr Gln Lys
305                 310                 315                 320

Ser Leu Ser Leu Ser Pro Gly Lys
            325

<210> SEQ ID NO 415
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Met Asp Ala Met Lys Arg Gly Leu Cys Cys Val Leu Leu Leu Cys Gly
1               5                   10                  15

Ala Val Phe Val Ser Pro Gly Ala Thr Ile Pro His Val Gln Lys
            20                  25                  30

Ser Val Asn Asn Asp Met Ile Val Thr Asp Asn Asn Gly Ala Val Lys
            35                  40                  45

Phe Pro Gln Leu Cys Lys Phe Cys Asp Val Arg Phe Ser Thr Cys Asp
        50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
        115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Asn Thr Ser Asn Pro
145                 150                 155                 160

Asp Thr Gly Gly Gly Thr His Thr Cys Pro Pro Cys Pro Ala Pro Glu
                165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
        195                 200                 205

Val Ser His Glu Asp Pro Glu Val Lys Phe Asn Trp Tyr Val Asp Gly
210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
        275                 280                 285

Pro Gln Val Tyr Thr Leu Pro Pro Cys Arg Glu Glu Met Thr Lys Asn
290                 295                 300

Gln Val Ser Leu Trp Cys Leu Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

```
Thr Pro Pro Val Leu Asp Ser Asp Gly Ser Phe Phe Leu Tyr Ser Lys
            340             345                 350

Leu Thr Val Asp Lys Ser Arg Trp Gln Gln Gly Asn Val Phe Ser Cys
            355             360                 365

Ser Val Met His Glu Ala Leu His Asn His Tyr Thr Gln Lys Ser Leu
    370             375                 380

Ser Leu Ser Pro Gly Lys
385             390

<210> SEQ ID NO 416
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65              70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Thr Gly Gly Gly Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Cys Arg Glu Glu Met Thr Lys Asn Gln Val Ser Leu Trp Cys Leu Val
        275                 280                 285

Lys Gly Phe Tyr Pro Ser Asp Ile Ala Val Glu Trp Glu Ser Asn Gly
```

```
                290                 295                 300
Gln Pro Glu Asn Asn Tyr Lys Thr Thr Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 417
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Thr His
            180                 185                 190

Thr Cys Pro Pro Cys Pro Ala Pro Glu Leu Leu Gly Gly Pro Ser Val
        195                 200                 205

Phe Leu Phe Pro Pro Lys Pro Lys Asp Thr Leu Met Ile Ser Arg Thr
    210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                245                 250                 255

Thr Lys Pro Arg Glu Glu Gln Tyr Asn Ser Thr Tyr Arg Val Val Ser
            260                 265                 270

Val Leu Thr Val Leu His Gln Asp Trp Leu Asn Gly Lys Glu Tyr Lys
        275                 280                 285
```

```
Cys Lys Val Ser Asn Lys Ala Leu Pro Ala Pro Ile Glu Lys Thr Ile
    290                 295                 300

Ser Lys Ala Lys Gly Gln Pro Arg Glu Pro Gln Val Tyr Thr Leu Pro
305                 310                 315                 320

Pro Cys Arg Glu Glu Met Thr Lys Asn Gln Val Ser Leu Trp Cys Leu
                325                 330                 335

Val Lys Gly Phe Tyr Pro Ser Asp Ile Ala Val Glu Trp Glu Ser Asn
                340                 345                 350

Gly Gln Pro Glu Asn Asn Tyr Lys Thr Thr Pro Pro Val Leu Asp Ser
            355                 360                 365

Asp Gly Ser Phe Phe Leu Tyr Ser Lys Leu Thr Val Asp Lys Ser Arg
370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415

<210> SEQ ID NO 418
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
                20                  25                  30

Arg His Ile Asn Asn Asp Met Ile Val Thr Asp Asn Asn Gly Ala Val
            35                  40                  45

Lys Phe Pro Gln Leu Cys Lys Phe Cys Asp Val Arg Phe Ser Thr Cys
50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
130                 135                 140

Glu Cys Asn Asp Asn Ile Ile Phe Ser Glu Glu Tyr Asn Thr Ser Asn
145                 150                 155                 160

Pro Asp Thr Gly Gly Gly Thr His Thr Cys Pro Pro Cys Pro Ala Pro
                165                 170                 175

Glu Leu Leu Gly Gly Pro Ser Val Phe Leu Phe Pro Pro Lys Pro Lys
            180                 185                 190

Asp Thr Leu Met Ile Ser Arg Thr Pro Glu Val Thr Cys Val Val Val
        195                 200                 205

Asp Val Ser His Glu Asp Pro Glu Val Lys Phe Asn Trp Tyr Val Asp
    210                 215                 220

Gly Val Glu Val His Asn Ala Lys Thr Lys Pro Arg Glu Glu Gln Tyr
225                 230                 235                 240
```

```
Asn Ser Thr Tyr Arg Val Val Ser Val Leu Thr Val His Gln Asp
                245                 250                 255

Trp Leu Asn Gly Lys Glu Tyr Lys Cys Lys Val Ser Asn Lys Ala Leu
            260                 265                 270

Pro Ala Pro Ile Glu Lys Thr Ile Ser Lys Ala Lys Gly Gln Pro Arg
            275                 280                 285

Glu Pro Gln Val Tyr Thr Leu Pro Pro Cys Arg Glu Glu Met Thr Lys
        290                 295                 300

Asn Gln Val Ser Leu Trp Cys Leu Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Tyr Ser
            340                 345                 350

Lys Leu Thr Val Asp Lys Ser Arg Trp Gln Gln Gly Asn Val Phe Ser
        355                 360                 365

Cys Ser Val Met His Glu Ala Leu His Asn His Tyr Thr Gln Lys Ser
370                 375                 380

Leu Ser Leu Ser Pro Gly Lys
385                 390

<210> SEQ ID NO 419
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Met Asp Ala Met Lys Arg Gly Leu Cys Cys Val Leu Leu Leu Cys Gly
1               5                   10                  15

Ala Val Phe Val Ser Pro Gly Ala Pro Pro Asn Arg Arg Thr Cys Val
            20                  25                  30

Phe Phe Glu Ala Pro Gly Val Arg Gly Ser Thr Lys Thr Leu Gly Glu
        35                  40                  45

Leu Leu Asp Thr Gly Thr Glu Leu Pro Arg Ala Ile Arg Cys Leu Tyr
    50                  55                  60

Ser Arg Cys Cys Phe Gly Ile Trp Asn Leu Thr Gln Asp Arg Ala Gln
65                  70                  75                  80

Val Glu Met Gln Gly Cys Arg Asp Ser Asp Glu Pro Gly Cys Glu Ser
                85                  90                  95

Leu His Cys Asp Pro Ser Pro Arg Ala His Pro Ser Pro Gly Ser Thr
            100                 105                 110

Leu Phe Thr Cys Ser Cys Gly Thr Asp Phe Cys Asn Ala Asn Tyr Ser
        115                 120                 125

His Leu Pro Pro Pro Gly Ser Pro Gly Thr Pro Gly Ser Gln Gly Pro
    130                 135                 140

Gln Ala Ala Pro Gly Glu Ser Ile Trp Met Ala Leu Thr Gly Gly Gly
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
```

```
                195                 200                 205
Pro Glu Val Lys Phe Asn Trp Tyr Val Asp Gly Val Glu Val His Asn
210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Pro Ile Glu Lys
            260                 265                 270

Thr Ile Ser Lys Ala Lys Gly Gln Pro Arg Glu Pro Gln Val Tyr Thr
        275                 280                 285

Leu Pro Pro Cys Arg Glu Glu Met Thr Lys Asn Gln Val Ser Leu Trp
290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
370                 375                 380

Lys
385

<210> SEQ ID NO 420
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
                85                  90                  95

Asp Phe Cys Asn Ala Asn Tyr Ser His Leu Pro Pro Gly Ser Pro
            100                 105                 110

Gly Thr Pro Gly Ser Gln Gly Pro Gln Ala Ala Pro Gly Glu Ser Ile
        115                 120                 125

Trp Met Ala Leu Thr Gly Gly Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160
```

```
Pro Lys Asp Thr Leu Met Ile Ser Arg Thr Pro Glu Val Thr Cys Val
            165                 170                 175

Val Val Asp Val Ser His Glu Asp Pro Glu Val Lys Phe Asn Trp Tyr
        180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
        210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
            245                 250                 255

Pro Arg Glu Pro Gln Val Tyr Thr Leu Pro Pro Cys Arg Glu Glu Met
            260                 265                 270

Thr Lys Asn Gln Val Ser Leu Trp Cys Leu Val Lys Gly Phe Tyr Pro
            275                 280                 285

Ser Asp Ile Ala Val Glu Trp Glu Ser Asn Gly Gln Pro Glu Asn Asn
        290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
            325                 330                 335

Phe Ser Cys Ser Val Met His Glu Ala Leu His Asn His Tyr Thr Gln
            340                 345                 350

Lys Ser Leu Ser Leu Ser Pro Gly Lys
            355                 360

<210> SEQ ID NO 421
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Met Asp Ala Met Lys Arg Gly Leu Cys Cys Val Leu Leu Leu Cys Gly
1               5                   10                  15

Ala Val Phe Val Ser Pro Gly Ala Met Glu Asp Glu Lys Pro Lys Val
            20                  25                  30

Asn Pro Lys Leu Tyr Met Cys Val Cys Glu Gly Leu Ser Cys Gly Asn
        35                  40                  45

Glu Asp His Cys Glu Gly Gln Gln Cys Phe Ser Ser Leu Ser Ile Asn
50                  55                  60

Asp Gly Phe His Val Tyr Gln Lys Gly Cys Phe Gln Val Tyr Glu Gln
65                  70                  75                  80

Gly Lys Met Thr Cys Lys Thr Pro Pro Ser Pro Gly Gln Ala Val Glu
            85                  90                  95

Cys Cys Gln Gly Asp Trp Cys Asn Arg Asn Ile Thr Ala Gln Leu Pro
            100                 105                 110

Thr Lys Gly Lys Ser Phe Pro Gly Thr Gln Asn Phe His Leu Glu Thr
        115                 120                 125

Gly Gly Gly Thr His Thr Cys Pro Pro Cys Pro Ala Pro Glu Leu Leu
        130                 135                 140

Gly Gly Pro Ser Val Phe Leu Phe Pro Pro Lys Pro Lys Asp Thr Leu
145                 150                 155                 160
```

```
Met Ile Ser Arg Thr Pro Glu Val Thr Cys Val Val Asp Val Ser
            165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
            195                 200                 205

Tyr Arg Val Val Ser Val Leu Thr Val Leu His Gln Asp Trp Leu Asn
            210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
            245                 250                 255

Val Cys Thr Leu Pro Pro Ser Arg Glu Glu Met Thr Lys Asn Gln Val
            260                 265                 270

Ser Leu Ser Cys Ala Val Lys Gly Phe Tyr Pro Ser Asp Ile Ala Val
            275                 280                 285

Glu Trp Glu Ser Asn Gly Gln Pro Glu Asn Asn Tyr Lys Thr Thr Pro
            290                 295                 300

Pro Val Leu Asp Ser Asp Gly Ser Phe Phe Leu Val Ser Lys Leu Thr
305                 310                 315                 320

Val Asp Lys Ser Arg Trp Gln Gln Gly Asn Val Phe Ser Cys Ser Val
            325                 330                 335

Met His Glu Ala Leu His Asn His Tyr Thr Gln Lys Ser Leu Ser Leu
            340                 345                 350

Ser Pro Gly Lys
            355

<210> SEQ ID NO 422
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
            20                  25                  30

Cys Phe Ser Ser Leu Ser Ile Asn Asp Gly Phe His Val Tyr Gln Lys
            35                  40                  45

Gly Cys Phe Gln Val Tyr Glu Gln Gly Lys Met Thr Cys Lys Thr Pro
        50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
            85                  90                  95

Thr Gln Asn Phe His Leu Glu Thr Gly Gly Gly Thr His Thr Cys Pro
            100                 105                 110

Pro Cys Pro Ala Pro Glu Leu Leu Gly Gly Pro Ser Val Phe Leu Phe
            115                 120                 125

Pro Pro Lys Pro Lys Asp Thr Leu Met Ile Ser Arg Thr Pro Glu Val
            130                 135                 140

Thr Cys Val Val Val Asp Val Ser His Glu Asp Pro Glu Val Lys Phe
```

```
                145                 150                 155                 160
Asn Trp Tyr Val Asp Gly Val Glu Val His Asn Ala Lys Thr Lys Pro
                165                 170                 175
Arg Glu Glu Gln Tyr Asn Ser Thr Tyr Arg Val Val Ser Val Leu Thr
                180                 185                 190
Val Leu His Gln Asp Trp Leu Asn Gly Lys Glu Tyr Lys Cys Lys Val
                195                 200                 205
Ser Asn Lys Ala Leu Pro Ala Pro Ile Glu Lys Thr Ile Ser Lys Ala
            210                 215                 220
Lys Gly Gln Pro Arg Glu Pro Gln Val Cys Thr Leu Pro Pro Ser Arg
225                 230                 235                 240
Glu Glu Met Thr Lys Asn Gln Val Ser Leu Ser Cys Ala Val Lys Gly
                245                 250                 255
Phe Tyr Pro Ser Asp Ile Ala Val Glu Trp Glu Ser Asn Gly Gln Pro
                260                 265                 270
Glu Asn Asn Tyr Lys Thr Thr Pro Pro Val Leu Asp Ser Asp Gly Ser
            275                 280                 285
Phe Phe Leu Val Ser Lys Leu Thr Val Asp Lys Ser Arg Trp Gln Gln
        290                 295                 300
Gly Asn Val Phe Ser Cys Ser Val Met His Glu Ala Leu His Asn His
305                 310                 315                 320
Tyr Thr Gln Lys Ser Leu Ser Leu Ser Pro Gly Lys
                325                 330

<210> SEQ ID NO 423
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Met Asp Ala Met Lys Arg Gly Leu Cys Cys Val Leu Leu Leu Cys Gly
1               5                   10                  15
Ala Val Phe Val Ser Pro Gly Ala Ala Leu Leu Pro Gly Ala Thr Ala
                20                  25                  30
Leu Gln Cys Phe Cys His Leu Cys Thr Lys Asp Asn Phe Thr Cys Val
            35                  40                  45
Thr Asp Gly Leu Cys Phe Val Ser Val Thr Glu Thr Thr Asp Lys Val
        50                  55                  60
Ile His Asn Ser Met Cys Ile Ala Glu Ile Asp Leu Ile Pro Arg Asp
65                  70                  75                  80
Arg Pro Phe Val Cys Ala Pro Ser Ser Lys Thr Gly Ser Val Thr Thr
                85                  90                  95
Thr Tyr Cys Cys Asn Gln Asp His Cys Asn Lys Ile Glu Leu Pro Thr
                100                 105                 110
Thr Val Lys Ser Ser Pro Gly Leu Gly Pro Val Glu Thr Gly Gly Gly
            115                 120                 125
Thr His Thr Cys Pro Pro Cys Pro Ala Pro Glu Leu Leu Gly Gly Pro
        130                 135                 140
Ser Val Phe Leu Phe Pro Pro Lys Pro Lys Asp Thr Leu Met Ile Ser
145                 150                 155                 160
Arg Thr Pro Glu Val Thr Cys Val Val Val Asp Val Ser His Glu Asp
                165                 170                 175
```

```
Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
            195                 200                 205

Val Ser Val Leu Thr Val Leu His Gln Asp Trp Leu Asn Gly Lys Glu
            210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Cys Thr
            245                 250                 255

Leu Pro Pro Ser Arg Glu Glu Met Thr Lys Asn Gln Val Ser Leu Ser
            260                 265                 270

Cys Ala Val Lys Gly Phe Tyr Pro Ser Asp Ile Ala Val Glu Trp Glu
            275                 280                 285

Ser Asn Gly Gln Pro Glu Asn Asn Tyr Lys Thr Thr Pro Pro Val Leu
            290                 295                 300

Asp Ser Asp Gly Ser Phe Phe Leu Val Ser Lys Leu Thr Val Asp Lys
305                 310                 315                 320

Ser Arg Trp Gln Gln Gly Asn Val Phe Ser Cys Ser Val Met His Glu
            325                 330                 335

Ala Leu His Asn His Tyr Thr Gln Lys Ser Leu Ser Leu Ser Pro Gly
            340                 345                 350

Lys

<210> SEQ ID NO 424
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Ala Leu Leu Pro Gly Ala Thr Ala Leu Gln Cys Phe Cys His Leu Cys
1               5                   10                  15

Thr Lys Asp Asn Phe Thr Cys Val Thr Asp Gly Leu Cys Phe Val Ser
            20                  25                  30

Val Thr Glu Thr Thr Asp Lys Val Ile His Asn Ser Met Cys Ile Ala
            35                  40                  45

Glu Ile Asp Leu Ile Pro Arg Asp Arg Pro Phe Val Cys Ala Pro Ser
50                  55                  60

Ser Lys Thr Gly Ser Val Thr Thr Thr Tyr Cys Cys Asn Gln Asp His
65                  70                  75                  80

Cys Asn Lys Ile Glu Leu Pro Thr Thr Val Lys Ser Ser Pro Gly Leu
            85                  90                  95

Gly Pro Val Glu Thr Gly Gly Gly Thr His Thr Cys Pro Pro Cys Pro
            100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
            165                 170                 175
```

-continued

```
Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
    210                 215                 220

Pro Arg Glu Pro Gln Val Cys Thr Leu Pro Pro Ser Arg Glu Glu Met
225                 230                 235                 240

Thr Lys Asn Gln Val Ser Leu Ser Cys Ala Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Val Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 425
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

```
Met Asp Ala Met Lys Arg Gly Leu Cys Cys Val Leu Leu Leu Cys Gly
1               5                   10                  15

Ala Val Phe Val Ser Pro Gly Ala Lys Lys Glu Asp Gly Glu Ser Thr
            20                  25                  30

Ala Pro Thr Pro Arg Pro Lys Val Leu Arg Cys Lys Cys His His His
        35                  40                  45

Cys Pro Glu Asp Ser Val Asn Asn Ile Cys Ser Thr Asp Gly Tyr Cys
    50                  55                  60

Phe Thr Met Ile Glu Glu Asp Ser Gly Leu Pro Val Val Thr Ser
65                  70                  75                  80

Gly Cys Leu Gly Leu Glu Gly Ser Asp Phe Gln Cys Arg Asp Thr Pro
                85                  90                  95

Ile Pro His Gln Arg Arg Ser Ile Glu Cys Cys Thr Glu Arg Asn Glu
            100                 105                 110

Cys Asn Lys Asp Leu His Pro Thr Leu Pro Pro Leu Lys Asn Arg Asp
        115                 120                 125

Phe Val Asp Gly Pro Ile His His Arg Thr Gly Gly Gly Thr His Thr
    130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205
```

```
Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Cys Thr Leu Pro Pro
            260                 265                 270

Ser Arg Glu Glu Met Thr Lys Asn Gln Val Ser Leu Ser Cys Ala Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Val Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 426
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426

Lys Lys Glu Asp Gly Glu Ser Thr Ala Pro Thr Pro Arg Pro Lys Val
1               5                   10                  15

Leu Arg Cys Lys Cys His His Cys Pro Glu Asp Ser Val Asn Asn
                20                  25                  30

Ile Cys Ser Thr Asp Gly Tyr Cys Phe Thr Met Ile Glu Glu Asp Asp
            35                  40                  45

Ser Gly Leu Pro Val Val Thr Ser Gly Cys Leu Gly Leu Glu Gly Ser
50                  55                  60

Asp Phe Gln Cys Arg Asp Thr Pro Ile Pro His Gln Arg Arg Ser Ile
65                  70                  75                  80

Glu Cys Cys Thr Glu Arg Asn Glu Cys Asn Lys Asp Leu His Pro Thr
                85                  90                  95

Leu Pro Pro Leu Lys Asn Arg Asp Phe Val Asp Gly Pro Ile His His
            100                 105                 110

Arg Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
```

|   |   |   | 195 |   |   |   | 200 |   |   |   | 205 |   |   |
|---|---|---|---|---|---|---|---|---|---|---|---|---|---|

Leu Asn Gly Lys Glu Tyr Lys Cys Lys Val Ser Asn Lys Ala Leu Pro
210                215                    220

Ala Pro Ile Glu Lys Thr Ile Ser Lys Ala Lys Gly Gln Pro Arg Glu
225                 230                235                 240

Pro Gln Val Cys Thr Leu Pro Pro Ser Arg Glu Glu Met Thr Lys Asn
                245                 250                 255

Gln Val Ser Leu Ser Cys Ala Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Val Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

-continued

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Met Asp Ala Met Lys Arg Gly Leu Cys Cys Val Leu Leu Leu Cys Gly
1               5                   10                  15

Ala Val Phe Val Ser Pro Gly Ala Ala Ile Leu Gly Arg Ser Glu Thr
            20                  25                  30

Gln Glu Cys Leu Phe Phe Asn Ala Asn Trp Glu Lys Asp Arg Thr Asn
        35                  40                  45

Gln Thr Gly Val Glu Pro Cys Tyr Gly Asp Lys Asp Lys Arg Arg His
    50                  55                  60

Cys Phe Ala Thr Trp Lys Asn Ile Ser Gly Ser Ile Glu Ile Val Lys
65                  70                  75                  80

Gln Gly Cys Trp Leu Asp Asp Ile Asn Cys Tyr Asp Arg Thr Asp Cys
                85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
        115                 120                 125

Gln Pro Thr Ser Asn Pro Val Thr Pro Lys Pro Thr Gly Gly Gly
    130                 135                 140

Thr His Thr Cys Pro Pro Cys Pro Ala Pro Glu Leu Leu Gly Gly Pro
145                 150                 155                 160

```
Ser Val Phe Leu Phe Pro Pro Lys Pro Lys Asp Thr Leu Met Ile Ser
            165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
            210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Ala Pro Ile Glu Lys
            245                 250                 255

Thr Ile Ser Lys Ala Lys Gly Gln Pro Arg Glu Pro Gln Val Cys Thr
            260                 265                 270

Leu Pro Pro Ser Arg Glu Glu Met Thr Lys Asn Gln Val Ser Leu Ser
            275                 280                 285

Cys Ala Val Lys Gly Phe Tyr Pro Ser Asp Ile Ala Val Glu Trp Glu
            290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Val Ser Lys Leu Thr Val Asp Lys
            325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys

<210> SEQ ID NO 452
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
            35                  40                  45

Gly Ser Ile Glu Ile Val Lys Gln Gly Cys Trp Leu Asp Asp Ile Asn
            50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
            85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
            115                 120                 125

Pro Glu Leu Leu Gly Gly Pro Ser Val Phe Leu Phe Pro Pro Lys Pro
            130                 135                 140
```

```
Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ala Pro Ile Glu Lys Thr Ile Ser Lys Ala Lys Gly Gln Pro
225                 230                 235                 240

Arg Glu Pro Gln Val Cys Thr Leu Pro Pro Ser Arg Glu Glu Met Thr
                245                 250                 255

Lys Asn Gln Val Ser Leu Ser Cys Ala Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Val
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly Lys
            340

<210> SEQ ID NO 453
<211> LENGTH: 368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Met Asp Ala Met Lys Arg Gly Leu Cys Cys Val Leu Leu Leu Cys Gly
1               5                   10                  15

Ala Val Phe Val Ser Pro Gly Ala Ser Gly Arg Gly Glu Ala Glu Thr
            20                  25                  30

Arg Glu Cys Ile Tyr Tyr Asn Ala Asn Trp Glu Leu Glu Arg Thr Asn
        35                  40                  45

Gln Ser Gly Leu Glu Arg Cys Glu Gly Glu Gln Asp Lys Arg Leu His
    50                  55                  60

Cys Tyr Ala Ser Trp Arg Asn Ser Ser Gly Thr Ile Glu Leu Val Lys
65                  70                  75                  80

Lys Gly Cys Trp Leu Asp Asp Phe Asn Cys Tyr Asp Arg Gln Glu Cys
                85                  90                  95

Val Ala Thr Glu Glu Asn Pro Gln Val Tyr Phe Cys Cys Cys Glu Gly
            100                 105                 110

Asn Phe Cys Asn Glu Arg Phe Thr His Leu Pro Glu Ala Gly Gly Pro
        115                 120                 125

Glu Val Thr Tyr Glu Pro Pro Pro Thr Ala Pro Thr Gly Gly Gly Thr
    130                 135                 140

His Thr Cys Pro Pro Cys Pro Ala Pro Glu Leu Leu Gly Gly Pro Ser
```

```
                145                 150                 155                 160
Val Phe Leu Phe Pro Pro Lys Pro Lys Asp Thr Leu Met Ile Ser Arg
                165                 170                 175

Thr Pro Glu Val Thr Cys Val Val Asp Val Ser His Glu Asp Pro
                180                 185                 190

Glu Val Lys Phe Asn Trp Tyr Val Asp Gly Val Glu Val His Asn Ala
                195                 200                 205

Lys Thr Lys Pro Arg Glu Glu Gln Tyr Asn Ser Thr Tyr Arg Val Val
                210                 215                 220

Ser Val Leu Thr Val Leu His Gln Asp Trp Leu Asn Gly Lys Glu Tyr
225                 230                 235                 240

Lys Cys Lys Val Ser Asn Lys Ala Leu Pro Ala Pro Ile Glu Lys Thr
                245                 250                 255

Ile Ser Lys Ala Lys Gly Gln Pro Arg Glu Pro Gln Val Cys Thr Leu
                260                 265                 270

Pro Pro Ser Arg Glu Glu Met Thr Lys Asn Gln Val Ser Leu Ser Cys
                275                 280                 285

Ala Val Lys Gly Phe Tyr Pro Ser Asp Ile Ala Val Glu Trp Glu Ser
                290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Val Ser Lys Leu Thr Val Asp Lys Ser
                325                 330                 335

Arg Trp Gln Gln Gly Asn Val Phe Ser Cys Ser Val Met His Glu Ala
                340                 345                 350

Leu His Asn His Tyr Thr Gln Lys Ser Leu Ser Leu Ser Pro Gly Lys
                355                 360                 365

<210> SEQ ID NO 454
<211> LENGTH: 343
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
                20                  25                  30

Glu Gln Asp Lys Arg Leu His Cys Tyr Ala Ser Trp Arg Asn Ser Ser
            35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr Gly Gly Gly Thr His Thr Cys Pro Pro Cys Pro Ala Pro
        115                 120                 125

Glu Leu Leu Gly Gly Pro Ser Val Phe Leu Phe Pro Pro Lys Pro Lys
    130                 135                 140
```

```
Asp Thr Leu Met Ile Ser Arg Thr Pro Glu Val Thr Cys Val Val Val
145                 150                 155                 160

Asp Val Ser His Glu Asp Pro Glu Val Lys Phe Asn Trp Tyr Val Asp
                165                 170                 175

Gly Val Glu Val His Asn Ala Lys Thr Lys Pro Arg Glu Glu Gln Tyr
            180                 185                 190

Asn Ser Thr Tyr Arg Val Val Ser Val Leu Thr Val Leu His Gln Asp
        195                 200                 205

Trp Leu Asn Gly Lys Glu Tyr Lys Cys Lys Val Ser Asn Lys Ala Leu
    210                 215                 220

Pro Ala Pro Ile Glu Lys Thr Ile Ser Lys Ala Lys Gly Gln Pro Arg
225                 230                 235                 240

Glu Pro Gln Val Cys Thr Leu Pro Pro Ser Arg Glu Glu Met Thr Lys
                245                 250                 255

Asn Gln Val Ser Leu Ser Cys Ala Val Lys Gly Phe Tyr Pro Ser Asp
            260                 265                 270

Ile Ala Val Glu Trp Glu Ser Asn Gly Gln Pro Glu Asn Asn Tyr Lys
        275                 280                 285

Thr Thr Pro Pro Val Leu Asp Ser Asp Gly Ser Phe Phe Leu Val Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 455
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Met Asp Ala Met Lys Arg Gly Leu Cys Cys Val Leu Leu Leu Cys Gly
1               5                   10                  15

Ala Val Phe Val Ser Pro Gly Ala Ser Gln Asn Gln Glu Arg Leu Cys
            20                  25                  30

Ala Phe Lys Asp Pro Tyr Gln Gln Asp Leu Gly Ile Gly Glu Ser Arg
        35                  40                  45

Ile Ser His Glu Asn Gly Thr Ile Leu Cys Ser Lys Gly Ser Thr Cys
    50                  55                  60

Tyr Gly Leu Trp Glu Lys Ser Lys Gly Asp Ile Asn Leu Val Lys Gln
65                  70                  75                  80

Gly Cys Trp Ser His Ile Gly Asp Pro Gln Glu Cys His Tyr Glu Glu
                85                  90                  95

Cys Val Val Thr Thr Thr Pro Pro Ser Ile Gln Asn Gly Thr Tyr Arg
            100                 105                 110

Phe Cys Cys Cys Ser Thr Asp Leu Cys Asn Val Asn Phe Thr Glu Asn
        115                 120                 125

Phe Pro Pro Pro Asp Thr Thr Pro Leu Ser Pro His Ser Phe Asn
        130                 135                 140

Arg Asp Glu Thr Gly Gly Gly Thr His Thr Cys Pro Pro Cys Pro Ala
145                 150                 155                 160
```

```
Pro Glu Leu Leu Gly Gly Pro Ser Val Phe Leu Phe Pro Pro Lys Pro
            165                 170                 175

Lys Asp Thr Leu Met Ile Ser Arg Thr Pro Glu Val Thr Cys Val Val
        180                 185                 190

Val Asp Val Ser His Glu Asp Pro Glu Val Lys Phe Asn Trp Tyr Val
    195                 200                 205

Asp Gly Val Glu Val His Asn Ala Lys Thr Lys Pro Arg Glu Glu Gln
210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
            245                 250                 255

Leu Pro Ala Pro Ile Glu Lys Thr Ile Ser Lys Ala Lys Gly Gln Pro
        260                 265                 270

Arg Glu Pro Gln Val Cys Thr Leu Pro Pro Ser Arg Glu Glu Met Thr
    275                 280                 285

Lys Asn Gln Val Ser Leu Ser Cys Ala Val Lys Gly Phe Tyr Pro Ser
290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Val
            325                 330                 335

Ser Lys Leu Thr Val Asp Lys Ser Arg Trp Gln Gln Gly Asn Val Phe
        340                 345                 350

Ser Cys Ser Val Met His Glu Ala Leu His Asn His Tyr Thr Gln Lys
    355                 360                 365

Ser Leu Ser Leu Ser Pro Gly Lys
370                 375

<210> SEQ ID NO 456
<211> LENGTH: 352
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Ser Gln Asn Gln Glu Arg Leu Cys Ala Phe Lys Asp Pro Tyr Gln Gln
1               5                   10                  15

Asp Leu Gly Ile Gly Glu Ser Arg Ile Ser His Glu Asn Gly Thr Ile
            20                  25                  30

Leu Cys Ser Lys Gly Ser Thr Cys Tyr Gly Leu Trp Glu Lys Ser Lys
        35                  40                  45

Gly Asp Ile Asn Leu Val Lys Gln Gly Cys Trp Ser His Ile Gly Asp
    50                  55                  60

Pro Gln Glu Cys His Tyr Glu Glu Cys Val Val Thr Thr Thr Pro Pro
65                  70                  75                  80

Ser Ile Gln Asn Gly Thr Tyr Arg Phe Cys Cys Cys Ser Thr Asp Leu
            85                  90                  95

Cys Asn Val Asn Phe Thr Glu Asn Phe Pro Pro Pro Asp Thr Thr Pro
        100                 105                 110

Leu Ser Pro Pro His Ser Phe Asn Arg Asp Glu Thr Gly Gly Gly Thr
    115                 120                 125

His Thr Cys Pro Pro Cys Pro Ala Pro Glu Leu Leu Gly Gly Pro Ser
```

```
                130                 135                 140
Val Phe Leu Phe Pro Pro Lys Pro Lys Asp Thr Leu Met Ile Ser Arg
145                 150                 155                 160

Thr Pro Glu Val Thr Cys Val Val Asp Val Ser His Glu Asp Pro
                165                 170                 175

Glu Val Lys Phe Asn Trp Tyr Val Asp Gly Val Glu Val His Asn Ala
                180                 185                 190

Lys Thr Lys Pro Arg Glu Glu Gln Tyr Asn Ser Thr Tyr Arg Val Val
                195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Cys Thr Leu
                245                 250                 255

Pro Pro Ser Arg Glu Glu Met Thr Lys Asn Gln Val Ser Leu Ser Cys
                260                 265                 270

Ala Val Lys Gly Phe Tyr Pro Ser Asp Ile Ala Val Glu Trp Glu Ser
                275                 280                 285

Asn Gly Gln Pro Glu Asn Asn Tyr Lys Thr Thr Pro Pro Val Leu Asp
                290                 295                 300

Ser Asp Gly Ser Phe Phe Leu Val Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
                340                 345                 350

<210> SEQ ID NO 457
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Met Asp Ala Met Lys Arg Gly Leu Cys Cys Val Leu Leu Leu Cys Gly
1               5                   10                  15

Ala Val Phe Val Ser Pro Gly Ala Pro Pro Asn Arg Arg Thr Cys Val
                20                  25                  30

Phe Phe Glu Ala Pro Gly Val Arg Gly Ser Thr Lys Thr Leu Gly Glu
            35                  40                  45

Leu Leu Asp Thr Gly Thr Glu Leu Pro Arg Ala Ile Arg Cys Leu Tyr
        50                  55                  60

Ser Arg Cys Cys Phe Gly Ile Trp Asn Leu Thr Gln Asp Arg Ala Gln
65                  70                  75                  80

Val Glu Met Gln Gly Cys Arg Asp Ser Asp Glu Pro Gly Cys Glu Ser
                85                  90                  95

Leu His Cys Asp Pro Ser Pro Arg Ala His Pro Ser Pro Gly Ser Thr
                100                 105                 110

Leu Phe Thr Cys Ser Cys Gly Thr Asp Phe Cys Asn Ala Asn Tyr Ser
            115                 120                 125

His Leu Pro Pro Pro Gly Ser Pro Gly Thr Pro Gly Ser Gln Gly Pro
        130                 135                 140
```

-continued

Gln Ala Ala Pro Gly Glu Ser Ile Trp Met Ala Leu Thr Gly Gly Gly
145                 150                 155                 160

Thr His Thr Cys Pro Pro Cys Pro Ala Pro Glu Leu Leu Gly Gly Pro
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
            245                 250                 255

Tyr Lys Cys Lys Val Ser Asn Lys Ala Leu Pro Ala Pro Ile Glu Lys
        260                 265                 270

Thr Ile Ser Lys Ala Lys Gly Gln Pro Arg Glu Pro Gln Val Cys Thr
    275                 280                 285

Leu Pro Pro Ser Arg Glu Glu Met Thr Lys Asn Gln Val Ser Leu Ser
290                 295                 300

Cys Ala Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
            325                 330                 335

Asp Ser Asp Gly Ser Phe Phe Leu Val Ser Lys Leu Thr Val Asp Lys
        340                 345                 350

Ser Arg Trp Gln Gln Gly Asn Val Phe Ser Cys Ser Val Met His Glu
    355                 360                 365

Ala Leu His Asn His Tyr Thr Gln Lys Ser Leu Ser Leu Ser Pro Gly
370                 375                 380

Lys
385

<210> SEQ ID NO 458
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Pro Pro Asn Arg Arg Thr Cys Val Phe Phe Glu Ala Pro Gly Val Arg
1               5                   10                  15

Gly Ser Thr Lys Thr Leu Gly Glu Leu Leu Asp Thr Gly Thr Glu Leu
            20                  25                  30

Pro Arg Ala Ile Arg Cys Leu Tyr Ser Arg Cys Cys Phe Gly Ile Trp
        35                  40                  45

Asn Leu Thr Gln Asp Arg Ala Gln Val Glu Met Gln Gly Cys Arg Asp
    50                  55                  60

Ser Asp Glu Pro Gly Cys Glu Ser Leu His Cys Asp Pro Ser Pro Arg
65                  70                  75                  80

Ala His Pro Ser Pro Gly Ser Thr Leu Phe Thr Cys Ser Cys Gly Thr
            85                  90                  95

Asp Phe Cys Asn Ala Asn Tyr Ser His Leu Pro Pro Gly Ser Pro
        100                 105                 110

Gly Thr Pro Gly Ser Gln Gly Pro Gln Ala Ala Pro Gly Glu Ser Ile
        115                 120                 125

Trp Met Ala Leu Thr Gly Gly Thr His Thr Cys Pro Pro Cys Pro
    130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
            195                 200                 205

Gln Tyr Asn Ser Thr Tyr Arg Val Val Ser Val Leu Thr Val Leu His
        210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Cys Thr Leu Pro Pro Ser Arg Glu Glu Met
            260                 265                 270

Thr Lys Asn Gln Val Ser Leu Ser Cys Ala Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Val Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360

<210> SEQ ID NO 459
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Val Asn Asn Asp Met Ile Val Thr Asp Asn Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95

Ile Thr Leu Glu Thr Val Cys His Asp Pro Lys Leu Pro Tyr His Asp

```
                100                 105                 110
Phe Ile Leu Glu Asp Ala Ala Ser Pro Lys Cys Ile Met Lys Glu Lys
            115                 120                 125

Lys Lys Pro Gly Glu Thr Phe Phe Met Cys Ser Cys Ser Ser Asp Glu
            130                 135                 140

Cys Asn Asp Asn Ile Ile Phe Ser Glu Glu Tyr Asn Thr Ser Asn Pro
145                 150                 155                 160

Asp Thr Gly Gly Gly Thr His Thr Cys Pro Pro Cys Pro Ala Pro Glu
            165                 170                 175

Leu Leu Gly Gly Pro Ser Val Phe Leu Phe Pro Pro Lys Pro Lys Asp
            180                 185                 190

Thr Leu Met Ile Ser Arg Thr Pro Glu Val Thr Cys Val Val Val Asp
            195                 200                 205

Val Ser His Glu Asp Pro Glu Val Lys Phe Asn Trp Tyr Val Asp Gly
210                 215                 220

Val Glu Val His Asn Ala Lys Thr Lys Pro Arg Glu Glu Gln Tyr Asn
225                 230                 235                 240

Ser Thr Tyr Arg Val Val Ser Val Leu Thr Val Leu His Gln Asp Trp
                245                 250                 255

Leu Asn Gly Lys Glu Tyr Lys Cys Lys Val Ser Asn Lys Ala Leu Pro
            260                 265                 270

Ala Pro Ile Glu Lys Thr Ile Ser Lys Ala Lys Gly Gln Pro Arg Glu
            275                 280                 285

Pro Gln Val Cys Thr Leu Pro Pro Ser Arg Glu Glu Met Thr Lys Asn
290                 295                 300

Gln Val Ser Leu Ser Cys Ala Val Lys Gly Phe Tyr Pro Ser Asp Ile
305                 310                 315                 320

Ala Val Glu Trp Glu Ser Asn Gly Gln Pro Glu Asn Asn Tyr Lys Thr
                325                 330                 335

Thr Pro Pro Val Leu Asp Ser Asp Gly Ser Phe Phe Leu Val Ser Lys
            340                 345                 350

Leu Thr Val Asp Lys Ser Arg Trp Gln Gln Gly Asn Val Phe Ser Cys
            355                 360                 365

Ser Val Met His Glu Ala Leu His Asn His Tyr Thr Gln Lys Ser Leu
            370                 375                 380

Ser Leu Ser Pro Gly Lys
385                 390

<210> SEQ ID NO 460
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
                20                  25                  30

Asp Val Arg Phe Ser Thr Cys Asp Asn Gln Lys Ser Cys Met Ser Asn
            35                  40                  45

Cys Ser Ile Thr Ser Ile Cys Glu Lys Pro Gln Glu Val Cys Val Ala
50                  55                  60
```

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Pro Gly Glu Thr Phe Phe
        100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp Thr Gly Gly Thr His Thr
130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
            195                 200                 205

Lys Pro Arg Glu Glu Gln Tyr Asn Ser Thr Tyr Arg Val Val Ser Val
210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Cys Thr Leu Pro Pro
            260                 265                 270

Ser Arg Glu Glu Met Thr Lys Asn Gln Val Ser Leu Ser Cys Ala Val
            275                 280                 285

Lys Gly Phe Tyr Pro Ser Asp Ile Ala Val Glu Trp Glu Ser Asn Gly
290                 295                 300

Gln Pro Glu Asn Asn Tyr Lys Thr Thr Pro Pro Val Leu Asp Ser Asp
305                 310                 315                 320

Gly Ser Phe Phe Leu Val Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
            355                 360                 365

<210> SEQ ID NO 461
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
                20                  25                  30

Ser Asp Val Glu Met Glu Ala Gln Lys Asp Glu Ile Ile Cys Pro Ser
            35                  40                  45

Cys Asn Arg Thr Ala His Pro Leu Arg His Ile Asn Asn Asp Met Ile
50                  55                  60

Val Thr Asp Asn Asn Gly Ala Val Lys Phe Pro Gln Leu Cys Lys Phe
 65                  70                  75                  80

Cys Asp Val Arg Phe Ser Thr Cys Asp Asn Gln Lys Ser Cys Met Ser
             85                  90                  95

Asn Cys Ser Ile Thr Ser Ile Cys Glu Lys Pro Gln Glu Val Cys Val
         100                 105                 110

Ala Val Trp Arg Lys Asn Asp Glu Asn Ile Thr Leu Glu Thr Val Cys
     115                 120                 125

His Asp Pro Lys Leu Pro Tyr His Asp Phe Ile Leu Glu Asp Ala Ala
 130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                 165                 170                 175

Ser Glu Glu Tyr Asn Thr Ser Asn Pro Asp Thr Gly Gly Thr His
             180                 185                 190

Thr Cys Pro Pro Cys Pro Ala Pro Glu Leu Leu Gly Gly Pro Ser Val
         195                 200                 205

Phe Leu Phe Pro Pro Lys Pro Lys Asp Thr Leu Met Ile Ser Arg Thr
     210                 215                 220

Pro Glu Val Thr Cys Val Val Val Asp Val Ser His Glu Asp Pro Glu
225                 230                 235                 240

Val Lys Phe Asn Trp Tyr Val Asp Gly Val Glu Val His Asn Ala Lys
                 245                 250                 255

Thr Lys Pro Arg Glu Glu Gln Tyr Asn Ser Thr Tyr Arg Val Val Ser
             260                 265                 270

Val Leu Thr Val Leu His Gln Asp Trp Leu Asn Gly Lys Glu Tyr Lys
         275                 280                 285

Cys Lys Val Ser Asn Lys Ala Leu Pro Ala Pro Ile Glu Lys Thr Ile
     290                 295                 300

Ser Lys Ala Lys Gly Gln Pro Arg Glu Pro Gln Val Cys Thr Leu Pro
305                 310                 315                 320

Pro Ser Arg Glu Glu Met Thr Lys Asn Gln Val Ser Leu Ser Cys Ala
                 325                 330                 335

Val Lys Gly Phe Tyr Pro Ser Asp Ile Ala Val Glu Trp Glu Ser Asn
             340                 345                 350

Gly Gln Pro Glu Asn Asn Tyr Lys Thr Thr Pro Pro Val Leu Asp Ser
         355                 360                 365

Asp Gly Ser Phe Phe Leu Val Ser Lys Leu Thr Val Asp Lys Ser Arg
     370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                 405                 410                 415

<210> SEQ ID NO 462
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Thr Ile Pro Pro His Val Gln Lys Ser Asp Val Glu Met Glu Ala Gln

-continued

```
1               5                   10                  15
Lys Asp Glu Ile Ile Cys Pro Ser Cys Asn Arg Thr Ala His Pro Leu
                20                  25                  30

Arg His Ile Asn Asn Asp Met Ile Val Thr Asp Asn Asn Gly Ala Val
                35                  40                  45

Lys Phe Pro Gln Leu Cys Lys Phe Cys Asp Val Arg Phe Ser Thr Cys
                50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
                100                 105                 110

Asp Phe Ile Leu Glu Asp Ala Ala Ser Pro Lys Cys Ile Met Lys Glu
                115                 120                 125

Lys Lys Lys Pro Gly Glu Thr Phe Phe Met Cys Ser Cys Ser Ser Asp
                130                 135                 140

Glu Cys Asn Asp Asn Ile Ile Phe Ser Glu Glu Tyr Asn Thr Ser Asn
145                 150                 155                 160

Pro Asp Thr Gly Gly Thr His Thr Cys Pro Pro Cys Pro Ala Pro
                165                 170                 175

Glu Leu Leu Gly Gly Pro Ser Val Phe Leu Phe Pro Pro Lys Pro Lys
                180                 185                 190

Asp Thr Leu Met Ile Ser Arg Thr Pro Glu Val Thr Cys Val Val Val
                195                 200                 205

Asp Val Ser His Glu Asp Pro Glu Val Lys Phe Asn Trp Tyr Val Asp
                210                 215                 220

Gly Val Glu Val His Asn Ala Lys Thr Lys Pro Arg Glu Glu Gln Tyr
225                 230                 235                 240

Asn Ser Thr Tyr Arg Val Val Ser Val Leu Thr Val Leu His Gln Asp
                245                 250                 255

Trp Leu Asn Gly Lys Glu Tyr Lys Cys Lys Val Ser Asn Lys Ala Leu
                260                 265                 270

Pro Ala Pro Ile Glu Lys Thr Ile Ser Lys Ala Lys Gly Gln Pro Arg
                275                 280                 285

Glu Pro Gln Val Cys Thr Leu Pro Pro Ser Arg Glu Glu Met Thr Lys
                290                 295                 300

Asn Gln Val Ser Leu Ser Cys Ala Val Lys Gly Phe Tyr Pro Ser Asp
305                 310                 315                 320

Ile Ala Val Glu Trp Glu Ser Asn Gly Gln Pro Glu Asn Asn Tyr Lys
                325                 330                 335

Thr Thr Pro Pro Val Leu Asp Ser Asp Gly Ser Phe Phe Leu Val Ser
                340                 345                 350

Lys Leu Thr Val Asp Lys Ser Arg Trp Gln Gln Gly Asn Val Phe Ser
                355                 360                 365

Cys Ser Val Met His Glu Ala Leu His Asn His Tyr Thr Gln Lys Ser
                370                 375                 380

Leu Ser Leu Ser Pro Gly Lys
385                 390

<210> SEQ ID NO 463
<211> LENGTH: 352
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 463

```
Met Asp Ala Met Lys Arg Gly Leu Cys Cys Val Leu Leu Leu Cys Gly
1               5                   10                  15

Ala Val Phe Val Ser Pro Gly Ala Asp Pro Val Lys Pro Ser Arg Gly
            20                  25                  30

Pro Leu Val Thr Cys Thr Cys Glu Ser Pro His Cys Lys Gly Pro Thr
        35                  40                  45

Cys Arg Gly Ala Trp Cys Thr Val Val Leu Val Arg Glu Gly Arg
50                  55                  60

His Pro Gln Glu His Arg Gly Cys Gly Asn Leu His Arg Glu Leu Cys
65                  70                  75                  80

Arg Gly Arg Pro Thr Glu Phe Val Asn His Tyr Cys Cys Asp Ser His
                85                  90                  95

Leu Cys Asn His Asn Val Ser Leu Val Leu Glu Ala Thr Gln Pro Pro
            100                 105                 110

Ser Glu Gln Pro Gly Thr Asp Gly Gln Leu Ala Thr Gly Gly Gly Thr
        115                 120                 125

His Thr Cys Pro Pro Cys Pro Ala Pro Glu Leu Leu Gly Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
210                 215                 220

Lys Cys Lys Val Ser Asn Lys Ala Leu Pro Ala Pro Ile Glu Lys Thr
225                 230                 235                 240

Ile Ser Lys Ala Lys Gly Gln Pro Arg Glu Pro Gln Val Tyr Thr Leu
                245                 250                 255

Pro Pro Cys Arg Glu Glu Met Thr Lys Asn Gln Val Ser Leu Trp Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350
```

<210> SEQ ID NO 464
<211> LENGTH: 328
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 464

```
Asp Pro Val Lys Pro Ser Arg Gly Pro Leu Val Thr Cys Thr Cys Glu
1               5                   10                  15

Ser Pro His Cys Lys Gly Pro Thr Cys Arg Gly Ala Trp Cys Thr Val
            20                  25                  30

Val Leu Val Arg Glu Glu Gly Arg His Pro Gln Glu His Arg Gly Cys
        35                  40                  45

Gly Asn Leu His Arg Glu Leu Cys Arg Gly Arg Pro Thr Glu Phe Val
    50                  55                  60

Asn His Tyr Cys Cys Asp Ser His Leu Cys Asn His Asn Val Ser Leu
65                  70                  75                  80

Val Leu Glu Ala Thr Gln Pro Pro Ser Glu Gln Pro Gly Thr Asp Gly
                85                  90                  95

Gln Leu Ala Thr Gly Gly Gly Thr His Thr Cys Pro Pro Cys Pro Ala
            100                 105                 110

Pro Glu Leu Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
130                 135                 140

Val Asp Val Ser His Glu Asp Pro Glu Val Lys Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Cys Arg Glu Glu Met Thr
225                 230                 235                 240

Lys Asn Gln Val Ser Leu Trp Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Gln Gly Asn Val Phe
    290                 295                 300

Ser Cys Ser Val Met His Glu Ala Leu His Asn His Tyr Thr Gln Lys
305                 310                 315                 320

Ser Leu Ser Leu Ser Pro Gly Lys
                325
```

<210> SEQ ID NO 465
<211> LENGTH: 356
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 465

Met Asp Ala Met Lys Arg Gly Leu Cys Cys Val Leu Leu Leu Cys Gly

```
1               5                   10                  15
Ala Val Phe Val Ser Pro Gly Ala Met Glu Asp Glu Lys Pro Lys Val
                20                  25                  30

Asn Pro Lys Leu Tyr Met Cys Val Cys Glu Gly Leu Ser Cys Gly Asn
                35                  40                  45

Glu Asp His Cys Glu Gly Gln Gln Cys Phe Ser Ser Leu Ser Ile Asn
    50                  55                  60

Asp Gly Phe His Val Tyr Gln Lys Gly Cys Phe Gln Val Tyr Glu Gln
65                  70                  75                  80

Gly Lys Met Thr Cys Lys Thr Pro Ser Pro Gly Gln Ala Val Glu
                85                  90                  95

Cys Cys Gln Gly Asp Trp Cys Asn Arg Asn Ile Thr Ala Gln Leu Pro
                100                 105                 110

Thr Lys Gly Lys Ser Phe Pro Gly Thr Gln Asn Phe His Leu Glu Thr
                115                 120                 125

Gly Gly Gly Thr His Thr Cys Pro Pro Cys Pro Ala Pro Glu Leu Leu
130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
                180                 185                 190

Val His Asn Ala Lys Thr Lys Pro Arg Glu Glu Gln Tyr Asn Ser Thr
                195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Cys Arg Glu Glu Met Thr Lys Asn Gln Val
                260                 265                 270

Ser Leu Trp Cys Leu Val Lys Gly Phe Tyr Pro Ser Asp Ile Ala Val
                275                 280                 285

Glu Trp Glu Ser Asn Gly Gln Pro Glu Asn Asn Tyr Lys Thr Thr Pro
                290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
                340                 345                 350

Ser Pro Gly Lys
        355

<210> SEQ ID NO 466
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466
```

Met Glu Asp Glu Lys Pro Lys Val Asn Pro Lys Leu Tyr Met Cys Val
1               5                   10                  15

Cys Glu Gly Leu Ser Cys Gly Asn Glu Asp His Cys Glu Gly Gln Gln
                20                  25                  30

Cys Phe Ser Ser Leu Ser Ile Asn Asp Gly Phe His Val Tyr Gln Lys
            35                  40                  45

Gly Cys Phe Gln Val Tyr Glu Gln Gly Lys Met Thr Cys Lys Thr Pro
        50                  55                  60

Pro Ser Pro Gly Gln Ala Val Glu Cys Cys Gln Gly Asp Trp Cys Asn
65                  70                  75                  80

Arg Asn Ile Thr Ala Gln Leu Pro Thr Lys Gly Lys Ser Phe Pro Gly
                85                  90                  95

Thr Gln Asn Phe His Leu Glu Thr Gly Gly Thr His Thr Cys Pro
                100                 105                 110

Pro Cys Pro Ala Pro Glu Leu Leu Gly Gly Pro Ser Val Phe Leu Phe
            115                 120                 125

Pro Pro Lys Pro Lys Asp Thr Leu Met Ile Ser Arg Thr Pro Glu Val
        130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
210                 215                 220

Lys Gly Gln Pro Arg Glu Pro Gln Val Tyr Thr Leu Pro Pro Cys Arg
225                 230                 235                 240

Glu Glu Met Thr Lys Asn Gln Val Ser Leu Trp Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 467
<211> LENGTH: 382
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Met Asp Ala Met Lys Arg Gly Leu Cys Cys Val Leu Leu Leu Cys Gly
1               5                   10                  15

Ala Val Phe Val Ser Pro Gly Ala Gln Asn Leu Asp Ser Met Leu His
                20                  25                  30

Gly Thr Gly Met Lys Ser Asp Ser Asp Gln Lys Lys Ser Glu Asn Gly
            35                  40                  45

Val Thr Leu Ala Pro Glu Asp Thr Leu Pro Phe Leu Lys Cys Tyr Cys
 50                  55                  60

Ser Gly His Cys Pro Asp Asp Ala Ile Asn Asn Thr Cys Ile Thr Asn
 65                  70                  75                  80

Gly His Cys Phe Ala Ile Ile Glu Glu Asp Asp Gln Gly Glu Thr Thr
                 85                  90                  95

Leu Ala Ser Gly Cys Met Lys Tyr Glu Gly Ser Asp Phe Gln Cys Lys
            100                 105                 110

Asp Ser Pro Lys Ala Gln Leu Arg Arg Thr Ile Glu Cys Cys Arg Thr
            115                 120                 125

Asn Leu Cys Asn Gln Tyr Leu Gln Pro Thr Leu Pro Pro Val Val Ile
130                 135                 140

Gly Pro Phe Phe Asp Gly Ser Ile Arg Thr Gly Gly Thr His Thr
145                 150                 155                 160

Cys Pro Pro Cys Pro Ala Pro Glu Leu Leu Gly Gly Pro Ser Val Phe
                165                 170                 175

Leu Phe Pro Pro Lys Pro Lys Asp Thr Leu Met Ile Ser Arg Thr Pro
            180                 185                 190

Glu Val Thr Cys Val Val Val Asp Val Ser His Glu Asp Pro Glu Val
            195                 200                 205

Lys Phe Asn Trp Tyr Val Asp Gly Val Glu Val His Asn Ala Lys Thr
            210                 215                 220

Lys Pro Arg Glu Glu Gln Tyr Asn Ser Thr Tyr Arg Val Val Ser Val
225                 230                 235                 240

Leu Thr Val Leu His Gln Asp Trp Leu Asn Gly Lys Glu Tyr Lys Cys
                245                 250                 255

Lys Val Ser Asn Lys Ala Leu Pro Ala Pro Ile Glu Lys Thr Ile Ser
            260                 265                 270

Lys Ala Lys Gly Gln Pro Arg Glu Pro Gln Val Tyr Thr Leu Pro Pro
            275                 280                 285

Cys Arg Glu Glu Met Thr Lys Asn Gln Val Ser Leu Trp Cys Leu Val
            290                 295                 300

Lys Gly Phe Tyr Pro Ser Asp Ile Ala Val Glu Trp Glu Ser Asn Gly
305                 310                 315                 320

Gln Pro Glu Asn Asn Tyr Lys Thr Thr Pro Pro Val Leu Asp Ser Asp
                325                 330                 335

Gly Ser Phe Phe Leu Tyr Ser Lys Leu Thr Val Asp Lys Ser Arg Trp
            340                 345                 350

Gln Gln Gly Asn Val Phe Ser Cys Ser Val Met His Glu Ala Leu His
            355                 360                 365

Asn His Tyr Thr Gln Lys Ser Leu Ser Leu Ser Pro Gly Lys
            370                 375                 380

<210> SEQ ID NO 468
<211> LENGTH: 360
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Gly Ala Gln Asn Leu Asp Ser Met Leu His Gly Thr Gly Met Lys Ser

```
1               5                   10                  15
Asp Ser Asp Gln Lys Ser Glu Asn Gly Val Thr Leu Ala Pro Glu
            20                  25                  30
Asp Thr Leu Pro Phe Leu Lys Cys Tyr Cys Ser Gly His Cys Pro Asp
            35                  40                  45
Asp Ala Ile Asn Asn Thr Cys Ile Thr Asn Gly His Cys Phe Ala Ile
50                  55                  60
Ile Glu Glu Asp Asp Gln Gly Glu Thr Thr Leu Ala Ser Gly Cys Met
65                  70                  75                  80
Lys Tyr Glu Gly Ser Asp Phe Gln Cys Lys Asp Ser Pro Lys Ala Gln
                85                  90                  95
Leu Arg Arg Thr Ile Glu Cys Cys Arg Thr Asn Leu Cys Asn Gln Tyr
                100                 105                 110
Leu Gln Pro Thr Leu Pro Pro Val Val Ile Gly Pro Phe Phe Asp Gly
                115                 120                 125
Ser Ile Arg Thr Gly Gly Gly Thr His Thr Cys Pro Pro Cys Pro Ala
130                 135                 140
Pro Glu Leu Leu Gly Gly Pro Ser Val Phe Leu Phe Pro Pro Lys Pro
145                 150                 155                 160
Lys Asp Thr Leu Met Ile Ser Arg Thr Pro Glu Val Thr Cys Val Val
                165                 170                 175
Val Asp Val Ser His Glu Asp Pro Glu Val Lys Phe Asn Trp Tyr Val
                180                 185                 190
Asp Gly Val Glu Val His Asn Ala Lys Thr Lys Pro Arg Glu Glu Gln
            195                 200                 205
Tyr Asn Ser Thr Tyr Arg Val Val Ser Val Leu Thr Val Leu His Gln
            210                 215                 220
Asp Trp Leu Asn Gly Lys Glu Tyr Lys Cys Lys Val Ser Asn Lys Ala
225                 230                 235                 240
Leu Pro Ala Pro Ile Glu Lys Thr Ile Ser Lys Ala Lys Gly Gln Pro
                245                 250                 255
Arg Glu Pro Gln Val Tyr Thr Leu Pro Pro Cys Arg Glu Glu Met Thr
                260                 265                 270
Lys Asn Gln Val Ser Leu Trp Cys Leu Val Lys Gly Phe Tyr Pro Ser
                275                 280                 285
Asp Ile Ala Val Glu Trp Glu Ser Asn Gly Gln Pro Glu Asn Asn Tyr
            290                 295                 300
Lys Thr Thr Pro Pro Val Leu Asp Ser Asp Gly Ser Phe Phe Leu Tyr
305                 310                 315                 320
Ser Lys Leu Thr Val Asp Lys Ser Arg Trp Gln Gln Gly Asn Val Phe
                325                 330                 335
Ser Cys Ser Val Met His Glu Ala Leu His Asn His Tyr Thr Gln Lys
                340                 345                 350
Ser Leu Ser Leu Ser Pro Gly Lys
                355                 360

<210> SEQ ID NO 469
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469
```

Met Asp Ala Met Lys Arg Gly Leu Cys Cys Val Leu Leu Leu Cys Gly
1               5                   10                  15

Ala Val Phe Val Ser Pro Gly Ala Ser Gly Pro Arg Gly Val Gln Ala
            20                  25                  30

Leu Leu Cys Ala Cys Thr Ser Cys Leu Gln Ala Asn Tyr Thr Cys Glu
        35                  40                  45

Thr Asp Gly Ala Cys Met Val Ser Ile Phe Asn Leu Asp Gly Met Glu
    50                  55                  60

His His Val Arg Thr Cys Ile Pro Lys Val Glu Leu Val Pro Ala Gly
65                  70                  75                  80

Lys Pro Phe Tyr Cys Leu Ser Ser Glu Asp Leu Arg Asn Thr His Cys
                85                  90                  95

Cys Tyr Thr Asp Tyr Cys Asn Arg Ile Asp Leu Arg Val Pro Ser Gly
            100                 105                 110

His Leu Lys Glu Pro Glu His Pro Ser Met Trp Gly Pro Val Glu Thr
        115                 120                 125

Gly Gly Gly Thr His Thr Cys Pro Pro Cys Pro Ala Pro Glu Leu Leu
        130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Cys Arg Glu Glu Met Thr Lys Asn Gln Val
            260                 265                 270

Ser Leu Trp Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
        290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 470
<211> LENGTH: 332
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

```
Ser Gly Pro Arg Gly Val Gln Ala Leu Leu Cys Ala Cys Thr Ser Cys
1               5                   10                  15

Leu Gln Ala Asn Tyr Thr Cys Glu Thr Asp Gly Ala Cys Met Val Ser
            20                  25                  30

Ile Phe Asn Leu Asp Gly Met Glu His His Val Arg Thr Cys Ile Pro
        35                  40                  45

Lys Val Glu Leu Val Pro Ala Gly Lys Pro Phe Tyr Cys Leu Ser Ser
    50                  55                  60

Glu Asp Leu Arg Asn Thr His Cys Cys Tyr Thr Asp Tyr Cys Asn Arg
65                  70                  75                  80

Ile Asp Leu Arg Val Pro Ser Gly His Leu Lys Glu Pro Glu His Pro
                85                  90                  95

Ser Met Trp Gly Pro Val Glu Thr Gly Gly Thr His Thr Cys Pro
                100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
                180                 185                 190

Val Leu His Gln Asp Trp Leu Asn Gly Lys Glu Tyr Lys Cys Lys Val
            195                 200                 205

Ser Asn Lys Ala Leu Pro Ala Pro Ile Glu Lys Thr Ile Ser Lys Ala
210                 215                 220

Lys Gly Gln Pro Arg Glu Pro Gln Val Tyr Thr Leu Pro Pro Cys Arg
225                 230                 235                 240

Glu Glu Met Thr Lys Asn Gln Val Ser Leu Trp Cys Leu Val Lys Gly
                245                 250                 255

Phe Tyr Pro Ser Asp Ile Ala Val Glu Trp Glu Ser Asn Gly Gln Pro
                260                 265                 270

Glu Asn Asn Tyr Lys Thr Thr Pro Pro Val Leu Asp Ser Asp Gly Ser
            275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330

<210> SEQ ID NO 471
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

Met Asp Ala Met Lys Arg Gly Leu Cys Cys Val Leu Leu Leu Cys Gly
1               5                   10                  15

Ala Val Phe Val Ser Pro Gly Ala Ala Leu Leu Pro Gly Ala Thr Ala
```

```
                20                  25                  30
Leu Gln Cys Phe Cys His Leu Cys Thr Lys Asp Asn Phe Thr Cys Val
            35                  40                  45

Thr Asp Gly Leu Cys Phe Val Ser Val Thr Glu Thr Thr Asp Lys Val
        50                  55                  60

Ile His Asn Ser Met Cys Ile Ala Glu Ile Asp Leu Ile Pro Arg Asp
65                  70                  75                  80

Arg Pro Phe Val Cys Ala Pro Ser Ser Lys Thr Gly Ser Val Thr Thr
                85                  90                  95

Thr Tyr Cys Cys Asn Gln Asp His Cys Asn Lys Ile Glu Leu Pro Thr
            100                 105                 110

Thr Val Lys Ser Ser Pro Gly Leu Gly Pro Val Glu Thr Gly Gly Gly
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Cys Arg Glu Glu Met Thr Lys Asn Gln Val Ser Leu Trp
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys

<210> SEQ ID NO 472
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Ala Leu Leu Pro Gly Ala Thr Ala Leu Gln Cys Phe Cys His Leu Cys
1               5                   10                  15

Thr Lys Asp Asn Phe Thr Cys Val Thr Asp Gly Leu Cys Phe Val Ser
```

```
                20              25              30
Val Thr Glu Thr Thr Asp Lys Val Ile His Asn Ser Met Cys Ile Ala
            35              40              45

Glu Ile Asp Leu Ile Pro Arg Asp Arg Pro Phe Val Cys Ala Pro Ser
        50              55              60

Ser Lys Thr Gly Ser Val Thr Thr Tyr Cys Cys Asn Gln Asp His
65              70              75              80

Cys Asn Lys Ile Glu Leu Pro Thr Thr Val Lys Ser Ser Pro Gly Leu
            85              90              95

Gly Pro Val Glu Thr Gly Gly Thr His Thr Cys Pro Pro Cys Pro
        100             105             110

Ala Pro Glu Leu Leu Gly Gly Pro Ser Val Phe Leu Phe Pro Pro Lys
            115             120             125

Pro Lys Asp Thr Leu Met Ile Ser Arg Thr Pro Glu Val Thr Cys Val
        130             135             140

Val Val Asp Val Ser His Glu Asp Pro Glu Val Lys Phe Asn Trp Tyr
145             150             155             160

Val Asp Gly Val Glu Val His Asn Ala Lys Thr Lys Pro Arg Glu Glu
            165             170             175

Gln Tyr Asn Ser Thr Tyr Arg Val Val Ser Val Leu Thr Val Leu His
        180             185             190

Gln Asp Trp Leu Asn Gly Lys Glu Tyr Lys Cys Lys Val Ser Asn Lys
            195             200             205

Ala Leu Pro Ala Pro Ile Glu Lys Thr Ile Ser Lys Ala Lys Gly Gln
        210             215             220

Pro Arg Glu Pro Gln Val Tyr Thr Leu Pro Pro Cys Arg Glu Glu Met
225             230             235             240

Thr Lys Asn Gln Val Ser Leu Trp Cys Leu Val Lys Gly Phe Tyr Pro
            245             250             255

Ser Asp Ile Ala Val Glu Trp Glu Ser Asn Gly Gln Pro Glu Asn Asn
        260             265             270

Tyr Lys Thr Thr Pro Pro Val Leu Asp Ser Asp Gly Ser Phe Phe Leu
            275             280             285

Tyr Ser Lys Leu Thr Val Asp Lys Ser Arg Trp Gln Gln Gly Asn Val
        290             295             300

Phe Ser Cys Ser Val Met His Glu Ala Leu His Asn His Tyr Thr Gln
305             310             315             320

Lys Ser Leu Ser Leu Ser Pro Gly Lys
            325

<210> SEQ ID NO 473
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 473

Met Asp Ala Met Lys Arg Gly Leu Cys Cys Val Leu Leu Leu Cys Gly
1               5               10              15

Ala Val Phe Val Ser Pro Gly Ala Lys Lys Glu Asp Gly Glu Ser Thr
            20              25              30

Ala Pro Thr Pro Arg Pro Lys Val Leu Arg Cys Lys Cys His His
        35              40              45
```

```
Cys Pro Glu Asp Ser Val Asn Asn Ile Cys Ser Thr Asp Gly Tyr Cys
 50                  55                  60

Phe Thr Met Ile Glu Glu Asp Asp Ser Gly Leu Pro Val Val Thr Ser
 65                  70                  75                  80

Gly Cys Leu Gly Leu Glu Gly Ser Asp Phe Gln Cys Arg Asp Thr Pro
                 85                  90                  95

Ile Pro His Gln Arg Arg Ser Ile Glu Cys Cys Thr Glu Arg Asn Glu
            100                 105                 110

Cys Asn Lys Asp Leu His Pro Thr Leu Pro Pro Leu Lys Asn Arg Asp
        115                 120                 125

Phe Val Asp Gly Pro Ile His His Arg Thr Gly Gly Gly Thr His Thr
130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205

Lys Pro Arg Glu Glu Gln Tyr Asn Ser Thr Tyr Arg Val Val Ser Val
210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Cys Arg Glu Glu Met Thr Lys Asn Gln Val Ser Leu Trp Cys Leu Val
        275                 280                 285

Lys Gly Phe Tyr Pro Ser Asp Ile Ala Val Glu Trp Glu Ser Asn Gly
290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 474
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 474

Lys Lys Glu Asp Gly Glu Ser Thr Ala Pro Thr Pro Arg Pro Lys Val
 1               5                  10                  15

Leu Arg Cys Lys Cys His His His Cys Pro Glu Asp Ser Val Asn Asn
                20                  25                  30

Ile Cys Ser Thr Asp Gly Tyr Cys Phe Thr Met Ile Glu Glu Asp Asp
            35                  40                  45
```

Ser Gly Leu Pro Val Val Thr Ser Gly Cys Leu Gly Leu Glu Gly Ser
            50                  55                  60

Asp Phe Gln Cys Arg Asp Thr Pro Ile Pro His Gln Arg Arg Ser Ile
 65                  70                  75                  80

Glu Cys Cys Thr Glu Arg Asn Glu Cys Asn Lys Asp Leu His Pro Thr
                 85                  90                  95

Leu Pro Pro Leu Lys Asn Arg Asp Phe Val Asp Gly Pro Ile His His
                100                 105                 110

Arg Thr Gly Gly Thr His Thr Cys Pro Pro Cys Pro Ala Pro Glu
                115                 120                 125

Leu Leu Gly Gly Pro Ser Val Phe Leu Phe Pro Lys Pro Lys Asp
        130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
                180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Cys Arg Glu Glu Met Thr Lys Asn
                245                 250                 255

Gln Val Ser Leu Trp Cys Leu Val Lys Gly Phe Tyr Pro Ser Asp Ile
                260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
        290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 475
<211> LENGTH: 342
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 475

Met Asp Ala Met Lys Arg Gly Leu Cys Cys Val Leu Leu Leu Cys Gly
 1               5                  10                  15

Ala Val Phe Val Ser Pro Gly Ala Gly Leu Lys Cys Val Cys Leu Leu
                 20                  25                  30

Cys Asp Ser Ser Asn Phe Thr Cys Gln Thr Glu Gly Ala Cys Trp Ala
        35                  40                  45

Ser Val Met Leu Thr Asn Gly Lys Glu Gln Val Ile Lys Ser Cys Val

```
            50                  55                  60
Ser Leu Pro Glu Leu Asn Ala Gln Val Phe Cys His Ser Ser Asn Asn
 65                  70                  75                  80

Val Thr Lys Thr Glu Cys Cys Phe Thr Asp Phe Cys Asn Asn Ile Thr
                 85                  90                  95

Leu His Leu Pro Thr Ala Ser Pro Asn Ala Pro Lys Leu Gly Pro Met
            100                 105                 110

Glu Thr Gly Gly Gly Thr His Thr Cys Pro Pro Cys Pro Ala Pro Glu
        115                 120                 125

Leu Leu Gly Gly Pro Ser Val Phe Leu Phe Pro Pro Lys Pro Lys Asp
130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Asn
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
210                 215                 220

Ala Pro Ile Glu Lys Thr Ile Ser Lys Ala Lys Gly Gln Pro Arg Glu
225                 230                 235                 240

Pro Gln Val Tyr Thr Leu Pro Pro Cys Arg Glu Glu Met Thr Lys Asn
                245                 250                 255

Gln Val Ser Leu Trp Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 476
<211> LENGTH: 318
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 476

Gly Leu Lys Cys Val Cys Leu Leu Cys Asp Ser Ser Asn Phe Thr Cys
 1               5                  10                  15

Gln Thr Glu Gly Ala Cys Trp Ala Ser Val Met Leu Thr Asn Gly Lys
            20                  25                  30

Glu Gln Val Ile Lys Ser Cys Val Ser Leu Pro Glu Leu Asn Ala Gln
        35                  40                  45

Val Phe Cys His Ser Ser Asn Asn Val Thr Lys Thr Glu Cys Cys Phe
50                  55                  60
```

```
Thr Asp Phe Cys Asn Asn Ile Thr Leu His Leu Pro Thr Ala Ser Pro
 65                  70                  75                  80

Asn Ala Pro Lys Leu Gly Pro Met Glu Thr Gly Gly Gly Thr His Thr
                 85                  90                  95

Cys Pro Pro Cys Pro Ala Pro Glu Leu Leu Gly Gly Pro Ser Val Phe
            100                 105                 110

Leu Phe Pro Pro Lys Pro Lys Asp Thr Leu Met Ile Ser Arg Thr Pro
        115                 120                 125

Glu Val Thr Cys Val Val Val Asp Val Ser His Glu Asp Pro Glu Val
    130                 135                 140

Lys Phe Asn Trp Tyr Val Asp Gly Val Glu Val His Asn Ala Lys Thr
145                 150                 155                 160

Lys Pro Arg Glu Glu Gln Tyr Asn Ser Thr Tyr Arg Val Val Ser Val
                165                 170                 175

Leu Thr Val Leu His Gln Asp Trp Leu Asn Gly Lys Glu Tyr Lys Cys
            180                 185                 190

Lys Val Ser Asn Lys Ala Leu Pro Ala Pro Ile Glu Lys Thr Ile Ser
        195                 200                 205

Lys Ala Lys Gly Gln Pro Arg Glu Pro Gln Val Tyr Thr Leu Pro Pro
210                 215                 220

Cys Arg Glu Glu Met Thr Lys Asn Gln Val Ser Leu Trp Cys Leu Val
225                 230                 235                 240

Lys Gly Phe Tyr Pro Ser Asp Ile Ala Val Glu Trp Glu Ser Asn Gly
                245                 250                 255

Gln Pro Glu Asn Asn Tyr Lys Thr Thr Pro Pro Val Leu Asp Ser Asp
            260                 265                 270

Gly Ser Phe Phe Leu Tyr Ser Lys Leu Thr Val Asp Lys Ser Arg Trp
        275                 280                 285

Gln Gln Gly Asn Val Phe Ser Cys Ser Val Met His Glu Ala Leu His
290                 295                 300

Asn His Tyr Thr Gln Lys Ser Leu Ser Leu Ser Pro Gly Lys
305                 310                 315
```

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

<210> SEQ ID NO 485

<400> SEQUENCE: 485

000

<210> SEQ ID NO 486

<400> SEQUENCE: 486

000

<210> SEQ ID NO 487

<400> SEQUENCE: 487

000

<210> SEQ ID NO 488

<400> SEQUENCE: 488

000

<210> SEQ ID NO 489

<400> SEQUENCE: 489

000

<210> SEQ ID NO 490

<400> SEQUENCE: 490

000

<210> SEQ ID NO 491

<400> SEQUENCE: 491

000

<210> SEQ ID NO 492

<400> SEQUENCE: 492

<210> SEQ ID NO 493

<400> SEQUENCE: 493

000

<210> SEQ ID NO 494

<400> SEQUENCE: 494

000

<210> SEQ ID NO 495

<400> SEQUENCE: 495

000

<210> SEQ ID NO 496

<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500
<211> LENGTH: 116
<212> TYPE: PRT
<213> ORGANISM: Homo sapiens

<400> SEQUENCE: 500

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110
```

Lys Pro Pro Thr
        115

<210> SEQ ID NO 501
<211> LENGTH: 150
<212> TYPE: PRT
<213> ORGANISM: Rattus sp.

<400> SEQUENCE: 501

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Pro
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 502
<211> LENGTH: 150
<212> TYPE: PRT
<213> ORGANISM: Sus sp.

<400> SEQUENCE: 502

Met Thr Ala Pro Trp Ala Ala Leu Ala Leu Leu Trp Gly Ser Leu Cys
1               5                   10                  15

Val Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150

<210> SEQ ID NO 503
<211> LENGTH: 150
<212> TYPE: PRT
<213> ORGANISM: Mus sp.

<400> SEQUENCE: 503

```
Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Pro Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150
```

<210> SEQ ID NO 504
<211> LENGTH: 150
<212> TYPE: PRT
<213> ORGANISM: Homo sapiens

<400> SEQUENCE: 504

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser
145                 150
```

<210> SEQ ID NO 505

```
<211> LENGTH: 150
<212> TYPE: PRT
<213> ORGANISM: Bos sp.

<400> SEQUENCE: 505

Met Thr Ala Pro Trp Ala Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Arg Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Val Gly Gly Leu Ser
145                 150

<210> SEQ ID NO 506
<211> LENGTH: 150
<212> TYPE: PRT
<213> ORGANISM: Xenopus sp.

<400> SEQUENCE: 506

Met Gly Ala Ser Val Ala Leu Thr Phe Leu Leu Leu Ala Thr Phe
1               5                   10                  15

Arg Ala Gly Ser Gly His Asp Glu Val Glu Thr Arg Glu Cys Ile Tyr
            20                  25                  30

Tyr Asn Ala Asn Trp Glu Leu Glu Lys Thr Asn Gln Ser Gly Val Glu
        35                  40                  45

Arg Leu Val Glu Gly Lys Lys Asp Lys Arg Leu His Cys Tyr Ala Ser
    50                  55                  60

Trp Arg Asn Asn Ser Gly Phe Ile Glu Leu Val Lys Lys Gly Cys Trp
65                  70                  75                  80

Leu Asp Asp Phe Asn Cys Tyr Asp Arg Gln Glu Cys Ile Ala Lys Glu
                85                  90                  95

Glu Asn Pro Gln Val Phe Phe Cys Cys Cys Glu Gly Asn Tyr Cys Asn
            100                 105                 110

Lys Lys Phe Thr His Leu Pro Glu Val Glu Thr Phe Asp Pro Lys Pro
        115                 120                 125

Gln Pro Ser Ala Ser Val Leu Asn Ile Leu Ile Tyr Ser Leu Leu Pro
    130                 135                 140

Ile Val Gly Leu Ser Met
145                 150

<210> SEQ ID NO 507
<211> LENGTH: 150
<212> TYPE: PRT
<213> ORGANISM: Homo sapiens
```

<400> SEQUENCE: 507

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
            115                 120                 125

Pro Val Thr Pro Lys Pro Pro Tyr Tyr Asn Ile Leu Leu Tyr Ser Leu
        130                 135                 140

Val Pro Leu Met Leu Ile
145                 150

<210> SEQ ID NO 508
<211> LENGTH: 154
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (8)..(8)
<223> OTHER INFORMATION: Thr, Ala or not present
<220> FEATURE:
<221> NAME/KEY: MOD_RES
<222> LOCATION: (121)..(121)
<223> OTHER INFORMATION: Pro, Ala, Val or Met

<400> SEQUENCE: 508

Met Thr Ala Pro Trp Ala Ala Xaa Leu Ala Leu Leu Trp Gly Ser Leu
1               5                   10                  15

Cys Ala Gly Ser Gly Arg Gly Glu Ala Glu Thr Arg Glu Cys Ile Tyr
            20                  25                  30

Tyr Asn Ala Asn Trp Glu Leu Glu Arg Thr Asn Gln Ser Gly Leu Glu
        35                  40                  45

Arg Leu Cys Glu Gly Glu Gln Asp Lys Arg Leu His Cys Tyr Ala Ser
    50                  55                  60

Trp Arg Asn Ser Ser Gly Thr Ile Glu Leu Val Lys Lys Gly Cys Trp
65                  70                  75                  80

Leu Asp Asp Phe Asn Cys Tyr Asp Arg Gln Glu Cys Val Ala Thr Glu
                85                  90                  95

Glu Asn Pro Gln Val Tyr Phe Cys Cys Cys Glu Gly Asn Phe Cys Asn
            100                 105                 110

Glu Arg Phe Thr His Leu Pro Glu Xaa Gly Gly Pro Glu Val Thr Tyr
            115                 120                 125

Glu Pro Lys Pro Pro Thr Ala Pro Thr Leu Leu Thr Val Leu Ala Tyr
        130                 135                 140

```
Ser Leu Leu Pro Ile Gly Gly Leu Ser Met
145                 150

<210> SEQ ID NO 509
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 509

His His His His His His
1               5
```